US008461209B2

(12) United States Patent
Yoshida et al.

(10) Patent No.: US 8,461,209 B2
(45) Date of Patent: Jun. 11, 2013

(54) MALONIC ACID SULFONAMIDE DERIVATIVE AND PHARMACEUTICAL USE THEREOF

(75) Inventors: Tomohiro Yoshida, Osaka (JP); Hiroshi Sakashita, Osaka (JP); Atsushi Numata, Osaka (JP); Saori Tahara, Osaka (JP); Hisashi Kawasumi, Osaka (JP)

(73) Assignee: Mitsubishi Tanabe Pharma Corporation, Osaka-shi (JP)

( * ) Notice: Subject to any disclaimer, the term of this patent is extended or adjusted under 35 U.S.C. 154(b) by 749 days.

(21) Appl. No.: 12/665,537

(22) PCT Filed: Jun. 19, 2008

(86) PCT No.: PCT/JP2008/061248
§ 371 (c)(1),
(2), (4) Date: Dec. 18, 2009

(87) PCT Pub. No.: WO2008/156142
PCT Pub. Date: Dec. 24, 2008

(65) Prior Publication Data
US 2010/0228026 A1    Sep. 9, 2010

(30) Foreign Application Priority Data

Jun. 20, 2007  (JP) .................................. 2007/163099

(51) Int. Cl.
*A61K 31/18* (2006.01)
*C07C 311/28* (2006.01)
*C07C 311/29* (2006.01)

(52) U.S. Cl.
USPC ................. 514/601; 564/80; 564/84; 564/95; 514/602; 514/605

(58) Field of Classification Search
USPC ................. 564/80, 84, 95; 514/601, 602, 605
See application file for complete search history.

(56) References Cited

U.S. PATENT DOCUMENTS

| 3,763,154 A | 10/1973 | Henniger et al. |
| 3,819,600 A | 6/1974 | Hamanaka et al. |
| 2004/0167176 A1 | 8/2004 | Alterman et al. |
| 2009/0069382 A1 | 3/2009 | Alterman et al. |
| 2009/0215847 A1 | 8/2009 | Alterman et al. |

FOREIGN PATENT DOCUMENTS

| GB | 1 339 708 | | 12/1973 |
| IN | 178290 | A | 3/1997 |
| JP | 48-85594 | A | 11/1973 |
| JP | 2004-533457 | A | 11/2004 |
| RU | 1824396 | A1 | 6/1993 |
| SU | 1824396 | A1 * | 6/1993 |
| WO | WO 03/064414 | A1 | 8/2003 |
| WO | WO 2004/046128 | A1 | 6/2004 |
| WO | WO 2004/046137 | A1 | 6/2004 |
| WO | WO 2004/046141 | A1 | 6/2004 |
| WO | WO 2004-085420 | A1 | 10/2004 |
| WO | WO 2006/109056 | A1 | 10/2006 |
| WO | WO 2006/109058 | A1 | 10/2006 |

OTHER PUBLICATIONS

Chakravarty et al., *Bioorganic & Medicinal Chemistry Letters*, 4(1): 75-80 (1994).
Cravotto et al., *Tetrahedron*, 52(40): 13007-13016 (1996).
Cravotto et al., *Tetrahedron*, 54: 1639-1646 (1998).
Desai et al., *Synthetic Communications*, 34(1): 25-32 (2004).
Donkor et al., *Eur. J. Med. Chem.*, 33: 15-22 (1998).
Gasparo et al., *Pharmacological Reviews*, 52(3): 415-472 (2000).
Harada et al., *Bioorganic & Medicinal Chemistry*, 9: 2955-2968 (2001).
Hin et al., *J. Org. Chem.*, 67: 7365-7368 (2002).
Hrubowchak et al., *Tetrahedron Letters*, 24(45): 4951-4954 (1983).
Ishizuka et al., *Synthesis*, 6: 784-788 (2000).
Jansen et al., *European Journal of Medicinal Chemistry*, 38: 855-865 (2003).
Niwayama et al., *J. Org. Chem.*, 65: 5834-5836 (2000).
Padgett et al., *J. Org. Chem.*, 44(20): 3492-3496 (1979).
Sakaki et al., *Bioorganic & Medicinal Chemistry Letters*, 8: 2241-2246 (1998).
Skarzewski, Jacek, *Synthesis*, 1125-1127 (Dec. 1990).
Smrcina et al., *Tetrahedron*, 53(38): 12867-12874 (1997).
Strube, R.E., *Organic Syntheses*, Coll. vol. 4: 417 (1963).
Toth et al., *Synthetic Communications*, 25(19): 3067-3074 (1995).
Wan et al., *J. Med. Chem.*, 47: 5995-6008 (2004).
Wu et al., *J. Med. Chem.*, 49: 7160-7168 (2006).
Nelson et al., Database CAPLUS [Online] Chemical Abstracts Service, Columbus, Ohio, STN Database accession No. 1980-93593 (1980).

* cited by examiner

*Primary Examiner* — Kamal Saeed
*Assistant Examiner* — Janet L Coppins
(74) *Attorney, Agent, or Firm* — Leydig, Voit & Mayer, Ltd.

(57) ABSTRACT

The invention provides a sulfonyl malonamide derivative, or a pharmacologically acceptable salt thereof or a solvate thereof, that has therapeutic and/or preventive effects(s) on various diseases due to its agonist action at $AT_2$ receptor, and is useful as a pharmaceutical agent for the treatment and/or prevention of diseases involving the renin-angiotensin-aldosterone system (RAAS).

16 Claims, No Drawings

MALONIC ACID SULFONAMIDE DERIVATIVE AND PHARMACEUTICAL USE THEREOF

TECHNICAL FIELD OF THE INVENTION

The present invention relates to a sulfonyl malonamide derivative that is a ligand for an angiotensin type 2 receptor (hereinafter to be indicated as $AT_2$ receptor), preferably having an agonist action at $AT_2$ receptor, and a pharmaceutical agent containing same.

BACKGROUND OF THE INVENTION

Biologically, angiotensinogen is converted via renin to angiotensin I, which is subsequently converted to angiotensin II (AngII) by converting enzymes such as angiotensin converting enzyme (ACE) and the like in vivo, resulting AngII has a potent and pleiotropic physiological action.

As receptors for AngII, the angiotensin type 1 receptor (hereinafter to be indicated as $AT_1$ receptor) and $AT_2$ receptor have been identified. It has been generally understood that conventionally well-known actions of AngII such as pressor effect on blood pressure, vasoconstriction and other effects are mainly mediated by classical $AT_1$ receptors. On the other hand, the physiological roles of $AT_2$ receptor have been rapidly revealed in recent years. The action via $AT_2$ receptor mostly opposes the effect mediated by $AT_1$ receptor in a number of cells and tissues and $AT_2$ receptor mainly acts toward the prevention of diseases progression in the course of the onset and the development, as evidenced by its antiproliferative, antihypertrophic and antihypertensive effects, promotion of apoptosis, inhibition of extracellular matrix production and the like. While $AT_2$ receptor is highly expressed in a wide range in fetal life, the expression level rapidly decreases after birth. However, it has become known that tissue-specific re-expression of $AT_2$ under pathological conditions, such as vascular injury, cardiovascular remodeling after myocardial infarction and the like, thereby the significance of $AT_2$ receptor involved in the prevention of the onset and progress of various diseases is much attracting attention.

Predicted pharmacological actions generally via $AT_2$ receptor activation have been reported in several papers including a paper from de Gasparo et al. (see non-patent reference 1). Thus, a variety of therapeutic or preventive effects in several diseases could be expected as pharmaceutical use of $AT_2$ receptor agonist. As its target diseases, various groups of disorders involving the renin-angiotensin-aldosterone system (hereinafter to be indicated as RAAS), such as metabolic diseases, cardiovascular diseases and the like are considered, and stroke, renal disease, cardiac disease, hypertension, diabetes, metabolic syndrome and the like can be given as examples.

As nonpeptidic $AT_2$ receptor agonist, 3-phenyl-2-thiophene sulfonamide or biphenyl sulfonamide compounds have heretofore been disclosed (see non-patent references 2, 3, patent references 1, 2, 3, 4, 5, 6, 7, 8, 9). However, the compounds described in these non-patent references and patent references are all characterized by a combination of a bisaryl structure and a sulfonamide group and the like, and a sulfonyl malonamide derivative is not clearly indicated or suggested.

While sulfonyl malonamide derivatives are known as herbicides (see patent reference 10), all of them are unsubstituted sulfonyl malonamide derivatives, and no reference is made to an $AT_2$ receptor agonist for a sulfonyl malonamide derivative having a substituent at 2-position of the malonamide structure.

The $AT_2$ receptor agonists reported up to current times have not been confirmed regarding the selectivity to other target molecules, pharmacokinetic property and/or safety. In addition, none of compounds successfully available or under development as a pharmaceutical product has been disclosed based on the mechanism of agonist action at $AT_2$ receptor.

non-patent reference 1: Pharmacol. Rev., 52, 415-472 (2000)
non-patent reference 2: J. Med. Chem., 47, 5995-6008 (2004)
non-patent reference 3: J. Med. Chem., 49, 7160-7168 (2006)
patent reference 1: WO02/096883
patent reference 2: WO06/109058
patent reference 3: WO03/064414
patent reference 4: WO04/046128
patent reference 5: WO04/046137
patent reference 6: WO04/085420
patent reference 7: WO06/109056
patent reference 8: WO06/109058
patent reference 9: WO04/046141
patent reference 10: Indian patent No. 178290

DISCLOSURE OF THE INVENTION

Problems to be Solved by the Invention

It is therefore an object of the present invention to provide a novel ligand, preferably a novel agonist, for an $AT_2$ receptor, which is expected as a pharmaceutical product, whereby to contribute to the development of therapeutic and/or preventive methods for various diseases.

Means of Solving the Problems

The present inventors have found that a certain kind of sulfonyl malonamide derivative has an agonist action at $AT_2$ receptor and conducted intensive studies. As a result, they have found that a novel sulfonyl malonamide derivative having a potent and selective agonist action at $AT_2$ receptor can be expected as a pharmaceutical product, which resulted in the completion of the present invention.

Accordingly, the present invention relates to the following sulfonyl malonamide derivative or a pharmacologically acceptable salt thereof, or a solvate thereof, and use of a ligand, agonist and the like comprising the same.

(1) A sulfonyl malonamide derivative represented by the following formula (I)

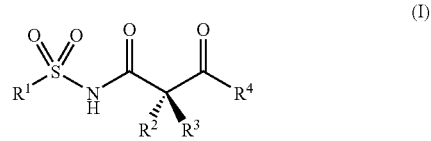

wherein $R^1$ is optionally substituted $C_{1-8}$ alkyl, optionally substituted $C_{2-6}$ alkenyl, optionally substituted $C_{2-6}$ alkynyl, optionally substituted $C_{3-10}$ cycloalkyl, optionally substituted cycloalkyl $C_{1-6}$ alkyl, optionally substituted heterocycle, optionally substituted aryl, optionally substituted aryl $C_{1-6}$ alkyl, optionally substituted aryloxy $C_{1-6}$ alkyl, optionally substituted aryl $C_{2-6}$ alkenyl, optionally substituted heteroaryl, optionally substituted heteroaryl $C_{1-6}$ alkyl, optionally substituted heteroaryloxy $C_{1-6}$ alkyl or optionally substituted heteroaryl $C_{2-6}$ alkenyl;

one of $R^2$ and $R^3$ is a hydrogen atom or a halogen atom, and the other is a halogen atom, optionally substituted $C_{1-6}$ alkyl, optionally substituted $C_{1-6}$ alkoxy, optionally substituted $C_{2-6}$ alkenyl, optionally substituted $C_{2-6}$ alkynyl, —$(CH_2)_n$—C(O)—$NR^5R^6$ (wherein n is an integer of 1 to 6, $R^5$ and $R^6$ are the same or different and each is a hydrogen atom, $C_{1-6}$ alkyl, optionally substituted aryl or optionally substituted heteroaryl, or $R^5$ and $R^6$ optionally form optionally substituted cyclic amino together with a nitrogen atom bonded thereto), optionally substituted $C_{3-10}$ cycloalkyl, optionally substituted heterocycle, optionally substituted $C_{3-10}$ cycloalkyl $C_{1-6}$ alkyl, optionally substituted heterocycle $C_{1-6}$ alkyl, optionally substituted aryl, optionally substituted aryl $C_{1-6}$ alkyl, optionally substituted aryloxy $C_{1-6}$ alkyl, optionally substituted aryl $C_{2-6}$ alkenyl, optionally substituted heteroaryl, optionally substituted heteroaryl $C_{1-6}$ alkyl, optionally substituted heteroaryloxy $C_{1-6}$ alkyl or optionally substituted heteroaryl $C_{2-6}$ alkenyl, or Fe and $R^3$ optionally form, together with a carbon atom bonded thereto, C=CX'Y' (wherein X' and Y' are the same or different and each is a hydrogen atom, optionally substituted $C_{1-6}$ alkyl, optionally substituted aryl or optionally substituted heteroaryl), or optionally substituted $C_{3-10}$ cycloalkyl; and
$R^4$ is the following formula

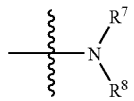

wherein $R^7$ and $R^8$ are the same or different and each is a hydrogen atom, optionally substituted $C_{1-6}$ alkyl, optionally substituted $C_{2-6}$ alkenyl, optionally substituted aryl, optionally substituted aryl $C_{1-6}$ alkyl, optionally substituted heteroaryl, optionally substituted heteroaryl $C_{1-6}$ alkyl, optionally substituted $C_{3-10}$ cycloalkyl or optionally substituted heterocycle, or $R^7$ and $R^8$ optionally form optionally substituted cyclic amino together with a nitrogen atom bonded thereto,
or a pharmacologically acceptable salt thereof, or a solvate thereof.
(2) The sulfonyl malonamide derivative of the above-mentioned (1), wherein $R^1$ is optionally substituted naphthyl, optionally substituted biphenyl, optionally substituted phenyl, optionally substituted thiophene, optionally substituted phenyl $C_{1-6}$ alkyl, optionally substituted phenoxy $C_{1-6}$ alkyl, optionally substituted thiazolyl $C_{1-6}$ alkyl, optionally substituted $C_{1-8}$ alkyl, optionally substituted $C_{2-6}$ alkenyl, optionally substituted $C_{3-10}$ cycloalkyl, or the following formula

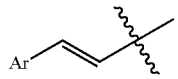

wherein Ar is optionally substituted phenyl, optionally substituted pyridyl or optionally substituted thiazolyl,
or a pharmacologically acceptable salt thereof, or a solvate thereof.
(3) The sulfonyl malonamide derivative of the above-mentioned (1), wherein one of $R^2$ and $R^3$ is a hydrogen atom, and the other is $C_{1-6}$ alkyl, allyl, prenyl, 2-propynyl, cyclopentyl, —$CH_2$—$R^9$ (wherein $R^9$ is cyclopropyl, cyano, optionally substituted cyclohexyl, optionally N-substituted 4-piperidinyl or —CO—$NR^5R^6$ wherein $R^5$ and $R^6$ are as defined above for (1)), —$(CH_2)_2$—$R^{9'}$ (wherein $R^{9'}$ is cyano, $C_{1-6}$ alkoxy, $C_{1-6}$ alkylthio, $C_{1-6}$ alkylsulfinyl, $C_{1-6}$ alkylsulfonyl, N-substituted-4-piperidinyl or N-substituted-4-piperazinyl), —$(CH_2)_n$—$Ar^1$ or —$CH_2$—CH=CH—$Ar^1$ (wherein n is an integer of 0 to 6, and $Ar^1$ is optionally substituted aryl or optionally substituted heteroaryl),
or a pharmacologically acceptable salt thereof, or a solvate thereof.
(4) The sulfonyl malonamide derivative of the above-mentioned (1), wherein $R^4$ is represented by the following formula

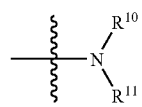

wherein $R^{10}$ and $R^{11}$ are the same or different and each is optionally substituted $C_{1-6}$ alkyl, optionally substituted $C_{2-6}$ alkenyl, optionally substituted aryl, optionally substituted aryl $C_{1-6}$ alkyl, optionally substituted heteroaryl, optionally substituted $C_{3-10}$ cycloalkyl or optionally substituted heterocycle, or $R^{10}$ and $R^{11}$ optionally form optionally substituted cyclic amino together with a nitrogen atom bonded thereto,
or a pharmacologically acceptable salt thereof, or a solvate thereof.
(5) An $AT_2$ receptor ligand comprising a sulfonyl malonamide derivative of any of the aforementioned (1) to (4), or a pharmacologically acceptable salt thereof, or a solvate thereof.
(6) The sulfonyl malonamide derivative of the above-mentioned (1), which is represented by the following formula (II)

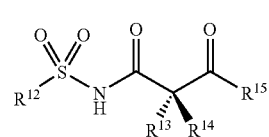

(II)

wherein $R^{12}$ is 2-naphthyl, trans-β-styryl, phenethyl, 3-phenoxypropyl or 4-phenylbutyl;
one of $R^{13}$ and $R^{14}$ is a hydrogen atom, and the other is isopropyl, isobutyl, neopentyl, allyl, —$CH_2$—$R^{16}$ wherein $R^{16}$ is optionally substituted $C_{3-10}$ cycloalkyl, optionally substituted heterocycle or —CO—$NR^5R^6$ (wherein $R^5$ and $R^6$ are as defined above for (1)), —$(CH_2)_2R^{16'}$ (wherein $R^{16'}$ is cyano or $C_{1-6}$ alkoxy), or —$(CH_2)_n$—$Ar^2$ (wherein n is an integer of 1 to 3, and $Ar^2$ is substituted phenyl or optionally substituted heteroaryl), or
$R^{13}$ and $R^{14}$ optionally form, together with a carbon atom bonded thereto, the following formula

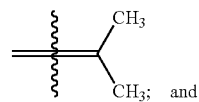

and $R^{15}$ is di($C_{1-6}$ alkyl)amino or the following formula

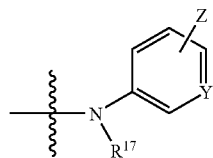

wherein Z is a hydrogen atom, a halogen atom or trifluoromethyl, Y is a nitrogen atom or CH, $R^{17}$ is ethyl, isopropyl or 3-pentyl, provided that when Y is a nitrogen atom, then Z is a hydrogen atom,
or a pharmacologically acceptable salt thereof, or a solvate thereof.

(7) The sulfonyl malonamide derivative of the above-mentioned (6), wherein $Ar^2$ for $R^{13}$ or $R^{14}$ is substituted phenyl represented by the following formula

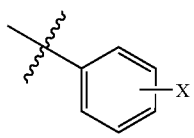

wherein X is a fluorine atom, a chlorine atom, a bromine atom, cyano, nitro, amino (excluding substitution at the ortho-position), —NHCOAr$^3$, —NHCOOAr$^3$, —NHCONHAr$^3$, —NHSO$_2$Ar$^3$, —OAr$^3$ (wherein Ar$^3$ is optionally substituted aryl or optionally substituted heteroaryl), —NHCOR$^{18}$ (wherein $R^{18}$ is optionally substituted $C_{1-6}$ alkyl, optionally substituted $C_{3-10}$ cycloalkyl, or optionally substituted heterocycle), optionally substituted $C_{1-6}$ alkoxycarbonyl, di($C_{1-6}$ alkyl)amino, optionally substituted $C_{1-6}$ alkoxy, optionally substituted heterocycle, optionally substituted aryl or optionally substituted heteroaryl,
or a pharmacologically acceptable salt thereof, or a solvate thereof.

(8) The sulfonyl malonamide derivative of the aforementioned (6), which is represented by the following formula (III)

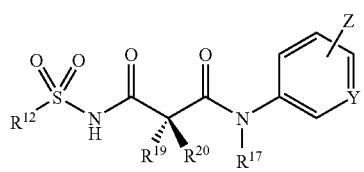

wherein $R^{12}$, $R^{17}$, Y and Z are as defined in the aforementioned (6), one of $R^{19}$ and $R^{20}$ is a hydrogen atom, and the other is isopropyl, isobutyl, neopentyl, allyl, cyclopropylmethyl or —CH$_2$—Ar$^2$ wherein Ar$^2$ is as defined for the aforementioned (6), or a pharmacologically acceptable salt thereof, or a solvate thereof.

(9) The sulfonyl malonamide derivative of the aforementioned (6), which is represented by the following formula (IV)

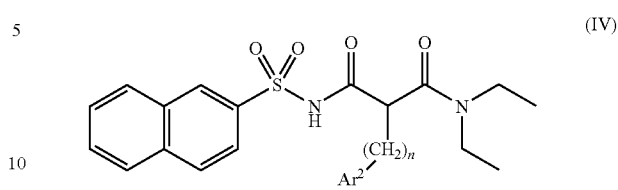

wherein n is an integer of 1 to 3, $Ar^2$ is as defined for the aforementioned (6),
or a pharmacologically acceptable salt thereof, or a solvate thereof.

(10) The sulfonyl malonamide derivative of the aforementioned (9), wherein $Ar^2$ is substituted phenyl represented by the following formula

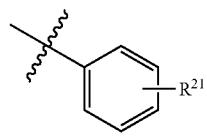

wherein $R^{21}$ is a fluorine atom, a chlorine atom, nitro, cyano, amino (excluding substitution at the ortho-position), dimethylamino, methoxy, trifluoromethoxy, methoxycarbonyl, phenyl, 2-pyridyloxy, 1-imidazolyl, 2-isoindolinyl, 1-oxo-2-isoindolinyl or the following formula

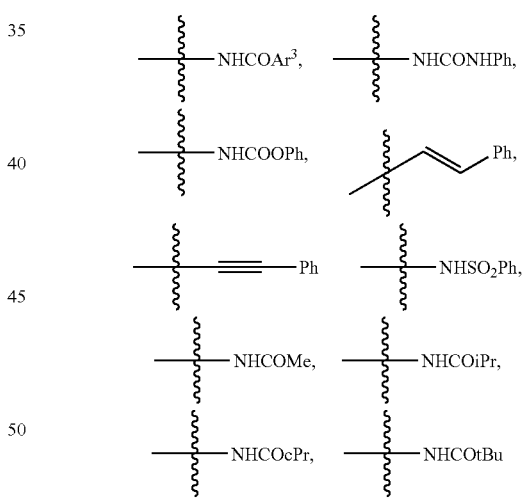

wherein $Ar^3$ is as defined for the aforementioned (7),
or a pharmacologically acceptable salt thereof, or a solvate thereof.

(11) The sulfonyl malonamide derivative of the aforementioned (9), wherein $Ar^2$ is substituted phenyl represented by the following formula

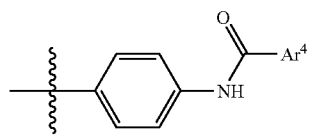

wherein Ar⁴ is 2-thienyl, 2-furyl, 4-pyridyl, 3-pyridyl, 2-pyridyl or the following formula

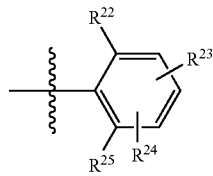

wherein $R^{22}$ and $R^{25}$ are the same or different and each is a hydrogen atom, amino, a fluorine atom, hydroxy, methoxy, methyl or a chlorine atom, $R^{23}$ is a hydrogen atom or a fluorine atom, and $R^{24}$ is a hydrogen atom, a fluorine atom, a chlorine atom, methyl, amino, methoxy or cyano, and n is 1, or a pharmacologically acceptable salt thereof, or a solvate thereof.

(12) The sulfonyl malonamide derivative of the aforementioned (6), which is the following compound:

N,N-diethyl-2-{4-[(2,6-difluorobenzoyl)amino]benzyl}-N'-(2-naphthylsulfonyl)malonamide, (2S)-2-[4-(benzoylamino)benzyl]-N,N-diethyl-N'-(2-naphthylsulfonyl)malonamide, (2S)—N,N-diethyl-2-{4-[(2-fluorobenzoyl)amino]benzyl}-N'-(2-naphthylsulfonyl)malonamide, (2S)—N,N-diethyl-2-{4-[(3-fluorobenzoyl)amino]benzyl}-N'-(2-naphthylsulfonyl)malonamide, (2S)—N,N-diethyl-2-{4-[(2,4-difluorobenzoyl)amino]benzyl}-N'-(2-naphthylsulfonyl)malonamide, (2S)—N,N-diethyl-2-{4-[(4-methylbenzoyl)amino]benzyl}-N'-(2-naphthylsulfonyl)malonamide, (2S)—N,N-diethyl-N'-(2-naphthylsulfonyl)-2-{4-[(2-thienoyl)amino]benzyl}malonamide, (2S)—N,N-diethyl-2-{4-[(2-furoyl)amino]benzyl}-N'-(2-naphthylsulfonyl)malonamide, (2S)-2-{4-[(2-amino-5-fluorobenzoyl)amino]benzyl}-N,N-diethyl-N'-(2-naphthylsulfonyl)malonamide, (2S)-2-{4-[(2-amino-6-fluorobenzoyl)amino]benzyl}-N,N-diethyl-N'-(2-naphthylsulfonyl)malonamide, (2S)—N,N-diethyl-N'-(2-naphthylsulfonyl)-2-{4-[(2-pyridylcarbonyl)amino]benzyl}malonamide, (2S)-2-{4-[(2-amino-4-chlorobenzoyl)amino]benzyl}-N,N-diethyl-N'-(2-naphthylsulfonyl)malonamide, (2S)-2-{4-[(2-aminobenzoyl)amino]benzyl}-N,N-diethyl-N'-(2-naphthylsulfonyl)malonamide, (2S)-2-{4-[(2-amino-5-chlorobenzoyl)amino]benzyl}-N,N-diethyl-N'-(2-naphthylsulfonyl)malonamide, (2S)-2-{4-[(2-amino-4,5-difluorobenzoyl)amino]benzyl}-N,N-diethyl-N'-(2-naphthylsulfonyl)malonamide, (2S)-2-{4-[(2-amino-4-fluorobenzoyl)amino]benzyl}-N,N-diethyl-N'-(2-naphthylsulfonyl)malonamide, (2S)-2-{4-[(2-amino-5-methylbenzoyl)amino]benzyl}-N,N-diethyl-N'-(2-naphthylsulfonyl)malonamide, 2-(4-fluorobenzyl)-N-isopropyl-N-(3-pyridyl)-N'-((E)-styrylsulfonyl)malonamide, 2-allyl-N-(4-fluorophenyl)-N-isopropyl-N'-((E)-styrylsulfonyl)malonamide, N-(4-fluorophenyl)-2-isobutyl-N-isopropyl-N'-((E)-styrylsulfonyl)malonamide, N-(4-fluorophenyl)-2-isobutyl-N-isopropyl-N'-phenethylsulfonylmalonamide, N-(4-fluorophenyl)-2-isobutyl-N-isopropyl-N'-(2-naphthylsulfonyl)malonamide, (2S or 2R)-2-cyclopropylmethyl-N-(4-fluorophenyl)-N-isopropyl-N'-((E)-2-styrylsulfonyl)malonamide, 2-cyclopropylmethyl-N-(4-fluorophenyl)-N-isopropyl-N'-phenethylsulfonylmalonamide, or 2-cyclopropylmethyl-N-(4-fluorophenyl)-N-isopropyl-N'-(2-naphthylsulfonyl)malonamide, or a pharmacologically acceptable salt thereof, or a solvate thereof.

(13) A pharmaceutical composition comprising the sulfonyl malonamide derivative of any of the aforementioned (6) to (12), or a pharmacologically acceptable salt thereof, or a solvate thereof as an active ingredient.

(14) An $AT_2$ receptor agonist comprising the sulfonyl malonamide derivative of any of the aforementioned (6) to (12), or a pharmacologically acceptable salt thereof, or a solvate thereof.

(15) The $AT_2$ receptor agonist of the aforementioned (14), comprising the sulfonyl malonamide derivative of the aforementioned (12), or a pharmacologically acceptable salt thereof, or a solvate thereof.

(16) The $AT_2$ receptor agonist of the aforementioned (15), which is $AT_2$ receptor selective.

Effect of the Invention

The novel sulfonyl malonamide derivative of the present invention has a potent and selective agonist action at $AT_2$ receptor, and is useful as a therapeutic or preventive drug for various diseases. As the target diseases, various groups of disorders involving RAAS, such as metabolic and cardiovascular diseases and the like are considered, and particularly stroke, renal disease, cardiac disease, hypertension, diabetes, metabolic syndrome and the like can be mentioned.

Each symbol used in the present specification is explained below.

Being optionally substituted means optionally having one or more substituents or being unsubstituted.

$C_{1-8}$ alkyl means a linear or branched chain hydrocarbon group having a carbon number of 1 to 8, such as methyl, ethyl, propyl, isopropyl, butyl, isobutyl, sec-butyl, tert-butyl, pentyl, isopentyl, neopentyl, hexyl, heptyl, octyl and the like.

$C_{1-6}$ alkyl means a linear or branched chain hydrocarbon group having a carbon number of 1 to 6, such as methyl, ethyl, propyl, isopropyl, butyl, isobutyl, sec-butyl, tert-butyl, pentyl, isopentyl, neopentyl, hexyl, isohexyl and the like.

$C_{2-6}$ alkenyl means a linear or branched unsaturated hydrocarbon group having a carbon number of 2 to 6 and containing one or more carbon-carbon double bonds, such as vinyl, allyl, 1-propenyl, isopropenyl, 2-butenyl, 1,3-butadienyl, 2-methyl-2-propenyl, prenyl, isopentenyl, 2-hexenyl and the like.

$C_{2-6}$ alkynyl means a linear or branched unsaturated hydrocarbon group having a carbon number of 2 to 6 and containing one or more carbon-carbon triple bond, such as ethynyl, 2-propynyl, 2-butynyl, 3-butynyl, 3-pentynyl, 5-hexynyl and the like.

$C_{3-10}$ cycloalkyl means a saturated cyclic hydrocarbon group having a carbon number of 3 to 10, such as cyclopropyl, cyclobutyl, cyclopentyl, cyclohexyl, cycloheptyl and the like. In addition, the cycloalkyl may be condensed with a benzene ring to form indane (e.g., indan-1-yl, indan-2-yl etc.), tetrahydronaphthalene (e.g., tetrahydronaphthalen-5-yl, tetrahydronaphthalen-6-yl etc.) and the like.

$C_{3-10}$ cycloalkyl $C_{1-6}$ alkyl means the above-mentioned "$C_{1-6}$ alkyl" substituted with the above-mentioned "$C_{3-10}$ cycloalkyl". The "$C_{1-6}$ alkyl" is preferably alkyl having a carbon number of 1 to 3, such as cyclopropylmethyl, 2-cyclobutylethyl, 3-cyclopentylpropyl, cyclohexylmethyl, 2-cyclohexylethyl, cycloheptylmethyl and the like.

Aryl means an aromatic hydrocarbon group preferably having a carbon number of 6 to 14, such as phenyl, naphthyl and the like. This group encompasses an ortho-fused bicyclic group having a ring atom of 8 to 10 wherein at least one ring is an aromatic ring (e.g., indenyl etc.) and the like.

Aryl $C_{1-6}$ alkyl means the above-mentioned "$C_{1-6}$ alkyl" substituted with the above-mentioned "aryl". Examples thereof include benzyl, benzhydryl, phenethyl, 1-phenylethyl, 3-phenylpropyl, 4-phenylbutyl, 5-phenylpentyl, 6-phenylhexyl, 1-naphthylmethyl, 2-naphthylmethyl, 2-(1-naphthyl)ethyl, 2-(2-naphthyl)ethyl, 3-(2-naphthyl)propyl, 4-(2-naphthyl)butyl and the like.

Aryloxy $C_{1-6}$ alkyl means the above-mentioned "$C_{1-6}$ alkyl" substituted with "aryloxy", wherein the aryl moiety of the "aryloxy" is as defined above for "aryl". The "$C_{1-6}$ alkyl" is preferably alkyl having a carbon number of 1 to 3, such as 2-phenoxyethyl, 3-phenoxypropyl, 2-(1-naphthoxy)ethyl, 2-(2-naphthoxy)ethyl, 3-(1-naphthoxy)propyl, 3-(2-naphthoxy)propyl and the like.

Aryl $C_{2-6}$ alkenyl means the above-mentioned "$C_{2-6}$ alkenyl" substituted with the above-mentioned "aryl". The "$C_{2-6}$ alkenyl" is preferably alkenyl having a carbon number of 2 to 4, such as trans-β-styryl, cinnamyl, 3-(1-naphthyl)-2-propenyl, 3-(2-naphthyl)-2-propenyl and the like.

Heteroaryl means an aromatic group containing, besides carbon atom, one or more (preferably 1 to 4) hetero atoms selected from an oxygen atom, a sulfur atom and a nitrogen atom. The group includes a 5- or 6-membered monocyclic group, an ortho-fused bicyclic group having 8 to 10 ring atoms (particularly benzo derivative) derived therefrom, a group obtained by fusion thereof with propenylene, trimethylene or tetramethylene, its stable N-oxide and the like. Examples of the group include pyrrolyl, furyl, thienyl, oxazolyl, isoxazolyl, imidazolyl, thiazolyl, isothiazolyl, pyrazolyl, triazolyl, tetrazolyl, 1,3,5-oxadiazolyl, 1,2,4-oxadiazolyl, 1,3,4-oxadiazolyl, 1,2,4-thiadiazolyl, pyridyl(2-pyridyl, 3-pyridyl, 4-pyridyl), pyrazinyl, pyrimidinyl, pyridazinyl, 1,2,4-triazinyl, 1,2,3-triazinyl, 1,3,5-triazinyl, benzoxazolyl, benzoisoxazolyl, benzothiazolyl, benzoisothiazolyl, benzoimidazolyl, oxazolopyridyl, imidazopyridazinyl, isothianaphthenyl, benzofuranyl, isobenzofuranyl, benzothienyl, chromenyl, isoindolyl, indolyl, indazolyl, isoquinolyl, quinolyl, phthalazinyl, quinoxalinyl, quinazolinyl, cinnolinyl, 2,1,3-benzoxadiazolyl, benzoxazinyl, pteridinyl and the like.

Heteroaryl $C_{1-6}$ alkyl means the above-mentioned "$C_{1-6}$ alkyl" substituted with the above-mentioned "heteroaryl". The "$C_{1-6}$ alkyl" is preferably alkyl having a carbon number of 1 to 5, such as 2-pyridylmethyl, 3-pyridylmethyl, 4-pyridylmethyl, 2-(2-pyridyl)ethyl, 2-(3-pyridyl)ethyl, 2-(4-pyridyl)ethyl, 3-(2-pyridyl)propyl, 3-(3-pyridyl)propyl, 3-(4-pyridyl)propyl, 2-thienylmethyl, 3-thienylmethyl, 2-(2-thienyl)ethyl, 3-(2-thienyl)propyl, 4-pyrazolylmethyl, 2-(4-pyrazolyl)ethyl, 3-(4-pyrazolyl)propyl, 2-thiazolylmethyl, 4-thiazolylmethyl, 5-thiazolylmethyl, 2-(2-thiazolyl)ethyl, 3-(2-thiazolyl)propyl, 2-(4-thiazolyl)ethyl, 3-(4-thiazolyl)propyl, 2-(5-thiazolyl)ethyl, 3-(5-thiazolyl)propyl, 2-oxazolylmethyl, 4-oxazolylmethyl, 5-oxazolylmethyl, 2-(2-oxazolyl)ethyl, 3-(2-oxazolyl)propyl, 2-(4-oxazolyl)ethyl, 3-(4-oxazolyl)propyl, 2-(5-oxazolyl)ethyl, 3-(5-oxazolyl)propyl, 4-(1,2,3-triazolyl)methyl, 5-tetrazolylmethyl, 2-(5-tetrazolyl)ethyl, 1-imidazolylmethyl, 2-(1-imidazolyl)ethyl, 6-benzoxazolylmethyl, 1-benzoimidazolylmethyl and the like.

Heteroaryl $C_{2-6}$ alkenyl means the above-mentioned "$C_{2-6}$ alkenyl" substituted with the above-mentioned "heteroaryl". The "$C_{2-6}$ alkenyl" is preferably alkenyl having a carbon number of 2 to 4, such as 2-pyridylethenyl, 3-pyridylethenyl, 4-pyridylethenyl, 2-thiazolylethenyl, 2-oxazolylethenyl, 3-(2-pyridyl)-2-propenyl, 3-(3-pyridyl)-2-propenyl, 3-(4-pyridyl)-2-propenyl, 3-(3-thienyl)-2-propenyl, 3-(4-isoquinolyl)-2-propenyl, 3-(3-benzothienyl)-2-propenyl and the like.

Heterocycle means a cyclic hydrocarbon group having 1 to 3 hetero atoms selected from a nitrogen atom, an oxygen atom, a sulfur atom and the like. The group is nonaromatic, and optionally saturated or partially unsaturated. The group includes not only monocycle but also spiro ring, with preference given to a 4- to 7-membered monocyclic group and a 10- or 11-membered spiro ring group. Examples of the group include azetidinyl, pyrrolidinyl, piperidinyl, piperazinyl, morpholino, 1,4-diazepanyl, 1,2,5,6-tetrahydropyridyl, tetrahydropyranyl, cyclopentanespiro-4'-piperidinyl and the like.

Furthermore, the above-mentioned heterocycle may be condensed with an aromatic ring. Examples of the fused ring include indolinyl, isoindolinyl, 1,2,3,4-tetrahydroquinolyl, 1,2,3,4-tetrahydroisoquinolyl, spiro[indane-1,4'-piperidin]-1'-yl and the like.

Heterocycle $C_{1-6}$ alkyl means the above-mentioned "$C_{1-6}$ alkyl" substituted with the above-mentioned "heterocycle". The "$C_{1-6}$ alkyl" is preferably alkyl having a carbon number of 1 to 3, such as 4-piperidinylmethyl, 2-(4-piperidinyl)ethyl, 2-(1-piperazinyl)ethyl and the like.

Cyclic amino means a cyclic hydrocarbon group containing at least one nitrogen atom, wherein the nitrogen atom is a bond of the group. The ring may further contain, besides the aforementioned nitrogen atom, 1 to 3 homologous or heterologous hetero atoms selected from, for example, a nitrogen atom, an oxygen atom and a sulfur atom. The group is nonaromatic, and optionally saturated or partially unsaturated. The group contains not only monocycle but also spiro ring, with preference given to a 4- to 7-membered monocyclic group and a 10- or 11-membered spiro ring group. Examples of the group include azetidino, pyrrolidino, piperidino, piperazino, morpholino, 1,4-diazepan-1-yl, 1,2,5,6-tetrahydropyridino, tetrahydroimidazolino, cyclopentanespiro-4'-piperidino and the like.

Furthermore, the above-mentioned cyclic amino may be condensed with an aromatic ring. Examples of the fused ring include indolino, isoindolino, 1,2,3,4-tetrahydroquinolino, 1,2,3,4-tetrahydroisoquinolino, spiro[indane-1,4'-piperidin]-1'-yl and the like.

Examples of the halogen atom include a chlorine atom, a bromine atom, a fluorine atom and an iodine atom.

Examples of the substituent of the "optionally substituted $C_{1-8}$ alkyl", "optionally substituted $C_{1-6}$ alkyl", "optionally substituted $C_{2-6}$ alkenyl", "optionally substituted $C_{2-6}$ alkynyl", "optionally substituted $C_{3-10}$ cycloalkyl", "optionally substituted heterocycle", "optionally substituted aryl" and "optionally substituted heteroaryl" include 1 to 3 substituents selected from substituent group A shown below, and the like.

The substituent of the "optionally substituted aryl", "optionally substituted $C_{3-10}$ cycloalkyl", "optionally substituted heteroaryl" or "optionally substituted heterocycle" moiety of the "optionally substituted $C_{3-10}$ cycloalkyl $C_{1-6}$ alkyl", "optionally substituted aryl $C_{1-6}$ alkyl", "optionally substituted aryloxy $C_{1-6}$ alkyl", "optionally substituted aryl $C_{2-6}$ alkenyl", "optionally substituted heteroaryl $C_{1-6}$ alkyl", "optionally substituted heteroaryloxy $C_{1-6}$ alkyl", "optionally substituted heteroaryl $C_{2-6}$ alkenyl" and "optionally substituted heterocycle $C_{1-6}$ alkyl" is similar to the substituent of the above-mentioned "optionally substituted aryl", "optionally substituted $C_{3-10}$ cycloalkyl", "optionally substituted heteroaryl" or "optionally substituted heterocycle".

Substituent group A: a halogen atom (as defined above), a hydroxyl group, nitro, cyano, trifluoromethyl, trifluoromethoxy, $C_{1-6}$ alkyl (as defined above), $C_{2-6}$ alkenyl (as defined above), $C_{2-6}$ alkynyl (as defined above), $C_{1-6}$ alkoxy, $C_{1-6}$ alkylthio, $C_{1-6}$ alkylsulfinyl, $C_{3-10}$ cycloalkyl (as defined above), $C_{3-10}$ cycloalkyl $C_{1-6}$ alkyl (as defined above), aryl (as defined above), aryloxy, aryl $C_{1-6}$ alkyl (as defined above), aryl $C_{2-6}$ alkenyl (as defined above), aryl $C_{2-6}$ alkynyl, heteroaryl (as defined above), heteroaryloxy, heteroaryl $C_{1-6}$ alkyl (as defined above), heterocycle (as defined above), oxo, —COOR$^a$, —CH$_2$COOR$^a$, —OCH$_2$COOR$_a$, —CONR$^b$R$^c$, —CH$_2$CONR$^b$R$^c$, —OCH$_2$CONR$^b$R$^c$, —COO(CH$_2$)$_2$NR$^e$R$^f$, —CONR$^d$SO$_2$T$^1$, —NR$^e$R$^f$, —NR$^g$CHO, —NR$^g$COT$^2$, —NR$^g$COOT$^2$, —NR$^g$CONR$^i$R$^j$, —NR$^h$SO$_2$T$^3$, —NHC(=NH)NH$_2$, —COT$^2$, —SO$_2$T$^3$, methylenedioxy, and ethyleneoxy.

The above-mentioned substituents may have 1 to 3 substituents selected from substituent group A at substitutable position(s).

Here, the "$C_{1-6}$ alkyl" moiety of the $C_{1-6}$ alkoxy is as defined above for "$C_{1-6}$ alkyl", and examples thereof include methoxy, ethoxy, propoxy, isopropoxy, butoxy, pentyloxy, hexyloxy and the like.

The "$C_{1-6}$ alkyl" moiety of the $C_{1-6}$ alkylthio is as defined above for "$C_{1-6}$ alkyl", and examples thereof include methylthio, ethylthio, propylthio, isopropylthio, butylthio, pentylthio, hexylthio and the like.

The "$C_{1-6}$ alkyl" moiety of the $C_{1-6}$ alkylsulfinyl is as defined above for "$C_{1-6}$ alkyl", and examples thereof include methylsulfinyl, ethylsulfinyl, propylsulfinyl, isopropylsulfinyl, butylsulfinyl, pentylsulfinyl, hexylsulfinyl and the like.

The aryl moiety of the aryloxy is as defined above for "aryl", and examples thereof include phenoxy, 1-naphthoxy, 2-naphthoxy and the like.

The aryl $C_{2-6}$ alkynyl means the above-mentioned "$C_{2-6}$ alkynyl" substituted with the above-mentioned "aryl". The "$C_{2-6}$ alkynyl" is preferably alkynyl having a carbon number of 2 to 4, such as phenylethynyl and the like.

The "heteroaryl" moiety of the heteroaryloxy is as defined above for "heteroaryl", and examples thereof include 2-pyridyloxy, 2-benzothiazolyloxy and the like.

In addition, R$^a$—R$^j$ are each a hydrogen atom, $C_{1-6}$ alkyl (as defined above), aryl (as defined above), aryl $C_{1-6}$ alkyl (as defined above), heteroaryl (as defined above) or heteroaryl $C_{1-6}$ alkyl (as defined above), respectively. These groups may further have 1 to 3 substituents selected from substituent group A, at substitutable position(s).

R$^b$ and R$^c$, R$^e$ and R$^f$, and R$^i$ and R$^j$ in —NR$^b$R$^c$, —NR$^e$R$^f$, —NR$^i$R$^j$ may form, together with a nitrogen atom bonded thereto, cyclic amino (as defined above) optionally further having 1 to 3 substituents selected from substituent group A at substitutable position(s). In addition, cyclic amino formed by —NR$^e$R$^f$ contains cyclic amino having oxo (e.g., 2-pyrrolidinon-1-yl, 1-oxoisoindolin-2-yl, succinimido, oxazolidin-2-on-3-yl, 2-benzoxazolinon-3-yl, phthalimido, 4-quinazolinon-3-yl etc.).

T$^1$-T$^3$ are each $C_{1-6}$ alkyl (as defined above), $C_{2-6}$ alkenyl (as defined above), $C_{2-6}$ alkynyl (as defined above), $C_{3-10}$ cycloalkyl (as defined above), $C_{3-10}$ cycloalkyl $C_{1-6}$ alkyl (as defined above), aryl (as defined above), aryl $C_{1-6}$ alkyl (as defined above), heteroaryl (as defined above), heteroaryl $C_{1-6}$ alkyl (as defined above), cyclic amino(as defined above) or heterocycle (as defined above). These groups may further have 1 to 3 substituents selected from substituent group A at substitutable position(s), and examples of aryl or heteroaryl having 1 to 3 substituent selected from substituent group A include 2-aminophenyl, 2-amino-5-fluorophenyl, 2-amino-6-fluorophenyl, 2-fluorophenyl, 4-methoxyphenyl, 5-chloro-2-pyridyl and the like.

In sulfonyl malonamide derivative represented by the formula (I), preferable embodiment of each substituent is explained as follows.

Preferred as R$^1$ is optionally substituted naphthyl, optionally substituted biphenyl, optionally substituted phenyl, optionally substituted thiophene, optionally substituted phenyl $C_{1-6}$ alkyl, optionally substituted phenoxy $C_{1-6}$ alkyl, optionally substituted thiazolyl $C_{1-6}$ alkyl, optionally substituted $C_{1-8}$ alkyl, optionally substituted $C_{1-6}$ alkenyl, optionally substituted $C_{3-10}$ cycloalkyl, and, a group represented by the following formula

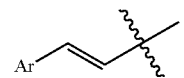

wherein Ar is as defined above. More preferably is 2-naphthyl, trans-β-styryl, phenethyl, 3-phenoxypropyl, 4-phenylbutyl, particularly preferably, 2-naphthyl.

Preferably, one of R$^2$ and R$^3$ is a hydrogen atom and the other is $C_{1-6}$ alkyl, allyl, prenyl, 2-propynyl, cyclopentyl, —CH$_2$—R$^9$ wherein R$^9$ is as defined above, —(CH$_2$)$_2$—R$^{9'}$ wherein R$^{9'}$ is as defined above, —(CH$_2$)$_n$—Ar or —CH$_2$—CH=CH—Ar$^1$ wherein n is an integer of 0 to 6, and Ar$^1$ is as defined above, or R$^2$ and R$^3$ form the following formula together with a carbon atom bonded thereto

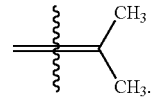

More preferably, one of them is a hydrogen atom, and the other is isopropyl, isobutyl, neopentyl, allyl, cyclopropylmethyl or —(CH$_2$)$_n$—Ar$^2$ wherein n is an integer of 1 to 3, and Ar$^2$ is as defined above. Still more preferably, either one is a hydrogen atom, and the other is —(CH$_2$)$_n$—Ar$^2$ wherein n is an integer of 1 to 3, and Ar$^2$ is as defined above. Here, n is preferably 1.

Preferred as Ar$^2$ for R$^2$ or R$^3$ is substituted phenyl. Here, preferred as the substituent of the substituted phenyl is a fluorine atom, a chlorine atom, a bromine atom, cyano, nitro, amino (excluding substitution at the ortho-position), —NHCOAr$^3$, —NHCOOAr$^3$, —NHCONHAr$^3$, —NHSO$_2$Ar$^3$, —OAr$^3$ wherein Ar$^3$ is as defined above, —NHCOR$^{18}$ wherein R$^{18}$ is as defined above, optionally substituted $C_{1-6}$ alkoxycarbonyl, di($C_{1-6}$ alkyl)amino, optionally substituted $C_{1-6}$ alkoxy (particularly, trifluoromethoxy), optionally substituted heterocycle, optionally substituted aryl, optionally substituted heteroaryl or the following formula

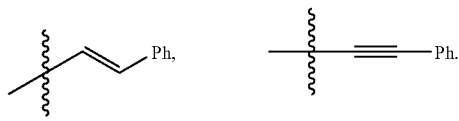

More preferably, Ar$^2$ is phenyl substituted with —NHCOAr$^4$ at the para-position, wherein Ar$^4$ is as defined above.

Preferred as R⁴ is the following formula

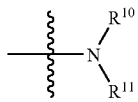

wherein $R^{10}$ and $R^{11}$ are as defined above. More preferably, $R^4$ is di($C_{1-6}$ alkyl)amino or the following formula

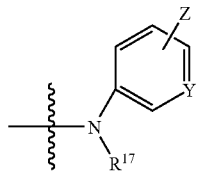

wherein Z, Y, and $R^{17}$ are as defined above, particularly preferably diethylamino.

Further preferable embodiment of the present invention encompasses sulfonyl malonamide derivatives represented by the above-mentioned formulas (II), (III) and (IV), a pharmacologically acceptable salt thereof, and a solvate thereof.

Particularly preferable sulfonyl malonamide derivatives are the following compounds:

N,N-diethyl-2-{4-[(2,6-difluorobenzoyl)amino]benzyl}-N'-(2-naphthylsulfonyl)malonamide, (2S)-2-[4-(benzoylamino)benzyl]-N,N-diethyl-N'-(2-naphthylsulfonyl)malonamide, (2S)—N,N-diethyl-2-{4-[(2-fluorobenzoyl)amino]benzyl}-N'-(2-naphthylsulfonyl)malonamide, (2S)—N,N-diethyl-2-{4-[(3-fluorobenzoyl)amino]benzyl}-N'-(2-naphthylsulfonyl)malonamide, (2S)—N,N-diethyl-2-{4-[(2,4-difluorobenzoyl)amino]benzyl}-N'-(2-naphthylsulfonyl)malonamide, (2S)—N,N-diethyl-2-{4-[(4-methylbenzoyl)amino]benzyl}-N'-(2-naphthylsulfonyl)malonamide, (2S)—N,N-diethyl-N'-(2-naphthylsulfonyl)-2-{4-[(2-thienoyl)amino]benzyl}malonamide, (2S)—N,N-diethyl-2-{4-[(2-furoyl)amino]benzyl}-N'-(2-naphthylsulfonyl)malonamide, (2S)-2-{4-[(2-amino-5-fluorobenzoyl)amino]benzyl}-N,N-diethyl-N'-(2-naphthylsulfonyl)malonamide, (2S)-2-{4-[(2-amino-6-fluorobenzoyl)amino]benzyl}-N,N-diethyl-N'-(2-naphthylsulfonyl)malonamide, (2S)—N,N-diethyl-N'-(2-naphthylsulfonyl)-2-{4-[(2-pyridylcarbonyl)amino]benzyl}malonamide, (2S)-2-{4-[(2-amino-4-chlorobenzoyl)amino]benzyl}-N,N-diethyl-N'-(2-naphthylsulfonyl)malonamide, (2S)-2-{4-[(2-aminobenzoyl)amino]benzyl}-N,N-diethyl-N'-(2-naphthylsulfonyl)malonamide, (2S)-2-{4-[(2-amino-5-chlorobenzoyl)amino]benzyl}-N,N-diethyl-N'-(2-naphthylsulfonyl)malonamide, (2S)-2-{4-[(2-amino-4,5-difluorobenzoyl)amino]benzyl}-N,N-diethyl-N'-(2-naphthylsulfonyl)malonamide, (2S)-2-{4-[(2-amino-4-fluorobenzoyl)amino]benzyl}-N,N-diethyl-N'-(2-naphthylsulfonyl)malonamide, (2S)-2-{4-[(2-amino-5-methylbenzoyl)amino]benzyl}-N,N-diethyl-N'-(2-naphthylsulfonyl)malonamide, 2-(4-fluorobenzyl)-N-isopropyl-N-(3-pyridyl)-N'-((E)-styrylsulfonyl)malonamide, 2-allyl-N-(4-fluorophenyl)-N-isopropyl-N'-((E)-styrylsulfonyl)malonamide, N-(4-fluorophenyl)-2-isobutyl-N-isopropyl-N'-((E)-styrylsulfonyl)malonamide, N-(4-fluorophenyl)-2-isobutyl-N-isopropyl-N'-phenethylsulfonylmalonamide, N-(4-fluorophenyl)-2-isobutyl-N-isopropyl-N'-(2-naphthylsulfonyl)malonamide, (2S or 2R)-2-cyclopropylmethyl-N-(4-fluorophenyl)-N-isopropyl-N'-((E)-2-styrylsulfonyl)malonamide, 2-cyclopropylmethyl-N-(4-fluorophenyl)-N-isopropyl-N'-phenethylsulfonylmalonamide, and 2-cyclopropylmethyl-N-(4-fluorophenyl)-N-isopropyl-N'-(2-naphthylsulfonyl)malonamide.

$AT_2$ receptor is an angiotensin type 2 receptor.

Being $AT_2$ receptor selective means that affinity of the compound for $AT_2$ receptor, expressed by Ki value, is at least 5-fold, preferably at least 20-fold, more potent than that for $AT_1$ receptor.

$AT_2$ receptor agonist is a substance that binds to $AT_2$ receptor and evokes intracellular signal transduction similar to natural ligand, angiotensin II.

A solvate means, a state where a solvent used for the reaction or crystallization is contained in crystal, without forming a covalent bond with the molecule or ion of the compound. Most solvents can form a solvate, and preferred as the solvate in the present invention is desirably a solvate with a solvent permitting use as a pharmaceutical product, specifically hydrate, ethanolate and the like.

Being pharmacologically acceptable means generally safe and harmless. Even if biologically undesirable, a substance might be preferable from other aspects, and includes those advantageous for not only use as pharmaceutical agents for human but also animal medicine. It means being useful for preparation of pharmaceutical compositions.

Examples of the pharmacologically acceptable salt include inorganic acid addition salts (e.g., salts with hydrochloric acid, hydrobromic acid, hydroiodic acid, sulfuric acid, phosphoric acid etc.), organic acid addition salts (e.g., salts with methanesulfonic acid, benzenesulfonic acid, p-toluenesulfonic acid, formic acid, acetic acid, trifluoroacetic acid, oxalic acid, citric acid, malonic acid, fumaric acid, glutaric acid, adipic acid, maleic acid, tartaric acid, succinic acid, mandelic acid, malic acid, pantothenic acid, methylsulfuric acid etc.), inorganic base addition salts (e.g., salts with sodium, potassium, calcium, magnesium etc.), salts with amino acid (e.g., salts with glutamic acid, aspartic acid, arginine, lysin etc.) and the like.

The sulfonyl malonamide derivative represented by the formula (I), or a pharmacologically acceptable salt thereof, or a solvate thereof (hereinafter to be sometimes referred to as "the compound of the present invention" simply) can show polymorphism. The compound of the present invention can be present as an optical isomer and a stereo isomer when it has an asymmetric carbon in molecule. Furthermore, the compound of the present invention can be present as one or more tautomer depending on unsaturated bond, kind of substituent, pH and the like. Therefore, the present invention encompasses any of the above-mentioned stereoisomers, optical isomers, polymorphs, tautomers, optional mixtures thereof and the like.

The compound of the present invention can be produced by various methods shown below.

Each symbol in the following reaction schemes is as defined above unless otherwise indicated. Each compound in the reaction schemes also includes salts as long as the reaction is not inhibited. While the compound obtained by each reaction can be directly used for the next reaction in the form of a reaction mixture or a crude product, or can be isolated from a reaction mixture according to conventional methods and can be easily purified by general separation means (e.g., recrystallization, distillation, chromatography etc.)

The production method of the compound represented by the formula (I) is shown in Scheme 1.

ethane, chloroform, carbon tetrachloride etc.), acetonitrile, N,N-dimethylformamide (DMF) and the like, and a mixed solvent thereof.

Examples of the base to be used include organic bases such as triethylamine (TEA), 4-dimethylaminopyridine (DMAP),

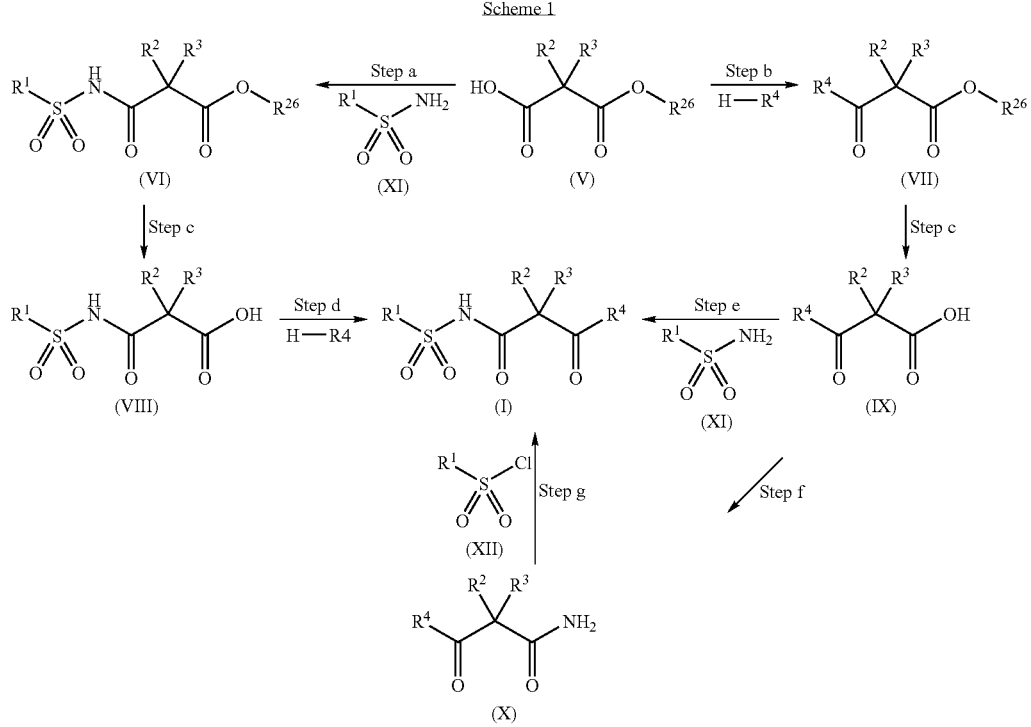

Scheme 1 wherein $R^1$, $R^2$, $R^3$ and $R^4$ are as defined above, and $R^{26}$ is a carboxyl-protecting group (e.g., methyl, ethyl, benzyl, tert-butyl etc.).

Step a: In this step, a compound represented by the formula (VI) is produced by subjecting a compound represented by the formula (V) and a compound represented by the formula (XI) to dehydration-condensation by a method well known in the field. For example, this step can be performed according to the methods described in Ishizuka et al., Synthesis, No. 6, 784-788 (2000), Jansen et al., Eur. J. Med. Chem., Vol. 38, 855-865 (2003), Chakravarty et al., Bioorg. Med. Chem. Lett., Vol. 4, 75-80 (1994), Sakaki et al., Bioorg. Med. Chem. Lett., Vol. 8, 2241-2246 (1998), Donkor et al., Eur. J. Med. Chem., Vol. 33, 15-22 (1998), or a method analogous thereto.

The compound represented by the formula (VI) can be produced by reacting an acidic compound represented by the formula (V) or a reactive derivative thereof with a compound represented by the formula (XI) using a dehydration-condensation agent in a solvent, in the presence of a base.

Examples of the reactive derivative of the acidic compound include acid anhydrides, activate esters (e.g., p-nitrophenyl ester, N-hydroxysuccinimide ester, pentafluorophenyl ester, 1-hydroxybenzotriazole ester etc.), acid halides (e.g., acid chloride, acid bromide etc.), imidazolide, mixed acid anhydrides (e.g., anhydrides with methyl carbonate, anhydride with ethyl carbonate etc.) and the like.

Examples of the solvent to be used include ether solvents (e.g., diethyl ether, tetrahydrofuran (THF), dioxane etc.), hydrocarbon solvents (e.g., benzene, toluene, hexane, heptane etc.), halogen solvents (e.g., dichloromethane, dichloro- N,N-diisopropylethylamine (DIPEA), triethylenediamine, 4-methylmorpholine, 1,8-diazabicyclo[5.4.0]undec-7-ene and the like, inorganic bases such as alkali metal or alkaline earth metal carbonates (e.g., sodium carbonate, potassium carbonate, cesium carbonate etc.), alkali metal or alkaline earth metal hydrogen carbonates (e.g., sodium hydrogen carbonate, potassium hydrogen carbonate etc.), alkali metal or alkaline earth metal hydroxides (e.g., sodium hydroxide, potassium hydroxide, cesium hydroxide etc.), alkali metal or alkaline earth metal hydrides (e.g., lithium hydride, sodium hydride, potassium hydride, calcium hydride etc.), metal amides (e.g., sodium amide, lithium diisopropylamide, lithium hexamethyldisilazide etc.), alkali metal alkoxides (e.g., potassium tert-butoxide, sodium tert-butoxide etc.) and the like.

Examples of the dehydration-condensation agent include condensation agents to be used for peptide synthesis and the like. Specific examples thereof include dicyclohexylcarbodiimide (DCC), N-ethyl-N'-(3-dimethylaminopropyl)carbodiimide (EDC) or a hydrochloride salt thereof, 2-chloro-1-methylpyridinium iodide, 2-ethoxy-1-ethoxycarbonyl-1,2-dihydroquinoline (EEDQ), carbodiimidazole (CDI), diethylphosphoryl cyanide, benzotriazol-1-yloxy-trispyrrolidinophosphonium hexafluorophosphate (PyBOP), diphenylphosphoryl azide (DPPA), propanephosphonic acid anhydride (PPA), isobutyl chloroformate, diethylacetyl chloride, trimethylacetyl chloride and the like. These condensation agents are used alone, or in combination with an activator such as N-hydroxysuccinimide (HONSu), hydroxybenzotriazole (HOBT), 3-hydroxy-4-oxo-3,4-dihydro-1,2,3-benzotriazine (HOOBT), DMAP and the like, preferably DMAP.

The compound represented by the formula (XI) is used in a proportion of about 50 to 1000 mol %, preferably about 100 to 600 mol %, per 1 mol of the compound represented by the formula (V), the condensation agent is used in a proportion of about 50 to 1000 mol %, preferably about 100 to 500 mol %, per 1 mol of the compound represented by the formula (V), and the base is used in a proportion of about 50 to 1000 mol %, preferably about 100 to 500 mol %, per 1 mol of the compound represented by the formula (V). The reaction temperature is about −30° C. to 100° C., preferably −10° C. to 80° C., and the reaction time is about 30 min to 96 hr, preferably 30 min to 48 hr.

Step b: In this step, a compound represented by the formula (VII) is produced by subjecting the compound represented by the formula (V) and amine (H—$R^4$) wherein $R^4$ is as defined above to dehydration-condensation.

The compound represented by the formula (VII) can be produced by reacting the acidic compound represented by the formula (V) or a reactive derivative with amine (H—$R^4$) using a dehydration-condensation agent in a solvent, in the presence of a base as necessary. The reactive derivative of acidic compound, the solvent, the base and the dehydration-condensation agent to be used are in the same manner as in Step a.

Step c: In this step, a compound represented by the formula (VIII) or the formula (IX) is produced by deprotecting the ester-protected carboxyl group of a compound represented by the formula (VI) or the formula (VII).

The reaction can be carried out according to a general deprotection to a carboxyl group. Examples of the base to be used include alkali metal or alkaline earth metal carbonates (e.g., sodium carbonate, potassium carbonate, cesium carbonate etc.), alkali metal or alkaline earth metal hydroxides (e.g., lithium hydroxide, sodium hydroxide, potassium hydroxide, cesium hydroxide etc.) and the like.

When $R^{26}$ is a benzyl group, it can be deprotected according to catalytic hydrogenation reaction using a metal catalyst such as palladium and the like. Examples of the solvent to be used for the reaction include alcohol solvents (e.g., methanol, ethanol etc.), ether solvents (e.g., THF, dioxane etc.) and the like, and a mixed solvent of these and water as necessary. The reaction temperature is about 0° C. to 100° C.

When $R^{26}$ is tert-butyl, it can be deprotected under acidic conditions of hydrochloric acid, trifluoroacetic acid and the like. Examples of the solvent to be used for the reaction include halogen solvents (e.g., dichloromethane, dichloroethane, chloroform, carbon tetrachloride etc.) and the like. The reaction temperature is about −10° C. to 60° C.

Step d: In this step, a compound represented by the formula (I) is produced from a compound represented by the formula (VIII) in the same manner as in Step b or according to a method analogous thereto.

Step e: In this step, a compound represented by the formula (I) is produced from a compound represented by the formula (IX) in the same manner as in step a or according to a method analogous thereto.

Step f: In this step, a compound represented by the formula (X) is produced from a compound represented by the formula (IX) in the same manner as in Step b or according to a method analogous thereto, using ammonia gas, an ammonia mixed solution (e.g., aqueous ammonia, ammonia/dioxane solution, ammonia/methanol solution etc.), or an ammonium salt (e.g., ammonium carbonate, ammonium hydrogen carbonate, ammonium chloride etc.) as an amine.

Step g: In this step, a compound represented by the formula (I) is produced by reacting a compound represented by the formula (X) with a compound represented by the formula (XII).

The compound represented by the formula (I) can be produced by reacting a compound represented by the formula (X) with a compound represented by the formula (XII) without solvent or in an appropriate solvent, in the presence of a base.

Examples of the base to be used include organic bases such as pyridine, TEA, DMAP, DIPEA, triethylenediamine, 4-methylmorpholine, 1,8-diazabicyclo[5.4.0]undec-7-ene and the like, alkali metal or alkaline earth metal carbonates (e.g., sodium carbonate, potassium carbonate, cesium carbonate etc.), alkali metal or alkaline earth metal hydrogen carbonates (e.g., sodium hydrogen carbonate, potassium hydrogen carbonate etc.), alkali metal or alkaline earth metal hydroxides (e.g., sodium hydroxide, potassium hydroxide, cesium hydroxide etc.), alkali metal or alkaline earth metal hydrides (e.g., lithium hydride, sodium hydride, potassium hydride, calcium hydride etc.), metal amides (e.g., sodium amide, lithium diisopropylamide, lithium hexamethyl disilazide etc.), alkali metal alkoxides (e.g., potassium tert-butoxide, sodium tert-butoxide etc.) and the like.

Examples of the solvent to be used include ether solvents (e.g., diethyl ether, THF, dioxane etc.), hydrocarbon solvents (e.g., benzene, toluene etc.), halogen solvents (e.g., dichloromethane, dichloroethane, chloroform, carbon tetrachloride etc.), acetonitrile, DMF and the like, and a mixed solvent thereof.

The compound represented by the formula (XII) is used in a proportion of about 50 to 1000 mol %, preferably about 100 to 600 mol %, per 1 mol of the compound represented by the formula (X), and the base is used in a proportion of about 50 to 2000 mol %, preferably about 200 to 1000 mol %, per 1 mol of the compound represented by the formula (X). The reaction temperature is about −30° C. to 100° C., preferably −10° C. to 80° C., and the reaction time is about 30 min to 96 hr, preferably 30 min to 48 hr.

When the compound represented by the formula (IX) in Scheme 1 is a compound represented by the formula (IX'), the compound can also be produced from a Meldrum's acid derivative represented by the formula (XIII) as shown in Scheme 2.

Scheme 2

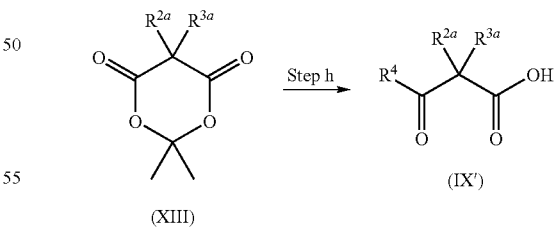

wherein $R^{2a}$ and $R^{3a}$ may form, together with the carbon atom they are bonded to, C=CX'Y' wherein X' and Y' are as defined above, or one of $R^{2a}$ and $R^{3a}$ is a hydrogen atom, and the other is alkyl, alkenyl, alkynyl, cycloalkylalkyl, arylalkyl, aryloxyalkyl, heteroarylalkyl, heteroaryloxyalkyl or heterocyclyl, each of which is optionally substituted, and $R^4$ is as defined above.

The Meldrum's acid derivative represented by the formula (XIII) can be produced according to methods well known in the field, for example, the methods described in Toth et al., Synth. Commun., Vol. 25, 3067-3074 (1995), Smrcina et al., Tetrahedron, Vol. 53, 12867-12874 (1997), Hin et al., J. Org. Chem., Vol. 67, 7365-7368 (2002), Desai et al., Synth. Commun., Vol. 34, 25-32 (2004), Hrubowchak et al., Tetrahedron Lett., Vol. 24, 4951-4954 (1983) and the like, or a method analogous thereto.

Step h: In this step, a compound represented by the formula (IX') is produced by reacting a Meldrum's acid derivative represented by the formula (XIII) with amine (H—$R^4$).

The compound represented by the formula (IX') can be produced by reacting a Meldrum's acid derivative represented by the formula (XIII) with amine (H—$R^4$) without solvent or in an appropriate solvent, in the presence of a silylating agent and, where necessary, an additive.

Examples of the solvent to be used include ether solvents (e.g., diethyl ether, THF, dioxane etc.), aromatic hydrocarbon solvents (e.g., benzene, toluene, chlorobenzene etc.), halogen solvents (e.g., dichloromethane, dichloroethane, chloroform, carbon tetrachloride etc.), acetonitrile, DMF, dimethyl sulfoxide (DMSO) and the like, and a mixed solvent thereof.

Examples of the silylating agent include N,O-bis(trimethylsilyl)trifluoroacetamide (BSTFA), N,O-bis(trimethylsilyl) acetamide (BSA), N-methyl-N-trimethylsilyl trifluoroacetamide (MSTFA), N-trimethylsilyl acetamide (TMSA) and the like. Preferred as the additive are DMAP and the like.

In this case, amine (H—$R^4$) is used in a proportion of about 50 to 1000 mol %, preferably about 100 to 600 mol %, per 1 mol of the compound represented by the formula (XIII), the silylating agent is used in a proportion of about 50 to 1000 mol %, preferably about 100 to 600 mol %, per 1 mol of the compound represented by the formula (XIII), and DMAP is used in a proportion of about 50 to 1000 mol %, preferably about 100 to 600 mol %, per 1 mol of the compound represented by the formula (XIII). The reaction temperature is about −30° C. to 100° C., preferably −10° C. to 80° C., and the reaction time is about 30 min to 96 hr, preferably 60 min to 48 hr.

The compound represented by the formula (V) in Scheme 1 is commercially available, or can be easily produced from commercially available malonic acid diester, for example, according to the methods described in Strube, Org. Synth. Coll. Vol. IV, 417 (1963), Niwayama, J. Org. Chem., Vol. 65, 5834-5836 (2000) and the like or a method analogous thereto. Alternatively, the compound represented by the formula (V'), i.e., the compound represented by the formula (V) wherein one of $R^2$ and $R^3$ is a hydrogen atom, can also be produced from the tricarboxylic acid triester derivative represented by the formula (XIV) as shown in Scheme 3.

Scheme 3

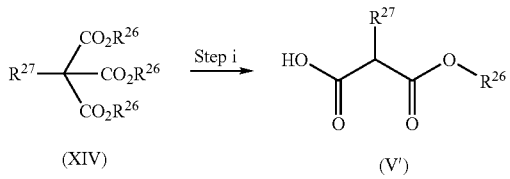

(XIV) (V')

wherein $R^{26}$ is as defined above, and when one of $R^2$ and $R^3$ is a hydrogen atom, $R^{27}$ is as defined for the other.

The tricarboxylic acid triester derivative represented by the formula (XIV) can be produced according to the methods well known in the field, for example, the methods described in Cravotto et al., Tetrahedron, Vol. 52, 13007-13016 (1996), Cravotto et al., Tetrahedron, Vol. 54, 1639-1646 (1998), Padgett et al., J. Org. Chem., Vol. 44, 3492-3496 (1979), Skarzewski, Synthesis, Vol. 12, 1125-1127 (1990) and the like, or a method analogous thereto.

Step i: In this step, a compound represented by the formula (V') is produced from a tricarboxylic acid triester derivative represented by the formula (XIV) by hydrolysis and decarboxylation reaction.

The reaction can be carried out according to a general deprotection to a carboxyl group, and a decarboxylation reaction proceeds following the deprotection. Examples of the base to be used include alkali metal or alkaline earth metal carbonates (e.g., sodium carbonate, potassium carbonate, cesium carbonate etc.), alkali metal or alkaline earth metal hydroxides (e.g., lithium hydroxide, sodium hydroxide, potassium hydroxide etc.) and the like. Examples of the solvent to be used for the reaction include alcohol solvents (e.g., methanol, ethanol etc.), ether solvents (e.g., THF, dioxane etc.) and the like, and a mixed solvent of these and water as necessary. The base is used in a proportion of about 200 mol % per 1 mol of the compound represented by the formula (XIV), and the reaction temperature is about 0° C. to 100° C.

The compounds represented by the formulas (XI) and (XII) in Scheme 1 are commercially available, or can be produced according to a method known per se, for example, the methods described in Harada et al., Bioorg. Med. Chem., Vol. 9, 2955-2968 (2001) and the like or a method analogous thereto.

For example, a compound represented by the formula (XVII), i.e. a compound represented by the formula (XI) wherein $R^1$ is a group represented by the following formula

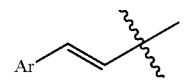

wherein Ar is as defined above, can be produced from Ar—CHO shown in Scheme 4.

Scheme 4

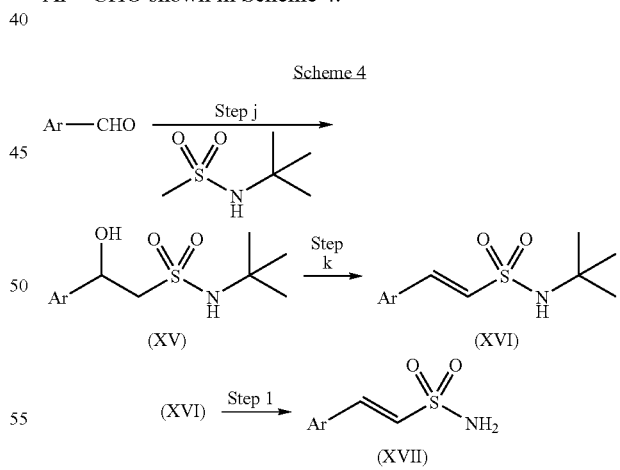

wherein Ar is as defined above.

Step j: In this step, a compound represented by the formula (XV) is produced by subjecting Ar—CHO and N-tert-butyl methanesulfonamide to aldol reaction.

The reaction can be carried out according to a general aldol reaction. Examples of the solvent to be used include ether solvents (e.g., THF, dioxane etc.) and the like. Examples of the base to be used include organic lithiums (e.g., methyl lithium, n-butyl lithium, sec-butyl lithium, tert-butyl lithium etc.), metal amides (e.g., lithium diisopropylamide, lithium hexamethyl disilazide etc.) and the like. The N-tert-butyl methanesulfonamide is used in a proportion of about 100 to 500 mol % per 1 mol of Ar—CHO, and the base is used in a proportion of about 200 to 1000 mol % per 1 mol of Ar—CHO. The reaction temperature is about −80° C. to 20° C., and the reaction time is about 30 min to 48 hr.

Step k: In this step, a compound represented by the formula (XVI) is produced by subjecting a compound represented by the formula (XV) to dehydration reaction.

The compound represented by the formula (XVI) can be produced by converting the hydroxyl group of a compound represented by the formula (XV) to a leaving group in a solvent in the presence of a base. Examples of the solvent to be used include ether solvents (e.g., diethyl ether, THF, dioxane etc.), aromatic hydrocarbon solvents (e.g., benzene, toluene, chlorobenzene etc.), halogen solvents (e.g., dichloromethane, dichloroethane, chloroform, carbon tetrachloride etc.), acetonitrile, DMF, DMSO and the like.

The conversion of the hydroxyl group to a leaving group is carried out using, for example, sulfonyl chlorides such as mesyl chloride, tosyl chloride and the like. Examples of the base include organic bases such as pyridine, TEA, DMAP, DIPEA, triethylenediamine, 4-methylmorpholine, 1,8-diazabicyclo[5.4.0]undec-7-ene and the like, alkali metal or alkaline earth metal carbonates (e.g., sodium carbonate, potassium carbonate, cesium carbonate etc.), alkali metal or alkaline earth metal hydrogen carbonates (e.g., sodium hydrogen carbonate, potassium hydrogen carbonate etc.), alkali metal or alkaline earth metal hydroxides (e.g., sodium hydroxide, potassium hydroxide, cesium hydroxide etc.) and the like.

The sulfonyl chloride is used in a proportion of about 100 to 500 mol % per 1 mol of the compound represented by the formula (XV), and the base is used in a proportion of about 200 to 1000 mol % per 1 mol of the compound represented by the formula (XV). The reaction temperature is about 0° C. to 100° C., and the reaction time is about 60 min to 48 hr.

Step l: In this step, a compound represented by the formula (XVII) is produced by removing the tert-butyl group from the compound represented by the formula (XVI).

The compound represented by the formula (XVII) can be produced by removing the tert-butyl group from the compound represented by the formula (XVI) using an acid such as hydrochloric acid, sulfuric acid, trifluoroacetic acid and the like, without solvent or in a halogen solvent (e.g., dichloromethane, dichloroethane, chloroform, carbon tetrachloride etc.).

A compound represented by the formula (XI'), i.e., a compound represented by the formula (XI) wherein $R^1$ is alkyl, arylalkyl, aryloxyalkyl or heteroarylalkyl, each of which is optionally substituted, can also be produced as shown in Scheme 5.

wherein $R^{1a}$ is alkyl, arylalkyl, aryloxyalkyl or heteroarylalkyl, each of which is optionally substituted, and $L^1$ is a leaving group.

Examples of the leaving group for $L^1$ include halogen atom, sulfonyloxy (e.g., methanesulfonyloxy, p-toluenesulfonyloxy etc.) and the like.

Step m: In this step, a compound represented by the formula (XIX) is produced from a compound represented by the formula (XVIII).

The compound represented by the formula (XIX) can be produced by reacting a compound represented by the formula (XVIII) with a sulfite in a solvent. Examples of the solvent include water, or a mixed solvent of water and an alcohol solvent (e.g., methanol, ethanol, propanol, isopropanol, n-butanol etc.), an ether solvent (e.g., THF, dioxane etc.), acetonitrile, DMF, DMSO and the like. Examples of the sulfite include sodium sulfite, potassium sulfite and the like. The sulfite is used in a proportion of about 100 to 1000 mold per 1 mol of the compound represented by the formula (XVIII). The reaction temperature is about 30° C. to 100° C., and the reaction time is about 60 min to 48 hr.

Step n: In this step, a compound represented by the formula (XX) is produced from a compound represented by the formula (XIX).

The compound represented by the formula (XX) can be produced by reacting a compound represented by the formula (XIX) with a chlorinating agent without solvent or in a solvent. Examples of the solvent include aromatic hydrocarbon solvents (e.g., benzene, toluene, chlorobenzene etc.), halogen solvents (e.g., dichloromethane, dichloroethane, chloroform, carbon tetrachloride etc.), DMF and the like. Examples of the chlorinating agent include thionyl chloride, phosphorus oxychloride, phosphorus pentachloride and the like. After completion of the reaction, the compound represented by the formula (XX) is generally obtained by evaporating the solvent and a chlorinating agent (in the case of thionyl chloride or phosphorus oxychloride). The chlorinating agent is used in excess per 1 mol of the compound represented by the formula (XIX). The reaction temperature is about 30° C. to 150° C., and the reaction time is about 60 min to 48 hr.

Step o: In this step, a compound represented by the formula (XI') is produced from a compound represented by the formula (XX).

The compound represented by the formula (XI') is produced by treating a compound represented by the formula (XX) with ammonia in a solvent. Examples of the solvent include halogen solvents (e.g., dichloromethane, dichloroethane, chloroform, carbon tetrachloride etc.) and the like. The compound can be produced by reacting a compound represented by the formula (XX) with ammonia gas or an ammonia mixed solution (e.g., aqueous ammonia, ammonia/dioxane solution, ammonia/methanol solution etc.) and the like.

A compound represented by the formula (V''), i.e., a compound represented by the formula (V) wherein one of $R^2$ and $R^3$ is a hydrogen atom, and the other is —$(CH_2)_n$—C(O)—$NR^5R^6$, can also be produced from a compound represented by the formula (XXI) as shown in Scheme 6. The compound represented by the formula (XXI) can be produced in the same manner as in the production of the aforementioned compound represented by the formula (XIV), or according to a method analogous thereto.

Scheme 5

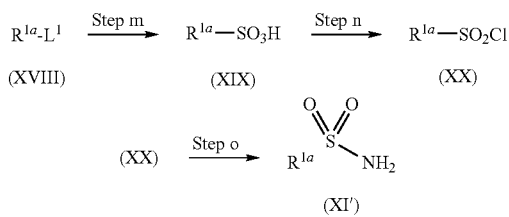

Scheme 6

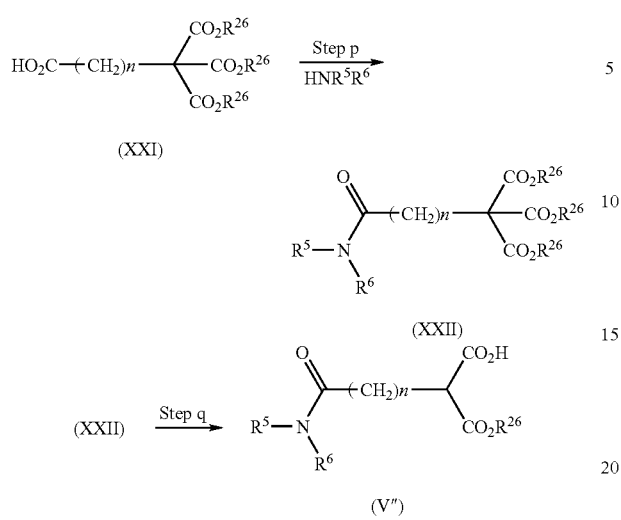

wherein $R^5$, $R^6$ and $R^{26}$ are as defined above, and n is an integer of 0 to 6.

Step p: In this step, a compound represented by the formula (XXII) is produced from a compound represented by the formula (XXI) in the same manner as in Step b, or according to a method analogous thereto.

Step q: In this step, a compound represented by the formula (V″) is produced from a compound represented by the formula (XXII) in the same manner as in Step i, or according to a method analogous thereto.

The production method of a compound represented by the formula (XXV). i.e., a compound represented by the formula (I) wherein one of $R^2$ and $R^3$ is a hydrogen atom, and the other is a group represented by the following formula

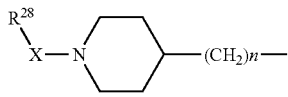

wherein n is an integer of 0 to 6, X is CO, $SO_2$, COO or CONH, $R^{28}$ is alkyl, alkenyl, alkynyl, cycloalkyl, cycloalkylalkyl, aryl, arylalkyl, heteroaryl, heteroarylalkyl or heterocyclyl, each of which is optionally substituted, and the cycloalkyl and heterocycle are optionally fused with a aromatic ring, is shown in Scheme 7.

Scheme 7

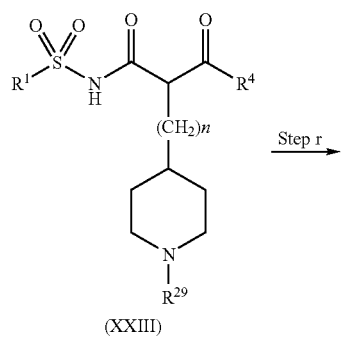

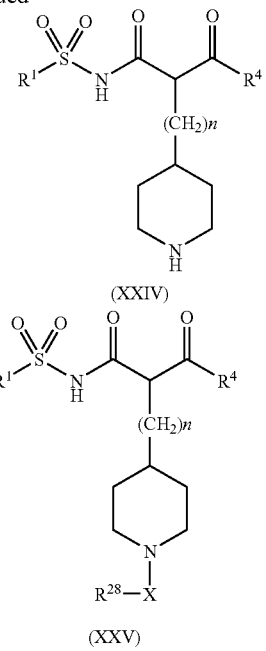

wherein $R^1$, $R^4$, $R^{28}$ and X are as defined above, n is an integer of 0 to 6, and $R^{29}$ is a conventional amino-protecting group.

Step r: In this step, a compound represented by the formula (XXIV) or a salt thereof is produced by subjecting a compound represented by the formula (XXIII) to deprotection.

For the reaction, general conditions for the deprotection of an amino-protecting group can be employed. For example, when $R^{29}$ is tert-butyloxycarbonyl (Boc), the deprotection can be carried out using an acid such as hydrochloric acid, sulfuric acid, trifluoroacetic acid and the like without solvent or in a halogen solvent (e.g., dichloromethane, dichloroethane, chloroform, carbon tetrachloride etc.). For example, when $R^{29}$ is benzyloxycarbonyl (Cbz), the deprotection can be carried out according to catalytic hydrogenation reaction using a palladium-carbon catalyst and the like to deprotect Cbz. Examples of the solvent to be used for the reaction include alcohol solvents (e.g., methanol, ethanol, isopropanol etc.), ether solvents (e.g., THF, dioxane etc.) and the like, and any reaction is generally carried out −20° C. to 80° C.

Step s: In this step, a compound represented by the formula (XXV) is produced by reacting a compound represented by the formula (XXIV) or a salt thereof with a sulfonyl chloride derivative: $R^{28}SO_2Cl$, carboxylic acid chloride derivative: $R^{28}COCl$, carboxylic acid derivative: $R^{28}CO_2H$, chloro carbonate derivative: $R^{28}OCOCl$ or isocyanate derivative: $R^{28}NCO$.

When the compound represented by the formula (XXV) is an amide derivative (X═CO), the reaction can be carried out using $R^{28}CO_2H$ in the same manner as in Step b, or according to a method analogous thereto. Alternatively, the reaction can be carried out using $R^{26}COCl$, in the presence of an organic base such as TEA, pyridine and the like, or an inorganic base such as alkali metal or alkaline earth metal carbonate (e.g., sodium carbonate, potassium carbonate, cesium carbonate etc.), alkali metal or alkaline earth metal hydroxide (e.g., sodium hydroxide, potassium hydroxide, cesium hydroxide etc.) and the like, in a solvent such as toluene, chloroform, dichloromethane, THF and the like, or in a mixed solvent thereof with water, at generally −20 to 80° C.

When the compound represented by the formula (XXV) is a sulfonamide derivative (X=SO$_2$), the reaction can be carried out using R$^{28}$SO$_2$Cl, in the same manner as in the above-mentioned reaction with R$^{28}$COCl, or according to a method analogous thereto.

When the compound represented by the formula (XXV) is a carbamate derivative (X=COO), the reaction can be carried out using R$^{28}$OCOCl, in the same manner as in the above-mentioned reaction with R$^{28}$COCl, or according to a method analogous thereto. When the compound represented by the formula (XXV) is a carbamide derivative (X=CONH), the reaction can be carried out using R$^{28}$NCO, in the same manner as in the above-mentioned reaction with R$^{28}$COCl, or according to a method analogous thereto.

The production method of a compound represented by the formula (XXVIII), i.e., a compound represented by the formula (I) wherein one of R$^2$ and R$^3$ is a hydrogen atom, and the other is a group represented by the following formula

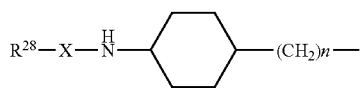

wherein R$^{28}$ and X are as defined above, n is an integer of 0 to 6, and the steric configuration of the cyclohexane ring is cis or trans, is shown in Scheme 8.

Scheme 8

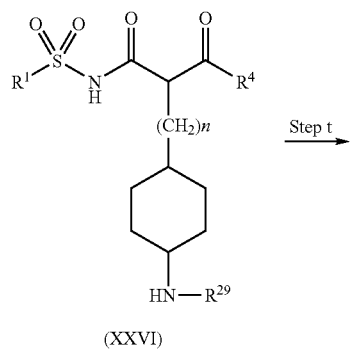

(XXVI)

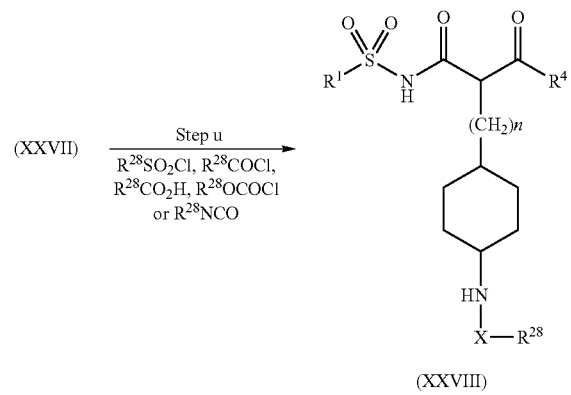

(XXVIII)

wherein R$^1$, R$^4$, R$^{28}$, R$^{29}$ and X are as defined above, and n is an integer of 0 to 6.

Step t: In this step, a compound represented by the formula (XXVII) or a salt thereof is produced from a compound represented by the formula (XXVI), in the same manner as in Step r, or according to a method analogous thereto.

Step u: In this step, a compound represented by the formula (XXVIII) is produced from a compound represented by the formula (XXVII) or a salt thereof, in the same manner as in Step s, or according to a method analogous thereto.

The production method of a compound represented by the formula (XXXI), i.e., a compound represented by the formula (I) wherein one of R$^2$ and R$^3$ is a hydrogen atom, and the other is a group represented by the following formula

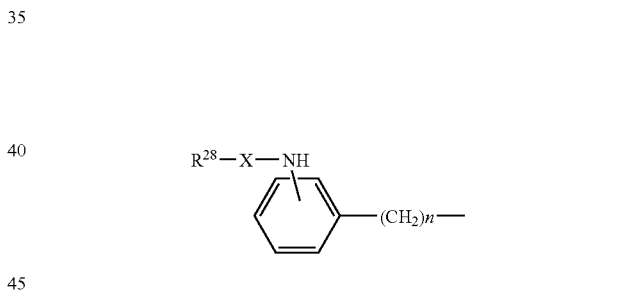

wherein R$^{28}$ and X are as defined above, n is an integer of 0 to 6, and ortho-substitution is excluded, is shown in Scheme 9.

Scheme 9

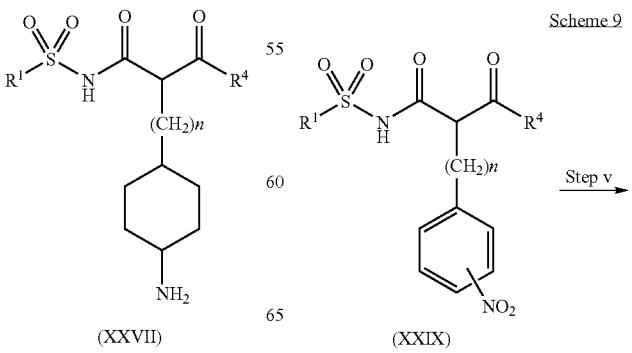

(XXIX)

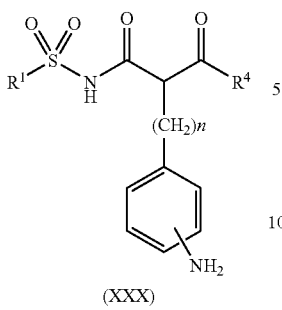

(XXX)

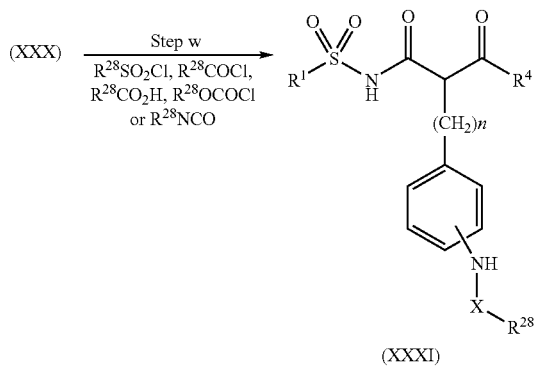

(XXXI)

wherein $R^1$, $R^4$, $R^{28}$ and X are as defined above, and n is an integer of 0 to 6.

Step v: In this step, a compound represented by the formula (XXX) or a salt thereof is produced by reducing a nitro compound represented by the formula (XXIX).

The reaction can be carried out according to a general reduction reaction of a nitro group. For example, a nitro compound represented by the formula (XXIX) can also be reduced according to catalytic hydrogenation reaction using a metal catalyst such as palladium and the like. Examples of the solvent to be used for the reaction include ethyl acetate, aromatic hydrocarbon solvents (e.g., benzene, toluene etc.), alcohol solvents (e.g., methanol, ethanol, isopropanol etc.), ether solvents (e.g., THF, dioxane etc.) and the like and, where necessary, a base such as TEA and the like may be added. The reaction temperature is generally 0° C. to 100° C.

Alternatively, the nitro compound can also be reduced using a metal such as zinc, iron and the like, or tin chloride. Examples of the solvent to be used for the reaction include DMF, acetic acid, alcohol solvents (e.g., methanol, ethanol, isopropanol etc.) and the like and, where necessary, a mixed solvent with an aqueous dilute hydrochloric acid can be used. Alternatively, the nitro compound can also be reduced using a metal catalyst such as iron chloride and the like in a mixed solvent of hydrazine and an alcohol solvent (e.g., methanol, ethanol, isopropanol etc.). Any reaction is carried out at generally 0° C. to 100° C.

Step w: In this step, a compound represented by the formula (XXXI) is produced from a compound represented by the formula (XXX) or a salt thereof in the same manner as in Step s, or according to a method analogous thereto.

The production method of a compound represented by the formula (XXXIV), i.e., a compound represented by the formula (I) wherein one of $R^2$ and $R^3$ is a hydrogen atom, and the other is a group represented by the following formula

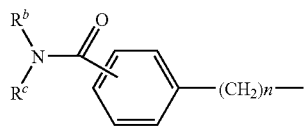

wherein $R^b$ and $R^c$ are as defined above, is shown in Scheme 10.

Scheme 10

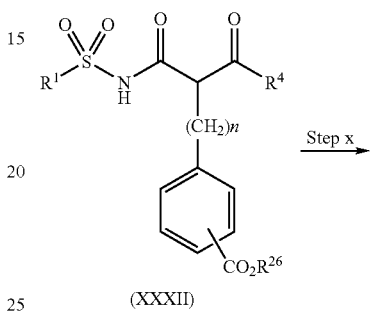

(XXXII)

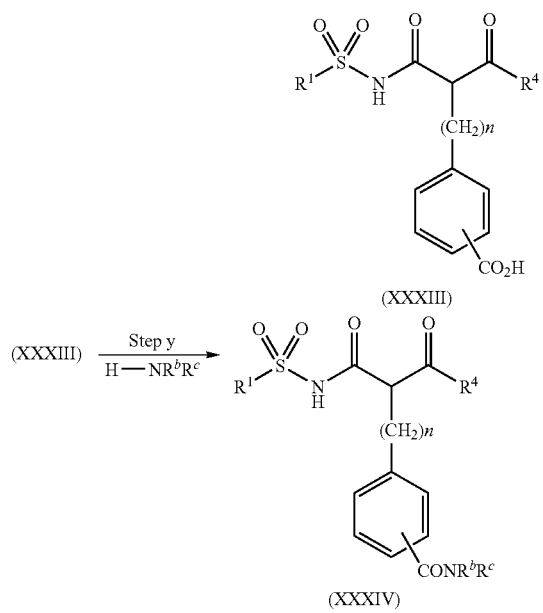

wherein $R^1$, $R^4$, $R^{26}$, $R^b$ and $R^c$ are as defined above, and n is an integer of 0 to 6.

Step x: In this step, a compound represented by the formula (XXXIII) is produced from a compound represented by the formula (XXXII) in the same manner as in Step c, or according to a method analogous thereto.

Step y: In this step, a compound represented by the formula (XXXIV) is produced from a compound represented by the formula (XXXIII) in the same manner as in Step b, or according to a method analogous thereto.

The production method of a compound represented by the formula (XXXVI), i.e., a compound represented by the formula (I) wherein one of $R^2$ and $R^3$ is a hydrogen atom, and the other is a group represented by the following formula

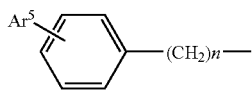

wherein Ar⁵ is aryl, heteroaryl and the like, each of which is optionally substituted, and n is an integer of 0 to 6, is shown in Scheme 11.

Scheme 11

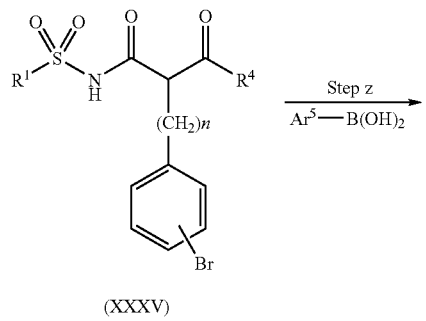

(XXXV)

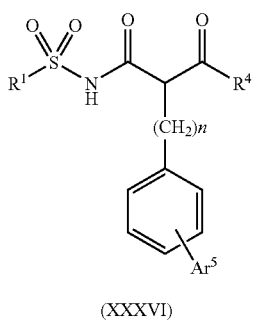

(XXXVI)

wherein $R^1$, $R^4$ and $Ar^5$ are as defined above, and n is an integer of 0 to 6.

Step z: In this step, a compound represented by the formula (XXXVI) is produced by subjecting a compound represented by the formula (XXXV) and $Ar^5$—B(OH)₂ to coupling reaction.

The reaction can be carried out according to a general Suzuki coupling reaction. Examples of the solvent to be used for the reaction include benzene, toluene, xylene, ethanol, DMF, DMSO, ethylene glycol dimethyl ether, water, dioxane and the like and a mixed solvent thereof. Examples of the coupling catalyst to be used include palladium catalysts (e.g., Pd(PPh₃)₄, Pd(OAc)₂/ligand (the ligand is, for example, PPh₃, P(o-Tol)₃, 1,1'-bis(diphenylphosphino)ferrocene and the like) and the like. Examples of the base to be used include inorganic bases such as sodium hydroxide, sodium carbonate, potassium carbonate, cesium carbonate and the like, or organic bases such as TEA, DIPEA and the like. $Ar^5$—B(OH)₂ is used in a proportion of about 100 to 500 mol % per 1 mol of the compound represented by the formula (XXXV), the coupling catalyst is used in a proportion of about 1 to 100 mol % per 1 mol of the compound represented by the formula (XXXV), and the base is used in a proportion of about 200 to 1000 mol % per 1 mol of the compound represented by the formula (XXXV). The reaction temperature is about 20° C. to 150° C., and the reaction time is about 1 to 100 hr.

The production method of a compound represented by the formula (XXXVIII), i.e., a compound represented by the formula (I) wherein one of $R^2$ and $R^3$ is a hydrogen atom, and the other is a group represented by the following formula

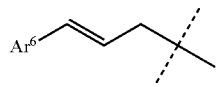

wherein Ar⁶ is aryl, heteroaryl and the like, each of which is optionally substituted, is shown in Scheme 12.

Scheme 12

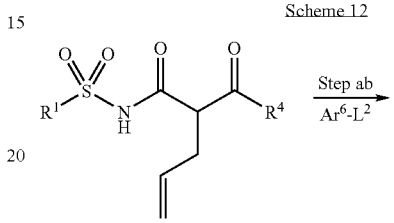

(XXXVII)

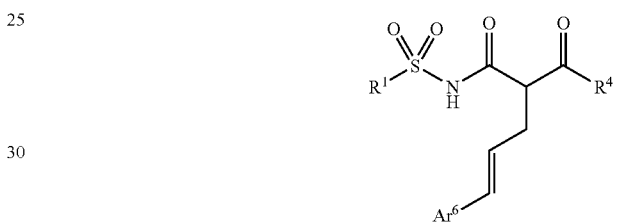

(XXXVIII)

wherein $R^1$, $R^4$ and $Ar^6$ are as defined above, and $L^2$ is a leaving group (a halogen atom, trifluoromethanesulfonyloxy etc.).

Step ab: In this step, a compound represented by the formula (XXXVIII) is produced by subjecting a compound represented by the formula (XXXVII) and $Ar^6$-$L^2$ to coupling reaction.

The reaction can be carried out according to a general Heck reaction using a palladium catalyst (e.g., Pd(PPh₃)₄, Pd(OAc)₂/PPh₃ etc.), in the presence of a base (e.g., potassium carbonate, calcium carbonate, TEA, diisopropylamine etc.), in a solvent such as THF, acetonitrile, N,N'-dimethylacetamide, DMF, 1-methyl-2-pyrrolidinone and the like, at room temperature to about 100° C. Where necessary, an additive (e.g., silver carbonate, potassium acetate etc.) may be added.

A compound represented by the formula (XXXX), i.e., a compound represented by the formula (I) wherein one of $R^2$ and $R^3$ is a hydrogen atom, and the other is a group represented by the following formula

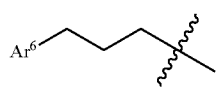

wherein Ar⁶ is as defined above, can also be produced as shown in Scheme 13.

Scheme 13

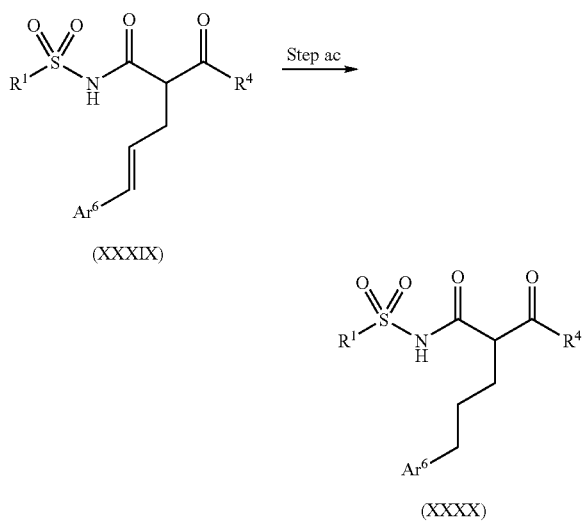

wherein $R^1$, $R^4$ and $Ar^6$ are as defined above.

Step ac: In this step, a compound represented by the formula (XXXX) is produced by reducing a compound represented by the formula (XXXIX).

The reaction can be carried out according to a general catalytic hydrogenation reaction using a palladium-carbon catalyst and the like. Examples of the solvent to be used for the reaction include ethyl acetate, aromatic hydrocarbon solvents (e.g., benzene, toluene etc.), alcohol solvents (e.g., methanol, ethanol, isopropanol etc.), ether solvents (e.g., THF, dioxane etc.) and the like, and the reaction temperature is generally 0° C. to 100° C.

A compound represented by the formula (XXXXII), i.e., a compound represented by the formula (I) wherein $R^1$ is a group represented by the following formula

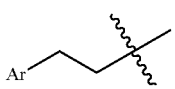

wherein Ar is as defined above, can also be produced as shown in Scheme 14.

Scheme 14

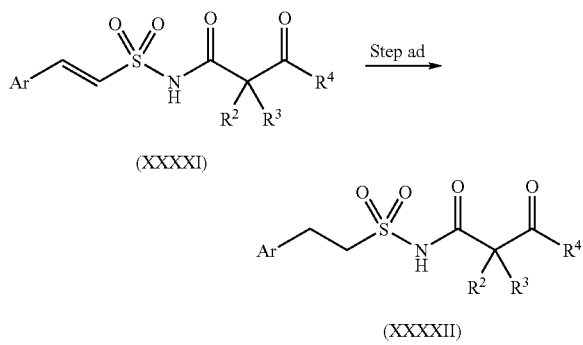

wherein $R^2$, $R^3$, $R^4$ and Ar are as defined above.

Step ad: In this step, a compound represented by the formula (XXXXII) is produced from a compound represented by the formula (XXXXI) in the same manner as in Step ac, or according to a method analogous thereto.

When the compound represented by the formula (I) is a racemate, it can also be resolved by a general optical resolution means well known in the pertinent field [for example, resolution using chiral amine ((+)-dehydroabiethylamine, optically active 2-amino-1-(4-nitrophenyl)-1,3-propanediol, optically active phenylethylamine and the like) described in CRC Handbook of Optical Resolution via Diastereomeric Salt Formation (CRC Press), resolution by chiral column chromatography] to give an S form or R form. Alternatively, a compound represented by the formula (IX) is resolved by a general optical resolution means and an S form or R form of the compound represented by the formula (I) can be produced according to a method described in, for example, Ishizuka et al., Synthesis, No. 6, 784-788 (2000), or a method analogous thereto.

The thus-produced compound of the present invention can be obtained at any purity by appropriately applying a known separation and purification means, such as concentration, extraction, chromatography, reprecipitation, recrystallization and the like.

Where necessary, the compound represented by the formula (I) can be converted to an inorganic base addition salt with sodium, potassium, calcium, magnesium etc., an inorganic acid addition salt with hydrochloric acid, sulfuric acid, phosphoric acid, hydrobromic acid etc., an organic acid addition salt with methanesulfonic acid, benzenesulfonic acid, p-toluenesulfonic acid, acetic acid etc., or a salt with amino acid such as glutamic acid, aspartic acid, arginine, lysin and the like. In addition, the compound represented by the formula (I) or a salt thereof can also be present as a solvate such as hydrate and the like.

The compound of the present invention has a potent agonist action at $AT_2$ receptor in mammals (e.g., human, monkey, dog, rat etc.).

Therefore, the compound of the present invention is useful as a novel $AT_2$ receptor agonist for the treatment or prevention of various diseases. Expected target diseases include various groups of disorders involving RAAS, such as metabolic and cardiovascular diseases and the like, particularly stroke, renal disease, cardiac disease, hypertension, diabetes, metabolic syndrome and the like.

Moreover, the compound of the present invention can be administered to a single subject simultaneously with other therapeutic or preventive drug(s), for example, a therapeutic or preventive drug for stroke, renal disease, cardiac disease, hypertension, diabetes, diabetic complications, hyperlipidemia and/or metabolic syndrome and the like, or in a staggered manner.

When the compound of the present invention is used in combination with other therapeutic or preventive drug(s), the compounding ratio thereof can be appropriately determined according to the subject to be administered, age, body weight and condition of the subject, administration time, dosage form, method of administration, pattern of combination and the like.

When the compound of the present invention is used as a therapeutic or preventive drug, the compound itself or a mixture of the compound and appropriate pharmacologically acceptable carrier, excipient, diluent and the like can be administered orally or parenterally in the form of powder, granule, tablet, capsule, injection and the like. The above-mentioned preparation contains an effective amount of the compound of the present invention.

The dose of the compound of the present invention varies depending on the administration route, target disease, condition, body weight or age of the subject and the like and can also be appropriately set according to the object. Generally, the dose for oral administration to an adult is 0.01-1000 mg/kg body weight/day, more preferably 0.05-500 mg/kg body weight/day, and an appropriate dose is preferably administered once a day or in several portions a day.

EXAMPLES

The present invention is explained in more detail in the following by referring to Examples, which are not to be construed as limitative.

$^1$H-NMR was measured at 300 or 400 MHz. The chemical shift of was expressed as relative delta (δ) value in parts per million (ppm) using tetramethylsilane (TMS) as the internal standard. For the coupling constant J, obvious multiplicity is shown using s (singlet), d (doublet), t (triplet), q (quartet), sept (septet), m (multiplet), dd (doublet of doublets), td (triplet of doublets), dt (doublet of triplets), brs (broad singlet) and the like in hertz (Hz). Mass spectrum (MS) was measured by liquid chromatography mass spectrometry and on a positive ion mode. The optical purity was measured by high performance liquid chromatography using a chiral column, and expressed by enantiomer excess (% e.e.) or diastereomer excess (% d.e.) based on the area value of R form and S form thereof. The optical rotation was represented by specific optical rotation $[\alpha]_D$. The thin-layer chromatography was performed using silica gel manufactured by Merck, and column chromatography was performed using silica gel manufactured by Fuji Silysia Chemical.

In extraction, moreover, organic solutions were dried over anhydrous sodium sulfate or anhydrous magnesium sulfate unless otherwise specified.

The solvents and reagents used for the experiments are shown by the following abbreviations.
tetrahydrofuran: THF
N,N-dimethylformamide: DMF
1-ethyl-3-(3-dimethylaminopropyl)carbodiimide hydrochloride: WSCI.HCl
1,1'-carbonyldiimidazole: CDI
1-hydroxybenzotriazole 1-hydrate: HOBt.H$_2$O
1,8-diazabicyclo[5.4.0]undec-7-ene: DBU Example 1

Synthesis of 2-benzyl-N,N-diethyl-N'-(2-naphthylsulfonyl)malonamide (1) monoethyl benzylmalonate To a solution of diethyl benzylmalonate (27.1 g) in ethanol (70 mL) was added a solution of potassium hydroxide (6.1 g) in ethanol (70 mL), and the mixture was stirred at room temperature for 18 hr. After concentration under reduced pressure, water (300 ml) and ether (100 mL) were added to extract the mixture. The aqueous layer was adjusted to pH=1-2 by the addition of concentrated hydrochloric acid, and the mixture was extracted with ethyl acetate (200 mL×2). The organic layer was washed with saturated brine and concentrated under reduced pressure to give the title compound (19.3 g) as an oil.

$^1$H-NMR (300 MHz, DMSO-d$_6$) δ1.08 (3H, t, J=7.2 Hz), 3.05 (2H, dd, J=9.3, 4.8 Hz), 3.67-3.72 (1H, m), 4.04 (2H, q, J=7.2 Hz), 7.17-7.30 (5H m), 12.94 (1H, brs).

(2) ethyl 2-benzyl-3-[(2-naphthylsulfonyl)amino]-3-oxopropionate

To a solution of the above-mentioned compound (5.53 g) in THF (100 mL) was added CDI (6.46 g), and the mixture was heated under reflux for 1 hr. The reaction mixture was allowed to cool to room temperature, naphthalene-2-sulfonamide (5.15 g) and DBU (4.10 mL) were added, and the mixture was stirred at room temperature for 20 hr. The reaction mixture was concentrated, 1 mol/L hydrochloric acid (100 mL) and ethyl acetate (200 mL) were added to extract the residue, and the organic layer was washed with saturated brine. After concentration, chloroform was added to the residue, and insoluble material was removed by filtration. The filtrate was concentrated, and the residue was purified by silica gel column chromatography to give the title compound (3.30 g) as an oil.

$^1$H-NMR (300 MHz, DMSO-d$_6$) δ0.94 (3H, t, J=7.0 Hz), 2.92-2.95 (2H, m), 3.71-3.78 (1H, m), 3.95 (2H, q, J=7.0 Hz), 6.99-7.08 (5H, m), 7.70-7.77 (3H, m), 8.07-8.25 (3H, m), 8.53 (1H, s), 12.53 (1H, brs).

(3) 2-benzyl-3-[(2-naphthylsulfonyl)amino]-3-oxopropionic acid

To a mixed solution of the above-mentioned compound (3.30 g) in THF (10 mL)/ethanol (50 mL) was added a solution of sodium hydroxide (1.0 g) in water (4 mL), and the mixture was stirred at room temperature for 15 hr. After concentration under reduced pressure, the residue was adjusted to pH=1-2 by the addition of 1 mol/L hydrochloric acid, and the mixture was extracted with ethyl acetate (100 mL×2). The organic layer was washed with saturated brine, and concentrated under reduced pressure to give the title compound (2.91 g) as a white solid.

$^1$H-NMR (300 MHz, DMSO-d$_6$) δ2.50-2.98 (2H, m), 3.67 (1H, dd, J=9.3, 6.0 Hz), 6.95-7.06 (5H, m), 7.69-7.79 (3H, m), 8.07-8.22 (3H, m), 8.51 (1H, s), 12.47 (1H, brs), 12.90 (1H, brs).

(4) 2-benzyl-N,N-diethyl-N'-(2-naphthylsulfonyl)malonamide

To a solution of the above-mentioned compound (690 mg) in DMF (10 mL) were added diethylamine (690 μL), HOBt.H$_2$O (330 mg) and WSCI.HCl (420 mg), and the mixture was stirred at room temperature for 18 hr. The mixture was adjusted to pH=1-2 by the addition of dilute hydrochloric acid (20 mL), and extracted with ethyl acetate (100 mL). The organic layer was washed with saturated brine and concentrated under reduced pressure. A mixed solution of hexane/ethyl acetate was added to the residue, and the precipitate was collected by filtration to give the title compound (473 mg) as a white solid.

$^1$H-NMR (300 MHz, DMSO-d$_6$) δ0.81-0.88 (6H, m), 2.91 (2H, d, J=7.2 Hz), 3.08-3.23 (4H, m), 3.80-3.85 (1H, m), 7.02-7.09 (5H, m), 7.70-7.80 (3H, m), 8.06-8.21 (3H, m), 8.53 (1H, s), 12.33 (1H, brs).
MS: 439(M+H)$^+$.

Example 2

Synthesis of N-{2-benzyl-3-[(2-naphthylsulfonyl)amino]-3-oxopropanoyl}-N-ethylglycine ethyl ester (1) N-ethylglycine ethyl ester hydrochloride To ethanol (30 mL) was added dropwise thionyl chloride (2.6 mL) at −10° C., and the mixture was stirred for 15 min. N-ethylglycine (1.0 g) was added to this solution at −10° C., and the mixture was allowed to warm to room temperature while stirring for 17 hr. The reaction mixture was concentrated under reduced pressure to give the title compound (1.63 g) as a white solid.

$^1$H-NMR (300 MHz, DMSO-$d_6$) δ1.19-1.27 (6H, m), 2.96 (2H, q, J=7.2 Hz), 3.93 (2H, s), 4.21 (2H, q, J=6.9 Hz), 9.54 (2H, brs).

(2) N-{2-benzyl-3-[(2-naphthylsulfonyl)amino]-3-oxopropanoyl}-N-ethylglycine ethyl ester In the same manner as in Example 1 (4), a crude product was obtained using the compound (582 mg) obtained by Example 1 (3) and the above-mentioned compound (310 mg). This was purified by silica gel column chromatography to give the title compound (342 mg) as a white solid.

$^1$H-NMR (300 MHz, DMSO-$d_6$) δ0.89 (3H, t, J=7.0 Hz), 1.08-1.22 (3H, m), 2.78-3.00 (2H, m), 3.22-3.35 (2H, m), 3.79-4.36 (5H, m), 6.90-7.10 (5H, m), 7.70-7.80 (3H, m), 8.08-8.24 (3H, m), 8.54 (1H, d, J=1.6 Hz), 12.36 (1H, brs).
MS: 525 (M+Na)$^+$.

Example 3

Synthesis of N-{2-benzyl-3-[(2-naphthylsulfonyl)amino]-3-oxopropanoyl}-N-ethylglycine To a mixture of the compound (250 mg) obtained by Example 2 in THF (10 mL)/water (3 mL) was added 1 mol/L aqueous sodium hydroxide solution (1.5 mL) at room temperature, and the mixture was stirred for 2.5 hr. After concentration under reduced pressure, the residue was adjusted to pH=1-2 by the addition of 1 mol/L hydrochloric acid and extracted with ethyl acetate (50 mL×2). The organic layer was washed with saturated brine and concentrated under reduced pressure to give the title compound (211 mg) as a white solid.

$^1$H-NMR (300 MHz, DMSO-$d_6$) δ0.88 (3H, t, J=6.9 Hz), 2.78-2.98 (2H, m), 3.19-3.34 (2H, m), 3.74-4.24 (3H, m), 6.91-7.08 (5H, m), 7.70-7.79 (3H, m), 8.07-8.22 (3H, m), 8.51-8.52 (1H, m), 12.30 (1H, brs), 12.51 (1H, brs).
MS: 469(M+H)$^+$.

Example 4

Synthesis of N-benzyl-N-{2-benzyl-3-[(2-naphthylsulfonyl)amino]-3-oxopropanoyl}glycine (1) N-benzyl-N-{2-benzyl-3-[(2-naphthylsulfonyl)amino]-3-oxopropanoyl}glycine ethyl ester In the same manner as in Example 1 (4), the title compound (1.29 g) was obtained as a white solid using the compound (930 mg) obtained by Example 1 (3) and N-benzylglycine ethyl ester (570 mg).
MS:559(M+H)$^+$.

(2) N-benzyl-N-{2-benzyl-3-[(2-naphthylsulfonyl)amino]-3-oxopropanoyl}glycine

In the same manner as in Example 3, the title compound (1.13 g) was obtained as a white solid using the above-mentioned compound (1.29 g).

$^1$H-NMR (300 MHz, DMSO-$d_6$) δ2.80-3.05 (2H, m), 3.75-4.25 (3H, m), 4.50-4.80 (2H, m), 6.84-7.25 (10H, m), 7.70-7.80 (3H, m), 8.07-8.10 (2H, m), 8.20-8.23 (1H, m), 8.52-8.53 (1H, m), 12.38 (2H, brs).
MS: 531(M+H)$^+$.

Example 5

Synthesis of 2-benzyl-N-(2-naphthylsulfonyl)-3-[4-(2-naphthylsulfonyl)piperazin-1-yl]-3-oxopropanamide (1) 2-benzyl-N-(2-naphthylsulfonyl)-3-(piperazin-1-yl)-3-oxopropanamide trifluoroacetate To a solution of the compound (1.0 g) obtained by Example 1 (3) in DMF (20 mL) were added 1-tert-butyloxycarbonylpiperazine (590 mg), HOBt.H$_2$O (480 mg), WSCI.HCl (600 mg) and N-methylmorpholine (290 μL), and the mixture was stirred at room temperature for 3.5 hr. The reaction mixture was adjusted to pH=4 by the addition of dilute hydrochloric acid (20 mL), and the precipitate was collected by filtration. Trifluoroacetic acid (10 mL) was added to this, and the mixture was stirred at room temperature for 13 hr. After concentration under reduced pressure, ether was added to the residue, and the mixture was subjected to decantation to give the title compound (1.47 g) as a white powder.
MS: 452(M+H)$^+$.

(2) 2-benzyl-N-(2-naphthylsulfonyl)-3-[4-(2-naphthylsulfonyl)piperazin-1-yl]-3-oxopropanamide To a solution of the above-mentioned compound (600 mg) in pyridine (5 mL) were added 4-dimethylaminopyridine (130 mg) and 2-naphthalenesulfonyl chloride (240 mg), and the mixture was stirred at room temperature for 16 hr. After concentration under reduced pressure, dilute hydrochloric acid was added to the residue, and the precipitate was collected by filtration. This was purified by silica gel column chromatography to give the title compound (265 mg) as a white powder.

$^1$H-NMR (300 MHz, DMSO-$d_6$) δ2.55-3.68 (10H, m), 3.88-3.97 (1H, m), 6.48-6.52 (1H, m), 6.75-6.79 (2H, m), 6.90-6.92 (2H, m), 7.63-8.51 (14H, m), 12.27 (1H, brs).
MS: 642(M+H)$^+$.

Example 6

Synthesis of N,N-diethyl-N'-(2-naphthylsulfonyl)-2-(4-nitrobenzyl)malonamide (1) dimethyl(4-nitrobenzyl)malonate To a solution of dimethyl malonate (5.53 g) in THF (100 mL) was added 60% sodium hydride (1.84 g) under ice-cooling, and the mixture was stirred for 30 min. 4-Nitrobenzyl bromide (9.04 g) was added to this mixture under ice-cooling, and the mixture was allowed to warm to room temperature while stirring for 4 hr. The reaction mixture was adjusted to pH=2-3 by the addition of dilute hydrochloric acid, the precipitate was removed by filtration, and the filtrate was extracted with ethyl acetate (200 mL). The organic layer was washed with saturated brine and concentrated under reduced pressure to give the title compound (7.66 g) as a pale-yellow solid.

$^1$H-NMR (300 MHz, DMSO-$d_6$) δ3.21 (2H, d, J=7.8 Hz), 3.60 (6H, s), 4.00 (1H, t, J=7.8 Hz), 7.51 (2H, d, J=8.4 Hz), 8.13 (2H, d, J=8.4 Hz).

(2) monomethyl(4-nitrobenzyl)malonate

To a solution (30 mL) of the above-mentioned compound (7.62 g) in methanol was added a solution of potassium hydroxide (1.45 g) in methanol (20 mL), and the mixture was stirred at room temperature for 56 hr. After concentration under reduced pressure, water (300 ml) and ether (100 mL) were added to extract the residue. The aqueous layer was adjusted to pH=1-2 by the addition of concentrated hydrochloric acid, and extracted with ethyl acetate (200 mL×2). The organic layer was washed with saturated brine and concentrated under reduced pressure to give the title compound (4.32 g) as a yellow solid.

$^1$H-NMR (300 MHz, DMSO-d$_6$) δ3.20 (2H, d, J=7.9 Hz), 3.61 (3H, s), 3.89 (1H, t, J=7.9 Hz), 7.53 (2H, d, J=8.5 Hz), 8.15 (2H, d, J=8.5 Hz), 13.00 (1H, brs).

(3) methyl 3-[(2-naphthylsulfonyl)amino]-2-(4-nitrobenzyl)-3-oxopropionate

In the same manner as in Example 1 (2), the title compound (5.49 g) was obtained as a pale-yellow powder using the above-mentioned compound (4.24 g).

$^1$H-NMR (300 MHz, DMSO-d$_6$) δ3.00-3.19 (2H, m), 3.57 (3H, s), 3.86-3.95 (1H, m), 7.23 (2H, d, J=8.5 Hz), 7.69-7.82 (5H, m), 8.03-8.07 (2H, m), 8.17-8.19 (1H, m), 8.48 (1H, s), 12.60 (1H, brs).

(4) 3-[(2-naphthylsulfonyl)amino]-2-(4-nitrobenzyl)-3-oxopropionic acid

To a solution of the above-mentioned compound (5.49 g) in THF (100 mL) was added a solution of sodium hydroxide (1.54 g) in water (12 mL). In the same manner as in Example 1 (3), the title compound (5.31 g) as a pale-yellow powder was obtained.

$^1$H-NMR (300 MHz, DMSO-d$_6$) δ2.97-3.18 (2H, m), 3.74-3.80 (1H, m), 7.22 (2H, d, J=8.5 Hz), 7.67-7.73 (3H, m), 7.78 (2H, d, J=8.5 Hz), 8.03 (2H, d, J=8.8 Hz), 8.16 (1H, d, J=7.9 Hz), 8.47 (1H, s), 12.54 (2H, brs).

(5) N,N-diethyl-N'-(2-naphthylsulfonyl)-2-(4-nitrobenzyl)malonamide

To the residue obtained in the same manner as in Example 1 (4) using the above-mentioned compound (5.31 g) was added methanol, and the precipitate was collected by filtration to give the title compound (2.63 g) as a white solid.

$^1$H-NMR (300 MHz, DMSO-d$_6$) δ0.86 (6H, t, J=7.6 Hz), 3.05 (2H, d, J=7.3 Hz), 3.12-3.20 (4H, m), 3.95 (1H, t, J=7.6 Hz), 7.31 (2H, d, J=8.6 Hz), 7.70-7.79 (3H, m), 7.88 (2H, d, J=8.6 Hz), 8.08 (2H, t, J=9.0 Hz), 8.19 (1H, d, J=7.9 Hz), 8.52 (1H, s), 12.40 (1H, brs).

MS: 484(M+H)$^+$.

Example 7

Synthesis of 2-(4-aminobenzyl)-N,N-diethyl-N'-(2-naphthylsulfonyl)malonamide

To a mixed suspension of the compound (2.53 g) obtained in Example 6 in ethanol (200 mL)/ethyl acetate (100 mL) was added 10% palladium/carbon (500 mg), and the mixture was heated under reflux under hydrogen atmosphere for 6 hr. After allowing to cool to room temperature, insoluble material was removed by filtration, and the filtrate was concentrated under reduced pressure to give the title compound (2.37 g) as a white powder. In some cases, the compound was further converted to a hydrochloride salt with 4 mol/L hydrochloric acid/ethyl acetate and used.

$^1$H-NMR (300 MHz, DMSO-d$_6$) δ0.82-0.88 (6H, m), 2.74 (2H, d, J=6.9 Hz), 3.06-3.20 (4H, m), 3.72 (1H, t, J=6.9 Hz), 6.37 (2H, d, J=8.4 Hz), 6.71 (2H, d, J=8.4 Hz), 7.65-7.78 (3H, m), 8.07 (1H, d, J=7.8 Hz), 8.13 (1H, d, J=9.0 Hz), 8.21 (1H, d, J=7.8 hz), 8.54 (1H, s).

MS: 454(M+H)$^+$.

Example 8

Synthesis of N,N-diethyl-2-(4-guanidinobenzyl)-N'-(2-naphthylsulfonyl)malonamide trifluoroacetic acid salt (1) [4-(N'',N'''-di-tert-butyloxycarbonylguanidino)benzyl]-N,N-diethyl-2-N'-(2-naphthylsulfonyl)malonamide To a solution of the compound (1.09 g) obtained in Example 7 in ethanol (10 mL) was added N,N'-di-tert-butyloxycarbonyl-1H-pyrazole-1-carboxamidine (745 mg) at room temperature, and the mixture was stirred for 2 hr. The precipitate was collected by filtration from the reaction mixture to give the title compound (1.44 g) as a white solid.

MS:696(M+H)$^+$.

(2) N,N-diethyl-2-(4-guanidinobenzyl)-N'-(2-naphthylsulfonyl)malonamide trifluoroacetic acid salt To the above-mentioned compound (1.44 g) was added 95% trifluoroacetic acid (20 mL), and the mixture was stirred at room temperature for 3 hr. The reaction mixture was concentrated under reduced pressure, ether was added to the residue, and the precipitate was collected by filtration to give the title compound (1.26 g) as a white solid.

$^1$H-NMR (300 MHz, DMSO-d$_6$) δ0.86 (6H, t, J=6.6 Hz), 2.93 (2H, d, J=6.9 Hz), 3.10-3.21 (4H, m), 3.87 (1H, t, J=6.9 Hz), 6.95 (2H, d, J=8.1 Hz), 7.12 (2H, d, J=8.1 Hz), 7.36 (4H, brs), 7.69-7.79 (3H, m), 8.07-8.08 (1H, d, J=8.1 Hz), 8.14 (1H, d, J=8.7 Hz), 8.22 (1H, d, J=7.8 Hz), 8.56 (1H, s), 9.67 (1H, s), 12.24 (1H, brs).

MS: 496(M+H)$^+$.

Example 9

Synthesis of 2-[4-(benzoylamino)benzyl]-N,N-diethyl-N'-(2-naphthylsulfonyl)malonamide To a solution of the compound (500 mg) obtained in Example 7 in pyridine (5 mL) were added benzoyl chloride (160 mg) and 4-dimethylaminopyridine in catalytic amount at room temperature, and the mixture was stirred for 3 hr. The reaction mixture was adjusted to pH=2-3 by the addition of dilute hydrochloric acid, the precipitate was collected by filtration, and washed with water to give the title compound (527 mg) as a white solid.

$^1$H-NMR (400 MHz, DMSO-d$_6$) δ0.86 (6H, t, J=6.9 Hz), 2.86-2.95 (2H, m), 3.09-3.22 (4H, m), 3.87 (1H, t, J=7.2 Hz), 7.05 (2H, d, J=8.2 Hz), 7.52-7.79 (8H, m), 7.96 (2H, d, J=8.2 Hz), 8.05 (1H, d, J=8.1 Hz), 8.14 (1H, d, J=8.8 Hz), 8.21 (1H, d, J=8.1 Hz), 8.56 (1H, s), 10.16 (1H, s), 12.37 (1H, brs).

MS: 558(M+H)$^+$.

Example 10

Synthesis of 2-[4-(acetylamino)benzyl]-N,N-diethyl-N'-(2-naphthylsulfonyl)malonamide In the same manner as in Example 9, the title compound (261 mg) was obtained as a white solid using hydrochloride salt (300 mg) of the compound obtained in Example 7 and acetic anhydride (70 μL).

$^1$H-NMR (400 MHz, DMSO-$d_6$) δ0.82-0.87 (6H, m), 2.02 (3H, s), 2.86 (2H, dd, J=7.2, 2.4 Hz), 3.07-3.20 (4H, m), 3.83 (1H, t, 7.2 Hz), 6.97 (2H, d, J=8.4 Hz), 7.33 (2H, d, J=8.4 Hz), 7.69-7.78 (3H, m), 8.07 (1H, d, J=8.0 Hz), 8.12 (1H, d, J=8.8 Hz), 8.21 (1H, d, J=8.0 Hz), 8.54 (1H, s), 9.81 (1H, s), 12.39 (1H, brs).

MS:496(M+H)$^+$.

Example 11

Synthesis of N,N-diethyl-2-[4-(isobutyrylamino)benzyl]-N'-(2-naphthylsulfonyl)malonamide In the same manner as in Example 9, the title compound (217 mg) was obtained as a white solid using hydrochloride salt (300 mg) of the compound obtained in Example 7 and isobutyryl chloride (77 μL).

$^1$H-NMR (400 MHz, DMSO-$d_6$) δ0.84-0.86 (6H, m), 1.10 (6H, d, J=7.2 Hz), 2.55 (1H, sept, J=7.2 Hz), 2.85-2.90 (2H, m), 3.08-3.17 (4H, m), 3.83 (1H, t, J=6.8 Hz), 6.98 (2H, d, J=8.4 Hz), 7.38 (2H, d, J=8.4 Hz), 7.68-7.78 (3H, m), 8.06 (1H, d, J=8.4 Hz), 8.11 (1H, d, J=8.8 Hz), 8.21 (1H, d, J=8.0 Hz), 8.55 (1H, s), 9.72 (1H, s), 12.26 (1H, brs).

MS: 524(M+H)$^+$.

Example 12

Synthesis of N,N-diethyl-N'-(2-naphthylsulfonyl)-2-[4-(pivaloylamino)benzyl]malonamide In the same manner as in Example 9, the title compound (307 mg) was obtained as a white solid using the compound (460 mg) obtained in Example 7 and trimethylacetyl chloride (128 μL).

$^1$H-NMR (400 MHz, DMSO-$d_6$) δ0.85 (6H, t, J=6.4 Hz), 1.22 (9H, s), 2.80-2.92 (2H, m), 3.10-3.30 (4H, m), 3.83 (1H, t, J=7.2 Hz), 6.99 (2H, d, J=8.4 Hz), 7.40 (2H, d, J=8.4 Hz), 7.69-7.78 (3H, m), 8.05 (1H, d, J=8.0 Hz), 8.11 (1H, d, J=8.4 Hz), 8.20 (1H, d, J=8.0 Hz), 8.54 (1H, s), 9.07 (1H, s), 12.27 (1H, brs).

MS: 538(M+H)$^+$.

Example 13

Synthesis of N,N-diethyl-N'-(2-naphthylsulfonyl)-2-[4-(propioloylamino)benzyl]malonamide To a solution of hydrochloride salt (240 mg) of the compound obtained in Example 7 in DMF (5 mL) were added WSCI.HCl (115 mg), 4-dimethylaminopyridine (120 mg) and propiolic acid (36 μL) at room temperature, and the mixture was stirred for 16 hr. The mixture was adjusted to pH=1-2 by the addition of dilute hydrochloric acid (30 mL) and extracted with ethyl acetate (50 mL×2). The organic layer was washed with saturated brine, concentrated under reduced pressure, and the residue was purified by silica gel column chromatography to give the title compound (46 mg) as a pale-yellow solid.

$^1$H-NMR (300 MHz, DMSO-$d_6$) δ0.81-0.87 (6H, m), 2.85-2.90 (2H, m), 3.08-3.18 (4H, m), 3.84 (1H, t, J=7.2 Hz), 4.41 (1H, s), 6.99 (2H, d, J=7.8 Hz), 7.34 (2H, d, J=7.8 Hz), 7.68-7.79 (3H, m), 8.06-8.12 (2H, m), 8.21 (1H, d, J=8.0 Hz), 8.54 (1H, s), 10.70 (1H, s), 12.30 (1H, brs).

MS: 506(M+H)$^+$.

Example 14

Synthesis of 2-{4-[(2-butynoyl)amino]benzyl}-N,N-diethyl-N'-(2-naphthylsulfonyl)malonamide In the same manner as in Example 13, the reaction mixture was obtained using hydrochloride salt (300 mg) of the compound obtained in Example 7 and 2-butynoic acid (57 mg). Dilute hydrochloric acid was added, and the precipitate was collected by filtration to give the title compound (170 mg) as a white solid.

$^1$H-NMR (300 MHz, DMSO-$d_6$) δ0.81-0.86 (6H, m), 1.88 (3H, s), 2.82-2.85 (2H, m), 3.08-3.18 (4H, m), 3.80 (1H, t, J=7.2 Hz), 6.95 (2H, d, J=8.4 Hz), 7.32 (2H, d, J=8.4 Hz), 7.67-7.76 (3H, m), 8.04 (1H, d, J=7.8 Hz), 8.09 (1H, d, J=8.7 Hz), 8.18 (1H, d, J=7.8 Hz), 8.52 (1H, s), 10.48 (1H, s), 12.31 (1H, brs).

MS: 520 (M+H)$^+$.

Example 15

Synthesis of 2-[4-(cyclopropylcarbonylamino)benzyl]-N,N-diethyl-N'-(2-naphthylsulfonyl)malonamide In the same manner as in Example 9, the title compound (81 mg) was obtained as a white solid using the compound (337 mg) obtained in Example 7 and cyclopropanecarbonyl chloride (67 μL).

$^1$H-NMR (400 MHz, DMSO-$d_6$) δ0.72-0.95 (10H, m), 1.67-1.80 (1H, m), 2.79-2.95 (2H, m), 3.03-3.25 (4H, m), 3.82 (1H, t, J=7.2 Hz), 6.97 (2H, d, J=8.4 Hz), 7.34 (2H, d, J=8.4 Hz), 7.66-7.82 (3H, m), 8.05 (1H, d, J=8.4 Hz), 8.10 (1H, d, J=8.4 Hz), 8.19 (1H, d, J=8.4 Hz), 8.53 (1H, s), 10.03 (1H, s), 12.28 (1H, brs).

MS: 522(M+H)$^+$.

Example 16

Synthesis of N,N-diethyl-2-{4-[(1-methylcyclopropyl)carbonylamino]benzyl}-N'-(2-naphthylsulfonyl)malonamide In the same manner as in Example 13, the title compound (366 mg) was obtained as a white solid using hydrochloride salt (430 mg) of the compound obtained in Example 7 and 1-methylcyclopropane-1-carboxylic acid (88 mg).

$^1$H-NMR (400 MHz, DMSO-$d_6$) δ0.58-0.68 (2H, m), 0.74-0.95 (6H, m), 1.02-1.13 (2H, m), 1.40 (3H, s), 2.54 (2H, s), 2.78-2.93 (2H, m), 3.01-3.23 (4H, m), 3.83 (1H, t, J=7.2 Hz), 6.97 (2H, d, J=8.4 Hz), 7.37 (2H, d, J=8.4 Hz), 7.62-7.82 (3H, m), 8.06 (1H, d, J=8.4 Hz), 8.11 (1H, d, J=8.4 Hz), 8.20 (1H, d, J=8.4 Hz), 8.54 (1H, s), 9.03 (1H, s), 12.30 (1H, brs).

MS: 536(M+H)$^+$.

Example 17

Synthesis of 2-{4-[(1-tert-butyloxycarbonyl-4-piperidinylcarbonyl)amino]benzyl}-N,N-diethyl-N'-(2-naphthylsulfonyl)malonamide In the same manner as in Example 1 (4), the reaction mixture was obtained using hydrochloride salt (430 mg) of the compound obtained in Example 7, N-tert-butyloxycarbonylisonipecotic acid (200 mg) and N-methylmorpholine (190 µL). Dilute hydrochloric acid was added, and the precipitate was collected by filtration to give the title compound (410 mg) as a white solid.

$^1$H-NMR (400 MHz, DMSO-$d_5$) δ0.82-0.86 (6H, m), 1.41 (9H, s), 1.41-1.52 (2H, m), 1.72-1.76 (2H, m), 2.67-2.89 (4H, m), 3.06-3.32 (5H, m), 3.72-3.78 (1H, m), 3.94-4.00 (2H, m), 6.98 (2H, d, J=8.8 Hz), 7.37 (2H, d, J=8.8 Hz), 7.67-7.76 (3H, m), 8.02-8.16 (3H, m), 8.49 (1H, brs), 9.80 (1H, s), 12.32 (1H, brs).

Example 18

Synthesis of N,N-diethyl-N'-(2-naphthylsulfonyl)-2-{4-[(4-piperidinylcarbonyl)amino]benzyl}malonamide trifluoroacetic acid salt To a solution of the compound (250 mg) obtained in Example 17 in methylene chloride (10 mL) was added trifluoroacetic acid (3 mL) at room temperature, and the mixture was stirred for 16 hr. After concentration under reduced pressure, an ether/chloroform mixture was added, and the precipitate was collected by filtration to give the title compound (247 mg) as a white solid.

$^1$H-NMR (400 MHz, DMSO-$d_6$) δ0.81-0.87 (6H, m), 1.75-1.97 (4H, m), 2.57-2.63 (1H, m), 2.78-3.28 (10H, m), 3.82 (1H, t, J=7.2 Hz), 7.01 (2H, d, J=8.4 Hz), 7.37 (2H, d, J=8.4 Hz), 7.68-7.77 (3H, m), 8.05 (1H, d, J=8.0 Hz), 8.10 (1H, d, J=8.4 Hz), 8.20 (1H, d, J=8.0 Hz), 8.26-8.33 (1H, brs), 8.54 (1H, s), 8.54-8.58 (1H, brs), 9.93 (1H, s), 12.34 (1H, brs).

MS: 565(M+H)$^+$.

Example 19

Synthesis of N,N-diethyl-2-{4-[(2-fluorobenzoyl)amino]benzyl}-N'-(2-naphthylsulfonyl)malonamide In the same manner as in Example 9, the title compound (204 mg) was obtained as a white solid using the compound (332 mg) obtained in Example 7 and 2-fluorobenzoyl chloride (87 µL).

$^1$H-NMR (400 MHz, DMSO-$d_6$) δ0.87 (6H, t, J=7.2 Hz), 2.83-2.98 (2H, m), 3.05-3.28 (4H, m), 3.86 (1H, t, J=7.2 Hz), 7.04 (2H, d, J=8.4 Hz), 7.28-7.40 (2H, m), 7.49 (2H, d, J=8.4 Hz), 7.53-7.80 (5H, m), 8.06 (1H, d, J=8.4 Hz), 8.12 (1H, d, J=8.4 Hz), 8.21 (1H, d, J=8.4 Hz), 8.56 (1H, s), 10.29 (1H, s), 12.27 (1H, brs).

MS: 576(M+H)$^+$.

Example 20

Synthesis of N,N-diethyl-2-{4-[(4-fluorobenzoyl)amino]benzyl}-N'-(2-naphthylsulfonyl)malonamide In the same manner as in Example 9, the title compound (261 mg) was obtained as a white solid using hydrochloride salt (300 mg) of the compound obtained in Example 7 and 4-fluorobenzoyl chloride (87 µL).

$^1$H-NMR (400 MHz, DMSO-$d_6$) δ0.86 (6H, t, J=6.8 Hz), 2.85-2.92 (2H, m), 3.09-3.35 (4H, m), 3.87 (1H, t, J=7.2 Hz), 7.04 (2H, d, J=8.4 Hz), 7.36-7.40 (2H, m), 7.52 (2H, d, J=8.4 Hz), 7.66-7.79 (3H, m), 8.02-8.06 (3H, m), 8.13 (1H, d, J=8.8 Hz), 8.21 (1H, d, J=8.0 Hz), 8.55 (1H, s), 10.16 (1H, s), 12.28 (1H, brs).

MS: 576(M+H)$^+$.

Example 21

Synthesis of N,N-diethyl-2-{4-[(3-fluorobenzoyl)amino]benzyl}-N'-(2-naphthylsulfonyl)malonamide In the same manner as in Example 9, the title compound (192 mg) was obtained as a white solid using hydrochloride salt (196 mg) of the compound obtained in Example 7 and 3-fluorobenzoyl chloride (48 µL).

$^1$H-NMR (400 MHz, DMSO-$d_6$) δ0.86 (6H, t, J=6.8 Hz), 2.82-2.96 (2H, m), 3.04-3.23 (4H, m), 3.87 (1H, t, J=7.2 Hz), 7.06 (2H, d, J=8.4 Hz), 7.40-7.49 (1H, m), 7.53 (2H, d, J=8.4 Hz), 7.57-7.86 (6H, m), 8.06 (1H, d, J=8.0 Hz), 8.13 (1H, d, J=8.4 Hz), 8.20 (1H, d, J=8.4 Hz), 8.55 (1H, s), 10.19 (1H, s).

MS: 576(M+H)$^+$.

Example 22

Synthesis of N,N-diethyl-2-{4-[(2,6-difluorobenzoyl)amino]benzyl}-N'-(2-naphthylsulfonyl)malonamide In the same manner as in Example 9, the title compound (184 mg) was obtained as a white solid using hydrochloride salt (207 mg) of the compound obtained in Example 7 and 2,6-difluorobenzoyl chloride (53 µL).

$^1$H-NMR (400 MHz, DMSO-$d_6$) δ0.87 (6H, t, J=6.8 Hz), 2.80-2.98 (2H, m), 3.04-3.23 (4H, m), 3.85 (1H, t, J=7.2 Hz), 7.06 (2H, d, J=8.4 Hz), 7.25 (2H, t, J=8.0 Hz), 7.46 (2H, d, J=8.4 Hz), 7.51-7.80 (4H, m), 8.06 (1H, d, J=8.0 Hz), 8.11 (1H, d, J=8.8 Hz), 8.21 (1H, d, J=8.0 Hz), 8.56 (1H, s), 10.69 (1H, s).

MS: 594(M+H)$^+$.

Example 23

Synthesis of N,N-diethyl-2-{4-[(2,4-difluorobenzoyl)amino]benzyl}-N'-(2-naphthylsulfonyl)malonamide In the same manner as in Example 13, the title compound (269 mg) was obtained as a white solid using hydrochloride salt (257 mg) of the compound obtained in Example 7 and 2,4-difluorobenzoic acid (83 mg).

$^1$H-NMR (400 MHz, DMSO-$d_6$) δ0.78-0.92 (6H, m), 2.81-2.97 (2H, m), 3.04-3.23 (4H, m), 3.72 (1H, m), 7.05 (2H, d, J=8.4 Hz), 7.22 (214 t, J=8.4 Hz), 7.41 (1H, t, J=8.4 Hz), 7.48 (1H, d, J=8.4 Hz), 7.60-7.7.83 (4H, m), 8.03 (2H, t, J=8.4 Hz), 8.13 (1H, d, J=8.0 Hz), 8.45 (1H, brs), 10.27 (1H, s).

MS: 594(M+H)$^+$.

Example 24

Synthesis of N,N-diethyl-2-{4-[(2-fluoro-4-methylbenzoyl)amino]benzyl}-N'-(2-naphthylsulfonyl)malonamide In the same manner as in Example 13, the title compound (193 mg) was obtained as a white solid using hydrochloride salt (252 mg) of the compound obtained in Example 7 and 2-fluoro-4-methylbenzoic acid (88 mg).

$^1$H-NMR (400 MHz, DMSO-$d_6$) δ0.86 (6H, t, J=7.2 Hz), 2.39 (3H, s), 2.83-3.00 (2H, m), 3.07-3.25 (4H, m), 3.86 (1H, t, J=7.2 Hz), 7.03 (2H, d, J=8.0 Hz), 7.11-7.22 (2H, m), 7.48 (2H, d, J=8.0 Hz), 7.56 (1H, t, J=8.0 Hz), 7.66-7.82 (3H, m), 8.06 (1H, d, J=8.0 Hz), 8.12 (1H, d, J=8.8 Hz), 8.20 (1H, d, J=8.0 Hz), 8.55 (1H, s), 10.16 (1H, s), 12.33 (1H, brs).
MS: 590(M+H)$^+$.

Example 25

Synthesis of N,N-diethyl-2-{4-[(2-methoxybenzoyl)amino]benzyl}-N'-(2-naphthylsulfonyl)malonamide In the same manner as in Example 9, the title compound (178 mg) was obtained as a white solid using the compound (505 mg) obtained in Example 7 and 2-methoxybenzoyl chloride (200 μL).
$^1$H-NMR (400 MHz, DMSO-d$_6$) δ0.86 (6H, t, J=7.0 Hz), 2.89 (2H, d, J=7.0 Hz), 3.08-3.23 (4H, m), 3.86 (1H, t, J=7.0 Hz), 3.91 (3H, s), 7.02 (2H, d, J=8.4 Hz), 7.08 (1H, t, J=7.4 Hz), 7.19 (1H, d, J=8.4 Hz), 7.47-7.55 (3H, m), 7.62-7.80 (4H, m), 8.06 (1H, d, J=8.1 Hz), 8.13 (1H, d, J=8.8 Hz), 8.21 (1H, d, J=8.1 Hz), 8.55 (1H, s), 10.01 (1H, s), 12.36 (1H, brs).
MS: 588(M+H)$^+$.

Example 26

Synthesis of N,N-diethyl-2-{4-[(4-methoxybenzoyl)amino]benzyl}-N'-(2-naphthylsulfonyl)malonamide In the same manner as in Example 9, the title compound (485 mg) was obtained as a white solid using the compound (488 mg) obtained in Example 7 and 4-methoxybenzoyl chloride (145 μL).
$^1$H-NMR (300 MHz, DMSO-d$_6$) δ0.86 (6H, t, J=7.0 Hz), 2.89 (2H, d, J=6.9 Hz), 3.03-3.23 (4H, m), 3.79-3.95 (4H, m), 7.03 (2H, d, J=8.7 Hz), 7.06 (2H, d, J=8.7 Hz), 7.53 (2H, d, J=8.7 Hz), 7.62-7.80 (3H, m), 7.96 (2H, d, J=8.7 Hz), 8.05 (1H, d, J=8.1 Hz), 8.13 (1H, d, J=8.1 Hz), 8.21 (1H, d, J=8.1 Hz), 8.55 (1H, s), 9.99 (1H, s), 13.26 (1H, brs).
MS: 588(M+H)$^+$.

Example 27

Synthesis of N,N-diethyl-2-{4-[(3-methoxybenzoyl)amino]benzyl}-N'-(2-naphthylsulfonyl)malonamide In the same manner as in Example 9, the title compound (199 mg) was obtained as a white solid using the compound (453 mg) obtained in Example 7 and 3-methoxybenzoyl chloride (135 μL).
$^1$H-NMR (400 MHz, DMSO-d$_6$) δ0.86 (3H, t, J=7.2 Hz), 0.86 (3H, t, J=6.8 Hz), 2.86-2.97 (2H, m), 3.07-3.24 (4H, m), 3.84 (3H, s), 3.87 (1H, t, J=7.2 Hz), 7.04 (2H, d, J=8.4 Hz), 7.16 (1H, dd, J=8.4, 2.0 Hz), 7.42-7.57 (5H, m), 7.64-7.81 (3H, m), 8.05 (1H, d, J=8.4 Hz), 8.13 (1H, d, J=8.4 Hz), 8.21 (1H, d, J=8.2 Hz), 8.56 (1H, s), 10.13 (1H, s), 12.36 (brs).
MS: 588(M+H)$^+$.

Example 28

Synthesis of N,N-diethyl-2-{4-[(2,6-dimethoxybenzoyl)amino]benzyl}-N'-(2-naphthylsulfonyl)malonamide In the same manner as in Example 9, the title compound (463 mg) was obtained as a white solid using the compound (520 mg) obtained in Example 7 and 2,6-dimethoxybenzoyl chloride (241 mg).
$^1$H-NMR (400 MHz, DMSO-d$_6$) δ0.76-0.90 (6H, m), 2.80-2.97 (2H, m), 3.04-3.25 (4H, m), 3.76 (6H, s), 3.85 (1H, d, J=7.2 Hz), 6.74 (2H, d, J=8.8 Hz), 6.99 (2H, d, J=8.4 Hz), 7.36 (1H, t, J=8.4 Hz), 7.50 (2H, d, J=8.4 Hz), 7.66-7.84 (3H, m), 8.06 (1H, d, J=8.0 Hz), 8.13 (1H, d, J=8.8 Hz), 8.22 (1H, d, J=8.0 Hz), 8.55 (1H, s), 10.14 (1H, s).
MS: 618(M+H)$^+$.

Example 29

Synthesis of N,N-diethyl-2-{4-[(2-hydroxybenzoyl)amino]benzyl}-N'-(2-naphthylsulfonyl)malonamide In the same manner as in Example 1 (4), a crude product was obtained using hydrochloride salt (357 mg) of the compound obtained in Example 7, 2-hydroxybenzoic acid (120 mg) and triethylamine (120 μL). This was purified by silica gel column chromatography to give the title compound (198 mg) as a white solid.
$^1$H-NMR (400 MHz, DMSO-d$_6$) δ0.86 (6H, t, J=7.0 Hz), 2.89-2.92 (2H, m), 3.12-3.21 (4H, m), 6.96-7.00 (4H, m), 7.41-7.47 (3H, m), 7.65-7.79 (3H, m), 7.97 (1H, dd, J=7.9, 1.3 Hz), 8.05 (1H, d, J=8.2 Hz), 8.12 (1H, d, J=8.7 Hz), 8.20 (1H, d, J=8.2 Hz), 8.54 (1H, d, J=1.0 Hz), 10.26 (1H, s), 11.85 (1H, s), 12.32 (1H, brs).
MS: 574(M+H)$^+$.

Example 30

Synthesis of N,N-diethyl-2-{4-[(3-methyl-2-hydroxybenzoyl)amino]benzyl}-N'-(2-naphthylsulfonyl)malonamide In the same manner as in Example 1 (4), a crude product was obtained using the compound (530 mg) obtained in Example 7 and 3-methyl-2-hydroxybenzoic acid (150 mg). This was purified by silica gel column chromatography to give the title compound (467 mg) as a white solid.
$^1$H-NMR (300 MHz, DMSO-d$_6$) δ0.87 (6H, t, J=6.9 Hz), 2.21 (3H, s), 2.92 (2H, d, J=7.8 Hz), 3.12-3.20 (4H, m), 3.87 (1H, t, J=7.8 Hz), 6.88 (1H, t, J=7.8 Hz), 7.06 (2H, d, J=8.4 Hz), 7.37-7.43 (3H, m), 7.65-7.92 (4H, m), 8.05 (1H, d, J=8.0 Hz), 8.13 (1H, d, J=8.7 Hz), 8.20 (1H, d, J=8.0 Hz), 8.54 (1H, d, J=0.9 Hz), 10.29 (1H, s), 12.28 (1H, brs), 12.63 (1H, s).
MS: 588(M+H)$^+$.

Example 31

Synthesis of N,N-diethyl-2-{4-[(2-methylbenzoyl)amino]benzyl}-N'-(2-naphthylsulfonyl)malonamide In the same manner as in Example 9, the title compound (534 mg) was obtained as a white solid using the compound (525 mg) obtained in Example 7 and 2-methylbenzoyl chloride (159 μL).
$^1$H-NMR (400 MHz, DMSO-d$_6$) δ0.86 (6H, t, J=7.2 Hz), 2.35 (3H, s), 2.89 (2H, d, J=6.8 Hz), 3.01-3.25 (4H, m), 3.85 (1H, d, J=6.8 Hz), 7.02 (2H, d, J=8.4 Hz), 7.31 (2H, d, J=7.6 Hz), 7.30-7.48 (2H, m), 7.44 (2H, d, J=7.6 Hz), 7.63-7.70 (1H, m), 7.76 (2H, d, J=7.2 Hz), 8.06 (1H, d, J=8.0 Hz), 8.13 (1H, d, J=8.0 Hz), 8.24 (1H, d, J=8.0 Hz), 8.57 (1H, s), 10.20 (1H, s), 12.37 (1H, brs).
MS: 572(M+H)$^+$.

Example 32

Synthesis of N,N-diethyl-2-{4-[(4-methylbenzoyl)amino]benzyl}-N'-(2-naphthylsulfonyl)malonamide In the same manner as in Example 9, the title compound (525 mg) was obtained as a white solid using the compound (497 mg) obtained in Example 7 and 4-methylbenzoyl chloride (146 μL).

$^1$H-NMR (400 MHz, DMSO-$d_6$) δ 0.78-0.95 (6H, m), 2.39 (3H, s), 2.82-2.96 (2H, m), 3.05-3.28 (4H, m), 3.86 (1H, t, J=7.4 Hz), 7.03 (2H, d, J=8.4 Hz), 7.34 (2H, d, J=8.4 Hz), 7.53 (2H, d, J=8.4 Hz), 7.61-7.82 (3H, m), 7.87 (2H, d, J=8.4 Hz), 8.05 (1H, d, J=8.4 Hz), 8.13 (1H, d, J=8.4 Hz), 8.22 (1H, d, J=8.4 Hz), 8.55 (1H, s), 10.07 (1H, s), 12.36 (1H, brs).
MS: 572(M+H)$^+$.

Example 33

Synthesis of N,N-diethyl-2-{4-[(3-methylbenzoyl)amino]benzyl}-N'-(2-naphthylsulfonyl)malonamide In the same manner as in Example 9, the title compound (416 mg) was obtained as a white solid using the compound (454 mg) obtained in Example 7 and 3-methylbenzoyl chloride (131 μL).

$^1$H-NMR (400 MHz, DMSO-$d_6$) δ 0.86 (6H, t, J=7.0 Hz), 2.41 (3H, s), 2.90 (2H, dd, J=4.2, 2.7 Hz), 3.06-3.28 (4H, m), 3.86 (1H, t, J=7.0 Hz), 7.03 (2H, d, J=8.4 Hz), 7.38-7.46 (2H, m), 7.53 (2H, d, J=8.4 Hz), 7.68 (1H, t, J=7.4 Hz), 7.71-7.80 (4H, m), 8.05 (1H, d, J=8.1 Hz), 8.13 (1H, d, J=8.1 Hz), 8.21 (1H, d, J=8.1 Hz), 8.55 (1H, s), 10.11 (1H, s), 12.36 (1H, brs).
MS: 572(M+H)$^+$.

Example 34

Synthesis of N,N-diethyl-2-{4-[(2,6-dimethylbenzoyl)amino]benzyl}-N'-(2-naphthylsulfonyl)malonamide In the same manner as in Example 9, the title compound (141 mg) was obtained as a white solid using the compound (950 mg) obtained in Example 7 and 2,6-dimethylbenzoyl chloride (390 mg).

$^1$H-NMR (400 MHz, DMSO-$d_6$) δ 0.87 (6H, t, J=6.8 Hz), 2.27 (6H, s), 2.89 (2H, d, J=6.8 Hz), 3.08-3.22 (4H, m), 3.85 (1H, d, J=6.8 Hz), 7.02 (2H, d, J=8.4 Hz), 7.10 (2H, d, J=8.4 Hz), 7.22 (1H, q, J=7.6 Hz), 7.51 (2H, d, J=8.4 Hz), 7.63-7.81 (3H, m), 8.66 (1H, d, J=8.0 Hz), 8.13 (1H, d, J=8.0 Hz), 8.22 (1H, d, J=8.0 Hz), 8.58 (1H, s), 10.26 (1H, s), 12.34 (1H, brs).
MS: 586(M+H)$^+$.

Example 35

Synthesis of 2-{4-[(4-chlorobenzoyl)amino]benzyl}-N,N-diethyl-N'-(2-naphthylsulfonyl)malonamide In the same manner as in Example 9, the title compound (484 mg) was obtained as a white solid using the compound (450 mg) obtained in Example 7 and 4-chlorobenzoyl chloride (126 μL).

$^1$H-NMR (400 MHz, DMSO-$d_6$) δ 0.85 (3H, t, J=7.2 Hz), 0.86 (3H, t, J=7.2 Hz), 2.90 (2H, dd, J=7.0, 2.0 Hz), 3.05-3.24 (4H, m), 3.87 (1H, t, J=7.2 Hz), 7.04 (2H, d, J=8.5 Hz), 7.52 (2H, d, J=8.4 Hz), 7.62 (2H, d, J=8.5 Hz), 7.66-7.80 (3H, m), 7.98 (2H, d, J=8.5 Hz), 8.05 (1H, d, J=8.1 Hz), 8.13 (1H, d, J=8.8 Hz), 8.20 (1H, d, J=8.1 Hz), 8.55 (1H, s), 10.22 (1H, s), 12.37 (1H, brs).
MS: 592(M+H)$^+$.

Example 36

Synthesis of 2-{4-[(2-chlorobenzoyl)amino]benzyl}-N,N-diethyl-N'-(2-naphthylsulfonyl)malonamide In the same manner as in Example 9, the title compound (300 mg) was obtained as a white solid using the compound (501 mg) obtained in Example 7 and 2-chlorobenzoyl chloride (140 μL).

$^1$H-NMR (400 MHz, DMSO-$d_6$) δ 0.86 (6H, t, J=7.2 Hz), 2.84-2.95 (2H, m), 3.07-3.24 (4H, m), 3.85 (1H, t, J=7.2 Hz), 7.03 (2H, d, J=8.5 Hz), 7.44-7.54 (4H, m), 7.56-7.60 (2H, m), 7.68-7.79 (3H, m), 8.06 (1H, d, J=8.0 Hz), 8.13 (1H, d, J=8.0 Hz), 8.22 (1H, d, J=8.0 Hz), 8.57 (1H, d, J=1.0 Hz), 10.42 (1H, s), 12.33 (1H, brs).
MS: 592(M+H)$^+$.

Example 37

Synthesis of 2-{4-[(3-chlorobenzoyl)amino]benzyl}-N,N-diethyl-N'-(2-naphthylsulfonyl)malonamide In the same manner as in Example 9, the title compound (461 mg) was obtained as a white solid using the compound (503 mg) obtained in Example 7 and 3-chlorobenzoyl chloride (142 μL).

$^1$H-NMR (400 MHz, DMSO-$d_6$) δ 0.86 (6H, t, J=7.2 Hz), 2.91 (2H, dd, J=7.2, 2.5 Hz), 3.06-3.23 (4H, m), 3.86 (1H, t, J=7.2 Hz), 7.05 (2H, d, J=8.5 Hz), 7.52 (2H, d, J=8.4 Hz), 7.54-7.61 (1H, m), 7.65-7.76 (3H, m), 7.77 (1H, dd, J=8.6, 1.6 Hz), 7.91 (1H, d, J=7.8 Hz), 7.98-8.02 (1H, m), 8.05 (1H, d, J=8.2 Hz), 8.12 (1H, d, J=8.7 Hz), 8.19 (1H, d, J=8.0 Hz), 8.54 (1H, s), 10.22 (1H, s), 12.34 (1H, brs).
MS: 592(M+H)$^+$.

Example 38

Synthesis of 2-{4-[(3,4-dichlorobenzoyl)amino]benzyl}-N,N-diethyl-N'-(2-naphthylsulfonyl)malonamide In the same manner as in Example 9, the title compound (401 mg) was obtained as a white solid using the compound (503 mg) obtained in Example 7 and 3,4-dichlorobenzoyl chloride (243 mg).

$^1$H-NMR (400 MHz, DMSO-$d_6$) δ 0.86 (6H, t, J=7.2 Hz) 2.91 (2H, dd, J=7.0, 2.1 Hz), 3.05-3.26 (4H, m), 3.87 (1H, t, J=7.2 Hz), 7.05 (2H, d, J=8.4 Hz), 7.50 (2H, d, J=8.5 Hz), 7.65-7.76 (2H, m), 7.77 (1H, dd, 8.7, 1.7 Hz), 7.83 (1H, d, J=8.4 Hz), 7.94 (1H, dd, J=8.5, 2.2 Hz), 8.05 (1H, d, J=8.0 Hz), 8.12 (1H, d, J=8.8 Hz), 8.18-8.24 (2H, m), 8.54 (1H, s), 10.27 (1H, s), 12.31 (1H, brs).
MS: 626(M+H)$^+$.

Example 39

Synthesis of N,N-diethyl-2-{4-[(5-fluoro-2-methoxybenzoyl)amino]benzyl}-N'-(2-naphthylsulfonyl)malonamide In the same manner as in Example 1 (4), a crude product was obtained using the compound (530 mg) obtained in Example 7 and 5-fluoro-2-methoxybenzoic acid (298 mg). This was purified by silica gel column chromatography to give the title compound (398 mg) as a white solid.
$^1$H-NMR (400 MHz, DMSO-$d_6$) δ0.87 (6H, t, J=7.2 Hz), 2.41-2.95 (2H, m), 3.07-3.22 (4H, m), 3.85 (1H, t, J=7.2 Hz), 3.90 (3H, s), 7.03 (2H, d, J=7.2 Hz), 7.14-7.25 (1H, m), 7.30-7.40 (1H, m), 7.40-7.53 (3H, m), 7.62-7.80 (3H, m), 8.05 (1H, d, J=8.0 Hz), 8.12 (1H, d, J=8.0 Hz), 8.20 (1H, d, J=8.0 Hz), 8.55 (1H, s), 10.07 (1H, s), 12.30 (1H, brs).
MS: 606(M+H)$^+$.

Example 40

Synthesis of N,N-diethyl-N'-(2-naphthylsulfonyl)-2-{4-[(2-trifluoromethylbenzoyl)amino]benzyl}malonamide In the same manner as in Example 9, the title compound (322 mg) was obtained as a white solid using the compound (292 mg) obtained in Example 7 and 2-trifluoromethylbenzoyl chloride (94 μL).
$^1$H-NMR (400 MHz, DMSO-$d_6$) δ0.86 (3H, t, J=7.2 Hz), 0.86 (3H, t, J=7.2), 2.85-2.95 (2H, m), 3.05-3.24 (4H, m), 3.86 (1H, t, J=7.2 Hz), 7.04 (2H, d, J=8.4 Hz), 7.48 (2H, d, J=8.4 Hz), 7.60-7.92 (7H, m), 8.06 (1H, d, J=8.4 Hz), 8.12 (1H, d, J=8.4 Hz), 8.20 (1H, d, J=8.4 Hz), 8.57 (1H, s), 10.11 (1H, s).
MS: 626(M+H)$^+$.

Example 41

Synthesis of 2-{4-[(3-cyanobenzoyl)amino]benzyl}-N,N-diethyl-N'-(2-naphthylsulfonyl)malonamide In the same manner as in Example 13, the reaction mixture was obtained using hydrochloride salt (250 mg) of the compound obtained in Example 7 and 3-cyanobenzoic acid (80 mg). Dilute hydrochloric acid was added, and the mixture was extracted with ethyl acetate. The organic layer was concentrated under reduced pressure to give the title compound (249 mg) as a white solid.
$^1$H-NMR (400 MHz, DMSO-$d_6$) δ0.86 (6H, t, J=7.2 Hz), 2.81-2.95 (2H, m), 3.04-3.28 (4H, m), 3.84 (1H, t, J=7.2 Hz), 7.07 (2H, d, J=8.4 Hz), 7.53 (2H, d, J=8.4 Hz), 7.60-7.83 (4H, m), 7.98-8.15 (3H, m), 8.19 (1H, d, J=8.4 Hz), 8.25 (1H, d, J=8.4 Hz), 8.40 (1H, s), 8.52 (1H, s), 10.30 (1H, s), 12.35 (1H, brs).
MS: 583(M+H)$^+$.

Example 42

Synthesis of N,N-diethyl-N'-(2-naphthylsulfonyl)-2-{4-[(2-nitrobenzoyl)amino]benzyl}malonamide In the same manner as in Example 13, the reaction mixture was obtained using hydrochloride salt (2.01 g) of the compound obtained in Example 7 and 2-nitrobenzoic acid (695 mg). Dilute hydrochloric acid was added, and the mixture was extracted with ethyl acetate. The organic layer was concentrated under reduced pressure to give the title compound (1.20 g) as a white solid.
$^1$H-NMR (400 MHz, DMSO-$d_6$) δ0.86 (6H, t, J=7.2 Hz), 2.81-2.99 (2H, m), 3.05-3.27 (4H, m), 3.86 (1H, t, J=7.2 Hz), 7.04 (2H, d, J=8.4 Hz), 7.45 (2H, d, J=8.4 Hz), 7.67-7.92 (6H, m), 8.07 (1H, d, J=8.0 Hz), 8.13 (1H, d, J=8.4 Hz), 8.15 (1H, d, J=8.4 Hz), 8.22 (1H, d, J=8.4 Hz), 8.57 (1H, s), 10.57 (1H, s), 12.32 (1H, brs).
MS: 603(M+H)$^+$.

Example 43

Synthesis of 2-{4-[(2-aminobenzoyl)amino]benzyl}-N,N-diethyl-N'-(2-naphthylsulfonyl)malonamide To a mixture of the compound (538 mg) obtained in Example 42 in ethanol (10 mL)/ethyl acetate (10 mL) was added 10% palladium/carbon (100 mg), and the mixture was stirred under hydrogen atmosphere at room temperature for 11 hr. Insoluble material was removed by filtration, and the filtrate was concentrated under reduced pressure to give the title compound (456 mg) as a brown powder.
$^1$H-NMR (400 MHz, DMSO-$d_6$) δ0.87 (6H, t, J=7.2 Hz), 2.88-2.93 (2H, m), 3.05-3.23 (4H, m), 3.86 (1H, t, J=7.2 Hz), 6.57 (1H, t, J=7.2 Hz), 6.76 (1H, d, J=8.4 Hz), 7.00 (2H, d, J=8.4 Hz), 7.46 (1H, t, J=7.2 Hz), 7.47 (2H, d, J=8.4 Hz), 7.61 (1H, d, J=7.6 Hz), 7.65-7.88 (3H, m), 8.06 (1H, d, J=8.0 Hz), 8.13 (1H, d, J=8.8 Hz), 8.20 (1H, d, J=8.0 Hz), 8.55 (1H, s), 9.88 (1H, s).
MS: 573(M+H)$^+$.

Example 44

Synthesis of 2-{4-[(4-aminobenzoyl)amino]benzyl}-N,N-diethyl-N'-(2-naphthylsulfonyl)malonamide (1) N,N-diethyl-N'-(2-naphthylsulfonyl)-2-{4-[(4-nitrobenzoyl)amino]benzyl}malonamide In the same manner as in Example 13, the reaction mixture was obtained using hydrochloride salt (491 mg) of the compound obtained in Example 7 and 4-nitrobenzoic acid (197 mg). Dilute hydrochloric acid was added, and the mixture was extracted with ethyl acetate. The organic layer was concentrated under reduced pressure to give the title compound (462 mg) as a white solid.

(2) 2-{4-[(4-aminobenzoyl)amino]benzyl}-N,N-diethyl-N'-(2-naphthylsulfonyl)malonamide In the same manner as in Example 43, the title compound (284 mg) was obtained as a pale-yellow powder using the above-mentioned compound (462 mg).
$^1$H-NMR (400 MHz, DMSO-$d_6$) δ0.86 (3H, t, J=7.2 Hz), 0.86 (3H, t, J=7.2 Hz), 2.80-2.97 (2H, m), 3.05-3.25 (4H, m), 3.85 (1H, t, J=7.2 Hz), 6.60 (2H, d, J=8.0 Hz), 6.99 (2H, d, J=8.0 Hz), 7.52 (2H, d, J=8.0 Hz), 7.62-7.81 (5H, m), 8.05 (1H, d, J=8.0 Hz), 8.12 (1H, d, J=8.4 Hz), 8.20 (1H, d, J=8.0 Hz), 8.54 (1H, s), 9.64 (1H, s).
MS: 573(M+H)$^+$.

Example 45

Synthesis of 2-{4-[(3-aminobenzoyl)amino]benzyl}-N,N-diethyl-N'-(2-naphthylsulfonyl)malonamide (1) N,N-diethyl-N'-(2-naphthylsulfonyl)-2-{4-[(3-nitrobenzoyl)amino]benzyl}malonamide In the same manner as in Example 13, the reaction mixture was obtained using hydrochloride salt (500 mg) of the compound obtained in Example 7 and 3-nitrobenzoic acid (195 mg). Dilute hydrochloric acid was added, and the mixture was extracted with ethyl acetate. The organic layer was concentrated under reduced pressure to give the title compound (444 mg) as a white solid.

(2) 2-{4-[(3-aminobenzoyl)amino]benzyl}-N,N-diethyl-N'-(2-naphthylsulfonyl)malonamide In the same manner as in Example 43, a crude product was obtained using the above-mentioned compound (444 mg). This was purified by silica gel column chromatography to give the title compound (293 mg) as a pale-yellow powder.

$^1$H-NMR (400 MHz, DMSO-d$_6$) δ0.86 (6H, t, J=7.2), 2.83-2.97 (2H, m), 3.04-3.25 (4H, m), 3.86 (1H, t, J=7.2 Hz), 6.75 (1H, d, J=8.0 Hz), 7.01 (2H, d, J=8.4 Hz), 7.04-7.21 (3H, m), 7.54 (2H, d, J=8.4 Hz), 7.62-7.78 (3H, m), 8.05 (2H, d, J=8.4 Hz), 8.12 (1H, d, J=8.8 Hz), 8.20 (1H, d, J=8.4 Hz), 8.54 (1H, s), 9.95 (1H, s).
MS: 573(M+H)$^+$.

Example 46

Synthesis of 2-{4-[(2-amino-3-methylbenzoyl)amino]benzyl}-N,N-diethyl-N'-(2-naphthylsulfonyl)malonamide In the same manner as in Example 13, the reaction mixture was obtained using hydrochloride salt (187 mg) of the compound obtained in Example 7 and 3-methylanthranilic acid (61 mg). Dilute hydrochloric acid was added, and the mixture was extracted with ethyl acetate. The organic layer was concentrated under reduced pressure to give the title compound (77 mg) as a white solid.

$^1$H-NMR (400 MHz, DMSO-d$_6$) δ0.81-0.90 (6H, m), 2.12 (3H, s), 2.83-2.95 (2H, m), 3.05-3.21 (4H, m), 3.81-3.89 (1H, m), 6.10 (2H, brs), 6.52-6.58 (1H, m), 7.01 (2H, d, J=8.2 Hz), 7.08-7.14 (1H, m), 7.46-7.50 (3H, m), 7.64-7.78 (3H, m), 8.05 (1H, d, J=8.1 Hz), 8.13 (1H, d, J=8.7 Hz), 8.21 (1H, d, J=8.1 Hz), 8.54 (1H, s), 9.89 (1H, s), 12.24 (1H, brs).
MS:587(M+H)$^+$.

Example 47

Synthesis of 2-{4-[(2-amino-5-chlorobenzoyl)amino]benzyl}-N,N-diethyl-N'-(2-naphthylsulfonyl)malonamide In the same manner as in Example 13, the title compound (45 mg) was obtained as a white solid using hydrochloride salt (187 mg) of the compound obtained in Example 7 and 5-chloroanthranilic acid (69 mg).

$^1$H-NMR (400 MHz, DMSO-d$_6$) δ0.87 (6H, t, d=7.0 Hz), 2.90 (2H, d, J=7.0 Hz), 3.06-3.22 (4H, m), 3.82-3.87 (1H, m), 6.45 (2H, brs), 6.78 (1H, d, J=8.8 Hz), 7.02 (2H, d, J=8.4 Hz), 7.21-7.24 (1H, m), 7.44 (2H, d, J=8.4 Hz), 7.66-7.79 (4H, m), 8.05 (1H, d, J=8.0 Hz), 8.12 (1H, d, J=8.7 Hz), 8.20 (1H, d, J=8.0 Hz), 8.54 (1H, s), 9.97 (1H, s), 12.22 (1H, brs).
MS: 607(M+H)$^+$.

Example 48

Synthesis of 2-{4-[(2-amino-5-fluorobenzoyl)amino]benzyl}-N,N-diethyl-N'-(2-naphthylsulfonyl)malonamide In the same manner as in Example 13, the title compound (51 mg) was obtained as a white solid using hydrochloride salt (187 mg) of the compound obtained in Example 7 and 5-fluoroanthranilic acid (63 mg).

$^1$H-NMR (400 MHz, DMSO-d$_6$) δ0.87 (6H, t, J=7.0 Hz), 2.85-2.92 (2H, m), 3.07-3.25 (4H, m), 3.85 (1H, t, J=7.1 Hz), 6.21 (2H, brs), 6.77 (1H, dd, J=8.9H, 5.0 Hz), 7.02 (2H, d, J=8.4 Hz), 7.09-7.14 (1H, m), 7.44-7.50 (3H, m), 7.68-7.79 (3H, m), 8.05 (1H, d, J=8.0 Hz), 8.13 (1H, d, J=8.7 Hz), 8.20 (1H, d, J=8.0 Hz), 8.55 (1H, s), 9.91 (1H, s), 12.21 (1H, brs).
MS: 591(M+H)$^+$.

Example 49

Synthesis of 2-{4-[(2-amino-3-chlorobenzoyl)amino]benzyl}-N,N-diethyl-N'-(2-naphthylsulfonyl)malonamide In the same manner as in Example 13, the reaction mixture was obtained using hydrochloride salt (187 mg) of the compound obtained in Example 7 and 3-chloroanthranilic acid (69 mg). Dilute hydrochloric acid was added, and the mixture was extracted with ethyl acetate. The organic layer was concentrated under reduced pressure to give the title compound (182 mg) as a white solid.

$^1$H-NMR (400 MHz, DMSO-d$_6$) δ0.80-0.91 (6H, m), 2.90 (2H, d, J=7.4 Hz), 3.09-3.28 (4H, m), 3.79-3.88 (1H, m), 6.39 (2H, brs), 6.68 (1H, t, J=7.8 Hz), 7.02 (2H, d, J=8.4 Hz), 7.44-7.47 (3H, m), 7.58-7.80 (4H, m), 8.05 (1H, d, J=8.0 Hz), 8.11 (1H, d, J=8.7 Hz), 8.19 (1H, d, J=8.0 Hz), 8.53 (1H, s), 10.07 (1H, s), 12.27 (1H, brs).
MS: 607(M+H)$^+$.

Example 50

Synthesis of 2-{4-[(2-amino-5-methylbenzoyl)amino]benzyl}-N,N-diethyl-N'-(2-naphthylsulfonyl)malonamide In the same manner as in Example 13, the title compound (74 mg) was obtained as a white solid using hydrochloride salt (300 mg) of the compound obtained in Example 7 and 5-methylanthranilic acid (111 mg).

$^1$H-NMR (400 MHz, DMSO-d$_6$) δ0.87 (6H, t, J=7.0 Hz), 2.22 (3H, s), 2.85-2.94 (2H, m), 3.07-3.28 (4H, m), 3.81-3.89 (1H, m), 6.08 (2H, brs), 6.68 (2H, d, J=8.4 Hz), 6.98-7.08 (3H, m), 7.42 (1H, s), 7.46 (2H, d, J=8.4 Hz), 7.64-7.80 (3H, m), 8.05 (1H, d, J=8.0 Hz), 8.13 (1H, d, J=8.8 Hz), 8.20 (1H, d, J=8.0 Hz), 8.54 (1H, s), 9.85 (1H, s), 12.23 (1H, brs).
MS: 587(M+H)$^+$.

Example 51

Synthesis of 2-{4-[(2-amino-4-chlorobenzoyl)amino]benzyl}-N,N-diethyl-N'-(2-naphthylsulfonyl)malonamide In the same manner as in Example 13, the title compound (86 mg) was obtained as a white solid using hydrochloride salt (300 mg) of the compound obtained in Example 7 and 4-chloroanthranilic acid (126 mg).

$^1$H-NMR (400 MHz, DMSO-d$_6$) δ0.80-0.91 (6H, m), 2.85-2.92 (2H, m), 3.07-3.25 (4H, m), 3.79-3.87 (1H, m), 6.56-6.64 (1H, m), 6.60 (2H, brs), 6.82 (1H, d, J=1.8 Hz), 7.01 (2H, d, J=8.5 Hz), 7.44 (2H, d, J=8.5 Hz), 7.62-7.79 (4H, m), 8.05 (1H, d, J=8.0 Hz), 8.12 (1H, d, J=8.2 Hz), 8.20 (1H, d, J=8.0 Hz), 8.53 (1H, s), 9.92 (1H, s), 12.30 (1H, brs).
MS: 607(M+H)$^+$.

Example 52

Synthesis of 2-{4-[(2-amino-4-fluorobenzoyl)amino]benzyl}-N,N-diethyl-N'-(2-naphthylsulfonyl)malonamide In the same manner as in Example 13, the title compound (87 mg) was obtained as a white solid using hydrochloride salt (300 mg) of the compound obtained in Example 7 and 4-fluoroanthranilic acid (114 mg).

$^1$H-NMR (400 MHz, DMSO-$d_6$) δ0.88 (6H, t, J=7.0 Hz), 2.85-2.92 (2H, m), 3.05-3.24 (4H, m), 3.84 (1H, t, J=6.9 Hz), 6.40 (1H, td, J=8.9, 2.4 Hz), 6.52 (1H, dd, J=11.8, 2.4 Hz), 6.67 (2H, brs), 7.01 (2H, d, J=8.4 Hz), 7.44 (2H, d, J=8.4 Hz), 7.65-7.80 (3H, m), 8.05 (1H, d, J=8.0 Hz), 8.12 (1H, d, J=8.7 Hz), 8.20 (1H, d, J=8.0 Hz), 8.54 (1H, s), 9.86 (1H, s), 12.29 (1H, brs).

MS: 591(M+H)$^+$.

Example 53

Synthesis of 2-{4-[(2-amino-3,5-dichlorobenzoyl)amino]benzyl}-N,N-diethyl-N'-(2-naphthylsulfonyl)malonamide In the same manner as in Example 13, the reaction mixture was obtained using hydrochloride salt (300 mg) of the compound obtained in Example 7 and 3,5-dichloroanthranilic acid (151 mg). Dilute hydrochloric acid was added, and the mixture was extracted with ethyl acetate. The organic layer was concentrated under reduced pressure to give the title compound (141 mg) as a white solid.

$^1$H-NMR (400 MHz, DMSO-$d_6$) δ0.87 (6H, t, J=7.0 Hz), 2.90 (2H, d, J=7.1 Hz), 3.07-3.25 (4H, m), 3.85 (1H, t, J=7.1 Hz), 6.51 (2H, brs), 7.03 (2H, d, J=8.4 Hz), 7.43 (2H, d, J=8.4 Hz), 7.58 (1H, d, J=2.2 Hz), 7.68-7.80 (4H, m), 8.05 (1H, d, J=8.0 Hz), 8.12 (1H, d, J=8.7 Hz), 8.20 (1H, d, J=8.0 Hz), 8.54 (1H, s), 10.16 (1H, s), 12.32 (1H, brs).

MS: 641(M+H)$^+$.

Example 54

Synthesis of 2-{4-[(2-amino-4,5-difluorobenzoyl)amino]benzyl}-N,N-diethyl-N'-(2-naphthylsulfonyl)malonamide In the same manner as in Example 13, the title compound (79 mg) was obtained as a white solid using hydrochloride salt (300 mg) of the compound obtained in Example 7 and 4,5-difluoroanthranilic acid (127 mg).

$^1$H-NMR (400 MHz, DMSO-$d_6$) δ0.86 (6H, t, J=7.0 Hz), 2.85-2.93 (2H, m), 3.07-3.24 (4H, m), 3.81-3.89 (1H, m), 6.55 (2H, brs), 6.72 (1H, dd, J=13.2, 7.3 Hz), 7.02 (2H, d, J=8.4 Hz), 7.43 (2H, d, J=8.4 Hz), 7.63-7.80 (4H, m), 8.05 (1H, d, J=8.0 Hz), 8.12 (1H, d, J=8.8 Hz), 8.20 (1H, d, J=8.0 Hz), 8.54 (1H, s), 9.86 (1H, s), 12.32 (1H, brs).

MS: 609(M+H)$^+$.

Example 55

Synthesis of 2-{4-[(2-amino-6-fluorobenzoyl)amino]benzyl}-N,N-diethyl-N'-(2-naphthylsulfonyl)malonamide In the same manner as in Example 13, the title compound (94 mg) was obtained as a white solid using hydrochloride salt (338 mg) of the compound obtained in Example 7 and 6-fluoroanthranilic acid (120 mg).

$^1$H-NMR (400 MHz, DMSO-$d_6$) δ0.87 (6H, t, J=6.9 Hz), 2.85-2.94 (2H, m), 3.05-3.24 (4H, m), 3.85 (1H, t, J=7.0 Hz), 5.76 (2H, brs), 6.40 (1H, t, J=9.0 Hz), 6.57 (1H, d, J=8.2 Hz), 7.02 (2H, d, J=8.2 Hz), 7.08-7.16 (1H, m), 7.49 (2H, d, J=8.2 Hz), 7.64-7.80 (3H, m), 8.06 (1H, d, J=8.0 Hz), 8.12 (1H, d, J=8.7 Hz), 8.20 (1H, d, J=8.0 Hz), 8.55 (1H, s), 10.16 (1H, s), 12.03 (1H, brs).

MS: 591(M+H)$^+$.

Example 56

Synthesis of N,N-diethyl-2-{4-[(2-methylaminobenzoyl)amino]benzyl}-N'-(2-naphthylsulfonyl)malonamide In the same manner as in Example 13, the title compound (100 mg) was obtained as a white solid using hydrochloride salt (242 mg) of the compound obtained in Example 7 and N-methylanthranilic acid (83 mg).

$^1$H-NMR (400 MHz, DMSO-$d_6$) δ0.86 (6H, t, J=7.2 Hz), 2.81 (3H, s), 2.90 (2H, d, J=6.0 Hz), 3.02-3.27 (4H, m), 3.85 (1H, t, J=7.2 Hz), 6.59-6.74 (2H, m), 7.02 (2H, d, J=8.4 Hz), 7.24-7.42 (2H, m), 7.47 (2H, d, J=8.4 Hz), 7.60-7.83 (3H, m), 8.05 (1H, d, J=8.0 Hz), 8.13 (1H, d, J=8.8 Hz), 8.20 (1H, d, J=8.0 Hz), 8.54 (1H, s), 9.95 (1H, s), 12.32 (1H, brs).

MS: 587(M+H)$^+$.

Example 57

Synthesis of 2-{4-[(2-acetylaminobenzoyl)amino]benzyl}-N,N-diethyl-N'-(2-naphthylsulfonyl)malonamide In the same manner as in Example 13, the title compound (103 mg) was obtained as a white solid using hydrochloride salt (239 mg) of the compound obtained in Example 7 and N-acetylanthranilic acid (81 mg).

$^1$H-NMR (400 MHz, DMSO-$d_6$) δ0.86 (3H, t, J=7.2 Hz), 0.88 (3H, t, J=7.2 Hz), 2.05 (3H, s), 2.91-3.28 (6H, m), 3.57 (1H, m), 7.17 (2H, d, J=8.4 Hz), 7.19-7.31 (2H, m), 7.43-7.61 (3H, m), 7.65 (1H, d, J=8.0 Hz), 7.74-8.06 (6H, m), 8.09 (1H, d, J=8.0 Hz), 8.29 (1H, brs).

MS: 615(M+H)$^+$.

Example 58

Synthesis of 2-{4-[(2-acetylamino-5-fluorobenzoyl)amino]benzyl}-N,N-diethyl-N'-(2-naphthylsulfonyl)malonamide In the same manner as in Example 13, the title compound (94 mg) was obtained as a white solid using hydrochloride salt (227 mg) of the compound obtained in Example 7 and N-acetyl-5-fluoroanthranilic acid (98 mg).

$^1$H-NMR (400 MHz, DMSO-$d_6$) δ0.86 (3H, t, J=7.2 Hz), 0.88 (3H, t, J=7.2 Hz), 2.04 (3H, s), 2.90-3.28 (6H, m), 3.59 (1H, m), 7.18 (2H, d, J=8.0 Hz), 7.20-7.32 (2H, m), 7.49-7.66 (2H, m), 7.66-7.84 (4H, m), 7.86-8.09 (3H, m), 8.32 (1H, s).

MS: 633(M+H)$^+$.

Example 59

Synthesis of N,N-diethyl-N'-(2-naphthylsulfonyl)-2-[4-(nicotinoylamino)benzyl]malonamide hydrochloride In the same manner as in Example 9, a white solid was obtained using the compound (310 mg) obtained in Example 7 and nicotinic acid chloride hydrochloride (365 mg). This was dissolved in ethanol (3 ml), 4 mol/L hydrochloric acid-ethyl acetate (200 μL) was added, and the precipitate was collected by filtration to give the title compound (255 mg) as a white solid.

$^1$H-NMR (400 MHz, DMSO-$d_6$) δ0.86 (6H, t, J=7.2 Hz), 2.85-2.94 (2H, m), 3.05-3.24 (4H, m), 3.90 (1H, t, J=7.2 Hz), 7.08 (2H, d, J=8.4 Hz), 7.54 (2H, d, J=8.4 Hz), 7.64-7.80 (4H, m), 8.06 (1H, d, J=8.0 Hz), 8.13 (1H, d, J=8.8 Hz), 8.21 (1H, d, J=8.0 Hz), 8.50 (1H, d, J=8.0 Hz), 8.55 (1H, d, J=1.2 Hz), 8.85 (1H, dd, J=4.4, 1.2 Hz), 9.20 (1H, d, J=2.0 Hz), 10.47 (1H, s), 12.34 (1H, brs).
MS: 559(M+H)$^+$.

Example 60

Synthesis of N,N-diethyl-N'-(2-naphthylsulfonyl)-2-{4-[(2-pyridylcarbonyl)amino]benzyl}malonamide hydrochloride In the same manner as in Example 9, the reaction mixture was obtained using the compound (340 mg) obtained in Example 7 and picolinic acid chloride hydrochloride (400 mg). The reaction mixture was adjusted to pH=1-2 by the addition of dilute hydrochloric acid and extracted with ethyl acetate (50 mL×2). After concentration under reduced pressure, the residue was dissolved in ethanol (3 ml), 4 mol/L hydrochloric acid-ethyl acetate (300 μL) was added, and the precipitate was collected by filtration to give the title compound (228 mg) as a pale-yellow solid.

$^1$H-NMR (400 MHz, DMSO-$d_6$) δ0.87 (6H, t, J=7.1 Hz), 2.91 (2H, d, J=7.2 Hz), 3.10-3.24 (4H, m), 3.89 (1H, t, J=7.2 Hz), 7.03 (2H, d, J=8.4 Hz), 7.62 (2H, d, J=8.4 Hz), 7.64-7.78 (4H, m), 8.04-8.12 (3H, m), 8.15 (1H, d, J=9.6 Hz), 8.19 (1H, d, J=8.7 Hz), 8.53 (1H, s), 8.76 (1H, d, J=4.6 Hz), 10.46 (1H, s), 12.31 (1H, brs).
MS: 559(M+H)$^+$.

Example 61

Synthesis of N,N-diethyl-2-[4-(isonicotinoylamino) benzyl]-N'-(2-naphthylsulfonyl)malonamide hydrochloride In the same manner as in Example 9, the title compound (16 mg) as a pale-brown solid was obtained using the compound (299 mg) obtained in Example 7 and isonicotinic acid chloride (128 mg).

$^1$H-NMR (400 MHz, DMSO-$d_6$) δ0.80-0.95 (6H, m), 2.85-2.96 (2H, m), 3.07-3.27 (4H, m), 3.85 (1H, m), 7.01 (2H, d, J=7.6 Hz), 7.50-7.63 (3H, m), 7.64-7.88 (4H, m), 8.06 (1H, d, J=8.1 Hz), 8.13 (1H, d, J=8.12 Hz), 8.21 (1H, d, J=8.1 Hz), 8.55 (2H, s), 10.42 (1H, s), 12.40 (1H.brs).
MS: 573(M+H)$^+$.

Example 62

Synthesis of N,N-diethyl-N'-(2-naphthylsulfonyl)-2-[4-(pyrazinylcarbonylamino)benzyl]malonamide In the same manner as in Example 13, the reaction mixture was obtained using hydrochloride salt (245 mg) of the compound obtained in Example 7 and pyrazinecarboxylic acid (66 mg). Dilute hydrochloric acid was added, and the mixture was extracted with ethyl acetate. The organic layer was concentrated under reduced pressure to give the title compound (213 mg) as a white solid.

$^1$H-NMR (400 MHz, DMSO-$d_6$) δ0.80-0.90 (6H, m), 2.91 (2H, d, J=7.2 Hz), 3.10-3.25 (4H, m), 3.87 (1H, t, J=7.2 Hz), 7.04 (2H, d, J=8.4 Hz), 7.62 (2H, d, J=8.4 Hz), 7.66-7.78 (3H, m), 8.04 (1H, d, J=8.0 Hz), 8.12 (1H, d, J=8.7 Hz), 8.19 (1H, d, J=8.0 Hz), 8.53 (1H, s), 8.82-8.83 (1H, m), 8.95 (1H, d, J=2.4 Hz), 9.30 (1H, d, J=1.2 Hz), 10.57 (1H, s), 12.31 (1H, brs).
MS: 560(M+H)$^+$.

Example 63

Synthesis of N,N-diethyl-2-{4-[(5-methyl-2-pyrazinylcarbonyl)amino]benzyl}-N'-(2-naphthylsulfonyl) malonamide In the same manner as in Example 13, the reaction mixture was obtained using hydrochloride salt (245 mg) of the compound obtained in Example 7 and 5-methyl-2-pyrazinecarboxylic acid (73 mg). Dilute hydrochloric acid was added, and the mixture was extracted with ethyl acetate. The organic layer was concentrated under reduced pressure to give the title compound (211 mg) as a white solid.

$^1$H-NMR (400 MHz, DMSO-$d_6$) δ0.87 (6H, t, J=7.0 Hz), 2.65 (3H, s), 2.90 (2H, d, J=7.2 Hz), 3.10-3.25 (4H, m), 3.87 (1H, t, J=7.2 Hz), 7.03 (2H, d, J=8.4 Hz), 7.61 (2H, d, J=8.4 Hz), 7.66-7.78 (3H, m), 8.04 (1H, d, J=8.0 Hz), 8.12 (1H, d, J=8.7 Hz), 8.19 (1H, d, J=8.0 Hz), 8.53 (1H, s), 8.71 (1H, s), 9.17 (1H, d, J=1.1 Hz), 10.48 (1H, s), 12.31 (1H, brs).
MS: 574(M+H)$^+$.

Example 64

Synthesis of N,N-diethyl-N'-(2-naphthylsulfonyl)-2-{4-[(5-pyrimidinylcarbonyl)amino] benzyl}malonamide In the same manner as in Example 13, the reaction mixture was obtained using hydrochloride salt (245 mg) of the compound obtained in Example 7 and 5-pyrimidinecarboxylic acid (66 mg). Dilute hydrochloric acid was added, and the mixture was extracted with ethyl acetate. The organic layer was concentrated under reduced pressure to give the title compound (230 mg) as a white solid.

$^1$H-NMR (400 MHz, DMSO-$d_6$) δ0.80-0.90 (6H, m), 2.85-2.96 (2H, m), 3.07-3.25 (4H, m), 3.86 (1H, t, J=7.2 Hz), 7.08 (2H, d, J=8.4 Hz), 7.52 (2H, d, J=8.4 Hz), 7.66-7.79 (3H, m), 8.05 (1H, d, J=8.0 Hz), 8.12 (1H, d, J=8.8 Hz), 8.20 (1H, d, J=8.0 Hz), 8.54 (1H, s), 9.23 (2H, s), 9.37 (1H, s), 10.47 (1H, s), 12.31 (1H, brs).
MS: 560(M+H)$^+$.

Example 65

Synthesis of 2-{4-[(3-amino-2-pyrazinylcarbonyl) amino]benzyl}-N,N-diethyl-N'-(2-naphthylsulfonyl) malonamide In the same manner as in Example 13, the reaction mixture was obtained using hydrochloride salt (500 mg) of the compound obtained in Example 7 and 3-amino-2-pyrazinecarboxylic acid (142 mg). Dilute hydrochloric acid was added, and the precipitate was collected by filtration to give the title compound (519 mg) as a white solid.

$^1$H-NMR (300 MHz, DMSO-$d_6$) δ0.87 (6H, t, J=7.2 Hz), 2.99 (2H, d, J=7.2 Hz), 3.08-3.27 (4H, m), 3.83 (1H, t, J=7.2 Hz), 7.01 (2H, d, J=8.7 Hz), 7.54 (2H, d, J=8.7 Hz), 7.58-7.78 (5H, m), 7.94 (1H, d, J=2.7 Hz), 8.05 (1H, d, J=8.1 Hz), 8.13

(1H, d, J=8.7 Hz), 8.20 (1H, d, J=8.1 Hz), 8.30 (1H, d, J=2.4 Hz), 8.53 (1H, s), 10.34 (1H, s), 12.31 (1H, brs).

Example 66

Synthesis of N,N-diethyl-2-{4-[(1-ethyl-1H-pyrazolyl-4-carbonyl)amino]benzyl}-N'-(2-naphthylsulfonyl)malonamide In the same manner as in Example 13, the reaction mixture was obtained using hydrochloride salt (530 mg) of the compound obtained in Example 7 and 1-ethyl-1H-pyrazole-4-carboxylic acid (151 mg). Dilute hydrochloric acid was added, and the precipitate was collected by filtration to give the title compound (273 mg) as a white solid.

$^1$H-NMR (400 MHz, DMSO-d$_6$) δ0.80-0.90 (6H, m), 1.41 (3H, t, J=7.2 Hz), 2.84-2.94 (2H, m), 3.06-3.26 (4H, m), 3.80-3.87 (1H, m), 4.19 (2H, q, J=7.2 Hz), 7.02 (2H, d, J=8.4 Hz), 7.47 (2H, d, J=8.4 Hz), 7.66-7.78 (3H, m), 8.02 (1H, s), 8.05 (1H, d, J=8.0 Hz), 8.12 (1H, d, J=8.8 Hz), 8.20 (1H, d, J=8.0 Hz), 8.35 (1H, s), 8.54 (1H, s), 9.70 (1H, s), 12.33 (1H, brs).

MS: 576(M+H)$^+$.

Example 67

Synthesis of N,N-diethyl-2-{4-[(5-methyl-1H-pyrazolyl-3-carbonyl)amino]benzyl}-N'-(2-naphthylsulfonyl)malonamide In the same manner as in Example 13, the reaction mixture was obtained using hydrochloride salt (280 mg) of the compound obtained in Example 7 and 5-methyl-1H-pyrazole-3-carboxylic acid (80 mg). Dilute hydrochloric acid was added, and the mixture was extracted with ethyl acetate. The organic layer was concentrated under reduced pressure to give the title compound (205 mg) as a white solid.

$^1$H-NMR (300 MHz, DMSO-d$_6$) δ0.84 (6H, t, J=6.9 Hz), 2.28 (3H, s), 2.86 (2H, d, J=7.2 Hz), 3.05-3.25 (4H, m), 3.84 (1H, t, J=7.2 Hz), 6.51 (1H, brs), 6.97 (2H, d, J=8.4 Hz), 7.53 (2H, d, J=8.4 Hz), 7.65-7.75 (3H, m), 8.04 (1H, d, J=7.8 Hz), 8.11 (1H, d, J=8.7 Hz), 8.19 (1H, d, J=7.8 Hz), 8.52 (1H, s), 9.82 (1H, s), 12.33 (1H, brs), 13.06 (1H, brs).

MS: 562(M+H)$^+$.

Example 68

Synthesis of N,N-diethyl-2-{4-[(3-methyl-4-isoxazolylcarbonyl)amino]benzyl}-N'-(2-naphthylsulfonyl)malonamide In the same manner as in Example 13, the title compound (328 mg) was obtained as a white solid using the compound (493 mg) obtained in Example 7 and 3-methyl-4-isoxazole carboxylic acid (161 mg).

$^1$H-NMR (400 MHz, DMSO-d$_6$) δ0.84 (3H, t, J=7.2 Hz), 0.86 (3H, t, J=7.2 Hz), 2.69 (3H, s), 2.82-2.93 (2H, m), 3.05-3.28 (4H, m), 3.85 (1H, d, J=7.2 Hz), 7.05 (2H, d, J=8.8 Hz), 7.44 (2H, d, J=8.4 Hz), 7.60-7.82 (3H, m), 8.05 (1H, d, J=8.0 Hz), 8.12 (1H, d, J=8.8 Hz), 8.20 (1H, d, J=8.0 Hz), 9.05 (1H, s), 9.91 (1H, s), 12.31 (1H, brs).

MS: 563(M+H)$^+$.

Example 69

Synthesis of N,N-diethyl-2-{4-[(2-furoyl)amino]benzyl}-N'-(2-naphthylsulfonyl)malonamide In the same manner as in Example 9, the title compound (270 mg) was obtained as a white solid using the compound (275 mg) obtained in Example 7 and 2-furoyl chloride (60 µL).

$^1$H-NMR (400 MHz, DMSO-d$_6$) δ0.86 (6H, t, J=7.2 Hz), 2.81-2.93 (2H, m), 3.02-3.25 (4H, m), 3.86 (1H, t, J=7.2 Hz), 7.04 (2H, d, J=8.4 Hz), 7.47 (2H, d, J=8.4 Hz), 7.62-7.90 (6H, m), 7.93 (1H, s), 8.06 (1H, d, J=8.4 Hz), 8.12 (1H, d, J=8.4 Hz), 8.20 (1H, d, J=8.4 Hz), 8.57 (1H, s), 10.45 (1H, s).

MS: 548(M+H)$^+$.

Example 70

Synthesis of N,N-diethyl-2-{4-[(5-methyl-2-furoyl)amino]benzyl}-N'-(2-naphthylsulfonyl)malonamide In the same manner as in Example 13, the reaction mixture was obtained using hydrochloride salt (297 mg) of the compound obtained in Example 7 and 5-methyl-2-furancarboxylic acid (80 mg). Dilute hydrochloric acid was added, and the mixture was extracted with ethyl acetate. The organic layer was concentrated under reduced pressure to give the title compound (192 mg) as a white solid.

$^1$H-NMR (400 MHz, DMSO-d$_6$) δ0.86 (6H, t, J=7.2 Hz), 2.39 (3H, s), 2.60-2.95 (2H, m), 3.04-3.26 (4H, m), 3.85 (1H, t, J=7.2 Hz), 6.32 (1H, d, J=2.8 Hz), 7.01 (2H, d, J=8.4 Hz), 7.22 (1H, d, J=2.8 Hz), 7.49 (2H, d, J=8.4 Hz), 7.61-7.80 (3H, m), 8.05 (1H, d, J=8.0 Hz), 8.12 (1H, d, J=8.8 Hz), 8.20 (1H, d, J=8.0 Hz), 8.54 (1H, s), 9.87 (1H, s), 12.32 (1H, brs).

MS: 562(M+H)$^+$.

Example 71

Synthesis of N,N-diethyl-2-{4-[(3-methyl-2-furoyl)amino]benzyl}-N'-(2-naphthylsulfonyl)malonamide In the same manner as in Example 13, the reaction mixture was obtained using hydrochloride salt (303 mg) of the compound obtained in Example 7 and 3-methyl-2-furancarboxylic acid (107 mg). Dilute hydrochloric acid was added, and the mixture was extracted with ethyl acetate. The organic layer was concentrated under reduced pressure to give the title compound (277 mg) as a white solid.

$^1$H-NMR (300 MHz, DMSO-d$_6$) δ0.83 (6H, t, J=7.2 Hz), 2.33 (3H, s), 2.86 (2H, d, J=6.9 Hz), 3.02-3.28 (4H, m), 3.69-3.84 (1H, m), 6.57 (1H, s), 6.98 (2H, d, J=8.4 Hz), 7.50 (2H, d, J=8.4 Hz), 7.58-7.85 (3H, m), 8.02 (1H, d, J=8.1 Hz), 8.08 (1H, d, J=9.0 Hz), 8.16 (1H, d, J=8.1 Hz), 8.48 (1H, s), 9.88 (1H, s), 12.39 (1H, brs).

MS: 562(M+H)$^+$.

Example 72

Synthesis of N,N-diethyl-N'-(2-naphthylsulfonyl)-2-{4-[(5-nitro-2-furoyl)amino]benzyl}malonamide In the same manner as in Example 13, the reaction mixture was obtained using hydrochloride salt (296 mg) of the compound obtained in Example 7 and 5-nitro-2-furancarboxylic acid (130 mg). Dilute hydrochloric acid was added, and the mixture was extracted with ethyl acetate. The organic layer was concentrated under reduced pressure to give the title compound (318 mg) as a white solid.

$^1$H-NMR (400 MHz, DMSO-d$_6$) δ0.86 (3H, t, J=7.2 Hz), 0.86 (3H, t, J=7.2 Hz), 2.91 (2H, d, J=7.2 Hz), 3.03-3.24 (4H, m), 3.87 (1H, t, J=7.2 Hz), 7.07 (2H, d, J=8.4 Hz), 7.48 (2H, d, J=8.4 Hz), 7.63 (1H, d, J=4.0 Hz), 7.64-7.80 (3H, m), 7.82 (1H, d, J=4.0 Hz), 8.06 (1H, d, J=8.4 Hz), 8.12 (1H, d, J=8.4 Hz), 8.19 (1H, d, J=8.0 Hz), 8.53 (1H, s), 10.49 (1H, s), 12.32 (1H, brs).

MS: 593(M+H)$^+$.

Example 73

Synthesis of 2-{4-[(5-bromo-2-furoyl)amino]benzyl}-N-diethyl-N'-(2-naphthylsulfonyl)malonamide In the same manner as in Example 13, the reaction mixture was obtained using hydrochloride salt (288 mg) of the compound obtained in Example 7 and 5-bromo-2-furancarboxylic acid (150 mg). Dilute hydrochloric acid was added, and the mixture was extracted with ethyl acetate. The organic layer was concentrated under reduced pressure to give the title compound (330 mg) as a white solid.

$^1$H-NMR (400 MHz, DMSO-d$_6$) δ0.85 (3H, t, J=7.2 Hz), 0.86 (3H, t, J=7.2 Hz), 2.90 (2H, d, J=4.8 Hz), 2.82-2.97 (4H, m), 3.86 (1H, t, J=7.2 Hz), 6.84 (1H, d, J=3.2 Hz), 7.03 (2H, d, J=8.4 Hz), 7.36 (1H, d, J=3.2 Hz), 7.47 (2H, d, J=8.4 Hz), 7.62-7.83 (3H, m), 8.05 (1H, d, J=8.0 Hz), 8.02 (1H, d, J=8.4 Hz), 8.20 (1H, d, J=8.0 Hz), 8.54 (1H, s), 10.08 (1H, s), 12.30 (1H, brs).

MS: 626(M+H)$^+$.

Example 74

Synthesis of N,N-diethyl-N'-2-{4-[(4,5-dimethyl-2-furoyl)amino]benzyl}-(2-naphthylsulfonyl)malonamide In the same manner as in Example 13, the reaction mixture was obtained using hydrochloride salt (308 mg) of the compound obtained in Example 7 and 4,5-dimethyl-2-furancarboxylic acid (84 mg). Dilute hydrochloric acid was added, and the mixture was extracted with ethyl acetate. The organic layer was concentrated under reduced pressure to give the title compound (222 mg) as a white solid.

$^1$H-NMR (400 MHz, DMSO-d$_6$) δ0.86 (3H, t, J=7.2 Hz), 0.87 (3H, t, J=7.2 Hz), 1.98 (3H, s), 2.31 (3H, s), 2.81-2.96 (2H, m), 3.04-3.27 (4H, m), 3.85 (1H, t, J=7.2 Hz), 7.00 (2H, d, J=8.8 Hz), 7.12 (1H, s), 7.49 (2H, d, J=8.4 Hz), 7.65-7.81 (3H, m), 8.05 (1H, d, J=8.0 Hz), 8.12 (1H, d, J=8.4 Hz), 8.20 (1H, d, J=8.0 Hz), 8.54 (1H, s), 9.80 (1H, s), 12.30 (1H, brs).

MS: 576(M+H)$^+$.

Example 75

Synthesis of N,N-diethyl-N'-(2-naphthylsulfonyl)-2-{4-[(2-thienoyl)amino]benzyl}malonamide In the same manner as in Example 9, the title compound (296 mg) was obtained as a white solid using the compound (301 mg) obtained in Example 7 and thiophene-2-carbonyl chloride (71 μL).

$^1$H-NMR (400 MHz, DMSO-d$_6$) δ0.85 (3H, t, J=7.2 Hz), 0.86 (3H, t, J=7.2 Hz), 2.81-2.96 (2H, m), 3.03-3.25 (4H, m), 3.88 (1H, t, J=7.2 Hz), 7.05 (2H, d, J=8.4 Hz), 7.19-7.57 (1H, m), 7.48 (2H, d, J=8.4 Hz), 7.60-7.92 (3H, m), 7.95-8.07 (2H, m), 8.12 (1H, d, J=8.4 Hz), 8.20 (1H, d, J=8.4 Hz), 8.55 (1H, s), 8.66-8.25 (1H, m), 10.12 (1H, s).

MS: 564(M+H)$^+$.

Example 76

Synthesis of N,N-diethyl-2-{4-[(5-methyl-2-thienoyl)amino]benzyl}-N'-(2-naphthylsulfonyl)malonamide In the same manner as in Example 13, the reaction mixture was obtained using hydrochloride salt (245 mg) of the compound obtained in Example 7 and 5-methyl-2-thiophenecarboxylic acid (84 mg). Dilute hydrochloric acid was added, and the precipitate was collected by filtration to give the title compound (257 mg) as a white solid.

$^1$H-NMR (400 MHz, DMSO-d$_6$) δ0.83-0.88 (6H, m), 2.85-2.94 (2H, m), 2.89 (3H, s), 3.07-3.23 (4H, m), 3.88 (1H, t, J=7.2 Hz), 6.92 (1H, d, J=3.8 Hz), 7.04 (2H, d, J=8.5 Hz), 7.47 (2H, d, J=8.5 Hz), 7.60-7.79 (3H, m), 7.83 (1H, d, J=3.8 Hz), 8.05 (1H, d, J=8.0 Hz), 8.12 (1H, d, J=8.8 Hz), 8.20 (1H, d, J=8.0 Hz), 8.54 (1H, d, J=1.0 Hz), 10.00 (1H, s), 12.34 (1H, brs).

MS:578(M+H)$^+$.

Example 77

Synthesis of 2-{4-[(5-chloro-2-thienoyl)amino]benzyl}-N,N-diethyl-N'-(2-naphthylsulfonyl)malonamide In the same manner as in Example 13, the reaction mixture was obtained using hydrochloride salt (245 mg) of the compound obtained in Example 7 and 5-chloro-2-thiophenecarboxylic acid (98 mg). Dilute hydrochloric acid was added, and the precipitate was collected by filtration to give the title compound (278 mg) as a white solid.

$^1$H-NMR (400 MHz, DMSO-d$_6$) δ0.83-0.88 (6H, m), 2.85-2.94 (2H, m), 3.07-3.24 (4H, m), 3.85 (1H, t, J=7.2 Hz), 7.05 (2H, d, J=8.5 Hz), 7.27 (1H, d, J=4.0 Hz), 7.44 (2H, d, J=8.5 Hz), 7.65-7.79 (3H, m), 7.90 (1H, d, J=4.0 Hz), 8.04 (1H, d, J=8.2 Hz), 8.11 (1H, d, J=8.4 Hz), 8.19 (1H, d, J=8.2 Hz), 8.53 (1H, s), 10.17 (1H, s), 12.30 (1H, brs).

MS: 598(M+H)$^+$.

Example 78

Synthesis of N,N-diethyl-2-{4-[(2,4-dimethyl-5-oxazolylcarbonyl)amino]benzyl}-N'-(2-naphthylsulfonyl)malonamide In the same manner as in Example 13, the reaction mixture was obtained using hydrochloride salt (245 mg) of the compound obtained in Example 7 and 2,4-dimethyl-5-oxazolecarboxylic acid (74 mg). Dilute hydrochloric acid was added, and the mixture was extracted with ethyl acetate. The organic layer was concentrated under reduced pressure to give the title compound (217 mg) as a white solid.

$^1$H-NMR (400 MHz, DMSO-d$_6$) δ0.83-0.87 (6H, m), 2.38 (3H, s), 2.50 (3H, s), 2.85-2.93 (2H, m), 3.07-3.24 (4H, m), 3.80-3.90 (1H, m), 7.01 (2H, d, J=8.5 Hz), 7.49 (2H, d, J=8.5 Hz), 7.65-7.78 (3H, m), 8.05 (1H, d, J=8.1 Hz), 8.12 (1H, d, J=8.7 Hz), 8.20 (1H, d, J=8.1 Hz), 8.54 (1H, s), 9.97 (1H, s), 12.28 (1H, brs).

MS: 577(M+H)$^+$.

Example 79

Synthesis of N,N-diethyl-2-{4-[(2,4-dimethyl-5-thiazolylcarbonyl)amino]benzyl}-N'-(2-naphthylsulfonyl)malonamide In the same manner as in Example 13, the reaction mixture was obtained using hydrochloride salt (245 mg) of the compound obtained in Example 7 and 2,4-dimethyl-5-thiazolecarboxylic acid (83 mg). Dilute hydrochloric acid was added, and the mixture was extracted with ethyl acetate. The organic layer was concentrated under reduced pressure to give the title compound (239 mg) as a white solid.

$^1$H-NMR (400 MHz, DMSO-$d_6$) δ0.86 (6H, t, J=6.8 Hz), 2.54 (3H, s), 2.66 (3H, s), 2.85-2.92 (2H, m), 3.06-3.23 (4H, m), 3.80-3.89 (1H, m), 7.02 (2H, d, J=8.3 Hz), 7.40 (2H, d, J=8.3 Hz), 7.69-7.79 (3H, m), 8.05 (1H, d, J=8.0 Hz), 8.12 (1H, d, J=8.8 Hz), 8.20 (1H, d, J=8.0 Hz), 8.54 (1H, s), 9.95 (1H, s), 12.30 (1H, brs).
MS: 593(M+H)$^+$.

Example 80

Synthesis of N,N-diethyl-N'-(2-naphthylsulfonyl)-2-{4-[(1-naphthoyl)amino]benzyl}malonamide In the same manner as in Example 9, the title compound (307 mg) was obtained as a white solid using hydrochloride salt (280 mg) of the compound obtained in Example 7 and 1-naphthoyl chloride (91 μL).

$^1$H-NMR (400 MHz, DMSO-$d_6$) δ0.81-0.93 (6H, m), 2.92 (2H, d, J=6.8 Hz), 3.10-3.25 (4H, m), 3.87 (1H, t, J=6.8 Hz), 7.06 (2H, d, J=8.4 Hz), 7.57-7.80 (9H, m), 8.01-8.24 (6H, m), 8.57 (1H, s), 10.46 (1H, s), 12.35 (1H, brs).
MS: 608(M+H)$^+$.

Example 81

Synthesis of N,N-diethyl-N'-(2-naphthylsulfonyl)-2-{4-[(8-quinolylcarbonyl)amino]benzyl}malonamide In the same manner as in Example 13, the reaction mixture was obtained using hydrochloride salt (245 mg) of the compound obtained in Example 7 and 8-quinolinecarboxylic acid (91 mg). Dilute hydrochloric acid was added, and the mixture was extracted with ethyl acetate. The organic layer was concentrated under reduced pressure to give the title compound (129 mg) as a white solid.

$^1$H-NMR (400 MHz, DMSO-$d_6$) δ0.84-0.90 (6H, m), 2.93 (2H, d, J=7.2 Hz), 3.10-3.25 (4H, m), 3.88 (1H, t, J=7.2 Hz), 7.08 (2H, d, J=8.3 Hz), 7.60 (2H, d, J=8.3 Hz), 7.63-7.71 (2H, m), 7.76-7.85 (3H, m), 8.03 (1H, d, J=8.0 Hz), 8.13 (1H, d, J=8.8 Hz), 8.20 (1H, d, J=8.0 Hz), 8.28 (1H, d, J=8.0 Hz), 8.54 (1H, s), 8.65 (1H, d, J=7.5 Hz), 9.18 (1H, d, J=4.4 Hz), 12.31 (1H, brs), 13.10 (1H, s).
MS: 609(M+H)$^+$.

Example 82

Synthesis of N,N-diethyl-2-{4-[(2-methyl-1H-benzimidazolyl-5-carbonyl)amino]benzyl}-N'-(2-naphthylsulfonyl)malonamide In the same manner as in Example 13, the reaction mixture was obtained using hydrochloride salt (245 mg) of the compound obtained in Example 7 and 2-methyl-1H-benzimidazolyle-5-carboxylic acid (93 mg). Dilute hydrochloric acid was added, and the mixture was extracted with ethyl acetate. The organic layer was concentrated under reduced pressure to give the title compound (14 mg) as a white solid.

$^1$H-NMR (400 MHz, DMSO-$d_6$) δ0.84-0.89 (6H, m), 2.55 (3H, s), 2.86-2.94 (2H, m), 3.07-3.25 (4H, m), 3.80-3.88 (1H, m), 7.03 (2H, d, J=8.5 Hz), 7.53-7.60 (3H, m), 7.67-7.79 (4H, m), 8.05 (1H, d, J=8.1 Hz), 8.11-8.14 (2H, m), 8.20 (1H, d, J=8.1 Hz), 8.53 (1H, s), 10.08 (1H, s), 12.50 (2H, brs).
MS: 612(M+H)$^+$.

Example 83

Synthesis of 2-{4-[(1H-benzimidazolylyl-2-carbonyl)amino]benzyl}-N,N-diethyl-N'-(2-naphthylsulfonyl)malonamide In the same manner as in Example 13, the reaction mixture was obtained using hydrochloride salt (245 mg) of the compound obtained in Example 7 and 1H-benzimidazolyle-2-carboxylic acid (85 mg). Dilute hydrochloric acid was added, and the mixture was extracted with ethyl acetate. The organic layer was concentrated under reduced pressure to give the title compound (188 mg) as a white solid.

$^1$H-NMR (400 MHz, DMSO-$d_6$) δ0.80-0.92 (6H, m), 2.85-2.94 (2H, m), 3.06-3.25 (4H, m), 3.88 (1H, t, J=7.2 Hz), 7.04 (2H, d, J=8.5 Hz), 7.28-7.40 (2H, m), 7.52-7.89 (7H, m), 8.05 (1H, d, J=8.1 Hz), 8.13 (1H, d, J=8.7 Hz), 8.20 (1H, d, J=8.1 Hz), 8.54 (1H, s), 10.74 (1H, s), 12.29 (1H, brs), 13.40 (1H, brs).
MS: 598(M+H)$^+$.

Example 84

Synthesis of N,N-diethyl-2-[4-(mesylamino)benzyl]-N'-(2-naphthylsulfonyl)malonamide In the same manner as in Example 9, the title compound (304 mg) as an orange solid was obtained using hydrochloride salt (300 mg) of the compound obtained in Example 7 and mesyl chloride (57 μL).

$^1$H-NMR (400 MHz, DMSO-$d_6$) δ0.81-0.86 (6H, m), 2.83-2.92 (2H, m), 2.90 (3H, s), 3.06-3.20 (4H, m), 3.83 (1H, t, J=7.2 Hz), 6.98-7.03 (4H, m), 7.50-7.53 (3H, m), 8.08 (1H, d, J=8.0 Hz), 8.14 (1H, d, J=8.8 Hz), 8.22 (1H, d, J=8.0 Hz), 8.57 (1H, d, J=1.2 Hz), 9.60 (1H, s).
MS: 532(M+H)$^+$.

Example 85

Synthesis of N,N-diethyl-N'-(2-naphthylsulfonyl)-2-[4-(phenylsulfonylamino)benzyl]malonamide In the same manner as in Example 9, the title compound (234 mg) as a pale-brown solid was obtained using hydrochloride salt (210 mg) of the compound obtained in Example 7 and benzenesulfonyl chloride (57 μL).

$^1$H-NMR (400 MHz, DMSO-$d_6$) δ0.73 (3H, t, J=7.2 Hz), 0.78 (3H, t, J=7.2 Hz), 2.75-2.87 (2H, m), 2.94-3.20 (4H, m), 3.76 (1H, t, J=7.4 Hz), 6.86-6.91 (4H, m), 7.45-7.59 (3H, m), 7.69-7.78 (5H, m), 8.08 (2H, t, J=9.4 Hz), 8.20 (1H, d, J=8.0 Hz), 8.56 (1H, s), 10.16 (1H, s), 12.29 (1H, brs).
MS: 594(M+H)$^+$.

Example 86

Synthesis of N,N-diethyl-N'-(2-naphthylsulfonyl)-2-[4-(tosylamino)benzyl]malonamide In the same manner as in Example 9, the title compound (574 mg) as a pale-brown solid was obtained using hydrochloride salt (500 mg) of the compound obtained in Example 7 and tosyl chloride (215 mg).

$^1$H-NMR (400 MHz, DMSO-d$_6$) δ0.70-0.81 (6H, m), 2.31 (3H, s), 2.73-2.86 (2H, m), 2.93-3.20 (4H, m), 3.71-3.78 (1H, m), 6.83-6.90 (4H, m), 7.30 (2H, d, J=8.4 Hz), 7.59 (2H, d, J=8.4H), 7.67-7.78 (3H, m), 8.03-8.10 (2H, m), 8.20 (1H, d, J=8.0 Hz), 8.54 (1H, s), 10.07 (1H, s), 12.22 (1H, brs).
MS: 608(M+H)$^+$.

Example 87

Synthesis of N,N-diethyl-N'-(2-naphthylsulfonyl)-2-[4-(phenoxycarbonylamino)benzyl]malonamide In the same manner as in Example 9, the title compound (185 mg) as a pale-brown solid was obtained using hydrochloride salt (260 mg) of the compound obtained in Example 7 and phenyl chlorocarbonate (70 µL).

$^1$H-NMR (300 MHz, DMSO-d$_6$) δ0.75-0.84 (6H, m), 2.88 (2H, d, J=7.2 Hz), 3.02-3.24 (4H, m), 3.84 (1H, t, J=7.2 Hz), 7.00 (2H, d, J=8.7 Hz), 7.21-7.50 (7H, m), 7.65-7.78 (3H, m), 8.04-8.22 (3H, m), 8.55 (1H, s), 10.09 (1H, s).
MS: 574(M+H)$^+$.

Example 88

Synthesis of 2-[4-(anilinocarbonylamino)benzyl]-N,N-diethyl-N'-(2-naphthylsulfonyl)malonamide To a solution of the compound (478 mg) obtained in Example 7 in THF (10 mL) were added 1 mol/L aqueous sodium hydroxide solution (3 mL) and phenyl isocyanate (120 µL), and the mixture was stirred at room temperature for 4 hr. The reaction mixture was adjusted to pH=1-2 by the addition of dilute hydrochloric acid and extracted with ethyl acetate (30 mL×2). The organic layer was washed with saturated brine, concentrated under reduced pressure, and washed with isopropanol (100 mL) to give the title compound (331 mg) as a white solid.

$^1$H-NMR (400 MHz, DMSO-d$_6$) δ0.86 (3H, t, J=7.0 Hz), 0.86 (3H, t, J=6.9 Hz), 2.87 (2H, d, J=7.0 Hz), 3.05-3.20 (4H, m), 3.83 (1H, t, J=7.0 Hz), 6.96 (2H, d, J=8.3 Hz), 7.20 (2H, d, J=8.3 Hz), 7.22-7.35 (2H, m), 7.45 (2H, d, J=8.1 Hz), 7.65-7.78 (3H, m), 8.06 (1H, d, J=8.0 Hz), 8.12 (1H, d, J=8.0 Hz), 8.20 (1H, d, J=8.0 Hz), 8.53 (2H, m), 8.60 (1H, s).
MS: 573(M+H)$^+$.

Example 89

Synthesis of N,N-diethyl-2-[4-(1-indolinylcarbonylamino)benzyl]-N'-(2-naphthylsulfonyl)malonamide To a solution of the compound obtained in Example 87 (418 mg) in THF (6 mL) were added indoline (84 µL) and triethylamine (540 µL), and the mixture was heated under reflux for 5.5 hr.

Dilute hydrochloric acid was added to the reaction mixture, and the mixture was extracted with ethyl acetate (50 mL×2). The extract was washed with saturated brine and concentrated under reduced pressure, and the residue was purified by silica gel column chromatography to give the title compound (198 mg) as a white solid. $^1$H-NMR (300 MHz, DMSO-d$_6$) δ0.85 (3H, t, J=7.2 Hz), 0.86 (3H, t, J=7.2 Hz), 2.82-2.93 (2H, m), 3.05-3.28 (6H, m), 3.81 (1H, t, J=7.2 Hz), 4.11 (2H, t, J=8.7 Hz), 6.90 (1H, m), 6.99 (2H, d, J=8.4 Hz), 7.13 (1H, m), 7.20 (1H, m), 7.32 (2H, d, J=8.4 Hz), 7.62-7.80 (5H, m), 7.87 (1H, d, J=8.2 Hz), 8.06 (1H, d, J=8.1 Hz), 8.14 (1H, d, J=8.1 Hz), 8.21 (1H, d, J=8.1 Hz), 8.40 (1H, s), 8.55 (1H, s), 12.30 (1H, brs).
MS: 599(M+H)$^+$.

Example 90

Synthesis of N,N-diethyl-2-[4-(N'',N''-diethylaminocarbonylamino)benzyl]-N'-(2-naphthylsulfonyl)malonamide To a mixed solution of the compound (520 mg) obtained in Example 87 in THF (40 mL)/pyridine (4 mL) were added diethylamine (2.0 mL) and 4-dimethylaminopyridine (14 mg), and mixture was stirred at room temperature for 18 hr. Dilute hydrochloric acid was added to the reaction solution, and the mixture was extracted with ethyl acetate (50 mL×2) The extract was washed with saturated brine and concentrated under reduced pressure to give the compound (256 mg) as a white solid.

$^1$H-NMR (400 MHz, DMSO-d$_6$) δ, 0.85 (6H, t, J=6.8), 1.15 (6H, t, J=6.8 Hz), 2.75-2.94 (2H, m), 3.03-3.24 (4H, m), 3.82 (1H, t, J=6.8 Hz), 6.92 (2H, d, J=8.4 Hz), 7.25 (2H, d, J=8.4 Hz), 7.64-7.85 (3H, m), 8.05 (1H, d, J=8.0 Hz), 8.12 (1H, d, J=8.4 Hz), 8.20 (1H, d, J=8.0 Hz), 8.54 (1H, s), 12.28 (1H, brs).
MS: 553(M+H)$^+$.

Example 91

Synthesis of (2S)—N,N-diethyl-N'-(2-naphthylsulfonyl)-2-(4-nitrobenzyl)malonamide To the compound (100 g) obtained in Example 6 and (+)-dehydroabiethylamine (70.8 g) was added methanol (2.7 L), and the mixture was dissolved by heating under reflux. The mixture was left standing and allowed to gradually cool to room temperature. Two days later, the precipitated solid was collected by filtration to give a (+)-dehydroabiethylamine salt (93.7 g, optical purity 43% d.e.) of the title compound as white crystals. 24.6 g thereof was dissolved in THF (400 mL) with heating, and the solution was allowed to gradually cool to room temperature and left standing for 1 day. The precipitate was collected by filtration. The filtrate was concentrated under reduced pressure and recrystallized from methanol (100 mL) in the same manner. The obtained crystals were combined, and recrystallized again from methanol (100 mL). The precipitate was collected by filtration to give a (+)-dehydroabiethylamine salt (12.3 g, optical purity>98% d.e.) of the title compound as white crystals. The salt (12.3 g) was suspended in ethanol (200 mL), 1 mol/L hydrochloric acid (50 mL) was added, and the mixture was desalted by stirring at room temperature for 3 hr. The precipitate was collected by filtration to give the title compound (7.23 g) as a white solid (optical purity>98% e.e.).

$^1$H-NMR and MS were the same as in Example 6.
specific optical rotation: [α]$_D$=+9° (c=1.28, chloroform).

Example 92

Synthesis of (2S)-2-[4-(benzoylamino)benzyl]-N,N-diethyl-N'-(2-naphthylsulfonyl)malonamide To a suspension of the compound (500 mg) obtained in Example 91 in THF (15 mL) were added triethylamine (160 µL) and 10% palladium/carbon (70 mg), and the mixture was stirred under hydrogen atmosphere at room temperature for 4 hr. Insoluble material was removed by filtration, benzoyl chloride (120 μL) was added to the filtrate under ice-cooling, and the mixture was stirred at room temperature for 17 hr. The mixture was concentrated under reduced pressure, dilute hydrochloric acid (30 mL) was added to the residue, and the precipitate was collected by filtration. The precipitate was triturated with ethanol/water to give the title compound (404 mg) as a white solid.

$^1$H-NMR and MS were same as in Example 9.

specific optical rotation: $[\alpha]_D=+42°$ (c=0.28, chloroform).

Example 93

Synthesis of (2S)—N,N-diethyl-2-{4-[(2-fluorobenzoyl)amino]benzyl}-N'-(2-naphthylsulfonyl)malonamide In the same manner as in Example 92, the title compound (336 mg) was obtained as a white solid using the compound (500 mg) obtained in Example 91 and 2-fluorobenzoyl chloride (124 μL).

$^1$H-NMR and MS were same as in Example 19.

specific optical rotation: $[\alpha]_D=+27°$ (c=0.61, chloroform).

Example 94

Synthesis of (2S)—N,N-diethyl-2-{4-[(3-fluorobenzoyl)amino]benzyl}-N'-(2-naphthylsulfonyl)malonamide In the same manner as in Example 92, the title compound (327 mg) was obtained as a white solid using the compound (500 mg) obtained in Example 91 and 3-fluorobenzoyl chloride (124 μL).

$^1$H-NMR and MS were same as in Example 21.

specific optical rotation: $[\alpha]_D=+31°$ (c=0.37, chloroform).

Example 95

Synthesis of (2S)—N,N-diethyl-2-{4-[(2,4-difluorobenzoyl)amino]benzyl}-N'-(2-naphthylsulfonyl)malonamide In the same manner as in Example 92, the title compound (489 mg) was obtained as a white solid using the compound (500 mg) obtained in Example 91 and 2,4-difluorobenzoyl chloride (127 μL).

$^1$H-NMR and MS were same as in Example 23.

specific optical rotation: $[\alpha]_D=+28°$ (c=0.56, chloroform).

Example 96

Synthesis of (2S)—N,N-diethyl-2-{4-[(4-methylbenzoyl)amino]benzyl}-N'-(2-naphthylsulfonyl)malonamide In the same manner as in Example 92, the title compound (273 mg) was obtained as a white solid using the compound (500 mg) obtained in Example 91 and 4-methylbenzoyl chloride (137 μL).

$^1$H-NMR and MS were same as in Example 32.

specific optical rotation: $[\alpha]_D=+35°$ (c=0.32, chloroform).

Example 97

Synthesis of (2S)—N,N-diethyl-N'-(2-naphthylsulfonyl)-2-{4-[(2-thienoyl)amino]benzyl}malonamide In the same manner as in Example 92, the title compound (382 mg) was obtained as a white solid using the compound (500 mg) obtained in Example 91 and thiophene-2-carbonyl chloride (111 μL).

$^1$H-NMR and MS were same as in Example 75.

specific optical rotation: $[\alpha]_D=+33°$ (c=0.35, chloroform).

Example 98

Synthesis of (2S)—N,N-diethyl-2-{4-[(2-furoyl)amino]benzyl}-N'-(2-naphthylsulfonyl)malonamide In the same manner as in Example 92, the title compound (352 mg) was obtained as a white solid using the compound (500 mg) obtained in Example 91 and 2-furoyl chloride (102 μL).

$^1$H-NMR and MS were same as in Example 69.

specific optical rotation: $[\alpha]_D=+33°$ (c=0.53, chloroform).

Example 99

Synthesis of (2S)-2-{4-[(2-amino-5-fluorobenzoyl)amino]benzyl}-N,N-diethyl-N'-(2-naphthylsulfonyl)malonamide The compound (5.79 g) obtained in Example 48 and (1S,2S)-(+)-2-amino-1-(4-nitrophenyl)-1,3-propanediol (2.08 g) were dissolved with heating in methanol (100 mL), and the solution was concentrated under reduced pressure to give an oil. The oil was dissolved with heating in isopropanol (100 mL), and the solution was stirred at 60° C. for 12 hr. The precipitate was collected by filtration and recrystallized from isopropanol (100 mL) to give (1S,2S)-(+)-2-amino-1-(4-nitrophenyl)-1,3-propanediol salt (2.20 g) of the title compound as white crystals (optical purity>98% d.e.). 0.5 mol/L Hydrochloric acid (200 mL) was added to a salt (15.6 g) obtained by repeating a similar operation, and the mixture was extracted with ethyl acetate (300 mL). After concentration under reduced pressure, the residue was triturated with ethanol to give the title compound (10.5 g) as a white solid (optical purity>98% e.e.).

$^1$H-NMR and MS were same as in Example 48.

specific optical rotation: $[\alpha]_D=+30°$ (c=0.325, chloroform).

Example 100

Synthesis of (2S)-2-{4-[(2-amino-6-fluorobenzoyl)amino]benzyl}-N,N-diethyl-N'-(2-naphthylsulfonyl)malonamide Resolution in the same manner as in Example 91 and using the compound (10.28 g) obtained in Example 55, (+)-dehydroabiethylamine (6.30 g) and ethanol gave a (+)-dehydroabiethylamine salt (3.62 g) (optical purity>98% d.e.) of the title compound as white crystals. A salt (6.80 g) obtained by repeating a similar operation was desalted in the same manner as in Example 91 to give the title compound (4.51 g) as a white solid (optical purity>98% e.e.).

$^1$H-NMR and MS were same as in Example 55.

specific optical rotation: $[\alpha]_D=+25°$ (c=0.515, chloroform).

Example 101

Synthesis of (2S)—N,N-diethyl-N'-(2-naphthylsulfonyl)-2-{4-[(2-pyridylcarbonyl)amino]benzyl}malonamide Resolution in the same manner as in Example 91 and using a free form of the compound (18.2 g) obtained in Example 60, (+)-dehydroabiethylamine (12.1 g) and methanol gave a (+)-dehydroabiethylamine salt (12.3 g) (optical purity>98% d.e.) of the title compound as white crystals. The salt was desalted with 2 equivalent amounts of hydrochloric acid in the same manner as in Example 91 to give the title compound (4.81 g) as a white solid (optical purity>98% e.e.).
$^1$H-NMR (400 MHz, CDCl$_3$) δ0.81 (3H, t, J=7.2 Hz), 1.03 (3H, t, J=7.2 Hz), 2.80-2.88 (2H, m), 3.01 (1H, dd, J=13.2, 5.0 Hz), 3.07-3.18 (2H, m), 3.44-3.53 (1H, m), 3.57 (1H, dd, J=10.1, 5.0 Hz), 7.05 (2H, d, J=8.4 Hz), 7.50 (1H, dd, J=8.0, 4.6 Hz), 7.56 (2H, d, J=8.4 Hz), 7.60-7.68 (2H, m), 7.90-7.94 (2H, m), 7.97-8.04 (3H, m), 8.28 (1H, d, J=7.8 Hz), 8.62 (1H, d, J=4.6 Hz), 8.68 (1H, s), 9.93 (1H, s), 10.97 (1H, s).
MS was the same as in Example 60.
specific optical rotation: $[\alpha]_D=+33°$ (c=0.32, chloroform).

Example 102

Synthesis of (2S)-2-(4-aminobenzyl)-N,N-diethyl-N'-(2-naphthylsulfonyl)malonamide To a mixed suspension of the compound (9.12 g) obtained in Example 91 in ethanol (50 mL)/ethyl acetate (50 mL) was added 10% palladium/carbon (1.00 g), and the mixture was stirred at room temperature under hydrogen atmosphere for 3 hr. The white precipitate was dissolved in chloroform, insoluble material was removed by filtration, and the filtrate was concentrated under reduced pressure to give the title compound (8.53 g) as a white powder.
$^1$H-NMR and MS were same as in Example 7.
specific optical rotation: $[\alpha]_D=+32°$ (c=0.65, chloroform).

Example 103

Synthesis of (2S)-2-{4-[(2-amino-4-chlorobenzoyl)amino]benzyl}-N,N-diethyl-N'-(2-naphthylsulfonyl)malonamide In the same manner as in Example 13, the title compound (668 mg) was obtained as a white solid using the compound (1.01 g) obtained in Example 102 and 4-chloroanthranilic acid (381 mg).
$^1$H-NMR and MS were same as in Example 51.
specific optical rotation: $[\alpha]_D=+33°$ (c=0.445, chloroform).

Example 104

Synthesis of (2S)-2-{4-[(2-aminobenzoyl)amino]benzyl}-N,N-diethyl-N'-(2-naphthylsulfonyl)malonamide In the same manner as in Example 13, the title compound (178 mg) was obtained as a white solid using the compound (1.02 g) obtained in Example 102 and anthranilic acid (309 mg). $^1$H-NMR and MS were same as in Example 43.

specific optical rotation: $[\alpha]_D=+29°$ (c=0.385, chloroform).

Example 105

Synthesis of (2S)-2-{4-[(2-amino-5-chlorobenzoyl)amino]benzyl}-N,N-diethyl-N'-(2-naphthylsulfonyl)malonamide In the same manner as in Example 13, the title compound (396 mg) was obtained as a white solid using the compound (1.01 g) obtained in Example 102 and 5-chloroanthranilic acid (382 mg).
$^1$H-NMR and MS were same as in Example 47.
specific optical rotation: $[\alpha]_D=+21°$ (c=0.475, chloroform).

Example 106

Synthesis of (2S)-2-{4-[(2-amino-4,5-difluorobenzoyl)amino]benzyl}-N,N-diethyl-N'-(2-naphthylsulfonyl)malonamide In the same manner as in Example 13, the title compound (503 mg) was obtained as a white solid using the compound (1.01 g) obtained in Example 102 and 4,5-difluoroanthranilic acid (424 mg).
$^1$H-NMR and MS were same as in Example 54.
specific optical rotation: $[\alpha]_D=+27°$ (c=0.575, chloroform).

Example 107

Synthesis of (2S)-2-{4-[(2-amino-4-fluorobenzoyl)amino]benzyl}-N,N-diethyl-N'-(2-naphthylsulfonyl)malonamide In the same manner as in Example 13, the title compound (715 mg) was obtained as a white solid using the compound (1.01 g) obtained in Example 102 and 4-fluoroanthranilic acid (340 mg).
$^1$H-NMR and MS were same as in Example 52.
specific optical rotation: $[\alpha]_D=+29°$ (c=0.525, chloroform).

Example 108

Synthesis of (2S)-2-{4-[(2-amino-5-methylbenzoyl)amino]benzyl}-N,N-diethyl-N'-(2-naphthylsulfonyl)malonamide In the same manner as in Example 13, the title compound (276 mg) was obtained as a white solid using the compound (1.80 g) obtained in Example 102 and 5-methylanthranilic acid (607 mg).
$^1$H-NMR and MS were same as in Example 50.
specific optical rotation: $[\alpha]_D=+25°$ (c=0.445, chloroform).

Example 109

Synthesis of N,N-diethyl-2-(4-dimethylaminobenzyl)-N'-(2-naphthylsulfonyl)malonamide To a solution of the compound (122 mg) obtained in Example 7 in THF (5 mL) were added 37% aqueous formaldehyde solution (0.5 mL) and sodium triacetoxyborohydride (230 mg), and the mixture was stirred at room temperature for 16 hr. Water (50 mL) was added to the reaction mixture, and the mixture was extracted with ethyl acetate (50 mL×2). The organic layer was washed with saturated brine and concentrated under reduced pressure to give the title compound (110 mg) as a white solid.

$^1$H-NMR (300 Mz, DMSO-d$_6$) δ0.88 (6H, t, J=7.1 Hz), 2.69-2.90 (2H, m), 2.75 (6H, s), 3.07-3.29 (4H, m), 3.68-3.75 (1H, m), 6.37 (2H, d, J=8.6 Hz), 6.78 (2H, d, J=8.6 Hz), 7.68-7.82 (3H, m), 8.05-8.25 (3H, m), 8.53 (1H, s), 12.26 (1H, brs).
MS: 482(M+H)$^+$.

Example 110

Synthesis of 2-(4-chlorobenzyl)-N,N-diethyl-N'-(2-naphthylsulfonyl)malonamide (1) diethyl 4-chlorobenzylmalonate In the same manner as in Example 6 (1), a crude product was obtained using diethyl malonate (13.6 g) and 4-chlorobenzyl bromide (17.5 g). This was purified by silica gel column chromatography to give the title compound (10.1 g) as an oil.

$^1$H-NMR (300 Mz, CDCl$_3$) δ1.22 (6H, t, J=6.9 Hz), 3.18 (2H, d, J=7.8 Hz), 3.60 (1H, t, J=7.7 Hz), 4.05-4.30 (4H, m), 7.14 (2H, d, J=8.4 Hz), 7.25 (2H, d, J=9.0 Hz).

(2) monomethyl 4-chlorobenzylmalonate

In the same manner as in Example 6 (2), the title compound (8.29 g) was obtained as an oil using the above-mentioned compound (10.1 g).

$^1$H-NMR (300 Mz, CDCl$_3$) δ3.10-3.29 (2H, m), 3.55-3.87 (4H, m), 7.08-7.32 (4H, m).

(3) methyl 2-(4-chlorobenzyl)-3-[(2-naphthylsulfonyl)amino]-3-oxopropionate

In the same manner as in Example 1 (2), the title compound (3.12 g) was obtained as an oil using the above-mentioned compound (2.00 g).

$^1$H-NMR (300 Mz, CDCl$_3$) δ3.00-3.90 (6H, m), 6.80 (2H, d, J=8.5 Hz), 6.90 (2H, d, J=8.7 Hz), 7.56-7.77 (2H, m), 7.84-8.08 (4H, m), 8.63 (1H, d, J=1.7 Hz).

(4) 2-(4-chlorobenzyl)-3-[(2-naphthylsulfonyl)amino]-3-oxopropionic acid disodium salt To a solution of the above-mentioned compound (3.12 g) in THF/ethanol (10 mL/20 mL) was added a solution of sodium hydroxide (0.867 g) in water (6 mL), and the mixture was stirred at room temperature for 18 hr. The precipitate was collected by filtration to give the title compound (2.41 g) as a white powder.

$^1$H-NMR (300 Mz, DMSO-d$_6$) δ2.75-2.96 (3H, m), 6.94-7.10 (4H, m), 7.49-7.64 (2H, m), 7.70-8.03 (7H, m), 8.24 (1H, s).

(5) 2-(4-chlorobenzyl)-N,N-diethyl-N'-(2-naphthylsulfonyl)malonamide

In the same manner as in Example 1 (4), a crude product was obtained using the above-mentioned compound (300 mg). This was purified by silica gel column chromatography to give the title compound (164 mg) as a white powder.

$^1$H-NMR (300 Mz, DMSO-d$_6$) δ0.74-0.92 (6H, m), 2.90 (2H, d, J=7.2 Hz), 3.01-3.29 (4H, m), 3.83 (1H, t, J=6.9 Hz), 7.00-7.14 (4H, m), 7.63-7.82 (3H, m), 8.01-8.29 (3H, m), 8.53 (1H, s), 12.38 (1H, brs).
MS: 473(M+H)$^+$.

Example 111

Synthesis of 2-(4-cyanobenzyl)-N,N-diethyl-N'-(2-naphthylsulfonyl)malonamide (1) diethyl 4-cyanobenzylmalonate In the same manner as in Example 6 (1), a crude product was obtained using diethyl malonate (13.6 g) and 4-cyanobenzyl bromide (16.7 g). This was purified by silica gel column chromatography to give the title compound (15.5 g) as an oil.

$^1$H-NMR (300 Mz, CDCl$_3$) δ1.22 (6H, t, J=7.2 Hz), 3.27 (2H, d, J=7.8 Hz), 3.64 (1H, t, J=7.5 Hz), 4.07-4.29 (4H, m), 7.34 (2H, d, J=8.1 Hz), 7.59 (2H, d, J=8.1 Hz).

(2) monoethyl (4-cyanobenzyl)malonate

To a solution of the above-mentioned compound (15.5 g) in ethanol (100 mL) were added a solution of potassium hydroxide (3.71 g) in ethanol (100 mL) and ethanol (50 mL), and the mixture was stirred at room temperature for 18 hr. The reaction mixture was concentrated under reduced pressure, water (100 mL) and ether (30 mL) were added to extract the residue. The aqueous layer was adjusted to pH=1-2 by the addition of 1 mol/L hydrochloric acid (100 mL), and extracted with ethyl acetate (200 mL). The organic layer was washed with brine and concentrated under reduced pressure to give the title compound (12.2 g) as an oil.

$^1$H-NMR (300 Mz, CDCl$_3$) δ1.22 (3H, t, J=6.9 Hz), 3.18-3.35 (2H, m), 3.70 (1H, t, J=7.6 Hz), 4.00-4.30 (2H, m), 7.35 (2H, d, J=8.2 Hz), 7.60 (2H, d, J=8.2 Hz).

(3) ethyl 2-(4-cyanobenzyl)-3-[(2-naphthylsulfonyl)amino]-3-oxopropionate

In the same manner as in Example 1 (2), the title compound (6.25 g) was obtained as an oil using the above-mentioned compound (4.00 g).

$^1$H-NMR (300 Mz, CDCl$_3$) δ1.17 (3H, J=7.2 Hz), 3.18 (2H, d, J=7.8 Hz), 3.52 (1H, t, J=7.2 Hz), 4.00-4.30 (2H, m), 7.01 (2H, d, J=8.1 Hz), 7.22 (2H, d, J=8.4 Hz), 7.52-7.79 (2H, m), 7.82-8.11 (4H, m), 8.63 (1H, s).

(4) 2-(4-cyanobenzyl)-3-[(2-naphthylsulfonyl)amino]-3-oxopropionic acid

To a solution of the above-mentioned compound (6.25 g) in THF/ethanol (20 mL/40 mL) was added a solution of sodium hydroxide (1.79 g) in water (12 mL), and the mixture was stirred at room temperature for 18 hr. The precipitate was collected by filtration, 0.5 mol/L hydrochloric acid (80 mL) and ethyl acetate (200 mL) were added to extract the precipitate. The organic layer was washed with brine and concentrated under reduced pressure to give the title compound (4.64 g) as a white powder.

$^1$H-NMR (300 Mz, CDCl$_3$) δ2.82-2.67 (2H, m), 3.63-3.81 (1H, m), 7.16 (2H, d, J=8.2 Hz), 7.39 (2H, d, J=8.2 Hz), 7.61-7.82 (3H, m), 8.09 (2H, d, J=8.6 Hz), 8.20 (1H, d, J=7.7 Hz), 8.50 (1H, d, J=1.2 Hz), 12.00-13.40 (1H, brs).

(5) 2-(4-cyanobenzyl)-N,N-diethyl-N'-(2-naphthylsulfonyl)malonamide

In the same manner as in Example 1 (4), a crude product was obtained using the above-mentioned compound (300 mg). This was purified by silica gel column chromatography to give the title compound (174 mg) as a white powder.

$^1$H-NMR (300 Mz, DMSO-$d_6$) δ0.76-0.91 (6H, m), 3.00 (2H, d, J=7.2 Hz), 3.02-3.31 (4H, m), 3.90 (1H, t, J=7.2 Hz), 7.24 (2H, d, J=8.4 Hz), 7.49 (2H, d, J=8.4 Hz), 7.86-7.81 (3H, m), 8.00-8.25 (3H, m), 8.52 (1H, s), 12.39 (1H, brs).

Example 112

Synthesis of N,N-diethyl-2-(4-methoxybenzyl)-N'-(2-naphthylsulfonyl)malonamide

(1) diethyl 4-methoxybenzylmalonate

In the same manner as in Example 6 (1), a crude product was obtained using diethyl malonate (25.6 g) and 4-methoxybenzyl chloride (25.0 g). This was purified by silica gel column chromatography to give the title compound (25.0 g) as an oil.

$^1$H-NMR (300 Mz, CDCl$_3$) δ1.21 (6H, t, J=7.5 Hz), 3.15 (2H, d, J=7.8 Hz), 3.60 (1H, t, J=7.8 Hz), 3.78 (3H, s), 4.02-4.27 (4H, m), 6.81 (2H, d, J=8.4 Hz), 7.12 (2H, d, J=8.1 Hz).

(2) monoethyl (4-methoxybenzyl)malonate

In the same manner as in Example 111 (2), the title compound (18.0 g) was obtained as an oil using the above-mentioned compound (25.0 g).

$^1$H-NMR (300 Mz, CDCl$_3$) δ1.22 (3H, t, J=7.1 Hz), 3.18 (2H, d, J=7.3 Hz), 3.65 (1H, t, J=7.5 Hz), 3.78 (3H, s), 4.17 (2H, q, J=7.2 Hz), 6.82 (2H, d, J=8.6 Hz), 7.12 (2H, d, J=8.6 Hz).

(3) ethyl 2-(4-methoxybenzyl)-3-[(2-naphthylsulfonyl)amino]-3-oxopropionate In the same manner as in Example 1 (2), the title compound (7.14 g) was obtained as an oil using the above-mentioned compound (4.08 g).

$^1$H-NMR (300 Mz, CDCl$_3$) δ1.14 (3H, t, J=7.1 Hz), 3.02-3.15 (2H, m), 3.45 (1H, t, J=7.0 Hz), 3.68 (3H, s), 4.01-4.20 (2H, m), 6.55 (2H, d, J=8.7 Hz), 6.81 (2H, J=8.6 Hz), 7.56-7.75 (2H, m), 7.95-8.10 (4H, m), 8.65 (1H, s).

(4) 2-(4-methoxybenzyl)-3-[(2-naphthylsulfonyl)amino]-3-oxopropionic acid

In the same manner as in Example 111 (4), the title compound (5.66 g) was obtained as a white powder using the above-mentioned compound (7.14 g).

$^1$H-NMR (300 Mz, CDCl$_3$) δ2.99-3.19 (2H, m), 3.58 (1H, t, J=6.7 Hz), 3.62 (3H, s), 6.47 (2H, d, J=8.7 Hz), 6.81 (2H, d, J=8.5 Hz), 7.53-7.72 (2H, m), 7.80-8.05 (4H, m), 7.00-8.00 (1H, brs), 8.63 (1H, s), 9.40-10.30 (1H, brs).

(5) N,N-diethyl-2-(4-methoxybenzyl)-N'-(2-naphthylsulfonyl)malonamide

In the same manner as in Example 1 (4), a crude product was obtained using the above-mentioned compound (550 mg). This was purified by silica gel column chromatography to give the title compound (189 mg) as a white powder.

$^1$H-NMR (300 Mz, DMSO-$d_6$) δ0.80-0.94 (6H, m), 2.70-2.95 (2H, m), 3.08-3.30 (4H, m), 3.63 (3H, s), 3.68-3.82 (1H, m), 6.59 (2H, d, J=8.7 Hz), 6.92 (2H, d, J=8.4 Hz), 7.64-7.84 (3H, m), 8.01-8.29 (3H, m), 8.54 (1H, s), 12.31 (1H, brs).

MS: 469(M+H)$^+$.

Example 113

Synthesis of N,N-diethyl-N'-(2-naphthylsulfonyl)-2-(4-pyridylmethyl)malonamide

(1) diethyl (4-pyridylmethyl)malonate

In the same manner as in Example 6 (1), a crude product was obtained using diethyl malonate (6.41 g) and 4-(bromomethyl)pyridine hydrobromide (10.1 g). This was purified by silica gel column chromatography to give the title compound (3.86 g) as an oil.

$^1$H-NMR (300 Mz, CDCl$_3$) δ1.22 (6H, t, J=7.1 Hz), 3.21 (2H, d, J=7.8 Hz), 3.58-3.71 (1H, m), 4.07-4.27 (4H, m), 7.09-7.17 (2H, m), 8.44-8.56 (2H, m).

(2) monoethyl (4-pyridylmethyl)malonate

In the same manner as in Example 111 (2), the title compound (1.89 g) was obtained as a white powder using the above-mentioned compound (3.86 g).

$^1$H-NMR (300 Mz, CDCl$_3$) δ0.97-1.16 (3H, m), 2.92-3.19 (2H, m), 3.70-4.15 (3H, m), 7.26 (2H, d, J=5.7 Hz), 8.46 (2H, d, J=5.4 Hz), 12.30-13.80 (1H, brs).

(3) ethyl 3-[(2-naphthylsulfonyl)amino]-3-oxo-2-(4-pyridylmethyl)propionate In the same manner as in Example 1 (2), the title compound (2.44 g) was obtained as an oil using the above-mentioned compound (1.89 g).

$^1$H-NMR (300 Mz, CDCl$_3$) δ1.04 (3H, t, J=7.2 Hz), 3.00-3.75 (3H, m), 3.91-4.09 (2H, m), 7.04 (2H, d, J=5.9 Hz), 7.40-8.05 (6H, m), 8.27 (2H, d, J=6.0 Hz), 8.24 (1H, s).

(4) 3-[(2-naphthylsulfonyl)amino]-3-oxo-2-(4-pyridylmethyl)propionic acid disodium salt In the same manner as in Example 110 (4), the title compound (1.27 g) was obtained as a white powder using the above-mentioned compound (3.86 g).

$^1$H-NMR (300 Mz, DMSO-$d_6$) δ2.79-3.00 (2H, m), 3.10-4.70 (1H, brs), 6.98-7.09 (2H, m), 7.50-7.63 (2H, m), 7.70-8.06 (4H, m), 8.18-8.29 (3H, m).

(5) N,N-diethyl-N'-(2-naphthylsulfonyl)-2-(4-pyridylmethyl)malonamide

In the same manner as in Example 1 (4), a crude product was obtained using the above-mentioned compound (200 mg). This was purified by silica gel column chromatography to give the title compound (38 mg) as a white powder.

$^1$H-NMR (300 Mz, DMSO-$d_6$) δ0.85 (6H, t, J=6.9 Hz), 2.95 (2H, d, J=7.2 Hz), 3.00-3.30 (4H, m), 3.89 (1H, t, J=7.5 Hz), 7.08 (2H, d, J=5.7 Hz), 7.60-7.80 (3H, m), 8.01-8.30 (5H, m), 8.54 (1H, s), 12.60 (1H, brs).

MS: 440(M+H)$^+$.

Example 114

Synthesis of N,N-diethyl-N'-(2-naphthylsulfonyl)-2-(3-nitrobenzyl)malonamide

(1) diethyl 3-nitrobenzylmalonate

In the same manner as in Example 6 (1), the title compound (7.02 g) was obtained as an oil using diethyl malonate (6.57 g) and 3-nitrobenzyl bromide (8.87 g).

(2) monoethyl (3-nitrobenzyl)malonate

In the same manner as in Example 111 (2), the title compound (4.00 g) was obtained as an oil using the above-mentioned compound (7.02 g).

$^1$H-NMR (400 Mz, CDCl$_3$) δ1.22-1.33 (6H, m), 3.15-3.20 (2H, m), 3.74 (1H, t, J=7.5 Hz), 4.18-4.28 (4H, m), 7.47-7.51 (1H, m), 7.58 (1H, d, J=7.7 Hz), 8.07-8.12 (2H, m).

(3) ethyl 3-(N,N-diethylamino)-2-(3-nitrobenzyl)-3-oxopropionate

To a solution of the above-mentioned compound (3.92 g) in methylene chloride (50 mL) was added oxalyl chloride (2.60 mL) under ice-cooling, and the mixture was stirred at room temperature for 1.5 hr. After concentration under reduced pressure, THF (50 mL) was added to the residue, and diethylamine (4.60 mL) was added under ice-cooling. After stirring for 20 min under the condition, the reaction mixture was adjusted to pH=2-3 by the addition of dilute hydrochloric acid and extracted with ethyl acetate (50 mL×2). The extract was washed with saturated brine and concentrated under reduced pressure, and the residue was purified by silica gel column chromatography to give the title compound (3.43 g) as an oil.

$^1$H-NMR (300 Mz, CDCl$_3$) δ0.99 (3H, t, J=7.5 Hz), 1.04 (3H, t, J=7.2 Hz), 1.25 (3H, t, J=7.2 Hz), 3.04-3.18 (1H, m), 3.25-3.48 (5H, m), 3.82 (1H, dd, J=9.0, 6.0 Hz), 4.19 (2H, q, J=7.2 Hz), 7.42-7.47 (1H, m), 7.60 (1H, d, J=7.5 Hz), 8.09 (1H, d, J=7.5 Hz), 8.10 (1H, s).

(4) 3-(N,N-diethylamino)-2-(3-nitrobenzyl)-3-oxopropionic acid

To a solution of the above-mentioned compound (2.99 g) in methanol (50 mL) was added 1 mol/L aqueous sodium hydroxide solution (14 mL), and the mixture was stirred at room temperature for 2 hr. After concentration under reduced pressure, the residue was adjusted to pH=2-3 by the addition of dilute hydrochloric acid and extracted with ethyl acetate (50 mL×2). The extract was washed with saturated brine and concentrated under reduced pressure to give the title compound (2.67 g) as a white solid.

$^1$H-NMR (400 Mz, CDCl$_3$) δ1.05 (3H, t, J=7.2 Hz), 1.08 (3H, t, J=7.2 Hz), 3.00-3.09 (2H, m), 3.09-3.22 (1H, m), 3.27-3.41 (2H, m), 3.49-3.61 (1H, In), 3.80-3.83 (1H, m), 7.48-7.52 (1H, m), 7.57 (1H, d, J=7.5 Hz), 8.05 (1H, s), 8.14 (1H, d, J=8.2 Hz).

(5) N,N-diethylamino-2-(3-nitrobenzyl)malonamide

To a solution of the above-mentioned compound (2.66 g) in methylene chloride (50 mL) were added oxalyl chloride (1.60 mL) and DMF (50 μL) under ice-cooling, and the mixture was stirred at room temperature for 2 hr. After concentration under reduced pressure, THF (50 mL) was added to the residue, and 28% aqueous ammonia (1.00 mL) was added under ice-cooling. After stirring at room temperature for 12 hr, the mixture was concentrated under reduced pressure, water was added to the residue, and the precipitate was collected by filtration to give the title compound (2.27 g) as a white solid.

$^1$H-NMR (400 Mz, DMSO-d$_6$) δ0.88-0.95 (6H, m), 3.05-3.40 (6H, m), 3.77 (1H, dd, J=8.7, 6.2 Hz), 7.12 (1H, brs), 7.37 (1H, brs), 7.54-7.58 (1H, m), 7.71 (1H, d, J=7.7 Hz), 8.06 (1H, d, J=7.8 Hz), 8.11 (1H, s).

(6) N,N-diethyl-N'-(2-naphthylsulfonyl)-2-(3-nitrobenzyl)malonamide

To a solution of the above-mentioned compound (250 mg) in THF (20 mL) was added 60% sodium hydride (40 mg) under ice-cooling, and the mixture was stirred at room temperature for 20 min. 2-Naphthalenesulfonyl chloride (230 mg) was added to the mixture at room temperature, and the mixture was stirred for 30 min. Additional 60% sodium hydride (40 mg) was added under ice-cooling, and the mixture was stirred at room temperature for 3 days. Water (50 mL) was added to the reaction mixture, and the mixture was extracted with ethyl acetate (50 mL×2). The extract was washed with saturated brine and concentrated under reduced pressure, and the residue was purified by silica gel column chromatography to give the title compound (144 mg) as a white solid.

$^1$H-NMR (400 Mz, CDCl$_3$) δ0.88 (3H, t, J=7.0 Hz), 1.02 (3H, t, J=7.0 Hz), 2.91-3.03 (2H, m), 3.09-3.20 (2H, m), 3.28 (1H, dd, J=13.2, 9.2 Hz), 3.42-3.51 (1H, m), 3.61 (1H, dd, J=9.2, 6.0 Hz), 7.20-7.32 (3H, m), 7.62-7.71 (2H, m), 7.92-8.03 (5H, m), 8.66 (1H, s), 10.72 (1H, s).

MS: 484(M+H)$^+$.

Example 115

Synthesis of 2-(3-aminobenzyl)-N,N-diethyl-N'-(2-naphthylsulfonyl)malonamide In the same manner as in Example 7, the title compound (83 mg) was obtained as a white powder using the compound (104 mg) obtained in Example 114 at room temperature.

$^1$H-NMR (400 Mz, CDCl$_3$) δ0.75-0.84 (3H, m), 0.97-1.06 (3H, m), 2.78-3.12 (5H, m), 3.47-3.55 (2H, m), 6.36 (1H, d, J=2.0 Hz), 6.43 (1H, d, J=7.6 Hz), 6.48 (1H, dd, J=7.6, 2.0 Hz), 6.93 (1H, t, J=7.6 Hz), 7.60-7.69 (2H, m), 7.91-8.02 (4H, m), 8.67 (1H, s).

MS: 454(M+H)$^+$.

Example 116

Synthesis of N,N-diethyl-N'-(2-naphthylsulfonyl)-2-(2-nitrobenzyl)malonamide

(1) diethyl 2-nitrobenzylmalonate

In the same manner as in Example 6 (1), a crude product was obtained using diethyl malonate (10.1 g) and 2-nitrobenzyl bromide (13.6 g). This was purified by silica gel column chromatography to give the title compound (13.9 g) as an oil.

$^1$H-NMR (400 Mz, CDCl$_3$) δ1.19-1.24 (6H, m), 3.51 (2H, d, J=7.6 Hz), 3.87 (1H, t, J=7.6 Hz), 4.10-4.24 (4H, m), 7.39-7.44 (2H, m), 7.51-7.55 (1H, m), 8.01 (1H, d, J=7.6 Hz).

(2) monoethyl (2-nitrobenzyl)malonate

In the same manner as in Example 111 (2), a crude product was obtained using the above-mentioned compound (13.8 g).

This was purified by silica gel column chromatography to give the title compound (3.75 g) as an oil.

$^1$H-NMR (400 Mz, CDCl$_3$) δ1.22 (3H, t, J=7.2 Hz), 3.45-3.56 (2H, m), 3.95 (1H, t, =7.2 Hz), 4.14-4.22 (2H, m), 7.42-7.46 (2H, m), 7.55 (1H, dd, J=8.0, 7.8 Hz), 8.03 (1H, d, J=8.0 Hz).

(3) ethyl 3-[(2-naphthylsulfonyl)amino]-2-(2-nitrobenzyl)-3-oxopropionate

In the same manner as in Example 1 (2), the title compound (860 mg) was obtained as a pale-yellow powder using the above-mentioned compound (910 mg).

$^1$H-NMR (400 Mz, CDCl$_3$) δ1.10-1.17 (3H, m), 3.34-3.48 (2H, m), 3.74 (1H, t, J=7.2 Hz), 4.06-4.18 (2H, m), 7.14-7.32 (3H, m), 7.63-7.69 (2H, m), 7.70-8.04 (5H, m), 8.64 (1H, s), 9.25 (1H, brs).

(4) N,N-diethyl-N'-(2-naphthylsulfonyl)-2-(2-nitrobenzyl)malonamide

To a solution of the above-mentioned compound (852 mg) in THF (10 mL) was added a solution of sodium hydroxide (292 mg) in water (2 mL), and the mixture was stirred at room temperature for 18 hr. After concentration under reduced pressure, the residue was adjusted to pH=2-3 by the addition of dilute hydrochloric acid and extracted with ethyl acetate (50 mL×2). After concentration under reduced pressure, the residue was subjected to the same manner as in Example 1 (4) to give a crude product. The crude product was purified by silica gel column chromatography to give the title compound (230 mg) as a pale-yellow powder.

$^1$H-NMR (400 Mz, CDCl$_3$) δ1.00-1.10 (6H, m), 3.12-3.41 (4H, m), 3.41-3.52 (2H, m), 3.95 (1H, dd, J=9.2, 6.4 Hz), 6.88-6.91 (2H, m), 7.21-7.25 (1H, m), 7.61-7.72 (2H, m), 7.93-8.03 (5H, m), 8.64 (1H, s), 11.01 (1H, s).

MS: 484(M+H)$^+$.

Example 117

Synthesis of N,N-diethyl-N'-(2-naphthylsulfonyl)-2-[4-(trifluoromethoxy)benzyl]malonamide (1) triethyl 2-[4-(trifluoromethoxy)phenyl]ethane-1,1,1-tricarboxylate To a solution of triethyl methanetricarboxylate (4.55 g) in DMF (40 mL) were added 4-(trifluoromethoxy)benzyl bromide (5.00 g), potassium iodide in catalytic amount and potassium carbonate (4.07 g), and the mixture was stirred at room temperature for 3 hr. Ethyl acetate (200 mL) and water (100 mL) were added to extract the reaction mixture. The extract was washed sequentially with water and brine, and concentrated under reduced pressure to give the title compound (7.97 g) as an oil.

$^1$H-NMR (300 Mz, CDCl$_3$) δ1.20 (9H, t, J=7.3 Hz), 3.51 (2H, s), 4.20 (6H, q, J=7.5 Hz), 7.09 (2H, d, J=8.7 Hz), 7.33 (2H, d, J=8.8 Hz).

(2) monoethyl (4-trifluoromethoxybenzyl)malonate

To a solution of the above-mentioned compound (7.97 g) in ethanol (30 mL) was added a solution of potassium hydroxide (2.20 g) in ethanol (50 mL), and the mixture was stirred at room temperature for 18 hr. The reaction mixture was concentrated, and the residue was adjusted to pH=2-3 by the addition of dilute hydrochloric acid and extracted with ethyl acetate (200 mL). The extract was washed with saturated brine and concentrated under reduced pressure to give the title compound (5.94 g) as an oil.

$^1$H-NMR (300 Mz, CDCl$_3$) δ1.20 (3H, t, J=7.2 Hz), 3.24 (2H, d, J=7.5 Hz), 3.68 (1H, t, J=7.5 Hz), 4.17 (2H, q, J=7.2 Hz), 7.14 (2H, d, J=8.4 Hz), 7.16-7.30 (2H, m).

(3) ethyl 3-[(2-naphthylsulfonyl)amino]-3-oxo-2-[4-(trifluoromethoxy)benzyl]propionate In the same manner as in Example 1 (2), the title compound (3.27 g) was obtained as an oil using the above-mentioned compound (2.97 g).

$^1$H-NMR (300 Mz, CDCl$_3$) δ1.12 (3H, t, J=6.8 Hz), 3.13 (2H, d, J=7.3 Hz), 3.48 (1H, t, J=6.9 Hz), 4.27 (2H, q, J=7.5 Hz), 6.85 (2H, d, J=8.1 Hz), 6.94 (2H, d, J=8.8 Hz), 7.57-7.75 (2H, m), 7.84-8.08 (4H, m), 8.65 (1H, s).

(4) 3-[(2-naphthylsulfonyl)amino]-3-oxo-2-[4-(trifluoromethoxy)benzyl]propionic acid In the same manner as in Example 111 (4), the title compound (2.36 g) was obtained as a white solid using the above-mentioned compound (3.27 g).

$^1$H-NMR (300 Mz, DMSO-d$_6$) δ2.73-3.15 (2H, m), 3.50-3.85 (1H, m), 6.95 (2H, d, J=8.2 Hz), 7.08 (2H, d, J=8.5 Hz), 7.58-7.89 (3H, m), 7.93-8.18 (2H, m), 8.20 (1H, d, J=8.0 Hz), 8.53 (1H, s), 11.60-13.80 (1H, brs).

(5) N,N-diethyl-N'-(2-naphthylsulfonyl)-2-[4-(trifluoromethoxy)benzyl]malonamide In the same manner as in Example 1 (4), a crude product was obtained using the above-mentioned compound (1.18 g). This was purified by silica gel column chromatography to give the title compound (530 mg) as a white powder.

$^1$H-NMR (300 Mz, DMSO-d$_6$) δ0.68-0.90 (6H, m), 2.95 (2H, d, J=7.2 Hz), 3.00-3.27 (4H, m), 3.86 (1H, t, J=7.2 Hz), 7.03 (2H, d, J=8.4 Hz), 7.15 (2H, d, J=9.0 Hz), 7.63-7.83 (3H, m), 8.02-8.26 (3H, m), 8.55 (1H, s), 12.34 (1H, brs).

MS: 523(M+H)$^+$.

Example 118

Synthesis of N,N-diethyl-2-(4-fluorobenzyl)-N'-(2-naphthylsulfonyl)malonamide (1) triethyl 2-(4-fluorophenyl)ethane-1,1,1-tricarboxylate In the same manner as in Example 117 (1), the title compound (13.5 g) was obtained as an oil using triethyl methanetricarboxylate (9.29 g) and 4-fluorobenzyl bromide (7.56 g).

$^1$H-NMR (300 Mz, CDCl$_3$) δ1.22 (9H, t, J=7.1 Hz), 3.49 (2H, s), 4.20 (6H, q, J=7.1 Hz), 6.92 (2H, t, J=8.7 Hz), 7.18-7.32 (2H, m).

(2) monoethyl (4-fluorobenzyl)malonate

In the same manner as in Example 117 (2), the title compound (10.0 g) was obtained as an oil using the above-mentioned compound (13.5 g).

$^1$H-NMR (300 Mz, CDCl$_3$) δ1.21 (3H, t, J=7.4 Hz), 3.10-3.27 (2H, m), 3.60-3.74 (1H, m), 4.15 (2H, q, J=6.9 Hz), 6.97 (2H, t, J=8.6 Hz), 7.10-7.24 (2H, m).

(3) ethyl 3-(N,N-diethylamino)-2-(4-fluorobenzyl)-3-oxopropionate

In the same manner as in Example 1 (4), the reaction mixture was obtained using the above-mentioned compound (3.30 g). Ethyl acetate (150 mL) and aqueous sodium hydrogen carbonate solution (120 mL) were added to extract the reaction mixture, and the organic layer was washed sequentially with 0.5 mol/L hydrochloric acid, water and brine. The organic layer was concentrated under reduced pressure to give the title compound (3.11 g) as an oil.
$^1$H-NMR (300 Mz, CDCl$_3$) δ0.96 (3H, t, J=7.3 Hz), 1.04 (3H, t, J=7.4 Hz), 1.23 (3H, t, J=7.4 Hz), 2.87-3.43 (6H, m), 3.66-3.78 (1H, m), 4.17 (2H, q, J=7.4 Hz), 6.94 (2H, t, J=8.9 Hz), 7.10-7.27 (2H, m).

(4) 3-(N,N-diethylamino)-2-(4-fluorobenzyl)-3-oxopropionic acid

To a solution of the above-mentioned compound (3.11 g) in THF (50 mL) were added 1 mol/L aqueous sodium hydroxide solution (12.6 mL) and ethanol (20 mL), and the mixture was stirred at room temperature for 3 days. After concentration under reduced pressure, 1 mol/L hydrochloric acid (50 mL) and ethyl acetate (100 mL) were added sequentially to extract the residue, and the organic layer was washed with brine. The organic layer was concentrated to give the title compound (2.77 g) as an oil.
$^1$H-NMR (300 Mz, CDCl$_3$) δ0.98 (3H, t, J=7.4 Hz), 1.07 (3H, t, J=7.3 Hz), 2.74-3.30 (6H, m), 3.65-3.78 (1H, m), 6.89-7.05 (2H, m), 7.10-7.24 (2H, m).

(5) N,N-diethyl-2-(4-fluorobenzyl)-N'-(2-naphthylsulfonyl)malonamide

In the same manner as in Example 1 (2), the title compound (1.29 g) was obtained as a white powder using the above-mentioned compound (1.39 g).
$^1$H-NMR (300 Mz, DMSO-d$_6$) δ0.70-0.96 (6H, m), 2.91 (2H, d, J=7.2 Hz), 3.00-3.38 (4H, m), 3.84 (1H, t, J=7.5 Hz), 6.85 (2H, t, J=8.7 Hz), 6.99-7.14 (2H, m), 7.60-7.83 (3H, m), 8.02-8.16 (2H, m), 8.21 (1H, d, J=8.1 Hz), 8.54 (1H, s), 12.29 (1H, brs).
MS: 457(M+H)$^+$.

Example 119

Synthesis of N,N-diethyl-2-(3,4-dimethoxybenzyl)-N'-(2-naphthylsulfonyl)malonamide

(1) 5-(3,4-dimethoxybenzyl)-2,2-dimethyl-1,3-dioxane-4,6-dione

Under ice-cooling, to formic acid (20 mL) was added dropwise triethylamine (29.6 mL). Then, 3,4-dimethoxybenzaldehyde (9.22 g) and Meldrum's acid (8.00 g) were added under ice-cooling, and the mixture was stirred at room temperature for 18 hr. The reaction mixture was poured into a mixture of ice (80 g) and 1 mol/L hydrochloric acid (50 mL), and the precipitate was collected by filtration to give the title compound (14.4 g) as a white solid.
$^1$H-NMR (300 Mz, CDCl$_3$) δ1.70 (3H, s), 1.77 (3H, s), 3.38 (2H, d, J=5.6 Hz), 3.86 (3H, s), 3.87 (3H, s), 4.14 (1H, t, J=5.8 Hz), 6.77-6.90 (1H, m), 6.92-7.09 (2H, m).

(2) 3-(N,N-diethylamino)-2-(3,4-dimethoxybenzyl)-3-oxopropionic acid

To a solution of diethylamine (1.99 g) in methylene chloride (40 mL) were added N, O-bis(trimethylsilyl)acetamide (6.66 mL) and 4-dimethylaminopyridine (1.66 g) under ice-cooling, and the mixture was stirred at room temperature for 2 hr. The above-mentioned compound (2.00 g) was added to the reaction mixture under ice-cooling, and the mixture was stirred at room temperature for 3 days. Under ice-cooling, methanol (10 mL) and water (50 mL) were added to extract the reaction mixture. The aqueous layer was acidified with 1 mol/L hydrochloric acid, and methylene chloride (50 mL) was added to extract the mixture. The organic layer was concentrated under reduced pressure, and the residue was purified by silica gel column chromatography to give the title compound (1.52 g) as a white powder.
$^1$H-NMR (300 Mz, CDCl$_3$) δ0.80-1.00 (6H, m), 2.80-2.97 (1H, m), 2.99-3.40 (5H, m), 3.74 (3H, s), 3.77 (3H, s), 3.78-3.89 (1H, m), 6.66-6.77 (1H, m), 6.80-6.98 (2H, m), 11.20-13.50 (1H, brs).

(3) N,N-diethyl-2-(3,4-dimethoxybenzyl)-N'-(2-naphthylsulfonyl)malonamide

In the same manner as in Example 1 (2), the title compound (518 mg) was obtained as a white powder using the above-mentioned compound (760 mg).
$^1$H-NMR (300 Mz, DMSO-d$_6$) δ0.91 (3H, t, J=7.0 Hz), 0.97 (3H, t, J=7.0 Hz), 2.77-2.98 (2H, m), 3.08-3.45 (4H, m), 3.60 (3H, s), 3.74 (3H, s), 3.78-3.89 (1H, m), 6.37-6.45 (1H, m), 6.60 (1H, t, J=7.8 Hz), 6.78 (1H, dd, J=8.2, 1.4 Hz), 7.64-7.84 (3H, m), 8.02-8.12 (2H, m), 8.13-8.22 (1H, m), 8.50 (1H, s), 12.20 (1H, brs).
MS: 499(M+H)$^+$.

Example 120

Synthesis of N,N-diethyl-2-(4-methoxycarbonylbenzyl)-N'-(2-naphthylsulfonyl)malonamide

(1) 5-(4-methoxycarbonylbenzyl)-2,2-dimethyl-1,3-dioxane-4,6-dione

In the same manner as in Example 119 (1), the title compound (8.57 g) was obtained as a white powder using methyl 4-formylbenzoate (9.11 g).
$^1$H-NMR (300 Mz, CDCl$_3$) δ1.59 (3H, s), 1.76 (3H, s), 3.53 (2H, d, J=5.0 Hz), 3.79 (1H, t, J=4.9 Hz), 3.90 (3H, s), 7.41 (2H, d, J=8.3 Hz), 7.96 (2H, d, J=8.3 Hz).

(2) 3-(N,N-diethylamino)-2-(4-methoxycarbonylbenzyl)-3-oxopropionic acid

In the same manner as in Example 119 (2), the title compound (1.82 g) was obtained as a white powder using the above-mentioned compound (2.34 g).
$^1$H-NMR (300 Mz, DMSO-d$_6$) δ0.71-0.97 (6H, m), 2.97-3.36 (6H, m), 3.83 (3H, s), 3.90-4.02 (1H, m), 7.35 (2H, d, J=8.1 Hz), 7.84 (2H, d, J=8.4 Hz).

(3) N,N-diethyl-2-(4-methoxycarbonylbenzyl)-N'-(2-naphthylsulfonyl)malonamide In the same manner as in Example 1 (2), the title compound (470 mg) was obtained as a white powder using the above-mentioned compound (909 mg).
$^1$H-NMR (300 Mz, DMSO-d$_6$) δ0.77-0.98 (6H, m), 2.99 (2H, d, J=7.5 Hz), 3.09-3.35 (4H, m), 3.83 (3H, s), 3.82-3.97 (1H, m), 7.16 (2H, d, J=8.4 Hz), 7.62 (2H, d, J=8.1 Hz), 7.67-7.83 (3H, m), 8.04-8.15 (2H, m), 8.18 (1H, d, J=7.8 Hz), 8.51 (1H, s), 12.35 (1H, brs).
MS: 497(M+H)$^+$.

Example 121

Synthesis of 2-(4-carboxybenzyl)-N,N-diethyl-N'-(2-naphthylsulfonyl)malonamide

To the compound (300 mg) obtained in Example 120 were added THF (20 mL), methanol (10 mL) and 1 mol/L aqueous sodium hydroxide solution (2.66 mL), and the mixture was stirred at room temperature for 3 days. The reaction mixture was concentrated, and water (30 mL) and chloroform (30 mL) were added to extract the residue. The aqueous layer was adjusted to pH=1-2 by the addition of 1 mol/L hydrochloric acid, and chloroform (30 mL) was added to extract the mixture. The organic layer was concentrated under reduced pressure to give the title compound (242 mg) as a white powder.

$^1$H-NMR (300 Mz, DMSO-d$_6$) δ0.63-0.94 (6H, m), 2.90-3.30 (6H, m), 3.89 (1H, t, J=7.2 Hz), 7.17 (2H, d, J=8.1 Hz), 7.60-7.82 (5H, m), 8.01-8.10 (2H, m), 8.19 (1H, d, J=7.8 Hz), 8.53 (1H, s), 12.34 (1H, brs), 12.78 (1H, brs).
MS: 483(M+H)$^+$.

Example 122

Synthesis of N,N-diethyl-2-[(2-methoxy-5-pyridyl)methyl]-N'-(2-naphthylsulfonyl)malonamide

(1) 5-(2-methoxy-5-pyridylmethyl)-2,2-dimethyl-1,3-dioxane-4,6-dione

Under ice-cooling, to formic acid (10 mL) was added dropwise triethylamine (14.8 mL). Then, 6-methoxy-3-pyridinecarboxaldehyde (3.81 g) and Meldrum's acid (4.00 g) were added under ice-cooling, and the mixture was stirred at room temperature for 18 hr. The reaction mixture was poured into ice-water, and ethyl acetate was added to extract the mixture. The organic layer was concentrated under reduced pressure. THF and then, ether were added to the residue, and the precipitate was collected by filtration to give the title compound (2.54 g) as a white powder.

$^1$H-NMR (300 Mz, CDCl$_3$) δ1.62 (3H, s), 1.76 (3H, s), 3.41 (2H, d, J=4.8 Hz), 3.72 (1H, t, J=4.5 Hz), 3.91 (3H, s), 6.67 (1H, d, J=8.7 Hz), 7.59 (1H, dd, J=8.4, 2.7 Hz), 8.13 (1H, d, J=2.4 Hz).

(2) 3-(N,N-diethylamino)-2-(2-methoxy-5-pyridyl)methyl-3-oxopropionic acid

In the same manner as in Example 119 (2), the title compound (1.41 g) was obtained as an oil using the above-mentioned compound (2.12 g).

$^1$H-NMR (300 Mz, DMSO-d$_6$) δ0.77-0.96 (6H, m), 2.88-3.32 (6H, m), 3.79 (3H, s), 3.84-3.96 (1H, m), 6.70 (1H, d, J=8.4 Hz), 7.55 (1H, dd, J=8.4, 2.4 Hz), 7.96 (1H, d, J=2.4 Hz).

(3) N,N-diethyl-2-[(2-methoxy-5-pyridyl)methyl]-N'-(2-naphthylsulfonyl)malonamide In the same manner as in Example 1 (2), the title compound (649 mg) was obtained as a white powder using the above-mentioned compound (705 mg).

$^1$H-NMR (300 Mz, DMSO-d$_6$) δ0.70-0.95 (6H, m), 2.70-2.90 (2H, m), 3.00-3.27 (4H, m), 3.75 (3H, s), 3.76-3.85 (1H, m), 6.50 (1H, d, J=8.6 Hz), 7.35 (1H, dd, J=8.6, 2.3 Hz), 7.63-7.89 (4H, m), 7.99-8.10 (2H, m), 8.21 (1H, d, J=7.9 Hz), 8.54 (1H, s), 12.34 (1H, brs).

Example 123

Synthesis of N,N-diethyl-2-(2-naphthylmethyl)-N'-(2-naphthylsulfonyl)malonamide

(1) diethyl (2-naphthylmethyl)malonate

In the same manner as in Example 6 (1), a crude product of the title compound was obtained using diethyl malonate (7.46 g) and 2-(bromomethyl)naphthalene (10.3 g).

(2) monoethyl (2-naphthylmethyl)malonate

In the same manner as in Example 1 (1), the title compound (2.88 g) was obtained as an oil using the above-mentioned crude product.

$^1$H-NMR (400 Mz, CDCl$_3$) δ1.18 (3H, t, J=7.2 Hz), 3.35-3.45 (2H, m), 3.81 (1H, J=7.7 Hz), 4.09-4.20 (2H, m), 7.33 (1H, dd, J=8.5, 1.4 Hz), 7.41-7.49 (2H, m), 7.66 (1H, s), 7.76-7.81 (3H, m).

(3) ethyl 2-(2-naphthylmethyl)-3-[(2-naphthylsulfonyl)amino]-3-oxopropionate In the same manner as in Example 1 (2), the title compound (290 mg) was obtained as a white powder using the above-mentioned compound (280 mg).

$^1$H-NMR (400 Mz, CDCl$_3$) δ1.00 (3H, t, J=7.2 Hz), 3.22-3.31 (2H, m), 3.73 (1H, t, J=7.2 Hz), 4.02 (2H, q, J=7.2 Hz), 7.04 (1H, dd, J=8.4, 1.2 Hz), 7.27-7.45 (5H, m), 7.50-7.54 (1H, m), 7.59-7.86 (6H, m), 8.60 (1H, s), 10.04 (1H, s).

(4) 2-(2-naphthylmethyl)-3-[(2-naphthylsulfonyl)amino]-3-oxopropionic acid

In the same manner as in Example 1 (3), the title compound (272 mg) was obtained using the above-mentioned compound (290 mg).

$^1$H-NMR (400 Mz, CDCl$_3$) δ3.30-3.38 (2H, m), 3.67 (1H, t, J=7.2 Hz), 7.02-7.05 (1H, m), 7.32-7.52 (5H, m), 7.63-7.74 (3H, m), 7.86-8.00 (4H, m), 8.61 (1H, s).

(5) N,N-diethyl-2-(2-naphthylmethyl)-N'-(2-naphthylsulfonyl)malonamide

In the same manner as in Example 1 (4), a crude product was obtained using the above-mentioned compound (290 mg). This was purified by silica gel column chromatography to give the title compound (151 mg) as a white powder.

$^1$H-NMR (400 Mz, DMSO-d$_6$) δ0.78-0.88 (6H, m), 3.06-3.23 (6H, m), 3.98 (1H, t, J=7.2 Hz), 7.24 (1H, dd, J=8.8, 1.6 Hz), 7.40-7.47 (2H, m), 7.54 (1H, s), 7.62-7.81 (6H, m), 7.96 (1H, d, J=8.8 Hz), 8.04 (1H, d, J=8.0 Hz), 8.17 (1H, d, J=8.0 Hz), 8.53 (1H, s), 12.37 (1H, brs).
MS: 489(M+H)$^+$.

Example 124

Synthesis of 2-(4-biphenylmethyl)-N,N-diethyl-N'-(2-naphthylsulfonyl)malonamide

(1) diethyl (4-biphenylmethyl)malonate

In the same manner as in Example 6 (1), a crude product of the title compound was obtained using diethyl malonate (5.02 g) and 4-(bromomethyl)biphenyl (7.75 g).

(2) monoethyl (4-biphenylmethyl)malonate

In the same manner as in Example 1 (1), the title compound (1.05 g) was obtained as a white solid using the above-mentioned crude product.

$^1$H-NMR (400 Mz, DMSO-d$_6$) δ1.18 (3H, t, J=6.8 Hz), 3.07-3.15 (2H, m), 3.74 (1H, t, J=8.0 Hz), 4.01-4.12 (2H, m), 7.31-7.36 (3H, m), 7.43-7.47 (2H, m), 7.58 (2H, d, J=8.0 Hz), 7.64 (2H, d, J=8.0 Hz), 12.86 (1H, brs).

(3) ethyl 2-(4-biphenylmethyl)-3-[(2-naphthylsulfonyl)amino]-3-oxopropionate In the same manner as in Example 1 (2), the title compound (910 mg) was obtained as a white powder using the above-mentioned compound (1.01 g).

$^1$H-NMR (400 Mz, DMSO-d$_6$) δ1.00 (3H, t, J=7.2 Hz), 2.94-3.03 (2H, m), 3.76-3.79 (1H, m), 4.01 (2H, q, J=7.2 Hz), 7.06 (2H, d, J=8.0 Hz), 7.29 (2H, d, J=8.0 Hz), 7.33-7.37 (1H, m), 7.43-7.51 (4H, m), 7.63-7.81 (3H, m), 8.02 (1H, d, J=8.4 Hz), 8.10 (1H, d, J=8.8 Hz), 8.19 (1H, d, J=8.0 Hz), 8.54 (1H, d, J=0.8 Hz), 12.55 (1H, brs).

(4) 2-(4-biphenylmethyl)-3-[(2-naphthylsulfonyl)amino]-3-oxopropionic acid

In the same manner as in Example 1 (3), the title compound (859 mg) was obtained using the above-mentioned compound (910 mg).

$^1$H-NMR (400 Mz, DMSO-d$_6$) δ2.91-3.01 (2H, m), 3.67-3.71 (1H, m), 7.02 (2H, d, J=8.0 Hz), 7.22 (2H, d, J=8.0 Hz), 7.33-7.38 (1H, m), 7.42-7.47 (4H, m), 7.64-7.91 (3H, m), 8.00 (1H, d, J=8.4 Hz), 8.07 (1H, d, J=8.8 Hz), 8.18 (1H, d, J=8.0 Hz), 8.53 (1H, s), 12.47 (1H, brs), 13.00 (1H, brs).

(5) 2-(4-biphenylmethyl)-N,N-diethyl-N'-(2-naphthylsulfonyl)malonamide

In the same manner as in Example 1 (4), the title compound (760 mg) was obtained as a white solid using the above-mentioned compound (782 mg).

$^1$H-NMR (400 Mz, CDCl$_3$) δ0.84 (3H, t, J=7.2 Hz), 1.03 (3H, t, J=7.2 Hz), 2.88-2.93 (2H, m), 3.04-3.19 (3H, m), 3.43-3.52 (1H, m), 3.59-3.63 (1H, m), 7.06 (2H, d, J=8.0 Hz), 7.31 (2H, d, J=8.0 Hz), 7.31-7.35 (1H, m), 7.39-7.47 (4H, m), 7.58-7.68 (2H, m), 7.89-8.05 (4H, m), 8.67 (1H, s).

MS: 515(M+H)$^+$.

Example 125

Synthesis of N,N-diethyl-2-[4-(1H-imidazol-1-yl)benzyl]-N'-(2-naphthylsulfonyl)malonamide hydrochloride To a solution of hydrochloride salt (550 mg) of the compound obtained in Example 7 in ethanol (4 mL) were added 35% aqueous formaldehyde solution (350 μL), 40% aqueous para-formaldehyde solution (600 μL) and 28% aqueous ammonia (250 μL), and the mixture was stirred at 50° C. for 3 hr. The mixture was concentrated under reduced pressure, and the residue was purified by silica gel column chromatography. This was dissolved in ethyl acetate (5 mL), 4 mol/L hydrochloric acid/ethyl acetate (1 mL) was added, and the precipitate was collected by filtration to give the title compound (295 mg) as a white solid.

$^1$H-NMR (400 Mz, DMSO-d$_6$) δ0.87 (6H, t, J=7.2 Hz), 2.96-3.10 (2H, m), 3.11-3.23 (4H, m), 4.03 (1H, t, J=7.2 Hz), 7.35 (2H, d, J=8.4 Hz), 7.52 (2H, d, J=8.4 Hz), 7.64-7.74 (2H, m), 7.81-7.84 (1H, m), 7.89 (1H, s), 8.03 (1H, d, J=8.4 Hz), 8.12 (1H, d, J=8.8 Hz), 8.17 (1H, s), 8.18 (1H, d, J=8.4 Hz), 8.54 (1H, d, J=0.8 Hz), 9.56 (1H, s), 12.80 (1H, brs).

MS:505(M+H)$^+$.

Example 126

Synthesis of 2-[4-(5-chloro-2-pyridyloxy)benzyl]-N,N -diethyl-N'-(2-naphthylsulfonyl)malonamide

(1) triethyl 2-[4-(5-chloro-2-pyridyloxy)phenyl]ethane-1,1,1-tricarboxylate

In the same manner as in Example 117 (1), the title compound (4.60 g) was obtained as an oil using triethyl methanetricarboxylate (2.60 g) and 4-(5-chloro-2-pyridyloxy)benzyl chloride (2.77 g).

$^1$H-NMR (400 Mz, CDCl$_3$) δ1.23 (9H, t, J=7.2 Hz), 3.52 (2H, s), 4.21 (6H, q, J=7.2 Hz), 6.83 (1H, d, J=8.8 Hz), 6.99 (2H, d, J=8.4 Hz), 7.32 (2H, d, J=8.4 Hz), 7.61 (1H, dd, J=8.8, 2.8 Hz), 8.10 (1H, d, J=2.8 Hz).

(2) monoethyl [4-(5-chloro-2-pyridyloxy)benzyl]malonate

In the same manner as in Example 117 (2), the title compound (2.96 g) was obtained as an oil using the above-mentioned compound (4.60 g).

$^1$H-NMR (400 Mz, DMSO-d$_6$) δ1.12 (3H, t, J=7.2 Hz), 3.02-3.12 (2H, m), 3.71 (1H, t, J=8.0 Hz), 4.07 (2H, q, J=7.2 Hz), 7.03-7.27 (5H, m), 7.94 (1H, dd, J=8.8, 2.8 Hz), 8.19 (1H, d, J=2.8 Hz), 12.90 (1H, brs).

(3) ethyl 2-[4-(5-chloro-2-pyridyloxy)benzyl]-3-(N,N-diethylamino)-3-oxopropionate In the same manner as in Example 1 (4), the reaction mixture was obtained using the above-mentioned compound (2.67 g). The reaction mixture was adjusted to pH=1-2 by the addition of dilute hydrochloric acid (50 mL) and extracted with ethyl acetate (100 mL). The organic layer was washed with water and saturated brine, and concentrated under reduced pressure to give the title compound (2.40 g) as an oil.

$^1$H-NMR (400 Mz, DMSO-d$_6$) δ0.88-0.93 (6H, m), 1.13 (3H, t, J=7.2 Hz), 3.01-3.28 (6H, m), 4.02-4.09 (3H, m), 7.01-7.03 (3H, m), 7.24 (2H, d, J=8.8 Hz), 7.93 (1H, dd, J=8.4, 2.4 Hz), 8.17 (1H, d, J=2.4 Hz).

(4) 2-[4-(5-chloro-2-pyridyloxy)benzyl]-3-(N,N-diethylamino)-3-oxopropionic acid In the same manner as in Example 1 (3), the title compound (1.91 g) was obtained as an oil using the above-mentioned compound (2.40 g).

$^1$H-NMR (400 Mz, DMSO-d$_6$) δ0.85-0.96 (6H, m), 2.97-3.34 (6H, m), 3.91 (1H, dd, J=9.2, 6.0 Hz), 7.00-7.03 (3H, m), 7.24 (1H, d, J=8.4 Hz), 7.93 (1H, dd, J=8.8, 2.8 Hz), 8.17 (1H, d, J=2.8 Hz), 12.56 (1H, brs).

(5) 2-[4-(5-chloro-2-pyridyloxy)benzyl]-N,N-diethyl-N'-(2-naphthylsulfonyl)malonamide In the same manner as in Example 1 (2), the title compound (1.03 g) was obtained as a white solid using the above-mentioned compound (1.91 g).

¹H-NMR (400 Mz, DMSO-d₆) δ0.88 (6H, t, J=7.2 Hz), 2.93 (2H, d, J=7.2 Hz), 3.10-3.25 (4H, m), 3.87 (1H, t, J=7.2 Hz), 6.81 (2H, d, J=8.4 Hz), 7.02-7.06 (3H, m), 7.65-7.74 (2H, m), 7.81 (1H, dd, J=8.8, 1.6 Hz), 7.93-7.96 (1H, m), 8.04 (1H, d, J=8.0 Hz), 8.12 (1H, d, J=8.8 Hz), 8.16-8.19 (2H, m), 8.55 (1H, s), 12.30 (1H, brs).
MS: 566(M+H)⁺.

Example 127

Synthesis of N,N-diethyl-N'-(2-naphthylsulfonyl)-2-[4-(2-pyridyloxy)benzyl]malonamide To a mixed solution of the compound (720 mg) obtained in Example 126 in ethanol (30 mL)/ethyl acetate (10 mL) was added 10% palladium/carbon (350 mg), and the mixture was stirred under hydrogen atmosphere for 42 hr. Insoluble material was removed by filtration, and the filtrate was concentrated under reduced pressure. The residue was purified by silica gel column chromatography to give the title compound (265 mg) as a white solid.
¹H-NMR (300 Mz, DMSO-d₆) δ0.88 (6H, t, J=6.9 Hz), 2.92 (2H, d, J=6.9 Hz), 3.05-3.23 (4H, m), 3.87 (1H, t, J=6.9 Hz), 6.78 (2H, d, J=8.4 Hz), 6.97 (1H, d, J=8.1 Hz), 7.03 (2H, d, J=8.4 Hz), 7.07-7.13 (1H, m), 7.60-7.87 (4H, m), 8.02-8.19 (4H, m), 8.55 (1H, s), 12.35 (1H, brs).
MS: 532(M+H)⁺.

Example 128

Synthesis of N,N-diethyl-N'-(2-naphthylsulfonyl)-2-[(2-phenyl-1,3-benzoxazol-6-yl)methyl]malonamide (1) ethyl 2-phenyl-1,3-benzoxazole-6-carboxylate To a solution of ethyl 3-hydroxy-4-nitrobenzoate (3.56 g) in ethyl acetate (100 mL) was added 10% palladium/carbon (600 mg), and the mixture was stirred under hydrogen atmosphere for 5 hr. Insoluble material was removed by filtration, and the filtrate was concentrated under reduced pressure. To a solution of the residue in methanol (100 mL) were added benzaldehyde (1.50 mL) and sodium sulfate (1.00 g), and the mixture was stirred at 45° C. for 16 hr. Insoluble material was removed by filtration, and the filtrate was concentrated under reduced pressure. To a solution of the residue in methylene chloride (100 mL) was added 2,3-dichloro-5,6-dicyano-1,4-benzoquinone (DDQ) (4.21 g), and the mixture was stirred at room temperature for 30 min. Saturated aqueous sodium hydrogen carbonate solution (300 mL) was added to the reaction mixture, and the mixture was extracted with chloroform (100 mL×2). The organic layer was washed with saturated brine. After concentration under reduced pressure, the residue was purified by silica gel column chromatography to give the title compound (3.60 g) as a pale-yellow solid.
¹H-NMR (300 Mz, CDCl₃) δ1.44 (3H, t, J=7.1 Hz), 4.43 (2H, q, J=7.1 Hz), 7.53-7.59 (3H, m), 7.90 (1H, d, J=8.4 Hz), 8.11 (1H, dd, J=8.4, 1.4 Hz), 8.27-8.30 (3H, m).

(2) 6-hydroxymethyl-2-phenyl-1,3-benzoxazole

To a solution of the above-mentioned compound (3.58 g) in THF (100 mL) was added lithium aluminum hydride (510 mg) under ice-cooling, and the mixture was stirred at room temperature for 39 hr. Saturated aqueous (+)-potassium sodium tartrate solution (300 mL) was added to the reaction mixture, and the mixture was extracted with ethyl acetate (200 mL×2). The organic layer was washed with saturated brine and concentrated under reduced pressure to give the title compound (2.60 g) as a white solid.
¹H-NMR (400 Mz, DMSO-d₆) δ4.65 (2H, d, J=5.6 Hz), 5.36 (1H, t, J=5.6 Hz), 7.37 (1H, d, J=8.0 Hz), 7.62-7.64 (3H, m), 7.71 (1H, s), 7.75 (1H, d, J=8.0 Hz), 8.19-8.22 (2H, m).

(3) 6-chloromethyl-2-phenyl-1,3-benzoxazole

To a solution of the above-mentioned compound (2.56 g) in chloroform (200 mL) was added thionyl chloride (2.73 mL), and the mixture was heated under reflux for 8 hr. Saturated aqueous sodium hydrogen carbonate solution (100 mL) was added to extract the reaction mixture. The organic layer was washed with saturated brine and concentrated under reduced pressure to give the title compound (2.69 g) as a pale-yellow solid.
¹H-NMR (400 Mz, DMSO-d₆) δ4.94 (2H, s), 7.51 (1H, dd, J=8.0, 1.2 Hz), 7.52-7.66 (3H, m), 7.81 (1H, d, J=8.0 Hz), 7.90 (1H, s), 8.20-8.23 (2H, m).

(4) triethyl 2-(2-phenyl-1,3-benzoxazol-6-yl)ethane-1,1,1-tricarboxylate

In the same manner as in Example 117 (1), the title compound (4.83 g) was obtained as an oil using triethyl methanetricarboxylate (2.56 g) and the above-mentioned compound (2.69 g).
¹H-NMR (400 Mz, CDCl₃) δ1.22 (9H, t, J=7.2 Hz), 3.67 (2H, s), 4.22 (6H, q, J=7.2 Hz), 7.24-7.27 (1H, m), 7.50-7.54 (3H, m), 7.61-7.63 (2H, m), 8.22-8.25 (2H, m).

(5) monoethyl [(2-phenyl-1,3-benzoxazol-6-yl)methyl]malonate

In the same manner as in Example 117 (2), the title compound (3.55 g) was obtained as a pale-yellow solid using the above-mentioned compound (4.83 g).
¹H-NMR (400 Mz, DMSO-d₆) δ1.03-1.10 (3H, m), 3.17-3.26 (2H, m), 3.82 (1H, t, J=8.0 Hz), 4.00-4.11 (2H, m), 7.29 (1H, dd, J=8.0, 1.2 Hz), 7.59-7.72 (5H, m), 8.18-8.20 (2H, m), 12.92 (1H, brs).

(6) ethyl 3-(N,N-diethylamino)-3-oxo-2-[(2-phenyl-1,3-benzoxazol-6-yl)methyl]propionate In the same manner as in Example 1 (4), the reaction mixture was obtained using the above-mentioned compound (820 mg). The reaction mixture was adjusted to pH=1-2 by the addition of dilute hydrochloric acid (50 mL) and extracted with ethyl acetate (100 mL). The organic layer was washed with water and saturated brine, and concentrated under reduced pressure to give the title compound (860 mg) as an oil.
¹H-NMR (300 Mz, CDCl₃) δ0.94 (3H, t, J=7.2 Hz), 1.04 (3H, t, J=7.2 Hz), 3.00-3.25 (2H, m), 3.25-3.49 (4H, m), 3.80-3.87 (1H, m), 4.19 (2H, q, J=7.2 Hz), 7.22 (1H, dd, J=8.1, 1.2 Hz), 7.48 (1H, d, J=1.2 Hz), 7.52-7.54 (3H, m), 7.66 (1H, d, J=8.1 Hz), 8.22-8.26 (2H, m).

(7) 3-(N,N-diethylamino)-3-oxo-2-[(2-phenyl-1,3-benzoxazol-6-yl)methyl]propionic acid In the same manner as in Example 1 (3), the title compound (630 mg) was obtained as a white powder using the above-mentioned compound (860 mg).
¹H-NMR (400 Mz, CDCl₃) δ0.95 (3H, t, J=7.2 Hz), 1.07 (3H, t, J=7.2 Hz), 2.67-2.75 (1H, m), 2.84-2.93 (1H, m), 3.06-3.14 (1H, m), 3.07-3.12 (2H, m), 3.56-3.64 (1H, m), 3.80 (1H, dd, J=9.6, 5.2 Hz), 7.20 (1H, dd, J=8.0, 1.2 Hz), 7.44 (1H, d, J=1.2 Hz), 7.52-7.56 (3H, m), 7.69 (1H, d, J=8.0 Hz), 8.23-8.26 (2H, m).

(8) N,N-diethyl-N'-(2-naphthylsulfonyl)-2-[(2-phenyl-1,3-benzoxazol-6-yl)methyl]malonamide In the same manner as in Example 1 (2), the title compound (361 mg) was obtained as a white solid using the above-mentioned compound (630 mg).

$^1$H-NMR (300 Mz, DMSO-$d_6$) $\delta$0.88 (3H, t, J=6.5 Hz), 3.09-3.24 (6H, m), 3.98 (1H, t, J=7.2 Hz), 7.12 (1H, d, J=8.3 Hz), 7.44 (1H, s), 7.51 (1H, d, J=8.3 Hz), 7.64-7.72 (6H, m), 7.94-8.02 (2H, m), 8.15-8.17 (3H, m), 8.52 (1H, s), 12.33 (1H, brs).

MS: 556(M+H)$^+$.

Example 129

Synthesis of N,N-diethyl-2-[4-(1,3-dihydro-2H-isoindol-2-yl)benzyl]-N'-(2-naphthylsulfonyl)malonamide hydrochloride To a solution of hydrochloride salt (200 mg) of the compound obtained in Example 7 in DMF (5 mL) were added O-xylene dibromide (110 mg) and potassium carbonate (260 mg), and the mixture was stirred at room temperature for 17 hr. The reaction mixture was adjusted to pH=1-2 by the addition of dilute hydrochloric acid, and the precipitate was collected by filtration to give the title compound (188 mg) as a white solid.

$^1$H-NMR (300 Mz, DMSO-$d_6$) $\delta$0.88-0.92 (6H, m), 2.67-2.88 (2H, m), 3.00-3.62 (5H, m), 4.46 (4H, s), 6.37 (2H, d, J=8.1 Hz), 6.90 (2H, d, J=8.1 Hz), 7.29-7.41 (4H, m), 7.55-7.68 (2H, m), 7.80 (1H, d, J=8.6 Hz), 7.83-8.07 (3H, m), 8.33 (1H, s), 12.22 (1H, brs).

MS: 556(M+H)$^+$.

Example 130

Synthesis of N,N-diethyl-N'-(2-naphthylsulfonyl)-2-[4-(1-oxo-1,3-dihydro-2H-isoindol-2-yl)benzyl]malonamide (1) N,N-diethyl-2-[4-(1,3-dioxo-1,3-dihydro-2H-isoindol-2-yl)benzyl]-N'-(2-naphthylsulfonyl)malonamide To a solution of hydrochloride salt (500 mg) of the compound obtained in Example 7 in pyridine (10 mL) was added phthaloyl chloride (150 μL) under ice-cooling, and the mixture was stirred at room temperature for 1.5 hr. The reaction mixture was adjusted to pH=1-2 by the addition of dilute hydrochloric acid, and the precipitate was collected by filtration. This was purified by silica gel column chromatography to give the title compound (140 mg) as a pale-yellow powder.

$^1$H-NMR (300 Mz, CDCl$_3$) $\delta$0.80 (3H, t, J=7.2 Hz), 1.02 (3H, t, J=7.2 Hz), 2.85 (2H, q, J=7.2 Hz), 2.94-3.19 (3H, m), 3.39-3.61 (2H, m), 7.04 (2H, d, J=8.4 Hz), 7.17 (2H, d, J=8.4 Hz), 7.21-7.27 (1H, m), 7.53-8.04 (9H, m), 8.65 (1H, s).

(2) N,N-diethyl-N'-(2-naphthylsulfonyl)-2-[4-(1-oxo-1,3-dihydro-2H-isoindol-2-yl)benzyl]malonamide To a solution of the above-mentioned compound (140 mg) in acetic acid (10 mL) was added zinc (300 mg), and the mixture was heated under reflux for 1 hr. Insoluble material was removed by filtration and, and the filtrate was concentrated under reduced pressure. The residue was purified by silica gel column chromatography to give the title compound (22 mg) as a white solid.

$^1$H-NMR (400 Mz, DMSO-$d_6$) $\delta$0.88-0.92 (6H, m), 2.98-2.97 (2H, m), 3.10-3.26 (4H, m), 8.85-3.92 (1H, m), 4.84 (2H, d, J=16.0 Hz), 7.08 (2H, d, J=8.4 Hz), 7.57 (2H, d, J=8.4 Hz), 7.56-7.70 (5H, m), 7.78-7.81 (2H, m), 8.03-8.05 (1H, m), 8.13 (1H, d, J=8.8 Hz), 8.17-8.20 (1H, m), 8.53 (1H, s), 12.31 (1H, brs).

MS: 570(M+H)$^+$.

Example 131

Synthesis of N,N-diethyl-2-{4-[(1,3-benzoxazol-2-yl)amino]benzyl}-N'-(2-naphthylsulfonyl)malonamide To a solution of the compound (450 mg) obtained in Example 7 in N-methyl-2-pyrrolidinone (2 mL) were added 2-chloro-1,3-benzoxazole (230 μL) and diisopropyl ethyl amine (500 μL), and the mixture was stirred at 100° C. for 10 hr. The reaction mixture was adjusted to pH=2-3 by the addition of dilute hydrochloric acid, and extracted with ethyl acetate (50 mL). The organic layer was washed with saturated brine and concentrated under reduced pressure. The residue was purified by silica gel column chromatography to give the title compound (256 mg) as a white solid.

$^1$H-NMR (300 MHz, DMSO-$d_6$) $\delta$0.85 (3H, t, J=7.3 Hz), 1.05 (3H, t, J=7.3 Hz), 2.80-3.30 (5H, m), 3.28-3.63 (2H, m), 7.02 (2H, d, J=8.4 Hz), 7.05-7.40 (6H, m), 7.49 (1H, d, J=7.4 Hz), 7.50-7.70 (2H, m), 7.85-8.08 (4H, m), 8.67 (1H, brs).

MS: 571(M+H)$^+$.

Example 132

Synthesis of N,N-diethyl-N'-(2-naphthylsulfonyl)-2-[4-(phenylethynyl)benzyl]malonamide (1) 2,2-dimethyl-5-[4-(phenylethynyl)benzyl]-1,3-dioxane-4,6-dione To a mixture of Meldrum's acid (688 mg) and 4-phenylethynylbenzoic acid (955 mg) in methylene chloride (30 mL) was added a solution of 4-dimethylaminopyridine (830 mg) and N, N'-dicyclohexylcarbodiimide (976 mg) in methylene chloride (15 mL) under ice-cooling, and the mixture was stirred at room temperature for 66 hr. Insoluble material was removed by filtration, and the filtrate was washed with 10% potassium hydrogen sulfate (30 mL) and saturated brine and concentrated under reduced pressure. The residue was dissolved in acetic acid (5 mL), and the solution was cooled to 0° C. Sodium borohydride (408 mg) was added, and the mixture was stirred at room temperature for 6 hr. Water (50 mL) was added to the reaction mixture, and the mixture was extracted with methylene chloride (50 mL×2). The organic layer was washed with saturated brine and concentrated under reduced pressure. The residue was washed with isopropanol, and the resulting precipitate was collected by filtration to give the title compound (654 mg) as a white solid.

$^1$H-NMR (300 MHz, CDCl$_3$) $\delta$1.56 (3H, s), 1.75 (3H, s), 3.50 (2H, d, J=4.8 Hz), 3.76 (1H, t, J=4.8 Hz), 7.28-7.40 (5H, m), 7.44-7.55 (4H, m).

(2) 3-(N,N-diethylamino)-3-oxo-2-[4-(phenylethynyl)benzyl]propionic acid

In the same manner as in Example 119 (2), the title compound (470 mg) was obtained as a white solid using the above-mentioned compound (654 mg).

$^1$H-NMR (300 MHz, CDCl$_3$) δ0.97 (3H, t, J=7.2 Hz), 1.09 (3H, t, J=7.2 Hz), 2.70-3.01 (2H, m), 3.05-3.19 (1H, m), 3.19-3.37 (1H, m), 3.52-3.68 (1H, m), 3.73 (1H, dd, J=9.6, 5.4 Hz), 7.18 (2H, d, J=8.1 Hz), 7.34 (3H, dd, J=6.0, 3.6 Hz), 7.46 (2H, d, J=8.1 Hz), 7.48-7.60 (2H, m).

(3) N,N-diethyl-N'-(2-naphthylsulfonyl)-2-[4-(phenylethynyl)benzyl]malonamide In the same manner as in Example 1 (2), a crude product was obtained using the above-mentioned compound (470 mg). This was washed with ethyl acetate, and the resulting precipitate was collected by filtration to give the title compound (365 mg) as a white solid.

$^1$H-NMR (400 MHz, DMSO-d$_6$) δ0.82 (3H, t, J=7.2 Hz), 1.03 (3H, t, J=7.2 Hz), 2.85 (2H, q, J=7.2 Hz), 3.02 (1H, dd, J=14.4, 4.8 Hz), 3.08-3.22 (2H, m), 3.40-3.52 (1H, m), 3.56 (1H, q, J=10.2 Hz), 7.01 (2H, d, J=8.1 Hz), 7.14 (2H, d, J=9.6 Hz), 7.31-7.40 (3H, m), 7.45-7.55 (2H, m), 7.58-7.70 (2H, m), 7.86-8.08 (5H, m), 8.67 (1H, brs).

MS: 539(M+H)$^+$.

Example 133

Synthesis of N,N-diethyl-N'-(2-naphthylsulfonyl)-2-{4-[(E)-2-phenylvinyl]benzyl}malonamide

(1) triethyl 2-{4-[(E)-2-phenylvinyl]phenyl}ethane-1,1,1-tricarboxylate

In the same manner as in Example 117 (1), the title compound (4.69 g) was obtained as an oil using triethyl methanetricarboxylate (2.5 mL) and 4-chloromethylstilbene (2.29 g).

$^1$H-NMR (300 MHz, CDCl$_3$) δ1.22 (9H, t, J=6.9 Hz), 3.53 (2H, s), 4.21 (6H, dd, J=14.1, 6.9 Hz), 7.07 (2H, s), 7.25-7.30 (2H, m), 7.37-7.42 (5H, m), 7.46-7.55 (2H, m).

(2) monoethyl {4-[(E)-2-phenylvinyl]benzyl}malonate

In the same manner as in Example 117 (2), the title compound (2.14 g) was obtained as a white solid using the above-mentioned compound (4.69 g).

$^1$H-NMR (300 MHz, CDCl$_3$) δ1.22 (3H, t, J=7.2 Hz), 3.26 (2H, d, J=7.5 Hz), 3.70 (1H, t, J=7.5 Hz), 4.18 (2H, q, J=7.2 Hz), 7.18-7.30 (3H, m), 7.35 (2H, t, J=7.2 Hz), 7.46 (2H, d, J=8.1 Hz), 7.49 (2H, d, J=8.1 Hz).

(3) ethyl 3-(N,N-diethylamino)-3-oxo-2-{4-[(E)-2-phenylvinyl]benzyl}propionate In the same manner as in Example 1 (4), the reaction mixture was obtained using the above-mentioned compound (2.14 g). The reaction mixture was adjusted to pH=1-2 by the addition of dilute hydrochloric acid (50 mL), and extracted with ethyl acetate (100 mL). The organic layer was washed with water and saturated brine, and concentrated under reduced pressure to give the title compound (2.63 g) as a white solid.

$^1$H-NMR (300 MHz, CDCl$_3$) δ0.98 (3H, t, J=7.2 Hz), 1.06 (3H, t, J=7.2 Hz), 1.24 (3H, t, J=7.2 Hz), 3.15-3.46 (6H, m), 3.78 (1H, dd, J=8.7, 2.4 Hz), 4.17 (2H, q, J=6.9 Hz), 7.07 (2H, d, J=3.3 Hz), 7.14-7.28 (2H, m), 7.28-7.49 (5H, m), 7.50 (2H, d, J=7.5 Hz).

(4) 3-(N,N-diethylamino)-3-oxo-2-{4-[(E)-2-phenylvinyl]benzyl}propionic acid In the same manner as in Example 1 (3), the title compound (2.53 g) was obtained as a white powder using the above-mentioned compound (2.63 g).

(5) N,N-diethyl-N'-(2-naphthylsulfonyl)-2-{4-[(E)-2-phenylvinyl]benzyl}malonamide In the same manner as in Example 1 (2), the title compound (448 mg) was obtained as a white solid using the above-mentioned compound (2.53 g).

$^1$H-NMR (400 MHz, DMSO-d$_6$) δ0.83 (3H, t, J=7.5 Hz), 1.04 (3H, t, J=7.2 Hz), 2.86 (2H, q, J=7.5 Hz), 3.00 (1H, dd, J=7.4, 5.4 Hz), 3.05-3.22 (2H, m), 3.39-3.50 (1H, m), 3.57 (1H, m), 6.97 (2H, d, J=7.2 Hz), 6.96 (2H, d, J=7.2 Hz), 7.21 (2H, d, J=8.1 Hz), 7.36 (2H, dd, J=15.0, 7.2 Hz), 7.48 (1H, d, J=7.2 Hz), 7.58-7.70 (2H, m), 7.85-8.08 (4H, m), 8.67 (1H, s), 10.96 (1H, brs).

MS: 541(M+H)$^+$.

Example 134

Synthesis of N,N-diethyl-N'-(2-naphthylsulfonyl)-2-(4-phenethylbenzyl)malonamide To a solution of the compound (412 mg) obtained in Example 133 in ethanol (40 mL) was added 10% palladium/carbon (100 mg), and the mixture was stirred under hydrogen atmosphere at room temperature for 14 hr. Insoluble material was removed by filtration, and the filtrate was concentrated under reduced pressure. The residue was purified by silica gel column chromatography to give the title compound (279 mg) as a white solid.

NMR (400 MHz, DMSO-d$_6$) δ0.60-0.98 (6H, m), 2.67-2.80 (4H, m), 2.80-2.95 (2H, m), 3.05-3.26 (4H, m), 3.82 (1H, t, J=7.2 Hz), 6.88 (4H, dd, J=13.0, 8.0 Hz), 7.14-7.22 (3H, m), 7.23-7.30 (2H, t, J=7.7 Hz), 7.71 (1H, t, J=7, 7 Hz) 7.77 (1H, t, J=7.0 Hz), 7.81 (1H, dd, J=8.6, 1.3 Hz), 8.09 (1H, d, J=8.1 Hz), 8.14 (1H, d, J=8.7 Hz), 8.20 (1H, d, J=8.1 Hz), 8.31 (1H, s), 12.26 (1H, brs).

MS: 543(M+H)$^+$.

Example 135

Synthesis of N,N-diethyl-2-[4-(2,5-dioxo-3-phenylimidazolidin-1-yl)benzyl]-N'-(2-naphthylsulfonyl)malonamide

(1) N,N-diethyl-2-{4-[(N"-ethoxycarbonyl-N"-phenyl)aminoacetyl]aminobenzyl}-N'-(2-naphthylsulfonyl)malonamide To a solution of N-phenylglycine (1.57 g) in THF (30 mL) were added ethyl chloroformate (1.60 mL) and triethylamine (4.00 mL) under ice-cooling, and the mixture was stirred at room temperature for 4 hr. The compound (453 mg) obtained in Example 7 was added to the reaction mixture, and the mixture was stirred at room temperature for 24 hr. The reaction solution was adjusted to pH=2-3 by the addition of dilute hydrochloric acid, and the mixture was extracted with ethyl acetate (100 mL×2). The organic layer was washed with saturated brine and concentrated under reduced pressure, and the residue was purified by silica gel column chromatography to give the title compound (587 mg) as a white solid.

$^1$H-NMR (400 MHz, DMSO-d$_6$) δ0.84 (3H, t, J=7.2 Hz), 0.85 (3H, t, J=7.2 Hz), 1.13 (3H, t, J=7.2 Hz), 2.80-2.94 (2H, m), 3.05-3.25 (4H, m), 3.84 (1H, t, J=7.4 Hz), 4.07 (2H, q, J=7.2 Hz), 4.38 (2H, s), 6.99 (2H, d, J=8.4 Hz), 7.10-7.43 (7H, m), 7.63-7.80 (3H, m), 8.04 (1H, d, J=8.0 Hz), 8.09 (1H, d, J=8.8 Hz), 8.19 (1H, d, J=8.0 Hz), 8.53 (1H, s), 9.95 (1H, s), 12.96 (1H, brs).

(2) N,N-diethyl-2-[4-(2,5-dioxo-3-phenylimidazolidin-1-yl)benzyl]-N'-(2-naphthylsulfonyl)malonamide To a solution of the above-mentioned compound (587 mg) in pyridine (10 mL) was added DBU (138 μL), and the mixture was heated under reflux. The reaction solution was adjusted to pH=2-3 by the addition of dilute hydrochloric acid and extracted with ethyl acetate (50 mL×2). The organic layer was washed with saturated brine and concentrated under reduced pressure, and the residue was purified by silica gel column chromatography to give the title compound (462 mg) as a white solid.

$^1$H-NMR (400 MHz, DMSO-d$_6$) δ0.57-0.73 (6H, m), 2.97 (2H, d, J=7.2 Hz), 3.03-3.45 (4H, m), 3.90 (1H, d, J=7.2 Hz), 4.64 (2H, s), 7.05-7.26 (6H, m), 7.44 (2H, t, J=8.4 Hz), 7.60-7.81 (5H, m), 8.07 (1H, d, J=8.4 Hz), 8.14 (1H, d, J=8.4 Hz), 8.19 (1H, d, J=8.4 Hz), 8.54 (1H, s), 12.34 (1H, brs).
MS: 613(M+H)$^+$.

Example 136

Synthesis of 2-{4-[benzoyl(methyl)amino]benzyl}-N,N-diethyl-N'-(2-naphthylsulfonyl)malonamide (1) 4-[benzoyl(methyl)amino]benzoic acid To a mixture of 4-(methylamino)benzoic acid (1.50 g) in THF (30 mL) and 1 mol/L aqueous sodium hydroxide solution (30 mL) was added dropwise benzoyl chloride (1.20 mL) under ice-cooling, and the mixture was stirred at room temperature for 14 hr. The reaction mixture was adjusted to pH=1-2 by the addition of dilute hydrochloric acid, and extracted with ethyl acetate (50 mL×2). The organic layer was washed with saturated brine and concentrated under reduced pressure. The residue was washed with a chloroform/hexane mixture and collected by filtration to give the title compound (1.81 g) as a white solid.

(2) 5-{4-[benzoyl(methyl)amino]benzyl}-2,2-dimethyl-1,3-dioxane-4,6-dione

In the same manner as in Example 132 (1), the title compound (2.05 g) was obtained as a white solid using the above-mentioned compound (1.81 g).

$^1$H-NMR (300 MHz, CDCl$_3$) δ1.54 (3H, s), 1.74 (3H, s), 3.41 (2H, d, J=4.8 Hz), 3.45 (3H, s), 3.70 (1H, t, J=5.1 Hz), 6.96 (2H, d, J=8.4 Hz), 7.08-7.35 (7H, m).

(3) 2-{4-[benzoyl(methyl)amino]benzyl}-3-(N,N-diethylamino)-3-oxopropionic acid

In the same manner as in Example 119 (2), the title compound (1.53 g) was obtained as an oil using the above-mentioned compound (2.05 g).

$^1$H-NMR (300 MHz, CDCl$_3$) δ0.96 (3H, t, J=6.9 Hz), 0.98 (3H, t, J=6.9 Hz), 2.55-2.90 (2H, m), 2.98-3.10 (1H, m), 3.16 (2H, d, J=7.5 Hz), 3.45 (3H, s), 3.46-72 (2H, m), 6.97 (2H, d, J=8.4 Hz), 7.00 (2H, d, J=8.4 Hz), 7.10-7.36 (5H, m).

(4) 2-{4-[benzoyl(methyl)amino]benzyl}-N,N-diethyl-N'-(2-naphthylsulfonyl)malonamide In the same manner as in Example 1 (2), the title compound (2.29 g) was obtained as a white solid using the above-mentioned compound (1.53 g).

$^1$H-NMR (400 MHz, DMSO-d$_6$) δ0.70-0.92 (6H, m), 2.84 (2H, d, J=8.0 Hz), 2.95-3.22 (4H, m), 3.25 (3H, s), 3.76 (1H, t, J=7.2 Hz), 6.82 (2H, d, J=8.4 Hz), 6.89 (2H, d, J=8.4 Hz), 7.12-7.28 (5H, m), 7.64-7.84 (3H, m), 8.08 (1H, d, J=8.0 Hz), 8.13 (1H, d, J=8.8 Hz), 8.20 (1H, d, J=8.4 Hz), 8.55 (1H, s), 12.23 (1H, brs).
MS: 572(M+H)$^+$.

Example 137

Synthesis of 2-[4-(benzoylamino)-3,5-dimethylbenzyl]-N,N-diethyl-N'-(2-naphthylsulfonyl)malonamide (1) 5-(3,5-dimethyl-4-nitrobenzyl)-2,2-dimethyl-1,3-dioxane-4,6-dione In the same manner as in Example 132 (1), the title compound (1.30 g) was obtained as a yellow solid using 3,5-dimethyl-4-nitrobenzoic acid (1.10 g).

$^1$H-NMR (400 MHz, CDCl$_3$) δ1.67 (3H, s), 1.78 (3H, s), 2.28 (6H, s), 3.43 (2H, d, J=4.8 Hz), 3.72 (1H, t, J=4.8 Hz), 7.11 (2H, s).

(2) 3-(N,N-diethylamino)-2-(3,5-dimethyl-4-nitrobenzyl)-3-oxopropionic acid

In the same manner as in Example 119 (2), the title compound (1.66 g) was obtained as a yellow powder using the above-mentioned compound (1.30 g).

$^1$H-NMR (400 MHz, DMSO-d$_6$) δ0.88 (3H, t, J=6.8 Hz), 0.90 (3H, t, J=6.8 Hz), 2.19 (6H, s), 2.95-3.40 (6H, m), 3.98 (1H, t, J=6.8 Hz), 7.11 (2H, s).

(3) N,N-diethyl-2-(3,5-dimethyl-4-nitrobenzyl)-N'-(2-naphthylsulfonyl)malonamide In the same manner as in Example 1 (2), the title compound (2.06 g) was obtained as a yellow powder using the above-mentioned compound (1.66 g).

$^1$H-NMR (300 MHz, DMSO-d$_6$) 0.85 (3H, t, J=6.9 Hz), 0.87 (3H, t, J=6.9 Hz), 2.07 (6H, s), 2.92 (2H, d, J=7.2 Hz), 3.02-3.27 (4H, m), 3.90 (1H, t, J=6.9 Hz), 6.98 (2H, s), 7.63-7.80 (3H, m), 8.06 (1H, d, J=8.1 Hz), 8.09 (1H, d, J=8.1 Hz), 8.20 (1H, d, J=8.1 Hz), 8.56 (1H, s), 12.38 (1H, brs).

(4) 2-(4-amino-3,5-dimethylbenzyl)-N,N-diethyl-N'-(2-naphthylsulfonyl)malonamide To a solution of the above-mentioned compound (1.91 g) in DMF (30 mL) was added tin(II) chloride dehydrate (4.18 g), and the mixture was heated at 60° C. for 6 hr. Water (50 mL) and chloroform (50 mL) were added to the reaction mixture, and the mixture was stirred for 30 min. After stirring, the mixture was neutralized to pH7 with 1 mol/L aqueous sodium hydroxide solution, and extracted with chloroform (50 mL×2). The organic layer was washed with saturated brine and concentrated under reduced pressure, and the residue was purified by silica gel column chromatography to give the title compound (631 mg) as a pale-yellow solid.
  $^1$H-NMR (400 MHz, DMSO-d$_6$) 0.79 (3H, t, J=7.2 Hz), 1.01 (3H, t, J=7.2 Hz), 2.04 (6H, s), 2.68-3.09 (5H, m), 3.45-3.60 (2H, m), 6.64 (2H, s), 7.60-7.75 (2H, m), 7.88-8.09 (5H, m), 8.68 (1H, s).

(5) 2-[4-(benzoylamino)-3,5-dimethylbenzyl]-N,N-diethyl-N'-(2-naphthylsulfonyl)malonamide In the same manner as in Example 9, a crude product was obtained using the above-mentioned compound (300 mg). This was purified by silica gel column chromatography to give the title compound (170 mg) as a white solid.
  $^1$H-NMR (400 MHz, DMSO-d$_6$) δ0.88 (6H, t, J=6.8 Hz), 2.03 (6H, s), 2.89 (2H, d, J=6.8 Hz), 3.03-3.25 (4H, m), 3.87 (1H, t, J=7.2 Hz), 6.83 (2H, s), 7.45-3.88 (6H, m), 7.98 (2H, d, J=8.0 Hz), 8.06 (1H, d, J=8.0 Hz), 8.14 (1H, d, J=8.4 Hz), 8.22 (1H, d, J=7.6 Hz), 8.59 (1H, s), 9.64 (1H, s), 12.37 (1H, brs).
  MS: 586(M+H)$^+$.

Example 138

Synthesis of N,N-diethyl-2-{4-[(2-fluorobenzoyl)amino]-3,5-dimethylbenzyl}-N'-(2-naphthylsulfonyl)malonamide In the same manner as in Example 9, a crude product was obtained using the compound (331 mg) obtained in Example 137 (4) and 4-fluorobenzoyl chloride (82 μL). This was purified by silica gel column chromatography to give the title compound (239 mg) as a white solid.
  $^1$H-NMR (400 MHz, DMSO-d$_6$) δ0.87 (6H, t, J=7.2 Hz), 2.07 (6H, s), 2.88 (2H, d, J=6.8 Hz), 3.04-3.28 (4H, m), 3.87 (1H, t, J=7.2 Hz), 6.83 (2H, s), 7.28-7.40 (2H, m), 7.64-7.80 (4H, m), 8.06 (1H, d, J=8.4 Hz), 8.13 (1H, d, J=8.4 Hz), 8.22 (1H, d, J=8.0 Hz), 8.58 (1H, s), 9.62 (1H, s), 12.35 (1H, brs).
  MS: 604(M+H)$^+$.

Example 139

Synthesis of N,N-diethyl-N'-(2-naphthylsulfonyl)-2-[4-(4-oxoquinazolin-3 (4H)-yl)benzyl]malonamide The compound (429 mg) obtained in Example 43 was dissolve in a mixed solution (1.5 mL) of ethanol/acetic acid (10/1), ethyl ortho-formate (187 μL) was added, and the mixture was heated under reflux for 7 hr. The reaction mixture was concentrated under reduced pressure, and the residue was purified by silica gel column chromatography to give the title compound (175 mg) as a white solid.
  $^1$H-NMR (400 MHz, DMSO-d$_6$) δ0.78-0.99 (6H, m), 3.01 (2H, d, J=7.2 Hz), 3.08-3.28 (4H, m), 3.94 (1H, t, J=7.2 Hz), 7.12-7.28 (4H, m), 7.75-7.95 (6H, m), 8.04 (1H, d, J=8.4 Hz), 8.07-8.29 (4H, m), 8.56 (1H, s), 12.39 (1H, brs).
  MS: 583(M+H)$^+$.

Example 140

Synthesis of N,N-diethyl-2-[4-(2-methyl-4-oxo-quinazoline-3(4H)-yl)benzyl]-N'-(2-naphthylsulfonyl)malonamide In the same manner as in Example 139, the title compound (132 mg) was obtained as a white solid using the compound (211 mg) obtained in Example 43 and ethyl orthoacetate (105 μL).
  $^1$H-NMR (400 MHz, DMSO-d$_6$) δ0.86 (3H, t, J=7.2 Hz), 0.87 (3H, t, J=7.2 Hz), 2.03 (3H, s), 2.95-3.08 (2H, m), 3.08-3.28 (4H, m), 3.93 (1H, t, J=7.2 Hz), 7.13-7.30 (4H, m), 7.52 (1H, t, J=8.0 Hz), 7.59-7.75 (3H, m), 7.79-7.88 (2H, m), 8.06 (1H, d, J=8.0 Hz), 8.11 (1H, d, J=8.4 Hz), 8.15 (1H, d, J=8.4 Hz), 8.21 (1H, d, J=8.4 Hz), 8.56 (1H, s), 12.36 (1H, brs).
  MS: 597(M+H)$^+$.

Example 141

Synthesis of N,N-diethyl-N'-(2-naphthylsulfonyl)-2-[4-(4-oxopteridin-3(4H)-yl)benzyl]malonamide In the same manner as in Example 139, the title compound (130 mg) was obtained as a white solid using the compound (214 mg) obtained in Example 65.
  $^1$H-NMR (300 MHz, DMSO-d$_6$) δ0.89 (3H, t, J=6.9 Hz), 0.90 (3H, t, J=6.9 Hz), 3.02 (2H, d, J=6.9 Hz), 3.08-3.28 (4H, m), 3.95 (1H, t, J=6.9 Hz), 7.23 (2H, d, J=8.4 Hz), 7.27 (2H, d, J=8.4 Hz), 7.62 (1H, t, J=7.2 Hz), 7.71 (1H, t, J=7.2 Hz), 7.82 (1H, d, J=8.7 Hz), 8.06 (1H, d, J=8.1 Hz), 8.16 (1H, d, J=9.0 Hz), 8.19 (1H, d, J=8.1 Hz), 8.50 (1H, s), 8.57 (1H, s), 8.94 (1H, d, J=2.1 Hz), 9.08 (1H, d, J=2.1 Hz), 12.43 (1H, brs).
  MS: 585(M+H)$^+$.

Example 142

Synthesis of N,N-diethyl-2-[4-(2-methyl-4-oxopteridin-3(4H)-yl)benzyl]-N'-(2-naphthylsulfonyl)malonamide In the same manner as in Example 139, the title compound (71 mg) was obtained as a white solid using the compound (221 mg) obtained in Example 65 and ethyl orthoacetate (305 μL).
  $^1$H-NMR (300 MHz, DMSO-d$_6$) δ0.85 (3H, t, J=7.2 Hz), 0.87 (3H, t, J=7.2 Hz), 2.10 (3H, s), 2.92-3.29 (6H, m), 3.95 (1H, t, J=6.9 Hz), 7.10-7.35 (4H, m), 7.55-7.78 (2H, m), 7.84 (1H, d, J=9.0 Hz), 8.06 (1H, d, J=8.1 Hz), 8.16 (1H, d, J=8.1 Hz), 8.22 (1H, d, J=8.1 Hz), 8.59 (1H, s), 8.85 (1H, s), 9.04 (1H, m), 12.38 (1H, brs).
  MS: 599(M+H)$^+$.

Example 143

Synthesis of N,N-diethyl-N'-(2-naphthylsulfonyl)-2-[4-(4-quinazolinylamino)benzyl]malonamide To a solution of hydrochloride salt (378 mg) of the compound obtained in Example 7 in isopropanol (10 mL) were added 4-chloroquinazoline (127 mg) and diisopropylethylamine (410 μL), and the mixture was heated under reflux for 5.5 hr. Additional 4-chloroquinazoline (127 mg) was added, and the mixture was heated under reflux for 7 hr. The reaction mixture was adjusted to pH=2-3 by the addition of dilute hydrochloric acid, and extracted with ethyl acetate (50 mL×2). The organic layer was washed with saturated brine and concentrated under reduced pressure, and the residue was purified by silica gel column chromatography to give the title compound (186 mg) as a white solid.
  $^1$H-NMR (400 MHz, DMSO-d$_6$) δ0.87-0.91 (6H, m), 2.97 (2H, d, J=7.1 Hz), 3.13-3.25 (4H, m), 3.93 (1H, t, J=7.1 Hz), 7.14 (2H, d, J=7.7 Hz), 7.48 (2H, d, J=7.7 Hz), 7.56-7.70 (2H, m), 7.75-7.91 (3H, m), 7.97-8.07 (2H, m), 8.16 (1H, d, J=8.7

Hz), 8.18 (1H, d, J=8.2 Hz), 8.55 (1H, s), 8.64-8.73 (1H, m), 8.73-8.82 (1H, m), 10.81 (1H, brs).
MS: 582(M+H)$^+$.

Example 144

Synthesis of N,N-diethyl-N'-(2-naphthylsulfonyl)-2-(4-nitrophenethyl)malonamide (1) triethyl 3-(4-nitrophenyl)propane-1,1,1-tricarboxylate To a solution of triethyl methanetricarboxylate (16.6 g) in ether (350 mL) were added 4-nitrophenethyl alcohol (8.00 g) and triphenylphosphine (25.0 g). 40% Diisopropyl azodicarboxylate/toluene solution (48.4 g) was added dropwise to the mixture under ice-cooling, and the mixture was stirred at room temperature for 18 hr. Insoluble material was removed by filtration, and the filtrate was washed with saturated aqueous sodium hydrogen carbonate solution (300 mL) and saturated brine. After concentration under reduced pressure, the residue was purified by silica gel column chromatography to give the title compound (12.2 g) as an oil.
$^1$H-NMR (400 MHz, CDCl$_3$) δ1.28-1.33 (9H, m), 2.39-2.43 (2H, m), 2.93-2.97 (2H, m), 4.29 (6H, q, J=7.2 Hz), 7.38 (2H, d, J=8.8 Hz), 8.15 (2H, d, J=8.8 Hz).

(2) monoethyl (4-nitrophenethyl)malonate

In the same manner as in Example 117 (2), the title compound (2.34 g) was obtained as an oil using the above-mentioned compound (3.17 g).
$^1$H-NMR (400 MHz, DMSO-d$_6$) δ1.19 (3H, t, J=7.2 Hz), 2.01-2.10 (2H, m), 2.74 (2H, dd, J=8.8, 6.0 Hz), 3.31-3.37 (1H, m), 4.12 (2H, q, J=7.2 Hz), 7.49 (2H, d, J=8.4 Hz), 8.17 (2H, d, J=8.4 Hz), 12.90 (1H, brs).

(3) ethyl 2-{[(2-naphthylsulfonyl)amino]carbonyl}-4-(4-nitrophenyl)butyrate

In the same manner as in Example 1 (2), the title compound (1.34 g) was obtained as an oil using the above-mentioned compound (2.34 g).
$^1$H-NMR (400 MHz, CDCl$_3$) δ1.24 (3H, t, J=7.2 Hz), 2.13-2.20 (2H, m), 2.65 (1H, t, J=8.0 Hz), 3.21 (1H, t, J=7.2 Hz), 4.19 (2H, q, J=7.2 Hz), 7.19 (2H, d, J=8.4 Hz), 7.65-7.71 (2H, m), 7.92 (2H, d, J=8.0 Hz), 7.97-8.04 (3H, m), 8.08 (2H, d, J=8.4 Hz), 8.69 (1H, s), 9.61 (1H, s).

(4) 2-{[(2-naphthylsulfonyl)amino]carbonyl}-4-(4-nitrophenyl)butyric acid

To a solution of the above-mentioned compound (1.33 g) in THF (30 mL) was added a solution of sodium hydroxide (333 mg) in water (1.5 mL) at room temperature, and the mixture was stirred for 3 hr. The reaction mixture was adjusted to pH=1-2 by the addition of dilute hydrochloric acid and extracted with ethyl acetate (50 mL×2). The organic layer was concentrated under reduced pressure to give the title compound (1.24 g) as a white powder.
$^1$H-NMR (400 MHz, CDCl$_3$) δ2.18-2.25 (2H, m), 2.68 (2H, t, J=8.0 Hz), 3.31 (1H, t, J=6.8 Hz), 7.20 (2H, d, J=8.8 Hz), 7.63-7.72 (2H, m), 7.93 (1H, d, J=7.6 Hz), 8.02-8.08 (5H, m), 8.70 (1H, s), 9.70 (1H, brs).

(5) N,N-diethyl-N'-(2-naphthylsulfonyl)-2-(4-nitrophenethyl)malonamide

In the same manner as in Example 1 (4), the reaction mixture was obtained using the above-mentioned compound (350 mg). The reaction mixture was adjusted to pH=1-2 by the addition of dilute hydrochloric acid, and the precipitate was collected by filtration to give the title compound (316 mg) as a white solid.
$^1$H-NMR (400 MHz, DMSO-d$_6$) δ0.83-0.95 (6H, m), 1.86-1.97 (2H, m), 2.45-2.55 (2H, m), 3.06-3.25 (4H, m), 3.55 (1H, t, J=6.8 Hz), 7.29 (2H, d, J=8.8 Hz), 7.68-7.77 (2H, m), 7.89 (1H, dd, J=8.8, 1.6 Hz), 8.07 (1H, d, J=8.0 Hz), 8.10 (2H, d, J=8.8 Hz), 8.16 (1H, d, J=8.0 Hz), 8.23 (1H, d, J=8.0 Hz), 8.62 (1H, s), 12.44 (1H, brs).
MS: 498(M+H)$^+$.

Example 145

Synthesis of 2-(4-aminophenethyl)-N,N-diethyl-N'-(2-naphthylsulfonyl)malonamide

In the same manner as in Example 7, the title compound (244 mg) was obtained as a white powder using the compound (292 mg) obtained in Example 144 at room temperature.
$^1$H-NMR (300 MHz, DMSO-d$_6$) δ0.86-0.93 (6H, m), 1.66-1.86 (2H, m), 2.11-2.25 (2H, m), 2.95-3.30 (4H, m), 3.45 (1H, t, J=7.0 Hz), 6.44 (2H, d, J=8.2 Hz), 6.62 (2H, d, J=8.2 Hz), 7.67-7.77 (2H, m), 7.87 (1H, dd, J=8.5, 1.5 Hz), 8.07 (1H, d, J=7.7 Hz), 8.15 (1H, d, J=8.7 Hz), 8.22 (1H, d, J=7.7 Hz), 8.60 (1H, s).
MS: 468(M+H)$^+$.

Example 146

Synthesis of N,N-diethyl-N'-(2-naphthylsulfonyl)-2-[(2E)-3-(4-nitrophenyl)-2-propen-1-yl]malonamide (1) triethyl (3E)-4-(4-nitrophenyl)-3-butene-1,1,1-tricarboxylate In the same manner as in Example 144 (1), the title compound (8.56 g) was obtained as an oil using triethyl methanetricarboxylate (10.1 g) and trans-4-nitrocinnamyl alcohol (5.18 g).
$^1$H-NMR (400 MHz, CDCl$_3$) δ1.24-1.30 (9H, m), 3.08 (2H, d, J=6.8 Hz), 4.24-4.31 (6H, m), 6.53 (1H, d, J=16.0 Hz), 6.60 (1H, dd, J=16.0, 6.8 Hz), 7.46 (2H, d, J=8.8 Hz), 8.15 (2H, d, J=8.8 Hz).

(2) monoethyl(trans-4-nitrocinnamyl)malonate

In the same manner as in Example 117 (2), a crude product was obtained using the above-mentioned compound (8.56 g). This was purified by silica gel column chromatography to give the title compound (2.33 g) as an oil.
$^1$H-NMR (400 MHz, CDCl$_3$) δ1.28 (3H, t, J=7.2 Hz), 2.85-2.93 (2H, m), 3.59 (1H, t, J=7.2 Hz), 4.25 (2H, q, J=7.2 Hz), 6.37 (1H, dt, J=16.0, 7.2 Hz), 6.57 (1H, d, J=16.0 Hz), 7.46 (2H, d, J=8.8 Hz), 8.17 (2H, d, J=8.8 Hz).

(3) ethyl (4E)-2-{[(2-naphthylsulfonyl)amino]carbonyl}-5-(4-nitrophenyl)-4-pentenoate In the same manner as in Example 1 (2), the title compound (195 mg) was obtained as an oil using the above-mentioned compound (2.32 g).
$^1$H-NMR (400 MHz, CDCl$_3$) δ1.13-1.21 (3H, m), 2.80 (2H, t, J=7.2 Hz), 3.55 (1H, t, J=7.2 Hz), 4.14-4.21 (2H, m), 6.12 (1H, dt, J=16.0, 7.2 Hz), 6.30 (1H, d, J=16.0 Hz), 7.12

(2H, d, J=8.8 Hz), 7.54-7.66 (2H, m), 7.80-7.84 (2H, m), 7.92 (2H, d, J=8.8 Hz), 7.91-8.00 (2H, m), 8.64 (1H, d, J=1.2 Hz), 9.89 (1H, brs).

(4) N,N-diethyl-N'-(2-naphthylsulfonyl)-2-[(2E)-3-(4-nitrophenyl)-2-propen-1-yl]malonamide The above-mentioned compound (195 mg) was subjected to hydrolysis in the same manner as in Example 144 (4) to give a carboxylic acid. The carboxylic acid was concentrated in the same manner as in Example 1 (4). After completion of the reaction, the reaction mixture was adjusted to pH=1-2 by the addition of dilute hydrochloric acid, and the precipitate was collected by filtration to give the title compound (100 mg) as a pale-yellow solid.
$^1$H-NMR (400 MHz, CDCl$_3$) δ1.10-1.54 (6H, m), 2.65-2.76 (2H, m), 3.26-3.35 (4H, m), 3.54 (1H, t, J=7.2 Hz), 6.02 (1H, dt, J=16.0, 8.0 Hz), 6.24 (1H, d, J=16.0 Hz), 7.07 (2H, d, J=8.4 Hz), 7.55-7.65 (2H, m), 7.79-7.85 (2H, m), 7.93-7.99 (4H, m), 8.62 (1H, s).
MS: 510(M+H)$^+$.

Example 147

Synthesis of 2-[3-(4-aminophenyl)propyl]-N,N-diethyl-N'-(2-naphthylsulfonyl)malonamide In the same manner as in Example 7, the title compound (24 mg) was obtained as a white solid using the compound (40 mg) obtained in Example 146.
$^1$H-NMR (400 MHz, DMSO-d$_6$) δ0.86-0.92 (6H, m), 1.12-1.40 (2H, m), 1.50-1.62 (2H, m), 2.20-2.35 (2H, m), 3.05-3.27 (4H, m), 3.52 (1H, t, J=6.8 Hz), 6.49 (2H, d, J=8.0 Hz), 6.69 (2H, d, J=8.0 Hz), 7.69-7.78 (2H, m), 7.83 (1H, dd, J=8.8, 1.9 Hz), 8.07 (1H, d, J=8.0 Hz), 8.11 (1H, d, J=8.7 Hz), 8.20 (1H, d, J=8.0 Hz), 8.58 (1H, s).
MS: 482(M+H)$^+$.

Example 148

Synthesis of 2-[(2E)-3-(4-aminophenyl)-2-propen-1-yl]-N,N-diethyl-N'-(2-naphthylsulfonyl)malonamide In the same manner as in Example 137 (4), the title compound (4 mg) was obtained as a pale-yellow solid using the compound (58 mg) obtained in Example 146 at room temperature.
$^1$H-NMR (400 MHz, CDCl$_3$) δ1.08 (6H, t, J=7.2 Hz), 2.57-2.72 (2H, m), 3.15-3.34 (4H, m), 3.47-3.55 (3H, m), 5.69 (1H, dt, J=15.6, 8.0 Hz), 6.18 (1H, d, J=15.6 Hz), 6.58 (2H, d, J=8.4 Hz), 6.93 (2H, d, J=8.4 Hz), 7.60-7.66 (2H, m), 7.88 (2H, d, J=8.8 Hz), 7.96-8.00 (2H, m), 8.65 (1H, s).
MS: 502(M+Na)$^+$.

Example 149

Synthesis of 2-[3-(4-tert-butyloxycarbonylaminophenyl)propyl]-N,N-diethyl-N'-(2-naphthylsulfonyl)malonamide

(1) triethyl 4-(4-tert-butyloxycarbonylaminophenyl)butane-1,1,1-tricarboxylate To a solution of the compound (3.95 g) obtained in Example 146 (1) in ethyl acetate (100 mL) was added di-tert-butyl dicarbonate (2.19 g), and the mixture was subjected to the same manner as in Example 7 at room temperature to give a crude product. This was purified by silica gel column chromatography to give the title compound (3.59 g) as an oil.
$^1$H-NMR (300 MHz, CDCl$_3$) δ1.26 (9H, t, J=7.3 Hz), 1.51 (9H, s), 1.72-1.85 (2H, m), 2.08-2.15 (2H, m), 2.59 (2H, t, J=8.6 Hz), 4.23 (6H, q, J=7.3 Hz), 7.09 (2H, d, J=8.6 Hz), 7.25 (2H, d, J=8.6 Hz).

(2) monoethyl [3-(4-tert-butyloxycarbonylaminophenyl)propyl]malonate

In the same manner as in Example 117 (2), the title compound (2.77 g) was obtained as an oil using the above-mentioned compound (3.53 g).
$^1$H-NMR (400 MHz, CDCl$_3$) δ1.28 (3H, t, J=7.2 Hz), 1.51 (9H, s), 1.60-1.74 (2H, m), 1.88-2.02 (2H, m), 2.60 (2H, t, J=7.2 Hz), 3.39 (1H, t, J=7.2 Hz), 4.22 (2H, q, J=7.2 Hz), 6.49 (1H, brs), 7.08 (2H, d, J=8.4 Hz), 7.25 (2H, d, J=8.4 Hz).

(3) ethyl 5-(4-tert-butyloxycarbonylaminophenyl)-2-{[(2-naphthylsulfonyl)amino]carbonyl}valerate In the same manner as in Example 1 (2), the title compound (2.42 g) was obtained as a white powder using the above-mentioned compound (2.77 g).
$^1$H-NMR (400 MHz, CDCl$_3$) δ1.21 (3H, t, J=7.2 Hz), 1.42-1.49 (2H, m), 1.52 (9H, s), 2.45 (2H, t, J=7.2 Hz), 3.19 (1H, t, J=7.2 Hz), 4.16 (2H, q, J=7.2 Hz), 6.39 (1H, s), 6.92 (2H, d, J=8.0 Hz), 7.19 (2H, d, J=8.0 Hz), 7.61-7.70 (2H, m), 7.92 (1H, d, J=8.0 Hz), 7.96-7.97 (2H, m), 8.01 (1H, d, J=8.0 Hz), 8.67 (1H, s), 9.70 (1H, brs).

(4) 5-(4-tert-butyloxycarbonylaminophenyl)-2-{[(2-naphthylsulfonyl)amino]carbonyl}valeric acid In the same manner as in Example 144 (4), the title compound (2.28 g) was obtained as a white powder using the above-mentioned compound (2.40 g).
$^1$H-NMR (400 MHz, DMSO-d$_6$) δ1.23-1.38 (2H, m), 1.48 (9H, s), 1.48-1.64 (2H, m), 2.29-2.41 (2H, m), 3.25-3.35 (1H, m), 6.84 (2H, d, J=8.4 Hz), 7.28 (2H, d, J=8.4 Hz), 7.67-7.78 (2H, m), 7.84 (1H, dd, J=8.4, 1.6 Hz), 8.06 (1H, d, J=8.4 Hz), 8.09 (1H, d, J=8.8 Hz), 8.20 (1H, d, J=8.4 Hz), 8.59 (1H, s), 9.22 (1H, s), 12.52 (1H, brs), 12.76 (1H, brs).

(5) 2-[3-(4-tert-butyloxycarbonylaminophenyl)propyl]-N,N-diethyl-N'-(2-naphthylsulfonyl)malonamide The above-mentioned compound (2.28 g) was subjected to the same manner as in Example 1 (4) to give the reaction mixture. The reaction mixture was adjusted to pH=3-4 by the addition of dilute hydrochloric acid, and the precipitate was collected by filtration to give the title compound (2.48 g) as a white solid.
$^1$H-NMR (300 MHz, DMSO-d$_6$) δ0.86-0.93 (6H, m), 1.11-1.41 (2H, m), 1.47 (9H, s), 1.50-1.62 (2H, m), 2.28-2.42 (2H, m), 3.08-3.22 (4H, m), 3.50-3.59 (1H, m), 6.87 (2H, d, J=8.4 Hz), 7.29 (2H, d, J=8.4 Hz), 7.68-7.78 (2H, m), 7.83 (1H, dd, J=8.7, 1.5 Hz), 8.07 (1H, d, J=8.1 Hz), 8.11 (1H, d, J=9.0 Hz), 8.20 (1H, d, 8.1 Hz), 8.58 (1H, s), 9.22 (1H, s), 12.38 (1H, brs).
MS:604(M+Na)$^+$.

Example 150

Synthesis of 2-[3-(4-acetylaminophenyl)propyl]-N,N-diethyl-N'-(2-naphthylsulfonyl)malonamide To a solution of the compound (210 mg) obtained in Example 147 in pyridine (4 mL) was added acetic anhydride (46 µL) at room temperature, and the mixture was stirred for 19 hr. The reaction mixture was adjusted to pH=1-2 by the addition of dilute hydrochloric acid, and the precipitate was collected by filtration to give the title compound (213 mg) as a white solid.

$^1$H-NMR (400 MHz, DMSO-d$_6$) δ0.85-0.94 (6H, m), 1.19-1.30 (1H, m), 1.30-1.42 (1H, m), 1.52-1.63 (2H, m), 2.02 (3H, s), 2.32-2.45 (2H, m), 3.06-3.24 (4H, m), 3.54 (1H, t, J=6.8 Hz), 6.91 (2H, d, J=8.4 Hz), 7.41 (2H, d, J=8.4 Hz), 7.69-7.85 (3H, m), 8.07 (1H, d, J=8.0 Hz), 8.11 (1H, d, J=8.8 Hz), 8.20 (1H, d, J=8.0 Hz), 8.58 (1H, s), 9.83 (1H, s), 12.40 (1H, brs). MS: 524(M+H)$^+$.

Example 151

Synthesis of 2-butyl-N,N-diethyl-N'-(2-naphthylsulfonyl)malonamide (1) monoethyl butylmalonate In the same manner as in Example 1 (1), the title compound (20.0 g) was obtained as an oil using diethyl butylmalonate (25.3 g).

$^1$H-NMR (300 MHz, DMSO-d$_6$) δ0.85 (3H, t, J=6.9 Hz), 1.15-1.33 (4H, m), 1.18 (3H, t, J=7.4 Hz), 1.69-1.78 (2H, m), 3.30 (1H, t, J=7.5 Hz), 4.11 (2H, q, J=6.9 Hz), 12.80 (1H, brs).

(2) 2-{[(2-naphthylsulfonyl)amino]carbonyl}hexanoic acid

In the same manner as in Example 1 (2), a crude product was obtained using the above-mentioned compound (1.15 g). This was subjected to hydrolysis in the same manner as in Example 1 (3) to give the title compound (1.61 g) as a white solid.

$^1$H-NMR (300 MHz, DMSO-d$_6$) δ0.86 (3H, t, J=6.9 Hz), 1.17-1.34 (4H, m), 1.61-1.75 (2H, m), 3.14-3.21 (1H, m), 7.67-7.90 (3H, m), 8.05-8.25 (3H, m), 8.59 (1H, s), 12.56 (2H, brs).

(3) 2-butyl-N,N-diethyl-N'-(2-naphthylsulfonyl)malonamide

In the same manner as in Example 1 (4), a crude product was obtained using the above-mentioned compound (350 mg). This was purified by silica gel column chromatography to give the title compound (64 mg) as a white solid.

$^1$H-NMR (300 MHz, DMSO-d$_6$) δ0.70 (3H, t, J=7.2 Hz), 0.86-0.95 (6H, m), 1.00-1.18 (4H, m), 1.49-1.63 (2H, m), 3.05-3.30 (4H, m), 3.46-3.55 (1H, m), 7.68-7.79 (2H, m), 7.85-7.88 (1H, m), 8.07 (1H, d, J=7.9 Hz), 8.16 (1H, d, J=8.4 Hz), 8.22 (1H, d, J=7.9 Hz), 8.59 (1H, s), 12.37 (1H, brs). MS: 405(M+H)$^+$.

Example 152

Synthesis of N,N-diethyl-N'-(2-naphthylsulfonyl)-2-(2-propynyl)malonamide (1) diethyl (2-propynyl)malonate To a mixed solution of triethyl methanetricarboxylate sodium salt (25.0 g) in toluene/DMF (120 mL/120 mL) was added propargyl bromide (25.0 g), and the mixture was stirred at 80° C. for 1.5 hr. After allowing to cool, dilute hydrochloric acid was added to the reaction mixture, and the mixture was extracted with ethyl acetate (60 mL). The organic layer was washed with saturated brine and concentrated under reduced pressure. The residue was dissolved in THF (30 mL), sodium ethoxide (7.60 g) was added, and the mixture was stirred at room temperature for 1 hr. 1 mol/L Hydrochloric acid (150 mL) was added, and the mixed solution was extracted with chloroform (100 mL). The organic layer was concentrated, and the residue was purified by silica gel column chromatography to give the title compound (35.0 g) as an oil.

$^1$H-NMR (300 Mz, CDCl$_3$) δ1.26-1.32 (6H, m), 2.04 (1H, s), 2.89-3.02 (3H, m), 4.22-4.32 (4H, m).

(2) monoethyl (2-propynyl)malonate

In the same manner as in Example 1 (1), the title compound (8.20 g) was obtained as an oil using the above-mentioned compound (19.8 g).

$^1$H-NMR (300 Mz, CDCl$_3$) δ 1.23-1.33 (3H, m), 2.18 (1H, s), 2.80-2.87 (2H, m), 3.60-3.65 (1H, m), 4.16-4.30 (2H, m).

(3) ethyl 2-{[(2-naphthylsulfonyl)amino]carbonyl}-4-pentynoate

To a solution of the above-mentioned compound (8.19 g) in DMF (30 mL) were added naphthalene-2-sulfonamide (9.97 g), 2-chloro-1-methylpyridinium iodide (14.7 g), diisopropyl ethyl amine (13.3 mL) and 4-dimethylaminopyridine (0.59 g), and the mixture was stirred at room temperature for 18 hr. The reaction mixture was adjusted to pH=2-3 by the addition of dilute hydrochloric acid, and ethyl acetate was added to extract the mixture. The organic layer was concentrated under reduced pressure, and the residue was purified by silica gel column chromatography to give the title compound (9.97 g) as a white powder.

$^1$H-NMR (300 Mz, CDCl$_3$) δ1.21-1.33 (3H, m), 1.95 (1H, s), 2.72-2.75 (2H, m), 3.38-3.43 (1H, m), 4.18-4.29 (2H, m), 7.60-7.69 (2H, m), 7.90-8.03 (4H, m), 8.68 (1H, s), 9.62 (1H, brs).

(4) 2-{[(2-naphthylsulfonyl)amino]carbonyl}-4-pentynoic acid

In the same manner as in Example 1 (3), the title compound (9.78 g) was obtained as a white powder using the above-mentioned compound (9.97 g).

$^1$H-NMR (300 Mz, CDCl$_3$) δ2.75-2.77 (1H, m), 3.47-3.52 (1H, m), 3.72-3.77 (2H, m), 7.60-7.70 (2H, m), 7.90-8.03 (5H, m), 8.68 (1H, s).

(5) N,N-diethyl-N'-(2-naphthylsulfonyl)-2-(2-propynyl)malonamide

In the same manner as in Example 1 (4), a crude product was obtained using the above-mentioned compound (1.82 g). This was purified by silica gel column chromatography to give the title compound (860 mg) as a white powder.

$^1$H-NMR (400 Mz, CDCl$_3$) δ1.09-1.12 (6H, m), 1.92 (1H, s), 2.63-2.77 (2H, m) 3.21-3.32 (2H, m), 3.34-3.42 (1H, m), 3.45-3.52 (1H, m), 3.57-3.68 (1H, m), 7.59-7.68 (2H, m), 7.89-8.02 (4H, m), 8.65 (1H, s), 10.58 (1H, brs). MS: 387(M+H)$^+$.

Example 153

Synthesis of 2-(2-cyanoethyl)-N,N-diethyl-N'-(2-naphthylsulfonyl)malonamide (1) monoethyl (2-cyanoethyl)malonate In the same manner as in Example 1 (1), the title compound (4.29 g) was obtained as an oil using diethyl (2-cyanoethyl) malonate (5.00 g).

¹H-NMR (300 Mz, CDCl₃) δ1.24-1.33 (3H, m), 2.26-2.32 (2H, m), 2.51-2.56 (2H, m), 3.56-3.59 (1H, m), 4.15-4.30 (2H, m).

(2) ethyl 4-cyano-2-{[(2-naphthylsulfonyl)amino]carbonyl}butyrate

In the same manner as in Example 152 (3), the title compound (2.43 g) was obtained as a white powder using the above-mentioned compound (2.50 g).
¹H-NMR (300 Mz, CDCl₃) δ1.20-1.32 (3H, m), 2.22-2.28 (2H, m), 2.49-2.58 (2H, m), 3.50-3.57 (1H, m), 4.18-4.28 (2H, m), 7.62-7.71 (2H, m), 7.72-7.94 (1H, m), 7.99-8.04 (3H, m), 8.67 (1H, s), 9.44 (1H, brs).

(3) 4-cyano-2-{[(2-naphthylsulfonyl)amino]carbonyl}butyric acid

In the same manner as in Example 1 (3), the title compound (1.94 g) was obtained as a white powder using the above-mentioned compound (2.43 g).
¹H-NMR (300 Mz, CDCl₃) δ2.21-2.25 (2H, m), 2.41-2.46 (2H, m), 3.01-3.52 (1H, m), 7.62-7.71 (2H, m), 7.71-7.92 (1H, m), 7.94-8.04 (3H, m), 8.68 (1H, s).

(4) 2-(2-cyanoethyl)-N,N-diethyl-N'-(2-naphthylsulfonyl)malonamide

In the same manner as in Example 1 (4), a crude product was obtained using the above-mentioned compound (1.00 g). This was purified by silica gel column chromatography to give the title compound (470 mg) as a white powder.
¹H-NMR (400 Mz, CDCl₃) δ1.09-1.14 (6H, m), 2.17-2.21 (2H, m), 2.27-2.39 (2H, m), 3.22-3.41 (3H, m), 3.43-3.55 (2H, m), 7.61-7.69 (2H, m), 7.91-8.03 (4H, m), 8.65 (1H, s), 10.56 (1H, s).
MS: 402(M+H)⁺.

Example 154

Synthesis of N,N-diethyl-N'-(2-naphthylsulfonyl)-2-(4-piperidinylmethyl)malonamide trifluoroacetic acid salt (1) 5-(1-tert-butyloxycarbonyl-4-piperidinylmethyl)-2,2-dimethyl-1,3-dioxane-4,6-dione In the same manner as in Example 132 (1), the title compound (10.8 g) was obtained as a white solid using N-(tert-butyloxycarbonyl)isonipecotic acid (8.68 g).
¹H-NMR (400 Mz, CDCl₃) δ1.07-1.22 (2H, m), 1.45 (9H, s), 1.57-1.73 (2H, m), 2.04-2.08 (2H, m), 2.63-2.74 (2H, m), 3.48 (1H, t, J=5.6 Hz), 4.00-4.18 (2H, m).

(2) 2-(1-tert-butyloxycarbonyl-4-piperidinylmethyl)-3-(N,N-diethylamino)-3-oxopropionic acid In the same manner as in Example 119 (2), the title compound (3.07 g) was obtained as a white solid using the above-mentioned compound (2.94 g).
¹H-NMR (400 MHz, DMSO-d₆) δ0.90-1.05 (5H, m), 1.11 (3H, t, J=7.2 Hz), 1.37 (9H, s), 1.52-1.76 (5H, m), 2.50-2.73 (2H, m), 3.23-3.48 (4H, m), 3.63 (1H, t, J=7.2 Hz), 3.81-3.95 (2H, m), 12.48 (1H, brs).

(3) 2-(1-tert-butyloxycarbonyl-4-piperidinylmethyl)-N,N-diethyl-N'-(2-naphthylsulfonyl)malonamide In the same manner as in Example 1 (4), a crude product was obtained using the above-mentioned compound (2.93 g). This was purified by silica gel column chromatography to give the title compound (1.73 g) as a white powder.
¹H-NMR (300 MHz, DMSO-d₆) δ0.75-1.75 (7H, m), 0.89 (3H, t, J=7.2 Hz), 0.96 (3H, t, J=7.2 Hz), 1.36 (9H, s), 2.23-2.54 (2H, m), 3.05-3.25 (4H, m), 3.55-3.64 (1H, m), 3.64-3.95 (2H, m), 7.67-7.79 (2H, m), 7.85-7.88 (1H, m), 8.07 (1H, d, J=7.1 Hz), 8.16 (1H, d, J=8.7 Hz), 8.22 (1H, d, J=7.5 Hz), 8.59 (1H, d, J=1.2 Hz), 12.32 (1H, brs).

(4) N,N-diethyl-N'-(2-naphthylsulfonyl)-2-(4-piperidinylmethyl)malonamide trifluoroacetic acid salt In the same manner as in Example 18, the title compound (1.77 g) was obtained as a white solid using the above-mentioned compound (1.73 g).
¹H-NMR (300 MHz, DMSO-d₆) δ0.85-0.93 (6H, m), 1.00-1.88 (7H, m), 2.57-2.84 (2H, m), 3.03-3.28 (6H, m), 3.55-3.64 (1H, m), 7.67-7.79 (2H, m), 7.85-7.89 (1H, m), 7.97-8.17 (1H, m), 8.07 (1H, d, J=8.0 Hz), 8.16 (1H, d, J=8.9 Hz), 8.22 (1H, d, J=8.0 Hz), 8.30-8.47 (1H, m), 8.60 (1H, d, J=1.0 Hz), 12.40 (1H, brs).
MS: 446(M+H)⁺.

Example 155

Synthesis of 2-(1-benzoyl-4-piperidinylmethyl)-N,N-diethyl-N'-(2-naphthylsulfonyl)malonamide To a mixed solution of the compound (250 mg) obtained in Example 154 in THF (10 mL) and 1 mol/L aqueous sodium hydroxide (1.5 mL) was added benzoyl chloride (104 μL) at room temperature, and the mixture was stirred for 24 hr. The reaction mixture was adjusted to pH=2-3 by the addition of dilute hydrochloric acid, and extracted with ethyl acetate (50 mL×2). The organic layer was washed with saturated brine and concentrated under reduced pressure to give the title compound (188 mg) as a white solid.
¹H-NMR (300 MHz, DMSO-d₆) δ0.80-1.08 (7H, m), 1.08-1.70 (6H, m), 3.10-3.49 (8H, m), 3.56-3.68 (1H, m), 7.29-7.45 (5H, m), 7.63-7.77 (2H, m), 7.85-7.88 (1H, m), 8.03-8.05 (1H, m), 8.14 (1H, d, J=8.8 Hz), 8.21 (1H, d, J=7.7 Hz), 8.59 (1H, d, J=1.0 Hz), 12.35 (1H, brs).
MS: 550(M+H)⁺.

Example 156

Synthesis of N,N-diethyl-N'-(2-naphthylsulfonyl)-2-(1-phenylsulfonyl-4-piperidinylmethyl)malonamide In the same manner as in Example 155, the title compound (205 mg) was obtained as a white solid using the compound (250 mg) obtained in Example 154 and benzenesulfonyl chloride (114 μL).
¹H-NMR (400 MHz, DMSO-d₆) δ0.74-1.08 (7H, m), 1.24-1.59 (4H, m), 1.80-1.86 (1H, m), 1.94-2.00 (1H, m), 3.08-3.19 (4H, m), 3.21-3.47 (3H, m), 3.50-3.56 (2H, m), 7.66-7.81 (8H, m), 7.96 (1H, d, J=9.6 Hz), 7.99 (1H, d, J=9.2 Hz), 8.17 (1H, d, J=8.4 Hz), 8.55 (1H, d, J=0.8 Hz), 12.30 (1H, brs).
MS: 586(M+H)⁺.

Example 157

Synthesis of N,N-diethyl-N'-(2-naphthylsulfonyl)-2-(1-phenoxycarbonyl-4-piperidinylmethyl)malonamide In the same manner as in Example 155, a crude product was obtained using the compound (250 mg) obtained in Example 154 and phenyl chlorocarbonate (112 µL). This was purified by silica gel column chromatography to give the title compound (208 mg) as a white solid.

$^1$H-NMR (400 MHz, DMSO-d$_6$) δ0.84-1.06 (7H, m), 1.10-1.68 (6H, m), 2.46-2.81 (2H, m), 3.12-3.29 (4H, m), 3.64 (1H, t, J=6.8 Hz), 3.78-4.08 (2H, m), 7.06-7.23 (3H, m), 7.36-7.40 (2H, m), 7.66-7.78 (2H, m), 7.87-7.90 (1H, m), 8.07 (1H, d, J=8.0 Hz), 8.18 (1H, d, J=8.8 Hz), 8.23 (1H, d, J=7.6 Hz), 8.61 (1H, s), 12.35 (1H, brs).

MS: 566(M+H)$^+$.

Example 158

Synthesis of N,N-diethyl-N'-(2-naphthylsulfonyl)-2-(1-phenylacetyl-4-piperidinylmethyl)malonamide In the same manner as in Example 155, the title compound (302 mg) was obtained as a white solid using the compound (373 mg) obtained in Example 154 and phenylacetic acid chloride (106 µL).

$^1$H-NMR (400 MHz, DMSO-d$_6$) δ0.67-0.99 (8H, m), 1.03-1.60 (5H, m), 2.16-2.33 (1H, m), 2.50-2.73 (1H, m), 3.08-3.28 (4H, m), 3.56-3.84 (4H, m), 4.18-4.30 (1H, m), 7.14-7.26 (3H, m), 7.28-7.32 (2H, m), 7.66-7.78 (2H, m), 7.86 (1H, d, J=8.8 Hz), 8.02-8.23 (3H, m), 8.60 (1H, s), 12.30 (1H, brs).

MS: 564(M+H)$^+$.

Example 159

Synthesis of 2-(1-anilinocarbonyl-4-piperidinylmethyl)-N,N-diethyl-N'-(2-naphthylsulfonyl)malonamide In the same manner as in Example 155, the title compound (223 mg) was obtained as a white solid using the compound (305 mg) obtained in Example 154 and phenyl isocyanate (72 µL).

$^1$H-NMR (400 MHz, DMSO-d$_6$) δ0.88-0.99 (8H, m), 1.05-1.19 (1H, m), 1.23-1.41 (1H, m), 2.39-2.52 (2H, m), 3.11-3.26 (4H, m), 3.60-3.68 (1H, m), 3.91-4.06 (2H, m), 6.92 (1H, d, J=8.0 Hz), 7.21 (2H, t, J=8.0 Hz), 7.43 (2H, d, J=8.0 Hz), 7.77-7.78 (2H, m), 7.86-7.89 (1H, m), 8.07 (1H, d, J=8.0 Hz), 8.17 (1H, d, J=8.8 Hz), 8.22 (1H, d, J=8.0 Hz), 8.35 (1H, s), 8.60 (1H, s), 12.32 (1H, brs).

MS: 565(M+H)$^+$.

Example 160

Synthesis of N,N-diethyl-2-[1-(1-naphthoyl)-4-piperidinylmethyl]-N'-(2-naphthylsulfonyl)malonamide In the same manner as in Example 155, the title compound (169 mg) was obtained as a white solid using the compound (272 mg) obtained in Example 154 and 1-naphthoyl chloride (73 µL).

$^1$H-NMR (400 MHz, DMSO-d$_6$) δ0.66-1.02 (7H, m), 1.02-1.39 (3H, m), 1.48-1.79 (3H, m), 2.45-2.78 (2H, m), 2.92-3.29 (5H, m), 3.57-3.66 (1H, m), 4.45-4.61 (1H, m), 7.30-7.43 (1H, m), 7.50-7.78 (6H, m), 7.81-7.88 (1H, m), 7.95-8.22 (5H, m), 8.59 (1H, s), 12.32 (1H, brs).

MS: 600(M+H)$^+$.

Example 161

Synthesis of 2-(1-benzyl-4-piperidinylmethyl)-N,N-diethyl-N'-(2-naphthylsulfonyl)malonamide hydrochloride To a solution of the compound (365 mg) obtained in Example 154 in chloroform (10 mL) were added benzaldehyde (67 µL) and sodium triacetoxyborohydride (280 mg), and the mixture was stirred at room temperature for 4 days. Water (50 mL) was added to the reaction mixture, and the mixture was extracted with chloroform (50 mL×2). The organic layer was washed with saturated brine and concentrated under reduced pressure. The residue was purified by silica gel column chromatography and converted to a hydrochloride salt with 4 mol/L hydrochloric acid-ethyl acetate (1 mL) to give the title compound (58 mg) as a white solid.

$^1$H-NMR (400 MHz, DMSO-d$_6$) δ0.82-0.95 (6H, m), 1.23-1.82 (7H, m), 2.62-2.79 (2H, m), 2.96-3.40 (6H, m), 3.60-3.69 (1H, m), 4.11-4.22 (2H, m), 7.46-7.54 (5H, m), 7.68-7.76 (2H, m), 7.85-7.89 (1H, m), 8.04 (1H, d, J=8.0 Hz), 8.11 (1H, d, J=8.8 Hz), 8.20 (1H, d, J=8.4 Hz), 8.58 (1H, s), 10.03 (1H, brs), 12.50 (1H, brs).

MS: 536(M+H)$^+$.

Example 162

Synthesis of 2-(1-benzylsulfonyl-4-piperidinylmethyl)-N,N-diethyl-N'-(2-naphthylsulfonyl)malonamide In the same manner as in Example 155, the title compound (68 mg) was obtained as a white solid using the compound (290 mg) obtained in Example 154 and benzylsulfonyl chloride (100 mg).

$^1$H-NMR (300 MHz, DMSO-d$_6$) δ0.80-1.01 (8H, m), 1.37-1.62 (5H, m), 2.28-2.51 (2H, m), 3.08-3.50 (6H, m), 3.56-3.63 (1H, m), 4.29 (2H, s), 7.30-7.40 (5H, m), 7.70-7.79 (2H, m), 7.87 (1H, dd, J=8.7, 1.8 Hz), 8.09 (1H, d, J=7.8 Hz), 8.17 (1H, d, J=8.7 Hz), 8.24 (1H, d, J=7.5 Hz), 8.61 (1H, d, J=1.8 Hz), 12.35 (1H, brs).

MS: 600(M+H)$^+$.

Example 163

Synthesis of 2-[1-(2-benzothiazolyl)-4-piperidinylmethyl]-N,N-diethyl-N'-(2-naphthylsulfonyl)malonamide To a solution of the compound (1.01 g) obtained in Example 154 in N-methylpyrrolidone (10 mL) were added 2-chlorobenzothiazole (445 µL) and diisopropyl ethyl amine (1.54 mL), and the mixture was stirred under nitrogen atmosphere at 100° C. for 2 hr. After allowing to cool, the reaction mixture was adjusted to pH=2-3 by the addition of dilute hydrochloric acid, and extracted with ethyl acetate (50 mL×2). The organic layer was washed with saturated brine and concentrated under reduced pressure, and the residue was purified by silica gel column chromatography to give the title compound (515 mg) as a white solid.

$^1$H-NMR (300 MHz, DMSO-d$_6$) δ0.83-1.70 (13H, m), 2.72-2.96 (2H, m), 3.10-3.25 (4H, m), 3.62-3.69 (1H, m), 3.71-3.96 (2H, m), 7.02-7.11 (1H, m), 7.21-7.30 (1H, m), 7.42 (1H, d, J=7.8 Hz), 7.66-7.77 (3H, m), 7.88 (1H, dd, J=8.7, 1.8 Hz), 8.09 (1H, d, J=8.1 Hz), 8.18 (1H, d, J=9.0 Hz), 8.23 (1H, d, J=7.5 Hz), 8.61 (1H, d, J=1.8 Hz), 12.39 (1H, brs).

MS: 579(M+H)$^+$.

Example 164

Synthesis of 2-[cis-4-(tert-butyloxycarbonylamino) cyclohexylmethyl]-N,N -diethyl-N'-(2-naphthylsulfonyl)malonamide (1) 5-[cis-4-(tert-butyloxycarbonylamino)cyclohexylmethyl]-2,2-dimethyl-1,3-dioxane-4,6-dione In the same manner as in Example 132 (1), the title compound (5.51 g) was obtained as a white solid using cis-4-(tert-butyloxycarbonylamino)cyclohexanecarboxylic acid (4.55 g).

$^1$H-NMR (300 MHz, DMSO-$d_6$) δ1.30-1.75 (9H, m), 1.38 (9H, s), 1.66 (3H, s), 1.80 (3H, s), 1.85-1.94 (2H, m), 3.38-3.49 (1H, m), 4.10-4.16 (1H, m), 6.76-6.75 (1H, m).

(2) 2-[cis-4-(tert-butyloxycarbonylamino)cyclohexylmethyl]-3-(N, N-diethylamino)-3-oxopropionic acid In the same manner as in Example 119 (2), the title compound (3.35 g) was obtained as an oil using the above-mentioned compound (4.00 g).

$^1$H-NMR (300 MHz, DMSO-$d_6$) δ0.93 (3H, t, J=7.2 Hz), 1.11 (3H, t, J=7.2 Hz), 1.20-1.78 (11H, m), 1.36 (9H, s), 3.19-3.48 (5H, m), 3.54-3.60 (1H, m), 6.60-6.70 (1H, m), 12.40 (1H, brs).

(3) 2-[cis-4-(tert-butyloxycarbonylamino)cyclohexylmethyl]-N,N -diethyl-N'-(2-naphthylsulfonyl)malonamide In the same manner as in Example 1 (2), the title compound (870 mg) was obtained as a white powder using the above-mentioned compound (3.34 g).

$^1$H-NMR (300 MHz, DMSO-$d_6$) δ0.81-1.76 (17H, m), 1.37 (9H, s), 3.06-3.21 (5H, m), 3.50-3.60 (1H, m), 6.58-6.66 (1H, m), 7.66-7.75 (2H, m), 7.82-7.90 (1H, m), 8.02-8.25 (3H, m), 8.58 (1H, s), 12.30 (1H, brs).

Example 165

Synthesis of 2-(cis-4-aminocyclohexylmethyl)-N,N-diethyl-N'-(2-naphthylsulfonyl)malonamide trifluoroacetic acid salt In the same manner as in Example 18, the title compound (790 mg) was obtained as a white solid using the compound (850 mg) obtained in Example 164.

$^1$H-NMR (400 MHz, DMSO-$d_6$) δ0.82-0.94 (6H, m), 1.18-1.65 (11H, m), 3.00-3.27 (5H, m), 3.55-3.59 (1H, m), 7.64 (3H, brs), 7.67-7.78 (2H, m), 7.86 (1H, dd, J=8.4, 1.6 Hz), 8.07 (1H, d, J=8.0 Hz), 8.15 (1H, d, J=8.8 Hz), 8.21 (1H, d, J=8.0 Hz), 8.59 (1H, s), 12.37 (1H, brs).

MS: 460(M+H)$^+$.

Example 166

Synthesis of 2-[cis-4-(benzoylamino)cyclohexylmethyl]-N,N -diethyl-N'-(2-naphthylsulfonyl)malonamide In the same manner as in Example 155, the title compound (100 mg) was obtained as a white powder using the compound (119 mg) obtained in Example 165 and benzoyl chloride (27 μL).

$^1$H-NMR (400 MHz, DMSO-$d_6$) δ0.84-0.98 (6H, m), 1.09-1.45 (7H, m), 1.45-1.71 (4H, m), 3.07-3.29 (4H, m), 3.59 (1H, t, J=6.8 Hz), 3.78-3.85 (1H, m), 7.41-7.52 (3H, m), 7.67-7.80 (4H, m), 7.86-7.88 (1H, m), 7.98 (1H, d, J=7.6 Hz), 8.07 (1H, d, J=8.4 Hz), 8.16 (1H, d, J=8.8 Hz), 8.22 (1H, d, J=8.0 Hz), 8.60 (1H, d, J=1.2 Hz), 12.32 (1H, brs).

MS: 564(M+H)$^+$.

Example 167

Synthesis of N,N-diethyl-N'-(2-naphthylsulfonyl)-2-[cis-4-(3-phenylureido)cyclohexylmethyl]malonamide In the same manner as in Example 155, the title compound (100 mg) was obtained as a white solid using the compound (126 mg) obtained in Example 165 and phenyl isocyanate (27 μL).

$^1$H-NMR (400 MHz, DMSO-$d_6$) δ0.83-1.63 (17H, m), 3.10-3.29 (4H, m), 3.57-3.67 (2H, m), 6.15 (1H, d, J=7.6 Hz), 6.85-6.89 (1H, m), 7.19-7.22 (2H, m), 7.35 (2H, d, J=8.0 Hz), 7.68-7.50 (2H, m), 7.87 (1H, dd, J=9.2, 2.0 Hz), 8.06 (1H, d, J=8.8 Hz), 8.16 (1H, d, J=8.8 Hz), 8.21-8.23 (2H, m), 8.60 (1H, s), 12.31 (1H, brs).

MS: 579(M+H)$^+$.

Example 168

Synthesis of N,N-diethyl-N'-(2-naphthylsulfonyl)-2-[cis-4-(pivaloylamino)cyclohexylmethyl]malonamide In the same manner as in Example 155, the title compound (86 mg) was obtained as a white solid using the compound (106 mg) obtained in Example 165 and pivaloyl chloride (25 μL).

$^1$H-NMR (400 MHz, DMSO-$d_6$) δ0.83-0.96 (6H, m), 1.06 (9H, s), 1.06-1.47 (9H, m), 1.57-1.70 (2H, m), 3.06-3.25 (4H, m), 3.50-3.60 (2H, m), 6.82 (1H, d, J=7.6 Hz), 7.70-7.75 (2H, m), 7.85-7.88 (1H, m), 8.07 (1H, d, J=8.0 Hz), 8.16 (1H, d, J=8.8 Hz), 8.22 (1H, d, J=8.0 Hz), 8.59 (1H, d, J=0.8 Hz), 12.32 (1H, brs).

MS: 544(M+H)$^+$.

Example 169

Synthesis of 2-[trans-4-(tert-butyloxycarbonylamino) cyclohexylmethyl]-N,N-diethyl-N'-(2-naphthylsulfonyl)malonamide (1) 5-[trans-4-(tert-butyloxycarbonylamino)cyclohexylmethyl]-2,2-dimethyl-1,3-dioxane-4,6-dione In the same manner as in Example 132 (1), the title compound (18.9 g) was obtained as a white solid using trans-4-(tert-butyloxycarbonylamino)cyclohexanecarboxylic acid (15.2 g).

$^1$H-NMR (300 MHz, DMSO-$d_6$) δ0.83-1.16 (4H, m), 1.37 (9H, s), 1.37-1.90 (7H, m), 1.66 (3H, s), 1.80 (3H, s), 3.07-3.33 (1H, m), 4.12-4.20 (1H, m), 6.60-6.70 (1H, m).

(2) 2-[trans-4-(tert-butyloxycarbonylamino)cyclohexylmethyl]-3-(N,N-diethylamino)-3-oxopropionic acid In the same manner as in Example 119 (2), the title compound (8.40 g) was obtained as a white powder using the above-mentioned compound (10.2 g).

¹H-NMR (400 MHz, DMSO-d₆) δ0.82-1.13 (11H, m), 1.35 (9H, s), 1.50-1.77 (6H, m), 3.04-3.17 (1H, m), 3.20-3.49 (4H, m), 3.59 (1H, t, J=7.2 Hz), 6.55-6.63 (1H, m), 12.43 (1H, brs).

(3) 2-[trans-4-(tert-butyloxycarbonylamino)cyclohexylmethyl]-N,N-diethyl-N'-(2-naphthylsulfonyl)malonamide In the same manner as in Example 1 (2), the title compound (7.20 g) was obtained as a white powder using the above-mentioned compound (8.30 g).

¹H-NMR (400 MHz, DMSO-d₆) δ0.74-1.05 (11H, m), 1.37 (9H, s), 1.37-1.72 (6H, m), 3.00-3.27 (5H, m), 3.59 (1H, t, J=7.2 Hz), 6.50-6.60 (1H, m), 7.65-7.77 (2H, m), 7.83-7.86 (1H, m), 8.07 (1H, d, J=8.0 Hz), 8.18 (1H, d, J=8.8 Hz), 8.22 (1H, d, J=7.6 Hz), 8.59 (1H, d, J=0.8 Hz), 12.30 (1H, brs).

Example 170

Synthesis of 2-(trans-4-aminocyclohexylmethyl)-N,N-diethyl-N'-(2-naphthylsulfonyl)malonamide trifluoroacetic acid salt In the same manner as in Example 18, the title compound (6.45 g) was obtained as a white solid using the compound (6.80 g) obtained in Example 169.

¹H-NMR (300 MHz, DMSO-d₆) δ0.78-1.23 (11H, m), 1.40-1.91 (6H, m), 2.79-2.93 (1H, m), 3.04-3.27 (4H, m), 3.60 (1H, t, J=6.8 Hz), 7.68 (3H, brs), 7.68-7.78 (2H, m), 7.85 (1H, d, J=8.6 Hz), 8.07 (1H, d, J=7.9 Hz), 8.16 (1H, d, J=8.8 Hz), 8.22 (1H, d, J=8.0 Hz), 8.59 (1H, s), 12.40 (1H, brs).
MS: 460(M+H)⁺.

Example 171

Synthesis of 2-[trans-4-(benzoylamino)cyclohexylmethyl]-N,N-diethyl-N'-(2-naphthylsulfonyl)malonamide In the same manner as in Example 155, the title compound (269 mg) was obtained as a white solid using the compound (323 mg) obtained in Example 170 and benzoyl chloride (27 μL).

¹H-NMR (300 MHz, DMSO-d₆) δ0.85-1.04 (9H, m), 1.07-1.29 (2H, m), 1.44-1.60 (3H, m), 1.66-1.81 (3H, m), 3.08-3.27 (4H, m), 3.59-3.71 (2H, m), 7.43-7.51 (3H, m), 7.68-7.76 (2H, m), 7.81-7.83 (2H, m), 7.86-7.88 (1H, m), 8.08 (1H, d, J=7.9 Hz), 8.18 (1H, d, J=8.8 Hz), 8.23 (1H, d, J=7.8 Hz), 8.60 (1H, s), 12.34 (1H, brs).
MS: 564(M+H)⁺.

Example 172

Synthesis of N,N-diethyl-2-[trans-4-(2-methoxybenzoylamino)cyclohexylmethyl]-N'-(2-naphthylsulfonyl)malonamide In the same manner as in Example 13, the title compound (454 mg) was obtained as a white solid using the compound (655 mg) obtained in Example 170 and 2-methoxybenzoic acid (174 mg).

¹H-NMR (400 MHz, DMSO-d₆) δ0.81-1.14 (11H, m), 1.39-1.82 (6H, m), 3.09-3.27 (4H, m), 3.55-3.66 (2H, m), 3.89 (3H, s), 7.00-7.04 (1H, m), 7.13 (1H, d, J=8.3 Hz), 7.43-7.47 (1H, m), 7.66-7.79 (4H, m), 7.86-7.89 (1H, m), 8.07 (1H, d, J=8.0 Hz), 8.17 (1H, d, J=8.7 Hz), 8.23 (1H, d, J=8.0 Hz), 8.60 (1H, s), 12.32 (1H, brs).
MS: 594(M+H)⁺.

Example 173

Synthesis of 2-{trans-4-[(2-benzoxazolyl)amino]cyclohexylmethyl}-N,N-diethyl-N'-(2-naphthylsulfonyl)malonamide In the same manner as in Example 163, the title compound (245 mg) was obtained as a pale-yellow solid using the compound (333 mg) obtained in Example 170 and 2-chlorobenzoxazole (140 μL).

¹H-NMR (400 MHz, DMSO-d₆) δ0.82-1.24 (11H, m), 1.42-2.00 (6H, m), 3.08-3.27 (4H, m), 3.36-3.46 (1H, m), 3.62 (1H, t, J=7.4 Hz), 6.94-6.98 (1H, m), 7.08-7.11 (1H, m), 7.22 (1H, d, J=7.5 Hz), 7.31 (1H, d, J=7.8 Hz), 7.67-7.74 (3H, m), 7.85-7.88 (1H, m), 8.07 (1H, d, J=7.9 Hz), 8.18 (1H, d, J=8.7 Hz), 8.22 (1H, d, J=7.8 Hz), 8.60 (1H, s), 12.34 (1H, brs).
MS: 577(M+H)⁺.

Example 174

Synthesis of 2-[2-(1-benzoyl-4-piperidinyl)ethyl]-N,N-diethyl-N'-(2-naphthylsulfonyl)malonamide (1) 5-[2-(1-tert-butyloxycarbonyl-4-piperidinyl)ethyl]-2,2-dimethyl-1,3-dioxane-4,6-dione In the same manner as in Example 132 (1), the title compound (3.15 g) was obtained as a white solid using 1-tert-butyloxycarbonyl-4-piperidinylacetic acid (4.96 g).

¹H-NMR (300 MHz, DMSO-d₆) δ0.83-1.41 (5H, m), 1.36 (9H, s), 1.55-1.96 (4H, m), 1.64 (3H, s), 1.77 (3H, s), 2.54-2.74 (2H, m), 3.80-3.94 (2H, m), 4.38-4.45 (1H, m).

(2) 2-[2-(1-tert-butyloxycarbonyl-4-piperidinyl)ethyl]-3-(N,N-diethylamino)-3-oxopropionic acid In the same manner as in Example 119 (2), the title compound (1.23 g) was obtained as an oil using the above-mentioned compound (3.13 g).

¹H-NMR (300 MHz, DMSO-d₆) δ0.80-1.20 (11H, m), 1.37 (9H, s), 1.52-1.74 (4H, m), 2.55-2.70 (2H, m), 3.18-3.53 (5H, m), 3.81-3.93 (2H, m), 12.43 (1H, brs).

(3) 2-[2-(1-tert-butyloxycarbonyl-4-piperidinyl)ethyl]-N,N-diethyl-N'-(2-naphthylsulfonyl)malonamide In the same manner as in Example 1 (2), the title compound (880 mg) was obtained as a white powder using the above-mentioned compound (1.22 g).

¹H-NMR (400 MHz, DMSO-d₅) δ0.63-1.31 (13H, m), 1.38 (9H, s), 1.50-1.67 (2H, m), 2.43-2.62 (2H, m), 3.08-3.25 (4H, m), 3.45-3.50 (1H, m), 3.73-3.84 (2H, m), 7.65-7.78 (2H, m), 7.85-7.88 (1H, m), 8.06 (1H, d, J=8.0 Hz), 8.15 (1H, d, J=8.8 Hz), 8.21 (1H, d, J=8.0 Hz), 8.59 (1H, s), 12.30 (1H, brs).

(4) N,N-diethyl-N'-(2-naphthylsulfonyl)-2-[2-(4-piperidinyl)ethyl]malonamide trifluoroacetic acid salt In the same manner as in Example 18, the title compound (900 mg) was obtained as a white powder using the above-mentioned compound (880 mg).

¹H-NMR (400 MHz, DMSO-d₆) δ0.87-0.92 (6H, m), 0.89-1.17 (4H, m), 1.31-1.40 (1H, m), 1.53-1.69 (4H, m), 2.68-2.82 (2H, m), 3.07-3.50 (7H, m), 7.67-7.77 (2H, m), 7.85-7.88 (1H, m), 7.95-8.08 (1H, m), 8.07 (1H, d, J=8.4 Hz), 8.16 (1H, d, J=8.4 Hz), 8.22 (1H, d, J=7.6 Hz), 8.31-8.40 (1H, m), 8.59 (1H, s), 12.33 (1H, brs).

(5) 2-[2-(1-benzoyl-4-piperidinyl)ethyl]-N,N-diethyl-N'-(2-naphthylsulfonyl)malonamide In the same manner as in Example 155, the title compound (152 mg) was obtained as a white solid using the above-mentioned compound (175 mg) and benzoyl chloride (39 μL).

¹H-NMR (400 MHz, DMSO-d₆) δ0.70-1.10 (11H, m), 1.20-1.65 (6H, m), 2.52-2.93 (2H, m), 3.08-3.25 (4H, m), 3.45-3.51 (2H, m), 4.22-4.42 (1H, m), 7.30-7.33 (2H, m), 7.42-7.44 (3H, m), 7.65-7.75 (2H, m), 7.87 (1H, dd, J=8.8, 1.6 Hz), 8.06 (1H, d, J=8.0 Hz), 8.16 (1H, d, J=8.8 Hz), 8.22 (1H, d, J=8.0 Hz), 8.60 (1H, d, J=1.6 Hz), 12.30 (1H, brs).

MS: 564(M+H)⁺.

Example 175

Synthesis of 2-[2-(1-anilinocarbonyl-4-piperidinyl)ethyl]-N,N -diethyl-N'-(2-naphthylsulfonyl)malonamide In the same manner as in Example 155, the title compound (151 mg) was obtained as a white solid using the compound (178 mg) obtained in Example 174 (4) and phenyl isocyanate (37 μL).

¹H-NMR (400 MHz, DMSO-d₆) δ0.71-1.08 (9H, m), 1.17-1.30 (2H, m), 1.40-1.66 (4H, m), 2.58-2.68 (2H, m), 3.07-3.26 (4H, m), 3.46-3.52 (1H, m), 3.95-4.04 (2H, m), 6.88-6.94 (1H, m), 7.19-7.23 (2H, m), 7.44-7.46 (2H, m), 7.68-7.71 (2H, m), 7.86-7.88 (1H, m), 8.01-8.07 (1H, m), 8.14 (1H, d, J=8.8 Hz), 8.17-8.23 (1H, m), 8.36 (1H, s), 8.59 (1H, d, J=0.8 Hz), 12.32 (1H, brs).

MS: 579(M+H)⁺.

Example 176

Synthesis of N,N-diethyl-N'-(2-naphthylsulfonyl)-2-[2-(1-nicotinoyl-4-piperidinyl)ethyl]malonamide hydrochloride To a solution of the compound (350 mg) obtained in Example 174 (4) in pyridine (2 mL) was added nicotinic acid chloride hydrochloride (326 mg) under ice-cooling, and the to mixture was stirred at room temperature for 2 hr. The mixture was concentrated under reduced pressure, and the residue was purified by silica gel column chromatography. This was converted to a hydrochloride salt with 4 mol/L hydrochloric acid-ethyl acetate to give the title compound (63 mg) as a white powder.

¹H-NMR (300 MHz, DMSO-d₆) δ0.76-1.68 (15H, m), 2.59-2.73 (1H, m), 2.84-3.05 (1H, m), 3.05-3.28 (4H, m), 3.28-3.48 (1H, m), 3.59 (1H, t, J=6.6 Hz), 4.23-4.40 (2H, m), 7.65-7.78 (2H, m), 7.78-7.90 (2H, m), 8.07 (1H, d, J=7.9 Hz), 8.16 (1H, d, J=8.8 Hz), 8.21-8.25 (3H, m), 8.60 (1H, s), 8.83-8.85 (2H, m), 12.48 (1H, brs).

MS: 565(M+H)⁺.

Example 177

Synthesis of 2-benzyl-N,N-diethyl-N'-(4-isobutylphenylsulfonyl)malonamide (1) 4-isobutylbenzenesulfonamide To chlorosulfonic acid (10 mL) was added dropwise isobutylbenzene (1.00 mL) under ice-cooling, and the mixture was stirred for 1 hr. Ice-water (100 mL) was added to the reaction mixture, and the mixture was extracted with ethyl acetate (100 mL×2). The organic layer was washed with saturated brine and concentrated under reduced pressure. 28% Aqueous ammonia (50 mL) was added dropwise to a solution of the residue in THF (20 mL) under ice-cooling, and the mixture was stirred at room temperature for 15 hr. The reaction mixture was adjusted to pH=1-2 by the addition of dilute hydrochloric acid, and extracted with ethyl acetate (100 mL×2). The organic layer was washed with saturated brine and concentrated under reduced pressure. The residue was purified by silica gel column chromatography to give the title compound (690 mg) as a white solid.

¹H-NMR (300 MHz, DMSO-d₆) δ0.86 (6H, d, J=6.6 Hz), 1.79-1.94 (1H, m), 2.52 (2H, d, J=7.2 Hz), 7.28 (2H, brs), 7.35 (2H, d, J=8.1 Hz), 7.73 (2H, d, J=8.1 Hz).

(2) ethyl 2-benzyl-3-[(4-isobutylphenylsulfonyl)amino]-3-oxopropionate

In the same manner as in Example 1 (2), the title compound (118 mg) was obtained as an oil using the above-mentioned compound (680 mg) and the compound (710 mg) obtained in Example 1 (1).

¹H-NMR (300 MHz, CDCl₃) δ0.92 (6H, d, J=6.6 Hz), 1.11 (3H, t, J=7.1 Hz), 1.83-1.98 (1H, m), 2.56 (2H, d, J=6.6 Hz), 3.14 (2H, d, J=7.2 Hz), 3.53 (1H, t, J=7.2 Hz), 4.08 (2H, q, J=7.1 Hz), 6.97-7.00 (2H, m), 7.15-7.18 (3H, m), 7.29 (2H, d, J=8.3 Hz), 7.92 (2H, d, J=8.3 Hz).

(3) 2-benzyl-3-[(4-isobutylphenylsulfonyl)amino]-3-oxopropionic acid

In the same manner as in Example 1 (3), the title compound (110 mg) was obtained as an oil using the above-mentioned compound (118 mg).

¹H-NMR (300 MHz, DMSO-d₆) δ0.87 (6H, d, J=6.9 Hz), 1.81-1.98 (1H, m), 2.56 (2H, d, J=7.2 Hz), 2.84-3.00 (2H, m), 3.60-3.70 (1H, m), 6.97-7.00 (2H, m), 7.14-7.16 (3H, m), 7.37 (2H, d, J=8.4 Hz), 7.67 (2H, d, J=8.4 Hz), 12.32 (1H, brs), 12.92 (1H, brs).

(4) 2-benzyl-N,N-diethyl-N'-(4-isobutylphenylsulfonyl)malonamide

In the same manner as in Example 1 (4), the title compound (67 mg) was obtained as an oil using the above-mentioned compound (110 mg).

¹H-NMR (300 MHz, CDCl₃) δ0.78 (3H, t, J=7.1 Hz), 0.90 (6H, d, J=6.6 Hz), 1.00 (3H, t, J=7.1 Hz), 1.85-1.97 (1H, m), 2.55 (2H, d, J=7.2 Hz), 2.78-2.88 (2H, m), 2.98-3.20 (3H, m), 3.38-3.52 (1H, m), 3.55-3.63 (1H, m), 7.05-7.08 (2H, m), 7.19-7.21 (3H, m), 7.30 (2H, d, J=8.4 Hz), 7.97 (2H, d, J=8.4 Hz), 10.08 (1H, brs).

MS: 445(M+H)⁺.

Example 178

Synthesis of N,N-diethyl-2-(4-nitrobenzyl)-N'-tosyl-malonamide (1) diethyl (4-nitrobenzyl) malonate In the same manner as in Example 6 (1), the title compound (27.2 g) was obtained as an oil using diethyl malonate (18.5 g).

$^1$H-NMR (300 Mz, CDCl$_3$) δ1.22 (6H, t, J=7.1 Hz), 3.32 (2H, d, J=7.8 Hz), 3.66 (1H, t, J=7.8 Hz), 4.05-4.29 (4H, m), 7.39 (2H, d, J=8.7 Hz), 8.15 (2H, d, J=8.7 Hz).

(2) monoethyl (4-nitrobenzyl)malonate

In the same manner as in Example 111 (2), the title compound (5.10 g) was obtained as an oil using the above-mentioned compound (7.40 g).

$^1$H-NMR (300 Mz, CDCl$_3$) δ1.23 (3H, t, J=7.1 Hz), 3.23-3.41 (2H, m), 3.74 (1H, t, J=7.7 Hz), 4.04-4.35 (2H, m), 7.40 (2H, d, J=8.6 Hz), 8.15 (2H, d, J=8.7 Hz), 9.65 (1H, brs).

(3) ethyl 2-(4-nitrobenzyl)-3-oxo-3-tosylaminopropionate

In the same manner as in Example 1 (2), the title compound (4.72 g) was obtained as an oil using the above-mentioned compound (3.00 g) and p-toluene-2-sulfonamide (1.92 g).

$^1$H-NMR (300 Mz, CDCl$_3$) δ1.23 (3H, t, J=7.0 Hz), 2.43 (3H, s), 2.98-3.36 (2H, m), 3.73 (1H, t, J=7.56 Hz), 4.14-4.25 (2H, m), 7.30-7.33 (2H, m), 7.39-7.42 (2H, m), 7.79-7.83 (2H, m), 8.14-8.19 (2H, m).

(4) N,N-diethyl-2-(4-nitrobenzyl)-N'-tosylmalonamide

The above-mentioned compound (4.72 g) was subjected to hydrolysis in the same manner as in Example 1 (3). In the same manner as in Example 1 (4), the title compound (1.06 g) was obtained as a white powder using the obtained carboxylic acid (2.16 g).

$^1$H-NMR (300 Mz, DMSO-d$_6$) δ0.88 (6H, t, J=7.2 Hz), 2.38 (3H, s), 3.03-3.05 (2H, m), 3.11-3.19 (4H, m), 3.91 (1H, t, J=7.2 Hz), 7.30-7.36 (4H, m), 7.65 (2H, d, J=8.1 Hz), 7.97 (2H, d, J=8.4 Hz), 12.22 (1H, brs).

MS: 448(M+H)$^+$.

Example 179

Synthesis of 2-(4-aminobenzyl)-N,N-diethyl-N'-tosylmalonamide

In the same manner as in Example 7, the title compound (92 mg) was obtained as a white powder using the compound (120 mg) obtained in Example 178 at room temperature.

$^1$H-NMR (300 Mz, DMSO-d$_6$) δ0.83-0.90 (6H, m), 2.39 (3H, s), 2.72 (2H, d, J=6.9 Hz), 3.10-3.17 (4H, m), 3.66-3.67 (1H, m), 6.35 (2H, J=8.1 Hz), 6.67 (2H, d, J=8.1 Hz), 7.38 (2H, d, J=8.1 Hz), 7.66 (2H, d, J=8.1 Hz).

MS: 418(M+H)$^+$.

Example 180

Synthesis of N'-(4-chlorophenylsulfonyl)-N,N-diethyl-2-(4-nitrobenzyl)malonamide (1) ethyl 3-[(4-chlorophenylsulfonyl)amino]-2-(4-nitrobenzyl)-3-oxopropionate In the same manner as in Example 152 (3), the title compound (1.95 g) was obtained as a white powder using the compound (2.00 g) obtained in Example 178 (2) and 4-chlorobenzenesulfonamide (1.44 g).

$^1$H-NMR (300 Mz, CDCl$_3$) δ1.20-1.25 (3H, m), 3.25-3.28 (2H, m), 3.56-3.61 (1H, m), 4.14-4.19 (2H, m), 7.39-7.42 (1H, m), 7.48-7.52 (2H, m), 7.85-7.88 (1H, m), 7.94-7.96 (2H, m), 8.13-8.16 (2H, m).

(2) 3-[(4-chlorophenylsulfonyl)amino]-2-(4-nitrobenzyl)-3-oxopropionic acid

In the same manner as in Example 1 (3), the title compound (1.01 g) was obtained as a white powder using the above-mentioned compound (1.95 g).

$^1$H-NMR (300 Mz, CDCl$_3$) δ3.31-3.39 (2H, m), 3.59-3.64 (1H, m), 7.20-7.23 (1H, m), 7.44-7.49 (1H, m), 7.49-7.54 (2H, in), 7.85-7.88 (1H, m), 7.94-7.97 (1H, m), 8.04-8.07 (1H, m), 8.16-8.19 (1H, m).

(3) N'-(4-chlorophenylsulfonyl)-N,N-diethyl-2-(4-nitrobenzyl)malonamide

In the same manner as in Example 1 (4), the title compound (140 mg) was obtained as a white powder using the above-mentioned compound (1.01 g).

$^1$H-NMR (300 Mz, DMSO-d$_6$) δ0.85-0.97 (6H, m), 3.05-3.11 (2H, m), 3.13-3.23 (4H, m), 3.93 (1H, t, J=7.5 Hz), 7.34 (2H, d, J=8.4 Hz), 7.63 (2H, d, J=8.4 Hz), 7.78 (2H, d, J=8.7 Hz), 7.99 (2H, d, J=8.7 Hz), 12.40 (1H, brs).

MS: 468(M+H)$^+$.

Example 181

Synthesis of 2-(4-aminobenzyl)-N'-(4-chlorophenylsulfonyl)-N,N-diethylmalonamide In the same manner as in Example 137 (4), the title compound (8 mg) was obtained as a white powder using the compound (116 mg) obtained in Example 180 at room temperature.

$^1$H-NMR (300 Mz, DMSO-d$_6$) δ0.86-0.87 (6H, m), 2.71-2.75 (1H, m), 3.03-3.15 (4H, m), 3.33-3.37 (2H, m), 6.41 (1H, d, J=7.8 Hz), 6.71 (1H, d, J=8.4 Hz), 7.33 (1H, d, J=8.7 Hz), 7.57 (1H, d, J=8.1 Hz), 7.65 (1H, d, J=8.7 Hz), 7.75-7.78 (2H, m), 7.99 (1H, d, J=8.7 Hz).

MS: 438(M+H)$^+$.

Example 182

Synthesis of N,N-diethyl-N'-(4-methoxyphenylsulfonyl)-2-(4-nitrobenzyl)malonamide (1) ethyl 3-[(4-methoxyphenylsulfonyl)amino]-2-(4-nitrobenzyl)-3-oxopropionate In the same manner as in Example 152 (3), the title compound (2.82 g) was obtained as a white powder using the compound (2.00 g) obtained in Example 178 (2) and 4-methoxybenzenesulfonamide (1.40 g).
$^1$H-NMR (300 Mz, CDCl$_3$) δ1.20 (3H, t, J=7.2 Hz), 2.17 (3H, s), 3.24-3.27 (2H, m), 3.51-3.55 (1H, m), 4.13-4.20 (2H, m), 6.97-6.99 (3H, m), 7.14-7.17 (1H, m), 7.85-7.88 (1H, m), 7.93-8.02 (3H, m).

(2) 3-[(4-methoxyphenylsulfonyl)amino]-2-(4-nitrobenzyl)-3-oxopropionic acid

In the same manner as in Example 1 (3), the title compound (2.64 g) was obtained as a white powder using the above-mentioned compound (2.82 g).
$^1$H-NMR (300 Mz, CDCl$_3$) δ2.07 (3H, s), 2.99-3.15 (2H, m), 3.68-3.71 (1H, m), 6.99-7.08 (2H, m), 7.16-7.26 (2H, m), 7.61-7.74 (2H, m), 7.92-7.95 (1H, m), 8.10-8.12 (1H, m).

(3) N,N-diethyl-N'-(4-methoxyphenylsulfonyl)-2-(4-nitrobenzyl)malonamide

In the same manner as in Example 1 (4), the title compound (980 mg) was obtained as a white powder using the above-mentioned compound (2.64 g).
$^1$H-NMR (300 Mz, DMSO-d$_6$) δ0.86-0.90 (6H, m), 3.03-3.13 (2H, m), 3.16-3.21 (4H, m), 3.32 (3H, s), 3.87-3.92 (1H, m), 7.06 (2H, d, J=9.0 Hz), 7.32 (2H, d, J=8.7 Hz), 7.71 (2H, d, J=8.7 Hz), 7.98 (2H, d, J=9.0 Hz), 12.14 (1H, brs).
MS: 464(M+H)$^+$.

Example 183

Synthesis of 2-(4-aminobenzyl)-N,N-diethyl-N'-(4-methoxyphenylsulfonyl)malonamide In the same manner as in Example 7, the title compound (170 mg) was obtained as a white powder using the compound (200 mg) obtained in Example 182 at room temperature.
$^1$H-NMR (300 Mz, DMSO-d$_6$) δ0.83-0.90 (6H, m), 2.72 (2H, d, J=6.9 Hz), 3.06-3.31 (4H, m), 3.64-3.62 (1H, m), 3.84 (3H, s), 6.36 (2H, d, J=8.4 Hz), 6.68 (2H, d, J=8.4 Hz), 7.10 (2H, d, J=8.7 Hz), 7.73 (2H, d, J=8.7 Hz).
MS: 434(M+H)$^+$.

Example 184

Synthesis of N,N-diethyl-N'-(1-naphthylsulfonyl)-2-(4-nitrobenzyl)malonamide (1) ethyl 3-[(1-naphthylsulfonyl)amino]-2-(4-nitrobenzyl)-3-oxopropionate In the same manner as in Example 152 (3), the title compound (3.17 g) was obtained as a white powder using the compound (2.00 g) obtained in Example 178 (2) and naphthalene-1-sulfonamide (1.55 g).
$^1$H-NMR (300 Mz, CDCl$_3$) δ0.88 (3H, t, J=6.9 Hz), 2.93-3.00 (2H, m), 3.76-3.89 (3H, m), 7.09-7.12 (2H, m), 7.55-7.72 (5H, m), 8.01-8.04 (1H, m), 8.21-8.28 (2H, m), 8.34-8.36 (1H, m), 12.75 (1H, brs).

(2) 3-[(1-naphthylsulfonyl)amino]-2-(4-nitrobenzyl)-3-oxopropionic acid

In the same manner as in Example 1 (3), the title compound (2.61 g) was obtained as a white powder using the above-mentioned compound (3.17 g).
$^1$H-NMR (300 Mz, CDCl$_3$) δ3.05-3.20 (2H, m), 3.64-3.66 (1H, m), 6.87-6.89 (2H, m), 7.48-7.65 (5H, m), 7.96-7.99 (1H, m), 8.18-8.21 (1H, m), 8.34-8.37 (1H, m), 8.48-8.51 (1H, m), 10.18 (1H, brs).

(3) N,N-diethyl-N'-(1-naphthylsulfonyl)-2-(4-nitrobenzyl)malonamide

In the same manner as in Example 1 (4), the title compound (1.18 g) was obtained as a white powder using the above-mentioned compound (2.61 g).
$^1$H-NMR (300 Mz, DMSO-d$_6$) δ0.68 (3H, t, J=6.9 Hz), 0.76 (3H, t, J=6.9 Hz), 2.89-3.09 (6H, m), 3.84-3.86 (1H, m), 7.21-7.24 (2H, m), 7.60-7.70 (3H, m), 7.82-7.85 (2H, m), 8.00-8.07 (1H, m), 8.26-8.30 (2H, m), 8.44 (1H, d, J=8.4 Hz), 12.67 (1H, brs).
MS: 484(M+H)$^+$.

Example 185

Synthesis of 2-(4-aminobenzyl)-N,N-diethyl-N'-(1-naphthylsulfonyl)malonamide

In the same manner as in Example 7, the title compound (290 mg) was obtained as a white powder using the compound (400 mg) obtained in Example 184.
$^1$H-NMR (300 Mz, DMSO-d$_6$) δ0.61-0.71 (6H, m), 2.63-2.71 (2H, m), 3.00-3.02 (4H, m), 3.60-3.63 (1H, m), 6.36 (2H, d, J=7.8 Hz), 6.71 (2H, d, J=7.8 Hz), 7.67-7.69 (3H, m), 8.09-8.29 (3H, m), 8.56 (1H, d, J=8.4 Hz).
MS: 454(M+H)$^+$.

Example 186

Synthesis of N,N-diethyl-N'-(7-methoxy-2-naphthylsulfonyl)-2-(4-nitrobenzyl)malonamide (1) 3-[(7-methoxy-2-naphthylsulfonyl)amino]-2-(4-nitrobenzyl)-3-oxopropionic acid In the same manner as in Example 152 (3), the ester form of the title compound was obtained using the compound (1.55 g) obtained in Example 178 (2) and 7-methoxynaphthalene-2-sulfonamide (1.37 g). In the same manner as in Example 1 (3), the title compound (1.53 g) was obtained as a white powder using this.
$^1$H-NMR (300 Mz, CDCl$_3$) δ2.97-3.13 (2H, m), 3.72-3.75 (1H, m), 3.89 (3H, s), 7.16-7.19 (1H, m), 7.34-7.38 (1H, m), 7.46-7.56 (3H, m), 7.73-7.76 (2H, m), 7.89-7.92 (2H, m), 8.11-8.14 (1H, m), 8.33 (1H, s), 12.77 (1H, brs).

(2) N,N-diethyl-N'-(7-methoxy-2-naphthylsulfonyl)-2-(4-nitrobenzyl)malonamide

In the same manner as in Example 1 (4), the title compound (450 mg) was obtained as a white powder using the above-mentioned compound (1.53 g).
$^1$H-NMR (300 Mz, DMSO-d$_6$) δ0.86 (6H, t, J=6.9 Hz), 3.04 (2H, d, J=7.5 Hz), 3.12-3.18 (4H, m), 3.90 (3H, s), 3.92-3.95 (1H, m), 7.26-7.29 (2H, m), 7.35-7.39 (1H, m), 7.58-7.61 (2H, m), 7.83-7.86 (2H, m), 7.93-8.00 (2H, m), 8.38 (1H, s), 12.30 (1H, brs).
MS: 514(M+H)$^+$.

Example 187

Synthesis of 2-(4-aminobenzyl)-N,N-diethyl-N'-(7-methoxy-2-naphthylsulfonyl)malonamide In the same manner as in Example 7, the title compound (46 mg) was obtained as a white powder using the compound (320 mg) obtained in Example 186.

$^1$H-NMR (300 Mz, DMSO-d$_6$) δ0.82-0.84 (6H, m), 2.73 (2H, d, J=6.0 Hz), 3.09-3.12 (4H, m), 3.65-3.70 (1H, m), 3.90 (3H, s), 6.34 (2H, d, J=8.1 Hz), 6.70 (2H, d, J=8.4 Hz), 7.36 (1H, d, J=9.0 Hz), 7.57-7.60 (2H, m), 7.94-8.03 (2H, m), 8.42 (1H, s).
MS: 484(M+H)$^+$.

Example 188

Synthesis of N'-(4-biphenylsulfonyl)-N,N-diethyl-2-(4-nitrobenzyl)malonamide (1) ethyl 3-(N,N-diethylamino)-2-(4-nitrobenzyl)-3-oxopropionate In the same manner as in Example 1 (4), the title compound (1.53 g) was obtained as a white powder using the compound (2.00 g) obtained in Example 178 (2).

$^1$H-NMR (300 Mz, CDCl$_3$) δ0.94-1.07 (6H, m), 1.22-1.26 (3H, m), 3.05-3.10 (2H, m), 3.30-3.42 (4H, m), 3.75-3.78 (1H, m), 4.15-4.22 (2H, m), 7.36-7.42 (2H, m), 8.12-8.14 (2H, m).

(2) 3-(N,N-diethylamino)-2-(4-nitrobenzyl)-3-oxo-propionic acid

In the same manner as in Example 1 (3), the title compound (1.09 g) was obtained as a pale-yellow powder using the above-mentioned compound (1.53 g).

$^1$H-NMR (300 Mz, CDCl$_3$) δ0.82-0.86 (6H, m), 3.05-3.14 (4H, m), 3.20-3.33 (2H, m), 3.99-4.04 (1H, m), 7.47-7.50 (2H, m), 8.09-8.12 (2H, m), 12.70 (1H, brs).

(3) N,N-diethyl-2-(4-nitrobenzyl)malonamide

To a solution of the above-mentioned compound (400 mg) in methylene chloride (10 mL) was added oxalyl chloride (180 μL) under ice-cooling, and the mixture was stirred at room temperature for 1 hr. The reaction mixture was concentrated under reduced pressure. THF (50 mL) was added, and the mixture was ice-cooled. 28% Aqueous ammonia (1 mL) was added, and the mixture was stirred for 1 hr. 1 mol/L Hydrochloric acid (100 mL) was added, and the mixture was extracted with ethyl acetate (50 mL). The organic layer was washed with saturated brine and concentrated under reduced pressure to give the title compound (250 mg) as a white powder.

$^1$H-NMR (300 Mz, CDCl$_3$) δ0.87-0.94 (6H, m), 3.04-3.10 (2H, m), 3.19-3.24 (4H, m), 3.37-3.76 (1H, m), 7.09 (1H, brs), 7.35 (1H, brs), 7.47-7.50 (2H, m), 8.10-8.13 (2H, m).

(4) N'-(4-biphenylsulfonyl)-N,N-diethyl-2-(4-nitrobenzyl)malonamide

To a solution of the above-mentioned compound (300 mg) and 4-biphenylsulfonyl chloride (260 mg) in THF (25 mL) was added 60% sodium hydride (80 mg) under ice-cooling, and the mixture was stirred at room temperature for 1 hr. 1 mol/L Hydrochloric acid (20 mL) was added to the reaction mixture under ice-cooling, and the mixture was extracted with ethyl acetate (20 mL). The organic layer was washed with saturated brine and concentrated under reduced pressure, and the residue was purified by silica gel column chromatography to give the title compound (380 mg) as a white powder.

$^1$H-NMR (300 Mz, DMSO-d$_6$) δ0.84-0.89 (6H, m), 3.01-3.15 (4H, m), 3.33-3.49 (1H, m), 3.49-3.62 (2H, m), 7.34-7.39 (3H, m), 7.44-7.49 (2H, m), 7.60-7.74 (6H, m), 7.98 (2H, d, J=8.4 Hz).
MS: 510(M+H)$^+$.

Example 189

Synthesis of 2-(4-aminobenzyl)-N'-(4-biphenylsulfonyl)-N,N-diethylmalonamide

In the same manner as in Example 7, the title compound (230 mg) was obtained as a white powder using the compound (300 mg) obtained in Example 188 at room temperature.

$^1$H-NMR (300 Mz, DMSO-d$_6$) δ0.84-0.90 (6H, m), 2.76 (1H, d, J=7.2 Hz), 3.16-3.18 (4H, m), 3.28-3.29 (2H, m), 6.39-6.43 (2H, m), 6.71-6.74 (2H, m), 7.44-7.54 (3H, m), 7.73-7.84 (2H, m), 7.86-7.87 (4H, m).
MS: 480(M+H)$^+$.

Example 190

Synthesis of N,N-diethyl-2-(4-nitrobenzyl)-N'-(2-tolylsulfonyl)malonamide

In the same manner as in Example 188 (4), the title compound (170 mg) was obtained as a white powder using the compound (300 mg) obtained in Example 188 (3) and 2-methylbenzenesulfonyl chloride (150 μL).

$^1$H-NMR (300 Mz, DMSO-d$_6$) δ0.86-0.91 (6H, m), 2.48 (3H, s), 3.04-3.07 (1H, m), 3.11-3.30 (4H, m), 3.93-3.97 (1H, m), 7.30-7.39 (4H, m), 7.54-7.56 (1H, m), 7.65-7.67 (1H, m), 7.90-8.05 (2H, m).
MS: 448(M+H)$^+$.

Example 191

Synthesis of 2-(4-aminobenzyl)-N,N-diethyl-N'-(2-tolylsulfonyl)malonamide

In the same manner as in Example 7, the title compound (158 mg) was obtained as a white powder using the compound (170 mg) obtained in Example 190 at room temperature.

$^1$H-NMR (300 Mz, DMSO-d$_6$) δ0.84-0.92 (6H, m), 2.43 (3H, s), 2.72-2.74 (2H, m), 3.12-3.17 (4H, m), 3.71 (1H, t, J=6.9 Hz), 6.38 (2H, d, J=8.3 Hz), 6.69 (2H, d, J=8.3 Hz), 7.35-7.38 (2H, m), 7.53-7.58 (1H, m), 7.86 (1H, d, J=8.1 Hz).
MS: 418(M+H)$^+$.

Example 192

Synthesis of N'-(4-tert-butylphenylsulfonyl)-N,N-diethyl-2-(4-nitrobenzyl)malonamide In the same manner as in Example 188 (4), the title compound (187 mg) was obtained as a white powder using the compound (300 mg) obtained in Example 188 (3) and 4-tert-butylbenzenesulfonyl chloride (230 mg).

$^1$H-NMR (300 Mz, DMSO-d$_6$) δ0.82-0.90 (6H, m), 1.28 (9H, s), 3.07-3.29 (6H, m), 3.91 (1H, t, J=7.2 Hz), 7.33 (2H, d, J=8.7 Hz), 7.58 (2H, d, J=8.7 Hz), 7.71 (2H, d, J=8.7 Hz), 7.98 (2H, d, J=8.7 Hz), 12.20 (1H, brs).

MS: 490(M+H)$^+$.

Example 193

Synthesis of 2-(4-aminobenzyl)-N'-(4-tert-butylphenylsulfonyl)-N,N-diethylmalonamide In the same manner as in Example 7, the title compound (100 mg) was obtained as a white powder using the compound (130 mg) obtained in Example 192 at room temperature.

$^1$H-NMR (300 Mz, DMSO-d$_6$) δ0.79-0.88 (6H, m), 1.29 (9H, s), 2.74 (2H, d, J=6.9 Hz), 3.08-3.32 (4H, m), 3.67-3.69 (1H, m), 6.37 (2H, d, J=8.4 Hz), 6.69 (2H, d, J=8.4 Hz), 7.60 (2H, d, J=8.7 Hz), 7.71 (2H, d, J=8.7 Hz).

MS: 460(M+H)$^+$.

Example 194

Synthesis of N,N-diethyl-2-(4-nitrobenzyl)-N'-(2-thienylsulfonyl)malonamide

In the same manner as in Example 188 (4), the title compound (390 mg) was obtained as a white powder using the compound (300 mg) obtained in Example 188 (3) and 2-thiophenesulfonyl chloride (180 mg).

$^1$H-NMR (300 Mz, DMSO-d$_6$) δ0.84-0.91 (6H, m), 3.06-3.21 (6H, m), 3.91 (1H, t, J=7.5 Hz), 7.14-7.17 (1H, m), 7.36 (2H, d, J=8.7 Hz), 7.67-7.68 (1H, m), 8.00-8.03 (3H, m).

MS: 440(M+H)$^+$.

Example 195

Synthesis of 2-(4-aminobenzyl)-N,N-diethyl-N'-(2-thienylsulfonyl)malonamide

In the same manner as in Example 137 (4), the title compound (52 mg) was obtained as a white powder using the compound (230 mg) obtained in Example 194 at room temperature.

$^1$H-NMR (300 Mz, DMSO-d$_6$) δ0.85-0.91 (6H, m), 2.74 (2H, d, J=6.3 Hz), 3.12-3.14 (4H, m), 3.65-3.67 (1H, m), 6.41 (2H, d, J=7.6 Hz), 6.73 (2H, d, J=7.6 Hz), 7.16 (1H, brs), 7.64 (1H, brs), 7.98 (1H, brs).

MS: 410(M+H)$^+$.

Example 196

Synthesis of N,N-diethyl-2-(4-nitrobenzyl)-N'-(4-trifluoromethylphenylsulfonyl)malonamide In the same manner as in Example 188 (4), the title compound (260 mg) was obtained as a white powder using the compound (300 mg) obtained in Example 188 (3) and 4-trifluoromethylbenzenesulfonyl chloride (240 mg).

$^1$H-NMR (300 Mz, DMSO-d$_6$) δ0.85-0.92 (6H, m), 3.07 (2H, d, J=7.5 Hz), 3.12-3.21 (4H, m), 3.95 (1H, t, J=7.5 Hz), 7.34 (2H, d, J=8.7 Hz), 7.93-8.02 (6H, m).

MS: 502(M+H)$^+$.

Example 197

Synthesis of 2-(4-aminobenzyl)-N,N-diethyl-N'-(4-trifluoromethylphenylsulfonyl)malonamide In the same manner as in Example 7, the title compound (120 mg) was obtained as a white powder using the compound (310 mg) obtained in Example 196.

$^1$H-NMR (300 Mz, DMSO-d$_6$) δ0.84 (3H, s), 0.86 (3H, s), 2.76 (2H, d, J=5.4 Hz), 3.12-3.17 (4H, m), 3.69 (1H, brs), 6.46 (2H, d, J=7.2 Hz), 6.76 (2H, d, J=7.2 Hz), 7.95-7.96 (4H, m).

MS: 472(M+H)$^+$.

Example 198

Synthesis of N,N-diethyl-N'-(5-dimethylaminonaphthyl-1-sulfonyl)-2-(4-nitrobenzyl)malonamide In the same manner as in Example 188 (4), the title compound (390 mg) was obtained as a white powder using the compound (300 mg) obtained in Example 188 (3) and 5-dimethylaminonaphthalene-1-sulfonyl chloride (270 mg).

$^1$H-NMR (300 Mz, DMSO-d$_6$) δ0.69 (3H, brs), 0.76 (3H, brs), 2.81 (6H, s), 2.87-3.18 (6H, m), 3.85 (1H, brs), 7.16-7.24 (3H, m), 7.51-7.54 (1H, m), 7.61-7.66 (1H, m), 7.83-7.85 (2H, m), 8.05-8.08 (1H, m), 8.22-8.29 (1H, m), 8.48-8.51 (1H, m), 12.62 (1H, brs).

MS: 527(M+H)$^+$.

Example 199

Synthesis of 2-(4-aminobenzyl)-N,N-diethyl-N'-(5-dimethylaminonaphthyl-1-sulfonyl)malonamide In the same manner as in Example 7, the title compound (100 mg) was obtained as a white powder using the compound (260 mg) obtained in Example 198 at room temperature.

$^1$H-NMR (300 Mz, DMSO-d$_6$) δ0.57-0.59 (3H, brs), 0.68-0.70 (3H, brs), 2.64-2.81 (9H, m), 2.99-3.01 (3H, m), 3.63 (1H, brs), 6.35-6.38 (2H, m), 6.71-6.74 (2H, m), 7.23-7.25 (1H, m), 7.57-7.66 (2H, m), 8.19-8.30 (2H, m), 8.48-8.50 (1H, m).

MS: 497(M+H)$^+$.

Example 200

Synthesis of N,N-diethyl-2-(4-nitrobenzyl)-N'-((E)-styrylsulfonyl)malonamide

In the same manner as in Example 188 (4), the title compound (310 mg) was obtained as a white powder using the compound (600 mg) obtained in Example 188 (3) and trans-β-styrenesulfonyl chloride (410 mg).

$^1$H-NMR (300 Mz, DMSO-d$_6$) δ0.87-0.97 (6H, m), 3.14-3.30 (6H, m), 3.94-3.96 (1H, m), 7.26 (1H, d, J=15.3 Hz), 7.43-7.48 (6H, m), 7.68-7.70 (2H, m), 8.03 (2H, d, J=8.4 Hz), 12.07 (1H, brs).

MS: 460(M+H)$^+$.

Example 201

Synthesis of 2-(4-aminobenzyl)-N,N-diethyl-N'-((E)-styrylsulfonyl)malonamide

In the same manner as in Example 137 (4), the title compound (60 mg) was obtained as a white powder using the compound (200 mg) obtained in Example 200 at room temperature.

¹H-NMR (300 Mz, DMSO-d₆) δ0.88-0.95 (6H, m), 2.83 (2H, d, J=6.6 Hz), 3.13-3.22 (4H, m), 3.73-3.74 (1H, m), 6.40 (2H, d, J=8.3 Hz), 6.81 (2H, d, J=8.3 Hz), 7.20 (1H, d, J=15.3 Hz), 7.45-7.55 (4H, m), 7.70-7.71 (2H, m).
MS: 430(M+H)⁺.

Example 202

Synthesis of 2-[4-(benzoylamino)benzyl]-N,N-diethyl-N'-((E)-styrylsulfonyl)malonamide In the same manner as in Example 9, the title compound (187 mg) was obtained as a white solid using the compound (193 mg) obtained in Example 201.
¹H-NMR (400 MHz, DMSO-d₆) δ0.86-1.05 (6H, m), 3.01 (2H, d, J=6.8 Hz), 3.08-3.40 (4H, m), 3.90 (1H, t, J=7.2 Hz), 7.10-7.28 (3H, m), 7.40-7.80 (11H, m), 7.94 (2H, d, J=7.2 Hz), 10.15 (1H, s), 12.00 (1H, brs).

Example 203

Synthesis of 2-[4-(benzoylamino)benzyl]-N'-(4-tert-butylphenylsulfonyl)-N,N-diethylmalonamide In the same manner as in Example 92, the title compound (1.70 g) was obtained as a white solid using the compound (1.62 g) obtained in Example 192.
¹H-NMR (400 MHz, DMSO-d₆) δ0.85-0.92 (6H, m), 1.29 (9H, s), 2.93 (2H, d, J=7.1 Hz), 3.10-3.24 (4H, m), 3.85 (1H, t, J=7.1 Hz), 7.05 (2H, d, J=8.4 Hz), 7.52-7.62 (7H, m), 7.72 (2H, d, J=8.4 Hz), 7.95 (2H, d, J=7.4 Hz), 10.19 (1H, s), 12.19 (1H, brs).
MS: 564(M+H)⁺.

Example 204

Synthesis of N,N-diethyl-2-(3-nitrobenzyl)-N'-((E)-styrylsulfonyl)malonamide (1) N,N-diethyl-2-(3-nitrobenzyl)malonamide In the same manner as in Example 188 (3), the title compound (2.27 g) was obtained as a white solid using the compound (2.66 g) obtained in Example 114 (4).
¹H-NMR (300 MHz, DMSO-d₆) δ0.88-0.95 (6H, m), 3.05-3.40 (6H, m), 3.77 (1H, dd, J=6.5, 4.7 Hz), 7.12 (1H, brs), 7.37 (1H, brs), 7.56 (1H, t, J=7.9 Hz), 7.72 (1H, d, J=7.9 Hz), 8.06 (1H, d, J=7.9 Hz), 8.11 (1H, s).

(2) N,N-diethyl-2-(3-nitrobenzyl)-N'-((E)-styrylsulfonyl)malonamide

In the same manner as in Example 188 (4), the title compound (150 mg) was obtained as a white solid using the above-mentioned compound (830 mg) and trans-β-styrenesulfonyl chloride (1.26 g).
¹H-NMR (300 MHz, CDCl₃) δ0.95 (3H, t, J=7.1 Hz), 1.04 (3H, t, J=7.1 Hz), 2.96-3.60 (6H, m), 3.75 (1H, dd, J=9.0, 6.1 Hz), 7.04 (1H, d, J=15.4 Hz), 7.35-7.54 (7H, m), 7.71 (1H, d, J=15.4 Hz), 8.06-8.08 (2H, m), 10.56 (1H, brs).

Example 205

Synthesis of 2-(3-aminobenzyl)-N,N-diethyl-N'-((E)-styrylsulfonyl)malonamide hydrochloride The compound (470 mg) obtained in Example 204 was reduced at room temperature in the same manner as in Example 137 (4), and the reduced product was converted to a hydrochloride salt with 4 mol/L hydrochloric acid-ethyl acetate (1 mL) to give the title compound (89 mg) as a pale-yellow powder.
¹H-NMR (400 MHz, DMS-d₆) δ0.85-1.03 (6H, m), 2.98-3.30 (6H, m), 3.93-3.97 (1H, m), 7.00-7.20 (3H, m), 7.20-7.36 (2H, m), 7.37 (1H, d, J=15.2 Hz), 7.45-7.50 (2H, m), 7.58 (1H, d, J=15.2 Hz), 7.74-7.76 (2H, m), 9.58 (3H, brs), 12.13 (1H, brs).
MS:430(M+H)⁺.

Example 206

Synthesis of N,N-diethyl-2-(4-methoxybenzyl)-N'-((E)-styrylsulfonyl)malonamide (1) ethyl 2-(4-methoxybenzyl)-3-oxo-3-[((E)-styrylsulfonyl)amino]propionate In the same manner as in Example 1 (2), the title compound (5.01 g) was obtained as an oil using the compound (4.08 g) obtained in Example 112 (2) and trans-β-styrenesulfonamide (2.74 g).
¹H-NMR (300 Mz, DMSO-d₆) δ1.08 (3H, t, J=7.0 Hz), 2.88-3.03 (2H, m), 3.56-3.80 (4H, m), 3.90-4.19 (2H, m), 6.73 (2H, d, J=8.5 Hz), 7.07 (2H, d, J=8.6 Hz), 7.28 (1H, d, J=15.5 Hz), 7.35-7.60 (4H, m), 7.67-7.81 (2H, m), 12.23 (1H, brs).

(2) 2-(4-methoxybenzyl)-3-oxo-3-[((E)-styrylsulfonyl)amino]propionic acid

In the same manner as in Example 1 (3), the title compound (3.56 g) was obtained as a white powder using the above-mentioned compound (5.01 g).
¹H-NMR (300 Mz, DMSO-d₆) δ2.88-3.03 (2H, m), 3.50-3.70 (4H, m), 6.70 (2H, d, J=8.7 Hz), 7.06 (2H, d, J=8.6 Hz), 7.23 (1H, J=15.4 Hz), 7.40-7.58 (4H, m), 7.61-7.79 (2H, m), 12.00 (1H, brs), 12.80 (1H, brs).

(3) N,N-diethyl-2-(4-methoxybenzyl)-N'-((E)-styrylsulfonyl)malonamide

In the same manner as in Example 1 (4), the title compound (980 mg) was obtained as a white powder using the above-mentioned compound (1.25 g).
¹H-NMR (300 Mz, DMSO-d₆) δ0.80-1.00 (6H, m), 2.83-3.31 (6H, m), 3.64 (3H, s), 3.71-3.88 (1H, m), 6.72 (2H, d, J=8.4 Hz), 7.08 (2H, d, J=8.4 Hz), 7.29 (1H, d, J=15.7 Hz), 7.40-7.59 (4H, m), 7.74 (2H, d, J=7.7 Hz), 12.00 (1H, brs).
MS: 445(M+H)⁺.

Example 207

Synthesis of N,N-diethyl-N'-((E)-styrylsulfonyl)-2-(4-trifluoromethoxybenzyl)malonamide (1) ethyl 3-oxo-3-[((E)-styrylsulfonyl)amino]-2-[4-(trifluoromethoxy)benzyl]propionate In the same manner as in Example 1 (2), the title compound (3.34 g) was obtained as an oil using the compound (2.97 g) obtained in Example 117 (2) and trans-β-styrenesulfonamide (1.64 g).
¹H-NMR (300 Mz, CDCl₃) δ1.16 (3H, t, J=7.1 Hz), 3.09-3.31 (2H, m), 3.48-3.61 (1H, m), 4.15 (2H, q, J=7.2 Hz), 6.89-7.64 (10H, m), 7.72 (1H, d, J=15.4 Hz).

(2) 3-oxo-3-[((E)-styrylsulfonyl)amino]-2-[4-(trifluoromethoxy)benzyl]propionic acid In the same manner as in Example 1 (3), the title compound (2.44 g) was obtained as a white powder using the above-mentioned compound (3.34 g).

$^1$H-NMR (300 Mz, DMSO-$d_6$) δ2.93-3.20 (2H, m), 3.60-3.78 (1H, m), 6.97-7.60 (9H, m), 7.60-7.80 (2H, m), 10.90-13.80 (2H, brs).

(3) N,N-diethyl-N'-((E)-styrylsulfonyl)-2-(4-trifluoromethoxybenzyl)malonamide

In the same manner as in Example 1 (4), the title compound (280 mg) was obtained as a white powder using the above-mentioned compound (1.22 g).

$^1$H-NMR (300 Mz, DMSO-$d_5$) δ0.80-1.00 (6H, m), 3.00-3.40 (6H, m), 3.89 (1H, t, J=7.2 Hz), 7.16 (2H, d, J=8.7 Hz), 7.20-7.35 (3H, m), 7.38-7.60 (4H, m), 7.65-7.80 (2H, m), 12.05 (1H, brs).

MS: 499(M+H)$^+$.

Example 208

Synthesis of N,N-diethyl-2-(4-fluorobenzyl)-N'-((E)-styrylsulfonyl)malonamide

In the same manner as in Example 1 (2), the title compound (755 mg) was obtained as a white powder using the compound (1.39 g) obtained in Example 118 (4) and trans-β-styrenesulfonamide (878 mg).

$^1$H-NMR (300 Mz, DMSO-$d_6$) δ0.80-1.00 (6H, m), 2.90-3.40 (6H, m), 3.86 (1H, t, J=7.2 Hz), 6.99 (2H, t, J=9.0 Hz), 7.11-7.33 (3H, m), 7.39-7.60 (4H, m), 7.64-7.79 (2H, m), 12.01 (1H, brs).

MS: 433(M+H)$^+$.

Example 209

Synthesis of N,N-diethyl-2-(3,4-dimethoxybenzyl)-N'-((E)-styrylsulfonyl)malonamide In the same manner as in Example 1 (2), the title compound (495 mg) was obtained as a white powder using the compound (760 mg) obtained in Example 119 (2) and trans-β-styrenesulfonamide (416 mg).

$^1$H-NMR (300 Mz, DMSO-$d_6$) δ0.96 (3H, t, J=7.2 Hz), 1.04 (3H, t, J=7.2 Hz), 2.88-3.09 (2H, m), 3.10-3.47 (4H, m), 3.71 (3H, s), 3.75 (3H, s), 3.80-3.94 (1H, m), 6.58-6.69 (1H, m), 6.71-6.90 (2H, m), 7.20 (1H, d, J=15.3 Hz), 7.39-7.59 (4H, m), 7.65-7.78 (2H, m), 11.91 (1H, brs).

MS: 475(M+H)$^+$.

Example 210

Synthesis of N,N-diethyl-2-(4-methoxycarbonylbenzyl)-N'-((E)-styrylsulfonyl)malonamide In the same manner as in Example 1 (2), the title compound (759 mg) was obtained as a white powder using the compound (909 mg) obtained in Example 120 (2) and trans-β-styrenesulfonamide (500 mg).

$^1$H-NMR (300 Mz, DMSO-$d_6$) δ0.79-1.00 (6H, m), 2.09 (3H, s), 3.00-3.37 (6H, m), 3.81 (3H, s), 3.94 (1H, t, J=7.5 Hz), 7.25 (1H, d, J=15.3 Hz), 7.29-7.39 (2H, m), 7.40-7.58 (4H, m), 7.67-7.84 (4H, m), 12.05 (1H, brs).

MS: 473(M+H)$^+$.

Example 211

Synthesis of N,N-diethyl-2-(4-hydroxycarbonylbenzyl)-N'-((E)-styrylsulfonyl)malonamide In the same manner as in Example 121, the title compound (254 mg) was obtained as a white powder using the compound (300 mg) obtained in Example 210.

$^1$H-NMR (300 Mz, DMSO-$d_6$) δ0.80-1.05 (6H, m), 3.00-3.45 (6H, m), 3.82-4.00 (1H, m), 7.18-7.34 (3H, m), 7.39-7.59 (4H, m), 7.64-7.85 (4H, m), 12.05 (1H, brs), 12.76 (1H, brs).

MS: 459(M+H)$^+$.

Example 212

Synthesis of N,N-diethyl-2-[(2-methoxy-5-pyridyl)methyl]-N'-((E)-styrylsulfonyl)malonamide In the same manner as in Example 1 (2), the title compound (502 mg) was obtained as a white powder using the compound (705 mg) obtained in Example 122 (2) and trans-β-styrenesulfonamide (425 mg).

$^1$H-NMR (300 Mz, DMSO-$d_6$) δ0.83-1.03 (6H, m), 2.86-3.01 (2H, m), 3.04-3.33 (4H, m), 3.76 (3H, s), 3.84 (1H, t, J=7.2 Hz), 6.64 (1H, d, J=8.4 Hz), 7.26 (1H, d, J=15.4 Hz), 7.43-7.60 (5H, m), 7.68-7.79 (2H, m), 7.96 (1H, s), 12.01 (1H, brs).

MS: 446(M+H)$^+$.

Example 213

Synthesis of 2-[4-(5-chloro-2-pyridyloxy)benzyl]-N,N-diethyl-N'-((E)-styrylsulfonyl)malonamide In the same manner as in Example 1 (2), the title compound (450 mg) was obtained as a white powder using the compound (770 mg) obtained in Example 126 (4) and trans-β-styrenesulfonamide (375 mg).

$^1$H-NMR (400 Mz, DMSO-$d_6$) δ0.88-1.02 (6H, m), 3.05 (2H, d, J=7.2 Hz), 3.10-3.31 (4H, m), 3.90 (1H, t, J=7.2 Hz), 6.94 (2H, d, J=8.4 Hz), 7.03 (1H, d, J=8.8 Hz), 7.21 (2H, d, J=8.4 Hz), 7.27 (1H, d, J=15.2 Hz), 7.40-7.48 (3H, m), 7.56 (1H, d, J=15.2 Hz), 7.70-7.72 (2H, m), 7.92-7.95 (1H, m), 8.15 (1H, d, J=2.4 Hz), 12.02 (1H, brs).

MS: 542(M+H)$^+$.

Example 214

Synthesis of 2-cyclopropylmethyl-N,N-diethyl-N'-((E)-styrylsulfonyl)malonamide (1) 5-cyclopropylmethyl-2,2-dimethyl-1,3-dioxane-4,6-dione To a solution of cyclopropanecarboxylic acid (17.2 g) in methylene chloride (800 mL) were added Meldrum's acid (28.8 g), WSCI.HCl (42.2 g) and 4-dimethylaminopyridine (39.1 g), and the mixture was stirred at room temperature for 18 hr. Water and then hydrochloric acid were added to acidify the reaction mixture, and the aqueous layer was removed by partitioning. Under ice-cooling, acetic acid (114 mL) and then sodium borohydride (18.9 g) were added slowly to the organic layer, and the mixture was stirred at room temperature for 3 days. Water and then hydrochloric acid were added to the reaction mixture, and the aqueous layer was removed by partitioning. The organic layer was concentrated to give a yellow powder. This was washed with ether/hexane to give the title compound (25.8 g) as a yellow powder.

$^1$H-NMR (300 Mz, CDCl$_3$) δ0.14-0.27 (2H, m), 0.43-0.52 (2H, m), 0.96-1.13 (1H, m), 1.78 (3H, s), 1.81 (3H, s), 1.97-2.09 (2H, m), 3.54 (1H, t, J=5.4 Hz).

(2) 2-cyclopropylmethyl-3-(N,N-diethylamino)-3-oxopropionic acid

In the same manner as in Example 119 (2), the title compound (1.05 g) was obtained as an oil using the above-mentioned compound (991 mg).

$^1$H-NMR (300 Mz, DMSO-d$_6$) δ(−0.20)-1.20 (11H, m), 1.35-1.71 (2H, m), 3.02-3.48 (4H, m), 3.50-3.65 (1H, m), 12.40 (1H, brs).

(3) 2-cyclopropylmethyl-N,N-diethyl-N'-((E)-styryl-sulfonyl)malonamide

In the same manner as in Example 1 (2), the title compound (137 mg) was obtained as a white powder using the above-mentioned compound (1.05 g) and trans-β-styrenesulfonamide (694 mg).

$^1$H-NMR (300 Mz, DMSO-d$_6$) δ(−0.07)-0.11 (2H, m), 0.18-0.42 (2H, m), 0.50-0.78 (1H, m), 0.96 (3H, t, J=6.9 Hz), 1.08 (3H, t, J=6.9 Hz), 1.31-1.54 (1H, m), 1.68-1.89 (1H, m), 3.02-3.47 (4H, m), 3.56-3.77 (1H, m), 7.32-7.62 (5H, m), 7.62-7.88 (2H, m), 12.08 (1H, brs).
MS: 379(M+H)$^+$.

Example 215

Synthesis of N,N-diethyl-2-(2-propynyl)-N'-((E)-styrylsulfonyl)malonamide (1) ethyl 2-{[((E)-styrylsulfonyl)amino]carbonyl}-4-pentynoate In the same manner as in Example 152 (3), the title compound (1.99 g) was obtained as a white powder using the compound (5.55 g) obtained in Example 152 (2) and trans-β-styrenesulfonamide (5.97 g).

$^1$H-NMR (300 Mz, CDCl$_3$) δ1.25-1.30 (3H, m), 2.05-2.07 (1H, m), 2.84-2.86 (2H, m), 3.48-3.52 (1H, m), 4.24-4.31 (2H, m), 7.04 (1H, d, J=15.6 Hz), 7.39-7.46 (3H, m), 7.51-7.54 (2H, m), 7.75 (1H, d, J=15.6 Hz), 9.45 (1H, brs).

(2) 2-{[((E)-styrylsulfonyl)amino]carbonyl}-4-pentynoic acid

In the same manner as in Example 1 (3), the title compound (2.08 g) was obtained as a white powder using the above-mentioned compound (1.99 g).

$^1$H-NMR (300 Mz, CDCl$_3$) δ2.09-2.12 (1H, m), 2.87-2.90 (2H, m), 3.61-3.57 (1H, m), 7.04 (1H, d, J=15.6 Hz), 7.42-7.46 (3H, m), 7.52-7.54 (2H, m), 7.76 (1H, d, J=15.6 Hz).

(3) N,N-diethyl-2-(2-propynyl)-N'-((E)-styrylsulfonyl)malonamide

In the same manner as in Example 1 (4), a crude product was obtained using the above-mentioned compound (1.04 g). This was purified by silica gel column chromatography to give the title compound (140 mg) as a white powder.

$^1$H-NMR (400 Mz, CDCl$_3$) δ1.08-1.28 (6H, m), 2.05 (1H, s), 2.80-2.85 (2H, m), 3.25-3.73 (4H, m), 4.21-4.22 (1H, m), 7.03 (1H, d, J=15.6 Hz), 7.39-7.47 (3H, m), 7.51-7.53 (2H, m), 7.71 (1H, d, J=15.6 Hz), 10.40 (1H, brs).
MS: 363(M+H)$^+$.

Example 216

Synthesis of 2-(2-cyanoethyl)-N,N-diethyl-N'-((E)-styrylsulfonyl)malonamide (1) ethyl 4-cyano-2-{[((E)-styrylsulfonyl)amino]carbonyl}butyrate In the same manner as in Example 152 (3), the title compound (880 mg) was obtained as a white powder using the compound (2.50 g) obtained in Example 153 (1) and trans-(3-styrenesulfonamide (2.47 g).

$^1$H-NMR (300 Mz, CDCl$_3$) δ1.26-1.32 (3H, m), 2.26-2.32 (2H, m), 2.49-2.53 (2H, m), 3.48-3.52 (1H, m), 4.24-4.32 (2H, m), 7.04 (1H, d, J=15.2 Hz), 7.26-7.57 (5H, m), 7.75 (1H, d, J=15.2 Hz), 9.38 (1H, brs).

(2) 4-cyano-2-{[((E)-styrylsulfonyl)amino]carbonyl}butyric acid

In the same manner as in Example 1 (3), the title compound (700 mg) was obtained as a white powder using the above-mentioned compound (800 mg).

$^1$H-NMR (300 Mz, CDCl$_3$) δ2.31-2.34 (2H, m), 2.54-2.57 (2H, m), 3.57-3.60 (1H, m), 7.04 (1H, d, J=15.6 Hz), 7.26-7.48 (3H, m), 7.53-7.55 (2H, m), 7.77 (1H, d, J=15.6 Hz).

(3) 2-(2-cyanoethyl)-N,N-diethyl-N'-((E)-styrylsulfonyl)malonamide

In the same manner as in Example 1 (4), a crude product was obtained using the above-mentioned compound (1.00 g). This was purified by silica gel column chromatography to give the title compound (210 mg) as a white powder.

$^1$H-NMR (400 Mz, CDCl$_3$) δ1.17 (3H, t, J=7.2 Hz), 1.23 (3H, t, J=7.2 Hz), 2.21-2.26 (2H, m), 2.42-2.52 (2H, m), 3.31-3.50 (4H, m), 3.63-3.67 (1H, m), 7.04 (1H, d, J=15.6 Hz), 7.41-7.46 (3H, m), 7.52-7.54 (2H, m), 7.72 (1H, d, J=15.6 Hz), 10.41 (1H, brs).
MS: 378(M+H)$^+$.

Example 217

Synthesis of N,N-diethyl-2-(4-nitrophenethyl)-N'-((E)-styrylsulfonyl)malonamide (1) ethyl 4-(4-nitrophenyl)-2-{[((E)-styrylsulfonyl)amino]carbonyl}butyrate In the same manner as in Example 1 (2), the title compound (1.52 g) was obtained as an oil using the compound (3.30 g) obtained in Example 144 (2) and trans-β-styrenesulfonamide (2.30 g).

$^1$H-NMR (300 Mz, CDCl$_3$) δ1.30 (3H, t, J=7.2 Hz), 2.24-2.31 (2H, m), 2.76-2.81 (2H, m), 3.31 (1H, t, J=7.2 Hz), 4.25

(2H, q, J=7.2 Hz), 7.05 (1H, d, J=15.6 Hz), 7.33 (2H, d, J=8.7 Hz), 7.41-7.55 (5H, m), 7.76 (1H, d, J=15.6 Hz), 8.15 (2H, d, J=8.7 Hz), 9.41 (1H, brs).

(2) 4-(4-nitrophenyl)-2-{[((E)-styrylsulfonyl)amino]carbonyl}butyric acid

In the same manner as in Example 1 (3), the title compound (1.42 g) was obtained as a white powder using the above-mentioned compound (1.52 g).

$^1$H-NMR (300 Mz, CDCl$_3$) δ2.15-2.36 (2H, m), 2.80-2.85 (2H, m), 3.36-3.42 (1H, m), 7.05-(1H, d, J=15.6 Hz), 7.33 (2H, d, J=8.7 Hz), 7.38-7.55 (5H, m), 7.77 (1H, d, J=15.6 Hz), 8.12-8.15 (2H, m), 9.40 (1H, brs).

(3) N,N-diethyl-2-(4-nitrophenethyl)-N'-((E)-styrylsulfonyl)malonamide

In the same manner as in Example 1 (4), the title compound (773 mg) was obtained as a white solid using the above-mentioned compound (800 mg).

$^1$H-NMR (400 Mz, DMSO-d$_6$) δ0.95-1.03 (6H, m), 1.99-2.08 (2H, m), 2.60-2.73 (2H, m), 3.13-3.59 (4H, m), 3.59 (1H, t, J=6.8 Hz), 7.41-7.48 (6H, m), 7.60 (1H, d, J=15.6 Hz), 7.50-7.77 (1H, m), 8.15 (2H, d, J=8.8 Hz), 12.13 (1H, brs).

MS: 474(M+H)$^+$.

Example 218

Synthesis of 2-(4-aminophenethyl)-N,N-diethyl-N'-((E)-styrylsulfonyl)malonamide In the same manner as in Example 137 (4), the title compound (40 mg) was obtained as a white powder using the compound (452 mg) obtained in Example 217 at room temperature.

$^1$H-NMR (400 Mz, DMSO-d$_6$) δ0.94-1.03 (6H, m), 1.79-1.97 (2H, m), 2.29-2.37 (2H, m), 3.11-3.34 (4H, m), 3.51 (1H, t, J=6.8 Hz), 6.48 (2H, d, J=8.4 Hz), 6.77 (2H, d, J=8.4 Hz), 7.42 (1H, d, J=15.6 Hz), 7.45-7.48 (3H, m), 7.58 (1H, d, J=15.6), 7.74-7.77 (2H, m).

MS: 444(M+H)$^+$.

Example 219

Synthesis of 2-(4-aminobenzyl)-N,N-diethyl-N'-phenethylsulfonylmalonamide

In the same manner as in Example 7, the title compound (29 mg) was obtained as a white powder using the compound (130 mg) obtained in Example 200 at room temperature.

$^1$H-NMR (300 Mz, DMSO-d$_6$) δ0.89-0.91 (6H, m), 2.79-2.89 (2H, m), 3.16-3.38 (8H, m), 3.73-3.74 (1H, m), 6.43 (2H, d, J=7.6 Hz), 6.82 (2H, d, J=7.6 Hz), 6.95 (1H, brs), 7.14-7.27 (1H, m), 7.46-7.54 (2H, m), 7.69 (1H, brs).

MS: 432(M+H)$^+$.

Example 220

Synthesis of 2-[4-(benzoylamino)benzyl]-N,N-diethyl-N'-phenethylsulfonylmalonamide In the same manner as in Example 92, a crude product was obtained using the compound (1.53 g) obtained in Example 200. To a mixed solution of this in ethanol (50 mL) and acetic acid (5 mL) was added 20% palladium hydroxide/carbon (500 mg), and the mixture was stirred under hydrogen atmosphere for 3 hr. Insoluble material was removed by filtration, and the filtrate was concentrated under reduced pressure. The residue was purified by silica gel column chromatography to give the title compound (27 mg) as a white solid.

$^1$H-NMR (400 Mz, DMSO-d$_6$) δ0.96-1.05 (6H, m), 2.78-3.12 (4H, m), 3.20-3.34 (4H, m), 3.51-3.64 (2H, m), 3.93-4.00 (1H, m), 7.19-7.31 (7H, m), 7.51-7.59 (3H, m), 7.68 (2H, d, J=8.5 Hz), 7.92 (2H, d, J=7.1 Hz), 10.18 (1H, s), 11.92 (1H, brs).

MS: 536(M+H)$^+$.

Example 221

Synthesis of N,N-diethyl-2-(4-methoxybenzyl)-N'-phenethylsulfonylmalonamide

To a mixed solution of the compound (660 mg) obtained in Example 206 in ethyl acetate (10 mL) and ethanol (10 mL) was added palladium black (400 mg), and the mixture was stirred under hydrogen atmosphere at room temperature for 21 hr. Insoluble material was removed by filtration, and the filtrate was concentrated under reduced pressure to give the title compound (339 mg) as a white solid.

$^1$H-NMR (300 Mz, DMSO-d$_6$) δ0.83-1.07 (6H, m), 2.63-3.07 (4H, m), 3.10-3.38 (4H, m), 3.45-3.62 (2H, m), 3.64 (3H, s), 3.80-3.93 (1H, m), 6.80 (2H, d, J=9.0 Hz), 7.09-7.38 (7H, m), 11.90 (1H, brs).

MS:447(M+H)$^+$.

Example 222

Synthesis of 2-(4-aminophenethyl)-N,N-diethyl-N'-phenethylsulfonylmalonamide In the same manner as in Example 221, a crude product was obtained using the compound (300 mg) obtained in Example 217. This was purified by silica gel column chromatography to give the title compound (95 mg) as a white solid.

$^1$H-NMR (400 Mz, DMSO-d$_6$) δ1.00 (3H, t, J=7.0 Hz), 1.07 (3H, t, J=7.0 Hz), 1.80-1.91 (1H, m), 2.00-2.11 (1H, m), 2.90-3.07 (2H, m), 3.11-3.34 (6H, m), 3.57-3.72 (3H, m), 6.98 (2H, d, J=7.6 Hz), 7.12 (2H, d, J=7.6 Hz), 7.20-7.32 (5H, m).

MS: 446(M+H)$^+$.

Example 223

Synthesis of N,N-diethyl-2-(4-nitrobenzyl)-N'-(4-phenoxyphenylsulfonyl)malonamide In the same manner as in Example 188 (4), the title compound (200 mg) was obtained as a white powder using the compound (300 mg) obtained in Example 188 (3) and 4-phenoxybenzenesulfonyl chloride (270 mg).

$^1$H-NMR (300 Mz, DMSO-d$_6$) δ0.84-0.91 (6H, m), 3.06-3.08 (2H, m), 3.14-3.15 (4H, m), 3.92 (1H, t, J=6.9 Hz), 7.04-7.15 (4H, m), 7.25-7.37 (3H, m), 7.45-7.50 (2H, m), 7.79 (2H, d, J=8.5 Hz), 8.02 (2H, d, J=8.5 Hz), 12.25 (1H, brs).

MS: 526(M+H)$^+$.

Example 224

Synthesis of 2-(4-aminobenzyl)-N,N-diethyl-N'-(4-phenoxyphenylsulfonyl)malonamide In the same manner as in Example 7, the title compound (120 mg) was obtained as a white powder using the compound (160 mg) obtained in Example 223 at room temperature.

¹H-NMR (300 Mz, DMSO-d₆) δ0.83-0.91 (6H, m), 2.73-2.75 (2H, m), 3.12-3.18 (4H, m), 3.66-3.68 (1H, m), 6.38 (2H, d, J=8.0 Hz), 6.71 (2H, d, J=8.0 Hz), 7.08-7.14 (4H, m), 7.24-7.28 (1H, m), 7.45-7.50 (2H, m), 7.79 (2H, d, J=9.0 Hz).
MS: 496(M+H)⁺.

Example 225

Synthesis of N,N-diethyl-N'-(5-isobutyl-2-thienylsulfonyl)-2-(4-nitrobenzyl)malonamide (1) ethyl 3-[(5-isobutyl-2-thienylsulfonyl)amino]-2-(4-nitrobenzyl)-3-oxopropionate In the same manner as in Example 152 (3), the title compound (2.22 g) was obtained as a white powder using the compound (2.40 g) obtained in Example 178 (2) and 5-isobutyl-2-thiophenesulfonamide (2.00 g).
¹H-NMR (300 Mz, CDCl₃) δ0.94 (3H, s), 0.95 (3H, s), 1.18-1.28 (3H, m), 1.96-1.98 (1H, m), 2.72-2.75 (2H, m), 3.29-3.32 (2H, m), 3.54-3.61 (1H, m), 4.14-4.19 (2H, m), 6.79-6.81 (1H, m), 7.21-7.24 (1H, m), 7.36-7.39 (1H, m), 7.70-7.71 (1H, m), 8.05-8.16 (2H, m), 9.41 (1H, brs).

(2) N,N-diethyl-N'-(5-isobutyl-2-thienylsulfonyl)-2-(4-nitrobenzyl)malonamide

The above-mentioned compound (2.22 g) was subjected to hydrolysis in the same manner as in Example 1 (3). In the same manner as in Example 1 (4), a crude product was obtained using this. The crude product was purified by silica gel column chromatography to give the title compound (620 mg) as a white powder.
¹H-NMR (300 Mz, DMSO-d₆) δ0.86 (6H, brs), 0.89 (6H, brs), 1.80-1.84 (1H, m), 2.70 (2H, d, J=6.9 Hz), 3.08-3.21 (6H, m), 3.92 (1H, t, J=6.9 Hz), 6.89 (1H, d, J=3.9 Hz), 7.38 (2H, d, J=8.7 Hz), 7.53 (1H, d, J=3.9 Hz), 8.03 (1H, d, J=8.7 Hz), 12.31 (1H, brs).
MS: 496(M+H)⁺.

Example 226

Synthesis of 2-(4-aminobenzyl)-N,N-diethyl-N'-(5-isobutyl-2-thienylsulfonyl)malonamide In the same manner as in Example 137 (4), the title compound (140 mg) as a brown solid was obtained using the compound (200 mg) obtained in Example 225.
¹H-NMR (300 Mz, DMSO-d₆) δ0.84-0.90 (12H, m), 1.82-1.86 (1H, m), 2.72 (2H, d, J=6.9 Hz), 2.77 (2H, d, J=7.2 Hz), 3.28-3.35 (4H, m), 3.67 (1H, t, J=7.2 Hz), 6.40 (2H, d, J=8.4 Hz), 6.73 (2H, d, J=8.4 Hz), 6.90 (1H, d, J=3.7 Hz), 7.50 (1H, d, J=3.7 Hz).
MS: 466(M+H)⁺.

Example 227

Synthesis of 2-(4-cyanobenzyl)-N-cyclohexyl-N'-(2-naphthylsulfonyl)malonamide

In the same manner as in Example 1 (4), the title compound (184 mg) was obtained as a white powder using the compound (300 mg) obtained in Example 111 (4) and cyclohexylamine (87 mg).
¹H-NMR (300 Mz, DMSO-d₆) δ0.89-0.1.27 (5H, m), 1.34-1.70 (5H, m), 2.29 (2H, d, J=7.6 Hz), 3.28-3.60 (2H, m), 7.25 (2H, d, J=8.1 Hz), 7.54 (2H, d, J=8.0 Hz), 7.59-7.84 (4H, m), 8.00-8.26 (3H, m), 8.53 (1H, s), 12.20 (1H, brs).
MS: 490(M+H)⁺.

Example 228

Synthesis of 2-(4-cyanobenzyl)-N-(2-naphthylsulfonyl)-3-[4-(4-nitrophenyl)-1-piperazinyl]-3-oxopropanamide In the same manner as in Example 1 (4), a crude product was obtained using the compound (300 mg) obtained in Example 111 (4) and 1-(4-nitrophenyl)piperazine (183 mg). This was purified by silica gel column chromatography to give the title compound (358 mg) as a white powder.
¹H-NMR (300 Mz, DMSO-d₆) δ2.91-3.74 (10H, m), 3.98-4.15 (1H, m), 6.83 (2H, d, J=9.3 Hz), 7.31 (2H, J=8.1 Hz), 7.56 (2H, d, J=8.1 Hz), 7.63-8.20 (8H, m), 8.55 (1H, s), 12.50 (1H, brs).
MS: 597(M+H)⁺.

Example 229

Synthesis of 2-(4-cyanobenzyl)-N-ethyl-N'-(2-naphthylsulfonyl)-N-phenylmalonamide In the same manner as in Example 1 (4), a crude product was obtained using the compound (300 mg) obtained in Example 111 (4) and N-ethylaniline (107 mg). This was purified by silica gel column chromatography to give the title compound (344 mg) as a white powder.
¹H-NMR (300 Mz, DMSO-d₆) δ0.87 (3H, t, J=7.2 Hz), 2.40-3.70 (5H, m), 6.93 (2H, d, J=7.5 Hz), 7.21 (2H, J=8.1 Hz), 7.10-8.30 (11H, m), 8.53 (1H, s), 12.10 (1H, brs).
MS: 512(M+H)⁺.

Example 230

Synthesis of 2-(4-cyanobenzyl)-3-[4-(5-cyano-2-pyridyl)-1-piperazinyl]-N-(2-naphthylsulfonyl)-3-oxopropanamide In the same manner as in Example 1 (4), a crude product was obtained using the compound (300 mg) obtained in Example 111 (4) and N-(5-cyano-2-pyridyl)piperazine (166 mg). This was purified by silica gel column chromatography to give the title compound (284 mg) as a white powder.
¹H-NMR (300 Mz, DMSO-d₆) δ2.80-3.00 (2H, m), 3.06-3.67 (8H, m), 3.88-4.00 (1H, m), 6.66 (1H, J=9.1 Hz), 7.20 (2H, J=8.3 Hz), 7.45 (2H, d, J=8.2 Hz), 7.49-7.80 (4H, m), 7.86-8.15 (3H, m), 8.38 (1H, d, J=2.3 Hz), 8.43 (1H, s), 12.32 (1H, brs).
MS: 579(M+H)⁺.

Example 231

Synthesis of 2-(4-cyanobenzyl)-N-(2-naphthylsulfonyl)-3-oxo-3-[4-(4-pyridyl)-1-piperazinyl]propanamide In the same manner as in Example 1 (4), a crude product was obtained using the compound (300 mg) obtained in Example 111 (4) and 1-(4-pyridyl)piperazine (144 mg). This was purified by silica gel column chromatography to give the title compound (109 mg) as a white powder.
¹H-NMR (300 Mz, DMSO-d₆) δ2.90-3.10 (2H, m), 3.13-3.95 (9H, m), 7.01 (2H, d, J=7.4 Hz), 7.31 (2H, d, J=8.2 Hz), 7.43-7.60 (4H, m), 7.76 (1H, dd, J=8.9, 1.4 Hz), 7.91 (2H, d, J=8.9 Hz), 7.95-8.06 (1H, m), 8.22 (2H, d, J=7.3 Hz), 8.30 (1H, s), 13.20 (1H, brs).
MS: 574(M+H)$^+$.

Example 232

Synthesis of N-ethyl-2-(4-methoxybenzyl)-N'-(2-naphthylsulfonyl)-N-phenylmalonamide In the same manner as in Example 1 (4), a crude product was obtained using the compound (550 mg) obtained in Example 112 (4) and N-ethylaniline (161 mg). This was purified by silica gel column chromatography to give the title compound (456 mg) as a white powder.
$^1$H-NMR (300 Mz, DMSO-d$_6$) δ0.88 (3H, t, J=6.9 Hz), 2.66-2.90 (2H, m), 3.30-3.70 (6H, m), 6.50-6.70 (4H, m), 6.95 (2H, d, J=7.2 Hz), 7.20-7.43 (3H, m), 7.61-7.83 (3H, m), 8.01-8.29 (3H, m), 8.54 (1H, s), 12.06 (1H, brs).
MS: 517(M+H)$^+$.

Example 233

Synthesis of 3-[4-(3,4-dicyanophenyl)-1-piperazinyl]-2-(4-methoxybenzyl)-N-(2-naphthylsulfonyl)-3-oxopropanamide In the same manner as in Example 1 (4), a crude product was obtained using the compound (550 mg) obtained in Example 112 (4) and N-(3,4-dicyanophenyl)piperazine (282 mg). This was purified by silica gel column chromatography to give the title compound (480 mg) as a yellow powder.
$^1$H-NMR (300 Mz, DMSO-d$_6$) δ2.70-3.70 (10H, m), 3.60 (3H, s), 3.88-4.06 (1H, m), 6.65 (2H, dd, J=7.0, 1.9 Hz), 6.98 (2H, d, J=8.7 Hz), 7.04-7.19 (1H, m), 7.45 (1H, d, J=2.4 Hz), 7.60-8.30 (7H, m), 8.56 (1H, s), 12.40 (1H, brs).
MS: 608(M+H)$^+$.

Example 234

Synthesis of N-diphenylmethyl-2-(4-methoxybenzyl)-N'-(2-naphthylsultonyl)malonamide In the same manner as in Example 1 (4), a crude product was obtained using the compound (300 mg) obtained in Example 112 (4) and benzhydrylamine (133 mg). This was purified by silica gel column chromatography to give the title compound (390 mg) as a white powder.
$^1$H-NMR (300 Mz, DMSO-d$_6$) δ2.79-2.95 (2H, m), 3.51-3.70 (4H, m), 5.95 (1H, d, J=7.8 Hz), 6.63 (2H, d, J=8.4 Hz), 6.85-7.09 (4H, m), 7.10-7.40 (8H, m), 7.64-7.84 (3H, m), 8.00-8.23 (3H, m), 8.55 (1H, s), 8.65 (1H, d, J=7.8 Hz), 12.19 (1H, brs).
MS: 579(M+H)$^+$.

Example 235

Synthesis of N-ethyl-N'-(2-naphthylsulfonyl)-2-(4-nitrobenzyl)-N-phenylmalonamide In the same manner as in Example 1 (4), a crude product was obtained using the compound (500 mg) obtained in Example 6 (4) and N-ethylaniline (141 mg). This was purified by silica gel column chromatography to give the title compound (242 mg) as a white powder.
$^1$H-NMR (300 Mz, DMSO-d$_6$) δ0.87 (3H, t, J=7.2 Hz), 2.88-3.12 (2H, m), 3.25-3.69 (3H, m), 6.94 (2H, d, J=7.5 Hz), 7.11 (2H, d, J=8.6 Hz), 7.29-7.48 (3H, m), 7.66-7.85 (3H, m), 7.94 (2H, d, J=8.8 Hz), 8.00-8.25 (3H, m), 8.51 (1H, s), 12.12 (1H, brs).
MS: 532(M+H)$^+$.

Example 236

Synthesis of 2-(4-aminobenzyl)-N-ethyl-N'-(2-naphthylsulfonyl)-N-phenylmalonamide In the same manner as in Example 7, the title compound (178 mg) was obtained as a white powder using the compound (198 mg) obtained in Example 235 at room temperature.
$^1$H-NMR (300 Mz, DMSO-d$_6$) δ0.88 (3H, t, J=7.1 Hz), 2.57-2.78 (2H, m), 3.20-3.61 (3H, m), 6.32 (2H, d, J=8.1 Hz), 6.46 (2H, d, J=8.1 Hz), 6.92 (2H, d, J=7.6 Hz), 7.20-7.43 (3H, m), 7.62-7.84 (3H, m), 8.10 (1H, d, J=7.8 Hz), 8.17 (1H, d, J=8.8 Hz), 8.23 (1H, d, J=7.8 Hz), 8.55 (1H, s).
MS: 501(M+H)$^+$.

Example 237

Synthesis of N,N-diisopropyl-N'-(2-naphthylsulfonyl)-2-(4-nitrobenzyl)malonamide (1) 2,2-dimethyl-5-(4-nitrobenzyl)-1,3-dioxane-4,6-dione In the same manner as in Example 119 (1), the title compound (38.4 g) was obtained as a white powder using 4-nitrobenzaldehyde (25.0 g).
$^1$H-NMR (300 Mz, CDCl$_3$) δ1.67 (3H, s), 1.79 (3H, s), 3.58 (2H, d, J=5.1 Hz), 3.82 (1H, t, J=5.1 Hz), 7.54 (2H, d, J=8.7 Hz), 8.15 (2H, d, J=8.7 Hz).

(2) 3-(N,N-diisopropylamino)-2-(4-nitrobenzyl)-3-oxopropionic acid

In the same manner as in Example 119 (2), the title compound (550 mg) was obtained as a white powder using the above-mentioned compound (2.07 g) and diisopropylamine (3.00 g).
$^1$H-NMR (400 Mz, DMSO-d$_6$) δ0.74 (3H, d, J=6.4 Hz), 1.04-1.07 (6H, m), 1.23 (3H, d, J=6.2 Hz), 3.08-3.20 (2H, m), 3.30-3.40 (1H, m), 3.98-4.07 (1H, m), 4.08-4.16 (1H, m), 7.50 (2H, d, J=8.6 Hz), 8.12 (2H, d, J=8.6 Hz), 12.64 (1H, brs).

(3) N,N-diisopropyl-N'-(2-naphthylsulfonyl)-2-(4-nitrobenzyl)malonamide

In the same manner as in Example 1 (2), the title compound (356 mg) was obtained as a white solid using the above-mentioned compound (520 mg).
$^1$H-NMR (300 Mz, DMSO-d$_6$) δ0.82 (3H, d, J=6.3 Hz), 1.01 (3H, d, J=6.6 Hz), 1.15 (3H, d, J=6.6 Hz), 1.19 (3H, d, J=6.6 Hz), 3.04 (2H, d, J=7.5 Hz), 3.27-3.40 (1H, m), 3.81-3.99 (2H, m), 7.29 (2H, d, J=8.4 Hz), 7.63-7.80 (3H, m), 7.85 (2H, d, J=8.4 Hz), 8.05-8.10 (2H, m), 8.19 (1H, d, J=7.8 Hz), 8.52 (1H, s), 12.30 (1H, brs).
MS: 512(M+H)$^+$.

Example 238

Synthesis of 2-[4-(benzoylamino)benzyl]-N,N-diisopropyl-N'-(2-naphthylsulfonyl)malonamide (1) 2-(4-aminobenzyl)-N,N-diisopropyl-N'-(2-naphthylsulfonyl)malonamide In the same manner as in Example 7, the title compound (281 mg) was obtained as a white solid using the compound (300 mg) obtained in Example 237.

(2) 2-[4-(benzoylamino)benzyl]-N,N-diisopropyl-N'-(2-naphthylsulfonyl)malonamide In the same manner as in Example 9, the title compound (121 mg) was obtained as a white solid using the above-mentioned compound (281 mg).

$^1$H-NMR (400 MHz, DMSO-$d_6$) δ0.83 (3H, d, J=6.4 Hz), 1.00 (3H, d, J=6.4 Hz), 1.18 (6H, t, J=6.8 Hz), 2.81-2.95 (2H, m), 3.32-3.40 (1H, m), 3.82-3.94 (1H, m), 3.86 (1H, t, J=6.8 Hz), 7.02 (2H, d, J=8.4 Hz), 7.25-7.80 (8H, m), 7.90-8.00 (3H, m), 8.04 (1H, d, J=8.8 Hz), 8.12 (1H, d, J=8.8 Hz), 8.20 (1H, d, J=8.8 Hz), 10.13 (1H, s), 12.22 (1H, brs).

MS: 586(M+H)$^+$.

Example 239

Synthesis of 2-[4-(benzoylamino)benzyl]-N-ethyl-N'-(2-naphthylsulfonyl)-N-phenylmalonamide In the same manner as in Example 9, the title compound (187 mg) was obtained as a white solid using the compound (155 mg) obtained in Example 236.

$^1$H-NMR (400 MHz, DMSO-$d_6$) δ0.80-0.93 (3H, m), 2.72-2.94 (2H, m), 3.39-3.62 (3H, m), 6.79 (2H, d, J=8.0 Hz), 6.95 (2H, d, J=8.0 Hz), 7.26-7.42 (3H, m), 7.46-7.62 (4H, m), 7.69-7.80 (3H, m), 7.94 (1H, d, J=7.2 Hz), 8.08 (1H, d, J=7.6 Hz), 8.17 (1H, d, J=8.8 Hz), 8.23 (1H, d, J=8.0 Hz), 8.55 (1H, s), 10.11 (1H, s), 12.12 (1H, brs).

MS: 606(M+H)$^+$.

Example 240

Synthesis of 2-[4-(benzoylamino)benzyl]-N,N-dimethyl-N'-(2-naphthylsulfonyl)malonamide (1) ethyl 3-[(2-naphthylsulfonyl)amino]-2-(4-nitrobenzyl)-3-oxopropionate In the same manner as in Example 1 (2), the title compound (9.02 g) as a pale-yellow powder was obtained using the compound (7.21 g) obtained in Example 178 (2).

$^1$H-NMR (300 Mz, CDCl$_3$) δ1.18 (3H, t, J=7.3 Hz), 3.12-3.29 (2H, m), 3.57 (1H, t, J=7.0 Hz), 4.03-4.30 (2H, m), 7.06 (2H, d, J=8.8 Hz), 7.56-7.92 (4H, m), 7.92-8.08 (4H, m), 8.63 (1H, d, J=1.0 Hz).

(2) ethyl 2-(4-aminobenzyl)-3-[(2-naphthylsulfonyl)amino]-3-oxopropionate

In the same manner as in Example 7, the title compound (15.4 g) as a pale-yellow powder was obtained using the above-mentioned compound (16.8 g) at room temperature.

$^1$H-NMR (300 Mz, DMSO-$d_6$) δ0.93 (3H, t, J=7.1 Hz), 2.66-2.89 (2H, m), 3.54-3.68 (1H, m), 3.93 (2H, q, J=7.1 Hz), 6.43 (2H, d, J=8.3 Hz), 6.74 (2H, d, J=8.2 Hz), 7.59-7.82 (3H, m), 7.97-8.32 (3H, s), 8.54 (1H, s).

(3) ethyl 2-[4-(benzoylamino)benzyl]-3-[(2-naphthylsulfonyl)amino]-3-oxopropionate In the same manner as in Example 9, the title compound (14.3 g) was obtained as a pale-yellow solid using the above-mentioned compound (15.4 g).

$^1$H-NMR (300 Mz, DMSO-$d_6$) δ0.95 (3H, t, J=7.2 Hz), 2.79-3.00 (2H, m), 3.60-3.80 (1H, m), 3.96 (2H, q, J=7.2 Hz), 7.03 (2H, d, J=8.4 Hz), 7.40-7.78 (8H, m), 7.82-8.29 (4H, m), 8.54 (1H, s), 10.17 (1H, s), 12.50 (1H, brs).

(4) 2-[4-(benzoylamino)benzyl]-3-[(2-naphthylsulfonyl)amino]-3-oxopropionic acid In the same manner as in Example 1 (3), the title compound (13.3 g) was obtained as a white powder using the above-mentioned compound (14.3 g).

$^1$H-NMR (300 Mz, DMSO-$d_6$) δ2.74-3.04 (2H, m), 3.57-3.76 (1H, m), 6.99 (2H, d, J=8.4 Hz), 7.40-7.78 (8H, m), 7.87-8.29 (5H, m), 8.52 (1H, s), 10.15 (1H, s), 12.40 (1H, brs), 12.95 (1H, brs).

(5) 2-[4-(benzoylamino)benzyl]-N,N-dimethyl-N'-(2-naphthylsulfonyl)malonamide

In the same manner as in Example 13, the title compound (102 mg) was obtained as a white powder using the above-mentioned compound (503 mg), dimethylamine hydrochloride (489 mg) and triethylamine (833 μL).

$^1$H-NMR (300 Mz, DMSO-$d_6$) δ2.73 (3H, s), 2.76 (3H, s), 2.65-2.99 (2H, m), 3.93 (1H, t, J=7.5 Hz), 7.05 (2H, d, J=8.4 Hz), 7.60-7.81 (8H, m), 7.89-8.26 (5H, m), 8.56 (1H, s), 10.17 (1H, s), 12.33 (1H, brs).

MS: 530(M+H)$^+$.

Example 241

Synthesis of 2-[4-(benzoylamino)benzyl]-N-ethyl-N-methyl-N'-(2-naphthylsulfonyl)malonamide In the same manner as in Example 13, the title compound (188 mg) was obtained as a white powder using the compound (503 mg) obtained in Example 240 (4) and N-ethylmethylamine (515 μL).

$^1$H-NMR (300 Mz, DMSO-$d_6$) δ0.74-0.98 (3H, m), 2.69, 2.73 (total 3H, each s), 2.77-3.00 (2H, m), 3.00-3.55 (2H, m), 3.78-4.02 (1H, m), 7.05 (2H, d, J=8.1 Hz), 7.39-7.84 (8H, m), 7.95 (2H, d, J=7.2 Hz), 8.06 (1H, d, J=7.8 Hz), 8.13 (1H, d, J=8.7 Hz), 8.21 (1H, d, J=7.8 Hz), 8.55 (1H, s), 10.16 (1H, s), 12.35 (1H, brs).

MS: 544(M+H)$^+$.

Example 242

Synthesis of 2-[4-(benzoylamino)benzyl]-N,N-dipropyl-N'-(2-naphthylsulfonyl)malonamide In the same manner as in Example 13, the title compound (351 mg) was obtained as a white powder using the compound (503 mg) obtained in Example 240 (4) and dipropylamine (165 μL).

¹H-NMR (300 Mz, DMSO-d₆) δ0.60 (3H, t, J=7.5 Hz), 0.69 (3H, t, J=0.5 Hz), 1.00-1.38 (4H, m), 2.70-3.20 (6H, m), 3.77-3.98 (1H, m), 7.05 (2H, d, J=8.4 Hz), 7.40-7.80 (8H, m), 7.96 (2H, d, J=7.2 Hz), 8.06 (1H, d, J=8.1 Hz), 8.13 (1H, d, J=8.7 Hz), 8.21 (1H, d, J=8.1 Hz), 8.55 (1H, s), 10.16 (1H, s), 12.36 (1H, brs).
MS: 586(M+H)⁺.

Example 243

Synthesis of 2-[4-(benzoylamino)benzyl]-N,N-dipentyl-N'-(2-naphthylsulfonyl)malonamide In the same manner as in Example 13, the title compound (256 mg) was obtained as a white powder using the compound (503 mg) obtained in Example 240 (4) and dipentylamine (189 μL).
¹H-NMR (300 Mz, DMSO-d₆) δ0.60-1.39 (18H, m), 2.70-3.24 (6H, m), 3.74-3.96 (1H, m), 7.05 (2H, d, J=8.4 Hz), 7.43-7.86 (8H, m), 7.88-7.98 (2H, m), 7.98-8.27 (3H, m), 8.56 (1H, s), 10.15 (1H, s), 12.34 (1H, brs).
MS: 642(M+H)⁺.

Example 244

Synthesis of 2-[(4-benzoylamino)benzyl]-N-(2-naphthylsulfonyl)-3-oxo-3-pyrrolidinopropanamide In the same manner as in Example 13, the title compound (264 mg) was obtained as a white powder using the compound (503 mg) obtained in Example 240 (4) and pyrrolidine (100 μL).
¹H-NMR (300 Mz, DMSO-d₆) δ1.41-1.80 (4H, m), 2.70-3.52 (6H, m), 3.61-3.81 (1H, m), 7.05 (2H, d, J=8.4 Hz), 7.38-7.83 (8H, m), 7.88-8.31 (5H, m), 8.55 (1H, s), 10.16 (1H, s), 12.31 (1H, brs).
MS: 556(M+H)⁺.

Example 245

Synthesis of 2-[(4-benzoylamino)benzyl]-N-(2-naphthylsulfonyl)-3-oxo-3-piperidinopropanamide In the same manner as in Example 13, the title compound (314 mg) was obtained as a white powder using the compound (503 mg) obtained in Example 240 (4) and piperidine (119 μL).
¹H-NMR (300 Mz, DMSO-d₆) δ0.91-1.53 (6H, m), 2.73-2.99 (2H, m), 3.03-3.49 (4H, m), 3.93 (1H, t, J=6.9 Hz), 7.05 (2H, d, J=8.4 Hz), 7.40-7.88 (8H, m), 7.96 (2H, d, J=6.9 Hz), 8.06 (1H, d, J=8.1 Hz), 8.14 (1H, d, J=8.7 Hz), 8.21 (1H, d, J=7.8 Hz), 8.56 (1H, s), 10.17 (1H, s), 12.29 (1H, brs).
MS: 570(M+H)⁺.

Example 246

Synthesis of 2-[(4-benzoylamino)benzyl]-3-morpholino-N-(2-naphthylsulfonyl)-3-oxopropanamide In the same manner as in Example 13, the title compound (346 mg) was obtained as a white powder using the compound (503 mg) obtained in Example 240 (4) and morpholine (105 μL).
¹H-NMR (300 Mz, DMSO-d₆) δ2.72-3.00 (2H, m), 3.00-3.55 (8H, m), 3.96 (1H, t, J=7.2 Hz), 7.08 (2H, d, J=8.4 Hz), 7.41-7.88 (8H, m), 7.88-8.30 (5H, m), 8.57 (1H, s), 10.18 (1H, s), 12.35 (1H, brs).
MS: 572(M+H)⁺.

Example 247

Synthesis of 2-[(4-benzoylamino)benzyl]-3-(4-methylpiperazino)-N-(2-naphthylsulfonyl)-3-oxopropanamide In the same manner as in Example 13, the title compound (256 mg) was obtained as a white powder using the compound (503 mg) obtained in Example 240 (4) and 1-methylpiperazine (133 μL).
¹H-NMR (300 Mz, DMSO-d₆) δ2.00-3.90 (14H, m), 7.08 (2H, d, J=7.5 Hz), 7.35-8.15 (13H, m), 8.32 (1H, s), 10.15 (1H, s).
MS: 585(M+H)⁺.

Example 248

Synthesis of 2-[4-(benzoylamino)benzyl]-N-ethyl-N-(4-fluorophenyl)-N'-(2-naphthylsulfonyl)malonamide In the same manner as in Example 13, the title compound (555 mg) was obtained as a white powder using the compound (503 mg) obtained in Example 240 (4) and N-ethyl-N-(4-fluorophenyl)amine (167 mg).
¹H-NMR (300 Mz, DMSO-d₆) δ0.88 (3H, t, J=7.0 Hz), 2.66-3.00 (2H, m), 3.20-3.64 (3H, m), 6.67-6.89 (2H, m), 6.89-7.26 (4H, m), 7.38-7.82 (8H, m), 7.82-8.00 (2H, m), 8.00-8.30 (3H, m), 8.55 (1H, s), 10.12 (1H, s), 12.03 (1H, brs).
MS: 624(M+H)⁺.

Example 249

Synthesis of 2-[4-(benzoylamino)benzyl]-N-(4-fluorophenyl)-N-isopropyl-N'-(2-naphthylsulfonyl)malonamide In the same manner as in Example 13, the title compound (473 mg) was obtained as a white powder using the compound (503 mg) obtained in Example 240 (4) and N-(4-fluorophenyl)-N-isopropylamine (184 mg).
¹H-NMR (300 Mz, DMSO-d₆) δ0.60-1.00 (6H, m), 2.60-2.80 (1H, m), 2.80-3.00 (1H, m), 3.10-3.39 (1H, m), 4.45-4.77 (1H, m), 6.65-7.00 (5H, m), 7.18-7.39 (1H, m), 7.39-7.64 (5H, m), 7.64-7.85 (3H, m), 7.95 (2H, d, J=6.9 Hz), 8.00-8.30 (3H, m), 8.56 (1H, s), 10.15 (1H, s), 12.00 (1H, brs).
MS: 638(M+H)⁺.

Example 250

Synthesis of 2-[4-(benzoylamino)benzyl]-N-isopropyl-N'-(2-naphthylsulfonyl)-N-(3-trifluoromethylphenyl)malonamide In the same manner as in Example 13, the title compound (439 mg) was obtained as a white powder using the compound (503 mg) obtained in Example 240 (4) and N-isopropyl-3-trifluoromethylaniline (244 mg).
¹H-NMR (300 Mz, DMSO-d₆) δ0.60-1.09 (6H, m), 2.65-3.07 (2H, m), 3.09-3.50 (1H, m), 4.55-4.82 (1H, m), 6.58-6.94 (2H, m), 6.98-8.33 (17H, m), 8.56 (1H, s), 10.15 (1H, s), 12.08 (1H, brs).
MS: 688(M+H)⁺.

Example 251

Synthesis of 2-[4-(benzoylamino)benzyl]-N-isopropyl-N'-(2-naphthylsulfonyl)-N-(3-pyridyl)malonamide In the same manner as in Example 13, the title compound (339 mg) was obtained as a white powder using the compound (503 mg) obtained in Example 240 (4) and N-isopropyl-N-(3-pyridyl)amine (163 mg).

$^1$H-NMR (300 Mz, DMSO-d$_6$) δ0.69-1.05 (6H, m), 2.60-3.08 (2H, m), 3.20-3.56 (1H, m), 4.54-4.83 (1H, m), 6.60-6.98 (2H, m), 6.98-8.38 (16H, m), 8.40-8.80 (2H, m), 10.16 (1H, s), 12.08 (1H, brs).

MS: 621(M+H)$^+$.

Example 252

Synthesis of 3-morpholino-N-(2-naphthylsulfonyl)-2-(4-nitrobenzyl)-3-oxopropanamide In the same manner as in Example 1 (4), a crude product was obtained using the compound (500 mg) obtained in Example 6 (4) and morpholine (204 μL). This was purified by silica gel column chromatography to give the title compound (304 mg) as a white powder.

$^1$H-NMR (300 Mz, DMSO-d$_6$) δ2.91-3.43 (11H, m), 4.5 (1H, t, J=7.4 Hz), 7.35 (2H, d, J=8.7 Hz), 7.63-7.84 (3H, m), 7.93 (2H, d, J=8.7 Hz), 8.00-8.25 (3H, m), 8.53 (1H, s).

MS: 498(M+H)$^+$.

Example 253

Synthesis of 2-(4-aminobenzyl)-3-morpholino-N-(2-naphthylsulfonyl)-3-oxopropanamide In the same manner as in Example 7, the title compound (164 mg) was obtained as a white powder using the compound (198 mg) obtained in Example 252 at room temperature.

$^1$H-NMR (300 Mz, DMSO-d$_6$) δ2.60-2.89 (2H, m), 2.95-3.55 (8H, m), 3.78 (1H, t, J=7.1 Hz), 6.39 (2H, d, J=8.3 Hz), 6.74 (2H, d, J=8.3 Hz), 7.64-7.87 (3H, m), 8.07 (1H, d, J=7.7 Hz), 8.12 (1H, d, J=7.5 Hz), 8.20 (1H, d, J=7.6 Hz), 8.59 (1H, s).

MS: 468(M+H)$^+$.

Example 254

Synthesis of 3-(4-methylpiperazino)-N-(2-naphthylsulfonyl)-2-(4-nitrobenzyl)-3-oxopropanamide In the same manner as in Example 1 (4), the title compound (355 mg) was obtained as a white powder using the compound (500 mg) obtained in Example 6 (4) and 1-methylpiperazine (234 mL).

$^1$H-NMR (300 Mz, DMSO-d$_6$) δ2.00-5.00 (6H, m), 2.60 (3H, brs), 2.94-3.11 (4H, m), 3.81 (1H, t, J=6.9 Hz), 7.34 (2H, d, J=5.6 Hz), 7.52-7.68 (2H, m), 7.75 (1H, d, J=8.4 Hz), 7.80-8.00 (4H, m), 8.03 (1H, d, J=6.8 Hz), 8.29 (1H, s).

MS: 511(M+H)$^+$.

Example 255

Synthesis of 2-(4-aminobenzyl)-3-(4-methylpiperazino)-N-(2-naphthylsulfonyl)-3-oxopropanamide In the same manner as in Example 7, the title compound (168 mg) was obtained as a white powder using the compound (270 mg) obtained in Example 254 at room temperature.

$^1$H-NMR (300 Mz, DMSO-d$_6$) δ2.00-4.00 (14H, m), 6.37 (2H, d, J=8.2 Hz), 6.74 (2H, d, J=8.2 Hz), 7.54-7.70 (2H, m), 7.77 (1H, dd, J=8.6, 1.4 Hz), 7.90-8.10 (3H, m), 8.32 (1H, s).

MS: 481(M+H)$^+$.

Example 256

Synthesis of N-(2-hydroxyethyl)-N-methyl-N'-(2-naphthylsulfonyl)-2-(4-nitrobenzyl)malonamide In the same manner as in Example 1 (4), a crude product was obtained using the compound (400 mg) obtained in Example 6 (4) and N-methylethanolamine (140 mg). This was purified by silica gel column chromatography to give the title compound (322 mg) as a white powder.

$^1$H-NMR (300 Mz, DMSO-d$_6$) δ2.76-2.87 (total 3H, each s), 2.90-3.70 (6H, m), 3.90-4.30 (1H, m), 7.22-7.40 (2H, m), 7.64-7.92 (5H, m), 8.00-8.24 (3H, m), 8.52 (1H, s), 11.90-12.60 (1H, m).

MS: 486(M+H)$^+$.

Example 257

Synthesis of 2-(4-aminobenzyl)-N-(2-hydroxyethyl)-N-methyl-N'-(2-naphthylsulfonyl)malonamide In the same manner as in Example 7, the title compound (209 mg) was obtained as a white powder using the compound (270 mg) obtained in Example 256.

$^1$H-NMR (300 Mz, DMSO-d$_6$) δ2.50-2.82 (5H, m), 3.06-3.59 (4H, m), 3.68-4.00 (1H, m), 4.38, 4.60 (total 1H, each brs), 6.29-6.40 (2H, m), 6.70 (2H, d, J=8.0 Hz), 7.64-7.88 (3H, m), 8.04-8.30 (3H, m), 8.53 (1H, m).

MS: 456(M+H)$^+$.

Example 258

Synthesis of N-diphenylmethyl-N'-(2-naphthylsulfonyl)-2-(4-nitrobenzyl)malonamide In the same manner as in Example 1 (4), a crude product was obtained using the compound (400 mg) obtained in Example 6 (4) and benzhydrylamine (171 mg). This was purified by silica gel column chromatography to give the title compound (155 mg) as a white powder.

$^1$H-NMR (300 Mz, DMSO-d$_6$) δ3.09 (2H, d, J=7.5 Hz), 3.69-3.89 (1H, m), 5.95 (1H, d, J=7.8 Hz), 6.97-7.76 (12H, m), 7.65-7.84 (3H, m), 7.91 (2H, d, J=8.5 Hz), 8.00-8.21 (3H, m), 8.54 (1H, m), 8.73 (1H, d, J=7.8 Hz), 12.32 (1H, brs).

MS: 594(M+H)$^+$.

Example 259

Synthesis of 2-(4-aminobenzyl)-N-diphenylmethyl-N'-(2-naphthylsulfonyl)malonamide In the same manner as in Example 7, the title compound (91 mg) was obtained as a white powder using the compound (135 mg) obtained in Example 258 at room temperature.

Example 260

Synthesis of N-ethyl-N'-(2-naphthylsulfonyl)-2-(4-nitrobenzyl)malonamide

In the same manner as in Example 1 (4), a crude product was obtained using the compound (400 mg) obtained in Example 6 (4) and 40% ethylamine-methanol solution (500 μL). This was purified by silica gel column chromatography to give the title compound (205 mg) as a white powder.
$^1$H-NMR (300 Mz, DMSO-$d_6$) δ0.91 (3H, t, J=6.9 Hz), 2.86-3.10 (4H, m), 3.54 (1H, t, J=7.7 Hz), 7.30 (2H, d, J=8.5 Hz), 7.62-7.80 (3H, m), 7.81-7.98 (3H, m), 8.05 (2H, t, J=7.7 Hz), 8.18 (1H, d, J=8.1 Hz), 8.52 (1H, s), 12.29 (1H, brs).
MS: 456(M+H)$^+$.

Example 261

Synthesis of 2-(4-aminobenzyl)-N-ethyl-N'-(2-naphthylsulfonyl)malonamide

In the same manner as in Example 7, the title compound (100 mg) was obtained as a white powder using the compound (145 mg) obtained in Example 260 at room temperature.
$^1$H-NMR (300 Mz, DMSO-$d_6$) δ0.89 (3H, t, J=7.2 Hz), 2.62-3.10 (4H, m), 3.34-3.52 (1H, m), 6.33 (2H, d, J=8.3 Hz), 6.69 (2H, d, J=8.3 Hz), 7.60-7.84 (4H, m), 8.07 (2H, t, J=9.2 Hz), 8.17 (1H, d, J=7.8 Hz), 8.51 (1H, s).
MS: 426(M+H)$^+$.

Example 262

Synthesis of N-(2-naphthylsulfonyl)-2-(4-nitrobenzyl)-3-oxo-3-(3-oxospiro[indane-1,4'-piperidin]-1'-yl)propanamide In the same manner as in Example 1 (4), a crude product was obtained using the compound (300 mg) obtained in Example 6 (4) and 3-oxospiro[indane-1,4'-piperidine] (141 mg). This was purified by silica gel column chromatography to give the title compound (90 mg) as a white powder.
$^1$H-NMR (300 Mz, DMSO-$d_6$) δ0.80-4.50 (13H, m), 7.09-8.25 (14H, m), 8.52 (1H, s), 12.47 (1H, brs).
MS: 612(M+H)$^+$.

Example 263

Synthesis of 2-(4-aminobenzyl)-N-(2-naphthylsulfonyl)-3-oxo-3-(3-oxospiro[indane-1,4'-piperidine]-1'-yl)propanamide In the same manner as in Example 7, the title compound (17 mg) was obtained as a white powder using the compound (72 mg) obtained in Example 262 at room temperature.
$^1$H-NMR (300 Mz, DMSO-$d_6$) δ0.80-4.48 (13H, m), 6.38 (1H, d, J=8.2 Hz), 6.47 (2H, d, J=8.2 Hz), 6.76 (1H, d, J=8.2 Hz), 6.82 (2H, d, J=8.2 Hz), 7.15-8.20 (10H, m), 8.49 (1H, brs).
MS: 582(M+H)$^+$.

$^1$H-NMR (300 Mz, DMSO-$d_6$) δ2.63-2.92 (2H, m), 3.39-3.47 (1H, m), 5.94 (1H, d, J=7.7 Hz), 6.36 (2H, d, J=8.3 Hz), 6.66-8.18 (19H, m), 8.56 (1H, d, J=7.9 Hz).
MS: 564(M+H)$^+$.

Example 264

Synthesis of 2-(4-aminobenzyl)-N,N-dipentyl-N'-(2-naphthylsulfonyl)malonamide (1) N,N-dipentyl-N'-(2-naphthylsulfonyl)-2-(4-nitrobenzyl)malonamide In the same manner as in Example 1 (4), a crude product was obtained using the compound (400 mg) obtained in Example 6 (4) and diamylamine (147 mg). This was purified by silica gel column chromatography to give the title compound (125 mg) as an oil.
$^1$H-NMR (300 Mz, CDCl$_3$) δ0.60-1.90 (18H, m), 2.70-3.75 (7H, m), 7.13 (2H, d, J=8.6 Hz), 7.50-8.10 (8H, m), 8.64 (1H, s), 10.60 (1H, brs).

(2) 2-(4-aminobenzyl)-N,N-dipentyl-N'-(2-naphthylsulfonyl)malonamide

In the same manner as in Example 7, the title compound (91 mg) as a pale-green powder was obtained using the above-mentioned compound (125 mg).
$^1$H-NMR (300 Mz, DMSO-$d_6$) δ0.60-1.50 (18H, m), 2.35-3.30 (6H, m), 3.59-3.72 (1H, m), 6.35 (2H, d, J=8.2 Hz), 6.71 (2H, d, J=8.2 Hz), 7.65-7.83 (3H, m), 8.06 (2H, t, J=8.3 Hz), 8.16 (1H, d, J=7.7 Hz), 8.52 (1H, s).
MS: 538(M+H)$^+$.

Example 265

Synthesis of N-ethyl-2-(4-methoxybenzyl)-N-phenyl-N'-((E)-styrylsulfonyl)malonamide In the same manner as in Example 1 (4), a crude product was obtained using the compound (1.25 g) obtained in Example 206 (2) and N-ethylaniline (364 mg). This was purified by silica gel column chromatography to give the title compound (610 mg) as a white powder.
$^1$H-NMR (300 Mz, DMSO-$d_6$) δ0.92 (3H, t, J=7.2 Hz), 2.71-2.96 (2H, m), 3.30-3.70 (6H, m), 6.68 (2H, d, J=8.4 Hz), 6.79 (2H, d, J=8.4 Hz), 6.99-7.17 (2H, m), 7.30 (1H, d, J=15.7 Hz), 7.35-7.82 (7H, m), 7.70-7.89 (2H, m), 11.78 (1H, brs).
MS: 493(M+H)$^+$.

Example 266

Synthesis of N-ethyl-2-(4-methoxybenzyl)-N'-phenethylsulfonyl-N-phenylmalonamide In the same manner as in Example 221, the title compound (72 mg) was obtained as a white powder using the compound (390 mg) obtained in Example 265.
$^1$H-NMR (300 Mz, DMSO-$d_6$) δ0.98 (3H, t, J=7.2 Hz), 2.65-3.01 (4H, m), 3.28-3.82 (8H, m), 6.59-6.95 (4H, m), 7.09-7.54 (10H, m), 11.75 (1H, brs).
MS: 495(M+H)$^+$.

Example 267

Synthesis of 2-(4-chlorobenzyl)-N-ethyl-N'-(2-naphthylsulfonyl)-N-phenylmalonamide (1) 2-(4-chlorobenzyl)-3-[(2-naphthylsulfonyl)amino]-3-oxopropionic acid To the compound (2.10 g) obtained in Example 110 (4) were added 0.5 mol/L hydrochloric acid (40 ml) and ethyl acetate (80 mL), and the organic layer was collected by partitioning and washed with brine. The organic layer was concentrated under reduced pressure to give the title compound (1.90 g) as a white solid.

$^1$H-NMR (300 Mz, DMSO-$d_6$) δ2.55-3.00 (2H, m), 3.58-3.74 (1H, m), 6.88-7.07 (4H, m), 7.60-7.87 (3H, m), 8.09 (2H, d, J=8.9 Hz), 8.20 (1H, d, J=7.7 Hz), 8.51 (1H, d, J=1.3 Hz), 12.44 (1H, brs), 13.00 (1H, brs).

(2) 2-(4-chlorobenzyl)-N-ethyl-N'-(2-naphthylsulfonyl)-N-phenylmalonamide

In the same manner as in Example 1 (4), a crude product was obtained using the above-mentioned compound (244 mg) and N-ethylaniline (71 mg). This was purified by silica gel column chromatography to give the title compound (125 mg) as a white powder.

$^1$H-NMR (300 Mz, DMSO-$d_6$) δ0.88 (3H, t, J=7.2 Hz), 2.67-3.61 (5H, m), 6.83 (2H, d, J=8.4 Hz), 6.94 (2H, d, J=8.1 Hz), 7.11 (2H, d, J=8.1 Hz), 7.26-7.50 (3H, m), 7.69-7.87 (3H, m), 8.08-8.30 (3H, m), 8.54 (1H, s), 12.11 (1H, brs).

MS: 521(M+H)$^+$.

Example 268

Synthesis of N-ethyl-N'-(2-naphthylsulfonyl)-N-phenyl-2-(4-pyridylmethyl)malonamide (1) 3-[(2-naphthylsulfonyl)amino]-3-oxo-2-(4-pyridyl)propionic acid To the compound (513 mg) obtained in Example 113 (4) were added 1 mol/L hydrochloric acid (2.5 mL) and water (10 mL), and the mixture was stirred at room temperature. The precipitate was collected by filtration to give the title compound (224 mg) as a white solid.

$^1$H-NMR (300 Mz, DMSO-$d_6$) δ2.80-3.02 (2H, m), 3.60-3.75 (1H, m), 7.01 (2H, d, J=5.9 Hz), 7.59-7.80 (3H, m), 7.96-8.24 (5H, m), 8.51 (1H, d, J=1.1 Hz).

(2) N-ethyl-N'-(2-naphthylsulfonyl)-N-phenyl-2-(4-pyridylmethyl)malonamide

In the same manner as in Example 1 (4), a crude product was obtained using the above-mentioned compound (224 mg) and N-ethylaniline (71 mg). This was purified by silica gel column chromatography to give the title compound (65 mg) as a white powder.

$^1$H-NMR (300 Mz, DMSO-$d_6$) δ0.87 (3H, t, J=7.0 Hz), 2.70-3.98 (2H, m), 3.19-3.60 (3H, m), 6.85 (2H, d, J=5.7 Hz), 6.94 (2H, d, J=7.7 Hz), 7.18-7.40 (3H, m), 7.59-7.82 (3H, m), 8.00-8.40 (5H, m), 8.53 (1H, s), 12.28 (1H, brs).

MS: 487(M+H)$^+$.

Example 269

Synthesis of N-ethyl-N'-(2-naphthylsulfonyl)-N-phenyl-2-(4-trifluoromethoxybenzyl)malonamide In the same manner as in Example 1 (4), a crude product was obtained using the compound (1.18 g) obtained in Example 117 (4) and N-ethylaniline (305 mg). This was purified by silica gel column chromatography to give the title compound (519 mg) as a white powder.

$^1$H-NMR (300 Mz, DMSO-$d_6$) δ0.87 (3H, t, J=7.2 Hz), 2.70-3.00 (2H, m), 3.25-3.66 (3H, m), 6.80-6.98 (4H, m), 7.06 (2H, d, J=8.4 Hz), 7.19-7.43 (3H, m), 7.65-7.84 (3H, m), 8.00-8.30 (3H, m), 8.59 (1H, s), 12.08 (1H, brs).

MS: 571(M+H)$^+$.

Example 270

Synthesis of N-ethyl-N-phenyl-N'-((E)-styrylsulfonyl)-2-(4-trifluoromethoxybenzyl)malonamide In the same manner as in Example 1 (4), a crude product was obtained using the compound (1.22 g) obtained in Example 207 (2) and N-ethylaniline (333 mg). This was purified by silica gel column chromatography to give the title compound (544 mg) as a white powder.

$^1$H-NMR (300 Mz, DMSO-$d_6$) δ0.91 (3H, t, J=7.2 Hz), 2.80-3.10 (2H, m), 3.26-3.67 (3H, m), 6.93-7.61 (14H, m), 7.69-7.88 (2H, m), 11.76 (1H, brs).

MS: 547(M+H)$^+$.

Example 271

Synthesis of N-ethyl-2-(3,4-dimethoxybenzyl)-N'-(2-naphthylsulfonyl)-N-phenylmalonamide (1) 3-(N-ethyl-N-phenylamino)-2-(3,4-dimethoxybenzyl)-3-oxopropionic acid In the same manner as in Example 119 (2), the title compound (428 mg) was obtained as a white powder using the compound (2.00 g) obtained in Example 119 (1) and N-ethylaniline (1.65 g).

$^1$H-NMR (300 Mz, CDCl$_3$) δ1.06 (3H, t, J=7.2 Hz), 2.97-3.29 (2H, m), 3.46-3.84 (6H, m), 3.87 (3H, s), 6.65-7.50 (8H, m).

(2) N-ethyl-2-(3,4-dimethoxybenzyl)-N'-(2-naphthylsulfonyl)-N-phenylmalonamide

In the same manner as in Example 1 (2), the title compound (9 mg) was obtained as a white powder using the above-mentioned compound (214 mg).

$^1$H-NMR (300 Mz, DMSO-$d_6$) δ0.90 (3H, t, J=7.2 Hz), 2.70-3.00 (2H, m), 3.30-3.70 (6H, m), 3.71 (3H, s), 6.22-6.34 (1H, m), 6.66-6.81 (2H, m), 6.83-7.10 (2H, m), 7.19-7.42 (3H, m), 7.63-7.80 (3H, m), 8.01-8.27 (3H, m), 8.52 (1H, s), 11.97 (1H, brs).

MS: 547(M+H)$^+$.

Example 272

Synthesis of N-ethyl-2-(3,4-dimethoxybenzyl)-N-phenyl-N'-((E)-styrylsulfonyl)malonamide In the same manner as in Example 1 (2), the title compound (69 mg) was obtained as a white powder using the compound (214 mg) obtained in Example 271 (1) and trans-β-styrenesulfonamide (101 mg).

$^1$H-NMR (300 Mz, DMSO-$d_6$) δ0.93 (3H, t, J=6.9 Hz), 2.75-3.10 (2H, m), 3.30-3.70 (6H, m), 3.73 (3H, s), 6.38-6.50 (1H, m), 6.77-6.94 (2H, m), 6.97-7.15 (2H, m), 7.25 (1H, d, J=15.3 Hz), 7.30-7.66 (7H, m), 7.63-7.80 (2H, m), 11.64 (1H, brs).

MS: 523(M+H)$^+$.

Example 273

Synthesis of N-ethyl-2-(3,4-methylenedioxybenzyl)-N'-(2-naphthylsulfonyl)-N-phenylmalonamide

(1) 2,2-dimethyl-5-(3,4-methylenedioxybenzyl)-1,3-dioxane-4,6-dione

In the same manner as in Example 119 (1), the title compound (8.34 g) was obtained as a white powder using 3,4-methylenedioxybenzaldehyde (8.33 g).
$^1$H-NMR (300 Mz, CDCl$_3$) δ1.54 (3H, s), 1.74 (3H, s), 3.41 (2H, d, J=4.8 Hz), 3.71 (1H, t, J=4.8 Hz), 5.92 (2H, s), 6.68-6.87 (3H, m).

(2) 3-(N-ethyl-N-phenylamino)-2-(3,4-methylenedioxybenzyl)-3-oxopropionic acid In the same manner as in Example 119 (2), the title compound (1.92 g) was obtained as a white solid using the above-mentioned compound (2.00 g) and N-ethylaniline (3.48 g).
$^1$H-NMR (300 Mz, DMSO-d$_6$) δ0.93 (3H, t, J=7.2 Hz), 2.86 (2H, d, J=7.5 Hz), 3.08-3.71 (3H, m), 5.98 (2H, s), 6.31-6.51 (2H, m), 6.54-6.96 (3H, m), 7.28-7.45 (3H, m), 12.45 (1H, brs).

(3) N-ethyl-2-(3,4-methylenedioxybenzyl)-N'-(2-naphthylsulfonyl)-N-phenylmalonamide In the same manner as in Example 1 (2), the title compound (563 mg) was obtained as a white powder using the above-mentioned compound (811 mg).
$^1$H-NMR (300 Mz, DMSO-d$_6$) δ0.89 (3H, t, J=7.2 Hz), 2.61-2.89 (2H, m), 3.20-3.69 (3H, m), 5.80-5.97 (2H, m), 6.17-6.34 (2H, m), 6.54 (1H, d, J=6.5 Hz), 6.96 (2H, d, J=7.2 Hz), 7.20-7.47 (3H, m), 7.60-7.85 (3H, m), 8.09 (1H, d, J=7.8 Hz), 8.16 (1H, d, J=8.7 Hz), 8.22 (1H, d, J=7.8 Hz), 8.53 (1H, s), 12.03 (1H, brs).
MS: 531(M+H)$^+$.

Example 274

Synthesis of N-ethyl-2-(3,4-methylenedioxybenzyl)-N-phenyl-N'-((E)-styrylsulfonyl)malonamide In the same manner as in Example 1 (2), the title compound (277 mg) was obtained as a white powder using the compound (811 mg) obtained in Example 273 (2) and trans-β-styrenesulfonamide (402 mg).
$^1$H-NMR (300 Mz, DMSO-d$_6$) δ0.93 (3H, t, J=7.2 Hz), 2.65-2.89 (2H, m), 3.30-3.72 (3H, m), 5.91 (2H, s), 6.29-6.47 (2H, m), 6.66 (1H, d, J=8.4 Hz), 7.00-7.19 (2H, m), 7.27 (1H, d, J=15.6 Hz), 7.36-7.81 (7H, m), 7.70-7.86 (2H, m), 11.72 (1H, brs).
MS: 507(M+H)$^+$.

Example 275

Synthesis of N-ethyl-2-(4-methoxycarbonylbenzyl)-N'-(2-naphthylsulfonyl)-N-phenylmalonamide

(1) 3-(N-ethyl-N-phenylamino)-2-(4-methoxycarbonylbenzyl)-3-oxopropionic acid In the same manner as in Example 119 (2), the title compound (1.50 g) was obtained as a white powder using the compound (2.34 g) obtained in Example 120 (1) and N-ethylaniline (3.88 g).
$^1$H-NMR (300 Mz, DMSO-d$_6$) δ0.91 (3H, t, J=7.2 Hz), 2.90-3.10 (2H, m), 3.20-3.68 (3H, m), 3.85 (3H, s), 6.35-7.00 (2H, m), 7.14 (2H, d, J=8.1 Hz), 7.20-7.50 (3H, m), 7.85 (2H, d, J=8.1 Hz).

(2) N-ethyl-2-(4-methoxycarbonylbenzyl)-N'-(2-naphthylsulfonyl)-N-phenylmalonamide In the same manner as in Example 1 (2), the title compound (542 mg) was obtained as a white powder using the above-mentioned compound (750 mg).
$^1$H-NMR (300 Mz, DMSO-d$_6$) δ0.87 (3H, t, J=7.2 Hz), 2.80-3.09 (2H, m), 3.20-3.70 (3H, m), 3.82 (3H, s), 6.83-7.01 (4H, m), 7.20-7.46 (3H, m), 7.59-7.81 (5H, m), 8.05-8.30 (3H, m), 8.52 (1H, s), 12.09 (1H, brs).
MS: 545(M+H)$^+$.

Example 276

Synthesis of 2-(4-carboxybenzyl)-N-ethyl-N'-(2-naphthylsulfonyl)-N-phenylmalonamide In the same manner as in Example 121, the title compound (193 mg) was obtained as a white powder using the compound (300 mg) obtained in Example 275.
$^1$H-NMR (300 Mz, DMSO-d$_6$) δ0.86 (3H, t, J=6.9 Hz), 2.78-3.07 (2H, m), 3.20-3.77 (3H, m), 6.83-7.01 (4H, m), 7.18-7.47 (3H, m), 7.59-7.87 (5H, m), 8.03-8.34 (3H, m), 8.45 (1H, s), 12.12 (1H, brs), 12.79 (1H, brs).
MS: 531(M+H)$^+$.

Example 277

Synthesis of N-ethyl-2-(4-methoxycarbonylbenzyl)-N-phenyl-N'-((E)-styrylsulfonyl)malonamide In the same manner as in Example 1 (2), the title compound (237 mg) was obtained as a white powder using the compound (750 mg) obtained in Example 275 (1) and trans-β-styrenesulfonamide (357 mg).
$^1$H-NMR (300 Mz, DMSO-d$_6$) δ0.91 (3H, t, J=7.2 Hz), 2.90-3.15 (2H, m), 3.35-3.68 (3H, m), 3.82 (3H, s), 7.00-7.13 (4H, m), 7.29 (1H, d, J=15.3 Hz), 7.34-7.60 (7H, m), 7.70-7.86 (4H, m), 11.80 (1H, brs).
MS: 521(M+H)$^+$.

Example 278

Synthesis of 2-(4-carboxybenzyl)-N-ethyl-N-phenyl-N'-((E)-styrylsulfonyl)malonamide In the same manner as in Example 121, the title compound (116 mg) was obtained as a white powder using the compound (180 mg) obtained in Example 277.
$^1$H-NMR (300 Mz, DMSO-d$_6$) δ0.91 (3H, t, J=7.2 Hz), 2.81-3.12 (2H, m), 3.35-3.69 (3H, m), 6.89-7.11 (4H, m), 7.28 (1H, d, J=15.3 Hz), 7.30-7.62 (7H, m), 7.65-7.90 (4H, m), 11.79 (1H, brs) 12.80 (1H, brs).
MS: 507(M+H)$^+$.

Example 279

Synthesis of N-ethyl-2-[(2-methoxy-5-pyridyl)methyl]-N'-(2-naphthylsulfonyl)-N-phenylmalonamide (1) 3-(N-ethyl-N-phenylamino)-2-[(2-methoxy-5-pyridyl)methyl]-3-oxopropionic acid In the same manner as in Example 119 (2), the title compound (1.46 g) was obtained as a white powder using the compound (2.12 g) obtained in Example 122 (1) and N-ethylaniline (3.87 g).
$^1$H-NMR (300 Mz, DMSO-$d_6$) δ0.93 (3H, t, J=7.1 Hz), 2.89 (2H, d, J=7.5 Hz), 3.20-3.69 (3H, m), 3.82 (3H, s), 6.71 (1H, d, J=8.4 Hz), 6.60-7.04 (2H, m), 7.29 (1H, dd, J=6.1, 2.3 Hz), 7.30-7.50 (3H, m), 7.77 (1H, d, J=2.2 Hz).

(2) N-ethyl-2-[(2-methoxy-5-pyridyl)methyl]-N'-(2-naphthylsulfonyl)-N-phenylmalonamide In the same manner as in Example 1 (2), the title compound (536 mg) was obtained as a white powder using the abovementioned compound (728 mg).
$^1$H-NMR (300 Mz, DMSO-$d_6$) δ0.88 (3H, t, J=6.9 Hz), 2.61-2.90 (2H, m), 3.30-3.65 (3H, m), 3.75 (3H, s), 6.49 (1H, d, J=9.0 Hz), 6.90-7.01 (2H, m), 7.07-7.15 (1H, m), 7.22-7.45 (3H, m), 7.61 (1H, s), 7.65-7.84 (3H, s), 8.04-8.30 (3H, m), 8.53 (1H, s), 12.04 (1H, brs).
MS: 518(M+H)$^+$.

Example 280

Synthesis of N-ethyl-2-[(2-methoxy-5-pyridyl)methyl]-N-phenyl-N'-((E)-styrylsulfonyl)malonamide In the same manner as in Example 1 (2), the title compound (346 mg) was obtained as a white powder using the compound (728 mg) obtained in Example 279 (1) and trans-β-styrenesulfonamide (375 mg).
$^1$H-NMR (300 Mz, DMSO-$d_6$) δ0.92 (3H, t, J=6.9 Hz), 2.70-3.05 (2H, m), 3.18-3.75 (3H, m), 3.76 (3H, s), 6.61 (1H, d, J=8.7 Hz), 7.00-7.14 (2H, m), 7.19-7.31 (2H, m), 7.32-7.61 (7H, m), 7.65-7.86 (3H, m), 11.73 (1H, brs).
MS: 494(M+H)$^+$.

Example 281

Synthesis of 2-[4-(benzyloxy)benzyl]-N-ethyl-N-phenyl-N'-((E)-styrylsulfonyl)malonamide (1) 5-[4-(benzyloxy)benzyl]-2,2-dimethyl-1,3-dioxane-4,6-dione In the same manner as in Example 119 (1), the title compound (10.4 g) was obtained as a pale-yellow powder using 4-benzyloxybenzaldehyde (11.8 g).
$^1$H-NMR (300 Mz, CDCl$_3$) δ1.46 (3H, s), 1.72 (3H, s), 3.44 (2H, d, J=4.8 Hz), 3.72 (1H, t, J=4.5 Hz), 5.03 (2H, s), 6.89 (2H, d, J=8.7 Hz), 7.17-7.49 (7H, m).

(2) 2-[4-(benzyloxy)benzyl]-3-(N-ethyl-N-phenylamino)-3-oxopropionic acid

In the same manner as in Example 119 (2), the title compound (354 mg) was obtained as a white powder using the above-mentioned compound (681 mg) and N-ethylaniline (969 mg).
$^1$H-NMR (300 Mz, DMSO-$d_6$) δ0.88 (3H, t, J=7.1 Hz), 2.73-2.95 (2H, m), 3.10-3.69 (3H, m), 5.12 (2H, s), 6.35-7.00 (6H, m), 7.10-7.50 (8H, m).

(3) 2-[4-(benzyloxy)benzyl]-N-ethyl-N-phenyl-N'-((E)-styrylsulfonyl)malonamide

In the same manner as in Example 1 (2), the title compound (167 mg) was obtained as a white powder using the above-mentioned compound (462 mg) and trans-β-styrenesulfonamide (462 mg).
$^1$H-NMR (300 Mz, DMSO-$d_6$) δ0.91 (3H, t, J=6.9 Hz), 2.60-3.78 (5H, m), 5.00 (2H, s), 6.70-6.90 (4H, m), 6.90-7.14 (2H, m), 7.18-7.58 (13H, m), 7.65-7.90 (2H, m), 11.76 (1H, brs).
MS: 569(M+H)$^+$.

Example 282

Synthesis of 2-[3-(benzyloxy)benzyl]-N-ethyl-N-phenyl-N'-((E)-styrylsulfonyl)malonamide (1) 5-[3-(benzyloxy)benzyl]-2,2-dimethyl-1,3-dioxane-4,6-dione In the same manner as in Example 119 (1), the title compound (371 mg) was obtained as a white powder using 3-benzyloxybenzaldehyde (950 mg).
$^1$H-NMR (300 Mz, CDCl$_3$) δ1.50 (3H, s), 1.73 (3H, s), 3.47 (2H, d, J=4.9 Hz), 3.74 (1H, t, J=4.9 Hz), 5.05 (2H, s), 6.79-7.00 (3H, m), 7.16-7.52 (6H, m).

(2) 2-[3-(benzyloxy)benzyl]-3-(N-ethyl-N-phenylamino)-3-oxopropionic acid

In the same manner as in Example 119 (2), the title compound (400 mg) was obtained as an oil using the above-mentioned compound (371 mg) and N-ethylaniline (528 mg).
$^1$H-NMR (300 Mz, DMSO-$d_6$) δ0.92 (3H, t, J=7.2 Hz), 2.80-2.98 (2H, m), 3.20-3.70 (3H, m), 5.01 (2H, s), 6.43-7.52 (14H, m), 12.60 (1H, brs).

(3) 2-[3-(benzyloxy)benzyl]-N-ethyl-N-phenyl-N'-((E)-styrylsulfonyl)malonamide

In the same manner as in Example 1 (2), the title compound (57 mg) was obtained as a white powder using the above-mentioned compound (400 mg) and trans-β-styrenesulfonamide (168 mg).
$^1$H-NMR (300 Mz, DMSO-$d_6$) δ0.92 (3H, t, J=6.9 Hz), 2.65-3.70 (5H, m), 4.97 (2H, s), 6.40-6.90 (3H, m), 6.94-7.20 (3H, m), 7.20-7.65 (13H, m), 7.69-7.90 (2H, m), 11.80 (1H, brs).
MS: 569(M+H)$^+$.

Example 283

Synthesis of N-ethyl-2-(4-methoxy-3-nitrobenzyl)-N-phenyl-N'-((E)-styrylsulfonyl)malonamide (1) 5-(4-methoxy-3-nitrobenzyl)-2,2-dimethyl-1,3-dioxane-4,6-dione In the same manner as in Example 214 (1), a crude product was obtained using 4-methoxy-3-nitrobenzoic acid (3.94 g). This was purified by silica gel column chromatography to give the title compound (1.08 g) as a pale-yellow solid.

¹H-NMR (300 Mz, DMSO-d₆) δ1.64 (3H, s), 1.82 (3H, s), 3.27 (2H, d, J=5.3 Hz), 3.89 (3H, s), 4.81 (1H, t, J=5.4 Hz), 7.28 (1H, d, J=8.6 Hz), 7.59 (1H, dd, J=8.8, 1.6 Hz), 7.83 (1H, d, J=1.2 Hz).

(2) 3-(N-ethyl-N-phenylamino)-2-(4-methoxy-3-nitrobenzyl)-3-oxopropionic acid

In the same manner as in Example 119 (2), the title compound (310 mg) was obtained as a white powder using the above-mentioned compound (1.08 g) and N-ethylaniline (1.69 g).
¹H-NMR (300 Mz, DMSO-d₆) δ0.91 (3H, t, J=7.0 Hz), 2.96 (2H, d, J=7.5 Hz), 3.20-3.70 (3H, m), 3.91 (3H, s), 6.25-7.10 (2H, m), 7.20-7.40 (5H, m), 7.46 (1H, s), 12.70 (1H, brs).

(3) N-ethyl-2-(4-methoxy-3-nitrobenzyl)-N-phenyl-N'-((E)-styrylsulfonyl)malonamide In the same manner as in Example 1 (2), the title compound (22 mg) was obtained as a white powder using the above-mentioned compound (310 mg) and trans-β-styrenesulfonamide (141 mg).
¹H-NMR (300 Mz, DMSO-d₆) δ0.91 (3H, t, J=7.2 Hz), 2.78-3.16 (2H, m), 3.25-3.70 (3H, m), 3.84 (3H, s), 6.94-7.05 (2H, m), 7.17 (1H, d, J=8.7 Hz), 7.20-784 (10H, m), 7.86-7.92 (2H, m), 11.74 (1H, brs).
MS: 538(M+H)⁺.

Example 284

Synthesis of N-ethyl-2-(4-methoxy-3-nitrobenzyl)-N'-(2-naphthylsulfonyl)-N-phenylmalonamide In the same manner as in Example 1 (2), the title compound (210 mg) was obtained as a white powder using the compound (294 mg) obtained in Example 283 (2).
¹H-NMR (300 Mz, DMSO-d₆) δ0.86 (3H, t, J=7.2 Hz), 2.70-3.07 (2H, m), 3.23-3.64 (3H, m), 3.83 (3H, s), 6.87 (2H, d, J=7.5 Hz), 6.99-7.18 (2H, m), 7.18-7.46 (4H, m), 7.60-7.85 (3H, m), 8.00-8.29 (3H, m), 8.55 (1H, s), 12.02 (1H, brs).
MS: 562(M+H)⁺.

Example 285

Synthesis of 2-(3-amino-4-methoxybenzyl)-N-ethyl-N'-(2-naphthylsulfonyl)-N-phenylmalonamide In the same manner as in Example 7, the title compound (132 mg) was obtained as a white powder using the compound (156 mg) obtained in Example 284 at room temperature.
¹H-NMR (300 Mz, DMSO-d₆) δ0.89 (3H, t, J=7.1 Hz), 2.50-2.90 (2H, m), 3.25-3.75 (3H, m), 3.65 (3H, s), 5.91 (1H, d, J=7.7 Hz), 6.17 (1H, d, J=1.0 Hz), 6.43 (1H, d, J=8.2 Hz), 6.88-7.01 (2H, m), 7.22-7.46 (3H, m), 7.61-7.87 (3H, m), 8.02-8.24 (3H, m), 8.53 (1H, s).
MS: 532(M+H)⁺.

Example 286

Synthesis of N-ethyl-2-(3-methoxy-4-nitrobenzyl)-N-phenyl-N'-((E)-styrylsulfonyl)malonamide (1) 5-(3-methoxy-4-nitrobenzyl)-2,2-dimethyl-1,3-dioxane-4,6-dione In the same manner as in Example 214 (1), the title compound (3.49 g) was obtained as a white powder using 3-methoxy-4-nitrobenzoic acid (3.94 g).

¹H-NMR (300 Mz, DMSO-d₆) δ1.67 (3H, s), 1.84 (3H, s), 3.34 (2H, d, J=5.5 Hz), 3.90 (3H, s), 4.84 (1H, t, J=5.6 Hz), 7.03 (1H, d, J=8.3 Hz), 7.32 (1H, s), 7.80 (1H, d, J=8.3 Hz).

(2) 3-(N-ethyl-N-phenylamino)-2-(3-methoxy-4-nitrobenzyl)-3-oxopropionic acid

In the same manner as in Example 119 (2), the title compound (962 mg) was obtained as a white powder using the above-mentioned compound (1.08 g) and N-ethylaniline (1.69 g).
¹H-NMR (300 Mz, DMSO-d₆) δ0.91 (3H, t, J=7.1 Hz), 2.89-3.09 (2H, m), 3.09-3.74 (3H, m), 3.76 (3H, s), 6.74 (2H, brs), 6.73 (1H, dd, J=8.3, 1.3 Hz), 6.95 (1H, d, J=0.9 Hz), 7.20-7.43 (3H, m), 7.79 (1H, d, J=8.2 Hz), 12.80 (1H, brs).

(3) N-ethyl-2-(3-methoxy-4-nitrobenzyl)-N-phenyl-N'-((E)-styrylsulfonyl)malonamide In the same manner as in Example 1 (2), the title compound (200 mg) was obtained as a white powder using the above-mentioned compound (310 mg) and trans-β-styrenesulfonamide (141 mg).
¹H-NMR (300 Mz, DMSO-d₆) δ0.92 (3H, t, J=7.1 Hz), 2.79-3.20 (2H, m), 3.26-3.70 (3H, m), 3.79 (3H, s), 6.70 (1H, d, J=8.3 Hz), 6.87 (1H, s), 6.90-7.88 (13H, m), 11.80 (1H, brs).
MS: 538(M+H)⁺.

Example 287

Synthesis of N-ethyl-2-(3-methoxy-4-nitrobenzyl)-N'-(2-naphthylsulfonyl)-N-phenylmalonamide In the same manner as in Example 1 (2), the title compound (318 mg) was obtained as a white powder using the compound (294 mg) obtained in Example 286 (2).
¹H-NMR (300 Mz, DMSO-d₆) δ0.88 (3H, t, J=7.1 Hz), 2.80-3.09 (2H, m), 3.26-3.69 (3H, m), 3.70 (3H, s), 6.54 (1H, d, J=8.3 Hz), 6.75 (1H, s), 6.89-7.00 (2H, m), 7.20-7.50 (3H, m), 7.58 (1H, d, J=8.3 Hz), 7.65-7.83 (3H, m), 8.02-8.29 (3H, m), 8.55 (1H, s), 11.10 (1H, brs).
MS: 562(M+H)⁺.

Example 288

Synthesis of 2-(4-amino-3-methoxybenzyl)-N-ethyl-N'-(2-naphthylsulfonyl)-N-phenylmalonamide In the same manner as in Example 7, the title compound (204 mg) was obtained as a white powder using the compound (240 mg) obtained in Example 287 at room temperature.
¹H-NMR (300 Mz, DMSO-d₆) δ0.88 (3H, t, J=6.9 Hz), 2.60-2.80 (2H, m), 3.24-3.67 (3H, m), 3.53 (3H, s), 6.05-6.20 (2H, m), 6.35 (1H, d, J=8.1 Hz), 6.90-7.05 (2H, m), 7.20-7.40 (3H, m), 7.62-7.80 (3H, m), 8.03-8.26 (3H, m), 8.55 (1H, s).
MS: 532(M+H)⁺.

Example 289

Synthesis of N-ethyl-2-(3-methoxy-2-nitrobenzyl)-N-phenyl-N'-((E)-styrylsulfonyl)malonamide (1) 5-(3-methoxy-2-nitrobenzyl)-2,2-dimethyl-1,3-dioxane-4,6-dione In the same manner as in Example 214 (1), the title compound (864 mg) was obtained as a white powder using 3-methoxy-2-nitrobenzoic acid (3.94 g).

¹H-NMR (300 Mz, DMSO-d₆) δ1.68 (3H, s), 1.84 (3H, s), 3.18 (2H, d, J=5.5 Hz), 3.87 (3H, s), 4.77 (1H, t, J=5.5 Hz), 7.07 (1H, d, J=7.9 Hz), 7.18 (1H, d, J=8.4 Hz), 7.48 (1H, t, J=8.1 Hz).

(2) 3-(N-ethyl-N-phenylamino)-2-(3-methoxy-2-nitrobenzyl)-3-oxopropionic acid

In the same manner as in Example 119 (2), the title compound (714 mg) was obtained as a white powder using the above-mentioned compound (864 mg) and N-ethylaniline (1.36 g).
¹H-NMR (300 Mz, DMSO-d₆) δ0.93 (3H, t, J=7.1 Hz), 2.66-2.80 (1H, m), 2.90-3.05 (1H, m), 3.25-3.70 (3H, m), 3.90 (3H, s), 6.15-7.60 (8H, m), 12.95 (1H, brs).

(3) N-ethyl-2-(3-methoxy-2-nitrobenzyl)-N-phenyl-N'-((E)-styrylsulfonyl)malonamide In the same manner as in Example 1 (2), the title compound (285 mg) was obtained as a white powder using the above-mentioned compound (714 mg) and trans-β-styrenesulfonamide (392 mg).
¹H-NMR (300 Mz, DMSO-d₆) δ0.92 (3H, t, J=7.1 Hz), 2.70-3.10 (2H, m), 3.35-3.70 (3H, m), 3.82 (3H, s), 6.60 (1H, d, J=7.8 Hz), 6.99-7.20 (3H, m), 7.22-7.60 (9H, m), 7.68-7.89 (2H, m), 11.75 (1H, brs).
MS: 538(M+H)⁺.

Example 290

Synthesis of N-ethyl-2-(4-methyl-3-nitrobenzyl)-N-phenyl-N'-((E)-styrylsulfonyl)malonamide (1) triethyl 2-(4-methyl-3-nitrophenyl)ethane-1,1,1-tricarboxylate In the same manner as in Example 117 (1), the title compound (16.5 g) was obtained as an oil using 4-methyl-3-nitrobenzyl chloride (8.06 g).
¹H-NMR (400 Mz, CDCl₃) δ1.25 (9H, t, J=7.2 Hz), 2.56 (3H, s), 3.53 (2H, s), 7.22 (1H, d, J=8.0 Hz), 7.47 (1H, dd, J=8.0, 1.6 Hz), 7.92 (1H, d, J=1.6 Hz).

(2) monoethyl(4-methyl-3-nitrobenzyl) malonate

In the same manner as in Example 117 (2), the title compound (12.2 g) was obtained as a yellow solid using the above-mentioned compound (16.5 g).
¹H-NMR (400 Mz, CDCl₃) δ1.25 (3H, t, J=7.2 Hz), 2.57 (3H, s), 3.23-3.33 (2H, m), 3.70 (1H, t, J=7.6 Hz), 4.15-4.23 (2H, m), 7.27 (1H, d, J=8.0 Hz), 7.37 (1H, dd, J=8.0, 1.6 Hz), 7.85 (1H, d, J=1.6 Hz).

(3) ethyl 3-(N-ethyl-N-phenylamino)-2-(4-methyl-3-nitrobenzyl)-3-oxopropionate

In the same manner as in Example 1 (4), the title compound (1.84 g) was obtained as a yellow solid using the above-mentioned compound (2.02 g) and N-ethylaniline (1.00 mL).
¹H-NMR (400 Mz, DMSO-d₆) δ0.92 (3H, t, J=7.2 Hz), 1.12 (3H, t, J=7.2 Hz), 2.50 (3H, s), 3.00-3.09 (2H, m), 3.43-3.65 (3H, m), 4.00 (2H, g, J=7.2 Hz), 6.76 (2H, brs), 7.26-7.28 (1H, m), 7.31-7.46 (4H, m), 7.60 (1H, d, J=1.2 Hz).

(4) 3-(N-ethyl-N-phenylamino)-2-(4-methyl-3-nitrobenzyl)-3-oxopropionic acid

In the same manner as in Example 1 (3), the title compound (1.54 g) was obtained as an oil using the above-mentioned compound (1.84 g).
¹H-NMR (400 Mz, DMSO-d₆) δ0.90 (3H, t, J=7.2 Hz), 2.50 (3H, s), 3.02 (2H, d, J=7.6 Hz), 3.32-3.39 (1H, m), 3.43-3.64 (2H, m), 6.72 (2H, brs), 7.26 (1H, dd, J=7.6, 1.6 Hz), 7.35 (3H, brs), 7.40 (1H, d, J=7.6 Hz), 7.58 (1H, d, J=1.6 Hz), 12.70 (1H, brs).

(5) N-ethyl-2-(4-methyl-3-nitrobenzyl)-N-phenyl-N'-((E)-styrylsulfonyl)malonamide In the same manner as in Example 1 (2), the title compound (296 mg) was obtained as a white solid using the above-mentioned compound (420 mg) and trans-β-styrenesulfonamide (216 mg).
¹H-NMR (400 Mz, DMSO-d₆) δ0.82-0.96 (3H, m), 2.42 (3H, s), 2.86-2.99 (1H, m), 3.05-3.16 (1H, m), 3.43-3.64 (3H, m), 7.03-7.05 (2H, m), 7.24-7.60 (11H, m), 7.78-7.80 (2H, m), 11.75 (1H, brs).

Example 291

Synthesis of 2-(3-amino-4-methylbenzyl)-N-ethyl-N-phenyl-N'-((E)-styrylsulfonyl)malonamide In the same manner as in Example 137 (4), the title compound (130 mg) was obtained as a pale-yellow solid using the compound (204 mg) obtained in Example 290 at room temperature.
¹H-NMR (400 Mz, DMSO-d₆) δ0.89-0.98 (3H, m), 1.96 (3H, s), 2.70-2.87 (2H, m), 3.40-3.53 (2H, m), 3.60-3.70 (1H, m), 6.01 (1H, d, J=7.2 Hz), 6.26 (1H, s), 6.69 (1H, d, J=7.2 Hz), 7.09-7.11 (2H, m), 7.29 (1H, d, J=15.6 Hz), 7.36-7.50 (6H, m), 7.55 (1H, d, J=15.6 Hz), 7.77-7.78 (2H, m).
MS: 492(M+H)⁺.

Example 292

Synthesis of 2-(3-benzoylamino-4-methylbenzyl)-N-ethyl-N-phenyl-N'-((E)-styrylsulfonyl)malonamide In the same manner as in Example 9, the title compound (71 mg) was obtained as a white solid using the compound (75 mg) obtained in Example 291.
¹H-NMR (400 Mz, DMSO-d₆) δ0.87-0.95 (3H, m), 2.49 (3H, s), 2.80-2.91 (1H, m), 2.96-3.07 (1H, m), 3.40-3.70 (3H, m), 6.76 (1H, d, J=7.9 Hz), 6.95 (1H, s), 7.04-7.10 (3H, m), 7.29-7.60 (10H, m), 7.73-7.82 (3H, m), 7.98 (2H, d, J=7.2 Hz), 9.79 (1H, s), 11.80 (1H, brs).
MS: 596(M+H)⁺.

Example 293

Synthesis of N-ethyl-2-(4-methyl-3-nitrobenzyl)-N'-(2-naphthylsulfonyl)-N-phenylmalonamide In the same manner as in Example 1 (2), the title compound (962 mg) was obtained as a white solid using the compound (1.12 g) obtained in Example 290 (4).

¹H-NMR (400 Mz, DMSO-d₆) δ0.81-0.90 (3H, m), 2.40 (3H, s), 2.85 (1H, dd, J=13.6, 5.6 Hz), 2.99 (1H, dd, J=13.6, 8.8 Hz), 3.39-3.57 (3H, m), 6.89 (2H, d, J=7.6 Hz), 7.08-7.15 (2H, m), 7.20-7.41 (3H, m), 7.52 (1H, s), 7.65-7.84 (3H, m), 8.11 (1H, d, J=8.0 Hz), 8.17 (1H, d, J=8.8 Hz), 8.24 (1H, d, J=8.0 Hz), 8.54 (1H, s), 12.07 (1H, brs).
MS: 546(M+H)⁺.

Example 294

Synthesis of 2-(3-amino-4-methylbenzyl)-N-ethyl-N'-(2-naphthylsulfonyl)-N-phenylmalonamide In the same manner as in Example 7, the title compound (620 mg) was obtained as a white solid using the compound (670 mg) obtained in Example 293 at room temperature.
¹H-NMR (400 Mz, DMSO-d₆) δ0.80-0.95 (3H, m), 1.94 (3H, s), 2.64-2.74 (2H, m), 3.36-3.49 (2H, m), 3.49-3.63 (1H, m), 5.87 (1H, d, J=7.6 Hz), 6.15 (1H, s), 6.58 (1H, d, J=7.6 Hz), 6.90-6.99 (2H, m), 7.25-7.39 (3H, m), 7.76-7.80 (3H, m), 8.10 (1H, d, J=8.0 Hz), 8.16 (1H, d, J=8.8 Hz), 8.22 (1H, d, J=8.0 Hz), 8.54 (1H, s).
MS: 516(M+H)⁺.

Example 295

Synthesis of 2-(3-benzoylamino-4-methylbenzyl)-N-ethyl-N'-(2-naphthylsulfonyl)-N-phenylmalonamide In the same manner as in Example 9, the title compound (148 mg) was obtained as a white solid using the compound (146 mg) obtained in Example 294.
¹H-NMR (400 Mz, DMSO-d₆) δ0.86 (3H, t, J=7.2 Hz), 2.15 (3H, s), 2.70-2.81 (1H, m), 2.86-2.96 (1H, m), 3.37-3.61 (3H, m), 6.66 (1H, d, J=7.3 Hz), 6.89-6.98 (4H, m), 7.18-7.40 (3H, m), 7.49-7.62 (3H, m), 7.70-7.82 (3H, m), 7.97-7.99 (2H, m), 8.09 (1H, d, J=8.0 Hz), 8.18 (1H, d, J=8.8 Hz), 8.24 (1H, d, J=8.0 Hz), 8.56 (1H, s), 9.78 (1H, s), 12.10 (1H, brs).
MS: 620(M+H)⁺.

Example 296

Synthesis of N-ethyl-2-(4-fluorobenzyl)-N'-(2-naphthylsulfonyl)-N-phenylmalonamide (1) ethyl 3-(N-ethyl-N-phenylamino)-2-(4-fluorobenzyl)-3-oxopropionate The compound (884 mg) obtained in Example 118 (2) and N-ethylaniline (1.67 g) were subjected to the same manner as in Example 1 (4) to give the reaction mixture. Ethyl acetate (150 mL) and aqueous sodium hydrogen carbonate solution (120 mL) were added to extract the mixture, and the organic layer was washed sequentially with 0.5 mol/L hydrochloric acid, water and saturated brine. The organic layer was concentrated under reduced pressure to give the title compound (940 mg) as an oil.
¹H-NMR (300 Mz, CDCl₃) δ1.03 (3H, t, J=7.2 Hz), 1.25 (3H, t, J=7.5 Hz), 2.93-3.09 (1H, m), 3.13-3.28 (1H, m), 3.32-3.46 (1H, m), 3.66 (2H, q, J=7.2 Hz), 4.14 (2H, q, J=6.9 Hz), 6.80-7.09 (4H, m), 7.09-7.50 (5H, m).

(2) 3-(N-ethyl-N-phenylamino)-2-(4-fluorobenzyl)-3-oxopropionic acid

In the same manner as in Example 111 (4), the title compound (837 mg) was obtained as an oil using the above-mentioned compound (940 mg).
¹H-NMR (300 Mz, CDCl₃) δ1.06 (3H, t, J=7.2 Hz), 2.90-3.04 (1H, m), 3.04-3.20 (1H, m), 3.35-3.48 (1H, m), 3.52-3.79 (2H, m), 6.80-7.50 (9H, m).

(3) N-ethyl-2-(4-fluorobenzyl)-N'-(2-naphthylsulfonyl)-N-phenylmalonamide

In the same manner as in Example 1 (2), the title compound (274 mg) was obtained as a white powder using the above-mentioned compound (418 mg).
¹H-NMR (300 Mz, DMSO-d₆) δ0.87 (3H, t, J=6.9 Hz), 2.65-2.94 (2H, m), 3.20-3.66 (3H, m), 6.71-6.97 (6H, m), 7.38-7.40 (3H, m), 7.63-7.82 (3H, m), 8.00-8.29 (3H, m), 8.54 (1H, s), 12.08 (1H, brs).
MS: 505(M+H)⁺.

Example 297

Synthesis of N-ethyl-2-(4-fluorobenzyl)-N-phenyl-N'-((E)-styrylsulfonyl)malonamide In the same manner as in Example 1 (2), the title compound (98 mg) was obtained as a white powder using the compound (418 mg) obtained in Example 296 (2) and trans-β-styrenesulfonamide (224 mg).
¹H-NMR (300 Mz, DMSO-d₆) δ0.91 (3H, t, J=7.2 Hz), 2.79-3.09 (2H, m), 3.38-3.70 (3H, m), 6.85-7.10 (6H, m), 7.29 (1H, d, J=15.3 Hz), 7.34-7.60 (7H, m), 7.70-7.89 (2H, m), 11.76 (1H, brs).
MS: 481(M+H)⁺.

Example 298

Synthesis of N-ethyl-2-[3-(4-fluorophenoxy)benzyl]-N-phenyl-N'-((E)-styrylsulfonyl)malonamide (1) triethyl 2-[3-(4-fluorophenoxy)phenyl]ethane-1,1,1-tricarboxylate In the same manner as in Example 117 (1), the title compound (1.56 g) was obtained as an oil using 3-(4-fluorophenoxy)benzyl bromide (1.01 g).
¹H-NMR (400 Mz, CDCl₃) δ1.20 (9H, t, J=7.2 Hz), 3.48 (2H, s), 4.17 (2H, q, J=7.2 Hz), 6.80-6.88 (2H, m), 7.91-7.02 (5H, m), 7.14-7.21 (1H, m).

(2) monoethyl[3-(4-fluorophenoxy)benzyl]malonate

In the same manner as in Example 117 (2), the title compound (1.19 g) was obtained as an oil using the above-mentioned compound (1.55 g).
¹H-NMR (400 Mz, CDCl₃) δ1.22 (3H, t, J=7.2 Hz), 3.23 (2H, dd, J=7.6, 4.4 Hz), 3.67 (1H, t, J=7.6 Hz), 4.17 (2H, q, J=7.2 Hz), 6.82-6.84 (2H, m), 6.92-6.97 (3H, m), 7.01-7.05 (2H, m), 7.22-7.26 (1H, m).

(3) ethyl 3-(N-ethyl-N-phenylamino)-2-[3-(4-fluorophenoxy)benzyl]-3-oxopropionate In the same manner as in Example 1 (4), the title compound (1.07 g) was obtained as an oil using the above-mentioned compound (1.19 g) and N-ethylaniline (550 µL).
¹H-NMR (300 Mz, CDCl₃) δ1.05 (3H, t, J=7.2 Hz), 1.24 (3H, t, J=7.2 Hz), 3.03 (1H, dd, J=13.2, 5.1 Hz), 3.20 (1H, dd, J=13.2, 9.6 Hz), 3.42 (1H, dd, J=9.6, 5.1 Hz), 3.67 (2H, q, J=7.2 Hz), 4.13 (2H, q, J=7.2 Hz), 6.60-6.68 (2H, 11), 6.77-7.05 (8H, m), 7.18-7.30 (3H, m).

(4) 3-(N-ethyl-N-phenylamino)-2-[3-(4-fluorophenoxy)benzyl]-3-oxopropionic acid In the same manner as in Example 1 (3), the title compound (1.00 g) was obtained as an oil using the above-mentioned compound (1.07 g).

$^1$H-NMR (300 Mz, DMSO-$d_6$) δ0.92 (3H, t, J=7.2 Hz), 2.91-2.94 (2H, m), 3.26-3.31 (1H, m), 3.41-3.68 (2H, m), 6.50-7.10 (6H, m), 7.10-7.44 (6H, m), 12.60 (1H, brs).

(5) N-ethyl-2-[3-(4-fluorophenoxy)benzyl]-N-phenyl-N'-((E)-styrylsulfonyl)malonamide In the same manner as in Example 1 (2), the title compound (260 mg) was obtained as a white powder using the above-mentioned compound (1.00 g) and trans-β-styrenesulfonamide (450 mg).

$^1$H-NMR (400 Mz, DMSO-$d_6$) δ0.88-0.95 (3H, m), 2.84-2.92 (1H, m), 2.98-3.06 (1H, m), 3.45-3.54 (2H, m), 3.54-3.65 (1H, m), 6.59 (1H, s), 6.74-6.82 (2H, m), 6.98-7.03 (4H, m), 7.12-7.60 (11H, m), 7.76-7.82 (2H, m), 11.74 (1H, brs). MS: 573(M+H)$^+$.

Example 299

Synthesis of N-ethyl-2-[3-(1H-imidazol-1-ylmethyl)benzyl]-N-phenyl-N'-((E)-styrylsulfonyl)malonamide

(1) triethyl 2-[3-(1H-imidazol-1-ylmethyl)phenyl]ethane-1,1,1-tricarboxylate In the same manner as in Example 144 (1), the title compound (1.13 g) was obtained as an oil using 3-(1H-imidazol-1-ylmethyl)benzyl alcohol (1.05 g).

$^1$H-NMR (400 Mz, DMSO-$d_6$) δ1.10 (9H, t, J=7.2 Hz), 3.37 (2H, s), 4.09 (6H, q, J=7.2 Hz), 5.14 (2H, s), 6.90 (1H, s), 7.06 (1H, s), 7.10-7.17 (3H, m), 7.22-7.28 (1H, m), 7.70 (1H, s).

(2) ethyl 3-(N-ethyl-N-phenylamino)-2-[3-(1H-imidazol-1-ylmethyl)benzyl]-3-oxopropionate The above-mentioned compound (1.10 g) was subjected to hydrolysis in the same manner as in Example 117 (2). In the same manner as in Example 1 (4), a crude product was obtained using this and N-ethylaniline (360 μL). The crude product was purified by silica gel column chromatography to give the title compound (655 mg) as an oil.

$^1$H-NMR (300 Mz, CDCl$_3$) δ1.02 (3H, t, J=7.2 Hz), 1.25 (3H, t, J=7.2 Hz), 3.00-3.10 (1H, m), 3.16-3.28 (1H, m), 3.37-3.45 (1H, m), 3.53-3.72 (3H, m), 4.14 (2H, q, J=7.2 Hz), 5.04 (2H, s), 6.58 (2H, m), 6.88-6.92 (2H, m), 7.02-7.04 (2H, m), 7.08 (1H, s), 7.18-7.35 (4H, m), 7.51 (1H, s).

(3) N-ethyl-2-[3-(1H-imidazol-1-ylmethyl)benzyl]-N-phenyl-N'-((E)-styrylsulfonyl)malonamide The above-mentioned compound (655 g) was subjected to hydrolysis in the same manner as in Example 1 (3). In the same manner as in Example 1 (2), the title compound (440 mg) was obtained as a white powder using this and trans-β-styrenesulfonamide (300 mg).

$^1$H-NMR (400 Mz, DMSO-$d_6$) δ0.82-0.93 (3H, m), 2.90 (1H, dd, J=13.2, 5.6 Hz), 3.00 (1H, dd, J=13.2, 8.0 Hz), 3.40-3.64 (3H, m), 5.33 (2H, s), 6.91-7.07 (4H, m), 7.17-7.81 (14H, m), 9.19 (1H, s), 11.83 (1H, brs).
MS: 543(M+H)$^+$.

Example 300

Synthesis of N-ethyl-2-{3-[(2-methyl-1H-benzimidazolyl-1-yl)methyl]benzyl}-N-phenyl-N'-((E)-styrylsulfonyl)malonamide

(1) methyl 3-[(2-methyl-1H-benzimidazol-1-yl)methyl]benzoate

To a solution of 2-methyl-1H-benzimidazolyle (2.25 g) in THF (100 mL) was added 60% sodium hydride (750 mg) under ice-cooling, and the mixture was stirred for 20 min. Methyl 3-(bromomethyl)benzoate (3.90 g) was added to the reaction mixture under ice-cooling, and the mixture was stirred at room temperature for 2 days. Water (100 mL) was added to the reaction mixture, and the mixture was extracted with ethyl acetate (100 mL×2). The organic layer was washed with saturated brine and concentrated under reduced pressure to give the title compound (3.97 g) as a pale-brown solid.

$^1$H-NMR (400 Mz, DMSO-$d_6$) δ2.50 (3H, s), 3.81 (3H, s), 5.58 (2H, s), 7.15-7.18 (2H, m), 7.36 (1H, d, J=7.6 Hz), 7.45-7.57 (3H, m), 7.74 (1H, s), 7.87 (1H, d, J=8.0 Hz).

(2) 3-[(2-methyl-1H-benzimidazolyl-1-yl)methyl]benzyl alcohol

To a solution of the above-mentioned compound (3.97 g) in THF (50 mL) was added in small amounts of lithium aluminum hydride (540 mg) under ice-cooling, and the mixture was allowed to warm to room temperature while stirring for 20 hr. Water (100 mL) was added to the reaction mixture, and the mixture was extracted with ethyl acetate (100 mL). The organic layer was washed with saturated brine and concentrated under reduced pressure to give the title compound (2.62 g) as a pale-yellow solid.

$^1$H-NMR (300 Mz, DMSO-$d_6$) δ2.51 (3H, s), 4.43 (2H, d, J=5.7 Hz), 5.16 (1H, t, J=5.7 Hz), 5.45 (2H, s), 6.95-7.00 (1H, m), 7.12-7.30 (5H, m), 7.44-7.56 (2H, m).

(3) 3-[(2-methyl-1H-benzimidazolyl-1-yl)methyl]benzyl chloride

To a solution of the above-mentioned compound (2.61 g) in chloroform (50 mL) was added thionyl chloride (4.0 mL), and the mixture was heated under reflux for 4 hr. Ice-water (200 mL), saturated sodium hydrogen carbonate (100 mL) and chloroform (100 mL) were added to extract the reaction mixture. The organic layer was washed with saturated brine, treated with activated carbon, and concentrated under reduced pressure to give the title compound (1.92 g) as a pale-brown solid.

$^1$H-NMR (300 Mz, DMSO-$d_6$) δ2.52 (3H, s), 4.72 (2H, s), 5.49 (2H, s), 7.00-7.17 (3H, m), 7.25 (1H, s), 7.27-7.35 (2H, m), 7.45-7.57 (2H, m).

(4) triethyl 2-{3-[(2-methyl-1H-benzimidazolyl-1-yl)methyl]phenyl}ethane-1,1,1-tricarboxylate In the same manner as in Example 117 (1), a crude product was obtained using the above-mentioned compound (1.65 g).

This was purified by silica gel column chromatography to give the title compound (2.68 g) as an oil.
$^1$H-NMR (300 Mz, CDCl$_3$) δ1.15 (9H, t, J=7.1 Hz), 2.56 (3H, s), 4.08 (6H, q, J=7.1 Hz), 5.27 (2H, s), 6.90-7.00 (2H, m), 7.08-7.33 (5H, m), 7.65-7.76 (1H, m).

(5) monoethyl{3-[(2-methyl-1H-benzimidazolyl-1-yl)methyl]benzyl}malonate

In the same manner as in Example 117 (2), a crude product was obtained using the above-mentioned compound (2.65 g). This was purified by silica gel column chromatography to give the title compound (800 mg) as an oil.
$^1$H-NMR (400 Mz, DMSO-d$_6$) δ0.99-1.06 (3H, m), 2.85 (3H, s), 2.97-3.09 (2H, m), 3.67-3.71 (1H, m), 3.92-4.00 (2H, m), 5.67 (2H, s), 7.16-7.31 (4H, m), 7.49-7.56 (2H, m), 7.78-7.82 (2H, m).

(6) ethyl 3-(N-ethyl-N-phenylamino)-2-{3-[(2-methyl-1H-benzimidazolyl-1-yl)methyl]benzyl}-3-oxopropionate In the same manner as in Example 1 (4), a crude product was obtained using the above-mentioned compound (800 mg) and N-ethylaniline (300 μL). This was purified by silica gel column chromatography to give the title compound (600 mg) as an oil.
$^1$H-NMR (400 Mz, DMSO-d$_6$) δ0.87 (3H, t, J=7.2 Hz), 1.08 (3H, t, J=7.2 Hz), 2.50 (3H, s), 2.84-2.96 (2H, m), 3.35-3.47 (3H, m), 3.94 (2H, q, J=7.2 Hz), 5.39 (2H, s), 6.62 (2H, brs), 6.84 (1H, s), 6.90 (1H, d, J=8.0 Hz), 7.02 (1H, d, J=7.9 Hz), 7.13-7.31 (6H, m), 7.41-7.44 (1H, m), 7.53-7.55 (1H, m).

(7) 3-(N-ethyl-N-phenylamino)-2-{3-[(2-methyl-1H-benzimidazolyl-1-yl)methyl]benzyl}-3-oxopropionic acid In the same manner as in Example 1 (3), the title compound (430 mg) was obtained as a white solid using the above-mentioned compound (655 mg).
$^1$H-NMR (300 Mz, DMSO-d$_6$) δ0.85 (3H, t, J=7.2 Hz), 2.51 (3H, s), 2.80-2.97 (2H, m), 3.23-3.45 (3H, m), 5.39 (2H, s), 6.60 (2H, brs), 6.86-6.90 (2H, m), 7.01 (1H, d, J=7.5 Hz), 7.13-7.36 (6H, m), 7.43-7.57 (2H, m), 12.61 (1H, brs).

(8) N-ethyl-2-{3-[(2-methyl-1H-benzimidazolyl-1-yl)methyl]benzyl}-N-phenyl-N'-((E)-styrylsulfonyl)malonamide In the same manner as in Example 1 (2), the title compound (182 mg) was obtained as a white solid using the above-mentioned compound (427 mg) and trans-β-styrenesulfonamide (177 mg).
$^1$H-NMR (400 Mz, DMSO-d$_6$) δ0.80-0.90 (3H, m), 2.83 (3H, s), 2.83-3.01 (2H, m), 3.37-3.59 (3H, m), 5.60 (2H, s), 6.88-6.98 (4H, m), 7.11 (1H, d, J=7.6 Hz), 7.19 (1H, t, J=7.6 Hz), 7.27-7.40 (4H, m), 7.46-7.58 (6H, m), 7.73-7.83 (4H, m), 11.80 (1H, brs).
MS: 607(M+H)$^+$.

Example 301

Synthesis of N-ethyl-2-(4-nitrophenethyl)-N-phenyl-N'-((E)-styrylsulfonyl)malonamide In the same manner as in Example 1 (4), the title compound (524 mg) was obtained as a white solid using the compound (690 mg) obtained in Example 217 (2) and N-ethylaniline (230 μL).

$^1$H-NMR (400 Mz, DMSO-d$_6$) δ0.97 (3H, t, J=6.8 Hz), 1.80-2.08 (2H, m), 2.53-2.57 (2H, m), 3.14 (1H, t, J=7.2 Hz), 3.49-3.71 (2H, m), 7.14-7.16 (2H, m), 7.27 (2H, d, J=8.8 Hz), 7.34-7.38 (4H, m), 7.48-7.49 (3H, m), 7.58 (1H, d, J=15.6 Hz), 7.80-7.82 (2H, m), 8.10 (2H, d, J=8.8 Hz), 11.72 (1H, brs).
MS: 522(M+H)$^+$.

Example 302

Synthesis of 2-(4-aminophenethyl)-N-ethyl-N-phenyl-N'-((E)-styrylsulfonyl)malonamide In the same manner as in Example 137 (4), the title compound (29 mg) was obtained as a white solid using the compound (257 mg) obtained in Example 301 at room temperature.
$^1$H-NMR (400 Mz, DMSO-d$_6$) δ0.97 (3H, t, J=7.2 Hz), 1.67-1.94 (2H, m), 2.15-2.27 (2H, m), 3.09-3.18 (1H, m), 3.52-3.67 (2H, m), 6.43 (2H, d, J=8.0 Hz), 6.63 (2H, d, J=8.0 Hz), 7.12-7.14 (2H, m), 7.30-7.36 (4H, m), 7.48-7.49 (3H, m), 7.55 (1H, d, J=15.6 Hz), 7.78-7.80 (2H, m).
MS: 492(M+H)$^+$.

Example 303

Synthesis of 2-(4-aminophenethyl)-N-ethyl-N'-phenethylsulfonyl-N-phenylmalonamide In the same manner as in Example 221, a crude product was obtained using the compound (240 mg) obtained in Example 301. The crude product was purified by silica gel column chromatography to give the title compound (86 mg) as a white solid.
$^1$H-NMR (400 Mz, DMSO-d$_6$) δ1.01 (3H, t, J=7.2 Hz), 1.76-1.82 (2H, m), 2.07-2.26 (2H, m), 2.85-3.08 (2H, m), 3.24 (1H, t, J=6.8 Hz), 3.47-3.80 (4H, m), 6.43 (2H, d, J=8.0 Hz), 6.59 (2H, d, J=8.0 Hz), 7.20-7.42 (10H, m).
MS: 494(M+H)$^+$.

Example 304

Synthesis of N-ethyl-N'-(2-naphthylsulfonyl)-2-(4-nitrophenethyl)-N-phenylmalonamide In the same manner as in Example 1 (4), the title compound (710 mg) was obtained as a white solid using the compound (850 mg) obtained in Example 144 (4) and N-ethylaniline (290 μL).
$^1$H-NMR (400 Mz, DMSO-d$_6$) δ0.88-0.98 (3H, m), 1.72-1.98 (2H, m), 2.35-2.48 (2H, m), 3.11 (1H, t, J=6.8 Hz), 3.43-3.67 (2H, m), 7.69-7.08 (2H, m), 7.14 (2H, d, J=8.8 Hz), 7.18-7.38 (3H, m), 7.70-7.85 (3H, m), 8.00 (2H, d, J=8.8 Hz), 8.06-8.11 (1H, m), 8.20 (1H, d, J=8.8 Hz), 8.26 (1H, d, J=8.0 Hz), 8.59 (1H, s), 12.03 (1H, brs).
MS: 546(M+H)$^+$.

Example 305

Synthesis of 2-(4-aminophenethyl)-N-ethyl-N'-(2-naphthylsulfonyl)-N-phenylmalonamide In the same manner as in Example 7, the title compound (600 mg) was obtained as a white solid using the compound (650 mg) obtained in Example 304 at room temperature.
$^1$H-NMR (400 Mz, DMSO-d$_6$) δ0.93 (3H, t, J=7.2 Hz), 1.60-1.85 (2H, m), 2.09 (2H, t, J=7.6 Hz), 3.11 (1H, t, J=6.8

Hz), 3.45-3.63 (2H, m), 6.41 (2H, d, J=8.4 Hz), 6.51 (2H, d, J=8.4 Hz), 6.99 (2H, d, J=7.6 Hz), 7.18-7.35 (3H, m), 7.70-7.83 (3H, m), 8.09 (1H, d, J=8.0 Hz), 8.19 (1H, d, J=8.8 Hz), 8.24 (1H, d, J=8.0 Hz), 8.56 (1H, s).

MS: 516(M+H)$^+$.

Example 306

Synthesis of N-ethyl-N-phenyl-2-(2-propynyl)-N'-((E)-styrylsulfonyl)malonamide

In the same manner as in Example 1 (4), a crude product was obtained using the compound (1.04 g) obtained in Example 215 (2) and N-ethylaniline (430 μL). This was purified by silica gel column chromatography to give the title compound (95 mg) as a white powder.

$^1$H-NMR (400 Mz, CDCl$_3$) δ1.17 (3H, brs), 2.04 (1H, s), 2.63-2.64 (1H, m), 2.65-2.71 (1H, m), 3.35-3.39 (1H, m), 3.74-3.84 (2H, m), 7.02 (1H, d, J=15.2 Hz), 7.15-7.17 (2H, m), 7.39-7.47 (7H, m), 7.51-7.53 (2H, m), 7.71 (1H, d, J=15.2 Hz).

MS: 411(M+H)$^+$.

Example 307

Synthesis of N-ethyl-N'-(2-naphthylsulfonyl)-N-phenyl-2-(2-propynyl)malonamide

In the same manner as in Example 1 (4), a crude product was obtained using the compound (4.00 g) obtained in Example 152 (4) and N-ethylaniline (1.53 mL). This was purified by silica gel column chromatography to give the title compound (98 mg) as a white powder.

$^1$H-NMR (400 Mz, CDCl$_3$) δ1.10 (3H, brs), 1.18-1.20 (1H, m) 1.88 (1H, s), 2.49-2.62 (1H, m), 2.63-2.88 (1H, m), 3.67-3.85 (2H, m), 6.67-7.19 (2H, m), 7.35-7.42 (3H, m), 7.60-7.69 (2H, m), 7.90-8.01 (4H, m), 8.66 (1H, s).

MS: 435(M+H)$^+$.

Example 308

Synthesis of N-ethyl-2-(4-fluorobenzyl)-N-(4-fluorophenyl)-N'-((E)-styrylsulfonyl)malonamide (1) ethyl 2-(4-fluorobenzyl)-3-oxo-3-[((E)-styrylsulfonyl)amino]propionate In the same manner as in Example 152 (3), the title compound (3.72 g) was obtained as an oil using the compound (10.0 g) obtained in Example 118 (2) and trans-β-styrenesulfonamide (7.06 g).

$^1$H-NMR (300 Mz, DMSO-d$_6$) δ1.07 (3H, t, J=6.9 Hz), 3.04 (2H, d, J=8.3 Hz), 3.75 (1H, t, J=7.6 Hz), 4.05 (2H, q, J=6.8 Hz), 6.80-7.80 (11H, m), 12.20 (1H, brs).

(2) 2-(4-fluorobenzyl)-3-oxo-3-[((E)-styrylsulfonyl)amino]propionic acid

In the same manner as in Example 1 (3), the title compound (2.58 g) was obtained as an oil using the above-mentioned compound (3.72 g).

$^1$H-NMR (300 Mz, DMSO-d$_6$) δ2.91-3.11 (2H, m), 3.58-3.72 (1H, m), 6.85-7.80 (11H, m), 12.10 (1H, brs), 12.50 (1H, brs).

(3) N-ethyl-2-(4-fluorobenzyl)-N-(4-fluorophenyl)-N'-((E)-styrylsulfonyl)malonamide In the same manner as in Example 13, the title compound (358 mg) was obtained as a white solid using the above-mentioned compound (755 mg) and N-ethyl-4-fluoroaniline (334 mg).

$^1$H-NMR (300 Mz, DMSO-d$_6$) δ0.91 (3H, t, J=7.2 Hz), 2.78-3.08 (2H, m), 3.11-3.67 (3H, m), 6.80-7.38 (9H, m), 7.38-7.61 (4H, m), 7.64-7.89 (2H, m), 11.70 (1H, brs).

MS: 499(M+H)$^+$.

Example 309

Synthesis of 2-(4-fluorobenzyl)-N-(4-fluorophenyl)-N-isopropyl-N'-((E)-styrylsulfonyl)malonamide In the same manner as in Example 13, the title compound (432 mg) was obtained as a white solid using the compound (755 mg) obtained in Example 308 (2) and 4-fluoro-N-isopropylaniline (368 mg).

$^1$H-NMR (300 Mz, DMSO-d$_6$) δ0.69-1.00 (6H, m), 2.76-2.93 (1H, m), 2.93-3.10 (1H, m), 3.12-3.45 (1H, m), 4.52-4.80 (1H, m), 6.60-7.19 (7H, m), 7.19-7.40 (2H, m), 7.40-7.63 (4H, m), 7.69-7.89 (2H, m), 11.67 (1H, brs).

MS: 513(M+H)$^+$.

Example 310

Synthesis of 2-(3-fluorobenzyl)-N-(4-fluorophenyl)-N-isopropyl-N'-((E)-styrylsulfonyl)malonamide (1) 5-(3-fluorobenzyl)-2,2-dimethyl-1,3-dioxane-4,6-dione In the same manner as in Example 119 (1), the title compound (9.96 g) was obtained as a white solid using 3-fluorobenzaldehyde (8.60 g).

$^1$H-NMR (400 Mz, CDCl$_3$) δ1.58 (3H, s), 1.76 (3H, s), 3.48 (2H, d, J=4.9 Hz), 3.73-3.76 (1H, m), 6.91-6.96 (1H, m), 7.01-7.11 (2H, m), 7.23-7.28 (1H, m).

(2) 3-[N-(4-fluorophenyl)-N-isopropylamino]-2-(3-fluorobenzyl)-3-oxopropionic acid In the same manner as in Example 119 (2), the title compound (740 mg) was obtained as a white solid using the above-mentioned compound (1.31 g) and 4-fluoro-N-isopropylaniline (1.68 g).

$^1$H-NMR (400 Mz, DMSO-d$_6$) δ0.70-0.88 (6H, m), 2.90-3.01 (2H, m), 3.16-3.18 (1H, m), 4.73-4.79 (1H, m), 5.95-5.99 (1H, m), 6.81-6.87 (2H, m), 7.03-7.10 (2H, m), 7.13-7.20 (1H, m), 7.29-7.35 (2H, m), 12.63 (1H, brs).

(3) 2-(3-fluorobenzyl)-N-(4-fluorophenyl)-N-isopropyl-N'-((E)-styrylsulfonyl)malonamide In the same manner as in Example 1 (2), the title compound (95 mg) was obtained as a white powder using the above-mentioned compound (260 mg) and trans-β-styrenesulfonamide (140 mg).

$^1$H-NMR (400 Mz, CDCl$_3$) δ0.90 (6H, brs), 2.95-2.97 (1H, m), 3.13-3.21 (2H, m), 4.88-4.99 (1H, m), 5.69-5.73 (1H, m), 6.74 (1H, d, J=9.4 Hz), 6.81-7.19 (5H, m), 7.22-7.26 (2H, m), 7.34-7.56 (6H, m), 7.71 (1H, d, J=15.0 Hz).
MS: 513(M+H)$^+$.

Example 311

Synthesis of 2-(3-fluorobenzyl)-N-(4-fluorophenyl)-N-isopropyl-N'-(2-naphthylsulfonyl)malonamide In the same manner as in Example 1 (2), the title compound (200 mg) was obtained as a white powder using the compound (480 mg) obtained in Example 310 (2).
$^1$H-NMR (400 Mz, CDCl$_3$) δ0.89 (6H, brs), 2.75-2.78 (1H, m), 3.00-3.10 (2H, m), 4.87-4.90 (1H, m), 5.69-5.73 (1H, m), 6.61-6.69 (3H, m), 6.77-6.82 (1H, m), 6.87-6.94 (2H, m), 7.11-7.25 (1H, m), 7.62-7.69 (2H, m), 7.91-8.02 (4H, m), 8.66 (1H, s), 10.34 (1H, s).
MS: 537(M+H)$^+$.

Example 312

Synthesis of 2-(4-cyanobenzyl)-N-(4-fluorophenyl)-N-isopropyl-N'-((E)-styrylsulfonyl)malonamide (1) 2-(4-cyanobenzyl)-3-oxo-3-[((E)-styrylsulfonyl)amino]propionic acid In the same manner as in Example 152 (3), the object compound was obtained using the compound (1.57 g) obtained in Example 111 (2) and trans-β-styrenesulfonamide (1.25 g). This was subjected to hydrolysis in the same manner as in Example 1 (3) to give the title compound (2.30 g) as a white powder.

(2) 2-(4-cyanobenzyl)-N-(4-fluorophenyl)-N-isopropyl-N'-((E)-styrylsulfonyl)malonamide In the same manner as in Example 1 (4), the title compound (395 mg) was obtained as a white powder using the above-mentioned compound (2.30 g) and 4-fluoro-N-isopropylaniline (920 mg).
$^1$H-NMR (400 Mz, CDCl$_3$) δ0.96 (6H, m), 3.15-3.25 (2H, m), 4.87-4.94 (1H, m), 5.98-6.02 (1H, m), 6.89-7.13 (6H, m), 7.26-7.53 (8H, m), 7.72 (1H, d, J=15.5 Hz), 10.16 (1H, brs).
MS: 520(M+H)$^+$.

Example 313

Synthesis of 2-(4-cyanobenzyl)-N-(4-fluorophenyl)-N-isopropyl-N'-(2-naphthylsulfonyl)malonamide (1) 2-(4-cyanobenzyl)-3-oxo-3-[(2-naphthylsulfonyl)amino]propionic acid In the same manner as in Example 152 (3), the object compound was obtained using the compound (1.57 g) obtained in Example 111 (2). This was subjected to hydrolysis in the same manner as in Example 1 (3) to give the title compound (2.51 g) as a white powder.

(2) 2-(4-cyanobenzyl)-N-(4-fluorophenyl)-N-isopropyl-N'-(2-naphthylsulfonyl)malonamide In the same manner as in Example 1 (4), the title compound (969 mg) was obtained as a white powder using the above-mentioned compound (2.51 g) and 4-fluoro-N-isopropylaniline (940 mg).
$^1$H-NMR (400 Mz, CDCl$_3$) δ0.96 (6H, brs), 2.82-2.86 (1H, m), 3.02-3.14 (2H, m), 4.84-4.91 (1H, m), 6.04-6.08 (1H, m), 6.69-6.73 (1H, m), 6.87-6.95 (3H, m), 7.31-7.33 (2H, m), 7.62-7.68 (2H, m), 7.69-8.02 (5H, m), 8.49 (1H, s), 12.03 (1H, brs).
MS: 544(M+H)$^+$.

Example 314

Synthesis of 2-(3-cyanobenzyl)-N-(4-fluorophenyl)-N-isopropyl-N'-((E)-styrylsulfonyl)malonamide (1) monoethyl(3-cyanobenzyl)malonate In the same manner as in Example 117 (1), the object compound was obtained using 3-cyanobenzyl bromide (4.22 g). This was subjected to hydrolysis in the same manner as in Example 117 (2) to give the title compound (6.32 g) as an oil.

(2) 2-(3-cyanobenzyl)-3-oxo-3-[((E)-styrylsulfonyl)amino]propionic acid

In the same manner as in Example 152 (3), the object compound was obtained using the above-mentioned compound (3.16 g) and trans-β-styrenesulfonamide (2.47 g). This was subjected to hydrolysis in the same manner as in Example 1 (3) to give the title compound (4.04 g) as a white powder.

(3) 2-(3-cyanobenzyl)-N-(4-fluorophenyl)-N-isopropyl-N'-((E)-styrylsulfonyl)malonamide In the same manner as in Example 1 (4), the title compound (668 mg) was obtained as a white powder using the above-mentioned compound (4.04 g) and 4-fluoro-N-isopropylaniline (1.61 g).
$^1$H-NMR (400 Mz, CDCl$_3$) δ0.96 (6H, brs), 2.99-3.03 (1H, m), 3.15-3.25 (2H, m), 4.87-4.93 (1H, m), 5.82-5.85 (1H, m), 6.89-6.96 (2H, m), 7.01-7.10 (2H, m), 7.30-7.37 (3H, m), 7.39-7.43 (3H, m), 7.46-7.58 (3H, m), 7.73 (1H, d, J=15.6 Hz), 10.14 (1H, brs).
MS: 520(M+H)$^+$.

Example 315

Synthesis of 2-(3-cyanobenzyl)-N-(4-fluorophenyl)-N-isopropyl-N'-(2-naphthylsulfonyl)malonamide (1) 2-(3-cyanobenzyl)-3-oxo-3-[(2-naphthylsulfonyl)amino]propionic acid In the same manner as in Example 152 (3), the object compound was obtained using the compound (3.16 g) obtained in Example 314 (1). This was subjected to hydrolysis in the same manner as in Example 1 (3) to give the title compound (3.96 g) as a white powder.

(2) 2-(3-cyanobenzyl)-N-(4-fluorophenyl)-N-isopropyl-N'-(2-naphthylsulfonyl)malonamide In the same manner as in Example 1 (4), the title compound (2.05 g) was obtained as a white powder using the above-mentioned compound (3.96 g) and 4-fluoro-N-isopropylaniline (1.49 g).
$^1$H-NMR (400 Mz, CDCl$_3$) δ0.97 (6H, brs), 2.85-2.97 (1H, m), 3.03-3.14 (2H, m), 4.84-4.91 (1H, m), 5.90-5.86 (1H, m), 6.65-6.69 (1H, m), 6.86-6.94 (2H, m), 7.10-7.12 (1H, m), 7.21-7.24 (1H, m), 7.44-7.50 (2H, m), 7.62-7.69 (3H, m), 7.71-8.07 (4H, m), 8.70 (1H, s).
MS: 544(M+H)$^+$.

Example 316

Synthesis of 2-(4-chlorobenzyl)-N-(4-fluorophenyl)-N-isopropyl-N'-(2-naphthylsulfonyl)malonamide In the same manner as in Example 13, the title compound (358 mg) was obtained as a white powder using the compound (418 mg) obtained in Example 267 (1) and 4-fluoro-N-isopropylaniline (184 mg).
$^1$H-NMR (300 Mz, DMSO-$d_6$) δ0.62-0.98 (6H, m), 2.60-2.82 (1H, m), 2.82-3.13 (1H, m), 3.15-3.45 (1H, m), 4.49-4.78 (1H, m), 6.60-7.00 (5H, m), 7.00-7.19 (2H, m), 7.19-7.40 (1H, m), 7.60-7.85 (3H, m), 7.97-8.35 (3H, m), 8.54 (1H, s), 11.98 (1H, brs).
MS: 553(M+H)$^+$.

Example 317

Synthesis of 2-(4-chlorobenzyl)-N-isopropyl-N'-(2-naphthylsulfonyl)-N-(3-pyridyl)malonamide hydrochloride In the same manner as in Example 13, the object compound was obtained using the compound (418 mg) obtained in Example 267 (1) and 3-(isopropylamino)pyridine (163 mg). This was dissolved in ethanol, 1 mol/L hydrochloric acid was added, and the mixture was concentrated under reduced pressure to give the title compound (74 mg) as a white solid.
$^1$H-NMR (300 Mz, DMSO-$d_6$) δ0.60-1.08 (6H, m), 2.39-3.10 (2H, m), 3.20-3.53 (1H, m), 4.48-4.78 (1H, m), 6.60-7.20 (4H, m), 7.25-7.90 (5H, m), 7.95-8.30 (3H, m), 8.30-8.60 (2H, m), 8.68-8.91 (1H, m), 12.00 (1H, brs).
MS: 536(M+H)$^+$.

Example 318

Synthesis of 2-(3-chlorobenzyl)-N-(4-fluorophenyl)-N-isopropyl-N'-((E)-styrylsulfonyl)malonamide (1) monoethyl(3-chlorobenzyl)malonate In the same manner as in Example 117 (1), the object compound was obtained using 3-chlorobenzyl bromide (3.46 g). This was subjected to hydrolysis in the same manner as in Example 117 (2) to give the title compound (5.72 g) as an oil.

(2) 2-(3-chlorobenzyl)-3-oxo-3-[((E)-styrylsulfonyl)amino]propionic acid

In the same manner as in Example 152 (3), the object compound was obtained using the above-mentioned compound (2.86 g) and trans-β-styrenesulfonamide (2.16 g). This was subjected to hydrolysis in the same manner as in Example 1 (3) to give the title compound (4.36 g) as a white powder.

(3) 2-(3-chlorobenzyl)-N-(4-fluorophenyl)-N-isopropyl-N'-((E)-styrylsulfonyl)malonamide In the same manner as in Example 1 (4), the title compound (1.89 g) was obtained as a white powder using the above-mentioned compound (4.36 g) and 4-fluoro-N-isopropylaniline (1.70 g).

$^1$H-NMR (400 Mz, CDCl$_3$) δ0.92 (6H, brs), 1.55-2.98 (1H, m), 3.12-3.20 (2H, m), 4.89-4.93 (1H, m), 5.63-5.67 (1H, m), 6.83-6.95 (3H, m), 7.01-7.07 (3H, m), 7.18-7.26 (1H, m), 7.27-7.29 (1H, m), 7.40-7.45 (3H, m), 7.52-7.54 (2H, m), 7.73 (1H, d, J=15.4 Hz), 10.24 (1H, brs).
MS: 531(M+H)$^+$.

Example 319

Synthesis of 2-(3-chlorobenzyl)-N-(4-fluorophenyl)-N-isopropyl-N'-(2-naphthylsulfonyl)malonamide (1) 2-(3-chlorobenzyl)-3-oxo-3-[(2-naphthylsulfonyl)amino]propionic acid In the same manner as in Example 152 (3), the object compound was obtained using the compound (2.86 g) obtained in Example 318 (1). This was subjected to hydrolysis in the same manner as in Example 1 (3) to give the title compound (4.37 g) as a white powder.

(2) 2-(3-chlorobenzyl)-N-(4-fluorophenyl)-N-isopropyl-N'-(2-naphthylsulfonyl)malonamide In the same manner as in Example 1 (4), the title compound (970 mg) was obtained as a white powder using the above-mentioned compound (4.37 g) and 4-fluoro-N-isopropylaniline (1.61 g).
$^1$H-NMR (400 Mz, CDCl$_3$) δ0.88 (6H, brs), 2.73-2.76 (1H, m), 2.99-3.09 (2H, m), 4.86-4.89 (1H, m), 5.62-5.66 (1H, m), 6.65-6.70 (1H, m), 6.79-6.84 (2H, m), 6.88-6.93 (2H, m), 7.09-7.21 (1H, m), 7.22-7.26 (1H, m), 7.61-7.70 (2H, m), 7.91-8.00 (5H, m), 8.67 (1H, s), 10.37 (1H, brs).
MS: 555(M+H)$^+$.

Example 320

Synthesis of N-(4-fluorophenyl)-N-isopropyl-N'-((E)-styrylsulfonyl)-2-(3-trifluoromethylbenzyl)malonamide (1) monoethyl(3-trifluoromethylbenzyl)malonate In the same manner as in Example 117 (1), the object compound was obtained using 3-trifluoromethylbenzyl bromide (5.00 g). This was subjected to hydrolysis in the same manner as in Example 117 (2) to give the title compound (6.72 g) as an oil.
$^1$H-NMR (400 Mz, CDCl$_3$) δ1.19-1.27 (3H, m), 3.30-3.34 (2H, m), 3.69-3.77 (1H, m), 4.10-4.21 (2H, m), 7.41-7.51 (4H, m).

(2) 3-[N-(4-fluorophenyl)-N-isopropylamino]-3-oxo-2-(3-trifluoromethylbenzyl)propionic acid In the same manner as in Example 1 (4), the object compound was obtained using the above-mentioned compound (6.72 g) and 4-fluoro-N-isopropylaniline (3.55 g). This was subjected to hydrolysis in the same manner as in Example 1 (3) to give the title compound (348 mg) as a white powder.

(3) N-(4-fluorophenyl)-N-isopropyl-N'-((E)-styrylsulfonyl)-2-(3-trifluoromethylbenzyl)malonamide In the same manner as in Example 1 (2), the title compound (47 mg) was obtained as a white powder using the above-mentioned compound (800 mg) and trans-β-styrenesulfonamide (370 mg).

¹H-NMR (400 Mz, CDCl₃) δ 0.92-0.94 (6H, m), 3.05-3.06 (1H, m), 3.17-3.23 (2H, m), 4.90-4.91 (1H, m), 6.80-6.82 (1H, m), 6.93 (2H, m), 7.00-7.05 (2H, m), 7.12-7.14 (2H, m), 7.41-7.57 (7H, m), 7.73 (1H, d, J=15.4 Hz).
MS: 563(M+H)⁺.

Example 321

Synthesis of N-(4-fluorophenyl)-N-isopropyl-N'-(2-naphthylsulfonyl)-2-(3-trifluoromethylbenzyl)malonamide In the same manner as in Example 1 (2), the title compound (193 mg) was obtained as a white powder using the compound (800 mg) obtained in Example 320 (2).
¹H-NMR (400 Mz, CDCl₃) δ 0.88-0.93 (6H, m), 1.56-2.86 (1H, m), 3.02-3.12 (2H, m), 5.82-5.85 (1H, m), 6.70-6.72 (1H, m), 6.73-6.83 (1H, m), 6.89-6.95 (3H, m), 7.32-7.34 (2H, m), 7.62-7.71 (3H, m), 7.89-8.00 (4H, m), 8.50 (1H, s), 8.66 (1H, brs).
MS: 587(M+H)⁺.

Example 322

Synthesis of 2-(4-fluorobenzyl)-N-isopropyl-N-(3-pyridyl)-N'-((E)-styrylsulfonyl)malonamide In the same manner as in Example 13, the title compound (390 mg) was obtained as a white powder using the compound (1.00 g) obtained in Example 308 (2) and 3-(isopropylamino)pyridine (433 mg).
¹H-NMR (300 Mz, DMSO-d₆) δ 0.69-0.97 (6H, m), 2.70-3.43 (3H, m), 4.57-4.80 (1H, m), 6.80-7.60 (11H, m), 7.60-7.86 (2H, m), 7.91-8.32 (1H, m), 8.66 (1H, s), 11.10-12.40 (1H, m).
MS: 496(M+H)⁺.

Example 323

Synthesis of 2-(4-fluorobenzyl)-N-(4-fluorophenyl)-N-(3-pentyl)-N'-((E)-styrylsulfonyl)malonamide In the same manner as in Example 13, the title compound (250 mg) was obtained as a white powder using the compound (377 mg) obtained in Example 308 (2) and 4-fluoro-N-(3-pentyl)aniline (218 mg).
¹H-NMR (300 Mz, DMSO-d₆) δ 0.59 (3H, t, J=7.2 Hz), 0.78 (3H, t, J=7.2 Hz), 0.90-1.33 (4H, m), 2.69-2.90 (1H, m), 2.90-3.10 (1H, m), 3.15-3.50 (1H, m), 4.20-4.43 (1H, m), 6.58-7.84 (13H, m), 7.84-7.96 (2H, m), 11.69 (1H, brs).
MS: 541(M+H)⁺.

Example 324

Synthesis of N-cyclohexyl-2-(4-fluorobenzyl)-N-(4-fluorophenyl)-N'-((E)-styrylsulfonyl)malonamide In the same manner as in Example 13, the title compound (217 mg) was obtained as a white powder using the compound (377 mg) obtained in Example 308 (2) and 4-fluoro-N-cyclohexylaniline (232 mg).
¹H-NMR (300 Mz, DMSO-d₆) δ 0.60-0.98 (3H, m), 1.02-1.35 (2H, m), 1.35-1.75 (5H, m), 2.70-2.90 (1H, m), 2.90-3.10 (1H, m), 3.18-3.47 (1H, m), 4.14-4.37 (1H, m), 6.68-6.90 (1H, m), 6.90-7.17 (6H, m), 7.17-7.40 (2H, m), 7.40-7.68 (4H, m), 7.69-7.90 (2H, m), 11.68 (1H, brs).
MS: 553(M+H)⁺.

Example 325

Synthesis of 2-(4-fluorobenzyl)-N-(4-fluorophenyl)-N'-((E)-styrylsulfonyl)-N-(4-tetrahydropyranyl)malonamide In the same manner as in Example 13, the title compound (184 mg) was obtained as a white powder using the compound (377 mg) obtained in Example 308 (2) and 4-fluoro-N-(4-tetrahydropyranyl)aniline (234 mg).
¹H-NMR (300 Mz, DMSO-d₆) δ 0.90-1.20 (2H, m), 1.33-1.68 (2H, m), 2.74-2.92 (1H, m), 2.92-3.10 (1H, m), 3.15-3.54 (3H, m), 3.64-3.85 (2H, m), 4.19-4.30 (1H, m), 6.70-7.16 (7H, m), 7.16-7.38 (2H, m), 7.38-7.67 (4H, m), 7.67-7.90 (2H, m), 11.70 (1H, brs).
MS: 555(M+H)⁺.

Example 326

Synthesis of 2-(4-fluorobenzyl)-N-(4-fluorophenyl)-N'-((E)-styrylsulfonyl)-N-(1-methyl-4-piperidinyl)malonamide In the same manner as in Example 13, the title compound (250 mg) was obtained as a white powder using the compound (377 mg) obtained in Example 308 (2) and 4-fluoro-N-(1-methyl-4-piperidinyl)aniline (250 mg).
¹H-NMR (300 Mz, DMSO-d₆) δ 1.00-1.40 (2H, m), 1.51-1.70 (1H, m), 1.70-1.90 (1H, m), 2.60 (3H, s), 2.70-3.70 (7H, m), 4.45-4.70 (1H, m), 6.10 (1H, brs), 6.77-7.25 (8H, m), 7.25-7.63 (6H, m), 8.80 (1H, brs).
MS: 568(M+H)⁺.

Example 327

Synthesis of 2-(4-fluorobenzyl)-N-(4-fluorophenyl)-N-isobutyl-N'-((E)-styrylsulfonyl)malonamide In the same manner as in Example 13, the title compound (160 mg) was obtained as a white powder using the compound (377 mg) obtained in Example 308 (2) and 4-fluoro-N-isobutylaniline (201 mg).
¹H-NMR (300 Mz, DMSO-d₆) δ 0.67 (3H, t, J=6.6 Hz), 0.77 (3H, t, J=6.6 Hz), 1.37-1.60 (1H, m), 2.77-2.92 (1H, m), 2.92-3.10 (1H, m), 3.14-3.55 (3H, m), 6.80-7.37 (9H, m), 7.37-7.65 (4H, m), 7.68-7.89 (2H, m), 11.72 (1H, brs).
MS: 527(M+H)⁺.

Example 328

Synthesis of 2-(4-fluorobenzyl)-N-isopropyl-N'-((E)-styrylsulfonyl)-N-(3-trifluoromethylphenyl)malonamide In the same manner as in Example 13, the title compound (158 mg) was obtained as a white powder using the compound (377 mg) obtained in Example 308 (2) and N-isopropyl-3-trifluoromethylaniline (244 mg).
¹H-NMR (300 Mz, DMSO-d₆) δ 0.68-1.03 (6H, m), 2.75-3.53 (3H, m), 4.59-4.89 (1H, m), 6.74-7.96 (15H, m), 11.70 (1H, brs).
MS: 563(M+H)⁺.

Example 329

Synthesis of 2-(4-fluorobenzyl)-N,N-diisopropyl-N'-((E)-styrylsulfonyl)malonamide In the same manner as in Example 13, the title compound (88 mg) was obtained as a white powder using the compound (870 mg) obtained in Example 308 (2) and diisopropylamine (646 μL).

$^1$H-NMR (300 Mz, DMSO-$d_6$) δ1.01 (6H, d, J=6.6 Hz), 1.09-1.30 (6H, m), 2.89-3.10 (2H, m), 3.19-3.48 (1H, m), 3.74-3.89 (1H, m), 3.89-4.05 (1H, m), 6.98 (2H, t, J=8.7 Hz), 7.10-7.34 (3H, m), 7.37-7.60 (4H, m), 7.60-7.92 (2H, m), 11.94 (1H, brs).

MS:461(M+H)$^+$.

Example 330

Synthesis of N-ethyl-2-(4-fluorobenzyl)-N-isopropyl-N'-((E)-styrylsulfonyl)malonamide In the same manner as in Example 13, the title compound (104 mg) was obtained as a white powder using the compound (377 mg) obtained in Example 308 (2) and N-ethylisopropylamine (174 mg).

$^1$H-NMR (300 Mz, DMSO-$d_6$) δ0.75-1.15 (9H, m), 2.90-3.25 (4H, m), 3.68-4.40 (2H, m), 6.91-7.08 (2H, m), 7.12-7.38 (3H, m), 7.38-7.58 (4H, m), 7.64-7.80 (2H, m), 12.01 (1H, brs).

MS: 447(M+H)$^+$.

Example 331

Synthesis of N-ethyl-N'-[(5-isobutyl-2-biphenyl)sulfonyl]-2-(4-nitrobenzyl)-N-phenylmalonamide (1) 3-{[(5-isobutyl-2-biphenyl)sulfonyl]amino}-2-(4-nitrobenzyl)-3-oxopropionic acid In the same manner as in Example 1 (2), the object compound was obtained using the compound (1.01 g) obtained in Example 178 (2) and 5-isobutylbiphenyl-2-sulfonamide (1.09 g). This was subjected to hydrolysis in the same manner as in Example 1 (3) to give the title compound (1.58 g) as an oil.

$^1$H-NMR (400 Mz, CDCl$_3$) δ0.85-0.98 (6H, m), 1.90-1.94 (1H, m), 2.54-2.59 (2H, m), 3.19-3.23 (1H, m), 3.35-3.37 (2H, m), 7.05-7.07 (2H, m), 7.11-7.43 (6H, m), 8.06-8.15 (2H, m), 8.17-8.20 (2H, m).

(2) N-ethyl-N'-[(5-isobutyl-2-biphenyl)sulfonyl]-2-(4-nitrobenzyl)-N-phenylmalonamide In the same manner as in Example 1 (4), the title compound (323 mg) was obtained as a white powder using the above-mentioned compound (1.58 g) and N-ethylaniline (380 mg).

$^1$H-NMR (300 Mz, DMSO-$d_6$) δ0.85-0.92 (9H, m), 1.85-1.87 (1H, m), 2.54 (2H, d, J=6.9 Hz), 2.75-2.76 (1H, m), 2.88-2.91 (1H, m), 3.19-3.20 (1H, m), 3.31-3.39 (1H, m), 3.64-3.65 (1H, m), 7.02-7.05 (7H, m), 7.27-7.42 (7H, m), 7.95-8.05 (3H, m), 11.68 (1H, brs).

MS: 614(M+H)$^+$.

Example 332

Synthesis of 2-(4-aminobenzyl)-N-ethyl-N'-[(5-isobutyl-2-biphenyl)sulfonyl]-N-phenylmalonamide In the same manner as in Example 7, the title compound (183 mg) was obtained as a white powder using the compound (250 mg) obtained in Example 331 at room temperature.

$^1$H-NMR (300 Mz, DMSO-$d_6$) δ0.86-0.93 (9H, m), 1.86-1.93 (2H, m), 2.55-2.57 (2H, m), 2.69-2.76 (2H, m), 3.64-3.71 (1H, m), 3.97-4.02 (1H, m), 6.75 (2H, d, J=8.1 Hz), 7.05-7.07 (6H, m), 7.19-7.43 (8H, m), 7.97 (1H, d, J=8.1 Hz).

MS: 584(M+H)$^+$.

Example 333

Synthesis of N'-(3-biphenylsulfonyl)-N-ethyl-2-(4-nitrobenzyl)-N-phenylmalonamide (1) 3-[(3-biphenylsulfonyl)amino]-2-(4-nitrobenzyl)-3-oxopropionic acid In the same manner as in Example 1 (2), the object compound was obtained using the compound (1.01 g) obtained in Example 178 (2) and biphenyl-3-sulfonamide (880 mg). This was subjected to hydrolysis in the same manner as in Example 1 (3) to give the title compound (1.17 g) as an oil.

(2) N'-(3-biphenylsulfonyl)-N-ethyl-2-(4-nitrobenzyl)-N-phenylmalonamide

In the same manner as in Example 1 (4), the title compound (382 mg) was obtained as a white powder using the above-mentioned compound (1.17 g) and N-ethylaniline (330 mg).

$^1$H-NMR (300 Mz, DMSO-$d_6$) δ0.87 (3H, t, J=6.9 Hz), 2.94-2.96 (1H, m), 3.02-3.05 (1H, m), 3.37-3.58 (3H, m), 6.94 (2H, d, J=7.2 Hz), 7.10 (2H, d, J=8.4 Hz), 7.27-7.30 (3H, m), 7.45-7.53 (3H, m), 7.68-7.79 (4H, m), 7.95-7.98 (2H, m), 8.04-8.05 (2H, m), 12.07 (1H, brs).

MS: 558(M+H)$^+$.

Example 334

Synthesis of 2-(4-aminobenzyl)-N'-(3-biphenylsulfonyl)-N-ethyl-N-phenylmalonamide In the same manner as in Example 7, the title compound (237 mg) was obtained as a white powder using the compound (280 mg) obtained in Example 333 at room temperature.

$^1$H-NMR (300 Mz, DMSO-$d_6$) δ0.87-0.88 (3H, brs), 2.67-2.68 (2H, m), 3.55-3.57 (3H, m), 6.29-6.41 (4H, m), 6.94-6.50 (2H, m), 7.29-7.30 (3H, m), 7.44-7.51 (3H, m), 7.71-7.79 (4H, m), 8.01-8.06 (2H, m).

MS: 528(M+H)$^+$.

Example 335

Synthesis of N-ethyl-2-(4-nitrobenzyl)-N-phenyl-N'-((E)-styrylsulfonyl)malonamide (1) ethyl 3-(N-ethyl-N-phenylamino)-2-(4-nitrobenzyl)-3-oxopropionate To a solution of the compound (3.00 g) obtained in Example 178 (2) in methylene chloride (10 mL) were added oxalyl chloride (1.43 mL) and DMF in catalytic amount under ice-cooling, and the mixture was stirred for 1 hr. After concentration under reduced pressure, the residue was dissolved in THF (10 mL), N-ethylaniline (1.55 mL) was added, and the mixture was stirred at room temperature for 1 hr. 1 mol/L Hydrochloric acid (100 mL) and ethyl acetate (100 mL) were added to extract the reaction mixture, and the organic layer was concentrated. The residue was purified by silica gel column chromatography to give the title compound (2.43 g) as an oil.

$^1$H-NMR (300 Mz, CDCl$_3$) δ1.01-1.06 (3H, m), 1.23-1.28 (3H, m), 3.18-3.20 (1H, m), 3.46-3.47 (1H, m), 3.60-3.63 (1H, m), 3.68-3.71 (2H, m), 4.12-4.16 (2H, m), 7.21-7.32 (7H, m), 8.10-8.13 (2H, m).

(2) 3-(N-ethyl-N-phenylamino)-2-(4-nitrobenzyl)-3-oxopropionic acid

In the same manner as in Example 1 (3), the title compound (1.35 g) was obtained as a white powder using the above-mentioned compound (2.43 g).

$^1$H-NMR (300 Mz, CDCl$_3$) δ1.04-1.09 (3H, m), 3.13-3.18 (1H, m), 3.26-3.29 (1H, m), 3.52-3.65 (2H, m), 3.75-3.77 (1H, m), 7.17-7.20 (3H, m), 7.34-7.36 (4H, m), 8.11-8.14 (2H, m).

(3) N-ethyl-2-(4-nitrobenzyl)-N-phenyl-N'-((E)-styrylsulfonyl)malonamide

To a solution of the above-mentioned compound (340 mg) in methylene chloride (10 mL) were added oxalyl chloride (500 μL) and DMF in catalytic amount under ice-cooling, and the mixture was stirred for 1 hr. After concentration under reduced pressure, the residue was dissolved in THF (10 mL) under ice-cooling, trans-β-styrenesulfonamide (180 mg) and 60% sodium hydride (80 mg) were added, and the mixture was stirred for 1 hr. 1 mol/L Hydrochloric acid (100 mL) and ethyl acetate (50 mL) were added to extract the reaction mixture, and the organic layer was concentrated. The residue was purified by silica gel column chromatography to give the title compound (270 mg) as a white powder.

$^1$H-NMR (300 Mz, DMSO-d$_6$) δ0.89 (3H, t, J=6.9 Hz), 2.97-3.01 (1H, m), 3.11-3.19 (1H, m), 3.48-3.60 (3H, m), 7.00-7.07 (2H, m), 7.21-7.28 (3H, m), 7.38-7.39 (3H, m), 7.45-7.47 (4H, m), 7.74-7.75 (2H, m), 8.02-8.04 (2H, m), 11.73 (1H, brs).

Example 336

Synthesis of 2-(4-aminobenzyl)-N-ethyl-N-phenyl-N'-((E)-styrylsulfonyl)malonamide In the same manner as in Example 137 (4), the title compound (93 mg) was obtained as a white powder using the compound (110 mg) obtained in Example 335 at room temperature.

$^1$H-NMR (300 Mz, DMSO-d$_6$) δ0.89 (3H, brs), 2.70-2.71 (1H, m), 2.86-2.87 (1H, m), 3.00-3.04 (1H, m), 3.54-3.55 (2H, m), 7.01-7.10 (4H, m), 7.12-7.13 (2H, m), 7.28 (1H, d, J=15.3 Hz), 7.37-7.38 (3H, m), 7.48-7.49 (3H, m), 7.56 (1H, d, J=15.3 Hz), 7.92-7.93 (2H, m).

MS: 478(M+H)$^+$.

Example 337

Synthesis of 2-[4-(benzoylamino)benzyl]-N-ethyl-N-phenyl-N'-((E)-styrylsulfonyl)malonamide In the same manner as in Example 9, the title compound (32 mg) was obtained as a white solid using the compound (33 mg) obtained in Example 336.

$^1$H-NMR (400 Mz, DMSO-d$_6$) δ0.93 (3H, t, J=7.2 Hz), 2.82-3.03 (2H, m), 3.43-3.57 (2H, m), 2.57-2.69 (1H, m), 6.88 (2H, d, J=8.0 Hz), 7.10 (2H, brs), 7.28 (1H, d, J=15.2 Hz), 7.36-7.63 (12H, m), 7.73-7.83 (2H, m), 7.93 (2H, d, J=7.2 Hz), 10.13 (1H, s), 11.76 (1H, brs).

MS: 582(M+H)$^+$.

Example 338

Synthesis of 2-(4-aminobenzyl)-N-ethyl-N'-phenethylsulfonyl-N-phenylmalonamide

In the same manner as in Example 7, the title compound (118 mg) was obtained as a white powder using the compound (130 mg) obtained in Example 335 at room temperature.

$^1$H-NMR (400 Mz, DMSO-d$_6$) δ0.89 (3H, brs), 2.84-3.00 (3H, m), 3.55-3.62 (6H, m), 6.89-7.03 (3H, m), 7.14-7.31 (4H, m), 7.38-7.44 (3H, m), 7.49-7.59 (3H, m), 7.78-7.79 (1H, m).

MS: 480(M+H)$^+$.

Example 339

Synthesis of N'-benzylsulfonyl-N-ethyl-2-(4-nitrobenzyl)-N-phenylmalonamide

In the same manner as in Example 1 (2), the title compound (112 mg) was obtained as a white powder using the compound (100 mg) obtained in Example 335 (2) and benzylsulfonamide (50 mg).

$^1$H-NMR (400 Mz, DMSO-d$_6$) δ0.95 (3H, brs), 2.90-2.95 (1H, m), 3.08-3.19 (1H, m), 3.44-3.64 (2H, m), 3.66-3.73 (1H, m), 4.63 (2H, s), 7.12-7.21 (2H, m), 7.30-7.32 (4H, m), 7.34-7.37 (3H, m), 7.47-7.50 (3H, m), 8.12-8.22 (2H, m), 11.57 (1H, brs).

MS: 496(M+H)$^+$.

Example 340

Synthesis of 2-(4-aminobenzyl)-N'-benzylsulfonyl-N-ethyl-N-phenylmalonamide

In the same manner as in Example 7, the title compound (310 mg) was obtained as a white powder using the compound (490 mg) obtained in Example 339 at room temperature.

$^1$H-NMR (400 Mz, DMSO-d$_6$) δ0.95 (3H, brs), 2.74-2.79 (2H, m), 3.38-3.43 (1H, m), 3.46-3.55 (1H, m), 3.66-3.75 (1H, m), 4.58 (2H, s), 6.38-6.52 (4H, m), 7.10-7.28 (4H, m), 7.30-7.37 (3H, m), 7.45-7.48 (3H, m).

MS: 466(M+H)$^+$.

Example 341

Synthesis of N-ethyl-2-(4-nitrobenzyl)-N-phenyl-N'-propylsulfonylmalonamide

In the same manner as in Example 1 (2), the title compound (379 mg) was obtained as a white powder using the compound (500 mg) obtained in Example 335 (2) and propylsulfonamide (180 mg).
$^1$H-NMR (400 Mz, DMSO-d$_6$) δ0.95 (6H, m), 1.46-1.61 (2H, m), 3.01-3.05 (1H, m), 3.13-3.19 (1H, m), 3.23-3.32 (2H, m), 3.49-3.56 (1H, m), 3.61-3.67 (2H, m), 7.17 (2H, d, J=6.4 Hz), 7.23 (2H, d, J=8.4 Hz), 7.48-7.51 (3H, m), 8.12 (2H, d, J=8.4 Hz), 11.59 (1H, brs).
MS: 448(M+H)$^+$.

Example 342

Synthesis of 2-(4-aminobenzyl)-N-ethyl-N-phenyl-N'-propylsulfonylmalonamide

In the same manner as in Example 7, the title compound (127 mg) was obtained as a white powder using the compound (200 mg) obtained in Example 341 at room temperature.
$^1$H-NMR (400 Mz, DMSO-d$_6$) δ0.95 (6H, m), 1.56-1.70 (2H, m), 2.76 (2H, d, J=6.8 Hz), 3.21-3.25 (2H, m), 3.37-3.66 (2H, m), 3.68-3.71 (1H, m), 6.36 (2H, d, J=8.0 Hz), 6.48 (2H, d, J=8.0 Hz), 7.17-7.28 (2H, m), 7.43-7.49 (3H, m).
MS: 418(M+H)$^+$.

Example 343

Synthesis of 2-(3-bromobenzyl)-N-ethyl-N'-(2-naphthylsulfonyl)-N-phenylmalonamide (1) diethyl(3-bromobenzyl)malonate In the same manner as in Example 6 (1), the title compound (12.5 g) was obtained as an oil using 3-bromobenzyl bromide (35.0 g).
$^1$H-NMR (300 Mz, CDCl$_3$) δ1.15-1.31 (6H, m), 3.16-3.19 (2H, m), 3.60-3.62 (1H, m), 4.09-4.22 (4H, m), 7.10-7.15 (2H, m), 7.30-7.34 (1H, m), 7.63-7.39 (1H, m).

(2) monoethyl(3-bromobenzyl)malonate

In the same manner as in Example 1 (1), the title compound (6.54 g) was obtained as an oil using the above-mentioned compound (7.00 g).

(3) 2-(3-bromobenzyl)-3-(N-ethyl-N-phenylamino)-3-oxopropionic acid

In the same manner as in Example 335 (1), the object compound was obtained using the above-mentioned compound (6.54 g). This was subjected to hydrolysis in the same manner as in Example 1 (3) to give the title compound (5.36 g) as a white powder.
$^1$H-NMR (300 Mz, CDCl$_3$) δ1.20-1.27 (3H, m), 2.99-3.03 (1H, m), 3.13-3.19 (1H, m), 3.45-3.49 (1H, m), 3.66-3.71 (2H, m), 6.99-7.00 (1H, m), 7.14-7.26 (3H, m), 7.33-7.47 (5H, m).

(4) 2-(3-bromobenzyl)-N-ethyl-N'-(2-naphthylsulfonyl)-N-phenylmalonamide

In the same manner as in Example 1 (2), the title compound (284 mg) was obtained as a white powder using the above-mentioned compound (300 mg).
$^1$H-NMR (300 Mz, DMSO-d$_6$) δ0.94-0.97 (3H, m), 2.92-2.95 (2H, m), 3.49-3.54 (2H, m), 3.62-3.70 (1H, m), 6.83-6.89 (2H, m), 6.97-7.04 (2H, m), 7.13-7.53 (5H, m), 7.60-7.80 (3H, m), 8.10-8.30 (3H, m), 12.12 (1H, brs).
MS: 567(M+H)$^+$.

Example 344

Synthesis of 2-(3-bromobenzyl)-N-ethyl-N-phenyl-N'-((E)-styrylsulfonyl)malonamide In the same manner as in Example 1 (2), the title compound (307 mg) was obtained as a white powder using the compound (540 mg) obtained in Example 343 (3) and trans-β-styrenesulfonamide (260 mg).
$^1$H-NMR (400 Mz, DMSO-d$_6$) δ1.17 (3H, t, J=7.2 Hz), 2.86-2.90 (1H, m), 2.97-3.03 (1H, m), 3.39-3.57 (3H, m), 6.95-6.97 (1H, m), 7.03 (2H, brs), 7.08-7.15 (2H, m), 7.22-7.35 (2H, m), 7.42-7.50 (3H, m), 7.50-7.59 (4H, m), 7.80-7.89 (2H, m), 11.78 (1H, brs).
MS: 545(M+H)$^+$.

Example 345

Synthesis of 2-(4-bromobenzyl)-N-ethyl-N-phenyl-N'-((E)-styrylsulfonyl)malonamide (1) monoethyl(4-bromobenzyl)malonate In the same manner as in Example 6 (1), the object compound was obtained using 4-bromobenzyl bromide (25.0 g). This was subjected to hydrolysis in the same manner as in Example 1 (1) to give the title compound (12.9 g) as an oil.
$^1$H-NMR (300 Mz, CDCl$_3$) δ1.21-1.28 (3H, m), 3.18-3.21 (2H, m), 3.80-3.83 (1H, m), 4.08-4.16 (2H, m), 7.07-7.10 (2H, m), 7.39-7.43 (2H, m).

(2) 2-(4-bromobenzyl)-3-(N-ethyl-N-phenylamino)-3-oxopropionic acid

In the same manner as in Example 1 (4), the object compound was obtained using the above-mentioned compound (5.00 g) and N-ethylaniline (2.40 g). This was subjected to hydrolysis in the same manner as in Example 1 (3) to give the title compound (5.28 g) as a white powder.

(3) 2-(4-bromobenzyl)-N-ethyl-N-phenyl-N'-((E)-styrylsulfonyl)malonamide

In the same manner as in Example 1 (2), the title compound (965 mg) was obtained as a white powder using the above-mentioned compound (2.00 g) and trans-β-styrenesulfonamide (970 mg).
$^1$H-NMR (400 Mz, DMSO-d$_6$) δ1.09 (3H, t, J=7.2 Hz), 2.83-2.88 (1H, m), 2.95-3.00 (1H, m), 3.44-3.59 (2H, m), 3.61-3.66 (1H, m), 6.90 (2H, d, J=8.4 Hz), 7.08 (2H, brs), 7.27-7.50 (6H, m), 7.50-7.80 (4H, m), 8.31-8.32 (2H, m), 11.77 (1H, brs).
MS: 543(M+H)$^+$.

Example 346

Synthesis of 2-(4-bromobenzyl)-N-ethyl-N'-(2-naphthylsulfonyl)-N-phenylmalonamide In the same manner as in Example 1 (2), the title compound (825 mg) was obtained as a white powder using the compound (2.00 g) obtained in Example 345 (2).

¹H-NMR (300 Mz, DMSO-d₆) δ0.85 (3H, t, J=7.2 Hz), 2.76-2.84 (2H, m), 3.40-3.52 (3H, m), 6.74 (2H, d, J=8.1 Hz), 6.92 (2H, d, J=7.5 Hz), 7.19-7.30 (5H, m), 7.71-7.78 (3H, m), 8.07-8.23 (3H, m), 8.53 (1H, s), 12.06 (1H, brs).

MS: 567(M+H)⁺.

Example 347

Synthesis of 2-(2-bromobenzyl)-N-ethyl-N-phenyl-N'-((E)-styrylsulfonyl)malonamide (1) monoethyl(2-bromobenzyl)malonate In the same manner as in Example 6 (1), the object compound was obtained using 2-bromobenzyl bromide (25.0 g). This was subjected to hydrolysis in the same manner as in Example 1 (1) to give the title compound (25.9 g) as an oil.

¹H-NMR (300 Mz, CDCl₃) δ1.18-1.26 (3H, m), 3.35-3.39 (2H, m), 3.88-3.93 (1H, m), 4.11-4.20 (2H, m), 7.08-7.14 (1H, m), 7.20-7.24 (2H, m), 7.53-7.56 (1H, m).

(2) 2-(2-bromobenzyl)-3-(N-ethyl-N-phenylamino)-3-oxopropionic acid

In the same manner as in Example 1 (4), the object compound was obtained using the above-mentioned compound (5.00 g) and N-ethylaniline (2.40 g). This was subjected to hydrolysis in the same manner as in Example 1 (3) to give the title compound (4.22 g) as a white powder.

¹H-NMR (300 Mz, CDCl₃) δ1.00-1.06 (3H, m), 3.22-3.28 (2H, m), 3.61-3.62 (1H, m), 3.71-3.74 (2H, m), 7.14-7.24 (3H, m), 7.32-7.48 (1H, m).

(3) 2-(2-bromobenzyl)-N-ethyl-N-phenyl-N'-((E)-styrylsulfonyl)malonamide

In the same manner as in Example 1 (2), the title compound (1.02 g) was obtained as a white powder using the above-mentioned compound (2.17 g) and trans-β-styrenesulfonamide (1.05 g).

¹H-NMR (400 Mz, DMSO-d₆) δ0.93 (3H, t, J=6.8 Hz), 2.98-3.01 (2H, m), 3.56-3.81 (3H, m), 7.09-7.12 (4H, m), 7.19-7.37 (2H, m), 7.47-7.48 (3H, m), 7.50-7.55 (5H, m), 7.78-7.78 (2H, m), 11.63 (1H, brs).

MS: 543(M+H)⁺.

Example 348

Synthesis of 2-(2-bromobenzyl)-N-ethyl-N'-(2-naphthylsulfonyl)-N-phenylmalonamide In the same manner as in Example 1 (2), the title compound (1.18 g) was obtained as a white powder using the compound (2.04 g) obtained in Example 347 (2).

¹H-NMR (400 Mz, DMSO-d₆) δ0.90 (3H, brs), 2.91-2.92 (1H, m), 3.05-3.06 (1H, m), 3.62-3.79 (3H, m), 6.82-7.05 (5H, m), 7.19-7.28 (3H, m), 7.33-7.44 (1H, m), 7.74-7.78 (3H, m), 8.10-8.13 (3H, m), 8.52 (1H, s), 11.97 (1H, brs).

MS: 567(M+H)⁺.

Example 349

Synthesis of N-ethyl-2-[2-(1-naphthyl)ethyl]-N-phenyl-N'-((E)-styrylsulfonyl)malonamide (1) 2,2-dimethyl-5-[2-(1-naphthyl)ethyl]-1,3-dioxane-4,6-dione In the same manner as in Example 132 (1), the title compound (3.02 g) was obtained as a pale-yellow powder using 1-naphthaleneacetic acid (3.72 g).

¹H-NMR (400 Mz, CDCl₃) δ1.76 (3H, s), 1.79 (3H, s), 2.51-2.56 (2H, m), 3.27-3.31 (2H, m), 3.57-3.60 (1H, m), 7.37-7.58 (4H, m), 7.34-7.76 (1H, m), 7.85-7.87 (1H, m), 8.19-8.21 (1H, m).

(2) 3-(N-ethyl-N-phenylamino)-2-[2-(1-naphthyl)ethyl]-3-oxopropionic acid

In the same manner as in Example 119 (2), the title compound (2.50 g) was obtained as an oil using the above-mentioned compound (2.05 g) and N-ethylaniline (3.50 g).

¹H-NMR (400 Mz, CDCl₃) δ1.11-1.23 (3H, m), 1.23-1.25 (1H, m), 2.89-2.93 (1H, m), 3.09-3.16 (1H, m), 3.29-3.31 (1H, m), 3.45-3.49 (1H, m), 3.63-3.70 (1H, m), 3.82-3.87 (1H, m), 6.96-6.97 (2H, m), 7.29-7.32 (5H, m), 7.48-7.51 (2H, m), 7.66-7.69 (1H, m), 7.82-7.84 (2H, m).

(3) N-ethyl-2-[2-(1-naphthyl)ethyl]-N-phenyl-N'-((E)-styrylsulfonyl)malonamide

In the same manner as in Example 1 (2), the title compound (44 mg) was obtained as a white powder using the above-mentioned compound (1.00 g) and trans-β-styrenesulfonamide (530 mg).

¹H-NMR (400 Mz, CDCl₃) δ1.07 (3H, brs), 2.14-2.23 (2H, m), 2.60-2.71 (2H, m), 3.18-3.22 (1H, m), 3.64-3.77 (1H, m), 3.79-3.82 (1H, m), 6.91 (2H, m), 7.04-7.16 (4H, m), 7.39-7.52 (6H, m), 7.53-7.54 (2H, m), 7.65-7.68 (3H, m), 7.73-7.78 (2H, m), 10.49 (1H, brs).

MS: 527(M+H)⁺.

Example 350

Synthesis of N-ethyl-2-[2-(1-naphthyl)ethyl]-N-phenyl-N'-(2-naphthylsulfonyl)malonamide In the same manner as in Example 1 (2), the title compound (251 mg) was obtained as a white powder using the compound (1.00 g) obtained in Example 349 (2).

¹H-NMR (400 Mz, CDCl₃) δ1.10 (3H, brs), 2.08-2.19 (2H, m), 2.68-2.81 (1H, m), 2.85-2.88 (1H, m), 3.12-3.16 (1H, m), 3.59-3.68 (1H, m), 3.76-3.84 (1H, m), 6.81-6.83 (2H, m), 6.99-7.02 (1H, m), 7.15-7.26 (4H, m), 7.36-7.59 (2H, m), 7.60-7.70 (4H, m), 7.75-7.95 (3H, m), 8.05-8.15 (2H, m), 8.79 (1H, s), 10.80 (1H, brs).

MS: 551(M+H)⁺.

Example 351

Synthesis of N-ethyl-2-[2-(2-naphthyl)ethyl]-N-phenyl-N'-((E)-styrylsulfonyl)malonamide (1) 2,2-dimethyl-5-[2-(2-naphthyl)ethyl]-1,3-dioxane-4,6-dione In the same manner as in Example 132 (1), the title compound (6.55 g) was obtained as a pale-yellow powder using 2-naphthaleneacetic acid (3.72 g).

$^1$H-NMR (400 Mz, CDCl$_3$) δ1.72 (3H, s), 1.76 (3H, s), 2.49-2.54 (2H, m), 3.01-3.05 (2H, m), 3.50-3.53 (1H, m), 7.38-7.48 (3H, m), 7.67 (1H, s), 7.78-7.83 (3H, m).

(2) 3-(N-ethyl-N-phenylamino)-2-[2-(2-naphthyl)ethyl]-3-oxopropionic acid

In the same manner as in Example 119 (2), the title compound (2.19 g) was obtained as an oil using the above-mentioned compound (2.09 g) and N-ethylaniline (3.50 g).

$^1$H-NMR (400 Mz, CDCl$_3$) δ1.12-1.20 (3H, m), 2.17-2.22 (1H, m), 2.23-2.28 (1H, m), 2.63-2.71 (1H, m), 2.74-2.80 (1H, m), 3.27-3.30 (1H, m), 3.61-3.70 (1H, m), 3.81-3.90 (1H, m), 6.98-7.00 (2H, m), 7.05-7.09 (1H, m), 7.15-7.20 (3H, m), 7.41-7.48 (3H, m), 7.67-7.72 (2H, m), 7.78-7.80 (1H, m).

(3) N-ethyl-2-[2-(2-naphthyl)ethyl]-N-phenyl-N'-((E)-styrylsulfonyl)malonamide

In the same manner as in Example 1 (2), the title compound (185 mg) was obtained as a white powder using the above-mentioned compound (1.00 g) and trans-β-styrenesulfonamide (910 mg).

$^1$H-NMR (400 Mz, CDCl$_3$) δ1.12 (3H, brs), 2.14-2.23 (2H, m), 2.60-2.71 (2H, m), 3.18-3.22 (1H, m), 3.64-3.77 (1H, m), 3.78-3.82 (1H, m), 6.90-6.92 (2H, m), 7.04-7.16 (5H, m), 7.26-7.52 (6H, m), 7.53-7.54 (2H, m), 7.65-7.68 (2H, m), 7.73-7.78 (2H, m), 10.49 (1H, brs).

MS:527(M+H)$^+$.

Example 352

Synthesis of N-ethyl-2-[2-(2-naphthyl)ethyl]-N'-(2-naphthylsulfonyl)-N-phenylmalonamide In the same manner as in Example 1 (2), the title compound (284 mg) was obtained as a white powder using the compound (1.00 g) obtained in Example 351 (2).

$^1$H-NMR (400 Mz, CDCl$_3$) δ1.10 (3H, brs), 2.03-2.10 (2H, m), 2.42-2.52 (2H, m), 3.06-3.09 (1H, m), 3.58-3.65 (1H, m), 3.74-3.81 (1H, m), 6.75-6.77 (2H, m), 7.00-7.02 (4H, m), 7.30-7.35 (1H, m), 7.41-7.44 (2H, m), 7.59-7.76 (4H, m), 7.89-7.91 (1H, m), 7.95-7.97 (1H, m), 8.01-8.03 (1H, m), 8.04-8.05 (2H, s), 8.70 (1H, s), 10.62 (1H, brs).

MS: 551(M+H)$^+$.

Example 353

Synthesis of N-ethyl-2-[2-(4-methoxyphenyl)ethyl]-N-phenyl-N'-((E)-styrylsulfonyl)malonamide (1) 5-[2-(4-methoxyphenyl)ethyl]-2,2-dimethyl-1,3-dioxane-4,6-dione In the same manner as in Example 132 (1), the title compound (4.59 g) was obtained as a pale-yellow powder using 4-methoxyphenylacetic acid (3.32 g).

$^1$H-NMR (400 Mz, CDCl$_3$) δ1.73 (3H, s), 1.79 (3H, s), 2.34-2.41 (2H, m), 2.77-2.83 (2H, m), 3.44-3.47 (1H, m), 3.79 (3H, s), 6.83-6.86 (2H, m), 7.16-7.25 (2H, m).

(2) 3-(N-ethyl-N-phenylamino)-2-[2-(4-methoxyphenyl)ethyl]-3-oxopropionic acid

In the same manner as in Example 119 (2), the title compound (2.10 g) was obtained as an oil using the above-mentioned compound (2.00 g) and N-ethylaniline (3.50 g).

$^1$H-NMR (400 Mz, CDCl$_3$) δ1.10-1.15 (3H, m), 1.92-2.05 (2H, m), 2.31-2.45 (1H, m), 2.49-2.55 (1H, m), 3.23-3.27 (1H, m), 3.64-3.72 (1H, m), 3.79 (3H, s), 3.82-3.88 (1H, m), 6.72-6.76 (2H, m), 6.90-7.02 (2H, m), 7.11-7.15 (2H, m), 7.37-7.43 (3H, m).

(3) N-ethyl-2-[2-(4-methoxyphenyl)ethyl]-N-phenyl-N'-((E)-styrylsulfonyl)malonamide In the same manner as in Example 1 (2), the title compound (303 mg) was obtained as a white powder using the above-mentioned compound (1.00 g) and trans-β-styrenesulfonamide (940 mg).

$^1$H-NMR (400 Mz, CDCl$_3$) δ1.15 (3H, brs), 2.06-2.08 (2H, m), 2.09-2.49 (2H, m), 3.17 (1H, t, J=7.2 Hz), 3.67-3.84 (5H, m), 6.69-6.73 (2H, m), 6.90-6.93 (2H, m), 7.00-7.08 (3H, m), 7.33-7.34 (3H, m), 7.39-7.44 (3H, m), 7.51-7.53 (2H, m), 7.71-7.75 (1H, m), 10.44 (1H, brs).

MS: 507(M+H)$^+$.

Example 354

Synthesis of N-ethyl-2-[2-(4-methoxyphenyl)ethyl]-N'-(2-naphthylsulfonyl)-N-phenylmalonamide In the same manner as in Example 1 (2), the title compound (527 mg) was obtained as a white powder using the compound (1.00 g) obtained in Example 353 (2).

$^1$H-NMR (400 Mz, CDCl$_3$) δ1.09 (3H, brs), 1.95-1.97 (2H, m), 2.20-2.30 (2H, m), 3.04 (1H, t, J=7.6 Hz), 3.59-3.67 (1H, m), 3.75-3.83 (4H, m), 6.64-6.67 (2H, m), 6.77-6.79 (2H, m), 6.84-6.86 (2H, m), 7.22-7.30 (3H, m), 7.60-7.90 (2H, m), 7.92-8.68 (4H, m), 8.68 (1H, s), 10.56 (1H, brs).

MS: 531(M+H)$^+$.

Example 355

Synthesis of 2-[2-(3-bromophenyl)ethyl]-N-ethyl-N-phenyl-N'-((E)-styrylsulfonyl)malonamide (1) 5-[2-(3-bromophenyl)ethyl]-2,2-dimethyl-1,3-dioxane-4,6-dione In the same manner as in Example 132 (1), the title compound (4.74 g) was obtained as a pale-yellow powder using 3-bromophenylacetic acid (4.30 g).

¹H-NMR (400 Mz, CDCl₃) δ1.77 (6H, s), 2.37-2.42 (2H, m), 2.79-2.83 (2H, m), 3.45-3.51 (1H, m), 7.17-7.20 (2H, m), 7.34-7.39 (2H, m).

(2) 2-[2-(3-bromophenyl)ethyl]-3-(N-ethyl-N-phenylamino)-3-oxopropionic acid

In the same manner as in Example 119 (2), the title compound (2.31 g) was obtained as an oil using the above-mentioned compound (2.30 g) and N-ethylaniline (3.50 g).
¹H-NMR (400 Mz, CDCl₃) δ1.09-1.17 (3H, m), 1.91-2.09 (1H, m), 2.10-2.18 (1H, m), 2.43-2.50 (1H, m), 2.55-2.61 (1H, m), 3.20-3.23 (1H, m), 3.64-3.71 (1H, m), 6.98-7.00 (1H, m), 7.04-7.68 (3H, m), 7.08 (1H, s), 7.27-7.29 (2H, m), 7.38-7.41 (3H, m).

(3) 2-[2-(3-bromophenyl)ethyl]-N-ethyl-N-phenyl-N'-((E)-styrylsulfonyl)malonamide In the same manner as in Example 1 (2), the title compound (11 mg) was obtained as a white powder using the above-mentioned compound (1.00 g) and trans-β-styrenesulfonamide (810 mg).
¹H-NMR (400 Mz, CDCl₃) δ1.10 (3H, brs), 2.02-2.12 (2H, m), 2.40-2.50 (2H, m), 3.11-3.15 (1H, m), 3.65-3.78 (1H, m), 3.79-3.85 (1H, m), 6.93-6.99 (5H, m), 7.01-7.05 (1H, m), 7.16-7.36 (4H, m), 7.40-7.45 (3H, m), 7.52-7.54 (2H, m), 7.73 (1H, d, J=15.6 Hz), 10.47 (1H, brs).
MS: 555(M+H)⁺.

Example 356

Synthesis of 2-[2-(3-bromophenyl)ethyl]-N-ethyl-N'-(2-naphthylsulfonyl)-N-phenylmalonamide In the same manner as in Example 1 (2), the title compound (56 mg) was obtained as a white powder using the compound (1.00 g) obtained in Example 355 (2).
¹H-NMR (400 Mz, CDCl₃) δ1.09 (3H, brs), 1.90-2.02 (2H, m), 2.19-2.34 (2H, m), 2.98-3.02 (1H, m), 3.57-3.66 (1H, m), 3.77-3.86 (1H, m), 6.78-6.85 (3H, m), 6.95-6.99 (2H, m), 7.03-7.30 (4H, m), 7.60-7.69 (2H, m), 7.90-8.04 (4H, m), 8.68 (1H, m), 10.59 (1H, brs).
MS: 579(M+H)⁺.

Example 357

Synthesis of 2-[2-(4-bromophenyl)ethyl]-N-ethyl-N-phenyl-N'-((E)-styrylsulfonyl)malonamide (1) 5-[2-(4-bromophenyl)ethyl]-2,2-dimethyl-1,3-dioxane-4,6-dione In the same manner as in Example 132 (1), the title compound (3.72 g) was obtained as a pale-yellow powder using 4-bromophenylacetic acid (4.30 g).
¹H-NMR (400 Mz, CDCl₃) δ1.76 (3H, s), 1.77 (3H, s), 2.36-2.41 (2H, m), 2.78-2.82 (2H, m), 3.45-3.51 (1H, m), 7.10-7.14 (2H, m), 7.41-7.44 (2H, m).

(2) 2-[2-(4-bromophenyl)ethyl]-3-(N-ethyl-N-phenylamino)-3-oxopropionic acid

In the same manner as in Example 119 (2), the title compound (2.57 g) was obtained as an oil using the above-mentioned compound (2.30 g) and N-ethylaniline (3.50 g).
¹H-NMR (400 Mz, CDCl₃) δ1.09-1.15 (3H, m), 1.92-1.99 (1H, m), 2.08-2.18 (1H, m), 2.42-2.49 (1H, m), 2.54-2.61 (1H, m), 3.18-3.21 (1H, m), 3.62-3.69 (1H, m), 3.83-3.92 (1H, m), 6.89-6.91 (2H, m), 7.01-7.03 (2H, m), 7.27-7.41 (5H, m).

(3) 2-[2-(4-bromophenyl)ethyl]-N-ethyl-N-phenyl-N'-((E)-styrylsulfonyl)malonamide In the same manner as in Example 1 (2), the title compound (57 mg) was obtained as a white powder using the above-mentioned compound (1.00 g) and trans-β-styrenesulfonamide (810 mg).
¹H-NMR (400 Mz, CDCl₃) δ1.10 (3H, brs), 1.90-2.07 (1H, m), 2.09-2.19 (1H, m), 2.36-2.44 (1H, m), 2.48-2.62 (1H, m), 3.11-3.14 (1H, m), 3.64-3.71 (1H, m), 3.76-3.83 (1H, m), 6.87 (2H, d, J=8.0 Hz), 6.94-6.96 (2H, m), 7.06 (1H, d, J=15.6 Hz), 7.29-7.39 (5H, m), 7.40-7.45 (3H, m), 7.52-7.54 (2H, m), 7.73 (1H, d, J=15.6 Hz), 10.51 (1H, brs).
MS: 555(M+H)⁺.

Example 358

Synthesis of 2-[2-(4-bromophenyl)ethyl]-N-ethyl-N'-(2-naphthylsulfonyl)-N-phenylmalonamide In the same manner as in Example 1 (2), the title compound (52 mg) was obtained as a white powder using the compound (1.00 g) obtained in Example 357 (2).
¹H-NMR (400 Mz, CDCl₃) δ1.07 (3H, brs), 1.90-2.01 (2H, m), 2.20-2.32 (2H, m), 2.98-3.02 (1H, m), 3.58-3.63 (1H, m), 3.77-3.82 (1H, m), 6.73 (2H, d, J=8.4 Hz), 6.81 (2H, d, J=7.6 Hz), 7.19-7.26 (4H, m), 7.29-7.32 (1H, m), 7.61-7.69 (2H, m), 7.90-8.04 (4H, m), 8.68 (1H, s), 10.63 (1H, brs).
MS: 579(M+H)⁺.

Example 359

Synthesis of 2-(3-biphenylmethyl)-N-ethyl-N-phenyl-N'-((E)-styrylsulfonyl)malonamide To a mixed solution of the compound (131 mg) obtained in Example 344 in toluene (10 mL)/ethanol (5 mL) were added phenylboronic acid (29 mg), tetrakis(triphenylphosphine)palladium (12 mg) and sodium carbonate (133 mg), and the mixture was heated under reflux for 8 hr. 1 mol/L Hydrochloric acid (10 mL) and ethyl acetate (30 mL) were added to extract the reaction mixture, and the organic layer was concentrated under reduced pressure. The residue was purified by silica gel column chromatography to give the title compound (20 mg) as a white powder.
¹H-NMR (300 Mz, CDCl₃) δ0.94-1.04 (3H, m), 2.98-3.09 (1H, m), 3.17-3.78 (1H, m), 3.31-3.34 (1H, m), 3.61-3.67 (2H, m), 6.83-7.02 (5H, m), 7.21-7.25 (7H, m), 7.44-7.53 (8H, m), 7.69-7.75 (2H, m), 10.40 (1H, brs).
MS: 539(M+H)⁺.

Example 360

Synthesis of 2-(3-biphenylmethyl)-N-ethyl-N'-(2-naphthylsulfonyl)-N-phenylmalonamide In the same manner as in Example 359, the title compound (21 mg) was obtained as a white powder using the compound (239 mg) obtained in Example 343.
¹H-NMR (400 Mz, CDCl₃) δ0.90-1.03 (3H, m), 2.85-3.30 (3H, m), 3.56-3.64 (2H, m), 6.81-6.99 (2H, m), 7.01-7.03

(2H, m), 7.12-7.13 (1H, m), 7.15-7.37 (4H, m), 7.40-7.49 (4H, m), 7.61-7.69 (2H, m), 7.90-8.03 (4H, m), 8.70 (1H, s), 10.60 (1H, brs).
MS: 563(M+H)$^+$.

Example 361

Synthesis of N-ethyl-2-[(4'-methoxy-4-biphenyl)methyl]-N-phenyl-N'-((E)-styrylsulfonyl)malonamide In the same manner as in Example 359, the title compound (60 mg) was obtained as a white powder using the compound (228 mg) obtained in Example 345 and (4-methoxyphenyl)boronic acid (456 mg).
$^1$H-NMR (300 Mz, CDCl$_3$) δ0.92 (3H, t, J=6.9 Hz), 2.94-3.01 (2H, m), 3.32-3.46 (2H, m), 3.61-3.76 (1H, m), 3.83 (3H, s), 6.90-6.98 (4H, m), 7.10-7.20 (2H, m), 7.30-7.56 (12H, m), 7.74-7.77 (2H, m), 11.76 (1H, brs).
MS: 569(M+H)$^+$.

Example 362

Synthesis of N-ethyl-2-[(4'-methoxy-4-biphenyl)methyl]-N'-(2-naphthylsulfonyl)-N-phenylmalonamide In the same manner as in Example 359, the title compound (167 mg) was obtained as a white powder using the compound (239 mg) obtained in Example 346 and (4-methoxyphenyl)boronic acid (456 mg).
$^1$H-NMR (300 Mz, DMSO-d$_6$) δ0.88 (3H, t, J=6.9 Hz), 2.85 (2H, d, J=6.9 Hz), 3.43-3.50 (2H, m), 3.55-3.57 (1H, m), 3.77 (3H, s), 6.75 (2H, d, J=8.1 Hz), 6.95-7.01 (4H, m), 7.19-7.22 (2H, m), 7.31-7.44 (5H, m), 7.68-7.78 (3H, m), 8.03-8.04 (1H, m), 8.12-8.19 (2H, m), 8.53 (1H, m), 12.07 (1H, brs).
MS: 593(M+H)$^+$.

Example 363

Synthesis of N-ethyl-2-[(4'-methoxy-4-biphenyl)methyl]-N'-phenethylsulfonyl-N-phenylmalonamide In the same manner as in Example 7, the title compound (43 mg) was obtained as a white powder using the compound (115 mg) obtained in Example 361 at room temperature.
$^1$H-NMR (300 Mz, DMSO-d$_6$) δ0.92 (3H, t, J=6.9 Hz), 2.94-2.95 (2H, m), 3.39-3.44 (5H, m), 3.47-3.60 (2H, m), 3.77 (3H, s), 6.89-6.98 (3H, m), 7.11-7.51 (13H, m), 7.75 (2H, d, J=6.9 Hz), 11.77 (1H, brs).
MS: 571(M+H)$^+$.

Example 364

Synthesis of 2-(2-biphenylmethyl)-N-ethyl-N-phenyl-N'-((E)-styrylsulfonyl)malonamide In the same manner as in Example 359, the title compound (263 mg) was obtained as a white powder using the compound (228 mg) obtained in Example 347.
$^1$H-NMR (300 Mz, DMSO-d$_6$) δ0.86 (3H, t, J=7.2 Hz), 2.70-2.90 (1H, m), 2.92-3.12 (1H, m), 3.15-3.34 (1H, m), 3.47-3.46 (2H, m), 6.71-6.74 (2H, m), 6.97-7.16 (2H, m), 7.18-7.19 (1H, m), 7.21-7.23 (3H, m), 7.32-7.46 (4H, m), 7.47-7.75 (6H, m), 8.28-8.29 (2H, m), 9.30 (1H, s), 11.67 (1H, brs).
MS: 539(M+H)$^+$.

Example 365

Synthesis of 2-(2-biphenylmethyl)-N-ethyl-N'-(2-naphthylsulfonyl)-N-phenylmalonamide In the same manner as in Example 359, the title compound (264 mg) was obtained as a white powder using the compound (239 mg) obtained in Example 348.
$^1$H-NMR (300 Mz, DMSO-d$_6$) δ0.84 (3H, t, J=6.9 Hz), 2.61-2.78 (1H, m), 2.80-3.01 (1H, m), 3.44-3.50 (3H, m), 6.74 (2H, d, J=8.1 Hz), 6.85-6.86 (2H, m), 7.07-7.18 (5H, m), 7.31-7.35 (1H, m), 7.56-7.63 (4H, m), 7.67-7.72 (3H, m), 8.12-8.20 (2H, m), 8.49 (1H, s), 9.31 (1H, s), 11.86 (1H, brs).
MS: 563(M+H)$^+$.

Example 366

Synthesis of 2-[(2-biphenyl)methyl]-N-ethyl-N'-phenethylsulfonyl-N-phenylmalonamide In the same manner as in Example 7, the title compound (44 mg) was obtained as a white powder using the compound (63 mg) obtained in Example 364.
$^1$H-NMR (300 Mz, CDCl$_3$) δ0.99-1.04 (3H, m), 1.45-1.58 (2H, m), 3.01-3.23 (4H, m), 3.51-3.57 (2H, m), 3.69-3.74 (1H, m), 6.70-6.76 (2H, m), 6.80-7.00 (1H, m), 7.13-7.49 (15H, m), 7.60-7.62 (1H, m), 9.89-9.93 (1H, m).
MS: 541(M+H)$^+$.

Example 367

Synthesis of 2-[2-(3-biphenyl)ethyl]-N-ethyl-N-phenyl-N'-((E)-styrylsulfonyl)malonamide In the same manner as in Example 359, the title compound (29 mg) was obtained as a white powder using the compound (279 mg) obtained in Example 355.
$^1$H-NMR (400 Mz, CDCl$_3$) δ1.09-1.12 (3H, m), 2.12-2.78 (2H, m), 2.49-2.62 (2H, m), 3.21 (1H, t, J=7.2 Hz), 3.66-3.77 (1H, m), 3.79-3.84 (1H, m), 6.98-7.01 (3H, m), 7.07 (1H, d, J=15.6 Hz), 7.23-7.28 (5H, m), 7.32-7.43 (7H, m), 7.44-7.53 (4H, m), 7.73 (1H, d, J=15.6 Hz), 10.44 (1H, brs).
MS: 553(M+H)$^+$.

Example 368

Synthesis of 2-[2-(4-biphenyl)ethyl]-N-ethyl-N-phenyl-N'-((E)-styrylsulfonyl)malonamide In the same manner as in Example 359, the title compound (18 mg) was obtained as a white powder using the compound (279 mg) obtained in Example 357.
$^1$H-NMR (400 Mz, CDCl$_3$) δ1.09-1.11 (3H, m), 2.09-2.17 (2H, m), 2.46-2.62 (2H, m), 3.21 (1H, t, J=6.0 Hz), 3.68-3.84 (2H, m), 6.98-6.99 (2H, m), 7.01-7.09 (3H, m), 7.29-7.36 (4H, m), 7.39-7.46 (7H, m), 7.52-7.56 (4H, m), 7.74 (1H, d, J=15.6 Hz), 10.48 (1H, brs).
MS: 553(M+H)$^+$.

Example 369

Synthesis of 2-[2-(4-biphenyl)ethyl]-N-ethyl-N'-(2-naphthylsulfonyl)-N-phenylmalonamide In the same manner as in Example 359, the title compound (50 mg) was obtained as a white powder using the compound (300 mg) obtained in Example 358.

¹H-NMR (400 Mz, CDCl₃) δ1.10-1.12 (3H, m), 2.00-2.10 (2H, m), 2.30-2.41 (2H, m), 3.06-3.09 (1H, m), 3.51-3.68 (1H, m), 3.76-3.85 (1H, m), 6.84-6.85 (2H, m), 6.93-6.95 (2H, m), 7.18-7.22 (3H, m), 7.31-7.36 (3H, m), 7.41-7.45 (2H, m), 7.52-7.62 (2H, m), 7.64-7.65 (2H, m), 7.68-7.66 (1H, m), 7.89-7.82 (1H, m), 7.96-8.06 (2H, m), 8.72 (1H, s), 10.6 (1H, brs).
MS: 577(M+H)⁺.

Example 370

Synthesis of 2-[2-(3-biphenyl)ethyl]-N-ethyl-N'-(2-naphthylsulfonyl)-N-phenylmalonamide In the same manner as in Example 359, the title compound (55 mg) was obtained as a white powder using the compound (300 mg) obtained in Example 356.
¹H-NMR (400 Mz, CDCl₃) δ1.02-1.09 (3H, m), 2.03-2.07 (2H, m), 2.30-2.42 (2H, m), 3.08 (1H, t, J=7.2 Hz), 3.58-3.67 (1H, m), 3.76-3.85 (1H, m), 6.83-6.87 (3H, m), 7.12 (1H, s), 7.16-7.24 (4H, m), 7.32-7.36 (2H, m), 7.41-7.48 (2H, m), 7.49-7.50 (2H, m), 7.58-7.87 (2H, m), 7.89-7.94 (1H, m), 7.96-7.99 (1H, m), 8.02-8.05 (2H, m), 8.69 (1H, s), 10.56 (1H, brs).
MS: 577(M+H)⁺.

Example 371

Synthesis of 2-[(1-benzyl-1H-pyrazol-4-yl)methyl]-N-ethyl-N-phenyl-N'-((E)-styrylsulfonyl)malonamide (1) ethyl 1-(tert-butoxycarbonyl)pyrazole-4-carboxylate To a solution of ethyl pyrazolecarboxylate (20.5 g) in ethanol (150 mL) were added a solution of di-tert-butyl dicarbonate (32.0 g) in ethanol (150 mL) and triethylamine (22 mL) at room temperature, and the mixture was stirred for 3 hr.
After concentration under reduced pressure, 10% aqueous citric acid solution (500 mL) was added to the residue, and the mixture was extracted with ethyl acetate (200 mL×2) and washed with saturated brine. The organic layer was concentrated under reduced pressure to give the title compound (34.7 g) as an oil.
¹H-NMR (400 Mz, CDCl₃) δ1.37 (3H, t, J=7.2 Hz), 1.67 (9H, s), 4.33 (2H, q, J=7.2 Hz), 8.06 (1H, s), 8.56 (1H, s).

(2) [1-(tert-butoxycarbonyl)-1H-pyrazol-4-yl]methanol

To a solution of the above-mentioned compound (34.7 g) in ether (400 mL) was added dropwise 1 mol/L diisobutylaluminum hydride-hexane solution (300 mL) at −78° C. for 1 hr, and the mixture was allowed to warm to room temperature and stirred for 3 days. The reaction mixture was washed with saturated aqueous (+)-potassium sodium tartrate solution (500 mL), and the organic layer was concentrated under reduced pressure. The residue was purified by silica gel column chromatography to give the title compound (4.15 g) as an oil.
¹H-NMR (400 Mz, DMSO-d₆) δ1.57 (9H, s), 4.38 (2H, d, J=5.6 Hz), 5.07 (1H, t, J=5.6 Hz), 7.73 (1H, s), 8.09 (1H, s).

(3) triethyl 2-[1-(tert-butoxycarbonyl)-1H-pyrazol-4-yl]ethane-1,1,1-tricarboxylate To a solution of the above-mentioned compound (4.12 g) in methylene chloride (100 mL) were added mesyl chloride (1.69 mL) and triethylamine (3.19 mL) under ice-cooling, and the mixture was stirred at room temperature for 3 hr. After the reaction mixture was concentrated under reduced pressure, the residue was dissolved in DMF (50 mL). Triethyl methanetricarboxylate (4.83 g), potassium carbonate (4.31 g) and potassium iodide in catalytic amount were added at room temperature, and the mixture was stirred for 16 hr. Water (300 mL) and hexane/ethyl acetate (1/1) (200 mL×2) were added to extract the reaction mixture, and the organic layer was washed with saturated brine. The organic layer was concentrated under reduced pressure, and the residue was purified by silica gel column chromatography to give the title compound (3.87 g) as an oil.
¹H-NMR (400 Mz, DMSO-d₆) δ1.17 (9H, t, J=7.2 Hz), 1.56 (9H, s), 3.24 (2H, s), 4.18 (6H, q, J=7.2 Hz), 7.61 (1H, s), 7.99 (1H, s).

(4) triethyl 2-(4-pyrazolyl)ethane-1,1,1-tricarboxylate

To a solution of the above-mentioned compound (2.72 g) in methylene chloride (50 mL) was added trifluoroacetic acid (20 ml) at room temperature, and the mixture was stirred for 17 hr. The reaction mixture was concentrated under reduced pressure, saturated aqueous sodium hydrogen carbonate solution (100 mL) was added to the residue, and the mixture was extracted with chloroform (100 mL×2). The organic layer was concentrated under reduced pressure to give the title compound (2.06 g) as an oil.
¹H-NMR (400 Mz, DMSO-d₆) δ1.16 (9H, t, J=7.2 Hz), 3.20 (2H, s), 4.14 (6H, q, J=7.2 Hz), 7.37 (2H, brs), 12.58 (1H, brs).

(5) triethyl 2-(1-benzyl-1H-pyrazol-4-yl)ethane-1,1,1-tricarboxylate

To a solution of the above-mentioned compound (710 mg) in DMF (10 mL) were added benzyl bromide (325 μL) and potassium carbonate (380 mg), and the mixture was stirred at 60° C. for 24 hr. Water (100 mL) was added to the reaction mixture, and the mixture was extracted with ethyl acetate (50 mL). The organic layer was concentrated under reduced pressure. The residue was purified by silica gel column chromatography to give the title compound (350 mg) as an oil.
¹H-NMR (400 Mz, CDCl₃) δ1.19 (9H, t, J=7.2 Hz), 3.29 (2H, s), 4.16 (6H, q, J=7.2 Hz), 5.21 (2H, s), 7.15-7.16 (2H, m), 7.25-7.32 (3H, m), 7.36 (1H, s), 7.40 (1H, s).

(6) monoethyl[(1-benzyl-1H-pyrazol-4-yl)methyl]malonate

In the same manner as in Example 117 (2), the title compound (248 mg) was obtained as an oil using the above-mentioned compound (330 mg).
¹H-NMR (400 Mz, CDCl₃) δ1.16 (3H, t, J=7.2 Hz), 3.01-3.09 (2H, m), 3.51-3.56 (1H, m), 4.08-4.17 (2H, m), 5.22 (2H, s), 7.11-7.17 (2H, m), 7.24 (1H, s), 7.24-7.31 (4H, m), 7.43 (1H, s), 10.07 (1H, brs).

(7) ethyl 2-[(1-benzyl-1H-pyrazol-4-yl)methyl]-3-(N-ethyl-N-phenylamino)-3-oxopropionate In the same manner as in Example 1 (4), the title compound (200 mg) was obtained as an oil using the above-mentioned compound (248 mg) and N-ethylaniline (124 μL).
¹H-NMR (400 Mz, CDCl₃) δ1.01 (3H, t, J=7.2 Hz), 1.23 (3H, t, J=7.2 Hz), 2.87 (1H, dd, J=14.4, 4.8 Hz), 3.10 (1H, dd, J=14.4, 10.4 Hz), 3.33 (1H, dd, J=10.4, 4.8 Hz), 3.56-3.72 (2H, m), 4.11 (2H, q, J=7.2 Hz), 5.23 (2H, dd, J=16.8, 14.8 Hz), 6.72 (2H, brs), 7.17 (1H, s), 7.21 (1H, s), 7.26-7.36 (8H, m).

(8) 2-[(1-benzyl-1H-pyrazol-4-yl)methyl]-3-(N-ethyl-N-phenylamino)-3-oxopropionic acid In the same manner as in Example 1 (3), the title compound (167 mg) was obtained as an oil using the above-mentioned compound (180 mg).
$^1$H-NMR (400 Mz, DMSO-$d_6$) δ0.89 (3H, t, J=7.2 Hz), 7.68-2.85 (2H, m), 3.10-3.18 (1H, m), 3.47-3.57 (2H, m), 5.26 (2H, s), 6.71 (2H, brs), 7.07 (1H, s), 7.27-7.39 (8H, m), 7.39 (1H, s).

(9) 2-[(1-benzyl-1H-pyrazol-4-yl)methyl]-N-ethyl-N-phenyl-N'-((E)-styrylsulfonyl)malonamide In the same manner as in Example 1 (2), the title compound (90 mg) was obtained as a white powder using the above-mentioned compound (168 mg) and trans-β-styrenesulfonamide (82 mg).
$^1$H-NMR (400 Mz, DMSO-$d_6$) δ0.89-0.96 (3H, m), 2.70 (1H, dd, J=13.6, 5.2 Hz), 2.87 (1H, dd, J=13.6, 8.4 Hz), 3.30-3.33 (1H, m), 3.48-3.63 (2H, m), 5.19 (2H, s), 7.00 (3H, brs), 7.15 (2H, d, J=7.2 Hz), 7.26-7.32 (8H, m), 7.45-7.52 (3H, m), 7.57 (1H, d, J=15.2 Hz), 7.78-7.80 (2H, m), 11.73 (1H, brs).
MS: 543(M+H)$^+$.

Example 372

Synthesis of N-ethyl-2-[(1-ethyl-1H-pyrazol-4-yl)methyl]-N-phenyl-N'-((E)-styrylsulfonyl)malonamide

(1) triethyl 2-(1-ethyl-1H-pyrazol-4-yl)ethane-1,1,1-tricarboxylate

In the same manner as in Example 371 (5), the title compound (240 mg) was obtained as an oil using the compound (710 mg) obtained in Example 371 (4) and ethyl iodide (440 μL).
$^1$H-NMR (400 Mz, CDCl$_3$) δ1.24 (9H, t, J=7.2 Hz), 1.43 (3H, t, J=7.2 Hz), 3.30 (2H, s), 4.09 (2H, q, J=7.2 Hz), 4.22 (6H, q, J=7.2 Hz), 7.33 (1H, s), 7.37 (1H, s).

(2) monoethyl[(1-ethyl-1H-pyrazol-4-yl)methyl]malonate

In the same manner as in Example 117 (2), the title compound (151 mg) was obtained as an oil using the above-mentioned compound (240 mg).
$^1$H-NMR (300 Mz, CDCl$_3$) δ1.27 (3H, t, J=7.3 Hz), 1.44 (3H, t, J=7.1 Hz), 3.10 (2H, d, J=7.3 Hz), 3.57 (1H, t, J=7.3 Hz), 4.10-4.25 (4H, m), 5.62 (1H, brs), 7.28 (1H, s), 7.38 (1H, s).

(3) ethyl 3-(N-ethyl-N-phenylamino)-2-[(1-ethyl-1H-pyrazol-4-yl)methyl]-3-oxopropionate In the same manner as in Example 1 (4), the title compound (90 mg) was obtained as an oil using the above-mentioned compound (151 mg) and N-ethylaniline (95 μL).
$^1$H-NMR (400 Mz, CDCl$_3$) δ1.04-1.10 (3H, m), 1.22-1.28 (3H, m), 1.46 (3H, t, J=7.2 Hz), 2.86-3.94 (1H, m), 3.08 (1H, dd, J=14.0, 10.0 Hz), 3.37 (1H, dd, J=10.0, 5.2 Hz), 3.71 (2H, q, J=7.2 Hz), 4.07-4.19 (4H, m), 6.83 (2H, brs), 7.17 (2H, s), 7.29-7.38 (3H, m).

(4) 3-(N-ethyl-N-phenylamino)-2-[(1-ethyl-1H-pyrazol-4-yl)methyl]-3-oxopropionic acid In the same manner as in Example 1 (3), the title compound (82 mg) was obtained as an oil using the above-mentioned compound (90 mg).
$^1$H-NMR (400 Mz, CDCl$_3$) δ1.05-1.12 (3H, m), 1.46 (3H, t, J=7.2 Hz), 2.91 (1H, dd, J=15.0, 5.2 Hz), 3.10 (1H, dd, J=15.0, 10.0 Hz), 3.42 (1H, dd, J=10.0, 5.2 Hz), 3.68-3.77 (2H, m), 4.09-4.18 (2H, m), 6.85 (2H, brs), 7.19 (1H, s), 7.21 (1H, s), 7.31-7.42 (3H, m), 8.76 (1H, brs).

(5) N-ethyl-2-[(1-ethyl-1H-pyrazol-4-yl)methyl]-N-phenyl-N'-((E)-styrylsulfonyl)malonamide In the same manner as in Example 1 (2), the title compound (87 mg) was obtained as a white powder using the above-mentioned compound (82 mg) and trans-β-styrenesulfonamide (50 mg).
$^1$H-NMR (400 Mz, DMSO-$d_6$) δ0.96 (3H, t, J=7.2 Hz), 1.23 (3H, t, J=7.2 Hz), 2.65-2.83 (2H, m), 3.50-3.69 (2H, m), 3.94 (2H, q, J=7.2 Hz), 6.88 (1H, s), 7.10-7.16 (2H, m), 7.17 (1H, s), 7.28-7.60 (8H, m), 7.75-7.85 (2H, m), 11.72 (1H, brs).
MS: 481(M+H)$^+$.

Example 373

Synthesis of N-ethyl-2-[(1-methyl-1H-pyrazol-4-yl)methyl]-N-phenyl-N'-((E)-styrylsulfonyl)malonamide

(1) triethyl 2-(1-methyl-1H-pyrazol-4-yl)ethane-1,1,1-tricarboxylate

In the same manner as in Example 371 (5), the title compound (220 mg) was obtained as an oil using the compound (710 mg) obtained in Example 371 (4) and methyl iodide (340 μL).
$^1$H-NMR (400 Mz, CDCl$_3$) δ1.25 (3H, t, J=7.2 Hz), 3.29 (2H, s), 3.83 (3H, s), 4.22 (2H, q, J=7.2 Hz), 7.33 (1H, s), 7.36 (1H, s).

(2) monoethyl[(1-methyl-1H-pyrazol-4-yl)methyl]malonate

In the same manner as in Example 117 (2), the title compound (120 mg) was obtained as an oil using the above-mentioned compound (220 mg).

(3) ethyl 3-(N-ethyl-N-phenylamino)-2-[(1-methyl-1H-pyrazol-4-yl)methyl]-3-oxopropionate In the same manner as in Example 1 (4), the title compound (90 mg) was obtained as an oil using the above-mentioned compound (120 mg) and N-ethylaniline (80 μL).
$^1$H-NMR (400 Mz, CDCl$_3$) δ1.08 (3H, t, J=7.2 Hz), 1.25 (3H, t, J=7.2 Hz), 2.90 (1H, dd, J=14.0, 5.6 Hz), 3.06 (1H, dd, J=14.0, 10.0 Hz), 3.38 (1H, dd, J=10.0, 5.6 Hz), 3.67-3.75 (2H, m), 3.85 (3H, s), 4.13 (2H, q, J=7.2 Hz), 6.89 (2H, brs), 7.12 (1H, s), 7.15 (1H, s), 7.31-7.38 (3H, m).

(4) 3-(N-ethyl-N-phenylamino)-2-[(1-methyl-1H-pyrazol-4-yl)methyl]-3-oxopropionic acid In the same manner as in Example 1 (3), the title compound (77 mg) was obtained as an oil using the above-mentioned compound (90 mg).
$^1$H-NMR (400 Mz, CDCl$_3$) δ1.09 (3H, t, J=7.2 Hz), 2.91 (1H, d, J=14.4, 5.6 Hz), 3.06 (1H, dd, J=14.4, 9.6 Hz), 3.43 (1H, dd, J=9.6, 5.6 Hz), 3.67-3.79 (2H, m), 3.87 (3H, s), 6.91 (2H, brs), 7.14 (1H, s), 7.19 (1H, s), 7.33-7.41 (3H, m), 8.57 (1H, brs).

(5) N-ethyl-2-[(1-methyl-1H-pyrazol-4-yl)methyl]-N-phenyl-N'-((E)-styrylsulfonyl)malonamide In the same manner as in Example 1 (2), the title compound (54 mg) was obtained as a white powder using the above-mentioned compound (77 mg) and trans-β-styrenesulfonamide (50 mg).
$^1$H-NMR (400 Mz, DMSO-d$_6$) δ0.95 (3H, t, J=7.2 Hz), 2.67-2.71 (1H, m), 2.79 (1H, dd, J=14.0, 7.6 Hz), 3.25-3.39 (1H, m), 3.46-3.59 (1H, m), 3.59-3.72 (1H, m), 3.65 (3H, s), 6.87 (1H, s), 7.14 (3H, brs), 7.30 (1H, d, J=15.6 Hz), 7.35-7.51 (6H, m), 7.56 (1H, d, J=15.6 Hz), 7.74-7.82 (2H, m), 11.73 (1H, brs).
MS: 467(M+H)$^+$.

Example 374

Synthesis of 2-{[1-(4-chlorophenyl)-1H-pyrazol-4-yl]methyl}-N-ethyl-N-phenyl-N'-((E)-styrylsulfonyl)malonamide (1) triethyl 2-[1-(4-chlorophenyl)-1H-pyrazol-4-yl]ethane-1,1,1-tricarboxylate In the same manner as in Example 117 (1), the title compound (1.71 g) was obtained as an oil using 4-(chloromethyl)-1-(4-chlorophenyl)-1H-pyrazole (920 mg).
$^1$H-NMR (400 Mz, DMSO-d$_6$) δ1.16 (9H, t, J=7.2 Hz), 3.28 (2H, s), 4.18 (2H, q, J=7.2 Hz), 7.54 (2H, d, J=8.8 Hz), 7.56 (1H, s), 7.79 (2H, d, J=8.8 Hz), 8.25 (1H, s).

(2) monoethyl{[1-(4-chlorophenyl)-1H-pyrazol-4-yl]methyl}malonate

In the same manner as in Example 117 (2), the title compound (1.31 g) was obtained as a white solid using the above-mentioned compound (1.71 g).
$^1$H-NMR (400 Mz, DMSO-d$_6$) δ1.13 (3H, t, J=7.2 Hz), 2.97 (2H, d, J=8.0 Hz), 3.69 (1H, t, J=8.0 Hz), 4.10 (2H, q, J=7.2 Hz), 7.54 (2H, d, J=8.8 Hz), 7.61 (1H, s), 7.80 (2H, d, J=8.8 Hz), 8.34 (1H, s), 12.98 (1H, brs).

(3) ethyl 2-{[1-(4-chlorophenyl)-1H-pyrazol-4-yl]methyl}-3-(N-ethyl-N-phenylamino)-3-oxopropionate In the same manner as in Example 1 (4), the title compound (310 mg) was obtained as an oil using the above-mentioned compound (410 mg) and N-ethylaniline (176 μL).
$^1$H-NMR (400 Mz, DMSO-d$_6$) δ0.96 (3H, t, J=7.2 Hz), 1.12 (3H, t, J=7.2 Hz), 2.85-2.97 (2H, m), 3.34-3.40 (1H, m), 3.52-3.68 (2H, m), 3.96-4.07 (2H, m), 6.90 (2H, brs), 7.33-7.42 (4H, m), 7.55 (2H, d, J=8.8 Hz), 7.80 (2H, d, J=8.8 Hz), 8.14 (1H, s).

(4) 2-{[1-(4-chlorophenyl)-1H-pyrazol-4-yl]methyl}-3-(N-ethyl-N-phenylamino)-3-oxopropionic acid In the same manner as in Example 1 (3), the title compound (247 mg) was obtained as a white solid using the above-mentioned compound (310 mg).
$^1$H-NMR (300 Mz, DMSO-d$_6$) δ0.95 (3H, t, J=7.8 Hz), 2.83-2.95 (2H, m), 3.18-3.33 (1H, m), 3.56-3.65 (2H, m), 6.88 (2H, brs), 7.36 (3H, brs), 7.37 (1H, s), 7.55 (2H, d, J=8.8 Hz), 7.80 (2H, d, J=8.8 Hz), 8.11 (1H, s), 12.63 (1h, brs).

(5) 2-{[1-(4-chlorophenyl)-1H-pyrazol-4-yl]methyl}-N-ethyl-N-phenyl-N'-((E)-styrylsulfonyl)malonamide In the same manner as in Example 1 (2), the title compound (135 mg) was obtained as a white powder using the above-mentioned compound (240 mg) and trans-β-styrenesulfonamide (110 mg).
$^1$H-NMR (400 Mz, DMSO-d$_6$) δ0.97 (3H, t, J=7.2 Hz), 2.84 (1H, dd, J=14.4, 6.0 Hz), 2.95 (1H, dd, J=14.4, 7.6 Hz), 3.46-3.70 (3H, m), 7.17-7.19 (2H, m), 7.29 (1H, s), 7.30 (1H, d, J=15.6 Hz), 7.36-7.51 (8H, m), 7.57 (1H, d, J=15.6 Hz), 7.71-7.78 (4H, m), 8.01 (1H, s), 11.76 (1H, brs).
MS: 563(M+H)$^+$.

Example 375

Synthesis of N-ethyl-2-{[1-(4-fluorobenzyl)-1H-pyrazol-4-yl]methyl}-N-phenyl-N'-((E)-styrylsulfonyl)malonamide (1) ethyl 1-(4-fluorobenzyl)-1H-pyrazole-4-carboxylate To a solution of ethyl pyrazolecarboxylate (10.1 g) in THF (200 mL) was added slowly 60% sodium hydride (3.17 g) under ice-cooling, and the mixture was stirred for 20 min. A solution of 4-fluorobenzyl bromide (14.3 g) in THF (25 mL) was added to the reaction mixture under ice-cooling, and the mixture was stirred at room temperature for 19 hr. Dilute hydrochloric acid was added to the reaction mixture, and the precipitate was collected by filtration to give the title compound (11.9 g) as a pale-yellow solid.
$^1$H-NMR (400 Mz, DMSO-d$_6$) δ1.25 (3H, t, J=7.2 Hz), 4.20 (2H, q, J=7.2 Hz), 5.35 (2H, s), 7.16-7.21 (2H, m), 7.33-7.36 (2H, m), 7.87 (1H, s), 8.48 (1H, s).

(2) [1-(4-fluorobenzyl)-1H-pyrazol-4-yl]methanol

In the same manner as in Example 128 (2), the title compound (4.99 g) was obtained as an oil using the above-mentioned compound (6.00 g).
$^1$H-NMR (300 Mz, CDCl$_3$) δ4.57 (2H, s), 5.24 (2H, s), 7.00-7.06 (2H, m), 7.19-7.27 (2H, m), 7.38 (1H, s), 7.53 (1H, s).

(3) 4-(chloromethyl)-1-(4-fluorobenzyl)-1H-pyrazole

To a solution of the above-mentioned compound (4.99 g) in chloroform (100 mL) was added thionyl chloride (2.10 mL), and the mixture was heated under reflux for 2 hr. The reaction mixture was concentrated under reduced pressure to give the title compound (5.44 g) as an oil.

¹H-NMR (300 Mz, CDCl₃) δ4.53 (2H, s), 5.24 (2H, s), 7.01-7.07 (2H, m), 7.19-7.26 (2H, m), 7.41 (1H, s), 7.56 (1H, s).

(4) triethyl 2-[1-(4-fluorobenzyl)-1H-pyrazol-4-yl]ethane-1,1,1-tricarboxylate

In the same manner as in Example 117 (1), the title compound (10.1 g) was obtained as an oil using the above-mentioned compound (5.44 g).

¹H-NMR (400 Mz, CDCl₃) δ1.21 (9H, t, J=7.2 Hz), 3.29 (2H, s), 4.18 (6H, q, J=7.2 Hz), 5.19 (2H, s), 6.97-7.02 (2H, m), 7.13-7.16 (2H, m), 7.35 (1H, s), 7.38 (1H, s).

(5) monoethyl{[1-(4-fluorobenzyl)-1H-pyrazol-4-yl]methyl}malonate

In the same manner as in Example 117 (2), the title compound (7.75 g) was obtained as a white solid using the above-mentioned compound (5.44 g).

¹H-NMR (400 Mz, DMSO-d₆) δ1.08 (3H, t, J=7.2 Hz), 2.84-2.89 (2H, m), 3.54 (1H, t, J=7.2 Hz), 5.23 (2H, s), 7.12-7.17 (2H, m), 7.21-7.24 (2H, m), 7.28 (1H, s), 7.57 (1H, s), 12.84 (1H, brs).

(6) ethyl 3-(N-ethyl-N-phenylamino)-2-{[1-(4-fluorobenzyl)-1H-pyrazol-4-yl]methyl}-3-oxopropionate In the same manner as in Example 1 (4), the title compound (1.40 g) was obtained as an oil using the above-mentioned compound (1.49 g) and N-ethylaniline (700 μL).

¹H-NMR (400 Mz, DMSO-d₆) δ0.91 (3H, t, J=7.2 Hz), 1.10 (3H, t, J=7.2 Hz), 2.73-2.89 (2H, m), 3.22 (1H, dd, J=9.6, 5.6 Hz), 3.50-3.59 (2H, m), 3.98 (2H, q, J=7.2 Hz), 5.24 (2H, s), 6.76 (2H, brs), 7.08 (1H, s), 7.14-7.19 (2H, m), 7.21-7.37 (5H, m), 7.40 (1H, s).

(7) 3-(N-ethyl-N-phenylamino)-2-{[1-(4-fluorobenzyl)-1H-pyrazol-4-yl]methyl}-3-oxopropionic acid In the same manner as in Example 1 (3), the title compound (1.21 g) was obtained as a white powder using the above-mentioned compound (1.37 g).

¹H-NMR (400 Mz, DMSO-d₆) δ0.89 (3H, t, J=7.2 Hz), 2.72 (1H, dd, J=14.0, 5.2 Hz), 2.82 (1H, dd, J=14.0, 9.6 Hz), 3.15 (1H, d, J=9.6, 5.2 Hz), 3.50-3.57 (2H, m), 5.24 (2H, s), 6.70 (2H, brs), 7.06 (1H, s), 7.15-7.20 (2H, m), 7.30-7.39 (5H, m), 7.39 (1H, s), 12.53 (1H, brs).

(8) N-ethyl-2-{[1-(4-fluorobenzyl)-1H-pyrazol-4-yl]methyl}-N-phenyl-N'-((E)-styrylsulfonyl)malonamide In the same manner as in Example 1 (2), the title compound (730 mg) was obtained as a white powder using the above-mentioned compound (1.20 g) and trans-β-styrenesulfonamide (550 mg).

¹H-NMR (400 Mz, DMSO-d₆) δ0.92 (3H, t, J=6.8 Hz), 2.70 (1H, dd, J=13.6, 4.4 Hz), 2.86 (1H, dd, J=13.6, 8.4 Hz), 3.25-3.38 (1H, m), 3.51-4.04 (2H, m), 5.18 (2H, s), 7.00 (3H, brs), 7.12-7.42 (9H, m), 7.49 (3H, brs), 7.58 (1H, d, J=15.6 Hz), 7.79 (2H, brs), 11.69 (1H, brs).

MS:561(M+H)⁺.

Example 376

Synthesis of 2-{[1-(2,4-difluorobenzyl)-1H-pyrazol-4-yl]methyl}-N-ethyl-N-phenyl-N'-((E)-styrylsulfonyl)malonamide (1) ethyl 1-(2,4-difluorobenzyl)-1H-pyrazole-4-carboxylate In the same manner as in Example 375 (1), the title compound (6.29 g) was obtained as a white solid using 2,4-difluorobenzyl bromide (5.02 g).

¹H-NMR (300 Mz, DMSO-d₆) δ1.26 (3H, t, J=6.9 Hz), 4.21 (2H, q, J=6.9 Hz), 5.41 (2H, s), 7.07-7.15 (1H, m), 7.24-7.40 (2H, m), 7.87 (1H, s), 8.44 (1H, s).

(2) [1-(2,4-difluorobenzyl)-1H-pyrazol-4-yl]methanol

In the same manner as in Example 128 (2), the title compound (3.76 g) was obtained as an oil using the above-mentioned compound (4.69 g).

¹H-NMR (300 Mz, CDCl₃) δ4.58 (2H, s), 5.28 (2H, s), 6.78-6.90 (2H, m), 7.16-7.24 (1H, m), 7.45 (1H, s), 7.52 (1H, s).

(3) 4-(chloromethyl)-1-(2,4-difluorobenzyl)-1H-pyrazole

In the same manner as in Example 375 (3), the title compound (3.01 g) was obtained as a white solid using the above-mentioned compound (3.72 g).

¹H-NMR (300 Mz, DMSO-d₆) δ4.69 (2H, s), 5.33 (2H, s), 7.03-7.14 (1H, m), 7.24-7.35 (2H, m), 7.52 (1H, s), 7.90 (1H, s).

(4) triethyl 2-[1-(2,4-difluorobenzyl)-1H-pyrazol-4-yl]ethane-1,1,1-tricarboxylate In the same manner as in Example 117 (1), the title compound (5.32 g) was obtained as an oil using the above-mentioned compound (2.88 g).

¹H-NMR (400 Mz, CDCl₃) δ1.22 (9H, t, J=7.2 Hz), 3.29 (2H, s), 4.19 (2H, q, J=7.2 Hz), 5.23 (2H, s), 6.78-6.84 (2H, m), 7.05-7.10 (1H, m), 7.38 (1H, s), 7.41 (1H, s).

(5) monoethyl{[1-(2,4-difluorobenzyl)-1H-pyrazol-4-yl]methyl}malonate

In the same manner as in Example 117 (2), the title compound (4.09 g) was obtained as an oil using the above-mentioned compound (5.32 g).

¹H-NMR (300 Mz, DMSO-d₆) δ1.10 (3H, t, J=7.2 Hz), 2.87 (2H, d, J=7.8 Hz), 3.55 (1H, t, J=7.8 Hz), 4.05 (2H, q, J=7.2 Hz), 5.27 (2H, s), 7.01-7.09 (1H, m), 7.16-7.28 (2H, m), 7.30 (1H, s), 7.57 (1H, s), 12.87 (1H, brs).

(6) ethyl 2-{[1-(2,4-difluorobenzyl)-1H-pyrazol-4-yl]methyl}-3-(N-ethyl-N-phenylamino)-3-oxopropionate In the same manner as in Example 1 (4), the title compound (2.40 g) was obtained as an oil using the above-mentioned compound (2.70 g) and N-ethylaniline (1.20 mL).

¹H-NMR (300 Mz, DMSO-d₆) δ0.92 (3H, t, J=7.1 Hz), 1.10 (3H, t, J=7.1 Hz), 2.70-2.89 (2H, m), 3.23 (1H, dd, J=9.0, 6.0 Hz), 3.55 (2H, q, J=7.1 Hz), 3.98 (2H, q, J=7.1 Hz), 5.29 (2H, s), 6.77 (2H, brs), 7.07 (1H, s), 7.07-7.12 (1H, m), 7.23-7.43 (5H, m), 7.38 (1H, s).

(7) 2-{[1-(2,4-difluorobenzyl)-1H-pyrazol-4-yl]methyl}-3-(N-ethyl-N-phenylamino)-3-oxopropionic acid In the same manner as in Example 1 (3), the title compound (2.25 g) was obtained as an oil using the above-mentioned compound (2.40 g).
¹H-NMR (300 Mz, DMSO-d₆) δ0.91 (3H, t, J=7.1 Hz), 2.68-2.87 (2H, m), 3.13-3.20 (1H, m), 3.55 (2H, q, J=7.1 Hz), 5.29 (2H, s), 6.73 (2H, brs), 7.06 (1H, s), 7.06-7.13 (1H, m), 7.25-7.40 (5H, m), 7.36 (1H, s), 12.50 (1H, brs).

(8) 2-{[1-(2,4-difluorobenzyl)-1H-pyrazol-4-yl]methyl}-N-ethyl-N-phenyl-N'-((E)-styrylsulfonyl)malonamide In the same manner as in Example 1 (2), the title compound (1.01 g) was obtained as a white solid using the above-mentioned compound (2.25 g) and trans-β-styrenesulfonamide (1.00 g).
¹H-NMR (300 Mz, DMSO-d₆) δ0.92 (3H, t, J=7.2 Hz), 2.60-2.76 (1H, m), 2.79-2.95 (1H, m), 3.21-3.32 (1H, m), 3.46-3.78 (2H, m), 5.22 (2H, s), 6.92-7.13 (4H, m), 7.13-7.62 (11H, m), 7.79-7.81 (2H, m), 11.72 (1H, brs).
MS:579(M+H)⁺.

Example 377

Synthesis of 2-{[1-(2-chlorobenzyl)-1H-pyrazol-4-yl]methyl}-N-ethyl-N-phenyl-N'-((E)-styrylsulfonyl)malonamide (1) triethyl 2-[1-(2-chlorobenzyl)-1H-pyrazol-4-yl]ethane-1,1,1-tricarboxylate In the same manner as in Example 371 (5), the title compound (1.12 g) was obtained as an oil using hydrochloride salt (2.15 g) of the compound obtained in Example 371 (4) and 2-chlorobenzyl bromide (800 μL).
¹H-NMR (400 Mz, CDCl₃) δ1.22 (9H, t, J=7.2 Hz), 3.31 (2H, s), 4.19 (2H, q, J=7.2 Hz), 5.35 (2H, s), 6.89-6.91 (1H, m), 7.17-7.24 (2H, m), 7.35-7.38 (1H, m), 7.42 (2H, s).

(2) monoethyl{[1-(2-chlorobenzyl)-1H-pyrazol-4-yl]methyl}malonate

In the same manner as in Example 117 (2), the title compound (840 mg) was obtained as an oil using the above-mentioned compound (1.12 g).
¹H-NMR (400 Mz, CDCl₃) δ1.24 (3H, t, J=7.2 Hz), 3.10-3.13 (2H, m), 3.55-3.59 (1H, m), 4.15-4.22 (2H, m), 5.38 (2H, s), 6.95-6.97 (1H, m), 7.18-7.24 (2H, m), 7.31 (1H, s), 7.34-7.39 (1H, m), 7.41 (1H, s).

(3) ethyl 2-{[1-(2-chlorobenzyl)-1H-pyrazol-4-yl]methyl}-3-(N-ethyl-N-phenylamino)-3-oxopropionate In the same manner as in Example 1 (4), the title compound (430 mg) was obtained as an oil using the above-mentioned compound (400 mg) and N-ethylaniline (180 μL).
¹H-NMR (400 Mz, CDCl₃) δ1.03 (3H, t, J=7.2 Hz), 1.23 (3H, t, J=7.2 Hz), 2.89 (1H, dd, J=14.4, 5.2 Hz), 3.10 (1H, dd, J=14.4, 10.0 Hz), 3.35 (1H, dd, J=10.0, 5.2 Hz), 4.12 (2H, q, J=7.2 Hz), 5.37 (2H, s), 6.80 (2H, brs), 7.10-7.12 (1H, m), 7.21-7.29 (7H, m), 7.38-7.40 (1H, m).

(4) 2-{[1-(2-chlorobenzyl)-1H-pyrazol-4-yl]methyl}-3-(N-ethyl-N-phenylamino)-3-oxopropionic acid In the same manner as in Example 1 (3), the title compound (260 mg) was obtained as a white powder using the above-mentioned compound (430 mg).
¹H-NMR (400 Mz, DMSO-d₆) δ0.91 (3H, t, J=7.2 Hz), 2.70-2.87 (2H, m), 3.13-3.21 (1H, m), 3.50-3.60 (2H, m), 5.37 (2H, s), 6.81 (2H, brs), 7.05-7.14 (1H, m), 7.10 (1H, s), 7.28-7.43 (5H, m), 7.37 (1H, s), 7.47-7.52 (1H, m), 12.54 (1H, brs).

(5) 2-{[1-(2-chlorobenzyl)-1H-pyrazol-4-yl]methyl}-N-ethyl-N-phenyl-N'-((E)-styrylsulfonyl)malonamide In the same manner as in Example 1 (2), the title compound (107 mg) was obtained as a white solid using the above-mentioned compound (255 mg) and trans-β-styrenesulfonamide (106 mg).
¹H-NMR (400 Mz, DMSO-d₆) δ0.92 (3H, t, J=7.2 Hz), 2.70 (1H, dd, J=14.0, 4.8 Hz), 2.87 (1H, dd, J=14.0, 8.4 Hz), 3.29-3.38 (1H, m), 3.48-3.66 (2H, m), 5.29 (2H, s), 6.91 (1H, d, J=7.6 Hz), 7.01-7.04 (3H, m), 7.29-7.36 (7H, m), 7.43-7.51 (4H, m), 7.56 (1H, d, J=15.6 Hz), 7.76-7.82 (2H, m), 11.67 (1H, brs).
MS: 577(M+H)⁺.

Example 378

Synthesis of 2-{[1-(2-chloro-5-pyridylmethyl)-1H-pyrazol-4-yl]methyl}-N-ethyl-N-phenyl-N'-((E)-styrylsulfonyl)malonamide (1) ethyl 1-(2-chloro-5-pyridylmethyl)-1H-pyrazole-4-carboxylate In the same manner as in Example 375 (1), the title compound (9.93 g) was obtained as a white solid using 2-chloro-5-(chloromethyl)pyridine (10.1 g).
¹H-NMR (400 Mz, CDCl₃) δ1.33 (3H, t, J=7.2 Hz), 4.29 (2H, q, J=7.2 Hz), 5.30 (2H, s), 7.33 (1H, d, J=8.4 Hz), 7.54 (1H, dd, J=8.4, 1.6 Hz), 7.91 (1H, s), 7.95 (1H, s), 8.35 (1H, d, J=1.6 Hz).

(2) [1-(2-chloro-5-pyridylmethyl)-1H-pyrazol-4-yl]methanol

In the same manner as in Example 128 (2), a crude product was obtained using the above-mentioned compound (9.90 g). This was purified by silica gel column chromatography to give the title compound (4.87 g) as an oil.
¹H-NMR (300 Mz, CDCl₃) δ1.69 (1H, t, J=5.1 Hz), 4.59 (2H, d, J=5.1 Hz), 5.27 (2H, s), 7.31 (1H, d, J=8.4 Hz), 7.43 (1H, s), 7.52 (1H, s), 7.55 (1H, s), 8.30 (1H, d, J=2.4 Hz).

(3) 4-(chloromethyl)-1-(2-chloro-5-pyridylmethyl)-1H-pyrazole

In the same manner as in Example 375 (3), the title compound (4.59 g) was obtained as a white solid using the above-mentioned compound (4.84 g).

¹H-NMR (300 Mz, DMSO-d₆) δ4.69 (2H, s), 5.37 (2H, s), 7.52 (1H, d, J=8.2 Hz), 7.56 (1H, s), 7.71 (1H, dd, J=8.2, 2.3 Hz), 7.98 (1H, s), 8.35 (1H, d, J=2.3 Hz).

(4) triethyl 2-[1-(2-chloro-5-pyridylmethyl)-1H-pyrazol-4-yl]ethane-1,1,1-tricarboxylate In the same manner as in Example 117 (1), a crude product was obtained using the above-mentioned compound (4.52 g). This was purified by silica gel column chromatography to give the title compound (7.33 g) as an oil.
¹H-NMR (300 Mz, CDCl₃) δ1.22 (9H, t, J=7.2 Hz), 3.29 (2H, s), 4.19 (6H, q, J=7.2 Hz), 5.22 (2H, s), 7.28 (1H, d, J=8.1 Hz), 7.38-7.47 (1H, m), 7.38 (1H, s), 7.43 (1H, s), 8.25 (1H, s).

(5) monoethyl{[1-(2-chloro-5-pyridylmethyl)-1H-pyrazol-4-yl]methyl}malonate

In the same manner as in Example 117 (2), the title compound (5.54 g) was obtained as an oil using the above-mentioned compound (7.23 g).
¹H-NMR (300 Mz, DMSO-d₆) δ1.08 (3H, t, J=7.1 Hz), 2.87 (2H, d, J=7.8 Hz), 3.56 (1H, t, J=7.8 Hz), 4.05 (2H, q, J=7.1 Hz), 5.32 (2H, s), 7.32 (1H, s), 7.49 (1H, d, J=7.6 Hz), 7.62-7.65 (1H, s), 7.65 (1H, s), 8.27 (1H, d, J=2.0 Hz), 12.91 (1H, brs).

(6) ethyl 2-{[1-(2-chloro-5-pyridylmethyl)-1H-pyrazol-4-yl]methyl}-3-(N-ethyl-N-phenylamino)-3-oxopropionate In the same manner as in Example 1 (4), the title compound (3.84 g) was obtained as an oil using the above-mentioned compound (3.87 g) and N-ethylaniline (1.73 mL).
¹H-NMR (400 Mz, CDCl₃) δ1.03 (3H, t, J=7.2 Hz), 1.24 (3H, t, J=7.2 Hz), 2.10 (1H, dd, J=14.4, 5.6 Hz), 3.07 (1H, dd, J=14.4, 9.6 Hz), 3.35 (1H, dd, J=9.6, 5.6 Hz), 3.61-3.73 (2H, m), 4.11 (2H, q, J=7.2 Hz), 5.22 (2H, s), 6.80 (2H, brs), 7.20-7.32 (6H, m), 7.53 (1H, dd, J=8.0, 2.4 Hz), 8.31 (1H, d, J=2.4 Hz).

(7) 2-{[1-(2-chloro-5-pyridylmethyl)-1H-pyrazol-4-yl]methyl}-3-(N-ethyl-N-phenylamino)-3-oxopropionic acid In the same manner as in Example 1 (3), the title compound (3.10 g) was obtained as a white solid using the above-mentioned compound (3.83 g).
¹H-NMR (300 Mz, DMSO-d₆) δ0.87 (3H, t, J=7.2 Hz), 2.66-2.87 (2H, m), 3.13-3.16 (1H, m), 3.42-3.62 (2H, m), 5.33 (2H, s), 6.71 (2H, brs), 7.10 (1H, s), 7.33 (3H, brs), 7.48 (1H, s), 7.52 (1H, d, J=8.4 Hz), 7.76 (1H, dd, J=8.4, 2.4 Hz), 8.37 (1H, d, J=2.4 Hz), 12.56 (1H, brs).

(8) 2-{[1-(2-chloro-5-pyridylmethyl)-1H-pyrazol-4-yl]methyl}-N-ethyl-N-phenyl-N'-((E)-styrylsulfonyl)malonamide In the same manner as in Example 1 (2), the title compound (1.23 g) was obtained as a white solid using the above-mentioned compound (3.06 g) and trans-β-styrenesulfonamide (1.35 g).
¹H-NMR (300 Mz, DMSO-d₆) δ0.92 (3H, t, J=7.2 Hz), 2.62-2.96 (2H, m), 3.30-3.36 (1H, m), 3.46-3.65 (2H, m), 5.27 (2H, s), 7.00-7.03 (3H, m), 7.30-7.67 (11H, m), 7.79-7.81 (2H, m), 8.25 (1H, d, J=2.1 Hz), 11.73 (1H, brs).
MS:578(M+H)⁺.

Example 379

Synthesis of N-ethyl-N-phenyl-2-{[1-(3-pyridylmethyl)-1H-pyrazol-4-yl]methyl}-N'-((E)-styrylsulfonyl)malonamide hydrochloride To a solution of the compound (340 mg) obtained in Example 378 in acetic acid (20 mL) was added zinc powder (780 mg), and the mixture was heated under reflux for 2 hr. Insoluble material was removed by filtration, and the filtrate was concentrated under reduced pressure. Ethyl acetate (10 mL) was added to the residue, and the precipitate was collected by filtration. This was purified by silica gel column chromatography to give the object compound, and this was converted to a hydrochloride salt with 1 mol/L hydrochloric acid-ethyl acetate to give the title compound (83 mg) as a white solid.
¹H-NMR (400 Mz, DMSO-d₆) δ0.92 (3H, t, J=7.2 Hz), 2.71 (1H, dd, J=14.0, 5.2 Hz), 2.85 (1H, dd, J=14.0, 8.0 Hz), 3.33-3.36 (1H, m), 3.48-3.65 (4H, m), 5.40 (2H, s), 7.04-7.06 (3H, m), 7.29 (1H, d, J=15.6 Hz), 7.36-7.38 (3H, m), 7.46-7.49 (4H, m), 7.56 (1H, d, J=15.6 Hz), 7.78-7.83 (3H, m), 8.03 (1H, d, J=8.0 Hz), 8.65 (1H, s), 8.74 (1H, d, J=5.6 Hz), 11.69 (1H, brs).
MS: 544(M+H)⁺.

Example 380

Synthesis of N-ethyl-N-phenyl-2-{[1-(2-pyridylmethyl)-1H-pyrazol-4-yl]methyl}-N'-((E)-styrylsulfonyl)malonamide hydrochloride (1) triethyl 2-[1-(2-pyridylmethyl)-1H-pyrazol-4-yl]ethane-1,1,1-tricarboxylate In the same manner as in Example 371 (5), the title compound (600 mg) was obtained as an oil using hydrochloride salt (2.00 g) of the compound obtained in Example 371 (4) and 2-(chloromethyl)pyridine hydrochloride (990 mg).
¹H-NMR (400 Mz, CDCl₃) δ1.23 (9H, t, J=7.2 Hz), 3.16 (2H, s), 4.20 (6H, q, J=7.2 Hz), 5.37 (2H, s), 6.89 (1H, d, J=7.6 Hz), 7.16-7.21 (1H, m), 7.44 (1H, s), 7.49 (1H, s), 7.59-7.64 (1H, m), 8.54-8.56 (1H, m).

(2) monoethyl{[1-(2-pyridylmethyl)-1H-pyrazol-4-yl]methyl}malonate

In the same manner as in Example 117 (2), the title compound (300 mg) was obtained as an oil using the above-mentioned compound (600 mg).
¹H-NMR (400 Mz, DMSO-d₆) δ1.12 (3H, t, J=7.2 Hz), 2.90 (2H, d, J=8.0 Hz), 3.56 (1H, t, J=8.0 Hz), 5.34 (2H, s), 6.90 (1H, d, J=7.6 Hz), 7.29 (1H, dd, J=7.6, 4.8 Hz), 7.31 (1H, s), 7.62 (1H, s), 7.71-7.75 (1H, m), 8.52 (1H, d, J=4.8 Hz), 12.85 (1H, brs).

(3) ethyl 3-(N-ethyl-N-phenylamino)-3-oxo-2-{[1-(2-pyridylmethyl)-1H-pyrazol-4-yl]methyl}propionate In the same manner as in Example 1 (4), the title compound (340 mg) was obtained as an oil using the above-mentioned compound (297 mg) and N-ethylaniline (150 μL).
¹H-NMR (400 Mz, CDCl₃) δ1.04 (3H, t, J=7.2 Hz), 1.23 (3H, t, J=7.2 Hz), 2.91 (1H, dd, J=14.4, 5.2 Hz), 3.11 (1H, dd, J=14.4, 9.6 Hz), 3.37 (1H, dd, J=9.6, 5.2 Hz), 3.60-3.78 (2H, m), 4.12 (2H, q, J=7.2 Hz), 5.37 (2H, s), 6.84 (2H, brs), 7.06 (1H, d, J=7.6 Hz), 7.17-7.23 (1H, m), 7.23-7.30 (5H, m), 7.59-7.66 (1H, m), 8.56 (1H, d, J=4.4 Hz).

(4) N-ethyl-N-phenyl-2-{[1-(2-pyridylmethyl)-1H-pyrazol-4-yl]methyl}-N'-((E)-styrylsulfonyl)malonamide hydrochloride The above-mentioned compound (330 mg) was subjected to hydrolysis in the same manner as in Example 1 (3). The reaction mixture was neutralized with dilute hydrochloric acid and concentrated under reduced pressure. In the same manner as in Example 1 (2), the object compound was obtained using the residue and trans-β-styrenesulfonamide (150 mg). This was converted to a hydrochloride salt with 1 mol/L hydrochloric acid-ethyl acetate to give the title compound (80 mg) as a white solid.
$^1$H-NMR (400 Mz, DMSO-$d_6$) δ0.87-0.98 (3H, m), 2.73 (1H, dd, J=14.0, 5.6 Hz), 2.88 (1H, dd, J=14.0, 7.6 Hz), 3.38 (1H, dd, J=7.6, 5.6 Hz), 3.51-3.64 (2H, m), 5.52 (2H, s), 7.07-7.09 (3H, m), 7.17 (1H, d, J=8.0 Hz), 7.29 (1H, d, J=15.6 Hz), 7.37-7.38 (3H, m), 7.45-7.49 (4H, m), 7.56 (1H, d, J=15.6 Hz), 7.62-7.66 (1H, m), 7.78-7.94 (2H, m), 8.10-8.14 (1H, m), 8.71 (1H, d, J=4.8 Hz), 11.72 (1H, brs).
MS: 544(M+H)$^+$.

Example 381

Synthesis of 2-{[1-(2-chloro-5-pyridylmethyl)-1H-pyrazol-4-yl]methyl}-N-ethyl-N-(4-fluorophenyl)-N'-((E)-styrylsulfonyl)malonamide (1) ethyl 2-{[1-(2-chloro-5-pyridylmethyl)-1H-pyrazol-4-yl]methyl}-3-[N-ethyl-N-(4-fluorophenyl)amino]-3-oxopropionate In the same manner as in Example 1 (4), the title compound (2.12 g) was obtained as an oil using the compound (2.51 g) obtained in Example 378 (5) and N-ethyl-4-fluoroaniline (1.24 g).
$^1$H-NMR (400 Mz, CDCl$_3$) δ0.99-1.03 (3H, m), 1.23 (3H, t, J=7.2 Hz), 2.89 (1H, dd, J=14.4, 5.2 Hz), 3.09 (1H, dd, J=14.4, 10.0 Hz), 3.32 (1H, dd, J=10.0, 5.2 Hz), 3.60-3.70 (2H, m), 4.09-4.14 (2H, m), 5.23 (2H, s), 6.94-7.05 (2H, m), 7.22-7.31 (5H, m), 7.52-7.55 (1H, m), 8.31 (1H, d, J=1.6 Hz).

(2) 2-{[1-(2-chloro-5-pyridylmethyl)-1H-pyrazol-4-yl]methyl}-3-[N-ethyl-N-(4-fluorophenyl)amino]-3-oxopropionic acid In the same manner as in Example 1 (3), the title compound (1.93 g) was obtained as a white solid using the above-mentioned compound (2.11 g).
$^1$H-NMR (300 Mz, DMSO-$d_6$) δ0.88 (3H, t, J=7.1 Hz), 2.69-2.87 (2H, m), 3.14-3.20 (1H, m), 3.41-3.63 (2H, m), 5.33 (2H, s), 6.76 (2H, brs), 7.04-7.21 (3H, m), 7.49-7.53 (2H, m), 7.76 (1H, dd, J=8.3, 2.3 Hz), 8.36 (1H, d, J=2.3 Hz), 12.53 (1H, brs).

(3) 2-{[1-(2-chloro-5-pyridylmethyl)-1H-pyrazol-4-yl]methyl}-N-ethyl-N-(4-fluorophenyl)-N'-((E)-styrylsulfonyl)malonamide In the same manner as in Example 1 (2), the title compound (1.27 g) was obtained as a white powder using the above-mentioned compound (1.91 g) and trans-β-styrenesulfonamide (810 mg).
$^1$H-NMR (300 Mz, DMSO-$d_6$) δ0.90 (3H, t, J=7.1 Hz), 2.63-2.92 (2H, m), 3.19-3.31 (1H, m), 3.47-3.60 (2H, m), 5.25 (2H, s), 7.00-7.21 (5H, m), 7.31 (1H, d, J=15.4 Hz), 7.41-7.59 (7H, m), 7.77-7.80 (2H, m), 8.24 (1H, d, J=2.1 Hz), 11.65 (1H, brs).
MS: 596(M+H)$^+$.

Example 382

Synthesis of N-ethyl-N-(4-fluorophenyl)-2-{[1-(3-pyridylmethyl)-1H-pyrazol-4-yl]methyl}-N'-((E)-styrylsulfonyl)malonamide hydrochloride In the same manner as in Example 379, the title compound (51 mg) was obtained as a white solid using the compound (1.24 g) obtained in Example 381.
$^1$H-NMR (400 Mz, DMSO-$d_6$) δ0.91 (3H, t, J=7.2 Hz), 2.64-2.90 (2H, m), 3.30-3.37 (1H, m), 3.48-3.60 (2H, m), 5.38 (2H, s), 7.08-7.21 (5H, m), 7.31 (1H, d, J=15.6 Hz), 7.48-7.49 (4H, m), 7.56 (1H, d, J=15.6 Hz), 7.73-7.80 (3H, m), 7.96 (1H, d, J=7.6 Hz), 8.61 (1H, s), 8.71 (1H, d, J=0.8 Hz), 11.68 (1H, brs).
MS: 562(M+H)$^+$.

Example 383

Synthesis of 2-{[1-(2-aminobenzyl)-1H-pyrazol-4-yl]methyl}-N-ethyl-N-phenyl-N'-((E)-styrylsulfonyl)malonamide (1) triethyl 2-[1-(2-nitrobenzyl)-1H-pyrazol-4-yl]ethane-1,1,1-tricarboxylate In the same manner as in Example 371 (5), the title compound (810 mg) was obtained as an oil using hydrochloride salt (1.13 g) of the compound obtained in Example 371 (4) and 2-nitrobenzyl bromide (700 mg).
$^1$H-NMR (400 Mz, CDCl$_3$) δ1.25 (9H, t, J=1.8 Hz), 4.22 (6H, q, J=1.8 Hz), 5.67 (2H, s), 6.69 (1H, d, J=7.6 Hz), 7.43-7.53 (2H, m), 7.46 (1H, s), 7.51 (1H, s), 8.09-8.11 (1H, m).

(2) monoethyl{[1-(2-nitrobenzyl)-1H-pyrazol-4-yl]methyl}malonate

In the same manner as in Example 117 (2), the title compound (630 mg) was obtained as an oil using the above-mentioned compound (810 mg).
$^1$H-NMR (400 Mz, DMSO-$d_6$) δ1.12 (3H, t, J=7.2 Hz), 2.91 (2H, d, J=8.0 Hz), 3.54-3.60 (1H, m), 4.07 (2H, q, J=7.2 Hz), 5.64 (2H, s), 6.70-6.75 (1H, m), 7.37 (1H, s), 7.51-7.70 (2H, m), 7.63 (1H, s), 8.06-8.11 (1H, m), 12.85 (1H, brs).

(3) ethyl 3-(N-ethyl-N-phenylamino)-2-{[1-(2-nitrobenzyl)-1H-pyrazol-4-yl]methyl}-3-oxopropionate In the same manner as in Example 1 (4), the title compound (568 mg) was obtained as an oil using the above-mentioned compound (630 mg) and N-ethylaniline (280 μL).
$^1$H-NMR (300 Mz, CDCl$_3$) δ1.08 (3H, t, J=7.1 Hz), 1.24 (3H, t, J=7.1 Hz), 2.88-3.17 (2H, m), 3.35-3.42 (1H, m), 3.60-3.82 (2H, m), 4.13 (2H, g, J=7.1 Hz), 5.67 (2H, s), 6.83-6.95 (3H, m), 7.26-7.36 (5H, m), 7.40-7.56 (2H, m), 8.11 (1H, d, J=7.8 Hz).

(4) 3-(N-ethyl-N-phenylamino)-2-{[1-(2-nitrobenzyl)-1H-pyrazol-4-yl]methyl}-3-oxopropionic acid In the same manner as in Example 1 (3), the title compound (450 mg) was obtained as a white powder using the above-mentioned compound (568 mg).
$^1$H-NMR (400 Mz, DMSO-d$_6$) δ0.93 (3H, t, J=7.2 Hz), 2.72-2.89 (2H, m), 3.18-3.25 (1H, m), 3.52-3.61 (2H, m), 5.64 (2H, s), 6.87 (2H, brs), 6.92-7.00 (1H, m), 7.14 (1H, s), 7.36 (3H, brs), 7.45 (1H, s), 7.53-7.61 (1H, m), 7.64-7.72 (1H, m), 8.05-8.10 (1H, m), 12.56 (1H, brs).

(5) N-ethyl-2-{[1-(2-nitrobenzyl)-1H-pyrazol-4-yl]methyl}-N-phenyl-N'-((E)-styrylsulfonyl)malonamide In the same manner as in Example 1 (2), the title compound (450 mg) was obtained as a pale-yellow solid using the above-mentioned compound (450 mg) and trans-β-styrenesulfonamide (200 mg).
$^1$H-NMR (400 Mz, DMSO-d$_6$) δ0.88-0.98 (3H, m), 2.66-3.93 (2H, m), 3.30-3.42 (1H, m), 3.49-3.65 (2H, m), 5.58 (2H, s), 6.70-6.77 (1H, m), 7.03-7.12 (3H, m), 7.27-7.69 (11H, m), 7.74-7.81 (2H, m), 8.06-8.11 (1H, m), 11.70 (1H, brs).

(6) 2-{[1-(2-aminobenzyl)-1H-pyrazol-4-yl]methyl}-N-ethyl-N-phenyl-N'-((E)-styrylsulfonyl)malonamide To a solution of the above-mentioned compound (430 mg) in ethanol (20 mL) were added acetic acid (1.0 mL) and zinc powder (500 mg), and the mixture was heated under reflux for 30 min. Insoluble material was removed by filtration, and the filtrate was concentrated under reduced pressure. Ethyl acetate (30 mL) was added to the residue, and the mixture was stirred. The precipitate was collected by filtration to give the title compound (187 mg) as a white solid.
$^1$H-NMR (300 Mz, DMSO-d$_6$) δ0.84 (3H, t, J=7.1 Hz), 2.58-2.90 (2H, m), 3.24-3.28 (1H, m), 3.39-3.50 (2H, m), 5.09 (2H, s), 5.24 (2H, brs), 6.48-6.55 (1H, m), 6.63-6.69 (1H, m), 6.80 (2H, brs), 6.95-7.42 (12H, m), 7.49-7.54 (2H, m).
MS: 558(M+H)$^+$.

Example 384

Synthesis of 2-{[1-(3-aminobenzyl)-1H-pyrazol-4-yl]methyl}-N-ethyl-N-phenyl-N'-((E)-styrylsulfonyl)malonamide (1) triethyl 2-[1-(3-nitrobenzyl)-1H-pyrazol-4-yl]ethane-1,1,1-tricarboxylate In the same manner as in Example 371 (5), the title compound (600 mg) was obtained as an oil using hydrochloride salt (1.13 g) of the compound obtained in Example 371 (4) and 3-nitrobenzyl bromide (560 mg).
$^1$H-NMR (400 Mz, CDCl$_3$) δ1.23 (9H, t, J=7.2 Hz), 3.31 (2H, s), 4.20 (2H, q, J=7.2 Hz), 5.33 (2H, s), 7.42-7.52 (4H, m), 8.01 (1H, s), 8.12-8.16 (1H, m).

(2) monoethyl{[1-(3-nitrobenzyl)-1H-pyrazol-4-yl]methyl}malonate

In the same manner as in Example 117 (2), the title compound (465 mg) was obtained as an oil using the above-mentioned compound (600 mg).
$^1$H-NMR (400 Mz, DMSO-d$_6$) δ1.09 (3H, t, J=7.2 Hz), 2.89 (2H, d, J=8.0 Hz), 3.56 (1H, t, J=8.0 Hz), 4.05 (2H, q, J=7.2 Hz), 5.42 (2H, s), 7.34 (1H, s), 7.58-7.69 (3H, m), 8.05 (1H, s), 8.14 (1H, d, J=7.6 Hz), 12.88 (1H, brs).

(3) ethyl 3-(N-ethyl-N-phenylamino)-2-{[1-(3-nitrobenzyl)-1H-pyrazol-4-yl]methyl}-3-oxopropionate In the same manner as in Example 1 (4), the title compound (400 mg) was obtained as an oil using the above-mentioned compound (465 mg) and N-ethylaniline (210 μL).
$^1$H-NMR (400 Mz, CDCl$_3$) δ1.02 (3H, t, J=7.2 Hz), 1.23 (3H, t, J=7.2 Hz), 2.91 (1H, dd, J=14.4, 5.6 Hz), 3.10 (1H, dd, J=14.4, 9.6 Hz), 3.37 (1H, dd, J=9.6, 5.6 Hz), 3.61-3.72 (2H, m), 4.12 (2H, q, J=7.2 Hz), 5.34 (2H, s), 6.83 (2H, brs), 7.24-7.38 (5H, m), 7.50-7.56 (2H, m), 8.09 (1H, s), 8.15-8.17 (1H, m).

(4) 3-(N-ethyl-N-phenylamino)-2-{[1-(3-nitrobenzyl)-1H-pyrazol-4-yl]methyl}-3-oxopropionic acid In the same manner as in Example 1 (3), the title compound (384 mg) was obtained as an oil using the above-mentioned compound (400 mg).
$^1$H-NMR (400 Mz, DMSO-d$_6$) δ0.86 (3H, t, J=7.2 Hz), 2.69-2.89 (2H, m), 3.12-3.20 (1H, m), 3.42-3.63 (2H, m), 4.03 (2H, q, J=7.2 Hz), 5.44 (2H, s), 6.71 (2H, brs), 7.13 (1H, s), 0.21-7.36 (3H, m), 7.50 (1H, s), 7.62-7.77 (2H, m), 8.13-8.17 (2H, m), 12.55 (1H, brs).

(5) N-ethyl-2-{[1-(3-nitrobenzyl)-1H-pyrazol-4-yl]methyl}-N-phenyl-N'-((E)-styrylsulfonyl)malonamide In the same manner as in Example 1 (2), the title compound (272 mg) was obtained as a white solid using the above-mentioned compound (375 mg) and trans-β-styrenesulfonamide (163 mg).
$^1$H-NMR (300 Mz, DMSO-d$_6$) δ0.89 (3H, t, J=7.2 Hz), 2.62-2.93 (2H, m), 7.15-3.31 (1H, m), 3.45-3.62 (2H, m), 5.37 (2H, s), 6.90-7.08 (3H, m), 7.20-7.64 (11H, m), 7.70-7.82 (2H, m), 8.03 (1H, s), 8.01-8.18 (1H, m), 11.68 (1H, brs).

(6) 2-{[1-(3-aminobenzyl)-1H-pyrazol-4-yl]methyl}-N-ethyl-N-phenyl-N'-((E)-styrylsulfonyl)malonamide In the same manner as in Example 383 (6), the title compound (107 mg) was obtained as a white solid using the above-mentioned compound (260 mg).
$^1$H-NMR (300 Mz, DMSO-d$_6$) δ0.88 (3H, t, J=7.1 Hz), 2.58-2.94 (2H, m), 3.24-3.30 (1H, m), 3.40-3.57 (2H, m), 5.02 (2H, s), 5.06 (2H, s), 6.32-6.50 (3H, m), 6.75-7.22 (10H, m), 7.29-7.43 (3H, m), 7.49-7.56 (2H, m).
MS: 558(M+H)$^+$.

Example 385

Synthesis of 2-[(1-benzyl-1H-pyrazol-4-yl)methyl]-N,N-diethyl-N'-((E)-styrylsulfonyl)malonamide (1) ethyl 2-[(1-benzyl-1H-pyrazol-4-yl)methyl]-3-(N,N-diethylamino)-3-oxopropionate In the same manner as in Example 1 (4), the title compound (3.62 g) was obtained as an oil using the compound (3.48 g) obtained in Example 371 (6).

¹H-NMR (300 Mz, DMSO-d₆) δ0.86-0.92 (6H, m), 1.12 (3H, t, J=7.1 Hz), 2.87 (2H, d, J=7.4 Hz), 3.15-3.24 (4H, m), 3.86 (1H, t, J=7.4 Hz), 4.04 (2H, q, J=7.4 Hz), 5.23 (2H, s), 7.15 (2H, d, J=7.2 Hz), 7.26-7.33 (4H, m), 7.50 (1H, s).

(2) 2-[(1-benzyl-1H-pyrazol-4-yl)methyl]-3-(N,N-diethylamino)-3-oxopropionic acid In the same manner as in Example 1 (3), the title compound (3.32 g) was obtained as an oil using the above-mentioned compound (3.62 g).
¹H-NMR (400 Mz, DMSO-d₆) δ0.82-0.91 (6H, m), 2.81-2.89 (2H, m), 3.11-3.30 (4H, m), 3.75 (1H, t, J=7.2 Hz), 5.23 (2H, s), 7.15 (2H, d, J=6.4 Hz), 7.25-7.33 (4H, m), 7.49 (1H, s), 12.56 (1H, brs).

(3) 2-[(1-benzyl-1H-pyrazol-4-yl)methyl]-N,N-diethyl-N'-((E)-styrylsulfonyl)malonamide In the same manner as in Example 1 (2), the title compound (2.02 g) was obtained as a white solid using the above-mentioned compound (3.32 g) and trans-β-styrenesulfonamide (1.85 g).
¹H-NMR (400 Mz, DMSO-d₆) δ0.90-0.96 (6H, m), 2.86 (2H, d, J=7.2 Hz), 3.11-3.27 (4H, m), 3.73 (1H, t, J=7.2 Hz), 5.17 (2H, s), 7.13 (2H, d, J=7.2 Hz), 7.23-7.32 (5H, m), 7.43-7.50 (4H, m), 7.56 (1H, d, J=15.2 Hz), 7.72 (2H, d, J=7.2 Hz), 11.99 (1H, brs).
MS: 495(M+H)⁺.

Example 386

Synthesis of N,N-diethyl-2-{[1-(4-fluorobenzyl)-1H-pyrazol-4-yl]methyl}-N'-((E)-styrylsulfonyl)malonamide (1) ethyl 3-(N,N-diethylamino)-2-{[1-(4-fluorobenzyl)-1H-pyrazol-4-yl]methyl}-3-oxopropionate In the same manner as in Example 1 (4), the title compound (1.71 g) was obtained as an oil using the compound (2.12 g) obtained in Example 375 (5).
¹H-NMR (400 Mz, CDCl₃) δ0.93-1.07 (6H, m), 1.26 (3H, t, J=7.2 Hz), 3.00-3.17 (3H, m), 3.24-3.40 (3H, m), 3.62-3.66 (1H, m), 4.15 (2H, q, J=7.2 Hz), 5.18 (2H, s), 6.97-7.03 (2H, m), 7.14-7.20 (2H, m), 7.21 (1H, s), 7.36 (1H, s).

(2) 3-(N,N-diethylamino)-2-{[1-(4-fluorobenzyl)-1H-pyrazol-4-yl]methyl}-3-oxopropionic acid In the same manner as in Example 1 (3), the title compound (1.48 g) was obtained as a pale-yellow solid using the above-mentioned compound (1.70 g).
¹H-NMR (300 Mz, DMSO-d₆) δ0.83-0.90 (6H, m), 2.83 (2H, d, J=7.2 Hz), 3.05-3.32 (4H, m), 3.74 (1H, t, J=7.2 Hz), 5.22 (2H, s), 7.11-7.25 (5H, m), 7.49 (1H, s), 12.58 (1H, brs).

(3) N,N-diethyl-2-{[1-(4-fluorobenzyl)-1H-pyrazol-4-yl]methyl}-N'-((E)-styrylsulfonyl)malonamide In the same manner as in Example 1 (2), the title compound (740 mg) was obtained as a white solid using the above-mentioned compound (1.48 g) and trans-β-styrenesulfonamide (780 mg).
¹H-NMR (400 Mz, DMSO-d₆) δ0.89-0.95 (6H, m), 2.86 (2H, d, J=7.2 Hz), 3.11-3.27 (4H, m), 3.72 (1H, t, J=7.2 Hz), 5.16 (2H, s), 7.09-7.23 (5H, m), 7.30 (1H, d, J=15.2 Hz), 7.43-7.48 (4H, m), 7.56 (1H, d, J=15.2 Hz), 7.73 (2H, dd, J=7.6, 1.6 Hz), 11.99 (1H, brs).
MS: 513(M+H)⁺.

Example 387

Synthesis of 2-{[1-(4-chlorobenzyl)-1H-pyrazol-4-yl]methyl}-N,N-diethyl-N'-((E)-styrylsulfonyl)malonamide (1) ethyl 1-(4-chlorobenzyl)-1H-pyrazole-4-carboxylate In the same manner as in Example 375 (1), the title compound (33.8 g) was obtained as a white solid using 4-chlorobenzyl chloride (25.0 g).
¹H-NMR (400 Mz, DMSO-d₆) δ1.26 (3H, t, J=7.2 Hz), 4.21 (2H, q, J=7.2 Hz), 5.37 (2H, s), 7.29 (2H, d, J=8.4 Hz), 7.42 (2H, d, J=8.4 Hz), 7.87 (1H, s), 8.47 (1H, s).

(2) [1-(4-chlorobenzyl)-1H-pyrazol-4-yl]methanol

In the same manner as in Example 128 (2), the title compound (8.20 g) was obtained as an oil using the above-mentioned compound (1.00 g).
¹H-NMR (400 Mz, CDCl₃) δ4.58 (2H, d, J=4.0 Hz), 5.24 (2H, s), 7.16 (2H, d, J=8.4 Hz), 7.30-7.34 (2H, m), 7.38 (1H, s), 7.53 (1H, s).

(3) 1-(4-chlorobenzyl)-4-(chloromethyl)-1H-pyrazole

In the same manner as in Example 375 (3), the title compound (8.19 g) was obtained as a white solid using the above-mentioned compound (7.97 g).
¹H-NMR (400 Mz, CDCl₃) δ4.52 (2H, s), 5.24 (2H, s), 7.15 (2H, d, J=8.4 Hz), 7.29-7.34 (2H, m), 7.40 (1H, s), 7.55 (1H, s).

(4) triethyl 2-[1-(4-chlorobenzyl)-1H-pyrazol-4-yl]ethane-1,1,1-tricarboxylate

In the same manner as in Example 117 (1), a crude product was obtained using the above-mentioned compound (8.18 g). The crude product was purified by silica gel column chromatography to give the title compound (12.3 g) as an oil.
¹H-NMR (400 Mz, CDCl₃) δ1.21 (9H, t, J=7.2 Hz), 3.29 (2H, s), 4.18 (6H, q, J=7.2 Hz), 5.19 (2H, s), 7.09 (2H, d, J=8.4 Hz), 7.28 (2H, d, J=8.4 Hz), 7.36 (1H, s), 7.39 (1H, s).

(5) monoethyl {[1-(4-chlorobenzyl)-1H-pyrazol-4-yl]methyl}malonate

In the same manner as in Example 117 (2), the title compound (9.30 g) was obtained as a white solid using the above-mentioned compound (12.3 g).
¹H-NMR (400 Mz, CDCl₃) δ1.21 (3H, t, J=6.8 Hz), 3.07-3.09 (2H, m), 3.55 (1H, t, J=7.2 Hz), 4.15-4.20 (2H, m), 5.21 (2H, s), 7.09 (2H, d, J=8.0 Hz), 7.24-7.28 (2H, m), 7.29 (1H, s), 7.39 (1H, s).

(6) ethyl 2-{[1-(4-chlorobenzyl)-1H-pyrazol-4-yl]methyl}-3-(N,N-diethylamino)-3-oxopropionate In the same manner as in Example 1 (4), the title compound (3.90 g) was obtained as an oil using the above-mentioned compound (4.71 g).

¹H-NMR (300 Mz, CDCl₃) δ0.98 (3H, t, J=7.2 Hz), 1.04 (3H, t, J=7.1 Hz), 1.22 (3H, t, J=7.1 Hz), 3.00-3.39 (6H, m), 4.15 (2H, q, J=7.1 Hz), 5.18 (2H, s), 7.11 (2H, d, J=8.3 Hz), 7.22 (1H, s), 7.28 (2H, d, J=8.3 Hz), 7.36 (1H, s).

(7) 2-{[1-(4-chlorobenzyl)-1H-pyrazol-4-yl]methyl}-3-(N,N-diethylamino)-3-oxopropionic acid In the same manner as in Example 1 (3), the title compound (3.60 g) was obtained as a white solid using the above-mentioned compound (3.88 g).
¹H-NMR (400 Mz, CDCl₃) δ1.04 (6H, t, J=7.2 Hz), 2.95-3.22 (5H, m), 3.46-3.55 (1H, m), 3.60-3.66 (1H, m), 5.20 (2H, s), 7.10-7.15 (2H, m), 7.22-7.36 (4H, m).

(8) 2-{[1-(4-chlorobenzyl)-1H-pyrazol-4-yl]methyl}-N,N-diethyl-N'-((E)-styrylsulfonyl)malonamide In the same manner as in Example 1 (2), the title compound (1.79 g) was obtained as a white solid using the above-mentioned compound (3.51 g) and trans-β-styrenesulfonamide (1.76 g).
¹H-NMR (400 Mz, DMSO-d₆) δ0.89-0.96 (6H, m), 2.86 (2H, d, J=7.2 Hz), 3.09-3.28 (4H, m), 3.73 (1H, t, J=7.2 Hz), 5.18 (2H, s), 7.15 (2H, d, J=8.0 Hz), 7.24-7.36 (4H, m), 7.43-7.49 (4H, m), 7.56 (1H, d, J=15.6 Hz), 7.37 (2H, d, J=8.0 Hz), 11.99 (1H, brs).
MS: 529(M+H)⁺.

Example 388

Synthesis of 2-{[1-(2-chloro-5-pyridylmethyl)-1H-pyrazol-4-yl]methyl}-N,N-diethyl-N'-((E)-styrylsulfonyl)malonamide (1) ethyl 2-{[1-(2-chloro-5-pyridylmethyl)-1H-pyrazol-4-yl]methyl}-3-(N,N-diethylamino)-3-oxopropionate In the same manner as in Example 1 (4), the title compound (1.15 g) was obtained as a white powder using the compound (1.63 g) obtained in Example 378 (5).
¹H-NMR (300 Mz, CDCl₃) δ0.99 (3H, t, J=7.2 Hz), 1.04 (3H, t, J=7.2 Hz), 1.22 (3H, t, J=7.2 Hz), 3.00-3.44 (6H, m), 3.62-3.69 (1H, m), 4.16 (2H, q, J=7.2 Hz), 5.21 (2H, s), 7.26-7.29 (2H, m), 7.38 (1H, s), 7.47 (1H, dd, J=8.1, 2.4 Hz), 8.25 (1H, d, J=2.4 Hz).

(2) 2-{[1-(2-chloro-5-pyridylmethyl)-1H-pyrazol-4-yl]methyl}-3-(N,N-diethylamino)-3-oxopropionic acid In the same manner as in Example 1 (3), the title compound (850 mg) was obtained as a white powder using the above-mentioned compound (1.15 g).
¹H-NMR (300 Mz, DMSO-d₆) δ0.81-0.89 (6H, m), 2.83 (2H, d, J=7.2 Hz), 3.10-3.31 (4H, m), 3.75 (1H, t, J=7.2 Hz), 5.30 (2H, s), 7.27 (1H, s), 7.49 (1H, d, J=8.1 Hz), 7.56 (1H, s), 7.64 (1H, dd, J=8.1, 2.4 Hz), 8.26 (1H, d, J=2.4 Hz), 12.56 (1H, brs).

(3) 2-{[1-(2-chloro-5-pyridylmethyl)-1H-pyrazol-4-yl]methyl}-N,N-diethyl-N'-((E)-styrylsulfonyl)malonamide In the same manner as in Example 1 (2), the title compound (442 mg) was obtained as a white solid using the above-mentioned compound (850 mg) and trans-β-styrenesulfonamide (430 mg).
¹H-NMR (300 Mz, DMSO-d₆) δ0.86-0.94 (6H, m), 2.86 (2H, d, J=6.6 Hz), 3.07-3.30 (4H, m), 3.71 (1H, t, J=6.6 Hz), 5.25 (2H, s), 7.26 (1H, s), 7.34 (1H, d, J=15.6 Hz), 7.45-7.47 (4H, m), 7.54-7.61 (2H, m), 7.73-7.76 (2H, m), 8.25 (1H, d, J=2.1 Hz), 12.07 (1H, brs).
MS: 530(M+H)⁺.

Example 389

Synthesis of 2-[(1-benzyl-1H-pyrazol-4-yl)methyl]-N,N-diethyl-N'-(2-naphthylsulfonyl)malonamide In the same manner as in Example 1 (2), the title compound (2.05 g) was obtained as a white solid using the compound (2.14 g) obtained in Example 358 (2).
¹H-NMR (400 Mz, DMSO-d₆) δ0.78-0.98 (6H, m), 2.73 (2H, m), 3.06-3.21 (4H, m), 3.70 (1H, t, J=7.2 Hz), 5.08 (1H, d, J=10.2 Hz), 5.14 (1H, d, J=10.2 Hz), 7.11 (2H, d, J=6.8 Hz), 7.15 (1H, s), 7.23-7.32 (3H, m), 7.34 (1H, s), 7.68-7.77 (2H, m), 7.81 (1H, dd, J=8.4, 1.6 Hz), 8.07 (1H, d, J=8.0 Hz), 8.12 (1H, d, J=8.4 Hz), 8.21 (1H, d, J=8.0 Hz), 8.57 (1H, d, J=1.6 Hz), 12.29 (1H, brs).
MS: 519(M+H)⁺.

Example 390

Synthesis of N,N-diethyl-2-{[1-(2-fluorobenzyl)-1H-pyrazol-4-yl]methyl}-N'-(2-naphthylsulfonyl)malonamide (1) ethyl 1-(2-fluorobenzyl)-1H-pyrazole-4-carboxylate In the same manner as in Example 375 (1), the title compound (1.90 g) was obtained as an oil using 2-fluorobenzyl bromide (1.53 g).
¹H-NMR (300 Mz, CDCl₃) δ1.33 (3H, t, J=7.2 Hz), 4.28 (2H, q, J=7.2 Hz), 5.36 (2H, s), 7.06-7.38 (4H, m), 7.92 (1H, s), 7.93 (1H, s).

(2) [1-(2-fluorobenzyl)-1H-pyrazol-4-yl]methanol

In the same manner as in Example 128 (2), a crude product was obtained using the above-mentioned compound (1.90 g), and the crude product was purified by silica gel column chromatography to give the title compound (860 mg) as an oil.
¹H-NMR (400 Mz, CDCl₃) δ1.54 (3H, t, J=5.2 Hz), 4.57 (2H, d, J=5.2 Hz), 5.33 (2H, s), 7.05-7.13 (2H, m), 7.17-7.20 (1H, m), 7.25-7.33 (1H, m), 7.44 (1H, s), 7.52 (1H, s).

(3) 1-(2-fluorobenzyl)-4-(chloromethyl)-1H-pyrazole

In the same manner as in Example 375 (3), the title compound (937 mg) was obtained as an oil using the above-mentioned compound (860 mg).
¹H-NMR (400 Mz, CDCl₃) δ4.53 (2H, s), 5.33 (2H, s), 7.06-7.34 (4H, m), 7.47 (1H, s), 7.54 (1H, s).

(4) triethyl 2-[1-(2-fluorobenzyl)-1H-pyrazol-4-yl]ethane-1,1,1-tricarboxylate

In the same manner as in Example 117 (1), the title compound (1.70 g) was obtained as an oil using the above-mentioned compound (937 mg).
¹H-NMR (400 Mz, CDCl₃) δ1.21 (9H, t, J=7.2 Hz), 3.30 (2H, s), 4.18 (6H, q, J=7.2 Hz), 5.28 (2H, s), 7.03-7.09 (3H, m), 7.25-7.28 (1H, m), 7.39 (1H, s), 7.40 (1H, s).

(5) monoethyl {[1-(2-fluorobenzyl)-1H-pyrazol-4-yl]methyl}malonate

In the same manner as in Example 117 (2), the title compound (1.24 g) was obtained as an oil using the above-mentioned compound (1.68 g).
$^1$H-NMR (400 Mz, CDCl$_3$) δ1.23 (3H, t, J=7.2 Hz), 3.09-3.14 (2H, m), 3.56 (1H, t, J=7.2 Hz), 4.17 (2H, q, J=7.2 Hz), 5.30 (2H, s), 7.04-7.13 (3H, m), 7.26-7.30 (1H, m), 7.30 (1H, s), 7.38 (1H, s).

(6) ethyl 3-(N,N-diethylamino)-2-{[1-(2-fluorobenzyl)-1H-pyrazol-4-yl]methyl}-3-oxopropionate In the same manner as in Example 1 (4), the title compound (1.06 g) was obtained as an oil using the above-mentioned compound (1.24 g).
$^1$H-NMR (300 Mz, DMSO-d$_6$) δ0.85-0.92 (6H, m), 1.12 (3H, t, J=7.0 Hz), 2.87 (2H, d, J=7.4 Hz), 3.15-3.23 (4H, m), 3.86 (1H, t, J=7.4 Hz), 4.04 (2H, q, J=7.0 Hz), 5.29 (2H, s), 7.03-7.22 (3H, m), 7.26 (1H, s), 7.30-7.39 (1H, m), 7.49 (1H, s).

(7) 3-(N,N-diethylamino)-2-{[1-(2-fluorobenzyl)-1H-pyrazol-4-yl]methyl}-3-oxopropionic acid In the same manner as in Example 1 (3), the title compound (962 mg) was obtained as an oil using the above-mentioned compound (1.04 g).
$^1$H-NMR (400 Mz, DMSO-d$_6$) δ0.83-0.91 (6H, m), 2.83-2.85 (2H, m), 3.12-3.27 (4H, m), 3.74 (1H, dd, J=8.0, 7.2 Hz), 5.28 (2H, s), 7.07-7.22 (3H, m), 7.24 (1H, s), 7.32-7.36 (1H, m), 7.47 (1H, s).

(8) N,N-diethyl-2-{[1-(2-fluorobenzyl)-1H-pyrazol-4-yl]methyl}-N'-(2-naphthylsulfonyl)malonamide In the same manner as in Example 1 (2), the title compound (577 mg) was obtained as a white solid using the above-mentioned compound (930 mg).
$^1$H-NMR (400 Mz, DMSO-d$_6$) δ0.77-0.88 (6H, m), 2.71-2.82 (2H, m), 3.04-3.20 (4H, m), 3.70 (1H, t, J=7.2 Hz), 5.15 (1H, d, J=10.2 Hz), 5.29 (1H, d, J=10.2 Hz), 7.01-7.05 (1H, m), 7.10-7.21 (3H, m), 7.31-7.37 (2H, m), 7.68-7.76 (2H, m), 7.82 (1H, dd, J=8.8, 1.6 Hz), 8.06 (1H, d, J=8.0 Hz), 8.13 (1H, d, J=8.8 Hz), 8.21 (1H, d, J=8.0 Hz), 8.57 (1H, d, J=1.6 Hz), 12.31 (1H, brs).
MS:537(M+H)$^+$.

Example 391

Synthesis of 2-{[1-(2-chlorobenzyl)-1H-pyrazol-4-yl]methyl}-N,N-diethyl-N'-(2-naphthylsulfonyl)malonamide (1) ethyl 2-{[1-(2-chlorobenzyl)-1H-pyrazol-4-yl]methyl}-3-(N,N-diethylamino)-3-oxopropionate In the same manner as in Example 1 (4), the title compound (389 mg) was obtained as an oil using the compound (410 mg) obtained in Example 377 (2).
$^1$H-NMR (400 Mz, CDCl$_3$) δ0.99-1.07 (6H, m), 1.22 (3H, t, J=7.2 Hz), 3.03-3.18 (3H, m), 3.23-3.42 (3H, m), 3.66 (1H, dd, J=9.6, 6.0 Hz), 4.16 (2H, q, J=7.2 Hz), 5.34 (2H, s), 6.98 (1H, dd, J=7.2, 1.2 Hz), 7.19-7.28 (3H, m), 7.36-7.38 (2H, m).

(2) 2-{[1-(2-chlorobenzyl)-1H-pyrazol-4-yl]methyl}-3-(N,N-diethylamino)-3-oxopropionic acid In the same manner as in Example 1 (3), the title compound (351 mg) was obtained as an oil using the above-mentioned compound (378 mg).
$^1$H-NMR (400 Mz, DMSO-d$_6$) δ0.90 (6H, t, J=7.2 Hz), 2.83-2.90 (2H, m), 3.10-3.30 (4H, m), 3.73-3.79 (1H, m), 5.33 (2H, s), 6.85-6.92 (1H, m), 7.24-7.36 (3H, m), 7.45-7.52 (2H, m), 12.52 (1H, brs).

(3) 2-{[1-(2-chlorobenzyl)-1H-pyrazol-4-yl]methyl}-N,N-diethyl-N'-(2-naphthylsulfonyl)malonamide In the same manner as in Example 1 (2), the title compound (150 mg) was obtained as a white solid using the above-mentioned compound (351 mg).
$^1$H-NMR (400 Mz, DMSO-d$_6$) δ0.75-0.88 (6H, m), 2.74-2.84 (2H, m), 3.07-3.21 (4H, m), 3.73 (1H, t, J=7.2 Hz), 5.22 (2H, s), 6.84 (1H, d, J=7.6 Hz), 7.20 (1H, s), 7.23-7.33 (2H, m), 7.36 (1H, s), 7.45 (1H, d, J=8.0 Hz), 7.67-7.84 (3H, m), 8.06 (1H, d, J=8.0 Hz), 8.12 (1H, d, J=8.8 Hz), 8.20 (1H, d, J=8.0 Hz), 8.57 (1H, s), 12.30 (1H, brs).
MS: 553(M+H)$^+$.

Example 392

Synthesis of N,N-diethyl-N'-(2-naphthylsulfonyl)-2-{[1-((2E)-3-phenyl-2-propen-1-yl)-1H-pyrazol-4-yl]methyl}malonamide (1) triethyl 2-[1-((2E)-3-phenyl-2-propen-1-yl)-1H-pyrazol-4-yl]ethane-1,1,1-tricarboxylate In the same manner as in Example 371 (5), the title compound (1.04 g) was obtained as an oil using hydrochloride salt (1.50 g) of the compound obtained in Example 371 (4) and trans-cinnamyl chloride (630 μL).
$^1$H-NMR (300 Mz, CDCl$_3$) δ1.23 (9H, t, J=7.1 Hz), 3.31 (2H, s), 4.20 (6H, q, J=7.1 Hz), 4.82 (1H, d, J=8.8 Hz), 6.26-6.54 (2H, m), 7.22-7.42 (7H, m).

(2) monoethyl {[1-((2E)-3-phenyl-2-propen-1-yl)-1H-pyrazol-4-yl]methyl}malonate

In the same manner as in Example 117 (2), the title compound (540 mg) was obtained as an oil using the above-mentioned compound (1.04 g).
$^1$H-NMR (400 Mz, DMSO-d$_6$) δ1.11 (3H, t, J=7.2 Hz), 2.89 (2H, d, J=7.6 Hz), 3.55 (1H, t, J=7.6 Hz), 4.05 (2H, q, J=7.2 Hz), 4.83 (1H, d, J=5.6 Hz), 6.37-6.52 (2H, m), 7.22-7.46 (6H, m), 7.53 (1H, s), 12.79 (1H, brs).

(3) ethyl 3-(N,N-diethylamino)-3-oxo-2-{[1-((2E)-3-phenyl-2-propen-1-yl)-1H-pyrazol-4-yl]methyl}propionate In the same manner as in Example 1 (4), the title compound (496 mg) was obtained as an oil using the above-mentioned compound (530 mg).
$^1$H-NMR (400 Mz, CDCl$_3$) δ0.98-1.11 (6H, m), 1.22 (3H, t, J=7.2 Hz), 3.04-3.20 (3H, m), 3.31-3.38 (3H, m), 3.67 (1H, dd, J=8.8, 6.4 Hz), 4.16 (2H, q, J=7.2 Hz), 4.81 (2H, d, J=6.4 Hz), 6.27-6.34 (1H, m), 6.54 (1H, d, J=16.0 Hz), 7.23-7.37 (7H, m).

(4) 3-(N,N-diethylamino)-3-oxo-2-{[1-((2E)-3-phenyl-2-propen-1-yl)-1H-pyrazol-4-yl]methyl}propionic acid In the same manner as in Example 1 (3), the title compound (430 mg) was obtained as a white powder using the above-mentioned compound (493 mg).

$^1$H-NMR (400 Mz, DMSO-$d_6$) δ0.92 (6H, t, J=7.2 Hz), 2.86 (2H, d, J=7.2 Hz), 3.10-3.26 (4H, m), 3.71-3.79 (1H, m), 4.81 (2H, d, J=6.0 Hz), 6.33-6.53 (2H, m), 7.25-7.41 (6H, m), 7.45 (1H, s), 12.48 (1H, brs).

(5) N,N-diethyl-N'-(2-naphthylsulfonyl)-2-{[1-((2E)-3-phenyl-2-propen-1-yl)-1H-pyrazol-4-yl]methyl}malonamide In the same manner as in Example 1 (2), the title compound (315 mg) was obtained as a white powder using the above-mentioned compound (423 mg).

$^1$H-NMR (400 Mz, DMSO-$d_6$) δ0.83-0.88 (6H, m), 2.78 (2H, d, J=7.2 Hz), 3.07-3.25 (4H, m), 3.71 (1H, t, J=7.2 Hz), 4.68-4.71 (2H, m), 6.27-6.35 (1H, m), 6.47 (1H, d, J=16.0 Hz), 7.15 (1H, s), 7.25-7.41 (6H, m), 7.65-7.83 (3H, m), 8.06 (1H, d, J=8.0 Hz), 8.13 (1H, d, J=8.8 Hz), 8.21 (1H, d, J=8.0 Hz), 8.56 (1H, s), 12.28 (1H, brs).
MS: 545(M+H)$^+$.

Example 393

Synthesis of N,N-diethyl-N'-(2-naphthylsulfonyl)-2-{[1-(3-phenylpropyl)-1H-pyrazol-4-yl]methyl}malonamide In the same manner as in Example 7, the title compound (150 mg) was obtained as a white powder using the compound (170 mg) obtained in Example 392 at room temperature.

$^1$H-NMR (300 Mz, DMSO-$d_6$) δ0.83-0.87 (6H, m), 1.85-1.99 (2H, m), 2.44 (2H, t, J=7.8 Hz), 2.75 (2H, d, J=7.2 Hz), 3.06-3.27 (4H, m), 3.70 (1H, t, J=7.2 Hz), 3.77-3.92 (2H, m), 7.13-7.29 (7H, m), 7.65-7.83 (3H, m), 8.05-8.23 (3H, m), 8.57 (1H, s), 12.34 (1H, brs).
MS: 547(M+H)$^+$.

Example 394

Synthesis of 2-[(1-ethyl-1H-pyrazol-4-yl)methyl]-N-(4-fluorophenyl)-N-isopropyl-N'-((E)-styrylsulfonyl)malonamide (1) 5-[(1-ethyl-1H-pyrazol-4-yl)methyl]-2,2-dimethyl-1,3-dioxane-4,6-dione In the same manner as in Example 132 (1), the title compound (12.6 g) was obtained as a yellow solid using 1-ethyl-1H-pyrazole-4-carboxylic acid (10.0 g).

$^1$H-NMR (400 Mz, DMSO-$d_6$) δ1.30 (3H, t, J=7.2 Hz), 1.58 (3H, s), 1.78 (3H, s), 3.08 (2H, d, J=4.4 Hz), 4.03 (2H, q, J=7.2 Hz), 4.71 (1H, t, J=4.4 Hz), 7.18 (1H, s), 7.43 (1H, s).

(2) 2-[(1-ethyl-1H-pyrazol-4-yl)methyl]-3-[N-(4-fluorophenyl)-N-isopropylamino]-3-oxopropionic acid In the same manner as in Example 119 (2), a crude product was obtained using the above-mentioned compound (2.19 g) and 4-fluoro-N-isopropylaniline (5.33 g). This was purified by silica gel column chromatography to give the title compound (1.77 g) as a white powder.

$^1$H-NMR (400 Mz, DMSO-$d_6$) δ9.86-0.96 (6H, m), 1.33 (3H, t, J=7.2 Hz), 2.71 (1H, dd, J=14.0, 5.6 Hz), 2.80 (1H, dd, J=14.0, 9.6 Hz), 3.01 (1H, dd, J=9.6, 5.6 Hz), 4.07 (2H, q, J=7.2 Hz), 4.75-4.83 (1H, m), 6.26-6.34 (1H, m), 7.03 (1H, s), 7.15-7.24 (2H, m), 7.26-7.32 (1H, m), 7.32 (1H, s), 12.52 (1H, brs).

(3) 2-[(1-ethyl-1H-pyrazol-4-yl)methyl]-N-(4-fluorophenyl)-N-isopropyl-N'-((E)-styrylsulfonyl)malonamide In the same manner as in Example 1 (2), the title compound (843 mg) was obtained as a white solid using the above-mentioned compound (1.76 g) and trans-β-styrenesulfonamide (930 mg).

$^1$H-NMR (400 Mz, DMSO-$d_6$) δ0.82-0.96 (6H, m), 1.24 (3H, t, J=7.2 Hz), 2.70 (1H, dd, J=14.0, 5.6 Hz), 2.84 (1H, dd, J=14.0, 8.0 Hz), 3.18 (1H, dd, J=8.0, 5.6 Hz), 3.95 (2H, q, J=7.2 Hz), 4.70-4.77 (1H, m), 6.97 (1H, s), 6.97-7.15 (3H, m), 7.22 (1H, s), 7.26-7.36 (1H, m), 7.31 (1H, d, J=15.2 Hz), 7.46-7.50 (3H, m), 7.56 (1H, d, J=15.2 Hz), 7.79-7.81 (2H, m), 11.61 (1H, brs).
MS: 513(M+H)$^+$.

Example 395

Synthesis of N-(4-fluorophenyl)-N-isopropyl-2-[(1-isopropyl-1H-pyrazol-4-yl)methyl]-N'-((E)-styrylsulfonyl)malonamide (1) 5-[(1-isopropyl-1H-pyrazol-4-yl)methyl]-2,2-dimethyl-1,3-dioxane-4,6-dione In the same manner as in Example 132 (1), the title compound (11.2 g) was obtained as a yellow solid using 1-isopropyl-1H-pyrazole-4-carboxylic acid (7.98 g).

$^1$H-NMR (400 Mz, DMSO-$d_6$) δ1.34 (6H, d, J=6.9 Hz), 1.57 (3H, s), 1.78 (3H, s), 3.08 (2H, d, J=4.5 Hz), 4.40 (1H, sept, J=6.9 Hz), 4.69 (1H, t, J=4.5 Hz), 7.18 (1H, s), 7.44 (1H, s).

(2) 3-[N-(4-fluorophenyl)-N-isopropylamino]-2-[(1-isopropyl-1H-pyrazol-4-yl)methyl]-3-oxopropionic acid In the same manner as in Example 119 (2), the title compound (2.31 g) was obtained as a pale-yellow powder using the above-mentioned compound (3.06 g) and 4-fluoro-N-isopropylaniline (7.04 g).

$^1$H-NMR (400 Mz, DMSO-$d_6$) δ0.82-0.95 (6H, m), 1.38 (6H, d, J=6.4 Hz), 2.71 (1H, dd, J=14.0, 5.2 Hz), 2.81 (1H, dd, J=14.0, 9.6 Hz), 3.01 (1H, dd, J=9.6, 5.2 Hz), 4.44 (1H, sept, J=6.4 Hz), 4.76-4.83 (1H, m), 6.22-6.26 (1H, m), 7.04 (1H, s), 7.11-7.21 (2H, m), 7.27-7.32 (1H, m), 7.35 (1H, s), 12.52 (1H, brs).

(3) N-(4-fluorophenyl)-N-isopropyl-2-[(1-isopropyl-1H-pyrazol-4-yl)methyl]-N'-((E)-styrylsulfonyl)malonamide In the same manner as in Example 1 (2), the title compound (1.53 g) was obtained as a white solid using the above-mentioned compound (2.29 g) and trans-β-styrenesulfonamide (1.16 g).

¹H-NMR (300 Mz, DMSO-d₆) δ0.86-0.92 (6H, m), 1.29 (6H, d, J=6.5 Hz), 2.64-2.89 (2H, m), 3.14-3.20 (1H, m), 4.32 (1H, sept, J=6.5 Hz), 4.68-4.79 (1H, m), 6.96 (1H, s), 6.96-7.16 (3H, m), 7.23 (1H, s), 7.27-7.39 (1H, m), 7.31 (1H, d, J=15.4 Hz), 7.43-7.52 (3H, m), 7.56 (1H, d, J=15.4 Hz), 7.79-7.81 (2H, m), 11.61 (1H, brs).
MS: 527(M+H)⁺.

Example 396

Synthesis of N-isopropyl-2-[(1-isopropyl-1H-pyrazol-4-yl)methyl]-N-(3-trifluoromethylphenyl)-N'-((E)-styrylsulfonyl)malonamide (1) 3-[N-isopropyl-N-(3-trifluoromethylphenyl) amino]-2-[(1-isopropyl-1H-pyrazol-4-yl)methyl]-3-oxopropionic acid In the same manner as in Example 119 (2), the title compound (931 mg) was obtained as a pale-yellow powder using the compound (2.00 g) obtained in Example 395 (1) and N-isopropyl-3-trifluoromethylaniline (6.10 g).
¹H-NMR (300 Mz, DMSO-d₆) δ0.87-0.96 (6H, m), 1.28-1.46 (6H, m), 2.64-3.00 (3H, m), 4.32-4.50 (1H, m), 4.65-4.90 (1H, m), 6.42-6.60 (1H, m), 7.03 (1H, d, J=5.7 Hz), 7.35-7.82 (4H, m), 12.94 (1H, brs).

(2) N-isopropyl-2-[(1-isopropyl-1H-pyrazol-4-yl)methyl]-N-(3-trifluoromethylphenyl)-N'-((E)-styrylsulfonyl)malonamide In the same manner as in Example 1 (2), the title compound (643 mg) was obtained as a white solid using the above-mentioned compound (931 mg) and trans-β-styrenesulfonamide (410 mg).
¹H-NMR (400 Mz, DMSO-d₆) δ0.85-1.01 (6H, m), 1.27 (6H, d, J=6.4 Hz), 2.68-2.91 (2H, m), 3.08-3.17 (1H, m), 4.29 (1H, sept, J=6.4 Hz), 4.78 (1H, sept, J=6.7 Hz), 6.83-6.93 (1H, m), 7.14-7.86 (12H, m), 11.65 (1H, brs).
MS: 577(M+H)⁺.

Example 397

Synthesis of N-(4-fluorophenyl)-N-isopropyl-2-[(1-isopropyl-1H-pyrazol-4-yl)methyl]-N'-(2-naphthylsulfonyl)malonamide In the same manner as in Example 1 (2), the title compound (1.00 g) was obtained as a white solid using the compound (1.38 g) obtained in Example 395 (2).
¹H-NMR (400 Mz, DMSO-d₆) δ0.78-0.90 (6H, m), 1.29-1.32 (6H, m), 2.62 (1H, dd, J=14.0, 5.8 Hz), 2.75 (1H, dd, J=14.0, 7.6 Hz), 3.10-3.18 (1H, m), 4.24 (1H, sept, J=6.6 Hz), 4.68 (1H, sept, J=6.7 Hz), 6.79-6.97 (3H, m), 6.89 (1H, s), 7.09 (1H, s), 7.25-7.34 (1H, m), 7.67-7.82 (3H, m), 8.07-8.28 (3H, m), 8.56 (1H, s), 11.92 (1H, brs).
MS: 551(M+H)⁺.

Example 398

Synthesis of 2-[(1-benzyl-1H-pyrazol-4-yl)methyl]-N-ethyl-N-phenyl-N'-{[(E)-2-(2-thiazolyl)ethenyl]sulfonyl}malonamide (1) N-tert-butyl-2-hydroxy-2-(2-thiazolyl)ethanesulfonamide To a solution of N-(tert-butyl)methanesulfonamide (3.44 g) in THF (30 mL) was added a 2.0 mol/L solution of lithium diisopropylamide in heptane/THF/ethylbenzene at −78° C., and the mixture was stirred at −40° C. for 45 min. The reaction mixture was again cooled to −78° C., and a solution of 2-thiazolecarboxyaldehyde (2.57 g) in THF (20 mL) was added dropwise. The reaction mixture was stirred at −78° C. for 1 hr, and then at room temperature for 1 hr, and poured into 1 mol/L hydrochloric acid (50 mL) containing ice, and the mixture was concentrated under reduced pressure. 1 mol/L Hydrochloric acid (50 mL) and ethyl acetate (300 mL) were added to extract the residue, and the organic layer was washed with saturated brine and concentrated under reduced pressure to give the title compound (3.05 g) as a pale-brown powder.
¹H-NMR (300 Mz, CDCl₃) δ1.41 (9H, s), 3.40-3.57 (1H, m), 3.80-3.92 (1H, m), 4.28 (1H, brs), 4.42 (1H, brs), 5.48-5.60 (1H, m), 7.37 (1H, d, J=3.6 Hz), 7.76 (1H, d, J=3.3 Hz).

(2) N-tert-butyl-[(E)-2-(2-thiazolyl)ethylene]sulfonamide

To a solution of the above-mentioned compound (3.05 g) in methylene chloride (30 mL) were added triethylamine (4.80 mL) and methanesulfonyl chloride (1.34 mL) under ice-cooling, and the mixture was heated under reflux for 3 hr. 1 mol/L Hydrochloric acid (100 mL) and methylene chloride were added to extract the reaction mixture, and the organic layer was concentrated under reduced pressure. The residue was purified by silica gel column chromatography to give the title compound (2.84 g) as an oil.
¹H-NMR (400 Mz, CDCl₃) δ1.39 (9H, s), 4.40 (1H, brs), 7.20 (1H, d, J=15.0 Hz), 7.48 (1H, d, J=3.3 Hz), 7.56 (1H, d, J=15.0 Hz), 7.94 (1H, d, J=3.3 Hz).

(3) [(E)-2-(2-thiazolyl)ethylene]sulfonamide

To the above-mentioned compound (2.84 g) was added trifluoroacetic acid (30 mL), and the mixture was stirred at room temperature for 18 hr. The reaction mixture was concentrated under reduced pressure, and the residue was adjusted to pH=8-9 by the addition of aqueous sodium hydrogen carbonate solution under ice-cooling. Ethyl acetate (100 mL) was added to extract the mixture, and the organic layer was washed with saturated brine, and concentrated under reduced pressure to give the title compound (1.39 g) as a red powder.
¹H-NMR (300 Mz, DMSO-d₆) δ7.29 (2H, brs), 7.36 (1H, d, J=14.5 Hz), 7.49 (1H, d, J=15.3 Hz), 7.94 (1H, d, J=3.1 Hz), 8.00 (1H, d, J=3.1 Hz).

(4) 2-[(1-benzyl-1H-pyrazol-4-yl)methyl]-N-ethyl-N-phenyl-N'-{[(E)-2-(2-thiazolyl)ethenyl]sulfonyl}malonamide In the same manner as in Example 152 (3), a condensed product was obtained using the above-mentioned compound (380 mg) and the compound (604 mg) obtained in Example 371 (6). This was subjected to hydrolysis in the same manner as in Example 1 (3) to give a white solid (578 mg). This and N-ethylaniline (156 mg) were condensed in the same manner as in Example 1 (4) to give a crude product, and the crude product was purified by silica gel column chromatography to give the title compound (60 mg) as a white powder.
¹H-NMR (400 Mz, DMSO-d₆) δ0.89-0.92 (3H, m), 2.50-2.70 (1H, m), 2.76-2.82 (1H, m), 2.95-2.97 (1H, m), 3.25-3.57 (2H, m), 5.22 (2H, s), 6.86-6.88 (2H, m), 7.04 (1H, s), 7.15-7.39 (11H, m), 7.84-7.94 (2H, m).
MS: 550(M+H)⁺.

Example 399

Synthesis of 2-[(1-benzyl-1H-pyrazol-4-yl)methyl]-N-ethyl-N-phenyl-N'-{[(E)-2-(3-pyridyl)ethenyl]sulfonyl}malonamide (1) N-tert-butyl-2-hydroxy-2-(3-pyridyl)ethanesulfonamide In the same manner as in Example 398 (1), the title compound (2.93 g) was obtained as a white powder using 3-pyridinecarboxyaldehyde (2.43 g).
$^1$H-NMR (300 Mz, CDCl$_3$) δ1.41 (9H, s), 3.21-3.52 (2H, m), 4.06 (1H, brs), 4.56 (1H, brs), 5.28-5.41 (1H, m), 7.28-7.39 (1H, m), 7.70-7.81 (1H, m), 8.49-8.68 (2H, m).

(2) N-tert-butyl-[(E)-2-(3-pyridyl)ethylene]sulfonamide

In the same manner as in Example 398 (2), the title compound (2.43 g) was obtained as a pale-brown powder using the above-mentioned compound (2.93 g).
$^1$H-NMR (300 Mz, CDCl$_3$) δ1.38 (9H, s), 4.41 (1H, brs), 6.90 (1H, d, J=15.7 Hz), 7.29-7.40 (1H, m), 7.46 (1H, d, J=15.5 Hz), 7.72-7.88 (1H, m), 8.56-8.69 (1H, m), 8.72 (1H, d, J=2.1 Hz).

(3) [(E)-2-(3-pyridyl)ethylene]sulfonamide

In the same manner as in Example 398 (3), the title compound (433 mg) was obtained as a pale-brown powder using the above-mentioned compound (2.43 g).
$^1$H-NMR (300 Mz, DMSO-d$_6$) δ7.19 (2H, brs), 7.25-7.53 (3H, m), 8.17 (1H, dd, J=6.1, 2.0 Hz), 8.59 (1H, dd, J=4.5, 1.3 Hz), 8.85 (1H, d, J=1.9 Hz).

(4) 2-[(1-benzyl-1H-pyrazol-4-yl)methyl]-N-ethyl-N-phenyl-N'-{[(E)-2-(3-pyridyl)ethenyl]sulfonyl}malonamide In the same manner as in Example 152 (3), a condensed product was obtained using the above-mentioned compound (368 mg) and the compound (604 mg) obtained in Example 371 (6). This was subjected to hydrolysis in the same manner as in Example 1 (3) to give a white solid (228 mg). This and N-ethylaniline (66 mg) were condensed in the same manner as in Example 1 (4) to give a crude product, and the crude product was purified by silica gel column chromatography to give the title compound (28 mg) as a white powder.
$^1$H-NMR (300 Mz, DMSO-d$_6$) δ0.90 (3H, t, J=6.8 Hz), 2.67-2.72 (2H, m), 2.82-2.88 (1H, m), 3.38-3.40 (2H, m), 5.20 (2H, s), 6.98-6.99 (3H, m), 7.13-7.15 (2H, m), 7.28-7.36 (7H, m), 7.54-7.65 (3H, m), 8.35-8.36 (1H, m), 8.68-8.69 (1H, m), 8.97-8.98 (1H, m), 11.78 (1H, brs).
MS: 544(M+H)$^+$.

Example 400

Synthesis of 2-[(1-benzyl-1H-pyrazol-4-yl)methyl]-N-ethyl-N-phenyl-N'-{[(E)-2-(4-fluorophenyl)ethenyl]sulfonyl}malonamide (1) N-tert-butyl-2-(4-fluorophenyl)-2-hydroxyethanesulfonamide In the same manner as in Example 398 (1), the title compound (9.27 g) was obtained as a pale-brown powder using 4-fluorobenzaldehyde (5.49 g).
$^1$H-NMR (400 Mz, CDCl$_3$) δ1.38 (9H, s), 3.29-3.31 (1H, m), 3.35-3.38 (1H, m), 4.11-4.13 (1H, m), 4.66-4.68 (1H, m), 5.24-5.30 (1H, m), 7.02-7.09 (2H, m), 7.32-7.38 (2H, m).

(2) N-tert-butyl-[(E)-2-(4-fluorophenyl)ethylene]sulfonamide

In the same manner as in Example 398 (2), the title compound (6.58 g) was obtained as an oil using the above-mentioned compound (9.27 g).
$^1$H-NMR (400 Mz, CDCl$_3$) δ1.38 (9H, s), 4.20 (1H, brs), 6.73 (1H, d, J=15.2 Hz), 7.04-7.12 (2H, m), 7.39-7.40 (1H, m), 7.44-7.48 (2H, m).

(3) [(E)-2-(4-fluorophenyl)ethylene]sulfonamide

In the same manner as in Example 398 (3), the title compound (1.56 g) was obtained as a red powder using the above-mentioned compound (6.58 g).
$^1$H-NMR (400 Mz, DMSO-d$_6$) δ7.09 (2H, brs), 7.19-7.34 (4H, m), 7.74-7.78 (2H, m).

(4) 2-[(1-benzyl-1H-pyrazol-4-yl)methyl]-N-ethyl-N-phenyl-N'-{[(E)-2-(4-fluorophenyl)ethenyl]sulfonyl}malonamide In the same manner as in Example 1 (2), the title compound (548 mg) was obtained as a white powder using the above-mentioned compound (302 mg) and the compound obtained in Example 371 (8).
$^1$H-NMR (400 Mz, CDCl$_3$) δ1.04 (3H, t, J=6.8 Hz), 2.85-2.89 (1H, m), 3.01-3.07 (1H, m), 3.35-3.39 (1H, m), 3.55-3.57 (1H, m), 3.73-3.76 (1H, m), 4.73-4.75 (2H, m), 5.24 (2H, s), 6.85 (1H, d, J=15.6 Hz), 7.08-7.21 (3H, m), 7.28-7.35 (8H, m), 7.47-7.52 (4H, m).
MS: 561(M+H)$^+$.

Example 401

Synthesis of N-ethyl-N-phenyl-2-{[1-(1-phenylethyl)-1H-pyrazol-4-yl]methyl}-N'-((E)-styrylsulfonyl)malonamide (1) (1-benzyl-1H-pyrazol-4-yl)methoxy-tert-butyldimethylsilane To a solution of (1-benzyl-1H-pyrazol-4-yl)methanol (3.84 g) in methylene chloride (100 mL) were added triethylamine (2.80 mL), 4-dimethylaminopyridine (100 mg) and tert-butyldimethylsilyl chloride (3.80 g) at room temperature, and the mixture was stirred for 2 hr. Saturated aqueous sodium hydrogen carbonate solution was added to the reaction mixture, and insoluble material was removed by filtration. Ethyl acetate (100 mL) was added to extract the filtrate, and the organic layer was washed with brine. The organic layer was concentrated under reduced pressure, and the residue was purified by silica gel column chromatography to give the title compound (6.00 g).
$^1$H-NMR (400 Mz, CDCl$_3$) δ0.08-0.10 (6H, m), 0.87-0.89 (9H, m), 0.91-0.94 (3H, m), 1.87-1.89 (2H, m), 4.57-4.61 (2H, m), 7.17-7.26 (2H, m), 7.29-7.33 (2H, m), 7.41-7.52 (2H, m).

(2) [1-(1-phenylethyl)-1H-pyrazol-4-yl]methanol

To a solution of the above-mentioned compound (1.00 g) in THF (50 mL) was added 2.6 mol/L n-butyl lithium-hexane solution (1.70 mL) under cooling to −78° C., and the mixture was stirred for 1 hr. Methyl iodide (1.20 mL) was added to the reaction mixture, and the mixture was stirred for 1 hr. After allowing to warm to room temperature, water was added to the reaction mixture, and the mixture was extracted with ethyl acetate (100 mL). The organic layer was washed with saturated brine. The organic layer was concentrated under reduced pressure. The residue was dissolved in THF (20 mL), tetrabutylammonium fluoride (5.0 mL) was added at room temperature, and the mixture was stirred for 1 hr. Water was added to the reaction mixture, and the mixture was extracted with ethyl acetate (100 mL). The organic layer was washed with saturated brine. The organic layer was concentrated under reduced pressure, and the residue was purified by silica gel column chromatography to give the title compound (2.76 g).
$^1$H-NMR (400 Mz, CDCl$_3$) δ1.88-1.90 (3H, m), 2.35 (2H, s), 4.52-4.56 (2H, m), 5.46-5.49 (1H, m), 7.13-7.25 (3H, m), 7.29-7.41 (2H, m), 7.55 (1H, s).

(3) 4-(chloromethyl)-1-(1-phenylethyl)-1H-pyrazole

In the same manner as in Example 375 (3), the title compound (1.57 g) was obtained using the above-mentioned compound (2.16 g).

(4) monoethyl {[1-(1-phenylethyl)-1H-pyrazol-4-yl]methyl}malonate

In the same manner as in Example 117 (1), the object compound was obtained using the above-mentioned compound (1.57 g). This was subjected to hydrolysis in the same manner as in Example 117 (2) to give the title compound (1.59 g) as an oil.
$^1$H-NMR (400 Mz, CDCl$_3$) δ1.23-1.33 (3H, m), 1.84 (3H, s), 3.15 (2H, s), 3.54-3.57 (1H, m), 4.25-4.27 (2H, m), 5.49-5.51 (2H, m), 7.11-7.13 (2H, m), 7.28-7.40 (4H, m).

(5) 3-oxo-2-{[1-(1-phenylethyl)-1H-pyrazol-4-yl]methyl}-3-[((E)-styrylsulfonyl)amino]propionic acid In the same manner as in Example 152 (3), the object compound was obtained using the above-mentioned compound (1.57 g) and trans-β-styrenesulfonamide (1.35 g). This was subjected to hydrolysis in the same manner as in Example 1 (3) to give the title compound (2.02 g) as a white solid.

(6) N-ethyl-N-phenyl-2-{[1-(1-phenylethyl)-1H-pyrazol-4-yl]methyl}-N'-((E)-styrylsulfonyl)malonamide In the same manner as in Example 1 (4), the title compound (69 mg) was obtained as a white powder using the above-mentioned compound (1.46 g) and N-ethylaniline (400 mg).
$^1$H-NMR (400 Mz, CDCl$_3$) δ1.00-1.03 (3H, m), 1.84-1.87 (3H, m), 2.81-2.86 (1H, m), 3.01-3.07 (1H, m), 3.22-3.26 (1H, m), 3.51-3.59 (1H, m), 3.65-3.71 (1H, m), 5.38-5.44 (1H, m), 7.02 (1H, d, J=15.6 Hz), 7.16-7.20 (3H, m), 7.24-7.35 (5H, m), 7.39-7.41 (5H, m), 7.43-7.52 (3H, m), 7.71 (1H, d, J=15.6 Hz), 10.20 (1H, brs).
MS: 557(M+H)$^+$.

Example 402

Synthesis of 2-[(1-benzyl-1H-pyrazol-4-yl)methyl]-N-ethyl-N-phenyl-N'-(4-tolylsulfonyl)malonamide (1) 2-[(1-benzyl-1H-pyrazol-4-yl)methyl]-3-oxo-3-[(4-tolylsulfonyl)amino]propionic acid In the same manner as in Example 152 (3), a condensed product was obtained using p-toluenesulfonamide (283 mg) and the compound (500 mg) obtained in Example 371 (6). This was subjected to hydrolysis in the same manner as in Example 1 (3) to give the title compound (670 mg) as a white solid.

(2) 2-[(1-benzyl-1H-pyrazol-4-yl)methyl]-N-ethyl-N-phenyl-N'-(4-tolylsulfonyl)malonamide In the same manner as in Example 1 (4), the title compound (170 mg) was obtained as a white powder using the above-mentioned compound (670 mg) and N-ethylaniline (190 mg).
$^1$H-NMR (400 Mz, CDCl$_3$) δ0.99 (3H, t, J=7.6 Hz), 2.42 (3H, s), 2.65-2.70 (1H, m), 2.90-2.96 (1H, m), 3.11-3.14 (1H, m), 3.46-3.53 (1H, m), 3.64-3.72 (1H, m), 5.20 (2H, m), 7.02 (1H, s), 7.11 (1H, s), 7.20-7.25 (2H, m), 7.25-7.37 (10H, m), 7.93 (2H, d, J=8.0 Hz), 10.24 (1H, brs).
MS: 531(M+H)$^+$.

Example 403

Synthesis of 2-[(1-benzyl-1H-pyrazol-4-yl)methyl]-N'-(4-chlorophenylsulfonyl)-N-ethyl-N-phenylmalonamide (1) 2-[(1-benzyl-1H-pyrazol-4-yl)methyl]-3-[(4-chlorophenylsulfonyl)amino]-3-oxopropionic acid In the same manner as in Example 152 (3), a condensed product was obtained using 4-chlorobenzenesulfonamide (317 mg) and the compound (500 mg) obtained in Example 371 (6). This was subjected to hydrolysis in the same manner as in Example 1 (3) to give the title compound (617 mg) as a white solid.

(2) 2-[(1-benzyl-1H-pyrazol-4-yl)methyl]-N'-(4-chlorophenylsulfonyl)-N-ethyl-N-phenylmalonamide In the same manner as in Example 1 (4), the title compound (94 mg) was obtained as a white powder using the above-mentioned compound (617 mg) and N-ethylaniline (167 mg).
$^1$H-NMR (400 Mz, CDCl$_3$) δ1.01-1.03 (3H, m), 2.63-2.72 (1H, m), 2.88-2.93 (1H, m), 3.13-3.17 (1H, m), 3.45-3.61 (1H, m), 3.65-3.72 (1H, m), 5.24 (2H, m), 6.95 (1H, s), 6.96 (1H, s), 7.00-7.26 (4H, m), 7.31-7.47 (6H, m), 7.48-7.52 (2H, m), 7.98 (2H, d, J=8.8 Hz), 10.47 (1H, brs).
MS: 551(M+H)$^+$.

Example 404

Synthesis of N-ethyl-N-(4-fluorophenyl)-2-{[1-(3-methyl-2-buten-1-yl)-1H-pyrazol-4-yl]methyl}-N'-((E)-styrylsulfonyl)malonamide (1) [1-(3-methyl-2-buten-1-yl)-1H-pyrazol-4-yl]methanol In the same manner as in Example 375 (1), the object compound (7.98 g) was obtained using 1-bromo-3-methyl-2-butene (5.00 g). In the same manner as in Example 128 (2), the title compound (4.92 g) was obtained as an oil using this.
$^1$H-NMR (400 Mz, CDCl$_3$) δ0.84-0.88 (1H, m), 1.77 (3H, s), 1.79 (3H, s), 4.57 (2H, s), 4.69-4.71 (2H, m), 5.42-5.45 (1H, m), 7.39 (1H, s), 7.49 (1H, s).

(2) 4-(chloromethyl)-1-(3-methyl-2-buten-1-yl)-1H-pyrazole

In the same manner as in Example 375 (3), the title compound (4.95 g) was obtained as an oil using the above-mentioned compound (4.92 g).

¹H-NMR (400 Mz, CDCl₃) δ1.77 (3H, s), 1.79 (3H, s), 4.54 (2H, s), 4.68-4.71 (2H, m), 5.41-5.45 (1H, m), 7.42 (1H, s), 7.51 (1H, s).

(3) monoethyl {[1-(3-methyl-2-buten-1-yl)-1H-pyrazol-4-yl]methyl}malonate

In the same manner as in Example 117 (1), the object compound was obtained using the above-mentioned compound (4.95 g). This was subjected to hydrolysis in the same manner as in Example 117 (2) to give the title compound (6.04 g) as an oil.
¹H-NMR (400 Mz, CDCl₃) δ1.25-1.33 (3H, m), 1.74 (3H, s), 1.77 (3H, s), 3.09-3.11 (2H, m), 3.54-3.58 (1H, m), 4.20-4.29 (2H, m), 4.66-4.68 (2H, m), 5.37-5.41 (1H, m), 7.23 (1H, s), 7.35 (1H, s).

(4) 2-{[1-(3-methyl-2-buten-1-yl)-1H-pyrazol-4-yl]methyl}-3-[((E)-styrylsulfonyl)amino]-3-oxopropionic acid In the same manner as in Example 152 (3), a condensed product was obtained using the above-mentioned compound (3.00 g) and trans-β-styrenesulfonamide (1.96 g). This was subjected to hydrolysis in the same manner as in Example 1 (3) to give the title compound (2.35 g) as a white solid.

(5) N-ethyl-N-(4-fluorophenyl)-2-{[1-(3-methyl-2-buten-1-yl)-1H-pyrazol-4-yl]methyl}-N'-((E)-styrylsulfonyl)malonamide In the same manner as in Example 1 (4), the title compound (158 mg) was obtained as a white powder using the above-mentioned compound (834 mg) and N-ethyl-4-fluoroaniline (278 mg).
¹H-NMR (400 Mz, CDCl₃) δ1.08 (3H, brs), 1.72-1.79 (6H, m), 2.85-2.89 (1H, m), 3.02-3.08 (1H, m), 3.22-3.26 (1H, m), 3.64-3.71 (2H, m), 4.65 (2H, d, J=7.2 Hz), 5.37-5.41 (1H, m), 7.00-7.05 (4H, m), 7.12 (1H, s), 7.18 (1H, s), 7.31-7.46 (3H, m), 7.48-7.54 (3H, m), 7.72 (1H, d, J=15.6 Hz), 10.23 (1H, brs).
MS: 539(M+H)⁺.

Example 405

Synthesis of 2-[(1-benzyl-1H-pyrazol-4-yl)methyl]-N-ethyl-N-(1-naphthyl)-N'-((E)-styrylsulfonyl)malonamide (1) ethyl 2-[(1-benzyl-1H-pyrazol-4-yl)methyl]-3-[N-ethyl-N-(1-naphthyl)amino]-3-oxopropionate To a solution of the compound (4.70 g) obtained in Example 371 (6) in toluene (80 mL) was added thionyl chloride (1.36 mL), and the mixture was stirred at 85° C. for 2 hr. After completion of the reaction, the mixture was concentrated under reduced pressure. 1.28 g of the residue was dissolved in acetonitrile (10 ml), triethylamine (666 μL) and N-ethyl-1-naphthylamine (685 mg) were added, and the mixture was stirred at room temperature for 1 hr. Ethyl acetate (50 mL) and dilute hydrochloric acid were added to extract the reaction mixture, and the organic layer was washed sequentially with 1 mol/L hydrochloric acid, aqueous sodium hydrogen carbonate solution and saturated brine. The organic layer was concentrated under reduced pressure, and the residue was purified by silica gel column chromatography to give the title compound (1.23 g) as an oil.
¹H-NMR (300 Mz, CDCl₃) δ0.88-1.33 (6H, m), 2.70-3.40 (4H, m), 3.75-4.40 (3H, m), 5.00-5.35 (2H, m), 6.20-8.00 (14H, m).

(2) 2-[(1-benzyl-1H-pyrazol-4-yl)methyl]-3-[N-ethyl-N-(1-naphthyl)amino]-3-oxopropionic acid In the same manner as in Example 1 (3), the title compound (1.18 g) was obtained as a pale-yellow solid using the above-mentioned compound (1.23 g).
¹H-NMR (300 Mz, DMSO-d₆) δ0.80-1.10 (3H, m), 2.55-3.40 (4H, m), 3.90-4.20 (1H, m), 5.05-5.45 (2H, m), 6.25-8.10 (14H, m), 12.50 (1H, brs).

(3) 2-[(1-benzyl-1H-pyrazol-4-yl)methyl]-N-ethyl-N-(1-naphthyl)-N'-((E)-styrylsulfonyl)malonamide In the same manner as in Example 1 (2), the title compound (33 mg) was obtained as a white solid using the above-mentioned compound (622 mg) and trans-β-styrenesulfonamide (246 mg).
¹H-NMR (300 Mz, DMSO-d₆) δ0.96 (3H, t, J=6.9 Hz), 2.78-3.06 (2H, m), 3.06-3.48 (2H, m), 3.85-4.09 (1H, m), 5.23 (2H, s), 6.96 (1H, s), 7.00-8.09 (20H, m), 11.49 (1H, brs).
MS: 593(M+H)⁺.

Example 406

Synthesis of 2-[(1-benzyl-1H-pyrazol-4-yl)methyl]-N-ethyl-N-(2-naphthyl)-N'-((E)-styrylsulfonyl)malonamide (1) ethyl 2-[(1-benzyl-1H-pyrazol-4-yl)methyl]-3-[N-ethyl-N-(2-naphthyl)amino]-3-oxopropionate In the same manner as in Example 405 (1), the title compound (1.27 g) was obtained as an oil using N-ethyl-2-naphthylamine hydrobromide (1.01 g).
¹H-NMR (300 Mz, CDCl₃) δ1.04 (3H, t, J=7.0 Hz), 1.23 (3H, t, J=7.4 Hz), 2.75-2.90 (1H, m), 3.03-3.20 (1H, m), 3.30-3.44 (1H, m), 3.70 (2H, brs), 4.01-4.20 (2H, m), 5.17-5.35 (2H, m), 7.10-7.89 (14H, m).

(2) 2-[(1-benzyl-1H-pyrazol-4-yl)methyl]-3-[N-ethyl-N-(2-naphthyl)amino]-3-oxopropionic acid In the same manner as in Example 1 (3), the title compound (1.15 g) was obtained as a pale-yellow solid using the above-mentioned compound (1.27 g).
¹H-NMR (300 Mz, DMSO-d₆) δ0.95 (3H, t, J=7.1 Hz), 2.60-2.78 (1H, m), 2.78-2.98 (1H, m), 3.09-3.30 (1H, m), 3.48-3.84 (2H, m), 5.28 (2H, s), 6.35-8.00 (14H, m), 12.55 (1H, brs).

(3) 2-[(1-benzyl-1H-pyrazol-4-yl)methyl]-N-ethyl-N-(2-naphthyl)-N'-((E)-styrylsulfonyl)malonamide In the same manner as in Example 1 (2), the title compound (140 mg) was obtained as a white powder using the above-mentioned compound (630 mg) and trans-β-styrenesulfonamide (249 mg).
¹H-NMR (300 Mz, DMSO-d₆) δ0.97 (3H, t, J=6.9 Hz), 2.57-3.02 (2H, m), 3.25-3.80 (3H, m), 5.18 (2H, s), 6.90-7.65 (16H, m), 7.69-8.00 (5H, m), 11.60 (1H, brs).
MS: 593(M+H)⁺.

Example 407

Synthesis of 2-[(1-benzyl-1H-pyrazol-4-yl)methyl]-3-(2,3-dihydro-1H-indol-1-yl)-3-oxo-N-((E)-styrylsulfonyl)propanamide (1) ethyl 2-[(1-benzyl-1H-pyrazol-4-yl)methyl]-3-oxo-3-[((E)-styrylsulfonyl)amino]propionate In the same manner as in Example 152 (3), the title compound (4.31 g) was obtained as an oil using the compound (3.00 g) obtained in Example 371 (6) and trans-β-styrenesulfonamide (1.68 g).

$^1$H-NMR (300 Mz, DMSO-$d_6$) δ1.06 (3H, t, J=7.1 Hz), 2.78-2.95 (2H, m), 3.54-3.68 (1H, m), 3.92-4.10 (2H, m), 5.00-5.32 (2H, m), 6.90-7.80 (14H, m), 12.25 (1H, brs).

(2) 2-[(1-benzyl-1H-pyrazol-4-yl)methyl]-3-oxo-3-[((E)-styrylsulfonyl)amino]propionic acid In the same manner as in Example 1 (3), the title compound (2.32 g) was obtained as a white powder using the above-mentioned compound (4.31 g).

$^1$H-NMR (300 Mz, DMSO-$d_6$) δ2.85 (2H, d, J=7.5 Hz), 3.55 (1H, t, J=7.2 Hz), 5.00-5.30 (2H, m), 7.00-7.95 (14H, m), 12.18 (1H, brs), 12.80 (1H, brs).

(3) 2-[(1-benzyl-1H-pyrazol-4-yl)methyl]-3-(2,3-dihydro-1H-indol-1-yl)-3-oxo-N-((E)-styrylsulfonyl)propanamide In the same manner as in Example 13, the title compound (47 mg) was obtained as a white solid using the above-mentioned compound (110 mg) and indoline (32 mg).

$^1$H-NMR (300 Mz, DMSO-$d_6$) δ2.80-4.22 (7H, m), 5.16 (2H, s), 6.90-7.66 (15H, m), 7.66-7.76 (2H, m), 8.00-8.15 (1H, m), 12.15 (1H, brs).
MS: 541(M+H)$^+$.

Example 408

Synthesis of 2-[(1-benzyl-1H-pyrazol-4-yl)methyl]-N-ethyl-N-(4-fluorophenyl)-N'-((E)-styrylsulfonyl)malonamide In the same manner as in Example 13, the title compound (111 mg) was obtained as a white solid using the compound (220 mg) obtained in Example 407 (2) and N-ethyl-4-fluoroaniline (84 mg).

$^1$H-NMR (300 Mz, DMSO-$d_6$) δ0.90 (3H, t, J=7.1 Hz), 2.58-2.92 (2H, m), 3.18-3.64 (3H, m), 5.18 (2H, s), 6.90-7.64 (16H, m), 7.66-7.85 (2H, m), 11.68 (1H, brs).
MS: 561(M+H)$^+$.

Example 409

Synthesis of 2-[(1-benzyl-1H-pyrazol-4-yl)methyl]-3-(3,4-dihydroquinolin-1(2H)-yl)-3-oxo-N-((E)-styrylsulfonyl)propanamide In the same manner as in Example 13, the title compound (235 mg) was obtained as a white solid using the compound (310 mg) obtained in Example 407 (2) and 1,2,3,4-tetrahydroquinoline (113 mg).

$^1$H-NMR (300 Mz, DMSO-$d_6$) δ1.52-1.83 (2H, m), 1.86-2.98 (4H, m), 3.18-4.10 (3H, m), 5.17 (2H, s), 6.40-7.65 (16H, m), 7.65-7.85 (2H, m), 12.05 (1H, brs).
MS: 555(M+H)$^+$.

Example 410

Synthesis of 2-[(1-benzyl-1H-pyrazol-4-yl)methyl]-N-ethyl-N-(3-pyridyl)-N'-((E)-styrylsulfonyl)malonamide hydrochloride In the same manner as in Example 13, the object compound was obtained using the compound (220 mg) obtained in Example 407 (2) and 3-(ethylamino)pyridine (73 mg). The compound was converted to a hydrochloride salt with hydrochloric acid-methanol solution to give the title compound (151 mg) as a white powder.

$^1$H-NMR (300 Mz, DMSO-$d_6$) δ0.93 (3H, t, J=7.2 Hz), 2.65-2.95 (2H, m), 3.20-3.80 (3H, m), 5.16 (2H, s), 6.95-7.86 (14H, m), 7.93-8.08 (2H, m), 8.54 (1H, brs), 8.66-8.79 (1H, s), 11.70 (1H, brs).
MS: 544(M+H)$^+$.

Example 411

Synthesis of 2-[(1-benzyl-1H-pyrazol-4-yl)methyl]-N-(4-ethoxycarbonylphenyl)-N-ethyl-N'-((E)-styrylsulfonyl)malonamide In the same manner as in Example 13, the title compound (338 mg) was obtained as a white solid using the compound (439 mg) obtained in Example 407 (2) and ethyl 4-(ethylamino)benzoate (232 mg).

$^1$H-NMR (300 Mz, DMSO-$d_6$) δ0.91 (3H, t, J=7.2 Hz), 1.31 (3H, t, J=7.2 Hz), 2.58-2.95 (2H, m), 3.10-3.45 (1H, m), 3.59 (2H, q, J=6.9 Hz), 4.32 (2H, q, J=7.2 Hz), 5.19 (2H, s), 6.82-7.38 (10H, m), 7.40-7.58 (4H, m), 7.69-7.81 (2H, m), 7.89 (2H, d, J=8.4 Hz), 11.68 (1H, brs).
MS: 615(M+H)$^+$.

Example 412

Synthesis of 2-[(1-benzyl-1H-pyrazol-4-yl)methyl]-N-(4-carboxyphenyl)-N-ethyl-N'-((E)-styrylsulfonyl)malonamide In the same manner as in Example 121, the title compound (191 mg) was obtained as a white powder using the compound (200 mg) obtained in Example 411.

$^1$H-NMR (300 Mz, DMSO-$d_6$) δ0.92 (3H, t, J=7.0 Hz), 2.58-2.92 (2H, m), 3.10-3.78 (3H, m), 5.18 (2H, s), 6.88-7.62 (14H, m), 7.65-7.81 (2H, m), 7.91 (2H, d, J=8.5 Hz), 11.65 (1H, brs), 13.10 (1H, brs).
MS: 587(M+H)$^+$.

Example 413

Synthesis of 2-[(1-benzyl-1H-pyrazol-4-yl)methyl]-N-(3-ethoxycarbonylphenyl)-N-ethyl-N'-((E)-styrylsulfonyl)malonamide In the same manner as in Example 13, the title compound (165 mg) was obtained as a white solid using the compound (439 mg) obtained in Example 407 (2) and ethyl 3-(ethylamino)benzoate (232 mg).

$^1$H-NMR (300 Mz, DMSO-$d_6$) δ0.92 (3H, t, J=6.9 Hz), 1.32 (3H, t, J=7.2 Hz), 2.60-2.94 (2H, m), 3.16-3.45 (1H, m), 3.59 (2H, q, J=6.9 Hz), 4.20-4.40 (2H, m), 5.17 (2H, s), 6.88-7.62 (14H, m), 7.62-7.80 (3H, m), 7.86-8.00 (1H, m), 11.65 (1H, brs).
MS: 615(M+H)$^+$.

Example 414

Synthesis of 2-[(1-benzyl-1H-pyrazol-4-yl)methyl]-N-(3-carboxyphenyl)-N-ethyl-N'-((E)-styrylsulfonyl)malonamide In the same manner as in Example 121, the title compound (76 mg) was obtained as a white powder using the compound (100 mg) obtained in Example 413.
$^1$H-NMR (300 Mz, DMSO-d$_6$) δ0.91 (3H, t, J=6.9 Hz), 2.55-2.95 (2H, m), 3.15-3.80 (3H, m), 5.16 (2H, s), 6.85-7.82 (17H, m), 7.85-8.00 (1H, m), 11.71 (1H, brs), 13.30 (1H, brs).
MS: 587(M+H)$^+$.

Example 415

Synthesis of 2-[(1-benzyl-1H-pyrazol-4-yl)methyl]-N-ethyl-N-[4-(hydroxymethyl)phenyl]-N'-((E)-styrylsulfonyl)malonamide In the same manner as in Example 13, the title compound (108 mg) was obtained as a white powder using the compound (220 mg) obtained in Example 407 (2) and 4-(ethylamino)benzyl alcohol (108 mg).
$^1$H-NMR (300 Mz, DMSO-d$_6$) δ0.90 (3H, t, J=7.2 Hz), 2.55-2.97 (2H, m), 3.20-3.65 (3H, m), 4.36-4.56 (2H, m), 5.19 (2H, s), 5.18-5.36 (1H, m), 6.74-7.65 (16H, m), 7.65-7.89 (2H, m), 11.72 (1H, brs).
MS: 573(M+H)$^+$.

Example 416

Synthesis of 2-[(1-benzyl-1H-pyrazol-4-yl)methyl]-N-ethyl-N-[3-(hydroxymethyl)phenyl]-N'-((E)-styrylsulfonyl)malonamide In the same manner as in Example 13, the title compound (180 mg) was obtained as a white powder using the compound (220 mg) obtained in Example 407 (2) and 3-(ethylamino)benzyl alcohol (91 mg).
$^1$H-NMR (300 Mz, DMSO-d$_6$) δ0.93 (3H, t, J=6.9 Hz), 2.54-2.97 (2H, m), 3.17-3.70 (3H, m), 4.49 (2H, s), 5.17 (2H, s), 5.30 (1H, brs), 6.77-7.62 (16H, m), 7.67-7.83 (2H, m), 11.72 (1H, brs).
MS: 573(M+H)$^+$.

Example 417

Synthesis of 2-[(1-benzyl-1H-pyrazol-4-yl)methyl]-N-(2-hydroxyethyl)-N-phenyl-N'-((E)-styrylsulfonyl)malonamide In the same manner as in Example 13, the title compound (172 mg) was obtained as a white powder using the compound (220 mg) obtained in Example 407 (2) and N-phenylethanolamine (82 mg).
$^1$H-NMR (300 Mz, DMSO-d$_6$) δ2.60-2.98 (2H, m), 3.19-3.70 (5H, m), 4.63 (1H, brs), 5.17 (2H, s), 6.79-7.63 (17H, m), 7.63-7.89 (2H, m), 11.72 (1H, brs).
MS: 559(M+H)$^+$.

Example 418

Synthesis of 2-[(1-benzyl-1H-pyrazol-4-yl)methyl]-N-isopropyl-N-phenyl-N'-((E)-styrylsulfonyl)malonamide In the same manner as in Example 13, the title compound (162 mg) was obtained as a white powder using the compound (220 mg) obtained in Example 407 (2) and N-isopropylaniline (81 mg).
$^1$H-NMR (300 Mz, DMSO-d$_6$) δ0.75-0.95 (6H, m), 2.50-2.70 (1H, m), 2.75-2.98 (1H, m), 3.00-3.20 (1H, m), 4.59-4.80 (1H, m), 5.20 (2H, s), 6.63-6.81 (1H, m), 6.83-7.64 (16H, m), 7.67-7.90 (2H, m), 11.63 (1H, brs).
MS: 557(M+H)$^+$.

Example 419

Synthesis of N-allyl-2-[(1-benzyl-1H-pyrazol-4-yl)methyl]-N-methyl-N'-((E)-styrylsulfonyl)malonamide In the same manner as in Example 13, the title compound (74 mg) was obtained as a white powder using the compound (220 mg) obtained in Example 407 (2) and N-methylallylamine (143 μL).
$^1$H-NMR (300 Mz, DMSO-d$_6$) δ2.64-2.94 (5H, m), 3.67-3.96 (3H, m), 4.86-5.10 (2H, m), 5.17 (2H, s), 5.50-5.70 (1H, m), 7.09-7.62 (12H, m), 7.66-7.80 (2H, m), 12.04 (1H, brs).
MS: 493(M+H)$^+$.

Example 420

Synthesis of 2-[(1-benzyl-1H-pyrazol-4-yl)methyl]-N-ethyl-N-(2-methoxyethyl)-N'-(2-naphthylsulfonyl)malonamide (1) ethyl 2-[(1-benzyl-1H-pyrazol-4-yl)methyl]-3-[(2-naphthylsulfonyl)amino]-3-oxopropionate In the same manner as in Example 152 (3), the title compound (4.62 g) was obtained as an oil using the compound (3.00 g) obtained in Example 371 (6).
$^1$H-NMR (300 Mz, DMSO-d$_6$) δ0.93 (3H, t, J=7.1 Hz), 2.69-2.88 (2H, m), 3.50-3.70 (1H, m), 2.82-4.20 (2H, m), 4.98-5.32 (2H, m), 6.90-8.65 (14H, m), 12.55 (1H, brs).

(2) 2-[(1-benzyl-1H-pyrazol-4-yl)methyl]-3-[(2-naphthylsulfonyl)amino]-3-oxopropionic acid In the same manner as in Example 1 (3), the title compound (2.23 g) was obtained as a white powder using the above-mentioned compound (4.62 g).
$^1$H-NMR (300 Mz, DMSO-d$_6$) δ2.62-2.84 (2H, m), 3.40-3.60 (1H, m), 4.94-5.18 (2H, m), 7.00-8.20 (13H, m), 8.56 (1H, s), 12.65 (2H, brs).

(3) 2-[(1-benzyl-1H-pyrazol-4-yl)methyl]-N-ethyl-N-(2-methoxyethyl)-N'-(2-naphthylsulfonyl)malonamide In the same manner as in Example 13, the title compound (62 mg) was obtained as a white powder using the above-mentioned compound (232 mg) and N-(2-methoxyethyl)ethylamine (62 mg).
$^1$H-NMR (300 Mz, DMSO-d$_6$) δ0.70-0.90 (3H, m), 2.63-2.86 (2H, m), 2.97-3.48 (9H, m), 3.68-3.90 (1H, m), 5.00-

5.20 (2H, m), 7.00-7.19 (3H, m), 7.19-7.43 (4H, m), 7.61-7.88 (3H, m), 8.00-8.29 (3H, m), 8.57 (1H, s), 12.10 (1H, brs).
MS: 549(M+H)$^+$.

Example 421

Synthesis of 2-[(1-benzyl-1H-pyrazol-4-yl)methyl]-N-[2-(dimethylamino)ethyl]-N-ethyl-N'-(2-naphthylsulfonyl)malonamide trifluoroacetic acid salt In the same manner as in Example 13, the object compound was obtained using the compound (232 mg) obtained in Example 420 (2) and N,N-dimethyl-N'-ethylethylenediamine (70 mg). This was treated with trifluoroacetic acid to give the title compound (41 mg) as a white powder.
MS: 562(M+H)$^+$.

Example 422

Synthesis of 2-[(1-benzyl-1H-pyrazol-4-yl)methyl]-N-(2-hydroxyethyl)-N-methyl-N'-(2-naphthylsulfonyl)malonamide In the same manner as in Example 13, the title compound (69 mg) was obtained as a white powder using the compound (232 mg) obtained in Example 420 (2) and N-methylethanolamine (45 mg).
$^1$H-NMR (300 Mz, DMSO-d$_6$) δ2.55-2.90 (5H, m), 2.95-4.05 (5H, m), 4.95-5.20 (2H, m), 6.96-7.40 (7H, m), 7.58-7.86 (3H, m), 7.97-8.30 (3H, m), 8.56 (1H, s), 12.30 (2H, brs).
MS: 521(M+H)$^+$.

Example 423

Synthesis of 2-[(1-benzyl-1H-pyrazol-4-yl)methyl]-3-morpholino-N-(2-naphthylsulfonyl)-3-oxopropanamide In the same manner as in Example 13, the title compound (160 mg) was obtained as a white powder using the compound (232 mg) obtained in Example 420 (2) and morpholine (52 mg).
$^1$H-NMR (300 Mz, DMSO-d$_6$) δ2.55-2.80 (2H, m), 2.97-3.50 (8H, m), 3.79 (1H, t, J=6.9 Hz), 5.00-5.25 (2H, m), 6.89-7.49 (7H, m), 7.78-7.87 (3H, m), 7.92-8.23 (3H, m), 8.58 (1H, s), 12.30 (1H, brs).
MS: 532(M+H)$^+$.

Example 424

Synthesis of 2-[(1-benzyl-1H-pyrazol-4-yl)methyl]-N-ethyl-N'-(2-naphthylsulfonyl)-N-phenylmalonamide In the same manner as in Example 13, the title compound (261 mg) was obtained as a white powder using the compound (200 mg) obtained in Example 420 (2) and N-ethylaniline (52 mg).
$^1$H-NMR (400 Mz, CDCl$_3$) δ0.99 (3H, t, J=7.2 Hz), 2.64-2.69 (1H, m), 2.88-2.96 (1H, m), 3.09-3.13 (1H, m), 3.46-3.52 (1H, m), 3.66-3.71 (1H, m), 5.10 (2H, s), 6.94 (1H, s), 7.08 (1H, s), 7.15-7.26 (5H, m), 7.29-7.35 (3H, m), 7.61-7.68 (3H, m), 7.89-8.01 (5H, m), 8.65 (1H, s), 10.39 (1H, brs).
MS: 567(M+H)$^+$.

Example 425

Synthesis of N-ethyl-2-{[2-(2,4-difluorophenyl)-4-thiazolyl]methyl}-N-phenyl-N'-((E)-styrylsulfonyl)malonamide (1) [2-(2,4-difluorophenyl)-4-thiazolyl]methanol In the same manner as in Example 128 (2), the title compound (1.23 g) was obtained as an orange solid using ethyl 2-(2,4-difluorophenyl)thiazolyl-4-carboxylate (1.93 g).
$^1$H-NMR (400 Mz, DMSO-d$_6$) δ4.66 (2H, d, J=6.0 Hz), 5.43 (1H, t, J=6.0 Hz), 7.25-7.30 (1H, m), 7.48-7.54 (1H, m), 7.61 (1H, s), 8.21-8.27 (1H, m).

(2) monoethyl {[2-(2,4-difluorophenyl)-4-thiazolyl]methyl}malonate

In the same manner as in Example 371 (3), the object compound was obtained using the above-mentioned compound (1.19 g). This was subjected to hydrolysis in the same manner as in Example 117 (2) to give the title compound (251 mg) as a white solid.
$^1$H-NMR (400 Mz, DMSO-d$_6$) δ1.13 (3H, t, J=7.2 Hz), 3.27 (2H, d, J=7.6 Hz), 4.10 (2H, q, J=7.2 Hz), 7.27-7.31 (1H, m), 7.48-7.55 (2H, m), 8.20-8.26 (1H, m), 13.00 (1H, brs).

(3) ethyl 3-(N-ethyl-N-phenylamino)-2-{[2-(2,4-difluorophenyl)-4-thiazolyl]methyl}-3-oxopropionate In the same manner as in Example 335 (1), the title compound (157 mg) was obtained as an oil using the above-mentioned compound (250 mg) and N-ethylaniline (200 μL).
$^1$H-NMR (300 Mz, DMSO-d$_6$) δ0.94 (3H, t, J=7.1 Hz), 1.13 (3H, t, J=7.1 Hz), 3.10-3.30 (3H, m), 3.58 (2H, q, J=7.1 Hz), 3.69-3.78 (1H, m), 4.03 (2H, q, J=7.1 Hz), 6.92 (2H, brs), 7.22-7.55 (6H, m), 7.96-8.06 (1H, m).

(4) 3-(N-ethyl-N-phenylamino)-2-{[2-(2,4-difluorophenyl)-4-thiazolyl]methyl}-3-oxopropionic acid In the same manner as in Example 1 (3), the title compound (81 mg) was obtained as an oil using the above-mentioned compound (156 mg).
$^1$H-NMR (300 Mz, CDCl$_3$) δ1.05 (3H, t, J=7.2 Hz), 3.31 (1H, dd, J=13.8, 4.8 Hz), 3.43 (1H, dd, J=13.8, 9.3 Hz), 3.60-3.79 (2H, m), 3.89 (1H, dd, J=9.3, 4.8 Hz), 6.85 (2H, brs), 6.93-7.03 (2H, m), 7.15 (1H, s), 7.15-7.30 (3H, m), 7.85 (1H, brs), 8.04-8.12 (1H, m).

(5) N-ethyl-2-{[2-(2,4-difluorophenyl)-4-thiazolyl]methyl}-N-phenyl-N'-((E)-styrylsulfonyl)malonamide In the same manner as in Example 1 (2), the title compound (95 mg) was obtained as a white powder using the above-mentioned compound (81 mg) and trans-β-styrenesulfonamide (36 mg).
$^1$H-NMR (300 Mz, DMSO-d$_6$) δ0.96 (3H, d, d=7.1 Hz), 3.07-3.30 (2H, m), 3.46-3.72 (2H, m), 3.80-3.91 (1H, m), 7.08-7.50 (12H, m), 7.57 (1H, d, J=16.1 Hz), 7.64-7.85 (2H, m), 8.06-8.20 (1H, m), 11.85 (1H, brs).
MS: 582(M+H)$^+$.

Example 426

Synthesis of 2-[(2-anilino-4-thiazolyl)methyl]-N-ethyl-N-phenyl-N'-((E)-styrylsulfonyl)malonamide (1) triethyl 2-(2-anilino-4-thiazolyl)ethane-1,1,1-tricarboxylate In the same manner as in Example 117 (1), the title compound (940 mg) was obtained as an oil using 2-anilino-4-(chloromethyl)thiazole (920 mg).

$^1$H-NMR (300 Mz, DMSO-$d_6$) δ1.14 (9H, t, J=7.2 Hz), 3.38 (2H, s), 4.17 (6H, q, J=7.2 Hz), 6.55 (1H, s), 6.87-6.94 (1H, m), 7.19-7.30 (2H, m), 7.56 (2H, d, J=8.4 Hz), 10.01 (1H, s).

(2) monoethyl [(2-anilino-4-thiazolyl)methyl]malonate

In the same manner as in Example 117 (2), the title compound (522 mg) was obtained as a pale-brown powder using the above-mentioned compound (910 mg).

$^1$H-NMR (300 Mz, CDCl$_3$) δ1.27 (3H, t, J=7.0 Hz), 3.20-3.36 (2H, m), 3.74 (1H, t, J=7.3 Hz), 4.22 (2H, q, J=7.0 Hz), 6.30 (1H, s), 7.10-7.20 (1H, m), 7.26-7.40 (5H, m).

(3) ethyl 2-[(2-anilino-4-thiazolyl)methyl]-3-(N-ethyl-N-phenylamino)-3-oxopropionate In the same manner as in Example 1 (4), the title compound (317 mg) was obtained as a pale-brown powder using the above-mentioned compound (510 mg) and N-ethylaniline (320 μL).

$^1$H-NMR (300 Mz, CDCl$_3$) δ1.07 (3H, t, J=7.0 Hz), 1.25 (3H, t, J=7.0 Hz), 3.09 (1H, dd, J=13.9, 4.5 Hz), 3.23 (1H, dd, J=13.9, 10.0 Hz), 3.61-3.80 (3H, m), 4.15 (2H, q, J=7.0 Hz), 6.32 (1H, s), 6.90 (2H, brs), 7.04-7.09 (1H, m), 7.16-7.38 (8H, m).

(4) 2-[(2-anilino-4-thiazolyl)methyl]-3-(N-ethyl-N-phenylamino)-3-oxopropionic acid In the same manner as in Example 1 (3), the title compound (292 mg) was obtained as a pale-brown powder using the above-mentioned compound (313 mg).

$^1$H-NMR (400 Mz, CDCl$_3$) δ1.06 (3H, t, J=7.2 Hz), 2.95-3.24 (2H, m), 3.57-3.75 (3H, m), 6.26 (1H, s), 6.94 (2H, brs), 7.07-7.14 (1H, m), 7.20-7.42 (8H, m).

(5) 2-[(2-anilino-4-thiazolyl)methyl]-N-ethyl-N-phenyl-N'-((E)-styrylsulfonyl)malonamide In the same manner as in Example 1 (2), the title compound (81 mg) was obtained as a white solid using the above-mentioned compound (292 mg) and trans-β-styrenesulfonamide (135 mg).

$^1$H-NMR (400 Mz, DMSO-$d_6$) δ0.95 (3H, t, J=7.2 Hz), 2.83-3.05 (2H, m), 3.47-3.53 (1H, m), 3.66-3.76 (2H, m), 6.27 (1H, s), 6.92-6.95 (1H, m), 7.18-7.20 (2H, m), 7.27-7.38 (6H, m), 7.47-7.58 (6H, m), 7.77-7.79 (2H, m), 10.04 (1H, s), 11.80 (1H, brs).

MS: 561(M+H)$^+$.

Example 427

Synthesis of 2-{[2-(4-chlorobenzyl)-4-thiazolyl]methyl}-N,N-diethyl-N'-((E)-styrylsulfonyl)malonamide (1) 2-(4-chlorobenzyl)-4-(chloromethyl)thiazole To a solution of 2-(4-chlorophenyl)thioacetamide (3.51 g) in 1,4-dioxane (20 mL) were added dichloroacetone (2.64 g) and sodium hydrogen carbonate (1.75 g) at room temperature, and the mixture was stirred for 3 days. Insoluble material was removed by filtration, thionyl chloride (1.52 mL) was added to the filtrate, and the mixture was heated at 70° C. for 30 min. The reaction mixture was adjusted to pH=8-9 by the addition of saturated aqueous sodium hydrogen carbonate solution, and extracted with ethyl acetate/hexane (1/1)(100 mL×2). The organic layer was washed with saturated brine, and concentrated under reduced pressure to give the title compound (4.19 g) as a pale-yellow solid.

$^1$H-NMR (400 Mz, DMSO-$d_6$) δ4.34 (2H, s), 4.78 (2H, s), 7.36-7.42 (4H, m), 7.61 (1H, s).

(2) triethyl 2-[2-(4-chlorobenzyl)-4-thiazolyl]ethane-1,1,1-tricarboxylate

In the same manner as in Example 117 (1), the title compound (7.35 g) was obtained as an oil using the above-mentioned compound (3.77 g).

$^1$H-NMR (400 Mz, DMSO-$d_6$) δ1.11 (9H, t, J=7.2 Hz), 3.48 (2H, s), 4.11 (6H, q, J=7.2 Hz), 4.34 (2H, s), 7.21 (1H, s), 7.30-7.40 (4H, m).

(3) monoethyl {[2-(4-chlorobenzyl)-4-thiazolyl]methyl}malonate

In the same manner as in Example 117 (2), the title compound (4.56 g) was obtained as an oil using the above-mentioned compound (7.35 g).

$^1$H-NMR (400 Mz, DMSO-$d_6$) δ1.08-1.13 (3H, m), 3.15 (2H, d, J=7.6 Hz), 3.77 (1H, t, J=7.6 Hz), 4.00-4.11 (2H, m), 4.28 (2H, s), 7.18 (1H, s), 7.32-7.40 (4H, m), 12.92 (1H, brs).

(4) ethyl 2-{[2-(4-chlorobenzyl)-4-thiazolyl]methyl}-3-(N,N-diethylamino)-3-oxopropionate In the same manner as in Example 1 (4), the title compound (570 mg) was obtained as an oil using the above-mentioned compound (1.16 g).

$^1$H-NMR (400 Mz, DMSO-$d_6$) δ0.85 (3H, t, J=7.2 Hz), 0.94 (3H, t, J=7.2 Hz), 1.12 (3H, t, J=7.2 Hz), 3.07-3.30 (6H, m), 4.01-4.13 (3H, m), 4.27 (2H, s), 7.11 (1H, s), 7.30-7.40 (4H, m).

(5) 2-{[2-(4-chlorobenzyl)-4-thiazolyl]methyl}-3-(N,N-diethylamino)-3-oxopropionic acid In the same manner as in Example 1 (3), the title compound (480 mg) was obtained as an oil using the above-mentioned compound (570 mg).

$^1$H-NMR (400 Mz, DMSO-$d_6$) δ0.84 (3H, t, J=7.2 Hz), 0.95 (3H, t, J=7.2 Hz), 3.04-3.29 (6H, m), 3.99-4.04 (1H, m), 4.27 (2H, s), 7.08 (1H, s), 7.31-7.40 (4H, m), 12.58 (1H, brs).

(6) 2-{[2-(4-chlorobenzyl)-4-thiazolyl]methyl}-N,N-diethyl-N'-((E)-styrylsulfonyl)malonamide In the same manner as in Example 1 (2), the title compound (250 mg) was obtained as a pale-brown powder using the above-mentioned compound (480 mg) and trans-β-styrenesulfonamide (230 mg).

$^1$H-NMR (400 Mz, DMSO-d$_6$) δ0.92 (3H, t, J=7.2 Hz), 1.01 (3H, t, J=7.2 Hz), 3.07-3.33 (6H, m), 4.11 (1H, t, J=7.2 Hz), 4.23 (2H, s), 7.08 (1H, s), 7.29-7.49 (8H, m), 7.58 (1H, d, J=15.6 Hz), 7.70 (2H, d, J=6.8 Hz), 12.05 (1H, brs).
MS: 546(M+H)$^+$.

Example 428

Synthesis of N-ethyl-2-{[2-(4-fluorophenyl)-4-oxazolyl]methyl}-N-phenyl-N'-((E)-styrylsulfonyl)malonamide

(1) triethyl 2-[2-(4-fluorophenyl)-4-oxazolyl]ethane-1,1,1-tricarboxylate

In the same manner as in Example 117 (1), the title compound (1.00 g) was obtained as an oil using 4-(chloromethyl)-2-(4-fluorophenyl)oxazole (520 mg).

$^1$H-NMR (400 Mz, CDCl$_3$) δ1.26 (9H, t, J=7.2 Hz), 3.49 (2H, s), 4.27 (6H, q, J=7.2 Hz), 7.09-7.14 (2H, m), 7.57 (1H, s), 7.95-7.98 (2H, m).

(2) monoethyl {[2-(4-fluorophenyl)-4-oxazolyl]methyl}malonate

In the same manner as in Example 117 (2), the title compound (750 mg) was obtained as a pale-yellow solid using the above-mentioned compound (1.00 g).

$^1$H-NMR (300 Mz, DMSO-d$_6$) δ1.15 (3H, t, J=7.1 Hz), 3.02 (2H, d, J=7.6 Hz), 3.74 (1H, t, J=7.6 Hz), 4.12 (2H, q, J=7.1 Hz), 7.34-7.40 (2H, m), 7.96 (1H, s), 7.96-8.01 (2H, m), 11.99 (1H, brs).

(3) ethyl 3-(N-ethyl-N-phenylamino)-2-{[2-(4-fluorophenyl)-4-oxazolyl]methyl}-3-oxopropionate In the same manner as in Example 1 (4), the title compound (690 mg) was obtained as an oil using the above-mentioned compound (750 mg) and N-ethylaniline (370 μL).

$^1$H-NMR (300 Mz, DMSO-d$_6$) δ0.96 (3H, t, J=7.2 Hz), 1.31 (3H, t, J=7.2 Hz), 2.84-3.08 (2H, m), 3.57-3.68 (3H, m), 4.03 (2H, q, J=7.2 Hz), 7.06 (2H, brs), 7.36-7.42 (5H, m), 7.88 (1H, s), 7.91-7.96 (2H, m).

(4) 3-(N-ethyl-N-phenylamino)-2-{[2-(4-fluorophenyl)-4-oxazolyl]methyl}-3-oxopropionic acid In the same manner as in Example 1 (3), the title compound (614 mg) was obtained as a white powder using the above-mentioned compound (660 mg).

$^1$H-NMR (400 Mz, DMSO-d$_6$) δ0.96 (3H, t, J=7.2 Hz), 2.86 (1H, dd, J=14.4, 4.8 Hz), 2.99 (1H, dd, J=14.4, 9.6 Hz), 3.56-3.62 (3H, m), 7.02 (2H, brs), 7.34-7.43 (5H, m), 7.86 (1H, s), 7.92-7.96 (2H, m), 12.75 (1H, brs).

(5) N-ethyl-2-{[2-(4-fluorophenyl)-4-oxazolyl]methyl}-N-phenyl-N'-((E)-styrylsulfonyl)malonamide In the same manner as in Example 1 (2), the title compound (311 mg) was obtained as a white solid using the above-mentioned compound (614 mg) and trans-β-styrenesulfonamide (295 mg).

$^1$H-NMR (300 Mz, DMSO-d$_6$) δ0.96 (3H, t, J=7.2 Hz), 2.86 (1H, dd, J=15.0, 5.4 Hz), 3.02 (1H, dd, J=15.0, 7.8 Hz), 3.55-3.69 (3H, m), 7.21 (2H, brs), 7.29-7.48 (9H, m), 7.56 (1H, d, J=15.6 Hz), 7.73-7.78 (3H, m), 7.88-7.93 (2H, m), 11.77 (1H, brs).
MS: 548(M+H)$^+$.

Example 429

Synthesis of 2-[(1-benzyl-1H-1,2,3-triazol-4-yl)methyl]-N-ethyl-N-phenyl-N'-((E)-styrylsulfonyl)malonamide

(1) ethyl 1-benzyl-1H-1,2,3-triazole-4-carboxylate

To a mixed solvent of toluene (100 mL)/ethanol (100 mL)/water (50 mL) were added benzyl bromide (10.7 g) and sodium azide (10.1 g), and the mixture was heated under reflux for 5 hr. A solution of ethyl acrylate (38.8 mL) in ethanol (200 mL) was added dropwise to the reaction mixture, and the mixture was heated under reflux for 12 hr. The reaction mixture was concentrated under reduced pressure, and the residue was purified by silica gel column chromatography to give the title compound (5.66 g) as an oil.

$^1$H-NMR (400 Mz, CDCl$_3$) δ1.37-1.40 (3H, m), 4.40-4.42 (2H, m), 5.58 (2H, s), 7.28-7.56 (5H, m), 7.96 (1H, s).

(2) 1-benzyl-4-(hydroxymethyl)-1H-1,2,3-triazole

In the same manner as in Example 128 (2), the title compound (4.15 g) was obtained as an oil using the above-mentioned compound (5.32 g).

$^1$H-NMR (400 Mz, CDCl$_3$) δ2.43-2.46 (1H, m), 4.75-4.77 (2H, m), 5.52 (2H, s), 7.27-7.28 (2H, m), 7.34-7.40 (3H, m), 7.44 (1H, s).

(3) 1-benzyl-4-(chloromethyl)-1H-1,2,3-triazole

In the same manner as in Example 128 (3), the title compound (3.66 g) was obtained as an oil using the above-mentioned compound (4.15 g).

$^1$H-NMR (400 Mz, CDCl$_3$) δ4.68 (2H, s), 5.52 (2H, s), 7.27-7.29 (2H, m), 7.36-7.41 (3H, m), 7.48 (1H, s).

(4) monoethyl [(1-benzyl-1H-1,2,3-triazol-4-yl)methyl]malonate

In the same manner as in Example 117 (1), the object compound was obtained using the above-mentioned compound (4.10 g). This was subjected to hydrolysis in the same manner as in Example 117 (2) to give the title compound (3.25 g) as an oil.

$^1$H-NMR (400 Mz, CDCl$_3$) δ1.23-1.31 (3H, m), 3.32-3.34 (2H, m), 3.84-3.88 (1H, m), 4.11-4.27 (2H, m), 5.48 (2H, m), 7.22-7.25 (3H, m), 7.33 (1H, s), 7.35-7.38 (2H, m).

(5) 2-[(1-benzyl-1H-1,2,3-triazol-4-yl)methyl]-3-oxo-3-[((E)-styrylsulfonyl)amino]propionic acid In the same manner as in Example 152 (3), the object compound was obtained using the above-mentioned compound (3.25 g) and trans-β-styrenesulfonamide (2.04 g). This was subjected to hydrolysis in the same manner as in Example 1 (3) to give the title compound (1.68 g) as a white powder.

¹H-NMR (400 Mz, CDCl₃) δ3.44-3.52 (3H, m), 3.76-3.84 (1H, m), 5.49 (2H, s), 7.00 (1H, d, J=15.2 Hz), 7.17-7.19 (2H, m), 7.23-7.43 (5H, m), 7.47-7.52 (4H, m), 7.67 (1H, d, J=15.2 Hz).

(6) 2-[(1-benzyl-1H-1,2,3-triazol-4-yl)methyl]-N-ethyl-N-phenyl-N'-((E)-styrylsulfonyl)malonamide In the same manner as in Example 1 (4), the title compound (606 mg) was obtained as a white powder using the above-mentioned compound (1.68 g) and N-ethylaniline (479 μL).
¹H-NMR (400 Mz, CDCl₃) δ1.01-1.05 (3H, m), 3.13-3.15 (1H, m), 3.24-3.26 (1H, m), 3.47-3.51 (1H, m), 3.64-3.68 (2H, m), 5.38-5.45 (2H, m), 6.80-6.95 (2H, m), 6.99 (1H, d, J=15.6 Hz), 7.22-7.26 (2H, m), 7.32-7.36 (7H, m), 7.42-7.50 (3H, m), 7.51-7.52 (2H, m), 7.67 (1H, d, J=15.6 Hz), 11.20 (1H, brs).
MS: 544(M+H)⁺.

Example 430

Synthesis of 2-[(1-benzyl-1H-1,2,3-triazol-4-yl)methyl]-N-ethyl-N-(4-fluorophenyl)-N'-((E)-styrylsulfonyl)malonamide In the same manner as in Example 1 (4), the title compound (182 mg) was obtained as a white powder using the compound (1.27 g) obtained in Example 429 (5) and N-ethyl-4-fluoroaniline (418 mg).
¹H-NMR (400 Mz, CDCl₃) δ1.01-1.09 (3H, m), 3.09-3.14 (1H, m), 3.25-3.31 (1H, m), 3.49-3.53 (1H, m), 3.57-3.68 (2H, m), 5.36-5.46 (2H, m), 6.88-6.89 (1H, m), 6.94-7.06 (3H, m), 7.23-7.25 (1H, m), 7.26-7.33 (3H, m), 7.39-7.44 (3H, m), 7.40-7.44 (3H, m), 7.46-7.52 (2H, m), 7.68 (1H, d, J=15.2 Hz), 10.11 (1H, brs).
MS: 562(M+H)⁺.

Example 431

Synthesis of 2-[(1-cyclohexyl-1H-tetrazol-5-yl)methyl]-N-ethyl-N-phenyl-N'-((E)-styrylsulfonyl)malonamide (1) triethyl 2-(1-cyclohexyl-1H-tetrazol-5-yl)ethane-1,1,1-tricarboxylate In the same manner as in Example 117 (1), the title compound (5.14 g) was obtained as an oil using 5-(chloromethyl)-1-cyclohexyl-1H-tetrazole (2.91 g).
¹H-NMR (400 Mz, DMSO-d₆) δ1.17 (9H, t, J=7.2 Hz), 1.20-1.31 (1H, m), 1.40-1.52 (2H, m), 1.63-1.87 (5H, m), 1.94-2.03 (2H, m), 3.66 (2H, s), 4.20 (6H, q, J=7.2 Hz), 4.48-4.57 (1H, m).

(2) monoethyl [(1-cyclohexyl-1H-tetrazol-5-yl)methyl]malonate

In the same manner as in Example 117 (2), the title compound (3.85 g) was obtained as an oil using the above-mentioned compound (5.14 g).
¹H-NMR (300 Mz, CDCl₃) δ1.20-1.56 (6H, m), 1.73-2.12 (7H, m), 3.41 (2H, d, J=7.4 Hz), 4.08-4.39 (4H, m).

(3) ethyl 2-[(1-cyclohexyl-1H-tetrazol-5-yl)methyl]-3-(N-ethyl-N-phenylamino)-3-oxopropionate In the same manner as in Example 1 (4), the title compound (1.08 g) was obtained as an oil using the above-mentioned compound (3.85 g) and N-ethylaniline (2.00 mL).

¹H-NMR (400 Mz, DMSO-d₆) δ0.96-1.04 (3H, m), 1.07-1.30 (4H, m), 1.37-1.52 (2H, m), 2.63-2.02 (7H, m), 3.22-3.42 (2H, m), 3.55-3.71 (2H, m), 3.87-3.95 (1H, m), 3.95-4.07 (2H, m), 4.40-4.50 (1H, m), 7.29 (2H, d, J=7.2 Hz), 7.36-7.51 (3H, m).

(4) 2-[(1-cyclohexyl-1H-tetrazol-5-yl)methyl]-3-(N-ethyl-N-phenylamino)-3-oxopropionic acid In the same manner as in Example 1 (3), the title compound (1.00 g) was obtained as a white powder using the above-mentioned compound (1.07 g).
¹H-NMR (400 Mz, CDCl₃) δ1.07 (3H, t, J=7.6 Hz), 1.23-1.52 (3H, m), 1.73-2.11 (7H, m), 3.25 (1H, dd, J=15.6, 5.2 Hz), 3.48 (1H, dd, J=15.6, 9.6 Hz), 3.69-4.09 (2H, m), 4.12 (1H, dd, J=9.6, 5.2 Hz), 4.20-4.33 (1H, m), 7.21-7.29 (2H, m), 7.37-7.50 (3H, m).

(5) 2-[(1-cyclohexyl-1H-tetrazol-5-yl)methyl]-N-ethyl-N-phenyl-N'-((E)-styrylsulfonyl)malonamide In the same manner as in Example 1 (2), the title compound (168 mg) was obtained as a white solid using the above-mentioned compound (970 mg) and trans-β-styrenesulfonamide (480 mg).
¹H-NMR (400 Mz, DMSO-d₆) δ0.86-1.00 (3H, m), 1.17-1.31 (1H, m), 2.35-2.52 (2H, m), 1.62-2.05 (7H, m), 3.08 (1H, dd, J=16.0, 4.8 Hz), 3.38 (1H, dd, J=16.0, 9.6 Hz), 3.49-3.61 (2H, m), 4.02 (1H, dd, J=9.6, 4.8 Hz), 4.46-4.52 (1H, m), 7.15-7.44 (5H, m), 7.31 (1H, d, J=15.6 Hz), 7.44-7.45 (3H, m), 7.58 (1H, d, J=15.6 Hz), 7.75-7.88 (2H, m), 11.88 (1H, brs).
MS: 537(M+H)⁺.

Example 432

Synthesis of 2-[(1-benzyl-1H-tetrazol-5-yl)methyl]-N-ethyl-N-phenyl-N'-((E)-styrylsulfonyl)malonamide (1) 3,3,3-(triethoxycarbonyl)propionic acid In the same manner as in Example 117 (1), the object compound was obtained using tert-butyl bromoacetate (10.4 g). This was dissolved in methylene chloride (100 mL), trifluoroacetic acid (30 mL) was added at room temperature, and the mixture was stirred for 20 hr. The reaction mixture was concentrated under reduced pressure, and water (200 mL) and chloroform (100 mL) were added to extract the residue. The organic layer was washed with saturated brine, and concentrated under reduced pressure to give the title compound (9.90 g) as an oil.
¹H-NMR (400 Mz, DMSO-d₆) δ1.18 (9H, t, J=7.2 Hz), 2.96 (2H, s), 4.18 (6H, q, J=7.2 Hz), 12.52 (1H, brs).

(2) N-benzyl-3,3,3-(triethoxycarbonyl)propanamide

In the same manner as in Example 1 (4), the title compound (2.99 g) was obtained as a white solid using the above-mentioned compound (2.45 g) and benzylamine (1.10 mL).
¹H-NMR (400 Mz, DMSO-d₆) δ1.17 (9H, t, J=7.2 Hz), 2.97 (2H, s), 4.15 (6H, q, J=7.2 Hz), 4.25 (2H, d, J=6.0 Hz), 7.21-7.33 (5H, m), 8.44 (1H, t, J=6.0 Hz).

(3) triethyl 2-(1-benzyl-1H-tetrazol-5-yl)ethane-1,1,1-tricarboxylate

To a solution of the above-mentioned compound (2.99 g) in methylene chloride (40 mL) was added phosphorus pentachloride (1.64 g) under ice-cooling, and the mixture was stirred at room temperature for 3 hr. Trimethylsilylazide (2.10 mL) was added to the reaction mixture under ice-cooling, and the mixture was stirred at room temperature for 28 hr. The reaction mixture was adjusted to pH=8 by the addition of saturated aqueous sodium hydrogen carbonate solution and extracted with chloroform (100 mL). The organic layer was washed with saturated brine, and concentrated under reduced pressure to give the title compound (3.19 g) as an oil.
$^1$H-NMR (300 Mz, CDCl$_3$) δ1.27 (9H, t, J=7.2 Hz), 3.50 (2H, s), 4.28 (6H, q, J=7.2 Hz), 5.62 (2H, s), 7.22-7.26 (3H, m), 7.36-7.38 (2H, m).

(4) monoethyl [(1-benzyl-1H-tetrazol-5-yl)methyl]malonate

In the same manner as in Example 117 (2), the title compound (2.40 g) was obtained as an oil using the above-mentioned compound (3.19 g).
$^1$H-NMR (300 Mz, DMSO-d$_6$) δ1.11-1.20 (3H, m), 3.29-3.37 (2H, m), 3.94-4.17 (3H, m), 5.70 (2H, s), 7.26-7.43 (5H, m), 13.05 (1H, brs).

(5) ethyl 2-[(1-benzyl-1H-tetrazol-5-yl)methyl]-3-(N-ethyl-N-phenylamino)-3-oxopropionate In the same manner as in Example 1 (4), the title compound (1.19 g) was obtained as an oil using the above-mentioned compound (2.40 g) and N-ethylaniline (1.20 mL).
$^1$H-NMR (400 Mz, CDCl$_3$) δ1.06 (3H, t, J=7.2 Hz), 1.22 (3H, t, J=7.2 Hz), 3.12 (1H, dd, J=15.6, 5.6 Hz), 3.39 (1H, dd, J=15.6, 10.0 Hz), 3.65-3.75 (2H, m), 4.02 (1H, dd, J=10.0, 5.6 Hz), 4.11 (2H, q, J=7.2 Hz), 5.56 (1H, d, J=15.6 Hz), 5.66 (1H, d, J=15.6 Hz), 7.21-7.26 (4H, m), 7.32-7.45 (6H, m).

(6) 2-[(1-benzyl-1H-tetrazol-5-yl)methyl]-3-(N-ethyl-N-phenylamino)-3-oxopropionic acid In the same manner as in Example 1 (3), the title compound (1.08 g) was obtained as a white powder using the above-mentioned compound (1.17 g).
$^1$H-NMR (400 Mz, DMSO-d$_6$) δ0.94-1.02 (3H, m), 3.22-3.28 (2H, m), 3.56-3.70 (2H, m), 3.76-3.80 (1H, m), 5.60 (1H, d, J=15.6 Hz), 5.65 (1H, d, J=15.6 Hz), 7.22-7.27 (4H, m), 7.34-7.49 (6H, m), 12.89 (1H, brs).

(7) 2-[(1-benzyl-1H-tetrazol-5-yl)methyl]-N-ethyl-N-phenyl-N'-((E)-styrylsulfonyl)malonamide In the same manner as in Example 1 (2), the title compound (460 mg) was obtained as a white solid using the above-mentioned compound (1.08 g) and trans-β-styrenesulfonamide (520 mg).
$^1$H-NMR (300 Mz, DMSO-d$_6$) δ0.94 (3H, t, J=7.1 Hz), 3.01-3.14 (1H, m), 3.36-3.45 (1H, m), 3.51-3.64 (2H, m), 3.95-4.04 (1H, m), 5.65 (2H, s), 7.16-7.51 (14H, m), 7.58 (1H, d, J=15.6 Hz), 7.78-7.88 (2H, m), 11.88 (1H, brs).
MS: 545(M+H)$^+$.

Example 433

Synthesis of 2-[(1-ethyl-1H-tetrazol-5-yl)methyl]-N-(4-fluorophenyl)-N-isopropyl-N'-((E)-styrylsulfonyl)malonamide (1) N-ethyl-3,3,3-(triethoxycarbonyl)propanamide In the same manner as in Example 1 (4), the title compound (2.04 g) was obtained as an oil using the compound (2.31 g) obtained in Example 432 (1) and 70% aqueous ethylamine solution (640 mg).
$^1$H-NMR (400 Mz, DMSO-d$_6$) δ1.00 (3H, t, J=7.2 Hz), 1.17 (9H, t, J=7.2 Hz), 2.73 (2H, s), 2.99-3.06 (2H, m), 4.15 (6H, q, J=7.2 Hz), 7.87-7.92 (1H, m).

(2) triethyl 2-(1-ethyl-1H-tetrazol-5-yl)ethane-1,1,1-tricarboxylate

In the same manner as in Example 432 (3), the title compound (2.13 g) was obtained as an oil using the above-mentioned compound (1.97 g).
$^1$H-NMR (400 Mz, CDCl$_3$) δ1.29 (9H, t, J=7.2 Hz), 1.58 (3H, t, J=7.2 Hz), 3.60 (2H, s), 4.31 (6H, q, J=7.2 Hz), 4.40 (2H, q, J=7.2 Hz).

(3) monoethyl [(1-ethyl-1H-tetrazol-5-yl)methyl]malonate

In the same manner as in Example 117 (2), the title compound (1.07 g) was obtained as an oil using the above-mentioned compound (2.13 g).
$^1$H-NMR (400 Mz, DMSO-d$_6$) δ1.22 (3H, t, J=6.8 Hz), 1.42 (3H, t, J=7.2 Hz), 3.35-3.42 (2H, m), 3.99 (1H, t, J=7.6 Hz), 4.09-4.37 (2H, m), 4.37-4.43 (2H, m), 13.21 (1H, brs).

(4) ethyl 2-[(1-ethyl-1H-tetrazol-5-yl)methyl]-3-[N-(4-fluorophenyl)-N-isopropylamino]-3-oxopropionate In the same manner as in Example 13, the title compound (940 mg) was obtained as an oil using the above-mentioned compound (1.05 g) and 4-fluoro-N-isopropylaniline (800 mg).
$^1$H-NMR (300 Mz, DMSO-d$_6$) δ0.90 (3H, d, J=6.9 Hz), 1.00 (3H, d, J=6.9 Hz), 1.14 (3H, t, J=7.2 Hz), 1.38 (3H, t, J=7.2 Hz), 3.24-3.27 (2H, m), 3.71 (1H, dd, J=10.8, 6.9 Hz), 3.94-4.10 (2H, m), 4.35 (2H, q, J=7.2 Hz), 4.75 (1H, sept, J=6.9 Hz), 7.23-7.39 (4H, m).

(5) 2-[(1-ethyl-1H-tetrazol-5-yl)methyl]-3-[N-(4-fluorophenyl)-N-isopropylamino]-3-oxopropionic acid In the same manner as in Example 1 (3), the title compound (852 mg) was obtained as a white powder using the above-mentioned compound (920 mg).
$^1$H-NMR (300 Mz, DMSO-d$_6$) δ0.90 (3H, d, J=6.7 Hz), 0.96 (3H, d, J=6.7 Hz), 1.34 (3H, t, J=7.2 Hz), 3.13-3.29 (2H, m), 3.58-3.67 (1H, m), 4.34 (2H, q, J=7.2 Hz), 4.75 (1H, sept, J=6.7 Hz), 7.18-7.36 (4H, m), 12.96 (1H, brs).

(6) 2-[(1-ethyl-1H-tetrazol-5-yl)methyl]-N-(4-fluorophenyl)-N-isopropyl-N'-((E)-styrylsulfonyl)malonamide In the same manner as in Example 1 (2), the title compound (480 mg) was obtained as a white solid using the above-mentioned compound (852 mg) and trans-β-styrenesulfonamide (440 mg).
$^1$H-NMR (300 Mz, DMSO-d$_6$) δ0.88 (6H, t, J=7.4 Hz), 1.39 (3H, t, J=7.2 Hz), 3.06 (1H, dd, J=15.9, 4.8 Hz), 3.34-3.42 (1H, m), 3.81 (1H, dd, J=9.5, 4.8 Hz), 4.37 (2H, q, J=7.2 Hz), 4.57-4.73 (1H, m), 6.94-7.15 (2H, m), 7.33-7.62 (7H, m), 7.69-7.88 (2H, m), 11.80 (1H, brs).
MS: 515(M+H)$^+$.

Example 434

Synthesis of N-(4-fluorophenyl)-N-isopropyl-2-[(1-methyl-1H-tetrazol-5-yl)methyl]-N'-((E)-styrylsulfonyl)malonamide (1) N-methyl-3,3,3-(triethoxycarbonyl)propanamide In the same manner as in Example 1 (4), the title compound (3.51 g) was obtained as an oil using the compound (5.04 g) obtained in Example 432 (1) and 2 mol/L methylamine-THF solution (9.55 mL).
$^1$H-NMR (300 Mz, CDCl$_3$) δ1.29 (9H, t, J=7.2 Hz), 2.31 (2H, s), 3.06 (3H, s), 4.29 (6H, q, J=7.2 Hz), 5.85 (1H, brs).

(2) triethyl 2-(1-methyl-1H-tetrazol-5-yl)ethane-1,1,1-tricarboxylate

In the same manner as in Example 432 (3), the title compound (1.47 g) was obtained as an oil using the above-mentioned compound (3.45 g).
$^1$H-NMR (400 Mz, CDCl$_3$) δ1.29 (9H, t, J=7.2 Hz), 3.61 (2H, s), 4.08 (3H, s), 4.31 (6H, q, J=7.2 Hz).

(3) monoethyl [(1-methyl-1H-tetrazol-5-yl)methyl]malonate

In the same manner as in Example 117 (2), the title compound (760 mg) was obtained as an oil using the above-mentioned compound (1.47 g).
$^1$H-NMR (300 Mz, DMSO-d$_6$) δ1.17 (3H, t, J=7.1 Hz), 3.29-3.36 (2H, m), 3.96 (1H, t, J=7.7 Hz), 4.02 (3H, s), 4.13 (2H, q, J=7.1 Hz), 13.07 (1H, brs).

(4) ethyl 3-[N-(4-fluorophenyl)-N-isopropylamino]-2-[(1-methyl-1H-tetrazol-5-yl)methyl]-3-oxopropionate In the same manner as in Example 13, the title compound (1.09 g) was obtained as an oil using the above-mentioned compound (760 mg) and 4-fluoro-N-isopropylaniline (620 mg).
$^1$H-NMR (300 Mz, CDCl$_3$) δ0.90 (3H, d, J=6.9 Hz), 1.05 (3H, d, J=6.9 Hz), 1.27 (3H, t, J=7.2 Hz), 3.20 (1H, dd, J=15.3, 4.8 Hz), 3.48 (1H, dd, J=15.3, 10.2 Hz), 3.90 (1H, dd, J=10.2, 4.8 Hz), 4.06 (3H, s), 4.15 (2H, q, J=7.2 Hz), 4.84 (1H, sept, J=6.9 Hz), 7.01-7.24 (4H, m).

(5) 3-[N-(4-fluorophenyl)-N-isopropylamino]-2-[(1-methyl-1H-tetrazol-5-yl)methyl]-3-oxopropionic acid In the same manner as in Example 1 (3), the title compound (820 mg) was obtained as a white powder using the above-mentioned compound (1.08 g).
$^1$H-NMR (400 Mz, DMSO-d$_6$) δ0.87-1.00 (6H, m), 3.17-3.31 (2H, m), 3.60 (1H, dd, J=8.4, 6.4 Hz), 3.96 (3H, s), 4.75 (1H, sept, J=6.8 Hz), 7.14-7.36 (4H, m), 12.91 (1H, brs).

(6) N-(4-fluorophenyl)-N-isopropyl-2-[(1-methyl-1H-tetrazol-5-yl)methyl]-N'-((E)-styrylsulfonyl)malonamide In the same manner as in Example 1 (2), the title compound (432 mg) was obtained as a white solid using the above-mentioned compound (765 mg) and trans-β-styrenesulfonamide (420 mg).
$^1$H-NMR (400 Mz, DMSO-d$_6$) δ0.86-0.91 (6H, m), 3.06 (1H, dd, J=15.6, 5.2 Hz), 3.35 (1H, dd, J=15.6, 9.2 Hz), 3.62-3.81 (1H, m), 3.98 (3H, s), 4.67 (1H, sept, J=6.8 Hz), 7.00-7.10 (2H, m), 7.27-7.43 (3H, m), 7.43-7.52 (3H, m), 7.57 (1H, d, J=15.6 Hz), 7.78-7.87 (2H, m), 11.77 (1H, brs).
MS: 501(M+H)$^+$.

Example 435

Synthesis of N-(4-fluorophenyl)-N-isopropyl-2-[(1-phenyl-1H-tetrazol-5-yl)methyl]-N'-((E)-styrylsulfonyl)malonamide (1) N-phenyl-3,3,3-(triethoxycarbonyl)propanamide In the same manner as in Example 1 (4), the title compound (2.22 g) was obtained as a yellow solid using the compound (2.00 g) obtained in Example 432 (1) and aniline (750 μL).
$^1$H-NMR (400 Mz, DMSO-d$_6$) δ1.18 (9H, t, J=7.2 Hz), 3.14 (2H, s), 4.19 (6H, q, J=7.2 Hz), 7.03 (1H, t, J=7.6 Hz), 7.28 (2H, t, J=7.6 Hz), 7.52 (2H, d, J=7.6 Hz), 10.05 (1H, s).

(2) triethyl 2-(1-phenyl-1H-tetrazol-5-yl)ethane-1,1,1-tricarboxylate

In the same manner as in Example 432 (3), the title compound (2.19 g) was obtained as an oil using the above-mentioned compound (2.05 g).
$^1$H-NMR (400 Mz, CDCl$_3$) δ1.28 (9H, t, J=7.2 Hz), 3.63 (2H, s), 4.30 (6H, q, J=7.2 Hz), 7.47-7.50 (2H, m), 7.57-7.61 (3H, m).

(3) monoethyl [(1-phenyl-1H-tetrazol-5-yl)methyl]malonate

In the same manner as in Example 117 (2), the title compound (1.40 g) was obtained as an oil using the above-mentioned compound (2.19 g).
$^1$H-NMR (400 Mz, DMSO-d$_6$) δ1.13-1.19 (3H, m), 3.29-3.89 (2H, m), 4.00-4.13 (3H, m), 7.62-7.75 (5H, m), 13.24 (1H, brs).

(4) ethyl 3-[N-(4-fluorophenyl)-N-isopropylamino]-3-oxo-2-[(1-phenyl-1H-tetrazol-5-yl)methyl]propionate In the same manner as in Example 13, the title compound (974 mg) was obtained as an oil using the above-mentioned compound (1.31 g) and 4-fluoro-N-isopropylaniline (830 mg).
$^1$H-NMR (300 Mz, DMSO-d$_6$) δ0.91 (3H, d, J=6.9 Hz), 1.00 (3H, d, J=6.9 Hz), 1.10 (3H, t, J=7.2 Hz), 3.18-3.38 (2H, m), 3.75-3.82 (1H, m), 3.91-4.02 (2H, m), 4.72 (1H, sept, J=6.9 Hz), 7.21-7.41 (5H, m), 7.63-7.70 (5H, m).

(5) 3-[N-(4-fluorophenyl)-N-isopropylamino]-3-oxo-2-[(1-phenyl-1H-tetrazol-5-yl)methyl]propionic acid In the same manner as in Example 1 (3), the title compound (690 mg) was obtained as a white powder using the above-mentioned compound (974 mg).

¹H-NMR (400 Mz, DMSO-d₆) δ0.88-1.02 (6H, m), 3.18-3.32 (2H, m), 3.72 (1H, t, J=7.6 Hz), 4.68-4.78 (1H, m), 7.21-7.40 (5H, m), 7.62-7.69 (5H, m), 12.93 (1H, brs).

(6) N-(4-fluorophenyl)-N-isopropyl-2-[(1-phenyl-1H-tetrazol-5-yl)methyl]-N'-((E)-styrylsulfonyl)malonamide In the same manner as in Example 1 (2), the title compound (255 mg) was obtained as a white solid using the above-mentioned compound (690 mg) and trans-β-styrenesulfonamide (320 mg).
¹H-NMR (300 Mz, DMSO-d₆) δ0.87 (6H, t, J=7.2 Hz), 3.09-3.30 (2H, m), 3.87-3.96 (1H, m), 4.64 (1H, sept, J=7.2 Hz), 6.98-7.08 (2H, m), 7.23-7.60 (7H, m), 7.67 (5H, brs), 7.80-7.82 (2H, m), 11.87 (1H, brs).
MS: 563(M+H)⁺.

Example 436

Synthesis of N,N-diethyl-N'-(2-naphthylsulfonyl)-2-[(1-phenyl-1H-tetrazol-5-yl)methyl]malonamide (1) ethyl 3-(N,N-diethylamino)-3-oxo-2-[(1-phenyl-1H-tetrazol-5-yl)methyl]propionate In the same manner as in Example 13, the title compound (1.82 g) was obtained as an oil using the compound (2.96 g) obtained in Example 435 (3) and diethylamine (1.30 mL).
¹H-NMR (300 Mz, CDCl₃) δ1.06 (3H, t, J=7.1 Hz), 1.24 (3H, t, J=7.1 Hz), 1.33 (3H, t, J=7.2 Hz), 3.19-3.30 (1H, m), 3.36-3.70 (5H, m), 4.17 (2H, q, J=7.2 Hz), 4.63 (1H, dd, J=8.1, 5.7 Hz), 7.59 (5H, brs).

(2) 3-(N,N-diethylamino)-3-oxo-2-[(1-phenyl-1H-tetrazol-5-yl)methyl]propionic acid In the same manner as in Example 1 (3), the title compound (1.63 g) was obtained as a white powder using the above-mentioned compound (1.80 g).
¹H-NMR (400 Mz, DMSO-d₆) δ0.88-0.96 (3H, m), 1.20 (3H, t, J=7.2 Hz), 3.17-3.45 (5H, m), 3.54-3.62 (1H, m), 4.37-4.41 (1H, m), 7.66-7.71 (5H, m), 12.97 (1H, brs).

(3) N,N-diethyl-N'-(2-naphthylsulfonyl)-2-[(1-phenyl-1H-tetrazol-5-yl)methyl]malonamide In the same manner as in Example 1 (2), the title compound (1.21 g) was obtained as a white solid using the above-mentioned compound (1.60 g).
¹H-NMR (400 Mz, DMSO-d₆) δ0.79 (3H, t, J=7.0 Hz), 0.98 (3H, t, J=7.0 Hz), 3.06-3.25 (6H, m), 4.41-4.45 (1H, m), 7.52-7.62 (5H, m), 7.68-7.82 (3H, m), 8.06 (1H, d, J=7.9 Hz), 8.11 (1H, d, J=8.7 Hz), 8.20 (1H, d, J=7.9 Hz), 8.55 (1H, s), 12.73 (1H, brs).
MS: 507(M+H)⁺.

Example 437

Synthesis of N-isopropyl-2-[(1-methyl-1H-tetrazol-5-yl)methyl]-N'-(2-naphthylsulfonyl)-N-(3-trifluoromethylphenyl)malonamide (1) ethyl 3-[N-isopropyl-N-(3-trifluoromethylphenyl)amino]-2-[(1-methyl-1H-tetrazol-5-yl)methyl]-3-oxopropionate In the same manner as in Example 13, the title compound (1.22 g) was obtained as a white solid using the compound (1.23 g) obtained in Example 434 (3) and N-isopropyl-3-trifluoromethylaniline (1.32 g).
¹H-NMR (400 Mz, DMSO-d₆) δ0.89-0.95 (3H, m), 0.96-1.04 (3H, m), 1.12-1.20 (3H, m), 3.23 (1H, dd, J=16.0, 5.9 Hz), 3.33-3.42 (1H, m), 3.97 (3H, s), 4.00-4.08 (2H, m), 4.79 (1H, sept, J=6.8 Hz), 7.50-7.66 (2H, m), 7.75-7.79 (1H, m), 7.82-7.90 (1H, m).

(2) 3-[N-isopropyl-N-(3-trifluoromethylphenyl)amino]-2-[(1-methyl-1H-tetrazol-5-yl)methyl]-3-oxopropionic acid In the same manner as in Example 1 (3), the title compound (1.01 g) was obtained as a white powder using the above-mentioned compound (1.22 g).
¹H-NMR (400 Mz, DMSO-d₆) δ0.89-1.02 (6H, m), 3.17-3.38 (2H, m), 3.51-3.55 (1H, m), 3.95 (3H, s), 4.79 (1H, sept, J=6.8 Hz), 7.51-7.59 (2H, m), 7.73-7.77 (1H, m), 7.80-7.89 (1H, m), 13.05 (1H, brs).

(3) N-isopropyl-2-[(1-methyl-1H-tetrazol-5-yl)methyl]-N'-(2-naphthylsulfonyl)-N-(3-trifluoromethylphenyl)malonamide In the same manner as in Example 1 (2), the title compound (830 mg) was obtained as a white solid using the above-mentioned compound (1.00 g).
¹H-NMR (400 Mz, DMSO-d₆) δ0.78-0.96 (6H, m), 2.95-3.24 (2H, m), 3.64-3.80 (1H, m), 3.91 (3H, s), 4.60-4.75 (1H, m), 6.94-7.32 (1H, m), 7.42-7.92 (6H, m), 8.02-8.30 (3H, m), 8.56 (1H, s), 12.12 (1H, brs).
MS: 575(M+H)⁺.

Example 438

Synthesis of N-ethyl-2-{2-[4-(4-nitrophenyl)-1-piperazinyl]-2-oxoethyl}-N-phenyl-N'-((E)-styrylsulfonyl)malonamide (1) triethyl 3-[4-(4-nitrophenyl)-1-piperazinyl]-3-oxopropane-1,1,1-tricarboxylate In the same manner as in Example 1 (4), the title compound (1.86 g) was obtained as a yellow solid using the compound (1.23 g) obtained in Example 432 (1) and 4-(4-nitrophenyl)piperazine (930 mg).
¹H-NMR (300 Mz, DMSO-d₆) δ1.18 (9H, t, J=7.2 Hz), 3.17 (2H, s), 3.42-3.71 (8H, m), 4.16 (6H, q, J=7.2 Hz), 7.02 (2H, d, J=9.6 Hz), 8.08 (2H, d, J=9.6 Hz).

(2) monoethyl {2-[4-(4-nitrophenyl)-1-piperazinyl]-2-oxoethyl}malonate

In the same manner as in Example 117 (2), the title compound (1.47 g) obtained as a yellow solid was using the above-mentioned compound (1.86 g).
¹H-NMR (400 Mz, DMSO-d₆) δ1.18 (3H, t, J=7.2 Hz), 2.92 (2H, d, J=8.0 Hz), 3.48-3.71 (9H, m), 4.05-4.15 (2H, m), 7.02 (2H, d, J=9.6 Hz), 8.08 (2H, d, J=9.6 Hz), 12.95 (1H, brs).

(3) ethyl 3-(N-ethyl-N-phenylamino)-2-{2-[4-(4-nitrophenyl)-1-piperazinyl]-2-oxoethyl}-3-oxopropionate In the same manner as in Example 1 (4), the title compound (330 mg) was obtained as a yellow powder using the above-mentioned compound (500 mg) and N-ethylaniline (175 μL).

¹H-NMR (400 Mz, CDCl₃) δ1.15 (3H, t, J=7.2 Hz), 1.24 (3H, t, J=7.2 Hz), 2.82 (1H, dd, J=16.4, 4.8 Hz), 3.15 (1H, dd, J=16.4, 9.2 Hz), 3.40-3.57 (4H, m), 3.70-3.83 (6H, m), 3.92 (1H, dd, J=9.2, 4.8 Hz), 4.11 (2H, q, J=7.2 Hz), 6.79-6.83 (2H, m), 7.34-7.47 (5H, m), 8.08-8.12 (2H, m).

(4) 3-(N-ethyl-N-phenylamino)-2-{2-[4-(4-nitrophenyl)-1-piperazinyl]-2-oxoethyl}-3-oxopropionic acid In the same manner as in Example 1 (3), the title compound (260 mg) was obtained as a yellow powder using the above-mentioned compound (330 mg).
¹H-NMR (400 Mz, DMSO-d₆) δ1.00 (3H, t, J=7.2 Hz), 2.73-2.90 (2H, m), 3.46-3.66 (11H, m), 7.01 (2H, d, J=9.6 Hz), 7.37-7.48 (5H, m), 8.08 (2H, d, J=9.6 Hz), 12.57 (1H, brs).

(5) N-ethyl-2-{2-[4-(4-nitrophenyl)-1-piperazinyl]-2-oxoethyl}-N-phenyl-N'-((E)-styrylsulfonyl)malonamide In the same manner as in Example 1 (2), the title compound (153 mg) was obtained as a yellow solid using the above-mentioned compound (251 mg) and trans-β-styrenesulfonamide (100 mg).
¹H-NMR (400 Mz, DMSO-d₆) δ0.96 (3H, t, J=7.2 Hz), 2.56-2.66 (1H, m), 2.88-2.98 (1H, m), 3.40-3.69 (11H, m), 7.01 (2H, d, J=9.6 Hz), 7.19-7.60 (10H, m), 7.72-7.88 (2H, m), 8.08 (2H, d, J=9.6 Hz), 11.72 (1H, brs).
MS: 620(M+H)⁺.

Example 439

Synthesis of 2-{2-[4-(4-aminophenyl)-1-piperazinyl]-2-oxoethyl}-N-ethyl-N-phenyl-N'-((E)-styrylsulfonyl)malonamide 2 hydrochloride In the same manner as in Example 137 (4), the object compound was obtained using the compound (135 mg) obtained in Example 438. This was converted to a hydrochloride salt with 4 mol/L hydrochloric acid-dioxane to give the title compound (45 mg) as a pale-brown solid.
¹H-NMR (400 Mz, DMSO-d₆) δ0.95 (3H, t, J=7.2 Hz), 2.61 (1H, dd, J=16.4, 4.4 Hz), 2.92-3.20 (5H, m), 3.46-3.68 (7H, m), 7.05 (2H, J=9.2 Hz), 7.22-7.58 (12H, m), 7.80-7.82 (2H, m), 9.98 (3H, brs), 11.70 (1H, brs).
MS: 590(M+H)⁺.

Example 440

Synthesis of 2-{2-[4-(5-cyano-2-pyridyl)-1-piperazinyl]-2-oxoethyl}-N-ethyl-N-phenyl-N'-((E)-styrylsulfonyl)malonamide (1) triethyl 3-[4-(5-cyano-2-pyridyl)-1-piperazinyl]-3-oxopropane-1,1,1-tricarboxylate In the same manner as in Example 1 (4), the title compound (2.08 g) was obtained as a white solid using the compound (1.31 g) obtained in Example 432 (1) and 1-(5-cyano-2-pyridyl)piperazine (1.02 g).
¹H-NMR (400 Mz, DMSO-d₆) δ1.18 (9H, t, J=7.2 Hz), 3.17 (2H, s), 3.53-3.74 (8H, m), 4.15 (6H, q, J=7.2 Hz), 6.94 (2H, d, J=9.2 Hz), 7.89 (1H, dd, J=9.2, 2.4 Hz), 8.52 (1H, d, J=2.4 Hz).

(2) ethyl 2-{2-[4-(5-cyano-2-pyridyl)-1-piperazinyl]-2-oxoethyl}-3-(N-ethyl-N-phenylamino)-3-oxopropionate In the same manner as in Example 117 (2), the object compound was obtained using the above-mentioned compound (2.08 g). This and N-ethylaniline (625 µL) were condensed in the same manner as in Example 1 (4) to give the title compound (422 mg) as an oil.
¹H-NMR (300 Mz, CDCl₃) δ1.15 (3H, t, J=7.1 Hz), 1.22-1.29 (3H, m), 2.76-2.87 (1H, m), 3.07-3.19 (1H, m), 3.68-3.96 (11H, m), 4.07-4.14 (2H, m), 6.63-6.67 (1H, m), 7.35-7.45 (5H, m), 7.63-7.68 (1H, m), 8.40 (1H, d, J=1.9 Hz).

(3) 2-{2-[4-(5-cyano-2-pyridyl)-1-piperazinyl]-2-oxoethyl}-3-(N-ethyl-N-phenylamino)-3-oxopropionic acid In the same manner as in Example 1 (3), the title compound (140 mg) was obtained as a white powder using the above-mentioned compound (400 mg).
¹H-NMR (400 Mz, CDCl₃) δ1.15 (3H, t, J=7.2 Hz), 2.82-2.90 (1H, m), 3.07-3.15 (1H, m), 3.62-3.86 (11H, m), 6.59 (2H, d, J=9.2 Hz), 7.35-7.45 (5H, m), 7.65 (1H, dd, J=9.2, 2.0 Hz), 8.42 (1H, d, J=2.0 Hz).

(4) 2-{2-[4-(5-cyano-2-pyridyl)-1-piperazinyl]-2-oxoethyl}-N-ethyl-N-phenyl-N'-((E)-styrylsulfonyl)malonamide In the same manner as in Example 1 (2), the title compound (50 mg) was obtained as a white solid using the above-mentioned compound (140 mg) and trans-β-styrenesulfonamide (60 mg).
¹H-NMR (400 Mz, DMSO-d₆) δ0.96 (3H, t, J=7.2 Hz), 2.56-2.64 (1H, m), 2.90-2.98 (1H, m), 3.40-3.77 (11H, m), 6.92 (1H, d, J=8.8 Hz), 7.19-7.60 (10H, m), 7.80 (2H, brs), 7.85-7.92 (1H, m), 8.50 (1H, d, J=2.0 Hz), 11.65 (1H, brs).
MS: 601(M+H)⁺.

Example 441

Synthesis of 2-[2-(3,4-dihydroisoquinolin-2(1H)-yl)-2-oxoethyl]-N-ethyl-N-phenyl-N'-((E)-styrylsulfonyl)malonamide (1) triethyl 3-(3,4-dihydroisoquinolin-2(1H)-yl)-3-oxopropane-1,1,1-tricarboxylate In the same manner as in Example 1 (4), the title compound (2.08 g) was obtained as an oil using the compound (1.70 g) obtained in Example 432 (1) and 1,2,3,4-tetrahydroisoquinoline (890 µL).
¹H-NMR (300 Mz, CDCl₃) δ1.28 (9H, t, J=7.1 Hz), 2.80-3.00 (2H, m), 3.27-3.28 (2H, m), 3.70-3.85 (2H, m), 4.28 (2H, q, J=7.1 Hz), 4.67-4.72 (2H, m), 7.06-7.22 (4H, m).

(2) monoethyl [2-(3,4-dihydroisoquinolin-2(1H)-yl)-2-oxoethyl]malonate

In the same manner as in Example 117 (2), the title compound (394 mg) was obtained as an oil using the above-mentioned compound (1.97 g).
¹H-NMR (300 Mz, DMSO-d₆) δ1.17 (3H, t, J=7.2 Hz), 2.70-2.97 (4H, m), 3.64-3.73 (3H, m), 4.09 (2H, q, J=7.2 Hz), 4.57 (1H, s), 4.68 (1H, s), 7.18-7.21 (4H, m), 12.88 (1H, brs).

(3) ethyl 2-[2-(3,4-dihydroisoquinolin-2(1H)-yl)-2-oxoethyl]-3-(N-ethyl-N-phenylamino)-3-oxopropionate In the same manner as in Example 1 (4), the title compound (204 mg) was obtained as an oil using the above-mentioned compound (390 mg) and N-ethylaniline (200 μL).

$^1$H-NMR (400 Mz, CDCl$_3$) δ1.09-1.29 (6H, m), 2.78-2.95 (3H, m), 3.15-3.24 (1H, m), 3.66-3.95 (5H, m), 4.10 (2H, q, J=7.2 Hz), 4.61-4.74 (2H, m), 7.08-7.22 (4H, m), 7.31-7.48 (5H, m).

(4) 2-[2-(3,4-dihydroisoquinolin-2(1H)-yl)-2-oxoethyl]-3-(N-ethyl-N-phenylamino)-3-oxopropionic acid In the same manner as in Example 1 (3), the title compound (190 mg) was obtained as a white powder using the above-mentioned compound (204 mg).

$^1$H-NMR (300 Mz, DMSO-d$_6$) δ0.99 (3H, t, J=7.1 Hz), 2.68-2.97 (4H, m), 3.53-3.72 (5H, m), 4.54-4.64 (2H, m), 7.17-7.21 (4H, m), 7.36-7.50 (5H, m), 12.47 (1H, brs).

(5) 2-[2-(3,4-dihydroisoquinolin-2(1H)-yl)-2-oxoethyl]-N-ethyl-N-phenyl-N'-((E)-styrylsulfonyl)malonamide In the same manner as in Example 1 (2), the title compound (112 mg) was obtained as a white solid using the above-mentioned compound (190 mg) and trans-β-styrenesulfonamide (91 mg).

$^1$H-NMR (300 Mz, DMSO-d$_6$) δ0.95 (3H, t, J=7.2 Hz), 2.54-2.75 (2H, m), 2.79-2.88 (1H, m), 2.92-3.05 (1H, m), 3.45-3.74 (5H, m), 4.52-4.62 (2H, m), 7.10-7.59 (14H, m), 7.74-7.85 (2H, m), 11.65 (1H, brs).

MS: 546(M+H)$^+$.

Example 442

Synthesis of 2-[(dimethylaminocarbonyl)methyl]-N-(4-fluorophenyl)-N-isopropyl-N'-((E)-styrylsulfonyl)malonamide

(1) triethyl 2-(dimethylaminocarbonyl)ethane-1,1,1-tricarboxylate

In the same manner as in Example 1 (4), the title compound (4.52 g) was obtained as an oil using the compound (4.17 g) obtained in Example 432 (1) and dimethylamine hydrochloride (1.41 g).

$^1$H-NMR (400 Mz, CDCl$_3$) δ1.29 (9H, t, J=7.2 Hz), 2.95 (3H, s), 3.06 (3H, s), 3.18 (2H, s), 4.28 (6H, q, J=7.2 Hz).

(2) monoethyl [(dimethylaminocarbonyl)methyl]malonate

In the same manner as in Example 117 (2), the title compound (2.48 g) was obtained as an oil using the above-mentioned compound (4.52 g).

$^1$H-NMR (400 Mz, CDCl$_3$) δ1.29 (3H, t, J=7.2 Hz), 2.97-3.11 (2H, m), 2.99 (3H, s), 3.08 (3H, s), 3.81 (1H, dd, J=7.2, 4.8 Hz), 4.22-4.28 (2H, m).

(3) ethyl 2-[(dimethylaminocarbonyl)methyl]-3-[N-(4-fluorophenyl)-N-isopropylamino]-3-oxopropionate In the same manner as in Example 13, the title compound (462 mg) was obtained as an oil using the above-mentioned compound (521 mg) and 4-fluoro-N-isopropylaniline (410 mg).

$^1$H-NMR (300 Mz, CDCl$_3$) δ1.01 (3H, d, J=6.8 Hz), 1.10 (3H, d, J=6.8 Hz), 1.23 (3H, t, J=7.1 Hz), 2.63-2.73 (1H, m), 2.91 (3H, s), 3.02 (3H, s), 3.08-3.18 (1H, m), 3.67-3.73 (1H, m), 4.09 (2H, q, J=7.1 Hz), 4.92-5.05 (1H, m), 7.00-7.21 (3H, m), 7.45-7.54 (1H, m).

(4) 2-[(dimethylaminocarbonyl)methyl]-3-[N-(4-fluorophenyl)-N-isopropylamino]-3-oxopropionic acid In the same manner as in Example 1 (3), the title compound (412 mg) was obtained as a white powder using the above-mentioned compound (462 mg).

$^1$H-NMR (300 Mz, DMSO-d$_6$) δ0.91 (3H, d, J=6.6 Hz), 0.96 (3H, d, J=6.6 Hz), 2.58-2.81 (2H, m), 2.66 (3H, s), 2.92 (3H, s), 3.32-3.37 (1H, m), 4.76 (1H, sept, J=6.6 Hz), 7.16-7.44 (4H, m), 12.43 (1H, brs).

(5) 2-[(dimethylaminocarbonyl)methyl]-N-(4-fluorophenyl)-N-isopropyl-N'-((E)-styrylsulfonyl)malonamide In the same manner as in Example 1 (2), the title compound (250 mg) was obtained as a white solid using the above-mentioned compound (400 mg) and trans-β-styrenesulfonamide (226 mg).

$^1$H-NMR (400 Mz, DMSO-d$_6$) δ0.89-0.91 (6H, m), 2.42-2.51 (1H, m), 2.75 (3H, s), 2.83-2.92 (1H, m), 2.93 (3H, s), 3.42-3.50 (1H, m), 4.67-4.77 (1H, m), 6.96-7.07 (2H, m), 7.28-7.40 (3H, m), 7.47-7.60 (4H, m), 7.78-7.86 (2H, m), 11.60 (1H, brs).

MS: 490(M+H)$^+$.

Example 443

Synthesis of N-(4-fluorophenyl)-N-isopropyl-2-[(pyrrolidinocarbonyl)methyl]-N'-((E)-styrylsulfonyl)malonamide

(1) triethyl 2-(pyrrolidinocarbonyl)ethane-1,1,1-tricarboxylate

In the same manner as in Example 1 (4), the title compound (5.60 g) was obtained as an oil using the compound (4.74 g) obtained in Example 432 (1) and pyrrolidine (1.64 mL).

$^1$H-NMR (300 Mz, CDCl$_3$) δ1.29 (9H, t, J=7.1 Hz), 1.80-2.00 (4H, m), 3.11 (2H, s), 3.48 (4H, t, J=6.7 Hz), 4.28 (6H, q, J=7.1 Hz).

(2) monoethyl [(pyrrolidinocarbonyl)methyl]malonate

In the same manner as in Example 117 (2), the title compound (3.46 g) was obtained as an oil using the above-mentioned compound (5.60 g).

$^1$H-NMR (400 Mz, CDCl$_3$) δ1.25-1.32 (3H, m), 1.88-2.07 (4H, m), 2.91 (1H, dd, J=16.8, 4.0 Hz), 3.03 (1H, dd, J=16.8, 7.2 Hz), 3.44-3.57 (4H, m), 3.82 (1H, dd, J=7.2, 4.0 Hz), 4.20-4.30 (2H, m).

(3) ethyl 3-[N-(4-fluorophenyl)-N-isopropylamino]-3-oxo-2-[(pyrrolidinocarbonyl)methyl]propionate In the same manner as in Example 13, the title compound (1.09 g) was obtained as an oil using the above-mentioned compound (980 mg) and 4-fluoro-N-isopropylaniline (680 mg).
$^1$H-NMR (300 Mz, DMSO-$d_6$) δ0.92 (3H, d, J=6.9 Hz), 1.00 (3H, d, J=6.9 Hz), 1.14 (3H, t, J=7.2 Hz), 1.69-1.90 (4H, m), 2.55-2.80 (2H, m), 3.18-3.47 (5H, m), 3.93-4.03 (2H, m), 4.77 (1H, sept, 6.9 Hz), 7.18-7.45 (4H, m).

(4) 3-[N-(4-fluorophenyl)-N-isopropylamino]-3-oxo-2-[(pyrrolidinocarbonyl)methyl]propionic acid In the same manner as in Example 1 (3), the title compound (963 mg) was obtained as a white powder using the above-mentioned compound (1.09 g).
$^1$H-NMR (400 Mz, DMSO-$d_6$) δ0.88-1.01 (6H, m), 1.69-1.90 (4H, m), 2.53-2.78 (2H, m), 3.20-3.30 (2H, m), 3.32-3.42 (3H, m), 4.71-4.82 (1H, m), 7.20-7.49 (4H, m), 12.49 (1H, brs).

(5) N-(4-fluorophenyl)-N-isopropyl-2-[(pyrrolidinocarbonyl)methyl]-N'-((E)-styrylsulfonyl)malonamide In the same manner as in Example 1 (2), the title compound (930 mg) was obtained as a white solid using the above-mentioned compound (1.05 g) and trans-β-styrenesulfonamide (550 mg).
$^1$H-NMR (400 Mz, DMSO-$d_6$) δ0.87-0.93 (6H, m), 1.69-1.90 (4H, m), 2.44 (1H, dd, J=16.0, 4.4 Hz), 2.81 (1H, dd, J=16.0, 9.6 Hz), 3.17-3.24 (2H, m), 3.31-3.42 (2H, m), 3.49 (1H, dd, J=9.6, 4.4 Hz), 4.69-4.76 (1H, m), 6.97-7.07 (2H, m), 7.28-7.38 (3H, m), 7.47-7.50 (3H, m), 7.56 (1H, d, J=15.6 Hz), 7.80-7.82 (2H, m), 11.62 (1H, brs).
MS: 516(M+H)$^+$.

Example 444

Synthesis of 2-allyl-N-ethyl-N'-(2-naphthylsulfonyl)-N-phenylmalonamide (1) monoethyl allylmalonate In the same manner as in Example 1 (1), the title compound (7.50 g) was obtained as an oil using diethyl allylmalonate (10.0 g).
$^1$H-NMR (300 Mz, CDCl$_3$) δ1.22-1.28 (3H, m), 2.04-2.70 (2H, m), 3.46-3.50 (1H, m), 4.09-4.16 (1H, m), 4.19-4.24 (2H, m), 5.07-5.17 (2H, m), 5.74-5.85 (1H, m).

(2) ethyl 2-allyl-3-[(2-naphthylsulfonyl)amino]-3-oxopropionate

In the same manner as in Example 152 (3), the title compound (15.5 g) was obtained as a white powder using the above-mentioned compound (7.50 g).
$^1$H-NMR (300 Mz, CDCl$_3$) δ1.23 (3H, t, J=7.2 Hz), 2.55-2.59 (2H, m), 3.27-3.31 (1H, t, J=7.2 Hz), 4.14-4.22 (2H, m), 4.94-4.99 (2H, m), 5.54-5.59 (1H, m), 7.59-7.70 (2H, m), 7.90-8.03 (4H, m), 8.67 (1H, s), 9.74 (1H, s).

(3) 2-allyl-3-[(2-naphthylsulfonyl)amino]-3-oxopropionic acid

In the same manner as in Example 1 (3), the title compound (15.0 g) was obtained as a white powder using the above-mentioned compound (15.5 g).

$^1$H-NMR (300 Mz, CDCl$_3$) δ2.62-2.64 (2H, m), 3.38 (1H, t, J=6.9 Hz), 4.95-5.01 (2H, m), 5.57-5.66 (1H, m), 7.60-7.70 (2H, m), 7.90-8.03 (4H, m), 8.67 (1H, s).

(4) 2-allyl-N-ethyl-N'-(2-naphthylsulfonyl)-N-phenylmalonamide

In the same manner as in Example 1 (4), the title compound (15.5 g) was obtained as a white powder using the above-mentioned compound (14.3 g) and N-ethylaniline (5.40 mL).
$^1$H-NMR (400 Mz, CDCl$_3$) δ0.95 (3H, brs), 2.13-2.25 (1H, m), 2.28-2.40 (1H, m), 3.46-3.51 (1H, m), 3.56-3.66 (2H, m), 4.71-4.79 (2H, m), 5.45-5.64 (1H, m), 7.03-7.05 (2H, m), 7.27-7.46 (3H, m), 7.71-7.96 (3H, m), 8.14-8.19 (1H, m), 8.21-8.30 (2H, m), 8.60 (1H, s), 12.02 (1H, brs).
MS: 437(M+H)$^+$.

Example 445

Synthesis of 2-allyl-N-(2-hydroxyethyl)-N-methyl-N'-((E)-styrylsulfonyl)malonamide (1) 2-allyl-3-oxo-3-[((E)-styrylsulfonyl)amino]propionic acid In the same manner as in Example 152 (3), the object compound was obtained using the compound (9.05 g) obtained in Example 444 (1) and trans-β-styrenesulfonamide (9.16 g). This was subjected to hydrolysis in the same manner as in Example 1 (3) to give the title compound (7.86 g) as a white powder.
$^1$H-NMR (300 Mz, CDCl$_3$) δ2.71-2.75 (2H, m), 3.46 (1H, t, J=6.9 Hz), 5.11-5.18 (2H, m), 5.70-5.79 (1H, m), 6.92 (1H, d, J=15.3 Hz), 7.42-7.77 (5H, m), 7.74 (1H, d, J=15.3 Hz), 9.52 (1H, brs).

(2) 2-allyl-N-(2-hydroxyethyl)-N-methyl-N'-((E)-styrylsulfonyl)malonamide

In the same manner as in Example 1 (4), the title compound (169 mg) was obtained as a white powder using the above-mentioned compound (500 mg) and 2-(methylamino)ethanol (240 mg).
$^1$H-NMR (400 Mz, CDCl$_3$) δ2.65 (3H, s), 3.01-3.13 (2H, m), 3.58-3.71 (2H, m), 3.77-3.87 (3H, m), 5.04-5.17 (2H, m), 5.68-5.78 (1H, m), 6.99-7.06 (1H, m), 7.39-7.42 (3H, m), 7.42-7.52 (2H, m), 7.66-7.72 (1H, m).
MS: 367(M+H)$^+$.

Example 446

Synthesis of 2-allyl-3-[4-(5-cyano-2-pyridyl)piperazino]-3-oxo-N-((E)-styrylsulfonyl)propanamide In the same manner as in Example 1 (4), the title compound (485 mg) was obtained as a white powder using the compound (500 mg) obtained in Example 445 (1) and 1-(5-cyano-2-pyridyl)piperazine (301 mg).
$^1$H-NMR (400 Mz, CDCl$_3$) δ2.66-2.69 (2H, m), 3.59-3.67 (5H, m), 3.68-3.82 (4H, m), 5.11-5.19 (2H, m), 5.67-5.77 (1H, m), 6.59 (1H, d, J=9.2 Hz), 7.03 (1H, d, J=15.2 Hz), 7.26-7.46 (3H, m), 7.50-7.51 (2H, m), 7.52-7.73 (2H, m), 8.42 (1H, s), 10.42 (1H, brs).
MS: 480(M+H)$^+$.

Example 447

Synthesis of 2-allyl-3-[4-(2-benzothiazolyl)piperazino]-3-oxo-N-((E)-styrylsulfonyl)propanamide In the same manner as in Example 1 (4), the title compound (860 mg) was obtained as a white powder using the compound (500 mg) obtained in Example 445 (1) and 1-(2-benzothiazolyl)piperazine (351 mg).

$^1$H-NMR (400 Mz, CDCl$_3$) δ2.63-2.73 (2H, m), 3.60-3.62 (2H, m), 3.66-3.71 (5H, m), 3.73-3.85 (2H, m), 5.12-5.19 (2H, m), 5.67-5.77 (1H, m), 7.04 (1H, d, J=15.6 Hz), 7.11-7.15 (1H, m), 7.31-7.49 (4H, m), 7.51-7.59 (2H, m), 7.61-7.63 (2H, m), 7.72 (1H, d, J=15.6 Hz), 10.43 (1H, brs).
MS: 511(M+H)$^+$.

Example 448

Synthesis of 2-allyl-3-oxo-N-((E)-styrylsulfonyl)-3-[4-(7-trifluoromethyl-4-quinolyl)piperazino]propanamide In the same manner as in Example 1 (4), the title compound (558 mg) was obtained as a white powder using the compound (500 mg) obtained in Example 445 (1) and 1-(7-trifluoromethyl-4-quinolyl)piperazine (341 mg).

$^1$H-NMR (400 Mz, CDCl$_3$) δ3.70-3.80 (5H, m), 3.82-4.02 (4H, m), 4.05-4.18 (2H, m), 5.13-5.21 (2H, m), 5.68-5.84 (1H, m), 6.90-7.07 (2H, m), 7.39-7.48 (4H, m), 7.49-7.53 (2H, m), 6.51-6.73 (1H, m), 7.01-7.85 (1H, m), 8.11-8.19 (1H, m), 8.63 (1H, s), 8.98 (1H, brs).
MS: 573(M+H)$^+$.

Example 449

Synthesis of 2-allyl-3-[4-(3,4-dimethylphenyl)piperazino]-3-oxo-N-((E)-styrylsulfonyl)propanamide In the same manner as in Example 1 (4), the title compound (366 mg) was obtained as a white powder using the compound (500 mg) obtained in Example 445 (1) and 1-(3,4-dimethylphenyl)piperazine (303 mg).

$^1$H-NMR (400 Mz, CDCl$_3$) δ1.50-1.70 (2H, m), 1.82-1.99 (2H, m), 2.21-2.23 (6H, m), 2.65-2.72 (4H, m), 3.12-3.23 (1H, m), 3.69-3.72 (1H, m), 3.96-3.99 (1H, m), 4.76-4.80 (1H, m), 5.08-5.21 (2H, m), 5.69-5.79 (1H, m), 6.88-6.95 (2H, m), 7.03-7.09 (2H, m), 7.38-7.41 (3H, m), 7.42-7.46 (2H, m), 7.53-7.71 (1H, m), 10.80-11.00 (1H, m).
MS: 481(M+H)$^+$.

Example 450

Synthesis of 2-allyl-N-diphenylmethyl-N'-((E)-styrylsulfonyl)malonamide

In the same manner as in Example 1 (4), the title compound (8 mg) was obtained as a white powder using the compound (500 mg) obtained in Example 445 (1) and benzhydrylamine (352 mg).

$^1$H-NMR (400 Mz, CDCl$_3$) δ2.67-2.69 (2H, m), 3.16-3.18 (1H, m), 5.07-5.14 (2H, m), 5.60-5.77 (1H, m), 6.17-6.19 (1H, m), 6.45-6.49 (1H, m), 7.00 (1H, d, J=15.6 Hz), 7.17-7.18 (4H, m), 7.28-7.32 (6H, m), 7.42-7.49 (3H, m), 7.50-7.51 (2H, m), 7.71 (1H, d, J=15.6 Hz), 10.09 (1H, m).
MS: 475(M+H)$^+$.

Example 451

Synthesis of 2-allyl-3-[4-(3-methyl-1-phenyl-5-pyrazolyl)piperazino]-3-oxo-N-((E)-styrylsulfonyl)propanamide In the same manner as in Example 1 (4), the title compound (20 mg) was obtained as a white powder using the compound (500 mg) obtained in Example 445 (1) and 1-(3-methyl-1-phenyl-5-pyrazolyl)piperazine (388 mg).

$^1$H-NMR (400 Mz, CDCl$_3$) δ2.28 (3H, s), 2.60-2.64 (3H, m), 2.81-2.88 (4H, m), 3.48-3.53 (2H, m), 3.68-3.70 (2H, m), 5.09-5.15 (2H, m), 5.64-5.71 (1H, m), 7.02 (1H, d, J=15.2 Hz), 7.27-7.31 (2H, m), 7.39-7.45 (5H, m), 7.50-7.52 (2H, m), 7.68-7.72 (3H, m), 10.45 (1H, brs).
MS: 534(M+H)$^+$.

Example 452

Synthesis of 2-allyl-N,N-diethyl-N'-((E)-styrylsulfonyl)malonamide

In the same manner as in Example 1 (4), the title compound (119 mg) was obtained as a white powder using the compound (500 mg) obtained in Example 445 (1).

$^1$H-NMR (400 Mz, CDCl$_3$) δ1.05-1.20 (6H, m), 2.60-2.66 (2H, m), 3.21-3.38 (3H, m), 3.51-3.58 (2H, m), 5.07-3.15 (2H, m), 5.65-5.76 (1H, m), 7.03 (1H, d, J=15.6 Hz), 7.39-7.46 (3H, m), 7.51-7.53 (2H, m), 7.71 (1H, d, J=15.6 Hz), 10.70 (1H, brs).
MS: 365(M+H)$^+$.

Example 453

Synthesis of 2-allyl-N-ethyl-N-phenyl-N'-((E)-styrylsulfonyl)malonamide

In the same manner as in Example 1 (4), the title compound (515 mg) was obtained as a white powder using the compound (500 mg) obtained in Example 445 (1) and N-ethylaniline (240 μL).

$^1$H-NMR (400 Mz, CDCl$_3$) δ1.10-1.17 (3H, m), 2.40-2.66 (2H, m), 3.20-3.32 (1H, m), 3.67-3.85 (2H, m), 5.01-5.06 (2H, m), 5.49-5.60 (1H, m), 7.03 (1H, d, J=15.6 Hz), 7.09-7.12 (2H, m), 7.30-7.42 (6H, m), 7.48-7.51 (2H, m), 7.69 (1H, d, J=15.6 Hz), 10.47 (1H, brs).
MS: 413(M+H)$^+$.

Example 454

Synthesis of 2-allyl-N-ethyl-N-(1-naphthyl)-N'-((E)-styrylsulfonyl)malonamide

In the same manner as in Example 1 (4), the title compound (108 mg) was obtained as a white powder using the compound (500 mg) obtained in Example 445 (1) and N-ethyl-1-naphthylamine (277 μL).

$^1$H-NMR (400 Mz, CDCl$_3$) δ1.15-1.22 (3H, m), 2.34-2.70 (2H, m), 2.92-3.30 (1H, m), 3.32-3.53 (1H, m), 4.19-4.40 (1H, m), 4.85-5.08 (2H, m), 5.31-5.59 (1H, m), 6.98-7.04 (1H, m), 7.22-7.76 (11H, m), 7.80-7.99 (2H, m), 10.10-10.04 (1H, brs).
MS: 463(M+H)$^+$.

Example 455

Synthesis of 2-allyl-N-ethyl-N-(1-naphthyl)-N'-(2-naphthylsulfonyl)malonamide

In the same manner as in Example 1 (4), the title compound (108 mg) was obtained as a white powder using the compound (540 mg) obtained in Example 444 (3) and N-ethyl-1-naphthylamine (279 μL).
$^1$H-NMR (400 Mz, CDCl$_3$) δ1.12-1.20 (3H, m), 2.19-2.45 (2H, m), 2.79-2.94 (1H, m), 3.21-3.53 (1H, m), 4.11-4.40 (1H, m), 4.66-4.88 (2H, m), 5.15-5.47 (1H, m), 6.82-6.97 (1H, m), 7.24-8.03 (12H, m), 8.62-8.67 (1H, m), 10.14-10.67 (1H, m).
MS: 487(M+H)$^+$.

Example 456

Synthesis of 2-allyl-N-ethyl-N-(2-naphthyl)-N'-{[(E)-2-(2-thiazolyl)ethenyl]sulfonyl}malonamide The compound (344 mg) obtained in Example 444 (1) and [(E)-2-(2-thiazolyl)ethylene]sulfonamide (380 mg) were condensed in the same manner as in Example 152 (3), and the condensed product was subjected to hydrolysis in the same manner as in Example 1 (3) to give a white powder (469 mg). In the same manner as in Example 1 (4), the title compound (84 mg) was obtained as a white powder using this and N-ethyl-2-naphthylamine (373 mg).
$^1$H-NMR (400 Mz, CDCl$_3$) δ1.30 (3H, m), 2.48-2.53 (1H, m), 2.56-2.64 (1H, m), 3.29 (1H, t, J=6.8 Hz), 3.82-3.89 (2H, m), 5.03-5.08 (2H, m), 5.49-5.59 (1H, m), 7.18-7.21 (1H, m), 7.39 (1H, d, J=14.8 Hz), 7.52-7.78 (4H, m), 7.81-7.83 (2H, m), 7.87-7.93 (2H, m), 7.97-7.98 (1H, m), 10.61 (1H, brs).
MS: 470(M+H)$^+$.

Example 457

Synthesis of 2-allyl-N-ethyl-N-(1-naphthyl)-N'-{[(E)-2-(2-thiazolyl)ethenyl]sulfonyl}malonamide In the same manner as in Example 456, the title compound (116 mg) was obtained as a white powder using N-ethyl-1-naphthylamine (514 μL).
$^1$H-NMR (400 Mz, CDCl$_3$) δ1.17-1.21 (3H, m), 2.30-2.70 (2H, m), 2.90-3.10 (1H, m), 4.20-4.40 (2H, m), 4.90-5.10 (2H, m), 5.30-5.60 (1H, m), 7.36-7.40 (1H, m), 7.47-7.59 (5H, m), 7.78-7.81 (1H, m), 7.91-7.94 (1H, m), 7.97-7.98 (3H, m), 10.25 (1H, brs).
MS: 470(M+H)$^+$.

Example 458

Synthesis of 2-allyl-N-ethyl-N-(2-naphthyl)-N'-{[(E)-2-(3-pyridyl)ethenyl]sulfonyl}malonamide The compound (344 mg) obtained in Example 444 (1) and [(E)-2-(3-pyridyl)ethylene]sulfonamide (369 mg) were condensed in the same manner as in Example 152 (3), and the condensed product was subjected to hydrolysis in the same manner as in Example 1 (3). In the same manner as in Example 1 (4), the title compound (25 mg) was obtained as a white powder using this and N-ethyl-2-naphthylamine (504 mg).
$^1$H-NMR (400 Mz, CDCl$_3$) δ1.22 (3H, t, J=7.2 Hz), 2.47-2.52 (2H, m), 2.56-2.63 (1H, m), 3.45-3.50 (1H, m), 3.69-3.87 (2H, m), 5.02-5.06 (2H, m), 5.51-5.58 (1H, m), 7.10-7.20 (2H, m), 7.35-7.38 (1H, m), 7.52-7.73 (2H, m), 7.81-7.83 (1H, m), 7.88-7.93 (4H, m), 8.65 (1H, s), 8.75 (1H, s).
MS: 464(M+H)$^+$.

Example 459

Synthesis of 2-allyl-N-(2,3-dichlorophenyl)-N-ethyl-N'-((E)-styrylsulfonyl)malonamide In the same manner as in Example 1 (4), the title compound (44 mg) was obtained as a white powder using the compound (928 mg) obtained in Example 445 (1) and 2,3-dichloro-N-ethylaniline (570 mg).
$^1$H-NMR (400 Mz, CDCl$_3$) δ1.12-1.18 (3H, m), 2.42-2.68 (2H, m), 3.02-3.10 (1H, m), 3.43-4.50 (1H, m), 3.93-4.26 (1H, m), 4.98-5.25 (2H, m), 5.50-5.79 (1H, m), 6.97-7.12 (2H, m), 7.21-7.31 (1H, m), 7.40-7.50 (3H, m), 7.55-7.65 (3H, m), 7.72 (1H, d, J=15.2 Hz).
MS: 480(M+H)$^+$.

Example 460

Synthesis of 2-allyl-N-(2,3-dimethylphenyl)-N-ethyl-N'-((E)-styrylsulfonyl)malonamide In the same manner as in Example 1 (4), the title compound (92 mg) was obtained as a white powder using the compound (928 mg) obtained in Example 445 (1) and 2,3-dimethyl-N-ethylaniline (448 mg).
$^1$H-NMR (400 Mz, CDCl$_3$) δ1.10-1.15 (3H, m), 2.09 (3H, s), 2.30 (3H, s), 2.40-2.45 (1H, m), 2.50-2.55 (1H, m), 3.04-3.15 (2H, m), 4.21-4.26 (1H, m), 4.97-5.04 (2H, m), 5.50-5.57 (1H, m), 6.78-6.80 (1H, m), 7.02 (1H, d, J=15.2 Hz), 7.07-7.11 (1H, m), 7.18-7.19 (1H, m), 7.39-7.44 (3H, m), 7.49-7.52 (2H, m), 7.70 (1H, d, J=15.2 Hz), 10.12 (1H, brs).
MS: 441(M+H)$^+$.

Example 461

Synthesis of 2-allyl-N-ethyl-N-(4-fluorophenyl)-N'-((E)-styrylsulfonyl)malonamide In the same manner as in Example 1 (4), the title compound (110 mg) was obtained as a white powder using the compound (928 mg) obtained in Example 445 (1) and N-ethyl-4-fluoroaniline (418 mg).
$^1$H-NMR (400 Mz, CDCl$_3$) δ1.13 (3H, brs), 2.45-2.59 (2H, m), 3.17-3.21 (1H, m), 3.66-3.81 (2H, m), 5.03-5.07 (2H, m), 5.49-5.58 (1H, m), 7.02 (1H, d, J=15.2 Hz), 7.09-7.15 (4H, m), 7.42-7.47 (3H, m), 7.50-7.52 (2H, m), 7.71 (1H, d, J=15.2 Hz), 10.28 (1H, brs).
MS: 431(M+H)$^+$.

Example 462

Synthesis of 2-allyl-N-methyl-N-(1-naphthyl)-N'-((E)-styrylsulfonyl)malonamide

In the same manner as in Example 1 (4), the title compound (458 mg) was obtained as a white powder using the compound (928 mg) obtained in Example 445 (1) and N-methyl-1-naphthylamine (581 mg).
$^1$H-NMR (400 Mz, CDCl$_3$) δ2.41-2.49 (2H, m), 3.12-3.16 (1H, m), 3.44 (3H, s), 4.87-5.08 (2H, m), 5.29-5.40 (1H, m), 7.03 (1H, d, J=15.6 Hz), 7.27-7.31 (1H, m), 7.32-7.61 (6H, m), 7.66-7.34 (2H, m), 7.89-7.91 (2H, m), 7.93-7.96 (2H, m), 10.06 (1H, brs).
MS: 449(M+H)$^+$.

Example 463

Synthesis of 2-allyl-N-(4-chlorophenyl)-N-ethyl-N'-((E)-styrylsulfonyl)malonamide In the same manner as in Example 1 (4), the title compound (707 mg) was obtained as a white powder using the compound (928 mg) obtained in Example 445 (1) and 4-chloro-N-ethylaniline (467 mg).

$^1$H-NMR (400 Mz, CDCl$_3$) δ1.14 (3H, brs), 2.46-2.59 (2H, m), 3.17-3.21 (1H, m), 3.66-3.71 (1H, m), 3.76-3.82 (1H, m), 5.03-5.07 (2H, m), 5.51-5.57 (1H, m), 7.00-7.06 (3H, m), 7.26-7.45 (5H, m), 7.51-7.53 (2H, m), 7.71 (1H, d, J=15.6 Hz), 10.25 (1H, brs).

MS: 447(M+H)$^+$.

Example 464

Synthesis of 2-allyl-N-(2,5-difluorophenyl)-N-ethyl-N'-((E)-styrylsulfonyl)malonamide In the same manner as in Example 1 (4), the title compound (92 mg) was obtained as a white powder using the compound (928 mg) obtained in Example 445 (1) and 2,5-difluoro-N-ethylaniline (425 mg).

$^1$H-NMR (400 Mz, CDCl$_3$) δ1.10-1.15 (3H, m), 2.40-2.70 (2H, m), 3.12-3.29 (1H, m), 3.47-3.67 (1H, m), 3.82-3.89 (1H, m), 4.97-5.10 (2H, m), 5.53-5.70 (1H, m), 6.91-6.94 (1H, m), 6.99-7.21 (4H, m), 7.31-7.43 (2H, m), 7.51-7.53 (2H, m), 7.71 (1H, d, J=15.6 Hz), 10.04-10.14 (1H, m).

MS: 449(M+H)$^+$.

Example 465

Synthesis of 2-allyl-N-(4-chlorophenyl)-N-methyl-N'-((E)-styrylsulfonyl)malonamide In the same manner as in Example 1 (4), the title compound (178 mg) was obtained as a white powder using the compound (928 mg) obtained in Example 445 (1) and 4-chloro-N-methylaniline (425 mg).

$^1$H-NMR (400 Mz, CDCl$_3$) δ2.47-2.59 (2H, m), 3.27-3.31 (4H, m), 5.03-5.08 (2H, m), 5.48-5.57 (1H, m), 7.00-7.09 (3H, m), 7.39-7.45 (5H, m), 7.51-7.53 (2H, m), 7.71 (1H, d, J=15.6 Hz), 10.18 (1H, brs).

MS: 432(M+H)$^+$.

Example 466

Synthesis of 2-allyl-N-ethyl-N-(2-fluorophenyl)-N'-((E)-styrylsulfonyl)malonamide In the same manner as in Example 1 (4), the title compound (263 mg) was obtained as a white powder using the compound (928 mg) obtained in Example 445 (1) and N-ethyl-2-fluoroaniline (418 mg).

$^1$H-NMR (400 Mz, CDCl$_3$) δ1.09-1.11 (3H, m), 2.40-2.70 (2H, m), 3.12-3.20 (1H, m), 3.51-3.57 (1H, m), 3.80-3.95 (1H, m), 4.96-5.08 (2H, m), 5.51-5.71 (1H, m), 6.99-7.04 (1H, m), 7.14-7.24 (4H, m), 7.50-7.55 (3H, m), 7.58-7.62 (2H, m), 7.88 (1H, d, J=15.2 Hz), 10.18-10.30 (1H, brs).

MS: 431(M+H)$^+$.

Example 467

Synthesis of 2-allyl-N-ethyl-N-(2,4,6-trifluorophenyl)-N'-((E)-styrylsulfonyl)malonamide In the same manner as in Example 1 (4), the title compound (108 mg) was obtained as a white powder using the compound (928 mg) obtained in Example 445 (1) and N-ethyl-2,4,6-trifluoroaniline (525 mg).

$^1$H-NMR (400 Mz, CDCl$_3$) δ1.17 (3H, brs), 2.46-2.53 (1H, m), 2.57-2.63 (1H, m), 3.05-3.09 (1H, m), 3.49-3.58 (1H, m), 3.84-3.93 (1H, m), 5.03-5.08 (2H, m), 5.51-5.61 (1H, m), 6.74-6.84 (2H, m), 7.00 (1H, d, J=15.6 Hz), 7.26-7.45 (3H, m), 7.51-7.53 (2H, m), 7.71 (1H, d, J=15.6 Hz), 9.91 (1H, brs).

MS: 467(M+H)$^+$.

Example 468

Synthesis of 2-allyl-N-ethyl-N-(2,4-difluorophenyl)-N'-((E)-styrylsulfonyl)malonamide In the same manner as in Example 1 (4), the title compound (5 mg) was obtained as a white powder using the compound (928 mg) obtained in Example 445 (1) and N-ethyl-2,4-difluoroaniline (550 mg).

$^1$H-NMR (400 Mz, CDCl$_3$) δ1.26-1.30 (3H, m), 2.66-2.70 (2H, m), 3.37-3.41 (1H, m), 4.20-4.25 (2H, m), 5.08-5.14 (2H, m), 5.70-5.72 (1H, m), 7.04 (1H, d, J=15.2 Hz), 7.40-7.45 (4H, m), 7.51-7.53 (4H, m), 7.73 (1H, d, J=15.2 Hz), 9.60 (1H, brs).

MS: 449(M+H)$^+$.

Example 469

Synthesis of 2-allyl-N-ethyl-N-(3,4-methylenedioxyphenyl)-N'-((E)-styrylsulfonyl)malonamide In the same manner as in Example 1 (4), the title compound (627 mg) was obtained as a white powder using the compound (928 mg) obtained in Example 445 (1) and N-ethyl-3,4-methylenedioxyaniline (496 mg).

$^1$H-NMR (400 Mz, CDCl$_3$) δ1.10 (3H, brs), 2.45-2.61 (2H, m), 3.29-3.32 (1H, m), 3.69-3.70 (2H, m), 5.03-5.08 (2H, m), 5.53-5.63 (1H, m), 6.04 (2H, s), 6.54-6.56 (2H, m), 6.78-6.80 (1H, m), 7.03 (1H, d, J=15.6 Hz), 7.32-7.40 (3H, m), 7.41-7.52 (2H, m), 7.70 (1H, d, J=15.6 Hz), 10.38 (1H, brs).

MS: 457(M+H)$^+$.

Example 470

Synthesis of 2-allyl-3-(5-bromo-2,3-dihydro-1H-indol-1-yl)-3-oxo-N-((E)-styrylsulfonyl)propanamide In the same manner as in Example 1 (4), the title compound (96 mg) was obtained as a white powder using the compound (928 mg) obtained in Example 445 (1) and 5-bromoindoline (594 mg).

$^1$H-NMR (400 Mz, CDCl$_3$) δ2.69-2.78 (2H, m), 3.17-3.21 (2H, m), 3.58-3.62 (1H, m), 4.05-4.21 (2H, m), 5.10-5.21 (2H, m), 5.71-5.81 (1H, m), 7.03 (1H, d, J=15.6 Hz), 7.33-7.39 (2H, m), 7.40-7.46 (3H, m), 7.50-7.52 (2H, m), 7.72 (1H, d, J=15.6 Hz), 8.11 (1H, d, J=8.4 Hz), 10.35 (1H, brs).

MS: 491(M+H)$^+$.

Example 471

Synthesis of 2-allyl-3-(6-fluoro-2-methyl-3,4-dihydroquinolin-1(2H)-yl)-3-oxo-N-((E)-styrylsulfonyl)propanamide In the same manner as in Example 1 (4), the title compound (236 mg) was obtained as a white powder using the compound (618 mg) obtained in Example 445 (1) and 6-fluoro-2-methyl-1,2,3,4-tetrahydroquinoline (330 mg).
$^1$H-NMR (400 Mz, CDCl$_3$) δ1.12 (3H, brs), 1.20-1.32 (1H, m), 2.34-2.61 (5H, m), 3.73-3.78 (1H, m), 4.75-4.80 (1H, m), 4.93-4.99 (2H, m), 5.30-5.39 (1H, m), 6.92-6.96 (3H, m), 7.07 (1H, d, J=15.2 Hz), 7.41-7.46 (3H, m), 7.53-7.55 (2H, m), 7.75 (1H, d, J=15.2 Hz), 10.29 (1H, brs).
MS: 457(M+H)$^+$.

Example 472

Synthesis of 2-allyl-N-benzyl-N-phenyl-N'-((E)-styrylsulfonyl)malonamide

In the same manner as in Example 1 (4), the title compound (268 mg) was obtained as a white powder using the compound (741 mg) obtained in Example 445 (1) and N-benzylaniline (439 mg).
$^1$H-NMR (400 Mz, CDCl$_3$) δ2.46-2.53 (1H, m), 2.57-2.64 (1H, m), 3.24-3.27 (1H, m), 4.78-4.82 (1H, m), 4.93-5.07 (3H, m), 5.49-5.59 (1H, m), 6.87 (2H, d, J=2.4 Hz), 7.01 (1H, d, J=15.2 Hz), 7.13-7.23 (2H, m), 7.28-7.36 (6H, m), 7.39-7.46 (3H, m), 7.49-7.52 (2H, m), 7.71 (1H, d, J=15.2 Hz), 10.36 (1H, brs).
MS: 475(M+H)$^+$.

Example 473

Synthesis of 2-allyl-3-(3,4-dihydroisoquinolin-2(1H)-yl)-3-oxo-N-((E)-styrylsulfonyl)propanamide In the same manner as in Example 1 (4), the title compound (650 mg) was obtained as a white powder using the compound (674 mg) obtained in Example 445 (1) and 1,2,3,4-tetrahydroisoquinoline (266 mg).
$^1$H-NMR (400 Mz, CDCl$_3$) δ2.62-2.75 (2H, m), 2.85-2.96 (2H, m), 3.71-3.78 (3H, m), 4.59-4.80 (2H, m), 4.98-5.17 (2H, m), 5.63-5.76 (1H, m), 7.03 (1H, d, J=15.6 Hz), 7.06-7.23 (4H, m), 7.26-7.45 (3H, m), 7.52-7.64 (2H, m), 7.72 (1H, d, J=15.6 Hz), 10.70-10.80 (1H, m).
MS: 425(M+H)$^+$.

Example 474

Synthesis of 2-allyl-N-ethyl-N-(4-methylthiophenyl)-N'-((E)-styrylsulfonyl)malonamide In the same manner as in Example 1 (4), the title compound (282 mg) was obtained as a white powder using the compound (618 mg) obtained in Example 445 (1) and N-ethyl-4-methylthioaniline (1.00 g).
$^1$H-NMR (400 Mz, CDCl$_3$) δ1.14 (3H, brs), 2.45-2.60 (5H, m), 3.23-3.26 (1H, m), 3.65-3.81 (2H, m), 5.02-5.07 (2H, m), 5.51-5.58 (1H, m), 6.99-7.05 (3H, m), 7.25-7.40 (2H, m), 7.40-7.45 (3H, m), 7.51-7.53 (2H, m), 7.71 (1H, d, J=15.2 Hz), 10.42 (1H, brs).
MS: 459(M+H)$^+$.

Example 475

Synthesis of 2-allyl-N-ethyl-N'-((E)-styrylsulfonyl)-N-(3-trifluoromethylphenyl)malonamide In the same manner as in Example 1 (4), the title compound (321 mg) was obtained as a white powder using the compound (618 mg) obtained in Example 445 (1) and N-ethyl-3-trifluoromethylaniline (1.00 g).
$^1$H-NMR (400 Mz, CDCl$_3$) δ1.14 (3H, brs), 2.45-2.51 (1H, m), 2.52-2.63 (1H, m), 3.10-3.14 (1H, m), 3.73-3.82 (2H, m), 5.05-5.24 (2H, m), 5.49-5.59 (1H, m), 7.03 (1H, d, J=15.6 Hz), 7.29-7.31 (1H, m), 7.33-7.46 (4H, m), 7.51-7.62 (2H, m), 7.65-7.70 (1H, m), 7.74-8.06 (2H, m), 10.31 (1H, brs).
MS: 481(M+H)$^+$.

Example 476

Synthesis of 2-allyl-N-ethyl-N'-((E)-styrylsulfonyl)-N-(4-trifluoromethylphenyl)malonamide In the same manner as in Example 1 (4), the title compound (398 mg) was obtained as a white powder using the compound (618 mg) obtained in Example 445 (1) and N-ethyl-4-trifluoromethylaniline (1.00 g).
$^1$H-NMR (400 Mz, CDCl$_3$) δ1.10-1.16 (3H, m), 2.45-2.52 (1H, m), 2.53-2.63 (1H, m), 3.16 (1H, t, J=7.2 Hz), 3.68-3.87 (2H, m), 5.04-5.08 (2H, m), 5.48-5.57 (1H, m), 7.02 (1H, d, J=15.6 Hz), 7.24-7.28 (2H, m), 7.39-7.45 (3H, m), 7.51-7.53 (2H, m), 7.61-7.73 (3H, m), 10.17 (1H, s).
MS: 481(M+H)$^+$.

Example 477

Synthesis of 2-allyl-N-methyl-N-(1-naphthylmethyl)-N'-((E)-styrylsulfonyl)malonamide In the same manner as in Example 1 (4), the title compound (89 mg) was obtained as a white powder using the compound (618 mg) obtained in Example 445 (1) and N-methyl-1-naphthylmethylamine hydrochloride (415 mg).
$^1$H-NMR (400 Mz, CDCl$_3$) 52.60-2.80 (2H, m), 2.88-3.15 (3H, m), 3.53-3.73 (1H, m), 4.93-5.28 (4H, m), 5.58-5.77 (1H, m), 6.99 (1H, d, J=15.6 Hz), 7.33-7.58 (9H, m), 7.71-8.09 (4H, m), 10.40-10.82 (1H, m).
MS: 463(M+H)$^+$.

Example 478

Synthesis of 2-allyl-N,N-dibenzyl-N'-((E)-styrylsulfonyl)malonamide

In the same manner as in Example 1 (4), the title compound (288 mg) was obtained as a white powder using the compound (618 mg) obtained in Example 445 (1) and dibenzylamine (394 mg).
$^1$H-NMR (400 Mz, CDCl$_3$) δ2.62-2.67 (2H, m), 3.65-3.69 (1H, m), 4.39-4.54 (3H, m), 4.84-4.88 (1H, m), 5.04-5.12 (2H, m), 5.60-5.66 (1H, m), 7.02 (1H, d, J=15.2 Hz), 7.07-7.09 (2H, m), 7.19-7.21 (2H, m), 7.29-7.34 (6H, m), 7.42-7.47 (3H, m), 7.51-7.53 (2H, m), 7.72 (1H, d, J=15.2 Hz), 10.43 (1H, brs).
MS: 489(M+H)$^+$.

Example 479

Synthesis of 2-allyl-N-ethyl-N-(3-fluorophenyl)-N'-((E)-styrylsulfonyl)malonamide In the same manner as in Example 1 (4), the title compound (372 mg) was obtained as a white powder using the compound (618 mg) obtained in Example 445 (1) and N-ethyl-3-fluoroaniline (278 mg).

$^1$H-NMR (400 Mz, CDCl$_3$) δ1.12 (3H, brs), 2.40-2.80 (2H, m), 3.21-3.69 (1H, m), 3.71-3.84 (2H, m), 5.04-5.22 (2H, m), 5.50-5.82 (1H, m), 6.85-6.93 (2H, m), 7.03 (1H, d, J=15.6 Hz), 7.11-7.16 (1H, m), 7.30-7.41 (5H, m), 7.42-7.47 (3H, m), 7.70 (1H, d, J=15.6 Hz), 10.30 (1H, brs).

MS: 431(M+H)$^+$.

Example 480

Synthesis of 2-allyl-N-ethyl-N-(4'-fluoro-4-biphenyl)-N'-((E)-styrylsulfonyl)malonamide In the same manner as in Example 1 (4), the title compound (241 mg) was obtained as a white powder using the compound (337 mg) obtained in Example 445 (1) and N-(4'-fluoro-4-biphenyl)-N-ethylamine (430 mg).

$^1$H-NMR (400 Mz, CDCl$_3$) δ1.12 (3H, brs), 2.40-2.65 (2H, m), 3.27-3.49 (1H, m), 3.70-3.89 (2H, m), 5.03-5.25 (2H, m), 5.52-5.85 (1H, m), 7.03 (1H, d, J=15.6 Hz), 7.09-7.22 (4H, m), 7.39-7.49 (3H, m), 7.51-7.54 (6H, m), 7.75 (1H, d, J=15.6 Hz), 10.40 (1H, brs).

MS: 507(M+H)$^+$.

Example 481

Synthesis of 2-allyl-N-(4-fluorophenyl)-N-isopropyl-N'-((E)-styrylsulfonyl)malonamide In the same manner as in Example 1 (4), the title compound (265 mg) was obtained as a white powder using the compound (618 mg) obtained in Example 445 (1) and 4-fluoro-N-isopropylaniline (306 mg).

$^1$H-NMR (400 Mz, CDCl$_3$) δ1.00 (3H, d, J=6.8 Hz), 1.09 (3H, d, J=6.8 Hz), 2.17-2.49 (1H, m), 2.52-2.58 (1H, m), 3.02-3.06 (1H, m), 4.93-4.97 (1H, m), 5.03-5.07 (2H, m), 5.50-5.57 (1H, m), 6.99-7.05 (3H, m), 7.09-7.14 (2H, m), 7.39-7.45 (3H, m), 7.50-7.52 (2H, m), 7.70 (1H, d, J=15.6 Hz), 10.29 (1H, brs).

MS: 445(M+H)$^+$.

Example 482

Synthesis of 2-allyl-N-isopropyl-N'-((E)-styrylsulfonyl)-N-(3-trifluoromethylphenyl)malonamide In the same manner as in Example 13, the title compound (96 mg) was obtained as a white powder using the compound (309 mg) obtained in Example 445 (1) and N-isopropyl-3-trifluoromethylaniline (244 mg).

$^1$H-NMR (300 Mz, DMSO-d$_6$) δ0.74-1.51 (6H, m), 2.15-2.60 (2H, m), 2.96-3.22 (1H, m), 4.67-5.00 (3H, m), 5.42-5.75 (1H, m), 7.13-7.95 (1H, m), 11.59 (1H, brs).

MS: 495(M+H)$^+$.

Example 483

Synthesis of 2-allyl-N-(4-fluorophenyl)-N-(3-pentyl)-N'-((E)-styrylsulfonyl)malonamide In the same manner as in Example 13, the title compound (357 mg) was obtained as a white powder using the compound (619 mg) obtained in Example 445 (1) and 4-fluoro-N-(3-pentyl)aniline (435 mg).

$^1$H-NMR (300 Mz, DMSO-d$_6$) δ0.69-0.90 (6H, m), 0.90-1.38 (4H, m), 2.11-2.32 (1H, m), 2.36-2.56 (1H, m), 3.06-3.23 (1H, m), 4.25-4.50 (1H, m), 4.78-4.99 (2H, m), 5.50-5.76 (1H, m), 6.84-7.04 (1H, m), 7.04-7.23 (2H, m), 7.23-7.40 (2H, m), 7.40-7.63 (4H, m), 7.69-7.91 (2H, m), 11.59 (1H, brs).

MS: 473(M+H)$^+$.

Example 484

Synthesis of 2-allyl-N-isopropyl-N-(3-pyridyl)-N'-((E)-styrylsulfonyl)malonamide In the same manner as in Example 13, the title compound (170 mg) was obtained as a white powder using the compound (619 mg) obtained in Example 445 (1) and 3-(isopropylamino)pyridine (327 mg).

$^1$H-NMR (300 Mz, DMSO-d$_6$) δ0.75-1.00 (6H, m), 2.13-2.55 (2H, m), 2.60-3.08 (1H, m), 4.60-5.00 (3H, m), 5.48-5.74 (1H, m), 7.00-7.90 (9H, m), 8.38 (1H, brs), 8.59 (1H, brs), 11.58 (1H, brs).

MS: 428(M+H)$^+$.

Example 485

Synthesis of 2-allyl-N-cyclohexyl-N-ethyl-N'-((E)-styrylsulfonyl)malonamide

In the same manner as in Example 13, the title compound (113 mg) was obtained as a white powder using the compound (619 mg) obtained in Example 445 (1) and N-ethylcyclohexylamine (305 mg).

$^1$H-NMR (300 Mz, DMSO-d$_6$) δ0.82-1.80 (13H, m), 2.31-2.52 (2H, m), 2.98-4.10 (4H, m), 4.89-5.05 (2H, m), 5.57-5.88 (1H, m), 7.23-7.61 (5H, m), 7.61-7.79 (2H, m), 12.14 (1H, brs).

MS: 419(M+H)$^+$.

Example 486

Synthesis of N-ethyl-N-(4-fluorophenyl)-2-(3-methyl-2-butenyl)-N'-((E)-styrylsulfonyl)malonamide (1) monoethyl (3-methyl-2-butenyl)malonate In the same manner as in Example 117 (1), the object compound was obtained using 1-bromo-3-methyl-2-butene (5.00 g). This was subjected to hydrolysis in the same manner as in Example 117 (2) to give the title compound (5.08 g) as an oil.

$^1$H-NMR (400 Mz, CDCl$_3$) δ1.26-1.33 (3H, m), 1.64 (3H, s), 1.69 (3H, s), 2.59-2.68 (2H, m), 3.37-3.43 (1H, m), 4.19-4.27 (2H, m), 5.06-5.10 (1H, m).

(2) 2-(3-methyl-2-butenyl)-3-oxo-3-[((E)-styrylsulfonyl)amino]propionic acid

In the same manner as in Example 152 (3), the object compound was obtained using the above-mentioned compound (3.00 g) and trans-β-styrenesulfonamide (2.75 g). This was subjected to hydrolysis in the same manner as in Example 1 (3) to give the title compound (3.84 g) as a white powder.
¹H-NMR (400 Mz, CDCl₃) δ2.11 (3H, s), 2.21 (3H, s), 3.39-3.45 (1H, m), 3.47-3.52 (1H, m), 5.01-5.10 (2H, m), 7.03 (1H, d, J=15.6 Hz), 7.21-7.54 (5H, m), 7.74 (1H, d, J=15.6 Hz), 9.42 (1H, brs).

(3) N-ethyl-N-(4-fluorophenyl)-2-(3-methyl-2-butenyl)-N'-((E)-styrylsulfonyl)malonamide In the same manner as in Example 1 (4), the title compound (201 mg) was obtained as a white powder using the above-mentioned compound (674 mg) and N-ethyl-4-fluoroaniline (278 mg).
¹H-NMR (400 Mz, CDCl₃) δ1.10-1.14 (3H, m), 1.50 (3H, s), 1.63 (3H, s), 2.41-2.44 (1H, m), 2.52-2.54 (1H, m), 3.11-3.15 (1H, m), 3.69-3.76 (2H, m), 4.86-4.88 (1H, m), 7.02-7.13 (5H, m), 7.41-7.45 (3H, m), 7.51-7.53 (2H, m), 7.71 (1H, d, J=15.2 Hz), 10.36 (1H, brs).
MS: 459(M+H)⁺.

Example 487

Synthesis of N-ethyl-N-(1-naphthyl)-2-propyl-N'-((E)-styrylsulfonyl)malonamide (1) monoethyl propylmalonate In the same manner as in Example 1 (1), the title compound (4.31 g) was obtained as an oil using diethyl propylmalonate (5.00 g).
¹H-NMR (300 Mz, CDCl₃) δ0.95 (3H, t, J=7.5 Hz), 1.08-1.48 (5H, m), 1.74-2.02 (2H, m), 3.39 (1H, t, J=7.2 Hz), 4.23 (2H, q, J=7.2 Hz), 7.27 (1H, brs).

(2) ethyl 3-oxo-2-propyl-3-[((E)-styrylsulfonyl)amino]propionate

In the same manner as in Example 152 (3), the title compound (8.17 g) was obtained as an oil using the above-mentioned compound (4.31 g) and trans-β-styrenesulfonamide (4.18 g).
¹H-NMR (300 Mz, CDCl₃) δ0.92 (3H, t, J=7.4 Hz), 1.07-1.48 (5H, m), 1.74-2.00 (2H, m), 3.32 (1H, t, J=7.4 Hz), 4.22 (2H, q, J=7.4 Hz), 6.89-7.79 (7H, m), 9.60 (1H, brs).

(3) 3-oxo-2-propyl-3-[((E)-styrylsulfonyl)amino]propionic acid

In the same manner as in Example 1 (3), the title compound (4.13 g) was obtained as an oil using the above-mentioned compound (8.17 g).
¹H-NMR (300 Mz, DMSO-d₆) δ0.84 (3H, t, J=7.4 Hz), 1.08-1.34 (2H, m), 1.50-1.78 (2H, m), 3.36 (1H, t, J=7.4 Hz), 7.07-7.80 (7H, m), 12.45 (2H, brs).

(4) N-ethyl-N-(1-naphthyl)-2-propyl-N'-((E)-styrylsulfonyl)malonamide

In the same manner as in Example 13, the title compound (186 mg) was obtained as a white powder using the above-mentioned compound (1.25 g) and N-ethyl-1-naphthylamine (822 mg).
¹H-NMR (300 Mz, DMSO-d₆) δ0.62 (3H, t, J=6.9 Hz), 0.80-1.47 (6H, m), 1.60-1.86 (1H, m), 2.70-2.87 (1H, m), 3.04-3.45 (1H, m), 3.97-4.18 (1H, m), 7.08-8.14 (14H, m), 11.36 (1H, brs).
MS: 465(M+H)⁺.

Example 488

Synthesis of N-ethyl-N-(4-fluorophenyl)-2-propyl-N'-((E)-styrylsulfonyl)malonamide In the same manner as in Example 13, the title compound (274 mg) was obtained as a white powder using the compound (1.25 g) obtained in Example 487 (3) and N-ethyl-4-fluoroaniline (668 mg).
¹H-NMR (300 Mz, DMSO-d₆) δ0.70 (3H, t, J=7.2 Hz), 0.96 (3H, t, J=7.2 Hz), 1.00-1.20 (2H, m), 1.40-1.83 (2H, m), 3.00-3.72 (3H, m), 6.97-7.61 (9H, m), 7.63-7.88 (2H, m), 11.62 (1H, brs).
MS: 432(M+H)⁺.

Example 489

Synthesis of N-(4-fluorophenyl)-N-isopropyl-2-propyl-N'-((E)-styrylsulfonyl)malonamide In the same manner as in Example 13, the title compound (627 mg) was obtained as a white powder using the compound (623 mg) obtained in Example 487 (3) and 4-fluoro-N-isopropylaniline (368 mg).
¹H-NMR (300 Mz, DMSO-d₆) δ0.71 (3H, t, J=7.5 Hz), 0.77-0.97 (6H, m), 0.97-1.20 (2H, m), 1.33-1.57 (1H, m), 1.57-1.78 (1H, m), 2.89-3.08 (1H, m), 4.61-4.86 (1H, m), 6.80-7.40 (5H, m), 7.40-7.60 (4H, m), 7.68-7.89 (2H, m), 11.54 (1H, brs).
MS: 447(M+H)⁺.

Example 490

Synthesis of N-(4-fluorophenyl)-N-isopropyl-2-isopropyl-N'-((E)-styrylsulfonyl)malonamide (1) monoethyl isopropylmalonate In the same manner as in Example 1 (1), the title compound (4.35 g) was obtained as an oil using diethyl isopropylmalonate (5.06 g).
¹H-NMR (300 Mz, DMSO-d₆) δ0.93 (6H, t, J=6.5 Hz), 1.18 (3H, t, J=7.2 Hz), 2.09-2.30 (1H, m), 3.07 (1H, d, J=8.3 Hz), 4.11 (2H, q, J=7.3 Hz), 12.80 (1H, brs).

(2) ethyl 2-[N-(4-fluorophenyl)-N-isopropylamino]carbonyl-3-methylbutyrate

In the same manner as in Example 13, the title compound (1.63 g) was obtained as an oil using the above-mentioned compound (1.39 g) and N-isopropyl-4-fluoroaniline (1.47 g).
¹H-NMR (300 Mz, CDCl₃) δ0.83 (3H, d, J=6.6 Hz), 0.92 (3H, d, J=6.9 Hz), 1.01 (3H, d, J=6.6 Hz), 1.07 (3H, d, J=6.6 Hz), 1.24 (3H, t, J=7.2 Hz), 2.33-2.55 (1H, m), 2.79 (1H, d, J=9.6 Hz), 4.00-4.24 (2H, m), 4.90-5.14 (1H, m), 6.95-7.24 (4H, m).

(3) 2-[N-(4-fluorophenyl)-N-isopropylamino]carbonyl-3-methylbutyric acid

In the same manner as in Example 1 (3), the title compound (1.48 g) was obtained as an oil using the above-mentioned compound (1.63 g).
¹H-NMR (300 Mz, DMSO-d₆) δ0.76 (3H, d, J=6.6 Hz), 0.83 (3H, d, J=6.7 Hz), 0.92 (3H, d, J=6.8 Hz), 1.00 (3H, d, J=6.8 Hz), 2.00-2.32 (1H, m), 2.65 (1H, d, J=9.5 Hz), 4.66-4.95 (1H, m), 7.05-7.40 (2H, m), 12.40 (1H, brs).

(4) N-(4-fluorophenyl)-N-isopropyl-2-isopropyl-N'-((E)-styrylsulfonyl)malonamide In the same manner as in Example 1 (2), the title compound (517 mg) was obtained as a white powder using the above-mentioned compound (1.48 g) and trans-β-styrenesulfonamide (890 mg).

$^1$H-NMR (300 Mz, DMSO-d$_6$) δ0.65-0.80 (12H, m), 2.11-2.37 (1H, m), 2.64-2.89 (1H, m), 4.63-4.83 (1H, m), 6.77-7.02 (1H, m), 7.05-7.25 (2H, m), 7.25-7.66 (6H, m), 7.66-7.89 (2H, m), 11.29 (1H, brs).

MS: 447(M+H)$^+$.

Example 491

Synthesis of N-(4-fluorophenyl)-2-isobutyl-N-isopropyl-N'-((E)-styrylsulfonyl)malonamide

(1) 4-methyl-2-{[((E)-styrylsulfonyl)amino]carbonyl}valeric acid

In the same manner as in Example 1 (1), the object compound was obtained using diethyl isobutylmalonate (10.0 g). This and trans-β-styrenesulfonamide (2.91 g) were condensed in the same manner as in Example 152 (3). The condensed product was subjected to hydrolysis in the same manner as in Example 1 (3) to give the title compound (4.99 g) as an oil.

(2) N-(4-fluorophenyl)-2-isobutyl-N-isopropyl-N'-((E)-styrylsulfonyl)malonamide In the same manner as in Example 1 (4), the title compound (269 mg) was obtained as a white powder using the above-mentioned compound (651 mg) and 4-fluoro-N-isopropylaniline (306 mg).

$^1$H-NMR (400 Mz, CDCl$_3$) δ0.62 (3H, d, J=7.2 Hz), 0.75 (3H, d, J=7.2 Hz), 0.94 (3H, d, J=7.2 Hz), 1.03 (3H, d, J=7.2 Hz), 1.43-1.49 (1H, m), 1.63-1.72 (2H, m), 3.03-3.06 (1H, m), 4.90-4.97 (1H, m), 7.01-7.05 (3H, m), 7.06-7.14 (2H, m), 7.39-7.51 (3H, m), 7.51-7.53 (2H, m), 7.71 (1H, d, J=15.5 Hz), 10.19 (1H, brs).

MS: 461(M+H)$^+$.

Example 492

Synthesis of N-(4-fluorophenyl)-N'-{[(E)-2-(4-fluorophenyl)ethenyl]sulfonyl}-2-isobutyl-N-isopropylmalonamide

(1) ethyl 2-{[N-(4-fluorophenyl)-N-isopropylamino]carbonyl}-4-methylvalerate In the same manner as in Example 1 (4), the title compound (5.97 g) was obtained as an oil using intermediate monoethyl isobutylmalonate (5.00 g) obtained in Example 491 (1) and 4-fluoro-N-isopropylaniline (4.08 g).

$^1$H-NMR (400 Mz, CDCl$_3$) δ0.97-0.98 (6H, m), 1.01-1.08 (6H, m), 1.24-1.31 (3H, m), 1.44-1.47 (1H, m), 1.66-1.79 (2H, m), 3.11 (1H, t, J=7.3 Hz), 4.08-4.13 (2H, m), 5.02 (1H, t, J=6.7 Hz), 7.07-7.14 (3H, m), 7.18-7.21 (1H, m).

(2) 2-{[N-(4-fluorophenyl)-N-isopropylamino]carbonyl}-4-methylvaleric acid

In the same manner as in Example 1 (3), the title compound (2.94 g) was obtained as an oil using the above-mentioned compound (5.00 g).

$^1$H-NMR (400 Mz, CDCl$_3$) δ0.50-0.55 (3H, m), 0.71-0.77 (3H, m), 1.04-1.52 (3H, m), 1.11-1.13 (3H, m), 1.47-1.60 (2H, m), 1.75-1.86 (1H, m), 2.35-3.13 (1H, m), 4.94-5.01 (1H, m), 7.09-7.26 (4H, m).

(3) N-(4-fluorophenyl)-N'-{[(E)-2-(4-fluorophenyl)ethenyl]sulfonyl}-2-isobutyl-N-isopropylmalonamide In the same manner as in Example 1 (2), the title compound (261 mg) was obtained as a white powder using the above-mentioned compound (295 mg) and [(E)-2-(4-fluorophenyl)ethylene]sulfonamide (201 mg).

$^1$H-NMR (400 Mz, CDCl$_3$) δ0.62 (3H, d, J=6.4 Hz), 0.75 (3H, d, J=6.4 Hz), 1.00 (3H, d, J=6.4 Hz), 1.10 (3H, d, J=6.4 Hz), 1.60-1.72 (2H, m), 3.02-3.06 (1H, m), 4.09-4.15 (1H, m), 4.90-4.97 (1H, m), 6.95 (1H, d, J=15.5 Hz), 7.03-7.15 (6H, m), 7.50-7.54 (2H, m), 7.67 (1H, d, J=15.5 Hz), 10.22 (1H, brs).

MS: 479(M+H)$^+$.

Example 493

Synthesis of N-(4-fluorophenyl)-2-isobutyl-N-isopropyl-N'-phenethylsulfonylmalonamide In the same manner as in Example 1 (2), the title compound (70 mg) was obtained as a white powder using the compound (295 mg) obtained in Example 492 (2) and phenethylsulfonamide (185 mg).

$^1$H-NMR (400 Mz, CDCl$_3$) δ0.66 (3H, d, J=6.4 Hz), 0.77 (3H, d, J=6.4 Hz), 1.02 (3H, d, J=6.4 Hz), 1.10 (3H, d, J=6.4 Hz), 1.46-1.53 (1H, m), 1.61-1.66 (1H, m), 3.04-3.17 (4H, m), 3.63-3.70 (2H, m), 4.92-4.95 (1H, m), 7.06-7.07 (2H, m), 7.08-7.23 (4H, m), 7.24-7.25 (1H, m), 7.30-7.34 (2H, m), 10.20 (1H, brs).

MS: 463(M+H)$^+$.

Example 494

Synthesis of N-(4-fluorophenyl)-2-isobutyl-N-isopropyl-N'-phenylsulfonylmalonamide In the same manner as in Example 1 (2), the title compound (78 mg) was obtained as a white powder using the compound (443 mg) obtained in Example 492 (2) and benzenesulfonamide (338 mg).

$^1$H-NMR (400 Mz, CDCl$_3$) δ0.56 (3H, d, J=6.6 Hz), 0.66 (3H, d, J=6.6 Hz), 0.98 (3H, d, J=6.6 Hz), 1.07 (3H, d, J=6.6 Hz), 1.22-1.27 (1H, m), 1.49-1.59 (2H, m), 2.91 (1H, t, J=7.4 Hz), 4.87-4.94 (1H, m), 6.77-6.99 (1H, m), 7.01-7.11 (3H, m), 7.51-7.55 (2H, m), 7.61-7.63 (1H, m), 8.04-8.06 (2H, m), 10.21 (1H, brs).

MS: 435(M+H)$^+$.

Example 495

Synthesis of N-(4-fluorophenyl)-2-isobutyl-N-isopropyl-N'-(2-naphthylsulfonyl)malonamide In the same manner as in Example 1 (2), the title compound (278 mg) was obtained as a white powder using the compound (443 mg) obtained in Example 492 (2) and naphthalene-2-sulfonamide (311 mg).
$^1$H-NMR (400 Mz, CDCl$_3$) δ0.54 (3H, d, J=6.7 Hz), 0.63 (3H, d, J=6.7 Hz), 0.94 (3H, d, J=6.7 Hz), 1.06 (3H, d, J=6.7 Hz), 1.20-1.28 (1H, m), 1.52-1.58 (2H, m), 2.90 (1H, t, J=7.8 Hz), 4.86-4.93 (1H, m), 6.67-6.71 (1H, m), 6.88-6.93 (1H, m), 6.97-7.01 (1H, m), 7.04-7.08 (1H, m), 7.60-7.69 (2H, m), 7.91-8.02 (4H, m), 8.65 (1H, s), 10.28 (1H, brs).
MS: 485(M+H)$^+$.

Example 496

Synthesis of N-(4-fluorophenyl)-2-isobutyl-N-isopropyl-N'-(3-phenoxypropylsulfonyl)malonamide (1) 3-phenoxypropanesulfonamide To a solution of 3-phenoxypropyl bromide (6.74 g) in water (67 mL) was added sodium sulfite (5.30 g), and the mixture was heated under reflux for 24 hr. Toluene was added to the reaction mixture, and the organic layer was concentrated under reduced pressure. The residue was dissolved in benzene (100 mL), and DMF (0.67 g) was added. Thionyl chloride (4.40 g) was added dropwise with stirring, and the mixture was heated under reflux for 4 hr. The reaction mixture was concentrated under reduced pressure, THF (100 mL) was added to the residue, and 28% aqueous ammonia was slowly added dropwise under ice-cooling. After completion of the reaction, the mixture was concentrated under reduced pressure, and the residue was purified by silica gel column chromatography to give the title compound (3.75 g).
$^1$H-NMR (400 Mz, DMSO-d$_6$) δ2.09-2.17 (2H, m), 3.11-3.15 (2H, m), 4.00-4.10 (2H, m), 6.91-6.93 (2H, m), 7.26-7.31 (3H, m), 7.43-7.46 (2H, m).

(2) N-(4-fluorophenyl)-2-isobutyl-N-isopropyl-N'-(3-phenoxypropylsulfonyl)malonamide In the same manner as in Example 1 (2), the title compound (208 mg) was obtained as a white powder using the compound (295 mg) obtained in Example 492 (2) and the abovementioned compound (215 mg).
$^1$H-NMR (400 Mz, CDCl$_3$) δ0.65 (3H, d, J=6.5 Hz), 0.77 (3H, d, J=6.5 Hz), 1.01 (3H, d, J=6.5 Hz), 1.10 (3H, d, J=6.5 Hz), 1.44-1.52 (1H, m), 1.62-1.72 (2H, m), 2.26-2.33 (2H, m), 3.08 (1H, t, J=7.2 Hz), 3.60-3.64 (2H, m), 4.07-4.09 (2H, m), 4.90-4.95 (1H, m), 6.94-6.98 (2H, m), 7.01-7.02 (1H, m), 7.04-7.08 (2H, m), 7.12-7.17 (2H, m), 7.28-7.30 (2H, m), 10.08 (1H, brs).
MS: 493(M+H)$^+$.

Example 497

Synthesis of N-(4-fluorophenyl)-2-isobutyl-N-isopropyl-N'-(4-phenylbutylsulfonyl)malonamide (1) 4-phenylbutanesulfonamide In the same manner as in Example 496 (1), the title compound (5.93 g) was obtained using 4-phenylbutyl bromide (5.00 g).
$^1$H-NMR (400 Mz, DMSO-d$_6$) δ1.69-1.74 (2H, m), 2.49-2.50 (2H, m), 2.53-2.61 (2H, m), 2.98-3.11 (2H, m), 6.71-6.72 (2H, m), 7.15-7.21 (3H, m), 7.26-7.29 (2H, m).

(2) N-(4-fluorophenyl)-2-isobutyl-N-isopropyl-N'-(4-phenylbutylsulfonyl)malonamide In the same manner as in Example 1 (2), the title compound (288 mg) was obtained as a white powder using the compound (443 mg) obtained in Example 492 (2) and the abovementioned compound (398 mg).
$^1$H-NMR (400 Mz, CDCl$_3$) δ0.76 (3H, d, J=6.5 Hz), 0.91 (3H, d, J=6.5 Hz), 1.02 (3H, d, J=6.5 Hz), 1.10 (3H, d, J=6.5 Hz), 1.42-1.54 (1H, m), 1.60-1.66 (2H, m), 1.75-1.88 (4H, m), 2.62-2.66 (2H, m), 3.05 (1H, t, J=7.6 Hz), 3.36-3.44 (2H, m), 4.89-4.96 (1H, m), 7.01-7.08 (2H, m), 7.11-7.18 (5H, m), 7.28-7.29 (2H, m), 9.93 (1H, brs).
MS: 491(M+H)$^+$.

Example 498

Synthesis of N'-(4-biphenylsulfonyl)-N-(4-fluorophenyl)-2-isobutyl-N-isopropylmalonamide In the same manner as in Example 1 (2), the title compound (568 mg) was obtained as a white powder using the compound (586 mg) obtained in Example 492 (2) and 4-biphenylsulfonamide (467 mg).
$^1$H-NMR (400 Mz, CDCl$_3$) δ0.56 (3H, d, J=6.4 Hz), 0.67 (3H, d, J=6.4 Hz), 0.98 (3H, d, J=6.4 Hz), 1.08 (3H, d, J=6.4 Hz), 1.26-1.27 (2H, m), 1.58-1.60 (1H, m), 2.92-2.96 (1H, m), 4.89-4.93 (1H, m), 6.80-6.87 (1H, m), 7.02-7.09 (3H, m), 7.42-7.50 (3H, m), 7.59-7.61 (2H, m), 7.72-7.74 (2H, m), 8.10-8.12 (2H, m), 10.27 (1H, brs).
MS: 511(M+H)$^+$.

Example 499

Synthesis of N-ethyl-N-(3-hydroxymethylphenyl)-2-isobutyl-N'-((E)-styrylsulfonyl)malonamide In the same manner as in Example 13, the title compound (262 mg) was obtained as a white powder using the compound (325 mg) obtained in Example 491 (1) and 3-(ethylamino)benzyl alcohol (181 mg).
$^1$H-NMR (300 Mz, DMSO-d$_6$) δ0.55 (3H, d, J=6.3 Hz), 0.65 (3H, d, J=6.6 Hz), 0.99 (3H, t, J=7.2 Hz), 1.12-1.70 (3H, m), 3.10-3.56 (2H, m), 3.59-3.80 (1H, m), 4.40-4.60 (2H, m), 5.15-5.38 (1H, m), 6.98-7.14 (1H, m), 7.19 (1H, s), 7.27-7.65 (7H, m), 7.65-7.86 (2H, m), 11.77 (1H, brs).
MS: 459(M+H)$^+$.

Example 500

Synthesis of N-(3-hydroxymethylphenyl)-2-isobutyl-N-isopropyl-N'-((E)-styrylsulfonyl)malonamide In the same manner as in Example 13, the title compound (33 mg) was obtained as a white powder using the compound (325 mg) obtained in Example 491 (1) and 3-(isopropylamino)benzyl alcohol (198 mg).
$^1$H-NMR (300 Mz, DMSO-d$_6$) δ0.58 (3H, d, J=6.3 Hz), 0.67 (3H, d, J=6.3 Hz), 0.74-1.03 (3H, m), 0.99 (3H, d, J=6.6 Hz), 1.12-1.49 (2H, m), 1.49-1.75 (1H, m), 2.89-3.18 (1H, m), 4.38-4.61 (2H, m), 4.61-4.83 (1H, m), 5.12-5.37 (1H, m), 6.73-7.92 (11H, m), 11.68 (1H, brs).
MS: 473(M+H)$^+$.

Example 501

Synthesis of 2-isobutyl-N-isopropyl-N'-((E)-styrylsulfonyl)-N-(3-trifluoromethylphenyl)malonamide In the same manner as in Example 13, the title compound (111 mg) was obtained as a white powder using the compound (325 mg) obtained in Example 491 (1) and N-isopropyl-3-trifluoromethylaniline (244 mg).
$^1$H-NMR (300 Mz, DMSO-$d_6$) δ0.24-0.78 (6H, m), 0.78-1.77 (9H, m), 2.84-3.15 (1H, m), 4.64-4.90 (1H, m), 7.16-7.95 (11H, m), 11.75 (1H, brs).
MS: 511(M+H)$^+$.

Example 502

Synthesis of 2-isobutyl-N-isopropyl-N-(3-pyridyl)-N'-((E)-styrylsulfonyl)malonamide hydrochloride In the same manner as in Example 13, the object compound was obtained using the compound (325 mg) obtained in Example 491 (1) and 3-(isopropylamino)pyridine (136 mg). 1 mol/L Hydrochloric acid was added to this, and the mixture was concentrated to give the title compound (45 mg) as a white powder.
$^1$H-NMR (300 Mz, DMSO-$d_6$) δ0.37-1.14 (12H, m), 1.14-1.75 (3H, m), 2.90-3.15 (1H, m), 4.61-4.91 (1H, m), 7.10-8.02 (9H, m), 8.30-8.88 (2H, m), 11.76 (1H, brs).
MS: 444(M+H)$^+$.

Example 503

Synthesis of 2-isobutyl-N-(2-hydroxyethyl)-N-phenyl-N'-((E)-styrylsulfonyl)malonamide In the same manner as in Example 13, the title compound (221 mg) was obtained as a white powder using the compound (325 mg) obtained in Example 491 (1) and N-phenylethanolamine (165 mg).
$^1$H-NMR (300 Mz, DMSO-$d_6$) δ0.53 (3H, d, J=6.3 Hz), 0.64 (3H, d, J=6.6 Hz), 1.17-1.67 (3H, m), 3.07-3.52 (3H, m), 3.52-3.71 (2H, m), 4.49-4.73 (1H, m), 7.14-7.60 (10H, m), 7.65-7.85 (2H, m), 11.77 (1H, brs).
MS: 445(M+H)$^+$.

Example 504

Synthesis of N-benzyl-2-isobutyl-N-isopropyl-N'-((E)-styrylsulfonyl)malonamide

In the same manner as in Example 13, the title compound (50 mg) was obtained as a white powder using the compound (325 mg) obtained in Example 491 (1) and N-isopropylbenzylamine (179 mg).
$^1$H-NMR (300 Mz, DMSO-$d_6$) δ0.50-1.10 (12H, m), 1.18-1.80 (3H, m), 3.10-4.68 (4H, m), 7.00-7.84 (12H, m), 12.19 (1H, brs).
MS: 457(M+H)$^+$.

Example 505

Synthesis of N-(4-fluorobenzyl)-2-isobutyl-N-isopropyl-N'-((E)-styrylsulfonyl)malonamide In the same manner as in Example 13, the title compound (91 mg) was obtained as a white powder using the compound (325 mg) obtained in Example 491 (1) and 4-fluoro-N-isopropylbenzylamine (201 mg).
$^1$H-NMR (300 Mz, DMSO-$d_6$) δ0.50-1.15 (12H, m), 1.15-1.80 (3H, m), 3.10-4.64 (4H, m), 6.85-7.80 (11H, m), 12.19 (1H, brs).
MS: 475(M+H)$^+$.

Example 506

Synthesis of N-(3-fluorobenzyl)-2-isobutyl-N-isopropyl-N'-((E)-styrylsulfonyl)malonamide In the same manner as in Example 13, the title compound (89 mg) was obtained as a white powder using the compound (325 mg) obtained in Example 491 (1) and 3-fluoro-N-isopropylbenzylamine (201 mg).
$^1$H-NMR (300 Mz, DMSO-$d_6$) δ0.50-1.18 (12H, m), 1.18-1.81 (3H, m), 3.13-4.64 (4H, m), 6.80-7.80 (11H, m), 12.22 (1H, brs).
MS: 475(M+H)$^+$.

Example 507

Synthesis of 2-isobutyl-N-isopropyl-N-phenethyl-N'-((E)-styrylsulfonyl)malonamide In the same manner as in Example 13, the title compound (28 mg) was obtained as a white powder using the compound (325 mg) obtained in Example 491 (1) and N-isopropylphenethylamine (196 mg).
$^1$H-NMR (300 Mz, DMSO-$d_6$) δ0.69-0.89 (6H, m), 0.89-1.18 (6H, m), 1.35-1.75 (3H, m), 2.45-4.22 (6H, m), 7.10-7.80 (12H, m), 12.11 (1H, brs).
MS: 471(M+H)$^+$.

Example 508

Synthesis of N-[2-(4-fluorophenyl)ethyl]-2-isobutyl-N-isopropyl-N'-((E)-styrylsulfonyl)malonamide In the same manner as in Example 13, the title compound (40 mg) was obtained as a white powder using the compound (325 mg) obtained in Example 491 (1) and 2-(4-fluorophenyl)-N-isopropylethylamine (218 mg).
$^1$H-NMR (300 Mz, DMSO-$d_6$) δ0.68-0.91 (6H, m), 0.91-1.20 (6H, m), 1.33-1.77 (3H, m), 2.57-4.38 (6H, m), 6.98-7.82 (11H, m), 12.08 (1H, brs).
MS: 489(M+H)$^+$.

Example 509

Synthesis of N-(4-fluorophenyl)-2-isobutyl-N-isopropyl-N'-{[(E)-2-(2-thiazolyl)ethenyl]sulfonyl}malonamide In the same manner as in Example 1 (2), the title compound (57 mg) was obtained as a white powder using the compound (295 mg) obtained in Example 492 (2) and [(E)-2-(2-thiazolyl)ethylene]sulfonamide (190 mg).
$^1$H-NMR (300 Mz, DMSO-$d_6$) δ60.61 (3H, d, J=6.3 Hz), 0.69 (3H, d, J=6.3 Hz), 0.88 (3H, d, J=6.9 Hz), 0.96 (3H, d, J=6.6 Hz), 1.25-1.48 (2H, m), 1, 54-1.75 (1H, m), 2.91-3.17 (1H, m), 4.60-4.88 (1H, m), 6.92-7.51 (5H, m), 7.60-7.89 (1H, m), 7.97-8.18 (2H, m), 11.92 (1H, brs).
MS: 468(M+H)$^+$.

Example 510

Synthesis of N-(4-fluorophenyl)-2-isobutyl-N-isopropyl-N'-{[2-(2-thiazolyl)ethyl]sulfonyl}malonamide (1) 2-(2-thiazolyl)ethanesulfonamide In the same manner as in Example 7, the title compound (270 mg) was obtained as a white powder using [(E)-2-(2-thiazolyl)ethylene]sulfonamide (500 mg) at room temperature.

$^1$H-NMR (300 Mz, DMSO-d$_6$) δ3.29-3.54 (4H, m), 6.98 (2H, brs), 7.64 (1H, d, J=3.2 Hz), 7.73 (1H, d, J=3.2 Hz).

(2) N-(4-fluorophenyl)-2-isobutyl-N-isopropyl-N'-{[2-(2-thiazolyl)ethyl]sulfonyl}malonamide In the same manner as in Example 1 (2), the title compound (177 mg) was obtained as a white powder using the above-mentioned compound (270 mg) and the compound (415 mg) obtained in Example 492 (2).

$^1$H-NMR (300 Mz, DMSO-d$_6$) δ0.54 (3H, d, J=6.6 Hz), 0.69 (3H, d, J=6.6 Hz), 0.93 (3H, d, J=6.6 Hz), 0.99 (3H, d, J=6.6 Hz), 1.16-1.39 (1H, m), 1.39-1.67 (2H, m), 3.10 (1H, t, J=6.6 Hz), 3.25-3.53 (2H, m), 3.82 (2H, t, J=7.5 Hz), 4.62-4.87 (1H, m), 7.12-7.40 (4H, m), 7.65 (1H, d, J=3.3 Hz), 7.74 (1H, d, J=3.6 Hz), 11.70 (1H, brs).

MS: 470(M+H)$^+$.

Example 511

Synthesis of N-(4-fluorophenyl)-2-isobutyl-N-isopropyl-N'-{[(E)-2-(3-pyridyl)ethenyl]sulfonyl}malonamide In the same manner as in Example 1 (2), the title compound (266 mg) was obtained as a white powder using the compound (295 mg) obtained in Example 492 (2) and [(E)-2-(3-pyridyl)ethylene]sulfonamide (184 mg).

$^1$H-NMR (300 Mz, DMSO-d$_6$) δ0.68 (3H, d, J=6.3 Hz), 0.83 (3H, d, J=6.3 Hz), 0.88 (3H, d, J=6.3 Hz), 0.96 (3H, d, J=6.6 Hz), 1.18-1.49 (2H, m), 1.51-1.78 (1H, m), 2.92-3.14 (1H, m), 4.59-4.88 (1H, m), 7.04-7.42 (4H, m), 7.43-7.70 (3H, m), 8.28 (1H, d, J=8.1 Hz), 8.57-8.70 (1H, m), 8.95 (1H, s), 11.80 (1H, brs).

MS: 462(M+H)$^+$.

Example 512

Synthesis of N-(4-fluorophenyl)-2-isopentyl-N-isopropyl-N'-((E)-2-styrylsulfonyl)malonamide (1) 5-isopentyl-2,2-dimethyl-1,3-dioxane-4,6-dione In the same manner as in Example 214 (1), the title compound (10.0 g) was obtained as a pale-yellow powder using isovaleric acid (12.3 g).

$^1$H-NMR (300 Mz, CDCl$_3$) δ0.92 (6H, d, J=6.6 Hz), 1.26-1.37 (2H, m), 1.48-1.70 (1H, m), 1.76 (3H, s), 1.78 (3H, s), 2.02-2.19 (2H, m), 3.49 (1H, t, J=4.8 Hz).

(2) 2-[N-(4-fluorophenyl)-N-isopropylamino]carbonyl-5-methylhexanoic acid

In the same manner as in Example 119 (2), the title compound (660 mg) was obtained as an oil using the above-mentioned compound (1.07 g) and 4-fluoro-N-isopropylaniline (2.14 g).

$^1$H-NMR (300 Mz, DMSO-d$_6$) δ0.79 (6H, d, J=6.6 Hz), 0.80-1.10 (8H, m), 1.20-1.43 (1H, m), 1.49-1.73 (2H, m), 2.84 (1H, t, J=7.4 Hz), 4.65-4.90 (1H, m), 7.10-7.40 (4H, m), 12.40 (1H, brs).

(3) N-(4-fluorophenyl)-2-isopentyl-N-isopropyl-N'-((E)-2-styrylsulfonyl)malonamide In the same manner as in Example 1 (2), the title compound (382 mg) was obtained as a white powder using the above-mentioned compound (660 mg) and trans-β-styrenesulfonamide (361 mg).

$^1$H-NMR (300 Mz, DMSO-d$_6$) δ0.62-0.83 (6H, m), 0.83-1.02 (8H, m), 1.25-1.40 (1H, m), 1.40-1.58 (1H, m), 1.58-1.78 (1H, m), 2.86-3.03 (1H, m), 4.62-4.82 (1H, m), 6.90-7.17 (2H, m), 7.17-7.40 (3H, m), 7.40-7.61 (4H, m), 7.69-7.90 (2H, m), 11.54 (1H, brs).

MS: 475(M+H)$^+$.

Example 513

Synthesis of N-(4-fluorophenyl)-N-isopropyl-2-neopentyl-N'-((E)-2-styrylsulfonyl)malonamide (1) 2,2-dimethyl-5-neopentyl-1,3-dioxane-4,6-dione In the same manner as in Example 119 (1), the title compound (8.52 g) was obtained as a white solid using trimethylacetoaldehyde (90 mL).

$^1$H-NMR (300 Mz, CDCl$_3$) δ0.97 (9H, s), 1.76 (3H, s), 1.84 (3H, s), 2.12 (2H, d, J=5.2 Hz), 3.30 (1H, t, J=5.2 Hz).

(2) 4,4-dimethyl-2-{[N-(4-fluorophenyl)-N-isopropylamino]carbonyl}valeric acid

In the same manner as in Example 119 (2), the title compound (472 mg) was obtained as a white solid using the above-mentioned compound (3.01 g) and 4-fluoro-N-isopropylaniline (8.47 g).

$^1$H-NMR (400 Mz, DMSO-d$_6$) δ0.66 (9H, s), 0.93 (3H, d, J=6.8 Hz), 0.99 (3H, d, J=6.8 Hz), 1.06 (2H, t, J=6.7 Hz), 2.90 (1H, t, J=6.0 Hz), 4.78 (1H, m), 7.64 (2H, brs), 8.31 (2H, brs).

(3) N-(4-fluorophenyl)-N-isopropyl-2-neopentyl-N'-((E)-2-styrylsulfonyl)malonamide In the same manner as in Example 1 (2), the title compound (212 mg) was obtained as a white solid using the above-mentioned compound (472 mg) and trans-β-styrenesulfonamide (291 mg).

$^1$H-NMR (400 Mz, DMSO-d$_6$) δ0.59 (9H, s), 0.83 (3H, d, J=6.8 Hz), 0.97 (3H, d, J=6.8 Hz), 1.53 (1H, dd, J=13.7, 5.7 Hz), 1.77 (1H, dd, J=13.7, 6.4 Hz), 3.06 (1H, t, J=5.9 Hz), 4.65-4.76 (1H, m), 7.10-7.40 (5H, m), 7.44-7.51 (3H, m), 7.55-7.62 (1H, m), 7.76-7.82 (2H, m), 11.73 (1H, s).

MS: 475(M+H)$^+$.

Example 514

Synthesis of 2-cyclopropylmethyl-N-ethyl-N-(4-fluorophenyl)-N'-((E)-2-styrylsulfonyl)malonamide (1) 2-cyclopropylmethyl-3-[N-ethyl-N-(4-fluorophenyl)amino]-3-oxopropionic acid In the same manner as in Example 119 (2), the title compound (750 mg) was obtained as an oil using the compound (740 mg) obtained in Example 214 (1) and N-ethyl-4-fluoroaniline (2.08 g).

$^1$H-NMR (300 Mz, DMSO-$d_6$) δ (−0.20)-(−0.02) (2H, m), 0.20-0.38 (2H, m), 0.40-0.61 (1H, m), 1.18 (3H, t, J=7.5 Hz), 1.54 (2H, d, J=7.2 Hz), 3.10-3.20 (1H, m), 3.65 (2H, q, J=7.2 Hz), 7.25-7.45 (4H, m), 12.50 (1H, brs).

(2) 2-cyclopropylmethyl-N-ethyl-N-(4-fluorophenyl)-N'-((E)-2-styrylsulfonyl)malonamide In the same manner as in Example 1 (2), the title compound (357 mg) was obtained as a white powder using the above-mentioned compound (750 mg) and trans-β-styrenesulfonamide (486 mg).

$^1$H-NMR (300 Mz, DMSO-$d_6$) δ (−0.35)-(−0.20) (1H, m), (−0.20)-(−0.02)(1H, m), 0.15-0.34 (2H, m), 0.45-0.64 (1H, m), 0.97 (3H, t, J=7.2 Hz), 1.20-1.43 (1H, m), 1.56-1.77 (1H, m), 3.18-3.75 (3H, m), 7.06-7.64 (9H, m), 7.66-7.95 (2H, m), 11.64 (1H, brs).

MS: 445(M+H)$^+$.

Example 515

Synthesis of 2-cyclopropylmethyl-N-(4-fluorophenyl)-N-isopropyl-N'-((E)-2-styrylsulfonyl)malonamide (1) 2-cyclopropylmethyl-3-[N-(4-fluorophenyl)-N-isopropylamino]-3-oxopropionic acid In the same manner as in Example 119 (2), the title compound (570 mg) was obtained as an oil using the compound (793 mg) obtained in Example 214 (1) and 4-fluoro-N-isopropylaniline (613 mg).

$^1$H-NMR (300 Mz, DMSO-$d_6$) δ (−0.26)-(−0.10)(2H, m), 0.19-0.38 (2H, m), 0.40-0.64 (1H, m), 0.88-1.06 (6H, m), 1.54 (2H, t, J=7.2 Hz), 3.01 (1H, t, J=6.9 Hz), 4.70-4.90 (1H, m), 7.15-7.40 (4H, m), 12.40 (1H, brs).

(2) 2-cyclopropylmethyl-N-(4-fluorophenyl)-N-isopropyl-N'-((E)-2-styrylsulfonyl)malonamide In the same manner as in Example 1 (2), the title compound (450 mg) was obtained as a white powder using the above-mentioned compound (570 mg) and trans-β-styrenesulfonamide (329 mg).

$^1$H-NMR (300 Mz, DMSO-$d_6$) δ (−0.30)-(−0.02) (2H, m), 0.18-0.36 (2H, m), 0.47-0.70 (1H, m), 0.80-1.06 (6H, m), 1.17-1.40 (1H, m), 1.65-1.86 (1H, m), 3.05-3.17 (1H, m), 4.62-4.86 (1H, m), 6.95-7.40 (5H, m), 7.40-7.63 (4H, m), 7.69-7.89 (2H, m), 11.55 (1H, brs).

MS: 459(M+H)$^+$.

Example 516

Synthesis of (2S or 2R)-2-cyclopropylmethyl-N-(4-fluorophenyl)-N-isopropyl-N'-((E)-2-styrylsulfonyl)malonamide To a suspension of the compound (19.2 g) obtained in Example 515 in methanol (300 mL) was added (S)-phenylethylamine (5.33 mL), and the mixture was stirred at room temperature to give a solution. The reaction mixture was concentrated under reduced pressure, diisopropylether (300 mL) was added to the residue, and the mixture was stirred at 60° C. for 20 min. Insoluble material was collected by filtration, and the obtained solid was subjected to the same operation with diisopropylether (100 mL×3) to give (S)-phenylethylamine salt (8.12 g) of the title compound as a white solid (optical purity>98% d.e.). To (S)-phenylethylamine salt (19.9 g) of the title compound obtained in the same manner as above were added ethyl acetate (500 mL) and 1 mol/L hydrochloric acid (500 mL), and the mixture was extracted. The organic layer was washed with saturated brine. The organic layer was concentrated under reduced pressure to give the title compound (16.2 g) as a white powder (optical purity>98% e.e.).

$^1$H-NMR and MS were same as in Example 515.

specific optical rotation: $[α]_D$=−64° (c=0.54, chloroform).

Example 517

Synthesis of N'-(3,5-dichlorophenylsulfonyl)-2-cyclopropylmethyl-N-(4-fluorophenyl)-N-isopropyl-malonamide (1) 2-cyclopropylmethyl-N-(4-fluorophenyl)-N-isopropylmalonamide In the same manner as in Example 114 (5), the title compound (864 mg) was obtained as a white powder using the compound (1.00 g) obtained in Example 515 (1).

$^1$H-NMR (400 Mz, CDCl$_3$) δ (−0.01)-0.01 (1H, m), 0.08-0.12 (1H, m), 0.39-0.46 (2H, m), 0.58-0.63 (1H, m), 1.02-1.04 (3H, m), 1.10-1.12 (3H, m), 1.65-1.69 (1H, m), 1.79-1.87 (1H, m), 3.03-3.07 (1H, m), 4.97-5.04 (1H, m), 5.24 (1H, brs), 7.05-7.17 (5H, m).

(2) N'-(3,5-dichlorophenylsulfonyl)-2-cyclopropylmethyl-N-(4-fluorophenyl)-N-isopropylmalonamide In the same manner as in Example 114 (6), the title compound (170 mg) was obtained as a white powder using the above-mentioned compound (585 mg) and 3,5-dichlorobenzenesulfonyl chloride (491 mg).

$^1$H-NMR (400 Mz, CDCl$_3$) δ (−0.12)-(−0.10)(2H, m), 0.33-0.36 (2H, m), 0.46-0.49 (1H, m), 1.01 (3H, d, J=6.4 Hz), 1.09 (3H, d, J=6.4 Hz), 1.59-1.64 (2H, m), 3.03 (1H, t, J=6.8 Hz), 4.91-4.98 (1H, m), 6.94-6.96 (1H, m), 7.03-7.06 (1H, m), 7.10-7.16 (2H, m), 7.59 (1H, s), 7.94 (2H, s), 10.68 (1H, brs).

MS: 501(M+H)$^+$.

Example 518

Synthesis of N'-(3,4-dichlorophenylsulfonyl)-2-cyclopropylmethyl-N-(4-fluorophenyl)-N-isopropyl-malonamide In the same manner as in Example 114 (6), the title compound (191 mg) was obtained as a white powder using the compound (200 mg) obtained in Example 517 (1) and 3,4-dichlorobenzenesulfonyl chloride (167 mg).

$^1$H-NMR (400 Mz, CDCl$_3$) δ (−0.29)-(−0.08)(2H, m), 0.29-0.38 (2H, m), 0.44-0.50 (1H, m), 1.00 (3H, d, J=6.4 Hz), 1.10 (3H, d, J=6.4 Hz), 1.53-1.67 (2H, m), 3.02 (1H, t, J=7.2 Hz), 4.91-4.98 (1H, m), 6.94-6.96 (1H, m), 7.02-7.06 (1H, m), 7.09-7.15 (2H, m), 7.60 (1H, d, J=8.8 Hz), 7.90 (1H, d, J=8.8 Hz), 8.16 (1H, s), 10.62 (1H, brs).

MS: 501(M+H)$^+$.

Example 519

Synthesis of N'-(4-chlorophenylsulfonyl)-2-cyclopropylmethyl-N-(4-fluorophenyl)-N-isopropylmalonamide In the same manner as in Example 1 (2), the title compound (105 mg) was obtained as a white powder using the compound (587 mg) obtained in Example 515 (1) and 4-chlorobenzenesulfonamide (383 mg).

$^1$H-NMR (400 Mz, CDCl$_3$) δ (−0.13)-(−0.12)(2H, m), 0.30-0.34 (2H, m), 0.45-0.46 (1H, m), 1.00 (3H, d, J=6.4 Hz), 1.09 (3H, d, J=6.4 Hz), 1.53-1.61 (2H, m), 2.99 (1H, t, J=7.2 Hz), 4.92-4.95 (1H, m), 6.91-6.92 (1H, m), 7.03-7.05 (1H, m), 7.08-7.13 (2H, m), 7.50 (2H, d, J=8.4 Hz), 7.99-8.02 (2H, m), 10.48 (1H, brs).

MS: 467(M+H)$^+$.

Example 520

Synthesis of N'-(4-tert-butylphenylsulfonyl)-2-cyclopropylmethyl-N-(4-fluorophenyl)-N-isopropylmalonamide In the same manner as in Example 114 (6), the title compound (552 mg) was obtained as a white powder using the compound (584 mg) obtained in Example 517 (1) and 4-tert-butylbenzenesulfonyl chloride (465 mg).

$^1$H-NMR (400 Mz, CDCl$_3$) δ (−0.18)-(−0.14) (2H, m), 0.24-0.30 (2H, m), 0.40-0.42 (1H, m), 0.99 (3H, d, J=5.2 Hz), 1.07 (3H, d, J=5.2 Hz), 1.33 (9H, s), 1.53-1.63 (2H, m), 2.95-2.97 (1H, m), 4.91-4.96 (1H, m), 6.80-6.81 (1H, m), 7.02-7.06 (3H, m), 7.52-7.54 (2H, m), 7.96-7.98 (2H, m), 10.22 (1H, brs).

MS: 489(M+H)$^+$.

Example 521

Synthesis of 2-cyclopropylmethyl-N-(4-fluorophenyl)-N-isopropyl-N'-(4-trifluoromethoxyphenylsulfonyl)malonamide In the same manner as in Example 114 (6), the title compound (211 mg) was obtained as a white powder using the compound (585 mg) obtained in Example 517 (1) and 4-trifluoromethoxybenzenesulfonyl chloride (521 mg).

$^1$H-NMR (400 Mz, CDCl$_3$) δ (−0.16)-(−0.14)(2H, m), 0.28-0.32 (2H, m), 0.42-0.45 (1H, m), 0.99 (3H, d, J=6.8 Hz), 1.09 (3H, d, J=6.8 Hz), 1.57-1.61 (2H, m), 2.99 (1H, t, J=7.2 Hz), 4.90-4.97 (1H, m), 6.87-6.91 (1H, m), 7.01-7.05 (1H, m), 7.08-7.12 (2H, m), 7.34 (2H, d, J=8.8 Hz), 8.13 (2H, d, J=8.8 Hz), 10.49 (1H, brs).

MS: 517(M+H)$^+$.

Example 522

Synthesis of 2-cyclopropylmethyl-N-(4-fluorophenyl)-N-isopropyl-N'-(4-tolylsulfonyl)malonamide In the same manner as in Example 1 (2), the title compound (267 mg) was obtained as a white powder using the compound (587 mg) obtained in Example 515 (1) and 4-toluenesulfonamide (342 mg).

$^1$H-NMR (400 Mz, CDCl$_3$) δ (−0.22)-(−0.09)(2H, m), 0.28-0.33 (2H, m), 0.43-0.44 (1H, m), 1.00 (3H, d, J=6.8 Hz), 1.08 (3H, d, J=6.8 Hz), 1.54-1.57 (2H, m), 2.43 (3H, s), 2.98 (1H, t, J=7.2 Hz), 4.94 (1H, t, J=6.8 Hz), 6.86-6.89 (1H, m), 7.02-7.11 (3H, m), 7.30-7.32 (2H, m), 7.93-7.95 (2H, m), 10.27 (1H, brs).

MS: 447(M+H)$^+$.

Example 523

Synthesis of 2-cyclopropylmethyl-N-(4-fluorophenyl)-N'-(4-isobutylphenylsulfonyl)-N-isopropylmalonamide In the same manner as in Example 1 (2), the title compound (202 mg) was obtained as a white powder using the compound (587 mg) obtained in Example 515 (1) and 4-isobutylbenzenesulfonamide (427 mg).

$^1$H-NMR (400 Mz, CDCl$_3$) δ (−0.19)-(−0.14) (2H, m), 0.24-0.30 (2H, m), 0.40-0.42 (1H, m), 0.89 (6H, d, J=6.4 Hz), 0.99 (3H, d, J=6.4 Hz), 1.08 (3H, d, J=6.4 Hz), 1.55-1.61 (2H, m), 1.87-1.90 (1H, m), 2.54 (2H, d, J=7.2 Hz), 2.97 (1H, t, J=7.2 Hz), 4.92-4.96 (1H, m), 6.84-6.87 (1H, m), 7.02-7.09 (3H, m), 7.27-7.29 (2H, m), 7.95 (2H, d, J=6.4 Hz), 10.26 (1H, brs).

MS: 489(M+H)$^+$.

Example 524

Synthesis of N'-(4-benzylsulfonyl)-2-cyclopropylmethyl-N-(4-fluorophenyl)-N-isopropylmalonamide In the same manner as in Example 1 (2), the title compound (193 mg) was obtained as a white powder using the compound (587 mg) obtained in Example 515 (1) and benzylsulfonamide (342 mg).

$^1$H-NMR (400 Mz, CDCl$_3$) δ0.41-0.43 (2H, m), 0.49-0.55 (1H, m), 0.98 (3H, d, J=6.8 Hz), 1.07 (3H, d, J=6.8 Hz), 1.49-1.50 (2H, m), 1.53-1.67 (2H, m), 3.05-3.13 (1H, m), 4.62 (2H, s), 4.82-4.91 (1H, m), 7.00-7.09 (2H, m), 7.10-7.23 (2H, m), 7.37 (5H, brs), 9.84 (1H, brs).

MS: 447(M+H)$^+$.

Example 525

Synthesis of 2-cyclopropylmethyl-N-(4-fluorophenyl)-N-isopropyl-N'-(4-methoxyphenylsulfonyl)malonamide In the same manner as in Example 1 (2), the title compound (70 mg) was obtained as a white powder using the compound (587 mg) obtained in Example 515 (1) and 4-methoxybenzenesulfonamide (374 mg).

$^1$H-NMR (400 Mz, CDCl$_3$) δ (−0.20)-(−0.09) (2H, m), 0.33-0.37 (2H, m), 0.39-0.48 (1H, m), 0.99 (3H, d, J=6.8 Hz), 1.64 (3H, d, J=6.8 Hz), 1.59-1.79 (2H, m), 2.98 (1H, t, J=7.2

Hz), 3.87 (3H, s), 4.89-5.01 (1H, m), 6.96-6.97 (1H, m), 6.98-7.01 (2H, m), 7.03-7.05 (1H, m), 7.07-7.52 (2H, m), 7.97-8.00 (2H, m), 10.23 (1H, brs).
MS: 463(M+H)$^+$.

Example 526

Synthesis of 2-cyclopropylmethyl-N-(4-fluorophenyl)-N-isopropyl-N'-propylsulfonylmalonamide In the same manner as in Example 1 (2), the title compound (37 mg) was obtained as a white powder using the compound (587 mg) obtained in Example 515 (1) and propylsulfonamide (648 mg).
$^1$H-NMR (400 Mz, CDCl$_3$) δ0.01-0.08 (2H, m), 0.42-0.49 (2H, m), 0.58-0.62 (1H, m), 1.03-1.12 (9H, m), 1.67-1.81 (2H, m), 1.83-1.91 (2H, m), 3.12 (1H, t, J=6.8 Hz), 3.34-3.38 (2H, m), 4.94-5.01 (1H, m), 7.05-7.20 (4H, m), 10.06 (1H, brs).
MS: 399(M+H)$^+$.

Example 527

Synthesis of 2-cyclopropylmethyl-N-(4-fluorophenyl)-N-isopropyl-N'-(4-phenoxyphenylsulfonyl)malonamide In the same manner as in Example 114 (6), the title compound (85 mg) was obtained as a white powder using the compound (200 mg) obtained in Example 517 (1) and 4-phenoxybenzenesulfonyl chloride (183 mg).
$^1$H-NMR (400 Mz, CDCl$_3$) δ (−0.13)-(−0.12)(2H, m), 0.25-0.30 (2H, m), 0.41-0.49 (1H, m), 1.00 (3H, d, J=7.2 Hz), 1.09 (3H, d, J=7.2 Hz), 1.59-1.61 (2H, m), 2.99-3.01 (1H, m), 4.94-4.96 (1H, m), 6.88-6.95 (1H, m), 7.02-7.13 (7H, m), 7.22-7.25 (1H, m), 7.38-7.43 (2H, m), 8.01 (2H, d, J=7.2 Hz), 10.32 (1H, brs).
MS: 525(M+H)$^+$.

Example 528

Synthesis of N'-(4-biphenylsulfonyl)-2-cyclopropylmethyl-N-(4-fluorophenyl)-N-isopropylmalonamide In the same manner as in Example 114 (6), the title compound (131 mg) was obtained as a white powder using the compound (200 mg) obtained in Example 517 (1) and 4-biphenylsulfonyl chloride (172 mg).
$^1$H-NMR (400 Mz, CDCl$_3$) δ (−0.15)-(−0.12)(2H, m), 0.27-0.33 (2H, m), 0.45-0.46 (1H, m), 1.00 (3H, d, J=6.8 Hz), 1.09 (3H, d, J=6.8 Hz), 1.59-1.64 (2H, m), 3.00 (1H, t, J=7.2 Hz), 4.93-4.97 (1H, m), 6.85-6.92 (1H, m), 7.03-7.09 (3H, m), 7.42-7.50 (3H, m), 7.59-7.62 (2H, m), 7.62-7.75 (2H, m), 8.11-8.13 (2H, m), 10.38 (1H, brs).
MS: 509(M+H)$^+$.

Example 529

Synthesis of 2-cyclopropylmethyl-N-(4-fluorophenyl)-N-isopropyl-N'-phenethylsulfonylmalonamide In the same manner as in Example 1 (2), the title compound (237 mg) was obtained as a white powder using the compound (587 mg) obtained in Example 515 (1) and phenethylsulfonamide (370 mg).
$^1$H-NMR (400 Mz, CDCl$_3$) δ0.02-0.07 (2H, m), 0.42-0.45 (2H, m), 0.54-0.59 (1H, m), 1.02 (3H, d, J=6.8 Hz), 1.11 (3H, d, J=6.8 Hz), 1.60-1.74 (2H, m), 3.09-3.15 (3H, m), 3.61-3.71 (2H, m), 4.93-5.00 (1H, m), 7.06-7.24 (7H, m), 7.29-7.33 (2H, m), 10.16 (1H, brs).
MS: 461(M+H)$^+$.

Example 530

Synthesis of 2-cyclopropylmethyl-N-(4-fluorophenyl)-N-isopropyl-N'-(2-naphthylsulfonyl)malonamide In the same manner as in Example 1 (2), the title compound (195 mg) was obtained as a white powder using the compound (587 mg) obtained in Example 515 (1) and naphthalene-2-sulfonamide (415 mg).
$^1$H-NMR (400 Mz, CDCl$_3$) δ (−0.20)-(−0.10) (2H, m), 0.21-0.33 (2H, m), 0.40-0.47 (1H, m), 0.97 (3H, d, J=6.9 Hz), 1.07 (3H, d, J=6.9 Hz), 1.56-1.65 (2H, m), 2.97 (1H, t, J=7.3 Hz), 4.91-4.97 (1H, m), 6.75-6.82 (1H, m), 6.97-7.09 (3H, m), 7.61-7.69 (2H, m), 7.91-8.02 (4H, m), 8.66 (1H, s), 10.43 (1H, brs).
MS: 483(M+H)$^+$.

Example 531

Synthesis of 2-cyclopropylmethyl-N-(4-fluorophenyl)-N-isopropyl-N'-(3-phenoxypropylsulfonyl)malonamide In the same manner as in Example 1 (2), the title compound (188 mg) was obtained as a white powder using the compound (587 mg) obtained in Example 515 (1) and 3-phenoxypropanesulfonamide (430 mg).
$^1$H-NMR (400 Mz, CDCl$_3$) δ0.01-0.05 (2H, m), 0.42-0.45 (2H, m), 0.57-0.60 (1H, m), 1.02 (3H, d, J=6.9 Hz), 1.11 (3H, d, J=6.9 Hz), 1.67-1.77 (2H, m), 2.27-2.33 (2H, m), 3.12-3.15 (1H, m), 3.59-3.66 (2H, m), 4.06-4.11 (2H, m), 4.93-5.00 (1H, m), 6.86-6.88 (2H, m), 6.94-7.15 (5H, m), 7.28-7.30 (2H, m), 10.21 (1H, brs).
MS: 491(M+H)$^+$.

Example 532

Synthesis of 2-cyclopropylmethyl-N-(4-fluorophenyl)-N-(3-pentyl)-N'-((E)-styrylsulfonyl)malonamide (1) 2-cyclopropylmethyl-3-[N-(4-fluorophenyl)-N-(3-pentyl)amino]-3-oxopropionic acid In the same manner as in Example 119 (2), the title compound (970 mg) was obtained as an oil using the compound (991 mg) obtained in Example 214 (1) and 4-fluoro-N-(3-pentyl)aniline (1.81 g).
$^1$H-NMR (300 Mz, DMSO-d$_6$) δ (−0.24)-(−0.05)(2H, m), 0.20-0.42 (2H, m), 0.42-0.60 (1H, m), 0.78-1.00 (6H, m), 1.07-1.70 (6H, m), 2.98-3.11 (1H, m), 4.34-4.57 (1H, m), 7.08-7.40 (4H, m), 12.45 (1H, brs).

(2) 2-cyclopropylmethyl-N-(4-fluorophenyl)-N-(3-pentyl)-N'-((E)-styrylsulfonyl)malonamide In the same manner as in Example 1 (2), the title compound (92 mg) was obtained as a white powder using the above-mentioned compound (970 mg) and trans-β-styrenesulfonamide (426 mg).
$^1$H-NMR (300 Mz, DMSO-d$_6$) δ (−0.28)-0.04 (2H, m), 0.13-0.39 (2H, m), 0.47-0.68 (1H, m), 0.68-0.98 (6H, m), 0.98-1.40 (5H, m), 1.70-1.96 (1H, m), 3.00-3.25 (1H, m), 4.29-4.51 (1H, m), 6.80-7.29 (3H, m), 7.29-7.70 (6H, m), 7.70-7.92 (2H, m), 11.58 (1H, brs).
MS: 487(M+H)⁺.

Example 533

Synthesis of 2-cyclopropylmethyl-N,N-diisopropyl-N'-((E)-styrylsulfonyl)malonamide (1) 2-cyclopropylmethyl-3-(N,N-diisopropylamino)-3-oxopropionic acid In the same manner as in Example 119 (2), the title compound (1.21 g) was obtained as an oil using the compound (991 mg) obtained in Example 214 (1) and diisopropylamine (1.40 mL).
$^1$H-NMR (300 Mz, DMSO-$d_6$) δ (−0.06)-0.09 (2H, m), 0.20-0.40 (2H, m), 0.49-0.72 (1H, m), 0.93-1.35 (12H, m), 1.38-1.58 (1H, m), 1.58-1.77 (1H, m), 3.32-3.50 (1H, m), 3.55-3.77 (1H, m), 4.08-4.30 (1H, m), 12.42 (1H, brs).

(2) 2-cyclopropylmethyl-N,N-diisopropyl-N'-((E)-styrylsulfonyl)malonamide

In the same manner as in Example 1 (2), the title compound (320 mg) was obtained as a white powder using the abovementioned compound (1.21 g) and trans-β-styrenesulfonamide (707 mg).
$^1$H-NMR (300 Mz, DMSO-$d_6$) δ (−0.18)-0.10 (2H, m), 0.19-0.38 (2H, m), 0.45-0.75 (1H, m), 0.99 (3H, t, J=6.6 Hz), 1.07 (3H, t, J=6.6 Hz), 1.10-1.43 (7H, m), 1.60-1.80 (1H, m), 3.19-3.47 (1H, m), 3.59 (1H, t, J=6.9 Hz), 3.75-4.00 (1H, m), 7.27-7.60 (5H, m), 7.60-7.80 (2H, m), 12.02 (1H, brs).
MS: 407(M+H)⁺.

Example 534

Synthesis of N-cyclohexyl-2-cyclopropylmethyl-N-isopropyl-N'-((E)-styrylsulfonyl)malonamide (1) 3-(N-cyclohexyl-N-isopropylamino)-2-cyclopropylmethyl-3-oxopropionic acid In the same manner as in Example 119 (2), the title compound (880 mg) was obtained as an oil using the compound (991 mg) obtained in Example 214 (1) and N-isopropylcyclohexylamine (2.83 g).
$^1$H-NMR (300 Mz, DMSO-$d_6$) δ (−0.10)-0.10 (2H, m), 0.20-0.42 (2H, m), 0.49-0.70 (1H, m), 0.70-1.80 (18H, m), 2.10-2.46 (1H, m), 2.80-4.30 (2H, m), 12.40 (1H, brs).

(2) N-cyclohexyl-2-cyclopropylmethyl-N-isopropyl-N'-((E)-styrylsulfonyl)malonamide In the same manner as in Example 1 (2), the title compound (120 mg) was obtained as a white powder using the abovementioned compound (880 mg) and trans-β-styrenesulfonamide (524 mg).
$^1$H-NMR (300 Mz, DMSO-$d_6$) δ (−0.18)-0.45 (4H, m), 0.50-1.88 (19H, m), 2.05-3.00 (1H, m), 3.15-4.00 (2H, m), 7.25-7.63 (5H, m), 7.63-7.79 (2H, m), 12.16 (1H, brs).
MS: 447(M+H)⁺.

Example 535

Synthesis of N'-butylsulfonyl-2-cyclopropylmethyl-N-(4-fluorophenyl)-N-isopropylmalonamide In the same manner as in Example 1 (2), the title compound (124 mg) was obtained as a white powder using the compound (587 mg) obtained in Example 515 (1) and 1-butanesulfonamide (274 mg).
$^1$H-NMR (300 Mz, DMSO-$d_6$) δ (−0.38)-(−0.20) (1H, m), (−0.14)-0.02 (1H, m), 0.15-0.33 (2H, m), 0.45-0.67 (1H, m), 0.88 (3H, t, J=7.2 Hz), 0.96 (6H, t, J=7.2 Hz), 1.30-1.77 (6H, m), 3.08-3.20 (1H, m), 3.20-3.44 (2H, m), 4.64-4.88 (1H, m), 7.10-7.42 (4H, m), 11.37 (1H, brs).
MS: 413(M+H)⁺.

Example 536

Synthesis of 2-cyclopropylmethyl-N-(4-fluorophenyl)-N-isopropyl-N'-octylsulfonylmalonamide In the same manner as in Example 1 (2), the title compound (490 mg) was obtained as a white powder using the compound (587 mg) obtained in Example 515 (1) and 1-octanesulfonamide (387 mg).
$^1$H-NMR (300 Mz, DMSO-$d_6$) δ (−0.39)-(−0.20) (1H, m), (−0.17)-0.02 (1H, m), 0.13-0.39 (2H, m), 0.42-0.67 (1H, m), 0.86 (3H, t, J=6.9 Hz), 0.96 (6H, t, J=7.2 Hz), 1.13-1.76 (14H, m), 3.13 (1H, t, J=6.6 Hz), 3.17-3.40 (2H, m), 4.63-4.89 (1H, m), 7.10-7.47 (4H, m), 11.36 (1H, brs).
MS: 469(M+H)⁺.

Example 537

Synthesis of 2-cyclopropylmethyl-N-(4-fluorophenyl)-N-isopropyl-N'-(2-methyl-2-propenylsulfonyl)malonamide (1) 2-methyl-2-propenesulfonamide To 2-methyl-2-propenesulfonic acid sodium salt (7.91 g) was added DMF (50 mL), thionyl chloride (7.26 mL) was added under ice-cooling, and the mixture was stirred at room temperature for 6 hr. The reaction mixture was poured into a mixed solution of ice-water (100 mL) and toluene (100 mL), and the mixture was extracted. The organic layer was concentrated under reduced pressure. THF (60 mL) was added to the residue, and then aqueous ammonia (40 mL) was added under ice-cooling. The mixture was stirred at room temperature for 18 hr. The reaction mixture was concentrated, and water and ethyl acetate were added to extract the residue. The organic layer was washed with saturated brine, and concentrated under reduced pressure to give the title compound (3.11 g) as an oil.
$^1$H-NMR (300 Mz, DMSO-$d_6$) δ 1.86 (3H, s), 3.69 (2H, s), 5.00 (1H, brs), 5.08 (1H, brs), 6.80 (2H, brs).

(2) 2-cyclopropylmethyl-N-(4-fluorophenyl)-N-isopropyl-N'-(2-methyl-2-propenylsulfonyl)malonamide In the same manner as in Example 1 (2), the title compound (390 mg) was obtained as a white powder using the compound (587 mg) obtained in Example 515 (1) and the abovementioned compound (270 mg).

¹H-NMR (300 Mz, DMSO-d₆) δ (−0.40)-(−0.20) (1H, m), (−0.17)-0.02 (1H, m), 0.15-0.35 (2H, m), 0.46-0.69 (1H, m), 0.81-1.09 (6H, m), 1.27-1.44 (1H, m), 1.60-1.79 (1H, m), 1.82 (3H, s), 2.97-3.19 (1H, m), 3.88-4.15 (2H, m), 4.66-4.88 (1H, m), 4.95 (1H, s), 5.12 (1H, s), 7.05-7.44 (4H, m), 11.42 (1H, brs).
MS: 411(M+H)⁺.

Example 538

Synthesis of N-(4-fluorophenyl)-N-isopropyl-2-(2-methoxyethyl)-N'-((E)-styrylsulfonyl)malonamide (1) 5-(2-methoxyethyl)-2,2-dimethyl-1,3-dioxane-4,6-dione In the same manner as in Example 214 (1), the title compound (930 mg) was obtained as an oil using methoxyacetic acid (3.60 g).
¹H-NMR (300 Mz, CDCl₃) δ1.76 (3H, s), 1.81 (3H, s), 5.61 (2H, q, J=5.6 Hz), 3.32 (3H, s), 3.63 (2H, t, J=5.9 Hz), 3.74 (1H, t, J=5.5 Hz).

(2) 2-{[N-(4-fluorophenyl)-N-isopropylamino]carbonyl}-4-methoxybutyric acid

In the same manner as in Example 119 (2), the title compound (600 mg) was obtained as a white powder using the above-mentioned compound (930 mg) and 4-fluoro-N-isopropylaniline (2.82 g).
¹H-NMR (300 Mz, DMSO-d₆) δ0.84-1.05 (6H, m), 1.70-2.01 (2H, m), 2.95-3.30 (6H, m), 4.65-4.90 (1H, m), 7.10-7.40 (4H, m), 12.50 (1H, brs).

(3) N-(4-fluorophenyl)-N-isopropyl-2-(2-methoxyethyl)-N'-((E)-styrylsulfonyl)malonamide In the same manner as in Example 1 (2), the title compound (164 mg) was obtained as a white powder using the above-mentioned compound (600 mg) and trans-β-styrenesulfonamide (341 mg).
¹H-NMR (300 Mz, DMSO-d₆) δ0.77-1.00 (6H, m), 1.67-1.85 (1H, m), 1.85-2.04 (1H, m), 2.97-3.26 (6H, m), 4.62-4.84 (1H, m), 6.95-7.15 (2H, m), 7.15-7.29 (1H, m), 7.29-7.40 (2H, m), 7.40-7.60 (4H, m), 7.69-7.90 (2H, m), 11.62 (1H, brs).
MS: 463(M+H)⁺.

Example 539

Synthesis of N-(4-fluorophenyl)-N-isopropyl-2-[2-(methylthio)ethyl]-N'-((E)-styrylsulfonyl)malonamide (1) 2,2-dimethyl-5-[2-(methylthio)ethyl]-1,3-dioxane-4,6-dione In the same manner as in Example 214 (1), the title compound (3.62 g) was obtained as a white powder using methylthioacetic acid (3.48 mL).
¹H-NMR (300 Mz, CDCl₃) δ1.78 (3H, s), 1.84 (3H, s), 2.09 (3H, s), 2.40 (2H, q, J=5.7 Hz), 2.80 (2H, t, J=6.9 Hz), 4.02 (1H, t, J=5.4 Hz).

(2) 2-{[N-(4-fluorophenyl)-N-isopropylamino]carbonyl}-4-methylthiobutyric acid

In the same manner as in Example 119 (2), the title compound (1.02 g) was obtained as a white solid using the above-mentioned compound (1.00 g) and 4-fluoro-N-isopropylaniline (2.82 g).
¹H-NMR (300 Mz, DMSO-d₆) δ0.82-1.02 (6H, m), 1.76-2.00 (5H, m), 2.31 (2H, t, J=7.1 Hz), 3.12 (1H, t, J=7.4 Hz), 4.68-4.88 (1H, m), 7.13-7.40 (4H, m), 12.60 (1H, brs).

(3) N-(4-fluorophenyl)-N-isopropyl-2-[2-(methylthio)ethyl]-N'-((E)-styrylsulfonyl)malonamide In the same manner as in Example 1 (2), the title compound (339 mg) was obtained as a white powder using the above-mentioned compound (1.02 g) and trans-β-styrenesulfonamide (551 mg).
¹H-NMR (300 Mz, DMSO-d₆) δ0.78-1.00 (6H, m), 1.68-1.85 (1H, m), 1.85-2.09 (4H, m), 2.14-2.40 (2H, m), 3.00-3.19 (1H, m), 4.60-4.84 (1H, m), 6.94-7.18 (2H, m), 7.18-7.40 (3H, m), 7.40-7.67 (4H, m), 7.67-7.89 (2H, m), 11.66 (1H, brs).
MS: 479(M+H)⁺.

Example 540

Synthesis of N-(4-fluorophenyl)-N-isopropyl-2-[2-(methylsulfinyl)ethyl]-N'-((E)-styrylsulfonyl)malonamide To a solution of the compound (100 mg) obtained in Example 539 in methanol (5 mL) was added a solution of sodium periodate (49 mg) in water (1 mL) under ice-cooling, and the mixture was stirred under ice-cooling for 2 hr. The reaction mixture was concentrated under reduced pressure, and 1 mol/L hydrochloric acid and ethyl acetate were added to extract the residue. The organic layer was washed with saturated brine, and concentrated under reduced pressure to give the title compound (103 mg) as a white powder.
¹H-NMR (300 Mz, DMSO-d₆) δ0.80-1.00 (6H, m), 1.75-1.95 (1H, m), 1.95-2.20 (1H, m), 2.35-2.58 (4H, m), 2.58-2.78 (1H, m), 3.09-3.33 (1H, m), 4.64-4.88 (1H, m), 6.91-7.17 (2H, m), 7.17-7.40 (3H, m), 7.40-7.67 (4H, m), 7.69-7.90 (2H, m), 11.68 (1H, brs).
MS: 495(M+H)⁺.

Example 541

Synthesis of N-(4-fluorophenyl)-N-isopropyl-2-[2-(methylsulfonyl)ethyl]-N'-((E)-styrylsulfonyl)malonamide To a solution of the compound (100 mg) obtained in Example 539 in methylene chloride (5 mL) was added m-chloroperbenzoic acid (79 mg), and the mixture was stirred at room temperature for 18 hr. Water, 1 mol/L hydrochloric acid and chloroform were added to extract the reaction mixture, and the organic layer was concentrated under reduced pressure. The residue was washed with THF-chloroform mixture to give the title compound (12 mg) as a white powder.
¹H-NMR (300 Mz, DMSO-d₆) δ0.92 (6H, d, J=6.7 Hz), 1.80-2.00 (1H, m), 2.00-2.28 (1H, m), 2.80-3.08 (5H, m), 3.08-3.35 (1H, m), 4.68-4.87 (1H, m), 6.88-7.09 (2H, m), 7.09-7.60 (7H, m), 7.62-7.89 (2H, m), 11.70 (1H, brs).
MS: 511(M+H)⁺.

Example 542

Synthesis of 2-(2-cyanoethyl)-N-ethyl-N-phenyl-N'-((E)-styrylsulfonyl)malonamide In the same manner as in Example 1 (4), a crude product was obtained using the compound (300 mg) obtained in

Example 543

Synthesis of 2-(2-cyanoethyl)-N-ethyl-N'-(2-naphthylsulfonyl)-N-phenylmalonamide In the same manner as in Example 1 (4), a crude product was obtained using the compound (1.00 g) obtained in Example 153 (3) and N-ethylaniline (379 μL). This was purified by silica gel column chromatography to give the title compound (687 mg) as a white powder.
$^1$H-NMR (400 Mz, CDCl$_3$) δ1.09 (3H, m), 1.91-2.02 (1H, m), 2.09-2.21 (3H, m), 3.11-3.15 (1H, m), 3.60-3.69 (1H, m), 3.82-3.91 (1H, m), 6.95-6.99 (2H, m), 7.35-7.62 (3H, m), 7.63-7.71 (2H, m), 7.92-7.93 (1H, m), 7.99-8.04 (3H, m), 8.67 (1H, s), 10.16 (1H, s).
MS: 450(M+H)$^+$.

Example 544

Synthesis of 2-(2-cyanoethyl)-N-(4-fluorophenyl)-N-isopropyl-N'-((E)-styrylsulfonyl)malonamide In the same manner as in Example 1 (4), a crude product was obtained using the compound (657 mg) obtained in Example 216 (2) and 4-fluoro-N-isopropylaniline (306 mg). This was purified by silica gel column chromatography to give the title compound (334 mg) as a white powder.
$^1$H-NMR (400 Mz, CDCl$_3$) δ1.05 (3H, d, J=6.8 Hz), 1.11 (3H, d, J=6.8 Hz), 2.03-2.09 (1H, m), 2.16-2.39 (3H, m), 3.09-3.14 (1H, m), 4.94-4.97 (1H, m), 7.00-7.09 (2H, m), 7.10-7.19 (3H, m), 7.43-7.47 (3H, m), 7.52-7.55 (2H, m), 7.72 (1H, d, J=15.6 Hz), 9.96 (1H, brs).
MS: 458(M+H)$^+$.

Example 545

Synthesis of 2-cyanomethyl-N-ethyl-N'-(2-naphthylsulfonyl)-N-phenylmalonamide (1) monoethyl (2-cyanomethyl) malonate In the same manner as in Example 117 (1), the object compound was obtained using chloroacetonitrile (1.63 mL). This was subjected to hydrolysis in the same manner as in Example 117 (2) to give the title compound (3.81 g) as an oil.
$^1$H-NMR (400 Mz, CDCl$_3$) δ1.32-1.36 (3H, m), 2.91-2.99 (2H, m), 3.69-3.79 (1H, m) 4.25-4.34 (2H, m).

(2) 2-cyanomethyl-3-(N-ethyl-N-phenylamino)-3-oxopropionic acid

In the same manner as in Example 1 (4), the object compound was obtained using the above-mentioned compound (3.81 g) and N-ethylaniline (2.70 mL). This was subjected to hydrolysis in the same manner as in Example 1 (3) to give the title compound (1.07 g) as an oil.

(3) 2-cyanomethyl-N-ethyl-N'-(2-naphthylsulfonyl)-N-phenylmalonamide

In the same manner as in Example 1 (2), the title compound (1.25 g) was obtained as a white powder using the above-mentioned compound (500 mg).
$^1$H-NMR (400 Mz, CDCl$_3$) δ1.19 (3H, m), 2.51-2.56 (1H, m), 2.80-2.87 (1H, m) 3.38-3.42 (1H, m), 3.73-3.87 (2H, m), 6.87-7.05 (2H, m), 7.39-7.40 (3H, m), 7.66-7.71 (2H, m), 7.92-8.03 (4H, m), 8.65 (1H, s), 9.77 (1H, brs).
MS: 436(M+H)$^+$.

Example 546

Synthesis of 2-cyanomethyl-N-ethyl-N-phenyl-N'-((E)-styrylsulfonyl)malonamide

In the same manner as in Example 1 (2), the title compound (66 mg) was obtained as a white powder using the compound (500 mg) obtained in Example 545 (2) and trans-β-styrenesulfonamide (372 mg).
$^1$H-NMR (400 Mz, CDCl$_3$) δ1.10-1.15 (3H, m), 2.61-2.74 (1H, m), 2.87-2.97 (1H, m), 3.47-3.53 (1H, m), 3.74-3.89 (2H, m), 6.91-7.02 (1H, m), 7.15-7.18 (2H, m), 7.21-7.57 (8H, m), 7.73 (1H, d, J=15.6 Hz), 9.48 (1H, brs).
MS: 412(M+H)$^+$.

Example 547

Synthesis of N-(4-fluorophenyl)-N-isopropyl-2-(2-propynyl)-N'-((E)-styrylsulfonyl)malonamide In the same manner as in Example 152 (3), the object compound was obtained using the compound (3.00 g) obtained in Example 152 (2) and trans-β-styrenesulfonamide (3.23 g). This was subjected to hydrolysis in the same manner as in Example 1 (3), and condensed with 4-fluoro-N-isopropylaniline (1.29 g) in the same manner as in Example 1 (4) to give a crude product. This was purified by silica gel column chromatography to give the title compound (1.25 g) as a white powder.
$^1$H-NMR (400 Mz, CDCl$_3$) δ1.04 (3H, d, J=6.8 Hz), 1.11 (3H, d, J=6.8 Hz), 2.04 (1H, s) 2.57-2.64 (1H, m), 2.70-2.77 (1H, m), 3.18-3.22 (1H, m), 4.94-4.99 (1H, m), 6.99-7.05 (2H, m), 7.09-7.15 (3H, m), 7.39-7.45 (3H, m), 7.50-7.53 (2H, m), 7.71 (1H, d, J=15.6 Hz), 9.87 (1H, brs).
MS: 443(M+H)$^+$.

Example 548

Synthesis of 2-cyclopentyl-N-(4-fluorophenyl)-N-isopropyl-N'-((E)-styrylsulfonyl)malonamide (1) monoethyl cyclopentylmalonate In the same manner as in Example 1 (1), the title compound (8.6 g) was obtained as an oil using diethyl cyclopentylmalonate (10.0 g).

2) 2-cyclopentyl-N-(4-fluorophenyl)-N-isopropyl-N'-((E)-styrylsulfonyl)malonamide In the same manner as in Example 152 (3), the object compound was obtained using the above-mentioned compound (540 mg) and trans-β-styrenesulfonamide (500 mg). This was subjected to hydrolysis in the same manner as in Example 1 (3), and condensed with 4-fluoro-N-isopropylaniline (414 mg) in the same manner as in Example 1 (4) to give a crude product. This was purified by silica gel column chromatography to give the title compound (103 mg) as a white powder.

$^1$H-NMR (400 Mz, CDCl$_3$) δ1.00 (3H, d, J=5.4 Hz), 1.03-1.10 (1H, m), 1.12 (3H, d, J=5.4 Hz), 1.26-1.31 (1H, m), 1.48-1.49 (4H, m), 1.55-1.62 (1H, m), 1.61-1.79 (1H, m), 2.31-2.42 (1H, m), 2.76 (1H, d, J=10.4 Hz), 4.93-5.02 (1H, m), 6.96-7.14 (5H, m), 7.39-7.50 (3H, m), 7.52-7.69 (2H, m), 7.71 (1H, d, J=15.4 Hz), 9.90 (1H, brs).
MS: 473(M+H)$^+$.

Example 549

Synthesis of N-ethyl-N'-(2-naphthylsulfonyl)-N-phenyl-2-[(2E)-3-(3-pyridyl)-2-propenyl]malonamide To a solution of the compound (436 mg) obtained in Example 444 in DMF (5 mL) were added 3-bromopyridine (237 mg), palladium acetate (145 mg), tetra-n-butylammonium chloride (416 mg), triphenylphosphine (52 mg) and potassium acetate (294 mg), and the mixture was stirred at 80° C. for 18 hr. Water and ethyl acetate were added to extract the reaction mixture, and the organic layer was concentrated under reduced pressure. The residue was purified by silica gel column chromatography to give the title compound (345 mg) as a white powder.

$^1$H-NMR (400 Mz, DMSO-d$_6$) δ0.92 (3H, brs), 2.39-2.45 (1H, m), 3.53-3.61 (3H, m), 6.23 (2H, s), 7.01-7.03 (2H, m), 7.08-7.40 (5H, m), 7.55-7.57 (1H, m), 7.59-7.79 (3H, m), 7.98-8.03 (2H, m), 8.14-8.16 (1H, m), 8.30-8.40 (2H, m), 8.52 (1H, s).
MS: 514(M+H)$^+$.

Example 550

Synthesis of N-ethyl-N'-(2-naphthylsulfonyl)-N-phenyl-2-[3-(3-pyridyl)propyl]malonamide In the same manner as in Example 7, the title compound (89 mg) was obtained as a white powder using the compound (100 mg) obtained in Example 549.

$^1$H-NMR (400 Mz, CDCl$_3$) δ1.09 (3H, brs), 1.29-1.36 (2H, m), 1.67-1.76 (2H, m), 2.27-2.38 (2H, m), 3.01-3.04 (1H, m), 3.57-3.82 (1H, m), 3.84-3.37 (1H, m), 6.89-6.90 (2H, m), 7.07-7.10 (1H, m), 7.17-7.19 (1H, m), 7.32-7.34 (3H, m), 7.60-7.69 (2H, m), 7.90-8.01 (4H, m), 8.21 (1H, s), 8.39 (1H, d, J=4.4 Hz), 8.67 (1H, s).
MS: 516(M+H)$^+$.

Example 551

Synthesis of N-ethyl-2-{(2E)-3-[4-(1H-imidazol-1-ylmethyl)phenyl]-2-propenyl}-N'-(2-naphthylsulfonyl)-N-phenylmalonamide In the same manner as in Example 549, the title compound (108 mg) was obtained as a white powder using the compound (436 mg) obtained in Example 444 and 1-(4-bromobenzyl)imidazole (356 mg).

$^1$H-NMR (400 Mz, CDCl$_3$) δ1.10 (3H, brs), 2.61-2.64 (2H, m), 3.60-3.69 (1H, m), 3.77-3.84 (1H, m), 5.24 (2H, s), 5.76-5.82 (1H, m), 6.09-6.20 (1H, m), 6.94-6.95 (1H, m), 7.03-7.20 (5H, m), 7.30-7.40 (5H, m), 7.58-7.67 (3H, m), 7.85-8.01 (5H, m) 8.65 (1H, s), 8.85 (1H, brs).
MS: 593(M+H)$^+$.

Example 552

Synthesis of N-ethyl-2-{3-[4-(1H-imidazol-1-ylmethyl)phenyl]propyl}-N'-(2-naphthylsulfonyl)-N-phenylmalonamide In the same manner as in Example 7, the title compound (17 mg) was obtained as a white powder using the compound (108 mg) obtained in Example 551 at room temperature.

$^1$H-NMR (400 Mz, CDCl$_3$) δ1.05-1.10 (3H, m), 1.35-1.40 (2H, m), 1.69-1.74 (2H, m), 2.36-2.42 (2H, m), 3.60-3.62 (2H, m), 3.82-3.84 (1H, m), 5.20 (2H, s), 6.89-6.90 (2H, m), 6.99-7.02 (2H, m), 7.07-7.08 (2H, m), 7.10-7.24 (2H, m), 7.31-7.32 (3H, m), 7.37-7.38 (1H, m) 7.63-7.65 (2H, m), 7.67-8.03 (4H, m), 8.65 (1H, s), 8.69 (1H, brs).
MS: 595(M+H)$^+$.

Example 553

Synthesis of N-ethyl-2-[(2E)-3-(2-naphthyl)-2-propenyl]-N'-(2-naphthylsulfonyl)-N-phenylmalonamide In the same manner as in Example 549, the title compound (14 mg) was obtained as a white powder using the compound (436 mg) obtained in Example 444 and 2-bromonaphthalene (310 mg).

$^1$H-NMR (400 Mz, CDCl$_3$) δ1.10 (3H, brs), 2.47-2.56 (1H, m), 2.60-2.81 (1H, m), 3.23-3.27 (1H, m), 3.63-3.66 (1H, m), 3.68-3.85 (1H, m), 5.81-5.87 (1H, m), 6.29 (1H, d, J=16.0 Hz), 6.95-6.97 (2H, m), 7.30-7.60 (7H, m), 7.65-7.85 (7H, m), 7.89-7.99 (2H, m), 8.67 (1H, s), 10.82 (1H, brs).
MS: 563(M+H)$^+$.

Example 554

Synthesis of N-ethyl-2-[3-(2-naphthyl)propyl]-N'-(2-naphthylsulfonyl)-N-phenylmalonamide In the same manner as in Example 7, the title compound (33 mg) was obtained as a white powder using the compound (34 mg) obtained in Example 553 at room temperature.

$^1$H-NMR (400 Mz, CDCl$_3$) δ1.08 (3H, m), 1.76-1.82 (2H, m), 2.46-2.53 (2H, m), 3.01-3.04 (2H, m), 3.52-3.60 (1H, m), 3.77-3.86 (1H, m), 6.81 (2H, d, J=7.6 Hz), 6.99-7.03 (3H, m), 7.05-7.31 (2H, m), 7.37-7.38 (2H, m), 7.41-7.43 (1H, m), 7.44-7.71 (4H, m), 7.74-8.01 (5H, m), 8.70 (1H, s) 10.60 (1H, brs).
MS: 565(M+H)$^+$.

Example 555

Synthesis of N-ethyl-2-[(2E)-3-(4-methoxyphenyl)-2-propenyl]-N'-(2-naphthylsulfonyl)-N-phenylmalonamide In the same manner as in Example 549, the title compound (11 mg) was obtained as a white powder using the compound (436 mg) obtained in Example 444 and 4-bromoanisole (281 mg).

$^1$H-NMR (400 Mz, CDCl$_3$) δ1.05 (3H, brs), 2.42-2.52 (1H, m), 2.54-2.70 (1H, m), 3.11-3.25 (1H, m), 3.64-3.71 (1H, m), 3.77-3.83 (4H, m), 5.17-5.76 (1H, m), 6.08-6.17 (1H, m), 6.65-6.78 (2H, m), 6.87-6.98 (3H, m), 7.29-7.41 (4H, m), 7.60-7.70 (2H, m), 7.85-7.90 (2H, m), 7.97-8.07 (2H, m), 8.67 (1H, s), 10.60 (1H, brs).
MS: 543(M+H)$^+$.

Example 556

Synthesis of N-ethyl-2-[3-(4-methoxyphenyl)propyl]-N'-(2-naphthylsulfonyl)-N-phenylmalonamide In the same manner as in Example 7, the title compound (11 mg) was obtained as a white powder using the compound (84 mg) obtained in Example 555 at room temperature.
$^1$H-NMR (400 Mz, DMSO-d$_6$) δ0.97 (3H, brs), 1.07-1.30 (2H, m), 1.45-1.70 (2H, m), 2.29-2.33 (2H, m), 3.10-3.20 (1H, m), 3.56-3.59 (2H, m), 3.72 (3H, s), 6.54-6.59 (1H, m), 6.71-6.75 (2H, m), 6.80-6.87 (1H, m), 7.01-7.09 (2H, m), 7.33-7.37 (2H, m), 7.47-7.51 (1H, m), 7.72-7.81 (3H, m), 8.11-8.16 (1H, m), 8.18-8.22 (1H, m), 8.24-8.35 (1H, m), 8.54 (1H, s), 11.98 (1H, brs).
MS:545(M+H)$^+$.

Example 557

Synthesis of 2-[(2E)-3-(4-biphenyl)-2-propenyl]-N-ethyl-N'-(2-naphthylsulfonyl)-N-phenylmalonamide In the same manner as in Example 549, the title compound (10 mg) was obtained as a white powder using the compound (436 mg) obtained in Example 444 and 4-bromobiphenyl (350 mg).
$^1$H-NMR (400 Mz, CDCl$_3$) δ1.10 (3H, brs), 2.52-2.61 (1H, m), 3.20-3.24 (1H, m), 3.64-3.69 (1H, m), 3.80-3.85 (1H, m), 5.71-5.75 (1H, m), 6.18 (1H, d, J=15.6 Hz), 6.96-7.06 (1H, m), 7.09-7.12 (2H, m), 7.33-7.41 (4H, m), 7.43-7.54 (5H, m), 7.55-7.63 (5H, m), 7.82-7.86 (2H, m), 7.95-7.99 (2H, m), 8.62 (1H, s).
MS: 589(M+H)$^+$.

Example 558

Synthesis of 2-[3-(4-biphenyl)propyl]-N-ethyl-N'-(2-naphthylsulfonyl)-N-phenylmalonamide In the same manner as in Example 7, the title compound (19 mg) was obtained as a white powder using the compound (94 mg) obtained in Example 557 at room temperature.
$^1$H-NMR (400 Mz, DMSO-d$_6$) δ0.93 (3H, brs), 1.12-1.40 (2H, m), 1.43-1.70 (2H, m), 2.33-2.51 (2H, m), 3.50-3.86 (3H, m), 7.04-7.06 (4H, m), 7.32-7.38 (2H, m), 7.44-7.50 (2H, m), 7.56-7.63 (4H, m), 7.71-7.76 (2H, m), 7.79-8.10 (3H, m), 8.16-8.55 (3H, m), 11.95 (1H, s) 12.28 (1H, brs).
MS: 591(M+H)$^+$.

Example 559

Synthesis of N-ethyl-2-[(2E)-3-(4-isoquinolyl)-2-propenyl]-N'-(2-naphthylsulfonyl)-N-phenylmalonamide In the same manner as in Example 549, the title compound (61 mg) was obtained as a white powder using the compound (436 mg) obtained in Example 444 and 4-bromoisoquinoline (363 mg).
$^1$H-NMR (400 Mz, CDCl$_3$) δ0.99 (3H, brs), 2.77-2.79 (1H, m), 3.28-3.30 (1H, m), 3.63-3.84 (1H, n), 3.86-3.93 (1H, m), 5.79-5.85 (1H, m), 6.69-6.65 (1H, m), 6.95-7.00 (2H, m), 7.30-7.37 (2H, m), 7.42-7.48 (3H, m), 7.48-7.58 (2H, m), 7.59-7.31 (3H, m), 7.73-8.05 (5H, m), 8.29 (1H, s), 8.65 (1H, s), 9.05 (1H, s).
MS: 564(M+H)$^+$.

Example 560

Synthesis of 2-[3-(benzothiophen-3-yl)-2-propenyl]-N-ethyl-N'-(2-naphthylsulfonyl)-N-phenylmalonamide In the same manner as in Example 549, the title compound (10 mg) was obtained as a white powder using the compound (436 mg) obtained in Example 444 and 3-bromobenzothiophene (319 mg).
$^1$H-NMR (400 Mz, CDCl$_3$) δ1.10 (3H, brs), 2.50-2.60 (1H, m), 2.60-2.70 (1H, m), 3.23-3.32 (1H, m), 3.60-3.69 (1H, m), 3.80-3.89 (1H, m), 5.72-5.79 (1H, m), 6.35 (1H, d, J=15.6 Hz), 6.96-6.99 (2H, m), 7.01-7.02 (1H, m), 7.30-7.37 (5H, m), 7.48-7.55 (2H, m), 7.58-7.80 (3H, m), 7.82-7.98 (3H, m), 8.60 (1H, s), 10.70 (1H, brs).
MS: 569(M+H)$^+$.

Example 561

Synthesis of N-ethyl-N'-(2-naphthylsulfonyl)-N-phenyl-2-[(2E)-3-(3-thienyl)-2-propenyl]malonamide In the same manner as in Example 549, the title compound (1 mg) was obtained as a white powder using the compound (436 mg) obtained in Example 444 and 3-bromothiophene (244 mg).
$^1$H-NMR (400 Mz, CDCl$_3$) δ1.08 (3H, brs), 2.40-2.48 (1H, in), 2.51-2.65 (1H, m), 3.16-3.19 (1H, m), 3.61-3.69 (1H, m), 3.78-3.85 (1H, m), 5.49-5.57 (1H, m), 6.16 (1H, d, J=15.6 Hz), 6.83-6.99 (4H, m), 7.16-7.18 (1H, m), 7.31-7.34 (3H, m), 7.52-7.68 (2H, m), 7.86-7.88 (2H, m), 7.92-7.99 (2H, m), 8.65 (1H, s), 10.60 (1H, brs).
MS: 519(M+H)$^+$.

Example 562

Synthesis of N-ethyl-2-[(2E)-3-(4-ethoxycarbonylphenyl)-2-propenyl]-N'-(2-naphthylsulfonyl)-N-phenylmalonamide In the same manner as in Example 549, the title compound (1.12 g) was obtained as a white powder using the compound (1.31 g) obtained in Example 444 and ethyl 4-bromobenzoate (1.24 g).
$^1$H-NMR (400 Mz, CDCl$_3$) δ1.07 (3H, brs), 1.42 (3H, brs), 2.49-2.55 (1H, m), 2.59-2.64 (1H, m), 3.19-3.23 (1H, m), 3.63-3.70 (1H, m), 3.78-3.85 (1H, m), 4.35-4.41 (2H, m), 5.75-5.83 (1H, m), 6.15 (1H, d, J=16.0 Hz), 6.93-6.96 (2H, m), 7.03-7.05 (2H, m), 7.31-7.37 (3H, m), 7.57-7.65 (2H, m), 7.81-7.84 (4H, m), 7.94-7.98 (2H, m), 8.63 (1H, s), 10.65 (1H, brs).
MS: 585(M+H)$^+$.

Example 563

Synthesis of N-ethyl-2-[3-(4-ethoxycarbonylphenyl)propyl]-N'-(2-naphthylsulfonyl)-N-phenylmalonamide In the same manner as in Example 7, the title compound (158 mg) was obtained as a white powder using the compound (1.10 g) obtained in Example 562 at room temperature.

¹H-NMR (400 Mz, CDCl₃) δ1.09 (3H, brs), 1.22-1.32 (2H, m), 1.41 (3H, brs), 1.68-1.73 (2H, m), 2.31-2.42 (2H, m), 2.99-3.03 (1H, m), 3.56-3.63 (1H, m), 3.82-3.87 (1H, m), 4.35-4.40 (2H, m), 6.87-6.94 (4H, m), 7.29-7.34 (3H, m), 7.61-7.69 (2H, m), 7.83-8.02 (6H, m), 8.67 (1H, s), 10.61 (1H, brs).
MS: 587(M+H)⁺.

Example 564

Synthesis of N-ethyl-2-[(2E)-3-(4-fluorophenyl)-2-propenyl]-N'-(2-naphthylsulfonyl)-N-phenylmalonamide In the same manner as in Example 549, the title compound (52 mg) was obtained as a white powder using the compound (436 mg) obtained in Example 444 and 4-bromo-1-fluorobenzene (263 mg).
¹H-NMR (400 Mz, CDCl₃) δ1.09 (3H, brs), 2.41-2.52 (1H, m), 2.54-2.67 (1H, m), 3.20-3.21 (1H, m), 3.61-3.70 (1H, m), 3.77-3.86 (1H, m), 5.54-5.72 (1H, m), 6.08 (1H, d, J=16.0 Hz), 6.71-6.88 (2H, m), 6.92-6.99 (4H, m), 7.31-7.35 (3H, m), 7.52-7.65 (2H, m), 7.82-7.89 (2H, m), 7.91-8.00 (2H, m), 8.65 (1H, s), 10.61 (1H, brs).
MS: 531(M+H)⁺.

Example 565

Synthesis of N-ethyl-2-[3-(4-fluorophenyl)propyl]-N'-(2-naphthylsulfonyl)-N-phenylmalonamide In the same manner as in Example 7, the title compound (11 mg) was obtained as a white powder using the compound (40 mg) obtained in Example 564 at room temperature.
¹H-NMR (400 Mz, CDCl₃) δ1.10 (3H, brs), 1.20-1.36 (2H, m), 1.61-1.82 (2H, m), 2.22-2.37 (2H, m), 2.98-3.02 (1H, m), 3.55-3.63 (1H, m), 3.79-3.88 (1H, m), 6.79-6.89 (5H, m), 7.13-7.20 (1H, m), 7.29-7.36 (3H, m), 7.60-7.63 (2H, m), 7.65-8.00 (4H, m), 8.71 (1H, s), 10.60 (1H, brs).
MS: 533(M+H)⁺.

Example 566

Synthesis of N-ethyl-N'-(2-naphthylsulfonyl)-2-{2-[4-(4-nitrophenyl)piperazino]ethyl}-N-phenylmalonamide (1) N-ethyl-5-hydroxy-1-(2-naphthylsulfonyl)-2-oxo-N-phenylpyrrolidine-3-carboxamide To a mixture of the compound (10.1 g) obtained in Example 444 in ethanol (60 mL)/water (60 mL) were added osmium tetroxide (200 mg) and sodium periodate (8.90 g), and the mixture was stirred at room temperature for 1.5 hr. Ethyl acetate and water were added to the reaction mixture, and the precipitate was collected by filtration to give the title compound (439 mg) as a white powder.
¹H-NMR (400 Mz, DMSO-d₆) δ0.91-0.97 (3H, m), 1.89-1.95 (1H, m), 2.63-2.67 (1H, m), 3.59-3.63 (2H, m), 3.65-3.70 (1H, m), 5.89-5.93 (1H, m), 6.91-6.93 (1H, m), 7.25-7.30 (2H, m), 7.33-7.37 (1H, m), 7.41-7.45 (2H, m), 7.69-7.78 (2H, m), 7.93-7.95 (1H, m), 8.05 (1H, d, J=8.0 Hz), 8.12-8.21 (2H, m), 8.63 (1H, brs).

(2) N-ethyl-N'-(2-naphthylsulfonyl)-2-{2-[4-(4-nitrophenyl)piperazino]ethyl}-N-phenylmalonamide To a solution of the above-mentioned compound (439 mg) in methylene chloride (5 mL) were added 1-(4-nitrophenyl)piperazine (228 mg), acetic acid (580 μL) and sodium triacetoxyborohydride (1.02 g), and the mixture was stirred at room temperature for 2 days. Water and chloroform were added to extract the reaction mixture, and the organic layer was concentrated under reduced pressure. The residue was purified by silica gel column chromatography to give the title compound (227 mg) as a white powder.
¹H-NMR (400 Mz, CDCl₃) δ1.07 (3H, t, J=7.2 Hz), 1.80-1.95 (1H, m), 1.97-2.04 (1H, m), 2.28-2.34 (1H, m), 2.46-2.53 (1H, m), 2.56-2.58 (4H, m), 3.39-3.42 (4H, m), 3.47-3.50 (1H, m), 3.56-3.64 (1H, m), 3.77-3.86 (1H, m), 6.77-6.81 (2H, m), 6.97-6.99 (2H, m), 7.29-7.32 (3H, m), 7.58-7.66 (2H, m), 7.88-8.01 (4H, m), 8.09-8.14 (2H, m), 8.64 (1H, brs).
MS: 630(M+H)⁺.

Example 567

Synthesis of 2-{2-[4-(4-aminophenyl)piperazino]ethyl}-N-ethyl-N'-(2-naphthylsulfonyl)-N-phenylmalonamide In the same manner as in Example 7, the title compound (89 mg) was obtained as a white powder using the compound (154 mg) obtained in Example 566 at room temperature.
¹H-NMR (400 Mz, DMSO-d₆) δ0.96 (3H, t, J=6.4 Hz), 1.06-1.19 (3H, m), 1.91-1.99 (2H, m), 2.82-2.84 (2H, m), 3.36-3.43 (3H, m), 3.51-3.61 (4H, m), 4.02-4.04 (1H, m), 6.50-6.52 (2H, m), 6.67-6.69 (2H, m), 7.18-7.28 (5H, m), 7.60-7.61 (2H, m), 7.80-7.82 (1H, m), 7.96-7.98 (2H, m), 8.05-8.06 (1H, m), 8.34 (1H, s).
MS: 600(M+H)⁺.

Example 568

Synthesis of N-ethyl-2,2-difluoro-N-(1-naphthyl)-N'-((E)-styrylsulfonyl)malonamide Diethyl difluoromalonate (1.00 g) was subjected to hydrolysis in the same manner as in Example 1 (1) to give the object compound as an oil. This and trans-β-styrenesulfonamide (1.94 g) were condensed in the same manner as in Example 152 (3), and the condensed product was subjected to hydrolysis in the same manner as in Example 1 (3). In the same manner as in Example 1 (4), a crude product was obtained using this and N-ethyl-1-naphthylamine (805 mg). This was purified by silica gel column chromatography to give the title compound (22 mg) as a white powder.
¹H-NMR (400 Mz, CDCl₃) δ1.85 (3H, t, J=6.8 Hz), 3.30-3.34 (1H, m), 4.35-4.38 (1H, m), 6.87 (1H, d, J=15.6 Hz), 7.27-7.30 (1H, m), 7.41-7.58 (8H, m), 7.67-7.87 (2H, m), 7.89-7.91 (2H, m).
MS: 459(M+H)⁺.

Example 569

Synthesis of N-(4-fluorophenyl)-N-isopropyl-2,2-dimethyl-N'-((E)-styrylsulfonyl)malonamide (1) 2,2-dimethyl-3-oxo-3-[((E)-styrylsulfonyl)amino]propionic acid Diethyl dimethylmalonate (10.0 g) was subjected to hydrolysis in the same manner as in Example 1 (1) to give the object compound as an oil. The carboxylic acid form (3.20 g) and trans-β-styrenesulfonamide (3.67 g) were condensed in the same manner as in Example 152 (3), and the condensed product was subjected to hydrolysis in the same manner as in Example 1 (3) to give the title compound (1.38 g) as a white powder.

$^1$H-NMR (400 Mz, CDCl$_3$) δ1.48 (6H, s), 7.07 (1H, d, J=14.4 Hz), 7.27-7.29 (3H, m), 7.40-7.42 (2H, m), 7.52-7.54 (2H, m), 7.71 (1H, d, J=14.4 Hz).

(2) N-(4-fluorophenyl)-N-isopropyl-2,2-dimethyl-N'-((E)-styrylsulfonyl)malonamide In the same manner as in Example 1 (4), a crude product was obtained using the above-mentioned compound (594 mg) and 4-fluoro-N-isopropylaniline (306 mg). This was purified by silica gel column chromatography to give the title compound (57 mg) as a white powder.

$^1$H-NMR (400 Mz, CDCl$_3$) δ1.02 (3H, s), 1.04 (3H, s), 1.90 (6H, brs), 4.89-4.93 (1H, brs), 6.99-7.10 (5H, m), 7.41-7.52 (3H, m), 7.53-7.55 (2H, m), 7.72 (1H, d, J=15.2 Hz), 8.45-8.48 (1H, brs).

MS: 433(M+H)$^+$.

Example 570

Synthesis of N-benzyl-N-phenyl-N'-((E)-styrylsulfonyl)cyclobutane-1,1-dicarboxamide (1) 1-{[((E)-styrylsulfonyl)amino]carbonyl}cyclobutanecarboxylic acid Diethyl 1,1-cyclobutanedicarboxylate (10.0 g) was subjected to hydrolysis in the same manner as in Example 1 (1) to give the object compound as an oil. The carboxylic acid form (3.44 g) and trans-β-styrenesulfonamide (3.67 g) were condensed in the same manner as in Example 152 (3), and the condensed product was subjected to hydrolysis in the same manner as in Example 1 (3) to give the title compound (3.02 g) as a white powder.

$^1$H-NMR (400 Mz, CDCl$_3$) δ1.97-2.07 (2H, m), 2.60-2.65 (2H, m), 2.70-2.73 (2H, m), 7.09 (1H, d, J=13.4 Hz), 7.31-7.34 (2H, m), 7.41-7.42 (3H, m), 7.53-7.54 (2H, m), 7.71 (1H, d, J=13.4 Hz).

(2) N-benzyl-N-phenyl-N'-((E)-styrylsulfonyl)cyclobutane-1,1-dicarboxamide

In the same manner as in Example 1 (4), a crude product was obtained using the above-mentioned compound (618 mg) and N-benzylaniline (367 mg). This was purified by silica gel column chromatography to give the title compound (249 mg) as a white powder.

$^1$H-NMR (400 Mz, CDCl$_3$) δ1.48-1.51 (2H, m), 1.87-1.89 (2H, m), 2.29-2.32 (2H, m), 4.88 (2H, s), 6.70-6.75 (2H, m), 6.85 (1H, d, J=15.6 Hz), 7.05-7.09 (2H, m), 7.16-7.20 (3H, m), 7.29-7.31 (3H, m), 7.41-7.46 (5H, m), 7.71 (1H, d, J=15.6 Hz), 8.75 (1H, brs).

MS: 475(M+H)$^+$.

Example 571

Synthesis of N,N-diethyl-N'-((E)-styrylsulfonyl)cyclobutane-1,1-dicarboxamide

In the same manner as in Example 1 (4), a crude product was obtained using the compound (618 mg) obtained in Example 570 (1). This was purified by silica gel column chromatography to give the title compound (26 mg) as a white powder.

$^1$H-NMR (400 Mz, CDCl$_3$) δ1.04-1.13 (6H, m), 1.70-1.90 (1H, m), 1.93-1.96 (1H, m), 2.57-2.63 (4H, m), 3.02-3.08 (2H, m), 3.33-3.38 (2H, m), 7.04 (1H, d, J=15.6 Hz), 7.41-7.52 (3H, m), 7.53-7.72 (2H, m), 7.74 (1H, d, J=15.6 Hz), 8.30 (1H, brs).

MS: 365(M+H)$^+$.

Example 572

Synthesis of N-(4-fluorophenyl)-N-isopropyl-N'-((E)-styrylsulfonyl)cyclobutane-1,1-dicarboxamide In the same manner as in Example 1 (4), a crude product was obtained using the compound (1.00 g) obtained in Example 570 (1) and 4-fluoro-N-isopropylaniline (490 mg). This was purified by silica gel column chromatography to give the title compound (71 mg) as a white powder.

$^1$H-NMR (400 Mz, CDCl$_3$) δ1.04-1.06 (6H, m), 1.49-1.53 (1H, m), 1.69-1.75 (1H, m), 1.82-1.86 (2H, m), 2.30-2.38 (2H, m), 4.89-4.92 (1H, m), 6.96-6.98 (4H, m), 7.09 (1H, d, J=15.6 Hz), 7.42-7.47 (3H, m), 7.54-7.56 (2H, m), 7.76 (1H, d, J=15.6 Hz), 8.63 (1H, brs).

MS: 445(M+H)$^+$.

Example 573

Synthesis of N-(4-fluorophenyl)-N-isopropyl-2-(1-methylethylidene)-N'-((E)-styrylsulfonyl)malonamide Diethyl (1-methylethylidene)malonate (5.00 g) was subjected to hydrolysis in the same manner as in Example 1 (1). The obtained carboxylic acid and trans-β-styrenesulfonamide (953 mg) were condensed in the same manner as in Example 152 (3), and the condensed product was subjected to hydrolysis in the same manner as in Example 1 (3). This and 4-fluoro-N-isopropylaniline (805 mg) were condensed in the same manner as in Example 1 (4) to give a crude product. This was purified by silica gel column chromatography to give the title compound (13 mg) as a white powder.

$^1$H-NMR (400 Mz, CDCl$_3$) δ0.80-1.10 (6H, m), 2.40-2.50 (6H, m), 5.50-5.80 (1H, m), 6.99-7.06 (2H, m), 7.09-7.14 (1H, m), 7.40-7.45 (4H, m), 7.50-7.54 (3H, m), 7.68-7.74 (1H, m), 10.30 (1H, brs).

MS: 445(M+H)$^+$.

Example 574

Synthesis of N,N-diethyl-N'-(2-naphthylsulfonyl)-2-(4-nitrobenzylidene)malonamide (1) 2,2-dimethyl-5-(4-nitrobenzylidene)-1,3-dioxane-4,6-dione To 4-nitrobenzaldehyde (15.1 g) were added a toluene (180 mL) solution, Meldrum's acid (14.4 g), piperidine (300 μL) and acetic acid (300 μL) at room temperature, and the mixture was stirred for 5 hr. Insoluble material was collected by filtration, and the obtained solid was washed with ethyl acetate (80 mL). The resulting precipitate was collected by filtration to give the title compound (19.3 g) as a pale-yellow solid.

$^1$H-NMR (300 Mz, DMSO-d$_6$) δ1.61 (6H, s), 8.07 (1H, d, J=8.7 Hz), 8.30 (2H, d, J=8.8 Hz), 8.51 (1H, s).

(2) 3-(N,N-diethylamino)-2-(4-nitrobenzylidene)-3-oxopropionic acid

In the same manner as in Example 119 (2), the title compound (1.22 g) was obtained as a white powder using the above-mentioned compound (15.2 g).

¹H-NMR (300 Mz, DMSO-d₆) δ0.83 (3H, t, J=7.1 Hz), 1.07 (3H, t, J=7.1 Hz), 3.00-3.70 (4H, m), 7.67 (1H, s), 7.79 (2H, d, J=8.8 Hz), 8.27 (2H, d, J=8.7 Hz).

(3) N,N-diethyl-N'-(2-naphthylsulfonyl)-2-(4-nitrobenzylidene)malonamide

In the same manner as in Example 1 (2), the title compound (930 mg) was obtained as a white powder using the above-mentioned compound (1.22 g).
¹H-NMR (300 Mz, DMSO-d₆) δ0.59 (3H, t, J=7.0 Hz), 0.97 (3H, t, J=7.0 Hz), 2.84-3.60 (4H, m), 7.50-8.39 (11H, m), 8.67 (1H, s).
MS: 482(M+H)⁺.

Example 575

Synthesis of 2-[4-(benzoylamino)benzylidene]-N,N-diethyl-N'-(2-naphthylsulfonyl)malonamide

(1) 2-(4-aminobenzylidene)-N,N-diethyl-N'-(2-naphthylsulfonyl)malonamide

In the same manner as in Example 137 (4), the title compound (50 mg) was obtained as a white powder using the compound (560 mg) obtained in Example 574.
¹H-NMR (300 Mz, CDCl₃) δ0.84 (3H, t, J=7.2 Hz), 1.23 (3H, t, J=7.2 Hz), 2.80-2.99 (1H, m), 3.04-3.39 (2H, m), 3.69-3.91 (1H, m), 6.55 (2H, d, J=8.7 Hz), 7.17 (2H, d, J=8.7 Hz), 7.46 (1H, s), 7.50-7.75 (2H, m), 7.83-8.12 (4H, m), 8.70 (1H, s).

(2) 2-[4-(benzoylamino)benzylidene]-N,N-diethyl-N'-(2-naphthylsulfonyl)malonamide In the same manner as in Example 9, the title compound (36 mg) was obtained as a white powder using the above-mentioned compound (50 mg).
¹H-NMR (300 Mz, DMSO-d₆) δ0.64 (3H, t, J=7.2 Hz), 1.03 (3H, t, J=7.2 Hz), 2.80-3.60 (4H, m), 7.37-8.30 (16H, m), 8.62 (1H, s), 10.45 (1H, s).
MS: 556(M+H)⁺.

Example 576

Synthesis of 2-[3-(benzoylamino)benzyl]-N,N-diethyl-N'-(2-naphthylsulfonyl)malonamide In the same manner as in Example 9, a crude product was obtained using the compound (170 mg) obtained in Example 115. This was purified by silica gel column chromatography to give the title compound (27 mg) as a white powder.
¹H-NMR (400 MHz, CDCl₃) δ0.87 (3H, t, J=7.2 Hz), 1.02 (3H, t, J=7.1 Hz), 2.92-3.20 (5H, m), 3.41-3.47 (1H, m), 3.61 (1H, dd, J=9.2, 5.8 Hz), 6.80 (1H, d, J=7.7 Hz), 7.14 (1H, t, J=7.7 Hz), 7.34 (1H, s), 7.49 (2H, t, J=7.2 Hz), 7.53-7.69 (4H, m), 7.79 (1H, brs), 7.85 (2H, d, J=7.2 Hz), 7.90 (1H, d, J=7.9 Hz), 7.96 (1H, d, J=8.8 Hz), 7.99-8.04 (2H, m), 8.67 (1H, s), 10.98 (1H, brs).
MS: 558(M+H)⁺.

Example 577

Synthesis of N,N-diethyl-N'-(2-naphthylsulfonyl)-2-{3-[(2-pyridylcarbonyl)amino]benzyl}malonamide The compound (150 mg) obtained in Example 115 and picolinic acid chloride hydrochloride (67 mg) were subjected to the same manner as in Example 9 to give the reaction mixture. The reaction mixture was adjusted to pH=1-2 by the addition of dilute hydrochloric acid and extracted with ethyl acetate (50 ml×2). After concentration under reduced pressure, and the residue was purified by silica gel column chromatography to give the title compound (84 mg) as a white powder.
¹H-NMR (400 MHz, CDCl₃) δ0.81 (3H, t, J=7.2 Hz), 0.99 (3H, t, J=7.1 Hz), 2.78-2.97 (2H, m), 3.01-3.21 (3H, m), 3.42-3.53 (1H, m), 3.63 (1H, dd, J=10.2, 5.1 Hz), 6.80 (1H, d, J=7.8 Hz), 7.13 (1H, t, J=7.8 Hz), 7.46-7.51 (2H, m), 7.58-7.69 (3H, m), 7.88-7.94 (2H, m), 7.97 (1H, d, J=8.8 Hz), 8.00-8.05 (2H, m), 8.27 (1H, d, J=7.8 Hz), 8.61 (1H, d, J=4.6 Hz), 8.68 (1H, s), 9.95 (1H, brs), 10.94 (1H, brs).
MS: 559(M+H)⁺.

Example 578

Synthesis of 2-{3-[(2-amino-5-fluorobenzoyl)amino]benzyl}-N,N-diethyl-N'-(2-naphthylsulfonyl)malonamide In the same manner as in Example 1 (4), a crude product was obtained using the compound (300 mg) obtained in Example 115 and 5-fluoroanthranilic acid (100 mg). This was purified by silica gel column chromatography to give the title compound (160 mg) as a white solid.
¹H-NMR (400 MHz, CDCl₃) δ0.86 (3H, t, J=7.2 Hz), 1.02 (3H, t, J=7.1 Hz), 2.85-3.20 (5H, m), 3.42-3.53 (1H, m), 3.60 (1H, dd, J=9.5, 5.6 Hz), 6.69 (1H, dd, J=8.9, 4.6 Hz), 6.81 (1H, d, J=7.9 Hz), 7.02 (1H, ddd, J=8.9, 7.8, 2.8 Hz), 7.13 (1H, t, J=7.9 Hz), 7.16 (1H, dd, J=9.2, 2.8 Hz), 7.33 (1H, s), 7.46 (1H, d, J=7.9 Hz), 7.58-7.69 (2H, m), 7.75 (1H, brs), 7.90 (1H, d, J=8.0 Hz), 7.96 (1H, d, J=8.8 Hz), 7.98-8.04 (2H, m), 8.67 (1H, s).
MS: 591(M+H)⁺.

Example 579

Synthesis of 2-{3-[(2-amino-6-fluorobenzoyl)amino]benzyl}-N,N-diethyl-N'-(2-naphthylsulfonyl)malonamide In the same manner as in Example 1 (4), a crude product was obtained using the compound (250 mg) obtained in Example 115 and 6-fluoroanthranilic acid (86 mg). This was purified by silica gel column chromatography to give the title compound (64 mg) as an oil.
¹H-NMR (400 MHz, CDCl₃) δ0.81 (3H, t, J=7.2 Hz), 1.01 (3H, t, J=7.1 Hz), 2.78-2.97 (2H, m), 2.98-3.20 (3H, m), 3.42-3.55 (1H, m), 3.61 (1H, dd, J=10.0, 5.0 Hz), 5.95 (2H, brs), 6.40 (1H, dd, J=13, 8.1 Hz), 6.48 (1H, d, J=8.3 Hz), 6.81 (1H, d, J=7.6 Hz), 7.07-7.19 (2H, m), 7.36 (1H, s), 7.42 (1H, d, J=8.2 Hz), 7.58-7.68 (2H, m), 7.90 (1H, d, J=7.8 Hz), 7.96 (1H, d, J=8.7 Hz), 7.99-8.05 (2H, m), 8.23 (1H, d, J=17 Hz), 8.67 (1H, s), 10.95 (1H, brs).
MS: 591(M+H)⁺.

Example 580

Synthesis of 2-[4-(benzoylamino)phenethyl]-N,N-diethyl-N'-(2-naphthylsulfonyl)malonamide In the same manner as in Example 9, a crude product was obtained using the compound (200 mg) obtained in Example 145. This was purified by silica gel column chromatography to give the title compound (180 mg) as a white solid.

¹H-NMR (400 MHz, CDCl₃) δ 0.94 (3H, t, J=7.2 Hz), 1.09 (3H, t, J=7.1 Hz), 1.97-2.08 (1H, m), 2.08-2.19 (1H, m), 2.44-2.58 (2H, m), 2.94-3.13 (2H, m), 3.20-3.30 (1H, m), 3.35 (1H, dd, J=8.3, 6.2 Hz), 3.39-3.50 (1H, m), 7.06 (2H, d, J=8.4 Hz), 7.46-7.53 (4H, m), 7.56 (1H, t, J=7.3 Hz), 7.59-7.69 (2H, m), 7.74 (1H, brs), 7.86 (2H, d, J=7.0 Hz), 7.91 (1H, d, J=8.0 Hz), 7.96 (1H, d, J=9.2 Hz), 7.99-8.05 (2H, m), 8.68 (1H, s), 10.94 (1H, brs).
MS: 572(M+H)⁺.

Example 581

Synthesis of N,N-diethyl-N'-(2-naphthylsulfonyl)-2-{4-[(2-pyridylcarbonyl)amino]phenethyl}malonamide In the same manner as in Example 577, the title compound (89 mg) was obtained as an oil using the compound (200 mg) obtained in Example 145.
¹H-NMR (400 MHz, CDCl₃) δ 0.93 (3H, t, J=7.2 Hz), 1.09 (3H, t, J=7.1 Hz), 1.97-2.09 (1H, m), 2.09-2.20 (1H, m), 2.44-2.58 (2H, m), 2.90-3.10 (2H, m), 3.18-3.30 (1H, m), 3.35 (1H, dd, J=8.3, 6.2 Hz), 3.38-3.50 (1H, m), 7.07 (2H, d, J=8.4 Hz), 7.48 (1H, ddd, J=7.5, 4.7, 1.1 Hz), 7.59-7.69 (4H, m), 7.88-7.93 (2H, m), 7.96 (1H, d, J=8.8 Hz), 8.00-8.04 (2H, m), 8.28 (1H, d, J=7.8 Hz), 8.61 (1H, d, J=4.4 Hz), 8.68 (1H, s), 9.96 (1H, brs), 10.94 (1H, brs).
MS: 573(M+H)⁺.

Example 582

Synthesis of 2-{4-[(2-amino-5-fluorobenzoyl)amino]phenethyl}-N,N-diethyl-N'-(2-naphthylsulfonyl)malonamide In the same manner as in Example 578, the title compound (91 mg) was obtained as a white solid using the compound (250 mg) obtained in Example 145.
¹H-NMR (400 MHz, CDCl₃) δ 0.95 (3H, t, J=7.1 Hz), 1.10 (3H, t, J=7.1 Hz), 1.95-2.20 (2H, m), 2.45-2.58 (2H, m), 2.95-3.15 (2H, m), 3.20-3.32 (1H, m), 3.36 (1H, dd, J=8.2, 6.3 Hz), 3.40-3.50 (1H, m), 6.69 (1H, dd, J=8.8, 4.5 Hz), 6.99-7.10 (3H, m), 7.17 (1H, dd, J=9.2, 2.7 Hz), 7.42 (2H, d, J=8.1 Hz), 7.59-7.73 (3H, m), 7.91 (1H, d, J=8.2 Hz), 7.96 (1H, d, J=8.7 Hz), 8.00-8.06 (2H, m), 8.68 (1H, s).
MS: 605(M+H)⁺.

Example 583

Synthesis of 2-{4-[(2-amino-6-fluorobenzoyl)amino]phenethyl}-N,N-diethyl-N'-(2-naphthylsulfonyl)malonamide In the same manner as in Example 579, the title compound (170 mg) was obtained as a white solid using the compound (250 mg) obtained in Example 145.
¹H-NMR (400 MHz, CDCl₃) δ 0.95 (3H, t, J=7.2 Hz), 1.09 (3H, t, J=7.1 Hz), 1.95-2.18 (2H, m), 2.43-2.57 (2H, m), 2.93-3.14 (2H, m), 3.20-3.30 (1H, m), 3.35 (1H, dd, J=8.3, 6.3 Hz), 3.39-3.50 (1H, m), 5.95 (2H, brs), 6.40 (1H, dd, J=13, 8.2 Hz), 6.48 (1H, d, J=8.2 Hz), 7.04 (2H, d, J=8.4 Hz), 7.13 (1H, td, J=8.2, 6.5 Hz), 7.44 (2H, d, J=8.4 Hz), 7.59-7.69 (2H, m), 7.91 (1H, d, J=7.9 Hz), 7.96 (1H, d, J=8.8 Hz), 8.00-8.04 (2H, m), 8.25 (1H, d, J=17 Hz), 8.68 (1H, s), 10.92 (1H, brs).
MS: 605(M+H)⁺.

Example 584

Synthesis of 2-{3-[4-(benzoylamino)phenyl]propyl}-N,N-diethyl-N'-(2-naphthylsulfonyl)malonamide In the same manner as in Example 9, a crude product was obtained using the compound (200 mg) obtained in Example 147. This was purified by silica gel column chromatography to give the title compound (160 mg) as a white solid.
¹H-NMR (400 MHz, CDCl₃) δ 1.05 (3H, t, J=7.2 Hz), 1.09 (3H, t, J=7.1 Hz), 1.44-1.55 (2H, m), 1.76-1.85 (2H, m), 2.41-2.57 (2H, m), 3.19 (2H, q, J=7.2 Hz), 3.23-3.48 (3H, m), 6.98 (2H, d, J=8.4 Hz), 7.44-7.69 (7H, m), 7.73 (1H, brs), 7.87 (2H, d, J=7.0 Hz), 7.91 (1H, d, J=8.1 Hz), 7.94 (1H, d, J=8.8 Hz), 7.96-8.04 (2H, m), 8.68 (1H, s), 10.83 (1H, brs).
MS: 586(M+H)⁺.

Example 585

Synthesis of N,N-diethyl-N'-(2-naphthylsulfonyl)-2-{3-[4-((2-pyridylcarbonyl)amino)phenyl]propyl}malonamide In the same manner as in Example 577, the title compound (180 mg) was obtained as an oil using the compound (200 mg) obtained in Example 147.
¹H-NMR (400 MHz, CDCl₃) δ 1.05 (3H, t, J=7.3 Hz), 1.09 (3H, t, J=7.2 Hz), 1.43-1.54 (2H, m), 1.76-1.87 (2H, m), 2.40-2.57 (2H, m), 3.18 (2H, q, J=7.2 Hz), 3.23-3.33 (1H, m), 3.35 (1H, t, J=7.4 Hz), 3.37-3.48 (1H, m), 6.99 (2H, d, J=8.4 Hz), 7.49 (1H, ddd, J=7.7, 4.8, 1.1 Hz), 7.57-7.70 (4H, m), 7.89-8.03 (5H, m), 8.30 (1H, d, J=7.7 Hz), 8.63 (1H, d, J=4.8 Hz), 8.66 (1H, s), 9.96 (1H, brs), 10.88 (1H, brs).
MS: 587(M+H)⁺.

Example 586

Synthesis of 2-{3-[4-((2-amino-5-fluorobenzoyl)amino)phenyl]propyl}-N,N-diethyl-N'-(2-naphthylsulfonyl)malonamide In the same manner as in Example 578, the title compound (210 mg) was obtained as a white solid using the compound (200 mg) obtained in Example 147.
¹H-NMR (400 MHz, CDCl₃) δ 1.06 (3H, t, J=7.1 Hz), 1.09 (3H, t, J=7.2 Hz), 1.43-1.54 (2H, m), 1.76-1.85 (2H, m), 2.40-2.58 (2H, m), 3.20 (2H, q, J=7.1 Hz), 3.23-3.48 (3H, m), 6.69 (1H, dd, J=8.9, 4.6 Hz), 6.97 (2H, d, J=8.4 Hz), 7.02 (1H, ddd, J=8.9, 7.9, 2.9 Hz), 7.19 (1H, dd, J=9.1, 2.9 Hz), 7.38 (2H, d, J=8.4 Hz), 7.59-7.72 (3H, m), 7.92 (1H, d, J=8.1 Hz), 7.95 (1H, d, J=8.8 Hz), 7.97-8.04 (2H, m), 8.66 (1H, s).
MS: 619(M+H)⁺.

Example 587

Synthesis of 2-{3-[4-((2-amino-6-fluorobenzoyl)amino)phenyl]propyl}-N,N-diethyl-N'-(2-naphthylsulfonyl)malonamide In the same manner as in Example 579, the title compound (130 mg) was obtained as a white solid using the compound (200 mg) obtained in Example 147.
¹H-NMR (400 MHz, CDCl₃) δ 1.05 (3H, t, J=7.1 Hz), 1.09 (3H, t, J=7.2 Hz), 1.40-1.53 (2H, m), 1.76-1.87 (2H, m), 2.40-2.56 (2H, m), 3.19 (2H, q, J=7.1 Hz), 3.23-3.50 (3H, m), 5.96 (2H, brs), 6.42 (1H, dd, J=13, 8.2 Hz), 6.49 (1H, d, J=8.2 Hz), 6.96 (2H, d, J=8.2 Hz), 7.14 (1H, td, J=8.2, 6.9 Hz), 7.39 (2H, d, J=8.2 Hz), 7.60-7.70 (2H, m), 7.91 (1H, d, J=8.0 Hz), 7.94 (1H, d, J=8.9 Hz), 7.97-8.05 (2H, m), 8.24 (1H, d, J=17 Hz), 8.66 (1H, s) 10.84 (1H, brs).

MS: 619(M+H)$^+$.

Example 588

Synthesis of 2-[4-(benzoylamino)benzyl]-N'-cyclohexylsulfonyl-N,N-diethylmalonamide (1) cyclohexanesulfonamide To a suspension of cyclohexanesulfonic acid sodium salt (2.5 g) in DMF (15 mL) was added thionyl chloride (1.96 mL) under ice-cooling, and the mixture was stirred at room temperature for 29 hr. The reaction mixture was added to a mixture of ice-cooled water (100 mL) and toluene (100 mL), and the mixture was extracted. The organic layer was concentrated under reduced pressure. THF (50 mL) was added to the residue, 28% aqueous ammonia (10 mL) was added dropwise to the solution under ice-cooling, and the mixture was stirred at room temperature for 17 hr. After concentration under reduced pressure, water (100 mL) and ethyl acetate (100 mL) were added to extract the residue. The organic layer was concentrated under reduced pressure to give the title compound (760 mg) as a white solid.

$^1$H-NMR (400 Mz, DMSO-d$_6$) δ1.04-1.37 (5H, m), 1.61-1.64 (1H, m), 1.77-1.80 (2H, m), 2.04-2.07 (2H, m), 2.70-2.77 (1H, m), 6.62 (2H, brs).

(2) N'-cyclohexylsulfonyl-N,N-diethyl-2-(4-nitrobenzyl)malonamide

To a suspension of the compound (1.37 g) obtained in Example 188 (2) in methylene chloride (50 mL) were added oxalyl chloride (800 μL) and DMF in catalytic amount under ice-cooling, and the mixture was stirred at room temperature for 1.5 hr. After concentration under reduced pressure, methylene chloride (8 mL) was added to the residue. Under ice-cooling, the solution was added dropwise to a mixture of the above-mentioned compound (760 mg) in THF (50 mL) and 4-dimethylaminopyridine (1.71 g). After stirring at room temperature for 17 hr, dilute hydrochloric acid (100 mL) was added, and the mixture was extracted with ethyl acetate (100 mL×2). The organic layer was concentrated under reduced pressure, and the residue was purified by silica gel chromatography to give the title compound (1.67 g) as a white solid.

$^1$H-NMR (300 Mz, DMSO-d$_6$) δ0.94-1.98 (17H, m), 3.17-3.33 (6H, m), 4.06 (1H, t, J=7.5 Hz), 7.54 (2H, d, J=9.0 Hz), 8.18 (2H, d, J=9.0 Hz), 11.76 (1H, brs).

(3) 2-[4-(benzoylamino)benzyl]-N'-cyclohexylsulfonyl-N,N-diethylmalonamide

To a mixed solution of the above-mentioned compound (1.67 g) in THF (50 mL) and triethylamine (1.06 mL) was added 10% palladium carbon (500 mg) under nitrogen atmosphere, and the mixture was stirred under hydrogen atmosphere at room temperature for 4 hr. Insoluble material was removed by filtration, benzoyl chloride (465 μL) was added to the filtrate under ice-cooling, and the mixture was stirred at room temperature for 15 hr. The reaction mixture was adjusted to pH=1-2 by the addition of dilute hydrochloric acid, and extracted with ethyl acetate (100 mL×2). The organic layer was concentrated under reduced pressure, and the residue was purified by silica gel chromatography to give the title compound (617 mg) as a white solid.

$^1$H-NMR (400 Mz, DMSO-d$_6$) δ0.97-1.35 (12H, m), 1.54-1.61 (2H, m), 1.67-1.81 (2H, m), 1.94-2.00 (1H, m), 2.96 (1H, dd, J=13.6, 6.4 Hz), 3.08 (1H, dd, J=13.6, 8.3 Hz), 3.19-3.28 (4H, m), 3.94-4.02 (1H, m), 7.20 (2H, d, J=8.5 Hz), 7.51-7.61 (3H, m), 7.69 (2H, d, J=8.5 Hz), 7.92 (1H, d, J=1.3 Hz), 7.94 (1H, s), 10.21 (1H, s), 11.64 (1H, s).

MS:514(M+H)$^+$.

The structures of the aforementioned Example compounds are shown in the following Tables 1 to 4.

TABLE 1

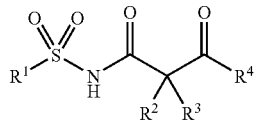

↑: same substituent as above

| Example | R$^1$ | R$^2$ | R$^3$ | R$^4$ |
|---|---|---|---|---|
| 1 | 2-naphthyl | benzyl | H | -N(Et)$_2$ |
| 2 | ↑ | ↑ | ↑ | -N(CH$_2$CO$_2$Et)(Et) |
| 3 | ↑ | ↑ | ↑ | -N(CH$_2$CO$_2$H)(Et) |

TABLE 1-continued
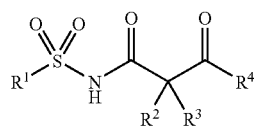
↑: same substituent as above
| Example | R¹ | R² | R³ | R⁴ |
|---|---|---|---|---|
| 4 | ↑ | ↑ | ↑ | 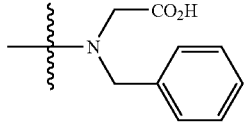 |
| 5 | ↑ | ↑ | ↑ | 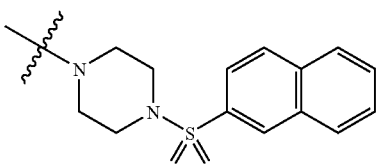 |
| 6 | ↑ | 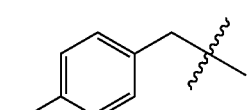 | ↑ | 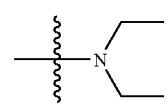 [SMILES: *N(CC)CC] |
| 7 | ↑ | 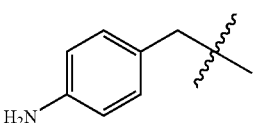 | ↑ | ↑ |
| 8 | ↑ | 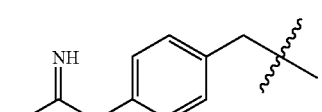 TFA | ↑ | ↑ |
TABLE 2
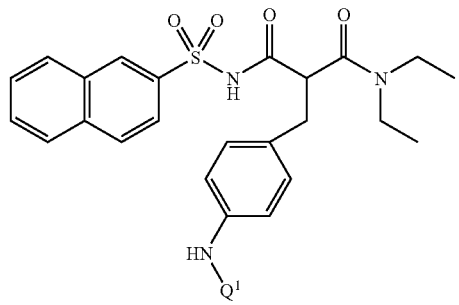
| Example | Q¹ |
|---|---|
| 9 | PhCO |
| 10 | Ac |
| 11 |  |
TABLE 2-continued
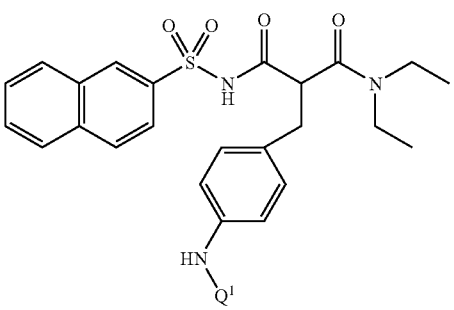
| Example | Q¹ |
|---|---|
| 12 | |

TABLE 2-continued

[Structure: naphthalene-SO2-NH-CH(C(=O)N(Et)2)-CH2-C6H4-NH-Q1]

| Example | Q¹ |
|---------|-----|
| 13 | propynoyl (HC≡C-C(=O)-C(CH3)-) |
| 14 | but-2-ynoyl (CH3-C≡C-C(=O)-C(CH3)-) |
| 15 | cyclopropyl-C(=O)-C(CH3)- |
| 16 | (1-methylcyclopropyl)-C(=O)-C(CH3)- |
| 17 | N-Boc-piperidin-4-yl-C(=O)-C(CH3)- |
| 18 | piperidin-4-yl-C(=O)-C(CH3)- · TFA |
| 19 | 2-fluorobenzoyl-C(CH3)- |
| 20 | 4-fluorobenzoyl-C(CH3)- |

TABLE 2-continued

[Structure: naphthalene-SO2-NH-CH(C(=O)N(Et)2)-CH2-C6H4-NH-Q1]

| Example | Q¹ |
|---------|-----|
| 21 | 3-fluorobenzoyl-C(CH3)- |
| 22 | 2,6-difluorobenzoyl-C(CH3)- |
| 23 | 2,4-difluorobenzoyl-C(CH3)- |
| 24 | 2-fluoro-4-methylbenzoyl-C(CH3)- |
| 25 | 2-methoxybenzoyl-C(CH3)- |
| 26 | 4-methoxybenzoyl-C(CH3)- |
| 27 | 3-methoxybenzoyl-C(CH3)- |

TABLE 2-continued

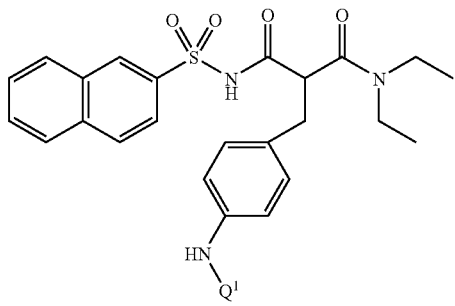

| Example | Q¹ |
|---|---|
| 28 | 2,6-dimethoxybenzoyl-C(CH₃)₂- |
| 29 | 2-hydroxybenzoyl-C(CH₃)₂- |
| 30 | 2-hydroxy-3-methylbenzoyl-C(CH₃)₂- |
| 31 | 2-methylbenzoyl-C(CH₃)₂- |
| 32 | 4-methylbenzoyl-C(CH₃)₂- |
| 33 | 3-methylbenzoyl-C(CH₃)₂- |
| 34 | 2,6-dimethylbenzoyl-C(CH₃)₂- |

TABLE 2-continued

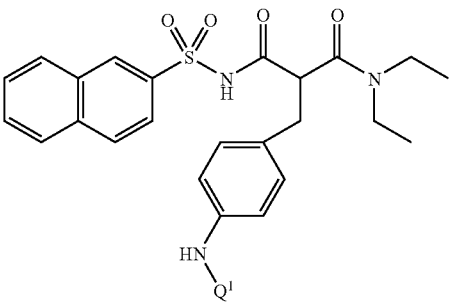

| Example | Q¹ |
|---|---|
| 35 | 4-chlorobenzoyl-C(CH₃)₂- |
| 36 | 2-chlorobenzoyl-C(CH₃)₂- |
| 37 | 3-chlorobenzoyl-C(CH₃)₂- |
| 38 | 3,4-dichlorobenzoyl-C(CH₃)₂- |
| 39 | 5-fluoro-2-methoxybenzoyl-C(CH₃)₂- |
| 40 | 2-trifluoromethylbenzoyl-C(CH₃)₂- |
| 41 | 3-cyanobenzoyl-C(CH₃)₂- |

TABLE 2-continued
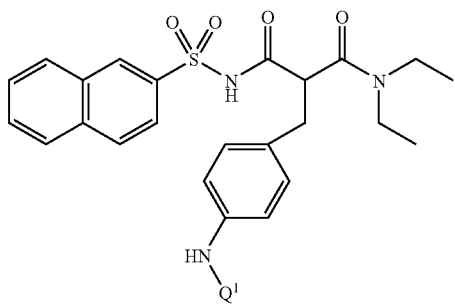
| Example | Q[1] |
|---|---|
| 42 | 2-nitrobenzoyl (2-NO2-C6H4-C(O)-) |
| 43 | 2-aminobenzoyl |
| 44 | 4-aminobenzoyl |
| 45 | 3-aminobenzoyl |
| 46 | 2-amino-3-methylbenzoyl |
| 47 | 2-amino-5-chlorobenzoyl |
| 48 | 2-amino-5-fluorobenzoyl |
TABLE 2-continued
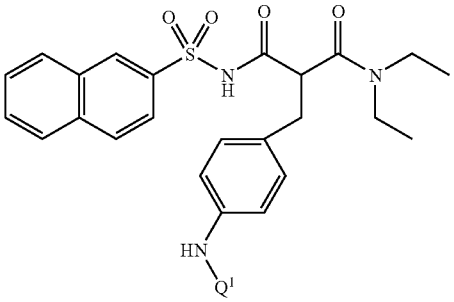
| Example | Q[1] |
|---|---|
| 49 | 2-amino-3-chlorobenzoyl |
| 50 | 2-amino-5-methylbenzoyl |
| 51 | 2-amino-4-chlorobenzoyl |
| 52 | 2-amino-4-fluorobenzoyl |
| 53 | 2-amino-3,5-dichlorobenzoyl |
| 54 | 2-amino-4,5-difluorobenzoyl |
| 55 | 2-amino-6-fluorobenzoyl |

TABLE 2-continued
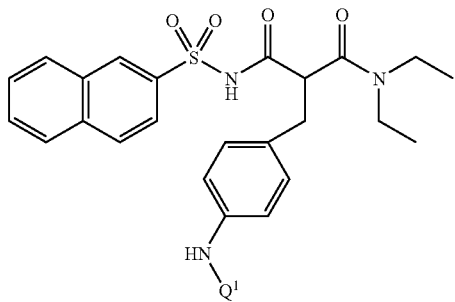
| Example | Q¹ |
|---|---|
| 56 | |
| 57 | |
| 58 | |
| 59 | |
| 60 | |
| 61 | |
| 62 | |
| 63 | |
TABLE 2-continued
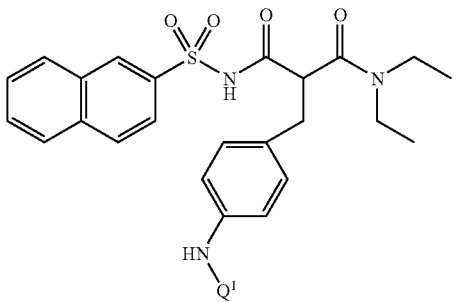
| Example | Q¹ |
|---|---|
| 64 | |
| 65 | |
| 66 | |
| 67 | |
| 68 | |
| 69 | |
| 70 | |
| 71 | |

TABLE 2-continued

| Example | Q¹ |
|---|---|
| 72 | 5-nitrofuran-2-yl C(=O)C(CH₃)- |
| 73 | 5-bromofuran-2-yl C(=O)C(CH₃)- |
| 74 | 4,5-dimethylfuran-2-yl C(=O)C(CH₃)- |
| 75 | thiophen-2-yl C(=O)C(CH₃)- |
| 76 | 5-methylthiophen-2-yl C(=O)C(CH₃)- |
| 77 | 5-chlorothiophen-2-yl C(=O)C(CH₃)- |
| 78 | 2,4-dimethyloxazol-5-yl C(=O)C(CH₃)- |
| 79 | 2,4-dimethylthiazol-5-yl C(=O)C(CH₃)- |
| 80 | naphthalen-1-yl C(=O)C(CH₃)- |
| 81 | quinolin-8-yl C(=O)C(CH₃)- |
| 82 | 2-methyl-1H-benzimidazol-5-yl C(=O)C(CH₃)- |
| 83 | 1H-benzimidazol-2-yl C(=O)C(CH₃)- |
| 84 | CH₃SO₂C(CH₃)- |
| 85 | PhSO₂C(CH₃)- |
| 86 | 4-methylphenyl-SO₂C(CH₃)- |
| 87 | PhOCO |
| 88 | PhNHCO |

TABLE 2-continued
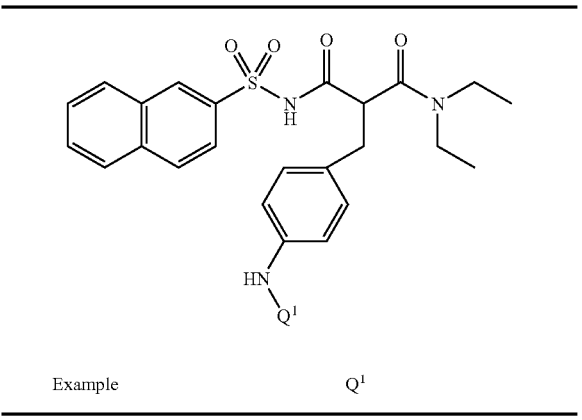
| Example | Q¹ |
|---|---|
| 89 | |
| 90 | |
TABLE 3
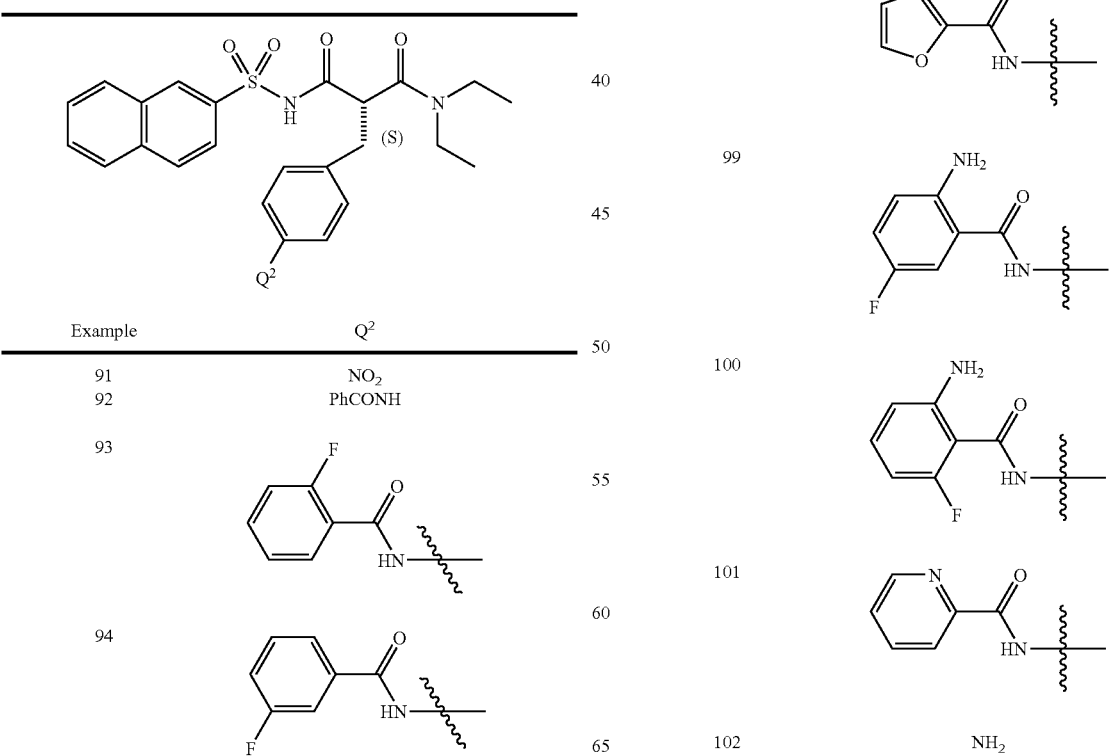
| Example | Q² |
|---|---|
| 91 | NO₂ |
| 92 | PhCONH |
| 93 | |
| 94 | |
TABLE 3-continued
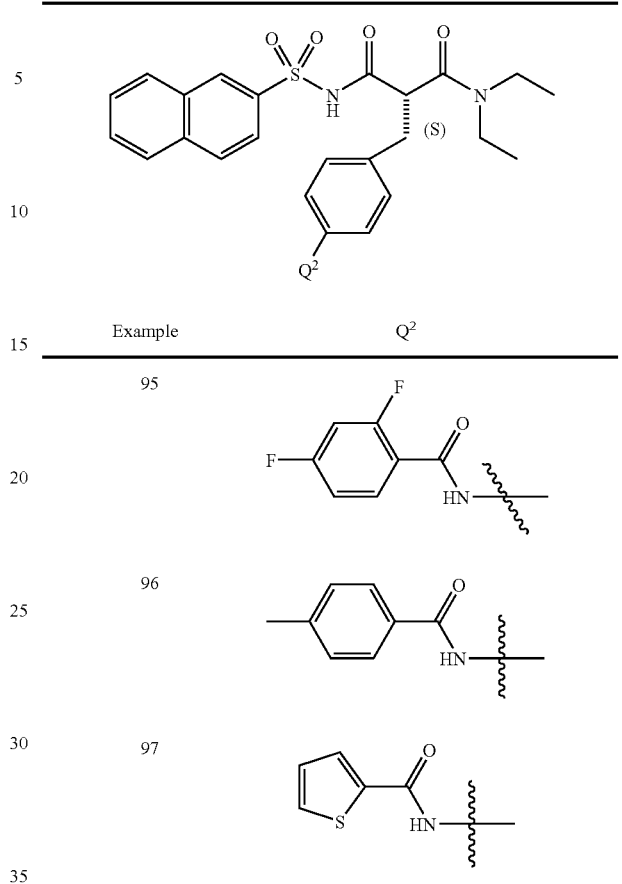
| Example | Q² |
|---|---|
| 95 | |
| 96 | |
| 97 | |
| 98 | |
| 99 | |
| 100 | |
| 101 | |
| 102 | NH₂ |

TABLE 3-continued
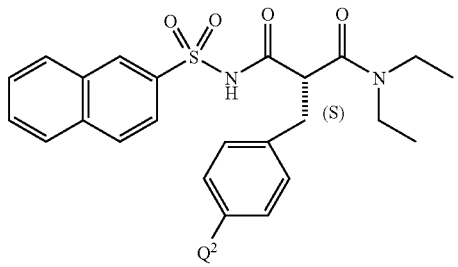
| Example | Q² |
|---|---|
| 103 | 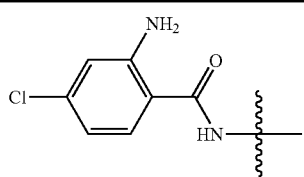 |
| 104 | 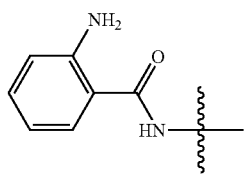 [SMILES: *NC(=O)c1ccccc1N] |
| 105 | 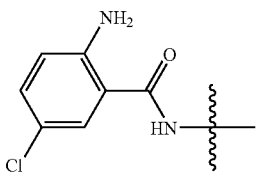 [SMILES: *NC(=O)c1cc(Cl)ccc1N] |
TABLE 3-continued
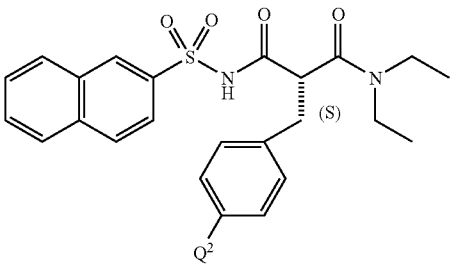
| Example | Q² |
|---|---|
| 106 | 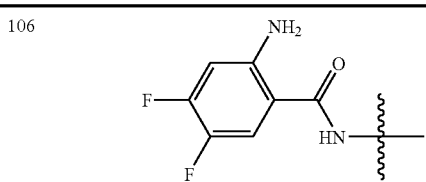 |
| 107 | 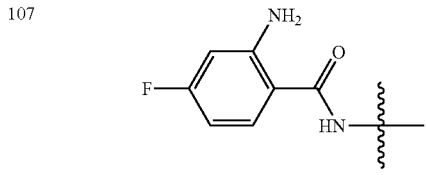 |
| 108 | 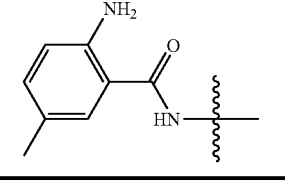 |

TABLE 4

| Example | R¹ | R² | R³ | R⁴ |
|---|---|---|---|---|
| 109 | 2-naphthyl | 4-(dimethylamino)benzyl | H | N,N-diethylaminomethyl |
| 110 | ↑ | 4-chlorobenzyl | ↑ | ↑ |
| 111 | ↑ | 4-cyanobenzyl | ↑ | ↑ |
| 112 | ↑ | 4-methoxybenzyl | ↑ | ↑ |
| 113 | ↑ | (pyridin-4-yl)methyl | ↑ | ↑ |
| 114 | ↑ | 3-nitrobenzyl | ↑ | ↑ |

↑: same substituent as above

TABLE 4-continued

| Example | R¹ | R² | R³ | R⁴ |
|---|---|---|---|---|
| 115 | ↑ | 3-H₂N-benzyl | ↑ | ↑ |
| 116 | ↑ | 2-NO₂-benzyl | ↑ | ↑ |
| 117 | ↑ | 4-F₃CO-benzyl | ↑ | ↑ |
| 118 | ↑ | 4-F-benzyl | ↑ | ↑ |
| 119 | ↑ | 3,4-diMeO-benzyl | ↑ | ↑ |
| 120 | ↑ | 4-MeO₂C-benzyl | ↑ | ↑ |

↑: same substituent as above

TABLE 4-continued

[Structure: R¹-S(O)₂-NH-C(O)-C(R²)(R³)-C(O)-R⁴]

↑: same substituent as above

| Example | R¹ | R² | R³ | R⁴ |
|---|---|---|---|---|
| 121 | ↑ | 4-(HO₂C)-C₆H₄-CH₂- | ↑ | ↑ |
| 122 | ↑ | (6-MeO-pyridin-3-yl)-CH₂- | ↑ | ↑ |
| 123 | ↑ | naphthalen-2-yl-CH₂- | ↑ | ↑ |
| 124 | ↑ | 4-phenyl-C₆H₄-CH₂- (biphenyl-4-ylmethyl) | ↑ | ↑ |
| 125 | ↑ | 4-(imidazol-1-yl)-C₆H₄-CH₂- · HCl | ↑ | ↑ |

TABLE 4-continued
| Example | R¹ | R² | R³ | R⁴ |
|---|---|---|---|---|
| 126 | ↑ | 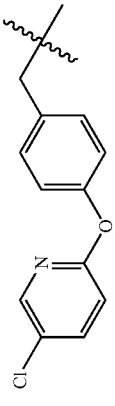 | ↑ | ↑ |
| 127 | ↑ | 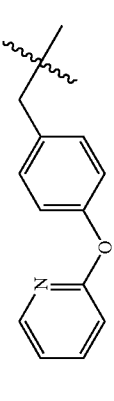 | ↑ | ↑ |
| 128 | ↑ | 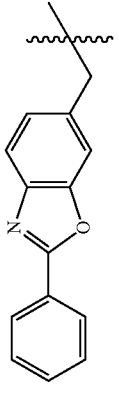 | ↑ | ↑ |
| 129 | ↑ | 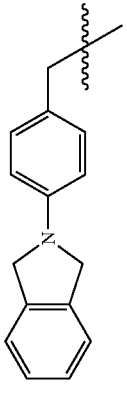 | ↑ | ↑ |
| 130 | ↑ | 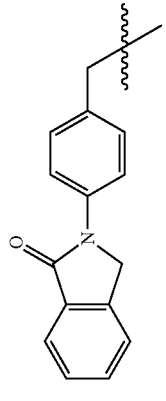 HCl | ↑ | ↑ |
↑: same substituent as above TABLE 4-continued Structure: R¹–S(O)₂–NH–C(O)–C(R²)(R³)–C(O)–R⁴

↑: same substituent as above

| Example | R¹ | R² | R³ | R⁴ |
|---|---|---|---|---|
| 131 | ↑ | benzoxazol-2-yl-NH-C₆H₄-CH₂- | ↑ | ↑ |
| 132 | ↑ | 4-(phenylethynyl)benzyl | ↑ | ↑ |
| 133 | ↑ | 4-styrylbenzyl | ↑ | ↑ |
| 134 | ↑ | 4-phenethylbenzyl | ↑ | ↑ |
| 135 | ↑ | 4-(3-phenyl-2,4-dioxoimidazolidin-1-yl)benzyl | ↑ | ↑ |

TABLE 4-continued
| Example | R¹ | R² | R³ | R⁴ |
|---|---|---|---|---|
| 136 | ↑ | 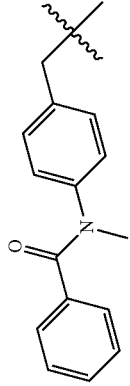 | ↑ | ↑ |
| 137 | ↑ | 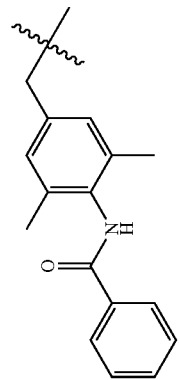 | ↑ | ↑ |
| 138 | ↑ | 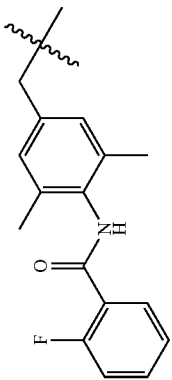 | ↑ | ↑ |
| 139 | ↑ | 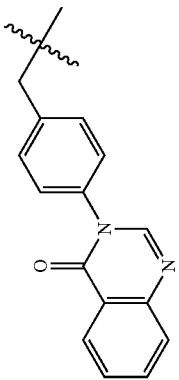 | ↑ | ↑ |
↑: same substituent as above TABLE 4-continued
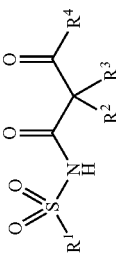
| Example | R¹ | R² | R³ | R⁴ |
|---|---|---|---|---|
| 140 | ↑ | [quinazolinone-benzyl structure] | ↑ | ↑ |
| 141 | ↑ | [pyrido-pyrimidinone-benzyl structure] | ↑ | ↑ |
| 142 | ↑ | [pyrido-pyrimidinone-benzyl structure] | ↑ | ↑ |
| 143 | ↑ | [isoquinoline-NH-benzyl structure] | ↑ | ↑ |
↑: same substituent as above TABLE 4-continued
| Example | R¹ | R² | R³ | R⁴ |
|---|---|---|---|---|
| 144 | ↑ | 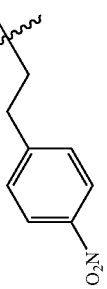 | ↑ | ↑ |
| 145 | ↑ | 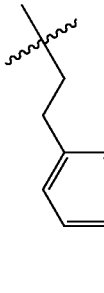 | ↑ | ↑ |
| 146 | ↑ | 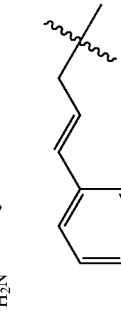 | ↑ | ↑ |
| 147 | ↑ | 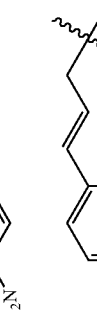 | ↑ | ↑ |
| 148 | ↑ | 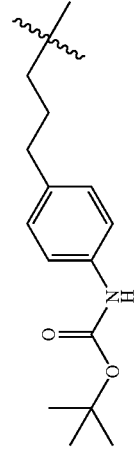 | ↑ | ↑ |
| 149 | ↑ | 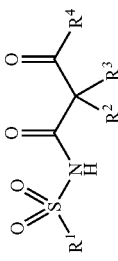 | ↑ | ↑ |
↑: same substituent as above TABLE 4-continued ↑: same substituent as above

| Example | R¹ | R² | R³ | R⁴ |
|---|---|---|---|---|
| 150 | ↑ | 4-acetamidophenethyl | ↑ | ↑ |
| 151 | ↑ | pentyl | ↑ | ↑ |
| 152 | ↑ | propargyl | ↑ | ↑ |
| 153 | ↑ | cyanoethyl | ↑ | ↑ |
| 154 | ↑ | (piperidin-4-yl)methyl TFA | ↑ | ↑ |
| 155 | ↑ | (1-benzoylpiperidin-4-yl)methyl | ↑ | ↑ |

TABLE 4-continued

↑: same substituent as above

| Example | R¹ | R² | R³ | R⁴ |
|---|---|---|---|---|
| 156 | ↑ | 4-piperidinylmethyl with N-phenylsulfonyl | ↑ | ↑ |
| 157 | ↑ | 4-piperidinylmethyl with N-phenoxycarbonyl | ↑ | ↑ |
| 158 | ↑ | 4-piperidinylmethyl with N-phenylacetyl | ↑ | ↑ |
| 159 | ↑ | 4-piperidinylmethyl with N-phenylcarbamoyl | ↑ | ↑ |

TABLE 4-continued

| Example | R¹ | R² | R³ | R⁴ |
|---|---|---|---|---|
| 160 | ↑ | [1-naphthoyl-piperidin-4-yl-methyl] | ↑ | ↑ |
| 161 | ↑ | [1-benzyl-piperidin-4-yl-methyl] HCl | ↑ | ↑ |
| 162 | ↑ | [1-(benzylsulfonyl)-piperidin-4-yl-methyl] | ↑ | ↑ |
| 163 | ↑ | [1-(benzothiazol-2-yl)-piperidin-4-yl-methyl] | ↑ | ↑ |
| 164 | ↑ | [4-(tert-butoxycarbonylmethyl)-cyclohexyl-methyl] | ↑ | ↑ |

↑: same substituent as above

TABLE 4-continued

| Example | R¹ | R² | R³ | R⁴ |
|---|---|---|---|---|
| 165 | ↑ | [cyclohexyl-CH₂- with H₂N-] | ↑ | ↑ |
| 166 | ↑ | [cyclohexyl-CH₂- with NHC(O)phenyl] TFA | ↑ | ↑ |
| 167 | ↑ | [cyclohexyl-CH₂- with NHC(O)NH-phenyl] | ↑ | ↑ |
| 168 | ↑ | [cyclohexyl-CH₂- with NHC(O)C(CH₃)₃] | ↑ | ↑ |
| 169 | ↑ | [cyclohexyl-CH₂- with NHC(O)O-tBu (Boc)] | ↑ | ↑ |

↑: same substituent as above

TABLE 4-continued
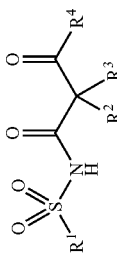
↑: same substituent as above
| Example | R¹ | R² | R³ | R⁴ |
|---|---|---|---|---|
| 170 | ↑ | H₂N-cyclohexyl-CH₂- TFA | ↑ | ↑ |
| 171 | ↑ | PhC(O)NH-cyclohexyl-CH₂- | ↑ | ↑ |
| 172 | ↑ | 2-MeO-C₆H₄-C(O)NH-cyclohexyl-CH₂- | ↑ | ↑ |
| 173 | ↑ | benzoxazol-2-yl-NH-cyclohexyl-CH₂- | ↑ | ↑ |

TABLE 4-continued

↑: same substituent as above

| Example | R¹ | R² | R³ | R⁴ |
|---|---|---|---|---|
| 174 | ↑ | 4-(1-benzoylpiperidin-4-yl)ethyl | ↑ | ↑ |
| 175 | ↑ | 4-(1-phenylcarbamoylpiperidin-4-yl)ethyl | ↑ | ↑ |
| 176 | ↑ | 4-(1-nicotinoylpiperidin-4-yl)ethyl | ↑ | ↑ |
| 177 | 4-isobutylphenyl | benzyl · HCl | ↑ | ↑ |

TABLE 4-continued

| Example | R¹ | R² | R³ | R⁴ |
|---|---|---|---|---|
| 178 | 4-methylphenyl | 4-nitrobenzyl | ↑ | ↑ |
| 179 | ↑ | 4-aminobenzyl | ↑ | ↑ |
| 180 | 4-chlorophenyl | 4-nitrobenzyl | ↑ | ↑ |
| 181 | ↑ | 4-aminobenzyl | ↑ | ↑ |
| 182 | 4-methoxyphenyl | 4-aminobenzyl | ↑ | ↑ |
| 183 | ↑ | 4-aminobenzyl | ↑ | ↑ |

↑: same substituent as above

TABLE 4-continued

| Example | R¹ | R² | R³ | R⁴ |
|---|---|---|---|---|
| 184 | 1-naphthyl | 4-nitrobenzyl | ↑ | ↑ |
| 185 | ↑ | 4-aminobenzyl | ↑ | ↑ |
| 186 | 6-methoxy-2-naphthyl | 4-nitrobenzyl | ↑ | ↑ |
| 187 | ↑ | 4-aminobenzyl | ↑ | ↑ |
| 188 | 4-biphenyl | 4-nitrobenzyl | ↑ | ↑ |

↑: same substituent as above

TABLE 4-continued
| Example | R¹ | R² | R³ | R⁴ |
|---------|----|----|----|----|
| 189 | 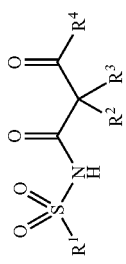 | 4-H₂N-C₆H₄-CH₂- | ↑ | ↑ |
| 190 | ↑ | 4-O₂N-C₆H₄-CH₂- | ↑ | ↑ |
| 191 | (4-tert-butylphenyl) | 4-H₂N-C₆H₄-CH₂- | ↑ | ↑ |
| 192 | ↑ | 4-O₂N-C₆H₄-CH₂- | ↑ | ↑ |
| 193 | ↑ | 4-H₂N-C₆H₄-CH₂- | ↑ | ↑ |
↑: same substituent as above TABLE 4-continued ↑: same substituent as above

| Example | R¹ | R² | R³ | R⁴ |
|---|---|---|---|---|
| 194 | thiophene | 4-NO₂-benzyl | ↑ | ↑ |
| 195 | ↑ | 4-NH₂-benzyl | ↑ | ↑ |
| 196 | 4-CF₃-phenyl | 4-NO₂-benzyl | ↑ | ↑ |
| 197 | ↑ | 4-NH₂-benzyl | ↑ | ↑ |
| 198 | 5-(dimethylamino)naphthalen-1-yl | 4-NO₂-benzyl | ↑ | ↑ |

TABLE 4-continued

| Example | R¹ | R² | R³ | R⁴ |
|---------|----|----|----|----|
| 199 | styryl | 4-aminobenzyl | ↑ | ↑ |
| 200 | ↑ | 4-nitrobenzyl | ↑ | ↑ |
| 201 | ↑ | 4-aminobenzyl | ↑ | ↑ |
| 202 | 4-tert-butylphenyl | 4-(benzamido)benzyl | ↑ | ↑ |
| 203 | styryl | ↑ | ↑ | ↑ |
| 204 | | 3-nitrobenzyl | ↑ | ↑ |

↑: same substituent as above

TABLE 4-continued

↑: same substituent as above

| Example | R¹ | R² | R³ | R⁴ |
|---|---|---|---|---|
| 205 | ↑ | 3-aminobenzyl · HCl | ↑ | ↑ |
| 206 | ↑ | 4-methoxybenzyl | ↑ | ↑ |
| 207 | ↑ | 4-trifluoromethoxybenzyl | ↑ | ↑ |
| 208 | ↑ | 4-fluorobenzyl | ↑ | ↑ |
| 209 | ↑ | 3,4-dimethoxybenzyl | ↑ | ↑ |
| 210 | ↑ | 4-(methoxycarbonyl)benzyl | ↑ | ↑ |

TABLE 4-continued

↑: same substituent as above

| Example | R¹ | R² | R³ | R⁴ |
|---|---|---|---|---|
| 211 | ↑ | 4-carboxyphenylmethyl | ↑ | ↑ |
| 212 | ↑ | (6-methoxypyridin-3-yl)methyl | ↑ | ↑ |
| 213 | ↑ | 4-(5-chloropyridin-2-yloxy)phenylmethyl | ↑ | ↑ |
| 214 | ↑ | cyclopropylmethyl | ↑ | ↑ |
| 215 | ↑ | propargyl | ↑ | ↑ |
| 216 | ↑ | 3-cyanopropyl | ↑ | ↑ |

TABLE 4-continued

| Example | R¹ | R² | R³ | R⁴ |
|---|---|---|---|---|
| 217 | ↑ | 4-O₂N-C₆H₄-CH₂CH₂- (wavy) | ↑ | ↑ |
| 218 | ↑ | 4-H₂N-C₆H₄-CH₂CH₂- (wavy) | ↑ | ↑ |
| 219 | PhCH₂CH₂- (wavy) | 4-H₂N-C₆H₄-CH₂- (wavy) | ↑ | ↑ |
| 220 | ↑ | 4-(PhC(O)NH)-C₆H₄-CH₂- (wavy) | ↑ | ↑ |
| 221 | ↑ | 4-MeO-C₆H₄-CH₂- (wavy) | ↑ | ↑ |

↑: same substituent as above

TABLE 4-continued

↑: same substituent as above

| Example | R¹ | R² | R³ | R⁴ |
|---|---|---|---|---|
| 222 | (4-phenoxyphenyl) | (4-aminophenyl ethyl) | ↑ | ↑ |
| 223 | ↑ | (4-nitrobenzyl) | ↑ | ↑ |
| 224 | (5-isobutylthiophen-2-yl) | (4-aminobenzyl) | ↑ | ↑ |
| 225 | ↑ | (4-nitrobenzyl) | ↑ | ↑ |
| 226 | ↑ | (4-aminobenzyl) | ↑ | ↑ |

TABLE 4-continued

| Example | R¹ | R² | R³ | R⁴ |
|---|---|---|---|---|
| 227 | 2-naphthyl | 4-cyanobenzyl | ↑ | cyclohexyl-NH- |
| 228 | ↑ | ↑ | ↑ | 4-(4-nitrophenyl)piperazin-1-yl |
| 229 | ↑ | ↑ | ↑ | N-ethyl-N-phenylamino |
| 230 | ↑ | ↑ | ↑ | 4-(5-cyanopyridin-2-yl)piperazin-1-yl |
| 231 | ↑ | ↑ | ↑ | 4-(pyridin-4-yl)piperazin-1-yl |
| 232 | ↑ | 4-methoxybenzyl | ↑ | N-ethyl-N-phenylamino |

↑: same substituent as above

TABLE 4-continued
| Example | R¹ | R² | R³ | R⁴ |
|---|---|---|---|---|
| 233 | ↑ | ↑ | ↑ | 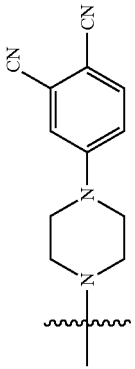 |
| 234 | ↑ | ↑ | ↑ | 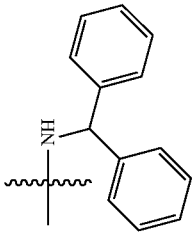 |
| 235 | ↑ | ↑ | ↑ | 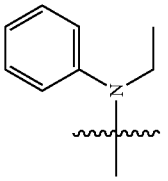 |
| 236 | ↑ | 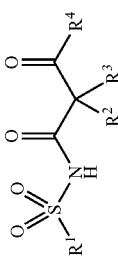 | ↑ | 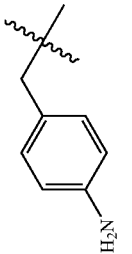 |
| 237 | ↑ | | ↑ | 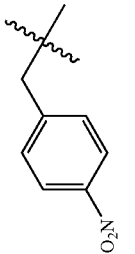 |
↑: same substituent as above TABLE 4-continued
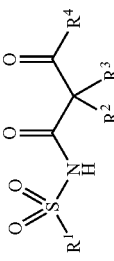
↑: same substituent as above
| Example | R¹ | R² | R³ | R⁴ |
|---|---|---|---|---|
| 238 | ↑ | (4-benzamidobenzyl) | ↑ | (N-ethyl-N-phenylamino) |
| 239 | ↑ | ↑ | ↑ | (N,N-dimethylamino) |
| 240 | ↑ | ↑ | ↑ | (N-ethyl-N-methylamino) |
| 241 | ↑ | ↑ | ↑ | (N,N-dipropylamino) |
| 242 | ↑ | ↑ | ↑ | |

TABLE 4-continued

↑: same substituent as above

| Example | R¹ | R² | R³ | R⁴ |
|---|---|---|---|---|
| 243 | ↑ | ↑ | ↑ | N(pentyl)(pentyl) |
| 244 | ↑ | ↑ | ↑ | pyrrolidin-1-yl |
| 245 | ↑ | ↑ | ↑ | piperidin-1-yl |
| 246 | ↑ | ↑ | ↑ | morpholin-4-yl |
| 247 | ↑ | ↑ | ↑ | 4-methylpiperazin-1-yl |
| 248 | ↑ | ↑ | ↑ | N-ethyl-N-(4-fluorophenyl)amino |

TABLE 4-continued

↑: same substituent as above

| Example | R¹ | R² | R³ | R⁴ |
|---|---|---|---|---|
| 249 | | | ↑ | 4-fluorophenyl(isopropyl)amino |
| 250 | ↑ | ↑ | ↑ | 3-(trifluoromethyl)phenyl(isopropyl)amino |
| 251 | ↑ | ↑ | ↑ | pyridin-3-yl(isopropyl)amino |
| 252 | ↑ | 4-nitrobenzyl | ↑ | morpholin-4-yl |
| 253 | ↑ | 4-aminobenzyl | ↑ | morpholin-4-yl |

TABLE 4-continued
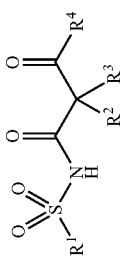
↑: same substituent as above
| Example | R¹ | R² | R³ | R⁴ |
|---|---|---|---|---|
| 254 | ↑ | 4-O₂N-benzyl | ↑ | N-methylpiperazinyl |
| 255 | ↑ | 4-H₂N-benzyl | ↑ | N-methylpiperazinyl |
| 256 | ↑ | 4-O₂N-benzyl | ↑ | N-methyl-N-(2-hydroxyethyl)amino |
| 257 | ↑ | 4-H₂N-benzyl | ↑ | N-methyl-N-(2-hydroxyethyl)amino |
| 258 | ↑ | 4-O₂N-benzyl | ↑ | benzhydrylamino |

TABLE 4-continued structure: R¹SO₂-NH-C(=O)-C(R²)(R³)-C(=O)-R⁴

↑: same substituent as above

| Example | R¹ | R² | R³ | R⁴ |
|---|---|---|---|---|
| 259 | ↑ | 4-(H₂N)-benzyl | ↑ | -C(CH₃)₂-NH-CH(Ph)₂ |
| 260 | ↑ | 4-(O₂N)-benzyl | ↑ | -C(CH₃)₂-NH-Et |
| 261 | ↑ | 4-(H₂N)-benzyl | ↑ | -C(CH₃)₂-NH-Et |
| 262 | ↑ | 4-(O₂N)-benzyl | ↑ | -C(CH₃)₂- (N-spiropiperidinyl-indanone) |

TABLE 4-continued

↑: same substituent as above

| Example | R¹ | R² | R³ | R⁴ |
|---|---|---|---|---|
| 263 | ↑ | 4-H₂N-benzyl | ↑ | spiro[indanone-piperidine] N-yl |
| 264 | ↑ | 4-H₂N-benzyl | ↑ | dipentylamino |
| 265 | styryl | 4-MeO-benzyl | ↑ | N-ethyl-N-phenylamino |
| 266 | phenethyl | 4-MeO-benzyl | ↑ | ↑ |
| 267 | 2-naphthyl | 4-Cl-benzyl | ↑ | ↑ |

TABLE 4-continued

↑: same substituent as above

| Example | R¹ | R² | R³ | R⁴ |
|---|---|---|---|---|
| 268 | ↑ | 4-pyridylmethyl | ↑ | ↑ |
| 269 | ↑ | 4-(trifluoromethoxy)benzyl | ↑ | ↑ |
| 270 | styryl | 4-(trifluoromethoxy)benzyl | ↑ | ↑ |
| 271 | 2-naphthyl | 3,4-dimethoxybenzyl | ↑ | ↑ |
| 272 | styryl | 3,4-dimethoxybenzyl | ↑ | ↑ |
| 273 | 2-naphthyl | benzo[1,3]dioxol-5-ylmethyl | ↑ | ↑ |

TABLE 4-continued
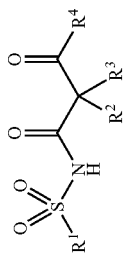
↑: same substituent as above
| Example | R¹ | R² | R³ | R⁴ |
|---|---|---|---|---|
| 274 | styryl | benzodioxole-CH2- | ↑ | ↑ |
| 275 | naphthyl | 4-(methoxycarbonyl)benzyl | ↑ | ↑ |
| 276 | ↑ | 4-carboxybenzyl | ↑ | ↑ |
| 277 | styryl | 4-(methoxycarbonyl)benzyl | ↑ | ↑ |
| 278 | ↑ | 4-carboxybenzyl | ↑ | ↑ |
| 279 | naphthyl | (6-methoxypyridin-3-yl)methyl | ↑ | ↑ |

TABLE 4-continued
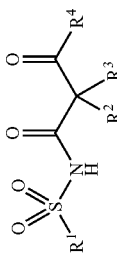
↑: same substituent as above
| Example | R¹ | R² | R³ | R⁴ |
|---|---|---|---|---|
| 280 | styryl | 4-(benzyloxy)benzyl | ↑ | ↑ |
| 281 | ↑ | ↑ | ↑ | ↑ |
| 282 | ↑ | 3-(benzyloxy)benzyl | ↑ | ↑ |
| 283 | ↑ | 4-methoxy-3-nitrobenzyl | ↑ | ↑ |
| 284 | naphthalen-2-yl | ↑ | ↑ | ↑ |

TABLE 4-continued

| Example | R¹ | R² | R³ | R⁴ |
|---|---|---|---|---|
| 285 | styryl | 4-MeO-3-H₂N-benzyl | ↑ | ↑ |
| 286 | naphthalen-2-yl | 3-MeO-4-O₂N-benzyl | ↑ | ↑ |
| 287 | ↑ | ↑ | ↑ | ↑ |
| 288 | styryl | 3-MeO-4-H₂N-benzyl | ↑ | ↑ |
| 289 | ↑ | 2-NO₂-3-MeO-benzyl | ↑ | ↑ |
| 290 | ↑ | 3-O₂N-4-methyl-benzyl | ↑ | ↑ |

↑: same substituent as above

TABLE 4-continued

| Example | R¹ | R² | R³ | R⁴ |
|---|---|---|---|---|
| 291 | ↑ | 3-amino-4-methylbenzyl | ↑ | ↑ |
| 292 | ↑ | 2-methyl-5-(benzamido)benzyl | ↑ | ↑ |
| 293 | naphthalen-2-yl | 4-methyl-3-nitrobenzyl | ↑ | ↑ |
| 294 | ↑ | 3-amino-4-methylbenzyl | ↑ | ↑ |
| 295 | ↑ | 2-methyl-5-(benzamido)benzyl | ↑ | ↑ |

↑: same substituent as above

TABLE 4-continued

![structure: R¹-S(O)₂-NH-C(=O)-C(R²)(R³)-C(=O)-R⁴]

↑: same substituent as above

| Example | R¹ | R² | R³ | R⁴ |
|---|---|---|---|---|
| 296 | styryl (PhCH=CH–) | 4-fluorobenzyl | ↑ | ↑ |
| 297 | ↑ | ↑ | ↑ | ↑ |
| 298 | ↑ | 3-(4-fluorophenoxy)benzyl | ↑ | ↑ |
| 299 | ↑ | 3-(imidazol-1-ylmethyl)benzyl | ↑ | ↑ |
| 300 | ↑ | 3-((2-methylbenzimidazol-1-yl)methyl)benzyl | ↑ | ↑ |
| 301 | ↑ | 4-nitrophenethyl | ↑ | ↑ |

TABLE 4-continued

| Example | R¹ | R² | R³ | R⁴ |
|---|---|---|---|---|
| 302 | phenethyl | 4-aminophenethyl | ↑ | ↑ |
| 303 | naphthalen-2-yl | 4-aminophenethyl | ↑ | ↑ |
| 304 | ↑ | 4-nitrophenethyl | ↑ | ↑ |
| 305 | styryl | 4-aminophenethyl | ↑ | ↑ |
| 306 | styryl | but-3-yn-1-yl | ↑ | ↑ |
| 307 | naphthalen-2-yl | ↑ | ↑ | ↑ |

↑: same substituent as above

TABLE 4-continued

| Example | R¹ | R² | R³ | R⁴ |
|---|---|---|---|---|
| 308 | cinnamyl | 4-fluorobenzyl | methyl | N-ethyl-4-fluoroanilino |
| 309 | ↑ | ↑ | ↑ | N-isopropyl-4-fluoroanilino |
| 310 | ↑ | 3-fluorobenzyl | ↑ | ↑ |
| 311 | 2-naphthylmethyl | ↑ | ↑ | ↑ |
| 312 | cinnamyl | 4-cyanobenzyl | ↑ | ↑ |

↑: same substituent as above

TABLE 4-continued

↑: same substituent as above

| Example | R¹ | R² | R³ | R⁴ |
|---|---|---|---|---|
| 313 | naphthalen-2-yl | | | |
| 314 | styryl | | | |
| 315 | naphthalen-2-yl | 3-cyanobenzyl | | |
| 316 | ↑ | 4-chlorobenzyl | | |
| 317 | ↑ | ↑ | ↑ | N-isopropyl-N-(pyridin-3-yl)amino · HCl |

TABLE 4-continued

↑: same substituent as above

| Example | R¹ | R² | R³ | R⁴ |
|---|---|---|---|---|
| 318 | styryl | 3-chlorobenzyl | | N(iPr)(4-fluorophenyl) |
| 319 | 2-naphthyl | ↑ | ↑ | ↑ |
| 320 | styryl | 3-(trifluoromethyl)benzyl | ↑ | ↑ |
| 321 | 2-naphthyl | ↑ | ↑ | ↑ |
| 322 | styryl | 4-fluorobenzyl | ↑ | N(iPr)(pyridin-3-yl) |

TABLE 4-continued
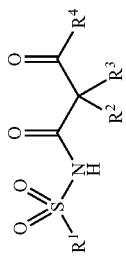
↑: same substituent as above
| Example | R¹ | R² | R³ | R⁴ |
|---|---|---|---|---|
| 323 | ↑ | ↑ | ↑ | 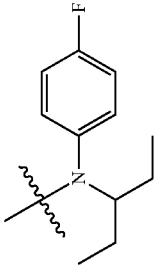 |
| 324 | ↑ | ↑ | ↑ | 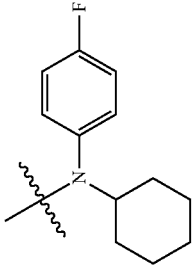 |
| 325 | ↑ | ↑ | ↑ | 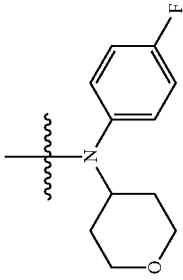 |
| 326 | ↑ | ↑ | ↑ | 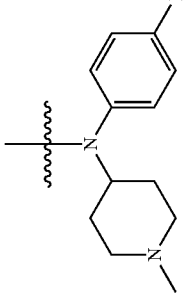 |

TABLE 4-continued
| Example | | R¹ | R² | R³ | R⁴ |
|---|---|---|---|---|---|
| 327 | | ↑ | ↑ | ↑ | 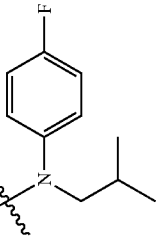 |
| 328 | | ↑ | ↑ | ↑ | 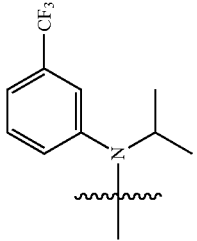 |
| 329 | | ↑ | ↑ | ↑ | 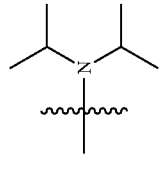 |
| 330 | | ↑ | ↑ | ↑ | 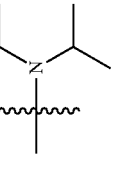 |
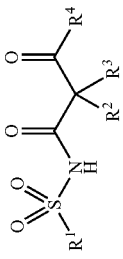
↑: same substituent as above TABLE 4-continued

| Example | R¹ | R² | R³ | R⁴ |
|---|---|---|---|---|
| 331 | biphenyl-isobutyl | 4-nitrobenzyl | ↑ | N-ethyl-N-phenyl |
| 332 | ↑ | 4-aminobenzyl | ↑ | ↑ |
| 333 | biphenyl | 4-nitrobenzyl | ↑ | ↑ |
| 334 | ↑ | 4-aminobenzyl | ↑ | ↑ |
| 335 | styryl | 4-nitrobenzyl | ↑ | ↑ |

↑: same substituent as above

TABLE 4-continued

Structure: R¹-S(=O)₂-NH-C(=O)-C(R²)(R³)-C(=O)-R⁴

↑: same substituent as above

| Example | R¹ | R² | R³ | R⁴ |
|---|---|---|---|---|
| 336 | ↑ | 4-aminobenzyl | ↑ | ↑ |
| 337 | ↑ | 4-(benzoylamino)benzyl | ↑ | ↑ |
| 338 | 2-phenylethyl | 4-aminobenzyl | ↑ | ↑ |
| 339 | benzyl | 4-nitrobenzyl | ↑ | ↑ |
| 340 | ↑ | 4-aminobenzyl | ↑ | ↑ |
| 341 | n-propyl | 3-nitrobenzyl | ↑ | ↑ |

TABLE 4-continued
| Example | R¹ | R² | R³ | R⁴ |
|---|---|---|---|---|
| 342 | ↑ | 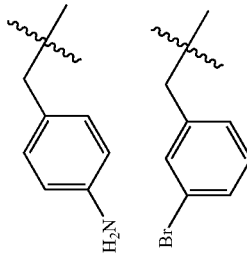 | ↑ | ↑ |
| 343 | 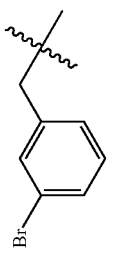 | 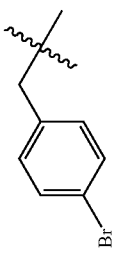 | ↑ | ↑ |
| 344 | 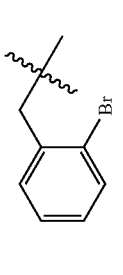 | ↑ | ↑ | ↑ |
| 345 | ↑ | 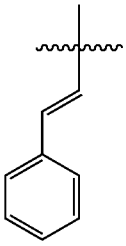 | ↑ | ↑ |
| 346 | 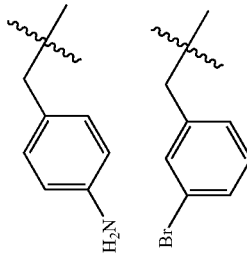 | ↑ | ↑ | ↑ |
| 347 | 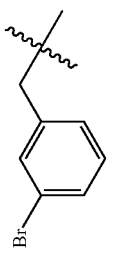 | 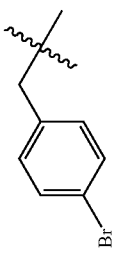 | ↑ | ↑ |
↑: same substituent as above TABLE 4-continued ↑: same substituent as above

| Example | R¹ | R² | R³ | R⁴ |
|---|---|---|---|---|
| 348 | 2-naphthyl | | ↑ | ↑ |
| 349 | styryl | 1-naphthylethyl | ↑ | ↑ |
| 350 | 2-naphthyl | | ↑ | ↑ |
| 351 | styryl | 2-naphthylethyl | ↑ | ↑ |
| 352 | 2-naphthyl | | ↑ | ↑ |

TABLE 4-continued
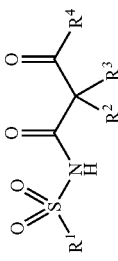
↑: same substituent as above
| Example | R¹ | R² | R³ | R⁴ |
|---|---|---|---|---|
| 353 | styryl | 4-MeO-phenethyl | ↑ | ↑ |
| 354 | naphthalen-2-yl | ↑ | ↑ | ↑ |
| 355 | styryl | 3-Br-phenethyl | ↑ | ↑ |
| 356 | naphthalen-2-yl | ↑ | ↑ | ↑ |
| 357 | styryl | 4-Br-phenethyl | ↑ | ↑ |
| 358 | naphthalen-2-yl | ↑ | ↑ | ↑ |

TABLE 4-continued

↑: same substituent as above

| Example | R¹ | R² | R³ | R⁴ |
|---|---|---|---|---|
| 359 | (E)-styryl | 3-biphenylmethyl | | |
| 360 | 2-naphthyl | ↑ | ↑ | ↑ |
| 361 | (E)-styryl | 4'-methoxy-4-biphenylmethyl (via CH₂) | ↑ | ↑ |
| 362 | 2-naphthyl | ↑ | ↑ | ↑ |
| 363 | phenethyl | ↑ | ↑ | ↑ |

TABLE 4-continued
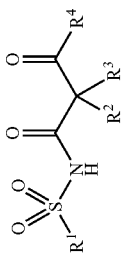
↑: same substituent as above
| Example | R¹ | R² | R³ | R⁴ |
|---|---|---|---|---|
| 364 | styryl | 2-benzylbiphenyl | ↑ | ↑ |
| 365 | naphthyl | ↑ | ↑ | ↑ |
| 366 | phenethyl | ↑ | ↑ | ↑ |
| 367 | styryl | 3-biphenyl-ethyl | ↑ | ↑ |
| 368 | ↑ | 4-biphenyl-ethyl | ↑ | ↑ |

TABLE 4-continued

| Example | R¹ | R² | R³ | R⁴ |
|---|---|---|---|---|
| 369 | 2-naphthyl | 3-biphenyl | ↑ | ↑ |
| 370 | ↑ | 1-benzyl-1H-pyrazol-4-ylmethyl | ↑ | ↑ |
| 371 | styryl | ↑ | ↑ | ↑ |
| 372 | ↑ | 1-ethyl-1H-pyrazol-4-ylmethyl | ↑ | ↑ |
| 373 | ↑ | 1-methyl-1H-pyrazol-4-ylmethyl | ↑ | ↑ |

↑: same substituent as above

TABLE 4-continued
| Example | R¹ | R² | R³ | R⁴ |
|---|---|---|---|---|
| 374 | ↑ | 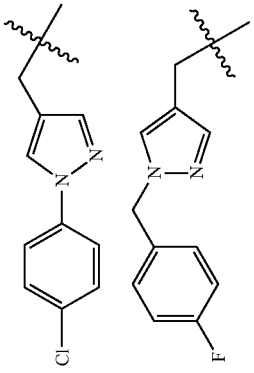 | ↑ | ↑ |
| 375 | ↑ | 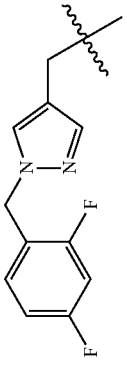 | ↑ | ↑ |
| 376 | ↑ | 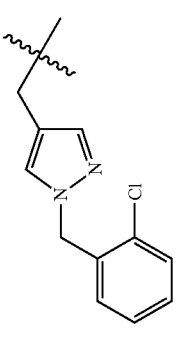 | ↑ | ↑ |
| 377 | ↑ | 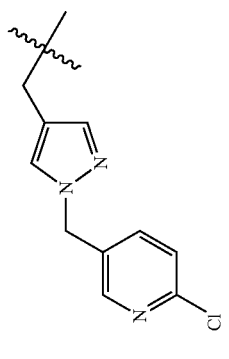 | ↑ | ↑ |
| 378 | ↑ | 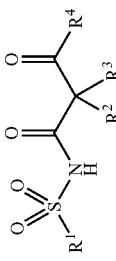 | ↑ | ↑ |
↑: same substituent as above TABLE 4-continued

| Example | R¹ | R² | R³ | R⁴ |
|---|---|---|---|---|
| 379 | ↑ | [3-pyridylmethyl-pyrazol-4-yl] | ↑ | ↑ |
| 380 | ↑ | [2-pyridylmethyl-pyrazol-4-yl] HCl | ↑ | ↑ |
| 381 | ↑ | [(6-chloropyridin-3-yl)methyl-pyrazol-4-yl] HCl | ↑ | N-ethyl-N-(4-fluorophenyl) |
| 382 | ↑ | [3-pyridylmethyl-pyrazol-4-yl] HCl | ↑ | ↑ |

↑: same substituent as above

TABLE 4-continued

↑: same substituent as above

| Example | R¹ | R² | R³ | R⁴ |
|---|---|---|---|---|
| 383 | ↑ | 1-(2-aminobenzyl)-pyrazol-4-yl-methyl | ↑ | N-ethyl-N-phenyl |
| 384 | ↑ | 1-(3-aminobenzyl)-pyrazol-4-yl-methyl | ↑ | ↑ |
| 385 | ↑ | 1-benzyl-pyrazol-4-yl-methyl | ↑ | N,N-diethyl |
| 386 | ↑ | 1-(4-fluorobenzyl)-pyrazol-4-yl-methyl | ↑ | ↑ |

TABLE 4-continued
| Example | R¹ | R² | R³ | R⁴ |
|---|---|---|---|---|
| 387 | 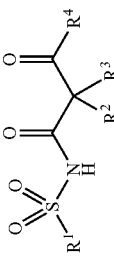 | 4-chlorobenzyl pyrazolylmethyl | ↑ | ↑ |
| 388 | ↑ | 6-chloropyridin-3-yl pyrazolylmethyl | ↑ | ↑ |
| 389 | ↑ | benzyl pyrazolylmethyl | ↑ | ↑ |
| 390 | ↑ | 2-fluorobenzyl pyrazolylmethyl | ↑ | ↑ |
| 391 | ↑ | 2-chlorobenzyl pyrazolylmethyl | ↑ | ↑ |
↑: same substituent as above TABLE 4-continued

| Example | R¹ | R² | R³ | R⁴ |
|---|---|---|---|---|
| 392 | | (1-cinnamyl-1H-pyrazol-4-yl)methyl | | |
| 393 | ↑ | (1-(3-phenylpropyl)-1H-pyrazol-4-yl)methyl | ↑ | ↑ |
| 394 | ↑ | (1-ethyl-1H-pyrazol-4-yl)methyl | ↑ | N-(4-fluorophenyl)-N-isopropyl |
| 395 | trans-cinnamyl | (1-isopropyl-1H-pyrazol-4-yl)methyl | ↑ | ↑ |

↑: same substituent as above

TABLE 4-continued

↑: same substituent as above

| Example | R¹ | R² | R³ | R⁴ |
|---------|----|----|----|----|
| 396 | ↑ | ↑ | ↑ | 3-CF₃-C₆H₄-N(iPr)- |
| 397 | 2-naphthyl | ↑ | ↑ | 4-F-C₆H₄-N(iPr)- |
| 398 | thiazol-2-yl-vinyl | 1-benzyl-pyrazol-4-ylmethyl | ↑ | C₆H₅-N(Et)- |
| 399 | pyridin-3-yl-vinyl | ↑ | ↑ | ↑ |

TABLE 4-continued

| Example | R¹ | R² | R³ | R⁴ |
|---|---|---|---|---|
| 400 | 4-F-C₆H₄-CH=CH- | 1-(1-phenylethyl)pyrazol-4-ylmethyl | ↑ | ↑ |
| 401 | C₆H₅-CH=CH- | 1-benzylpyrazol-4-ylmethyl | ↑ | ↑ |
| 402 | 4-methylphenyl- | ↑ | ↑ | ↑ |
| 403 | 4-Cl-C₆H₄- | ↑ | ↑ | ↑ |

↑: same substituent as above

TABLE 4-continued

| Example | R¹ | R² | R³ | R⁴ |
|---|---|---|---|---|
| 404 | (E)-styryl | 1-(3-methylbut-2-enyl)-1H-pyrazol-4-ylmethyl | ↑ | N-ethyl-N-(4-fluorophenyl)amino |
| 405 | (E)-styryl | 1-benzyl-1H-pyrazol-4-ylmethyl | ↑ | N-ethyl-N-(naphthalen-1-yl)amino |
| 406 | ↑ | ↑ | ↑ | N-ethyl-N-(naphthalen-2-yl)amino |
| 407 | ↑ | ↑ | ↑ | indolin-1-yl |

↑: same substituent as above

TABLE 4-continued

↑: same substituent as above

| Example | R¹ | R² | R³ | R⁴ |
|---|---|---|---|---|
| 408 | ↑ | ↑ | ↑ | 4-fluorophenyl(ethyl)amino |
| 409 | ↑ | ↑ | ↑ | 3,4-dihydroquinolin-1(2H)-yl |
| 410 | ↑ | ↑ | ↑ | pyridin-3-yl(ethyl)amino · HCl |
| 411 | ↑ | ↑ | ↑ | 4-(ethoxycarbonyl)phenyl(ethyl)amino |

TABLE 4-continued

↑: same substituent as above

| Example | R¹ | R² | R³ | R⁴ |
|---|---|---|---|---|
| 412 | ↑ | ↑ | ↑ | 4-carboxyphenyl-N(Et)- (attached via quaternary carbon with methyl) |
| 413 | ↑ | ↑ | ↑ | 3-(ethoxycarbonyl)phenyl-N(Et)- |
| 414 | ↑ | ↑ | ↑ | 3-carboxyphenyl-N(Et)- |
| 415 | ↑ | ↑ | ↑ | 4-(hydroxymethyl)phenyl-N(Et)- |

TABLE 4-continued

↑: same substituent as above

| Example | R¹ | R² | R³ | R⁴ |
|---|---|---|---|---|
| 416 | | | | 3-(hydroxymethyl)phenyl-N-ethyl amine |
| 417 | ↑ | ↑ | ↑ | N-phenyl-N-(2-hydroxyethyl) amine |
| 418 | ↑ | ↑ | ↑ | N-phenyl-N-isopropyl amine |
| 419 | ↑ | ↑ | ↑ | N-allyl-N-methyl amine |
| 420 | 2-naphthyl | ↑ | ↑ | N-(2-methoxyethyl)-N-ethyl amine |

TABLE 4-continued
| Example | R¹ | R² | R³ | R⁴ |
|---|---|---|---|---|
| 421 | ↑ | ↑ | ↑ | 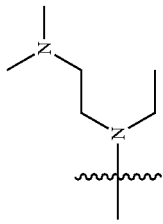 |
| 422 | ↑ | ↑ | ↑ | 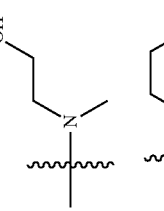 TFA |
| 423 | ↑ | ↑ | ↑ | 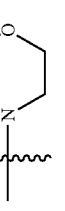 |
| 424 | ↑ | ↑ | ↑ | 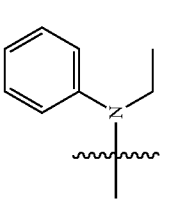 |
| 425 | 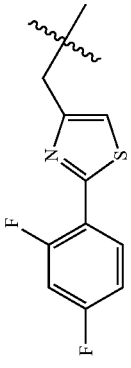 | 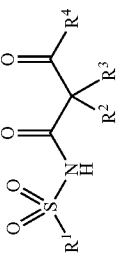 | ↑ | ↑ |
↑: same substituent as above TABLE 4-continued

| Example | R¹ | R² | R³ | R⁴ |
|---|---|---|---|---|
| 426 | ↑ | (structure: thiazole with NH-phenyl) | ↑ | N,N-diethylamino |
| 427 | ↑ | (structure: thiazole with 4-chlorobenzyl) | ↑ | N-ethyl-N-phenylamino |
| 428 | ↑ | (structure: oxazole with 4-fluorophenyl) | ↑ | ↑ |
| 429 | ↑ | (structure: triazole with benzyl) | ↑ | ↑ |

↑: same substituent as above

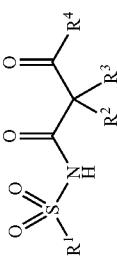

TABLE 4-continued

↑: same substituent as above

| Example | R¹ | R² | R³ | R⁴ |
|---|---|---|---|---|
| 434 | ↑ | | | |
| 435 | ↑ | | | |
| 436 | (2-naphthyl) | (1-methyl-tetrazol-5-yl-methyl) | ↑ | (N,N-diethylamino) |
| 437 | ↑ | (1-methyl-tetrazol-5-yl-methyl) | ↑ | N-isopropyl-N-(3-trifluoromethylphenyl)amino |

TABLE 4-continued
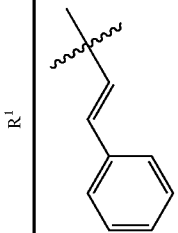
↑: same substituent as above
| Example | R¹ | R² | R³ | R⁴ |
|---|---|---|---|---|
| 438 | 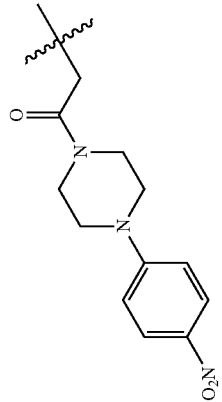 | piperazinyl-C₆H₄-NO₂ acyl | ↑ | N-ethyl-N-phenyl |
| 439 | ↑ | piperazinyl-C₆H₄-NH₂ acyl 2HCl | ↑ | ↑ |
| 440 | ↑ | piperazinyl-pyridyl-CN acyl | ↑ | ↑ |
| 441 | ↑ | tetrahydroisoquinolinyl acyl | ↑ | ↑ |

TABLE 4-continued

↑: same substituent as above

| Example | R¹ | R² | R³ | R⁴ |
|---|---|---|---|---|
| 442 | ↑ | | ↑ | 4-fluorophenyl-N-isopropyl |
| 443 | ↑ | N,N-dimethylacetamide | ↑ | ↑ |
| 444 | 2-naphthyl | 1-(pyrrolidin-1-yl)ethanone | ↑ | N-ethyl-N-phenyl |
| 445 | styryl (E) | allyl | ↑ | 2-(N-methylamino)ethanol |
| 446 | ↑ | ↑ | ↑ | 4-(5-cyanopyridin-2-yl)piperazin-1-yl |

TABLE 4-continued

↑: same substituent as above

| Example | R¹ | R² | R³ | R⁴ |
|---|---|---|---|---|
| 447 | ↑ | ↑ | ↑ | benzothiazol-2-yl piperazine |
| 448 | ↑ | ↑ | ↑ | 7-(trifluoromethyl)quinolin-4-yl piperazine |
| 449 | ↑ | ↑ | ↑ | 4-(3,4-dimethylphenyl)piperazine |
| 450 | ↑ | ↑ | ↑ | diphenylmethylamino |

TABLE 4-continued

↑: same substituent as above

| Example | R¹ | R² | R³ | R⁴ |
|---|---|---|---|---|
| 451 |  |  |  | piperazinyl-(3-methyl-1-phenyl-pyrazol-5-yl) with methyl |
| 452 | ↑ | ↑ | ↑ | N,N-diethyl with methyl |
| 453 | ↑ | ↑ | ↑ | N-ethyl-N-phenyl with methyl |
| 454 | ↑ | ↑ | ↑ | N-ethyl-N-(naphth-1-yl) with methyl |
| 455 | 2-naphthyl with methyl | ↑ | ↑ | ↑ |

TABLE 4-continued

![structure: R¹-SO₂-NH-C(=O)-C(R²)(R³)-C(=O)-R⁴]

↑: same substituent as above

| Example | R¹ | R² | R³ | R⁴ |
|---|---|---|---|---|
| 456 | (E)-CH=CH-(thiazol-2-yl) | | | N-ethyl-N-(naphthalen-2-yl) |
| 457 | ↑ | ↑ | ↑ | N-ethyl-N-(naphthalen-1-yl) |
| 458 | (E)-CH=CH-(pyridin-3-yl) | ↑ | ↑ | N-ethyl-N-(naphthalen-2-yl) |
| 459 | (E)-CH=CH-(phenyl) | ↑ | ↑ | N-ethyl-N-(2,3-dichlorophenyl) |

TABLE 4-continued
| Example | R¹ | R² | R³ | R⁴ |
|---|---|---|---|---|
| 460 | ↑ | ↑ | ↑ | 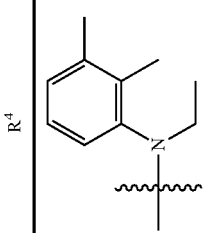 |
| 461 | ↑ | ↑ | ↑ | 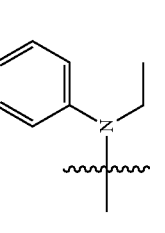 |
| 462 | ↑ | ↑ | ↑ | 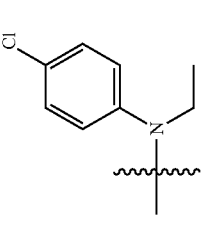 |
| 463 | ↑ | ↑ | ↑ | 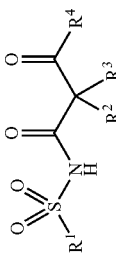 |
↑: same substituent as above TABLE 4-continued
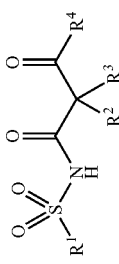
↑: same substituent as above
| Example | R¹ | R² | R³ | R⁴ |
|---|---|---|---|---|
| 464 | ↑ | ↑ | ↑ | 2,5-difluorophenyl-N-ethyl |
| 465 | ↑ | ↑ | ↑ | 4-chlorophenyl-N-methyl |
| 466 | ↑ | ↑ | ↑ | 2-fluorophenyl-N-ethyl |
| 467 | ↑ | ↑ | ↑ | 2,4,6-trifluorophenyl-N-ethyl |

TABLE 4-continued

| Example | R¹ | R² | R³ | R⁴ |
|---|---|---|---|---|
| 468 | ↑ | ↑ | ↑ | 2,4-difluorophenyl-N-ethyl |
| 469 | ↑ | ↑ | ↑ | benzo[1,3]dioxol-5-yl-N-ethyl |
| 470 | ↑ | ↑ | ↑ | 5-bromoindolin-1-yl |
| 471 | ↑ | ↑ | ↑ | 6-fluoro-2-methyl-1,2,3,4-tetrahydroquinolin-1-yl |

↑: same substituent as above

TABLE 4-continued

↑: same substituent as above

| Example | R¹ | R² | R³ | R⁴ |
|---|---|---|---|---|
| 472 | | | | N(phenyl)(benzyl) |
| 473 | ↑ | ↑ | ↑ | 1,2,3,4-tetrahydroisoquinolin-2-yl |
| 474 | ↑ | ↑ | ↑ | N-ethyl-N-(4-methylthiophenyl) |
| 475 | ↑ | ↑ | ↑ | N-ethyl-N-(3-trifluoromethylphenyl) |

TABLE 4-continued

↑: same substituent as above

| Example | R¹ | R² | R³ | R⁴ |
|---|---|---|---|---|
| 476 | ↑ | ↑ | ↑ | N-ethyl-4-(trifluoromethyl)phenyl |
| 477 | ↑ | ↑ | ↑ | N-methyl-(naphthalen-1-ylmethyl) |
| 478 | ↑ | ↑ | ↑ | N,N-dibenzyl |
| 479 | ↑ | ↑ | ↑ | N-ethyl-3-fluorophenyl |

TABLE 4-continued

↑: same substituent as above

| Example | R¹ | R² | R³ | R⁴ |
|---|---|---|---|---|
| 480 | ↑ | ↑ | ↑ | N-ethyl-N-(4'-fluorobiphenyl-4-yl) |
| 481 | ↑ | ↑ | ↑ | N-isopropyl-N-(4-fluorophenyl) |
| 482 | ↑ | ↑ | ↑ | N-isopropyl-N-(3-trifluoromethylphenyl) |

TABLE 4-continued
| Example | R¹ | R² | R³ | R⁴ |
|---|---|---|---|---|
| 483 | 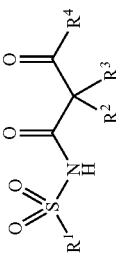 | ↑ | ↑ | 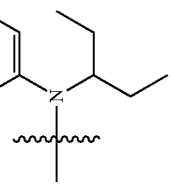 |
| 484 | | ↑ | ↑ | 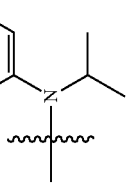 |
| 485 | | ↑ | ↑ | 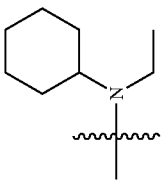 |
↑: same substituent as above TABLE 4-continued
| Example | R¹ | R² | R³ | R⁴ |
|---|---|---|---|---|
| 486 | ↑ |  | ↑ | 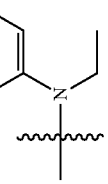 |
| 487 | ↑ |  | ↑ | 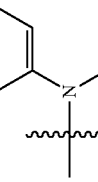 |
| 488 | ↑ | ↑ | ↑ |  |
↑: same substituent as above TABLE 4-continued
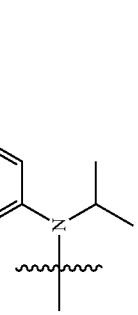
↑: same substituent as above
| Example | R¹ | R² | R³ | R⁴ |
|---|---|---|---|---|
| 489 | ↑ | ↑ | ↑ | 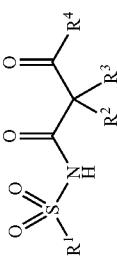 |
| 490 | ↑ | ↑ | ↑ | ↑ |
| 491 | ↑ | ↑ | ↑ | ↑ |
| 492 | | | ↑ | ↑ |
| 493 | | | ↑ | ↑ |

TABLE 4-continued

| Example | R¹ | R² | R³ | R⁴ |
|---|---|---|---|---|
| 494 | phenyl | ↑ | ↑ | ↑ |
| 495 | naphthyl | ↑ | ↑ | ↑ |
| 496 | phenoxyethyl | ↑ | ↑ | ↑ |
| 497 | phenylbutyl | ↑ | ↑ | ↑ |
| 498 | biphenyl | ↑ | ↑ | ↑ |

↑: same substituent as above

TABLE 4-continued

↑: same substituent as above

| Example | R¹ | R² | R³ | R⁴ |
|---|---|---|---|---|
| 499 | (E)-styryl-CH2- | | | 3-(hydroxymethyl)phenyl-N(Et)- |
| 500 | ↑ | ↑ | ↑ | 3-(hydroxymethyl)phenyl-N(iPr)- |
| 501 | ↑ | ↑ | ↑ | 3-(CF3)phenyl-N(iPr)- |
| 502 | ↑ | ↑ | ↑ | pyridin-3-yl-N(iPr)- · HCl |

TABLE 4-continued

↑: same substituent as above

| Example | R¹ | R² | R³ | R⁴ |
|---|---|---|---|---|
| 503 | ↑ | ↑ | ↑ | N-phenyl, N-(2-hydroxyethyl), methyl |
| 504 | ↑ | ↑ | ↑ | N-benzyl, N-isopropyl, methyl |
| 505 | ↑ | ↑ | ↑ | N-(4-fluorobenzyl), N-isopropyl, methyl |
| 506 | ↑ | ↑ | ↑ | N-(3-fluorobenzyl), N-isopropyl, methyl |

TABLE 4-continued

↑: same substituent as above

| Example | R¹ | R² | R³ | R⁴ |
|---|---|---|---|---|
| 507 | ↑ | ↑ | ↑ | phenethyl-N(iPr)(Me)- |
| 508 | ↑ | ↑ | ↑ | 4-fluorophenethyl-N(iPr)(Me)- |
| 509 | (E)-2-(thiazol-2-yl)vinyl-C(Me)₂- | ↑ | ↑ | 4-fluorophenyl-N(iPr)(Me)- |

TABLE 4-continued

↑: same substituent as above

| Example | R¹ | R² | R³ | R⁴ |
|---|---|---|---|---|
| 510 | thiazol-2-ylethyl | ↑ | ↑ | ↑ |
| 511 | (pyridin-3-yl)vinyl | ↑ | ↑ | ↑ |
| 512 | styryl | isobutyl | ↑ | ↑ |
| 513 | ↑ | neopentyl | ↑ | ↑ |
| 514 | ↑ | cyclopropylmethyl | ↑ | N-ethyl-N-(4-fluorophenyl) |

TABLE 4-continued
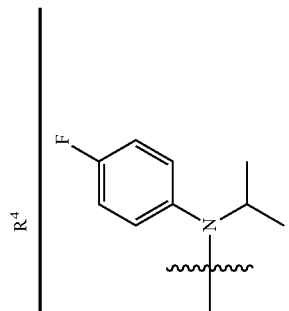
↑: same substituent as above
| Example | R¹ | R² | R³ | R⁴ |
|---|---|---|---|---|
| 515 | ↑ | ↑ | ↑ |  |
| 516 | ↑ | 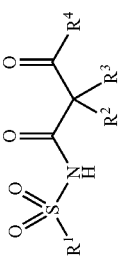 ↑ (optically active form) | ↑ | ↑ |
| 517 | 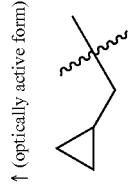 | ↑ | ↑ | ↑ |
| 518 | 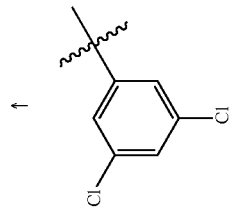 | ↑ | ↑ | ↑ |
| 519 | 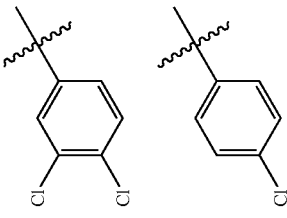 | ↑ | ↑ | ↑ |

TABLE 4-continued
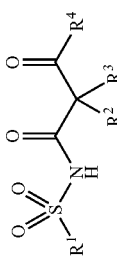
↑: same substituent as above
| Example | R¹ | R² | R³ | R⁴ |
|---|---|---|---|---|
| 520 | 4-tert-butylphenyl | ↑ | ↑ | ↑ |
| 521 | 4-(trifluoromethoxy)phenyl | ↑ | ↑ | ↑ |
| 522 | 4-methylphenyl | ↑ | ↑ | ↑ |
| 523 | 4-isobutylphenyl | ↑ | ↑ | ↑ |
| 524 | benzyl | ↑ | ↑ | ↑ |

TABLE 4-continued
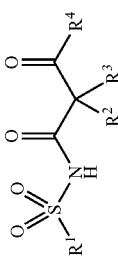
↑: same substituent as above
| Example | R¹ | R² | R³ | R⁴ |
|---|---|---|---|---|
| 525 | 4-methoxyphenyl | ↑ | ↑ | ↑ |
| 526 | butyl | ↑ | ↑ | ↑ |
| 527 | 4-phenoxyphenyl | ↑ | ↑ | ↑ |
| 528 | biphenyl | ↑ | ↑ | ↑ |
| 529 | phenethyl | ↑ | ↑ | ↑ |

TABLE 4-continued

↑: same substituent as above

| Example | R¹ | R² | R³ | R⁴ |
|---|---|---|---|---|
| 530 | 2-naphthyl | | | |
| 531 | phenoxypropyl | ↑ | ↑ | ↑ |
| 532 | styryl (PhCH=CH-) | ↑ | ↑ | N(4-F-C₆H₄)(CH(Et)₂) |
| 533 | ↑ | ↑ | ↑ | N(iPr)₂ |

TABLE 4-continued

↑: same substituent as above

| Example | R¹ | R² | R³ | R⁴ |
|---|---|---|---|---|
| 534 | ↑ | ↑ | ↑ | N-cyclohexyl-N-isopropyl |
| 535 | n-pentyl | ↑ | ↑ | N-(4-fluorophenyl)-N-isopropyl |
| 536 | n-octyl | ↑ | ↑ | ↑ |
| 537 | isobutenyl-methyl | ↑ | ↑ | ↑ |
| 538 | styryl | 2-methoxyethyl | ↑ | ↑ |

TABLE 4-continued

![structure: R¹-SO2-NH-C(=O)-C(R²)(R³)-C(=O)-R⁴]

↑: same substituent as above

| Example | R¹ | R² | R³ | R⁴ |
|---|---|---|---|---|
| 539 | ↑ | ![CH2CH2SCH3] | ↑ | ↑ |
| 540 | ↑ | ![CH2CH2S(=O)CH3] | ↑ | ↑ |
| 541 | ↑ | ![CH2CH2S(=O)2CH3] | ↑ | ↑ |
| 542 | ↑ | ![CH2CH2CN] | ↑ | ↑ |
| 543 | ![2-naphthyl] | ↑ | ↑ | ![N-ethyl-N-phenyl methyl] |

TABLE 4-continued
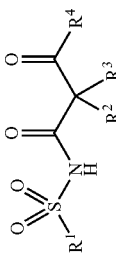
↑: same substituent as above
| Example | R¹ | R² | R³ | R⁴ |
|---|---|---|---|---|
| 544 | styryl | ↑ | ↑ | N(4-F-C₆H₄)(iPr) |
| 545 | 2-naphthyl | CH₂CN | ↑ | N(C₆H₅)(Et) |
| 546 | styryl | ↑ | ↑ | ↑ |
| 547 | ↑ | CH₂C≡CH | ↑ | N(4-F-C₆H₄)(iPr) |

TABLE 4-continued

| Example | R¹ | R² | R³ | R⁴ |
|---|---|---|---|---|
| 548 | naphthyl | cyclopentylmethyl | | N-ethyl-N-phenylamino-methyl |
| 549 | ↑ | 3-pyridyl-CH=CH-CH₂- | ↑ | ↑ |
| 550 | ↑ | 3-pyridyl-CH₂CH₂CH₂- | ↑ | ↑ |
| 551 | ↑ | 4-(imidazol-1-ylmethyl)phenyl-CH=CH- | ↑ | ↑ |
| 552 | ↑ | 4-(imidazol-1-ylmethyl)phenyl-CH₂CH₂- | ↑ | ↑ |
| 553 | ↑ | 2-naphthyl-CH=CH- | ↑ | ↑ |

↑: same substituent as above

TABLE 4-continued

Structure: R¹–S(O)₂–NH–C(O)–C(R²)(R³)–C(O)–R⁴

↑: same substituent as above

| Example | R¹ | R² | R³ | R⁴ |
|---|---|---|---|---|
| 554 | ↑ | naphthalen-2-yl-(CH₂)₂– | ↑ | ↑ |
| 555 | ↑ | (E)-4-MeO-C₆H₄–CH=CH– | ↑ | ↑ |
| 556 | ↑ | 4-MeO-C₆H₄–(CH₂)₂– | ↑ | ↑ |
| 557 | ↑ | (E)-4-phenyl-C₆H₄–CH=CH– | ↑ | ↑ |
| 558 | ↑ | 4-phenyl-C₆H₄–(CH₂)₂– | ↑ | ↑ |

TABLE 4-continued

| Example | R¹ | R² | R³ | R⁴ |
|---|---|---|---|---|
| 559 | ↑ | isoquinolin-4-yl-CH=CH-CH₂- | ↑ | ↑ |
| 560 | ↑ | benzothiophen-3-yl-CH=CH-CH₂- | ↑ | ↑ |
| 561 | ↑ | thiophen-3-yl-CH=CH-CH₂- | ↑ | ↑ |
| 562 | ↑ | 4-(EtO₂C)-C₆H₄-CH=CH-CH₂- | ↑ | ↑ |
| 563 | ↑ | 4-(EtO₂C)-C₆H₄-CH₂-CH₂-CH₂- | ↑ | ↑ |
| 564 | ↑ | 4-F-C₆H₄-CH=CH-CH₂- | ↑ | ↑ |

↑: same substituent as above

TABLE 4-continued

↑: same substituent as above

| Example | R¹ | R² | R³ | R⁴ |
|---|---|---|---|---|
| 565 | | | | |
| 566 | ↑ | ↑ | ↑ | ↑ |
| 567 | ↑ | ↑ | ↑ | ↑ |
| 568 | | F, F | | |
| 569 | ↑ | Me, Me | | ↑ |

TABLE 4-continued

↑: same substituent as above

| Example | R¹ | R² | R³ | R⁴ |
|---|---|---|---|---|
| 570 | (naphthalen-2-yl) | (cyclobutyl) | | N(phenyl)(benzyl) |
| 571 | ↑ | ↑ | | N(Et)₂ |
| 572 | ↑ | ↑ | | N(iPr)(4-fluorophenyl) |
| 573 | ↑ | (tert-butyl CH=C) | | ↑ |
| 574 | ↑ | (4-nitrophenyl CH=C) | | N(Et)₂ |

TABLE 4-continued
↑: same substituent as above
| Example | R¹ | R² | R³ | R⁴ |
|---|---|---|---|---|
| 575 | ↑ | 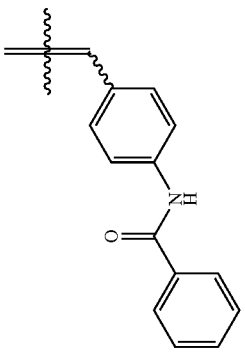 | H | ↑ |
| 576 | ↑ | 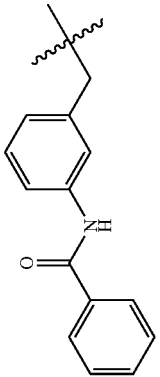 | ↑ | ↑ |
| 577 | ↑ | 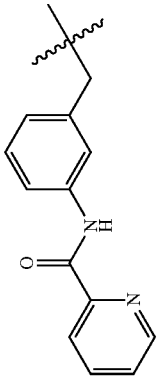 | ↑ | ↑ |
| 578 | ↑ | 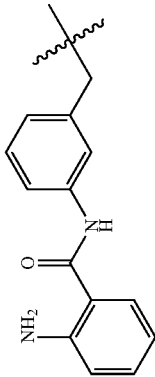 | ↑ | ↑ |

TABLE 4-continued
| Example | R¹ | R² | R³ | R⁴ |
|---|---|---|---|---|
| 579 | ↑ | 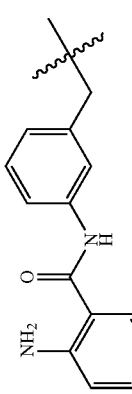 | ↑ | ↑ |
| 580 | ↑ | 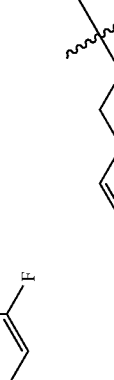 | ↑ | ↑ |
| 581 | ↑ | 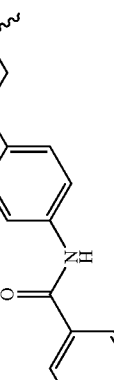 | ↑ | ↑ |
| 582 | ↑ | 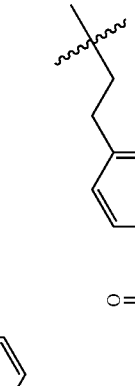 | ↑ | ↑ |
↑: same substituent as above TABLE 4-continued
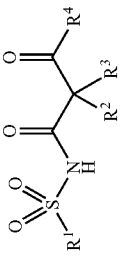
↑: same substituent as above
| Example | R¹ | R² | R³ | R⁴ |
|---|---|---|---|---|
| 583 | ↑ | (2-amino-6-fluorobenzamide-phenyl-propyl) | ↑ | ↑ |
| 584 | ↑ | (benzamide-phenyl-propyl) | ↑ | ↑ |
| 585 | ↑ | (pyridine-2-carboxamide-phenyl-propyl) | ↑ | ↑ |
| 586 | ↑ | (2-amino-5-fluorobenzamide-phenyl-propyl) | ↑ | ↑ |

TABLE 4-continued
| Example | R¹ | R² | R³ | R⁴ |
|---|---|---|---|---|
| | | ↑: same substituent as above | | |
| 587 | 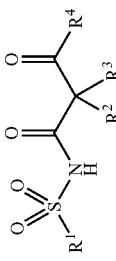 | 2-amino-6-fluorobenzamido-phenylpropyl | ↑ | ↑ |
| 588 | | 4-benzamidobenzyl | ↑ | ↑ |

It was clarified from the following Experimental Examples 1 to 3 that the compound of the present invention selectively binds to $AT_2$ receptor and/or shows an agonist action at $AT_2$ receptor.

Experimental Example 1

Affinity for $AT_1$ Receptor

Using a commercially available receptor membrane fraction (PerkinElmer, Cat No. 6110533) obtained from CHO cells expressing human recombinant $AT_1$ receptor, a receptor binding assay was performed. $^{125}I$-[$Sar^1$, $Ile^8$]-Ang II (2.4 kBq, final concentration 0.3 nmol/L) and various concentrations of the compound of the present invention were added to a solution of 50 mmol/L Tris-HCl (pH 7.4), 125 mmol/L NaCl, 6.5 mmol/L $MgCl_2$ and 1 mmol/L EDTA containing the receptor membrane fraction, and the mixture was incubated at room temperature for 60 min. Bound or free $^{125}I$-[$Sar^1$, $Ile^8$]-Ang II was separated with a glass fiber filter (Millipore, MultiScreen FB Plate), and the radioactivity of [$Sar^1$, $Ile^8$]-Ang II bound to the receptor was determined. $IC_{50}$ value which shows the concentration of the compound of the present invention necessary for inhibiting the binding of $^{125}I$-[$Sar^1$, $Ile^8$]-Ang II to the receptor by 50% was calculated from the concentration-response curve. On the other hand, Kd value of $^{125}I$-[$Sar^1$, $Ile^8$]-Ang II for $AT_1$ receptor in the absence of the compound of the present invention was determined by Scatchard analysis. Using the $IC_{50}$ value obtained from the concentration-response curve and the Kd value of $^{125}I$-[$Sar^1$, $Ile^8$]-Ang II, the Ki value of the compound of the present invention was calculated and used as an index of the affinity for $AT_1$ receptor.

Experimental Example 2

Affinity for $AT_2$ Receptor

Using a commercially available receptor membrane fraction (PerkinElmer, Cat No. 6110538) obtained from HeLa cells expressing human recombinant $AT_2$ receptor, a receptor binding assay was performed. $^{125}I$-[$Sar^1$, $Ile^8$]-Ang II (0.8 kBq, final concentration 0.1 nmol/L) and various concentrations of the compound of the present invention were added to a solution of 50 mmol/L Tris-HCl (pH 7.4), 125 mmol/L NaCl, 6.5 mmol/L $MgCl_2$ and 1 mmol/L EDTA containing the receptor membrane fraction, and the mixture was incubated at room temperature for 90 min. Bound or free $^{125}I$-[$Sar^1$, $Ile^8$]-Ang II was separated with a glass fiber filter (Millipore, MultiScreen FB Plate), and the radioactivity of $^{125}I$-[$Sar^1$, $Ile^8$]-Ang II bound to the receptor was determined. $IC_{50}$ value which shows the concentration of the compound of the present invention necessary for inhibiting the binding of $^{125}I$-[$Sar^1$, $Ile^8$]-Ang II to the receptor by 50% was calculated from the concentration-response curve. On the other hand, Kd value of $^{125}I$-[$Sar^1$, $Ile^8$]-Ang II for $AT_2$ receptor in the absence of the compound of the present invention was determined by Scatchard analysis. Using the $IC_{50}$ value obtained from the concentration-response curve and the Kd value of $^{125}I$-[$Sar^1$, $Ile^8$]-Ang II, the Ki value of the compound of the present invention was calculated and used as an index of the affinity for $AT_2$ receptor.

Experimental Example 3

(Agonist Action at $AT_2$ Receptor

According to the method of Stroth et al (Mol. Brain Res. 78 (2000), 175-180), the agonist action at $AT_2$ receptor of the compound of the present invention was examined. To be specific, PC12W cells (rat adrenal pheochromocytoma) cultured in a growth medium were subsequently cultured in a low-serum medium, and finally serum-deprived for 3 hr. Then, NGF (final concentration 3-30 ng/mL) and various concentrations of the compound of the present invention were added, and they were incubated at 37° C., 5% $CO_2$ for 10 min. Thereafter, the cells were lysed on ice for 30 min, and the amount of phosphorylated ERK in the cell lysis solution was detected by a Phospho-p44/42 MAPK-recognizing antibody. Using the decreasing effect on phosphorylated ERK as an index, the agonist action at $AT_2$ receptor of the compound of the present invention was examined.

The affinity (Ki value) of the compounds of the present invention for $AT_2$ receptor as determined by the aforementioned method is shown in the following. All the compounds showed an agonist action at $AT_2$ receptor and the affinity for $AT_1$ receptor of Ki>500 nmol/L.

TABLE 5

| Example No. | Affinity for $AT_2$ receptor (Ki, nmol/L) |
| --- | --- |
| 22 | 8.0 |
| 87 | 23 |
| 92 | 2.3 |
| 99 | 0.9 |
| 100 | 1.8 |
| 101 | 16 |
| 103 | 3.2 |
| 104 | 3.3 |
| 105 | 5.4 |
| 106 | 1.6 |
| 107 | 1.6 |
| 108 | 9.7 |
| 147 | 34 |
| 322 | 6.4 |
| 371 | 12 |
| 441 | 11 |
| 475 | 13 |
| 481 | 9.0 |
| 491 | 9.2 |
| 493 | 5.2 |
| 495 | 8.4 |
| 496 | 12 |
| 516 | 6.1 |
| 529 | 10 |
| 530 | 13 |

This application is based on a patent application No. 2007-163099 filed in Japan, the contents of which are incorporated in full herein by this reference. In addition, the references cited herein, including patent reference and non-patent reference, are hereby incorporated in full by reference, to the extent that they have been disclosed herein.

The invention claimed is:
1. A sulfonyl malonamide derivative represented by the following formula (I)

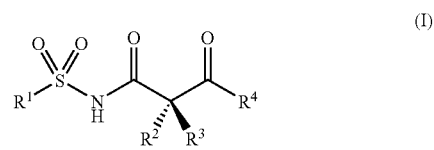

wherein $R^1$ is optionally substituted $C_{1-8}$ alkyl, optionally substituted $C_{2-6}$ alkenyl, optionally substituted $C_{2-6}$ alkynyl, optionally substituted $C_{3-10}$ cycloalkyl, optionally substituted $C_{3-10}$ cycloalkyl $C_{1-6}$ alkyl, optionally substituted heterocycle, optionally substituted aryl, optionally substituted aryl $C_{1-6}$ alkyl, optionally substituted aryloxy $C_{1-6}$ alkyl, optionally substituted aryl $C_{2-6}$ alkenyl, optionally substituted heteroaryl, optionally substituted heteroaryl $C_{1-6}$ alkyl, optionally substituted heteroaryloxy $C_{1-6}$ alkyl or optionally substituted heteroaryl $C_{2-6}$ alkenyl;

one of $R^2$ and $R^3$ is a hydrogen atom or a halogen atom, and the other is a halogen atom, optionally substituted $C_{1-6}$ alkyl, optionally substituted $C_{1-6}$ alkoxy, optionally substituted $C_{2-6}$ alkenyl, optionally substituted $C_{2-6}$ alkynyl, —$(CH_2)_n$—$C(O)$—$NR^5R^6$ (wherein n is an integer of 1 to 6, $R^5$ and $R^6$ are the same or different and each is a hydrogen atom, $C_{1-6}$ alkyl, optionally substituted aryl or optionally substituted heteroaryl, or $R^5$ and $R^6$ optionally form optionally substituted cyclic amino together with a nitrogen atom bonded thereto), optionally substituted $C_{3-10}$ cycloalkyl, optionally substituted heterocycle, optionally substituted $C_{3-10}$ cycloalkyl $C_{1-6}$ alkyl, optionally substituted heterocycle $C_{1-6}$ alkyl, optionally substituted aryl, optionally substituted aryl $C_{1-6}$ alkyl, optionally substituted aryloxy $C_{1-6}$ alkyl, optionally substituted aryl $C_{2-6}$ alkenyl, optionally substituted heteroaryl, optionally substituted heteroaryl $C_{1-6}$ alkyl, optionally substituted heteroaryloxy $C_{1-6}$ alkyl or optionally substituted heteroaryl $C_{2-6}$ alkenyl, or $R^2$ and $R^3$ optionally form, together with a carbon atom bonded thereto, C=CX'Y' (wherein X' and Y' are the same or different and each is a hydrogen atom, optionally substituted $C_{1-6}$ alkyl, optionally substituted aryl or optionally substituted heteroaryl), or optionally substituted $C_{3-10}$ cycloalkyl; and $R^4$ is the following formula

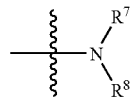

wherein $R^7$ and $R^8$ are the same or different and each is a hydrogen atom, optionally substituted $C_{1-6}$ alkyl, optionally substituted $C_{2-6}$ alkenyl, optionally substituted aryl, optionally substituted aryl $C_{1-6}$ alkyl, optionally substituted heteroaryl, optionally substituted heteroaryl $C_{1-6}$ alkyl, optionally substituted $C_{3-10}$ cycloalkyl or optionally substituted heterocycle, or $R^7$ and $R^8$ optionally form optionally substituted cyclic amino together with a nitrogen atom bonded thereto, or a pharmacologically acceptable salt thereof.

2. The sulfonyl malonamide derivative of claim 1, wherein $R^1$ is optionally substituted naphthyl, optionally substituted biphenyl, optionally substituted phenyl, optionally substituted thiophene, optionally substituted phenyl $C_{1-6}$ alkyl, optionally substituted phenoxy $C_{1-6}$ alkyl, optionally substituted thiazolyl $C_{1-6}$ alkyl, optionally substituted $C_{1-8}$ alkyl, optionally substituted $C_{2-6}$ alkenyl, optionally substituted $C_{3-10}$ cycloalkyl, or the following formula

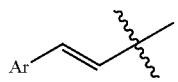

wherein Ar is optionally substituted phenyl, optionally substituted pyridyl or optionally substituted thiazolyl, or a pharmacologically acceptable salt thereof.

3. The sulfonyl malonamide derivative of claim 1, wherein one of $R^2$ and $R^3$ is a hydrogen atom, and the other is $C_{1-6}$ alkyl, allyl, prenyl, 2-propynyl, cyclopentyl, —$CH_2$—$R^9$ (wherein $R^9$ is cyclopropyl, cyano, optionally substituted cyclohexyl, optionally N-substituted 4-piperidinyl or —CO—$NR^5R^6$ wherein $R^5$ and $R^6$ are as defined in claim 1), —$(CH_2)_2$—$R^{9'}$ (wherein $R^{9'}$ is cyano, $C_{1-6}$ alkoxy, $C_{1-6}$ alkylthio, $C_{1-6}$ alkylsulfinyl, $C_{1-6}$ alkylsulfonyl, N-substituted-4-piperidinyl or N-substituted-4-piperazinyl), —$(CH_2)_n$—$Ar^1$ or —$CH_2$—$CH$=$CH$—$Ar^1$ (wherein n is an integer of 0 to 6, and $Ar^1$ is optionally substituted aryl or optionally substituted heteroaryl), or a pharmacologically acceptable salt thereof.

4. The sulfonyl malonamide derivative of claim 1, wherein $R^4$ is represented by the following formula

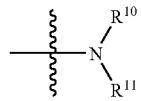

wherein $R^{10}$ and $R^{11}$ are the same or different and each is optionally substituted $C_{1-6}$ alkyl, optionally substituted $C_{2-6}$ alkenyl, optionally substituted aryl, optionally substituted aryl $C_{1-6}$ alkyl, optionally substituted heteroaryl, optionally substituted $C_{3-10}$ cycloalkyl or optionally substituted heterocycle, or $R^{10}$ and $R^{11}$ optionally form optionally substituted cyclic amino together with a nitrogen atom bonded thereto, or a pharmacologically acceptable salt thereof.

5. An $AT_2$ receptor ligand comprising a sulfonyl malonamide derivative of claim 1, or a pharmacologically acceptable salt thereof.

6. The sulfonyl malonamide derivative of claim 1, which is represented by the following formula (II)

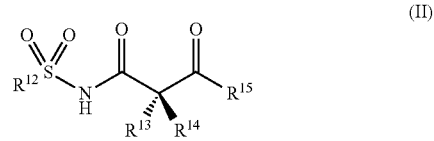

(II)

wherein $R^{12}$ is 2-naphthyl, trans-β-styryl, phenethyl, 3-phenoxypropyl or 4-phenylbutyl;

one of $R^{13}$ and $R^{14}$ is a hydrogen atom, and the other is isopropyl, isobutyl, neopentyl, allyl, —$CH_2$—$R^{16}$ wherein $R^{16}$ is optionally substituted $C_{3-10}$ cycloalkyl, optionally substituted heterocycle or —CO—$NR^5R^6$ (wherein $R^5$ and $R^6$ are as defined in claim 1), —$(CH_2)_2$—$R^{16'}$ (wherein $R^{16'}$ is cyano or $C_{1-6}$ alkoxy), or —$(CH_2)_n$—$Ar^2$ (wherein n is an integer of 1 to 3, and $Ar^2$ is substituted phenyl or optionally substituted heteroaryl), or $R^{13}$ and $R^{14}$ optionally form, together with a carbon atom bonded thereto, the following formula

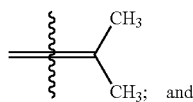

$R^{15}$ is di($C_{1-6}$ alkyl)amino or the following formula

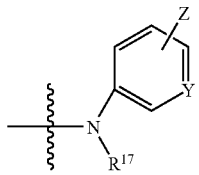

wherein Z is a hydrogen atom, a halogen atom or trifluoromethyl, Y is a nitrogen atom or CH, $R^{17}$ is ethyl, isopropyl or 3-pentyl, provided that when Y is a nitrogen atom, then Z is a hydrogen atom, or a pharmacologically acceptable salt thereof.

7. The sulfonyl malonamide derivative of claim 6, wherein $Ar^2$ for $R^{13}$ or $R^{14}$ is substituted phenyl represented by the following formula

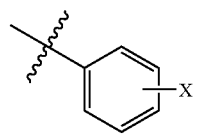

wherein X is a fluorine atom, a chlorine atom, a bromine atom, cyano, nitro, amino (excluding substitution at the ortho-position), —NHCOAr$^3$, —NHCOOAr$^3$, —NHCONHAr$^3$, —NHSO$_2$Ar$^3$, —OAr$^3$ (wherein Ar$^3$ is optionally substituted aryl or optionally substituted heteroaryl), —NHCOR$^{18}$ (wherein R$^{18}$ is optionally substituted C$_{1-6}$ alkyl, optionally substituted C$_{3-10}$ cycloalkyl, or optionally substituted heterocycle), optionally substituted C$_{1-6}$ alkoxycarbonyl, di(C$_{1-6}$ alkyl)amino, optionally substituted C$_{1-6}$ alkoxy, optionally substituted heterocycle, optionally substituted aryl or optionally substituted heteroaryl, or a pharmacologically acceptable salt thereof.

8. The sulfonyl malonamide derivative of claim 6, which is represented by the following formula (III)

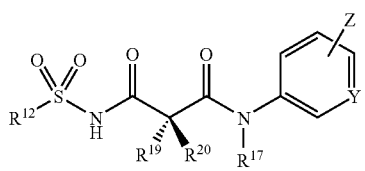

wherein $R^{12}$, $R^{17}$, Y and Z are as defined in claim 6, one of $R^{19}$ and $R^{20}$ is a hydrogen atom, and the other is isopropyl, isobutyl, neopentyl, allyl, cyclopropylmethyl or —CH$_2$—Ar$^2$ wherein Ar$^2$ is as defined in claim 6, or a pharmacologically acceptable salt thereof.

9. The sulfonyl malonamide derivative of claim 6, which is represented by the following formula (IV)

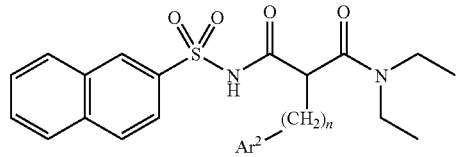

wherein n is an integer of 1 to 3, $Ar^2$ is as defined in claim 6, or a pharmacologically acceptable salt thereof.

10. The sulfonyl malonamide derivative of claim 9, wherein $Ar^2$ is substituted phenyl represented by the following formula

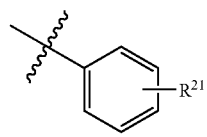

wherein $R^{21}$ is a fluorine atom, a chlorine atom, nitro, cyano, amino (excluding substitution at the ortho-position), dimethylamino, methoxy, trifluoromethoxy, methoxycarbonyl, phenyl, 2-pyridyloxy, 1-imidazolyl, 2-isoindolinyl, 1-oxo-2-isoindolinyl or the following formula

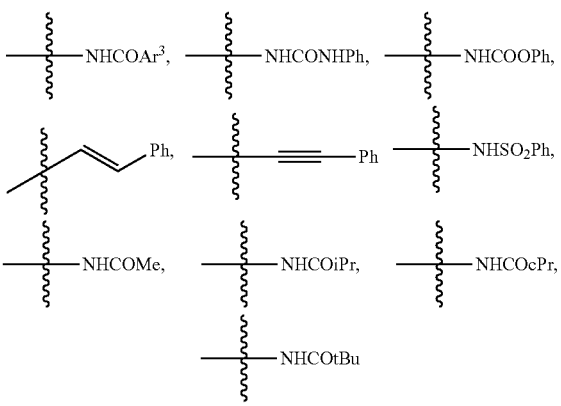

wherein $Ar^3$ is optionally substituted aryl or optionally substituted heteroaryl, or a pharmacologically acceptable salt thereof.

11. The sulfonyl malonamide derivative of claim 9, wherein $Ar^2$ is substituted phenyl represented by the following formula

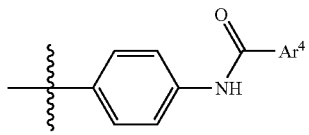

wherein $Ar^4$ is 2-thienyl, 2-furyl, 4-pyridyl, 3-pyridyl, 2-pyridyl or the following formula

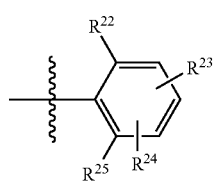

wherein $R^{22}$ and $R^{25}$ are the same or different and each is a hydrogen atom, amino, a fluorine atom, hydroxy, methoxy, methyl or a chlorine atom, $R^{23}$ is a hydrogen atom or a fluorine atom, and $R^{24}$ is a hydrogen atom, a fluorine atom, a chlorine atom, methyl, amino, methoxy or cyano, and n is 1, or a pharmacologically acceptable salt thereof.

12. The sulfonyl malonamide derivative of claim 6, which is the following compound:

N,N-diethyl-2-[4-[(2,6-difluorobenzoyl)amino]benzyl]-N'-(2-naphthylsulfonyl)malonamide,
(2S)-2-[4-(benzoylamino)benzyl]-N,N-diethyl-N'-(2-naphthylsulfonyl)malonamide,
(2S)—N,N-diethyl-2-{4-[(2-fluorobenzoyl)amino]benzyl}-N'-(2-naphthylsulfonyl)malonamide,
(2S)—N,N-diethyl-2-{4-[(3-fluorobenzoyl)amino]benzyl}-N'-(2-naphthylsulfonyl)malonamide,
(2S)—N,N-diethyl-2-[4-[(2,4-difluorobenzoyl)amino]benzyl]-N'-(2-naphthylsulfonyl)malonamide,
(2S)—N,N-diethyl-2-{4-[(4-methylbenzoyl)amino]benzyl}-N'-(2-naphthylsulfonyl)malonamide,
(2S)—N,N-diethyl-N'-(2-naphthylsulfonyl)-2-{4-[(2-thienoyl)amino]benzyl}malonamide,
(2S)—N,N-diethyl-2-{4-[(2-furoyl)amino]benzyl}-N'-(2-naphthylsulfonyl)malonamide,
(2S)-2-{4-[(2-amino-5-fluorobenzoyl)amino]benzyl}-N,N-diethyl-N'-(2-naphthylsulfonyl)malonamide,
(2S)-2-{4-[(2-amino-6-fluorobenzoyl)amino]benzyl}-N,N-diethyl-N'-(2-naphthylsulfonyl)malonamide,
(2S)—N,N-diethyl-N'-(2-naphthylsulfonyl)-2-{4-[(2-pyridylcarbonyl)amino]benzyl}malonamide,
(2S)-2-{4-[(2-amino-4-chlorobenzoyl)amino]benzyl}-N,N-diethyl-N'-(2-naphthylsulfonyl)malonamide,
(2S)-2-{4-[(2-aminobenzoyl)amino]benzyl}-N,N-diethyl-N'-(2-naphthylsulfonyl)malonamide,
(2S)-2-{4-[(2-amino-5-chlorobenzoyl)amino]benzyl}-N,N-diethyl-N'-(2-naphthylsulfonyl)malonamide,
(2S)-2-{4-[(2-amino-4,5-difluorobenzoyl)amino]benzyl}-N,N-diethyl-N'-(2-naphthylsulfonyl)malonamide,
(2S)-2-{4-[(2-amino-4-fluorobenzoyl)amino]benzyl}-N,N-diethyl-N'-(2-naphthylsulfonyl)malonamide,
(2S)-2-{4-[(2-amino-5-methylbenzoyl)amino]benzyl}-N,N-diethyl-N'-(2-naphthylsulfonyl)malonamide,
2-(4-fluorobenzyl)-N-isopropyl-N-(3-pyridyl)-N'-((E)-styrylsulfonyl)malonamide,
2-allyl-N-(4-fluorophenyl)-N-isopropyl-N'-((E)-styrylsulfonyl)malonamide,
N-(4-fluorophenyl)-2-isobutyl-N-isopropyl-N'-((E)-styrylsulfonyl)malonamide,
N-(4-fluorophenyl)-2-isobutyl-N-isopropyl-N'-phenethylsulfonylmalonamide,
N-(4-fluorophenyl)-2-isobutyl-N-isopropyl-N'-(2-naphthylsulfonyl)malonamide,
(2S or 2R)-2-cyclopropylmethyl-N-(4-fluorophenyl)-N-isopropyl-N'-((E)-2-styrylsulfonyl)malonamide,
2-cyclopropylmethyl-N-(4-fluorophenyl)-N-isopropyl-N'-phenethylsulfonylmalonamide, or
2-cyclopropylmethyl-N-(4-fluorophenyl)-N-isopropyl-N'-(2-naphthylsulfonyl)malonamide, or a pharmacologically acceptable salt thereof.

13. A pharmaceutical composition comprising the sulfonyl malonamide derivative of claim 6, or a pharmacologically acceptable salt thereof as an active ingredient.

14. An $AT_2$ receptor agonist comprising the sulfonyl malonamide derivative of claim 6, or a pharmacologically acceptable salt thereof.

15. An $AT_2$ receptor agonist comprising the sulfonyl malonamide derivative of claim 12, or a pharmacologically acceptable salt thereof.

16. The $AT_2$ receptor agonist of claim 15, which is $AT_2$ receptor selective.

* * * * *